(12) United States Patent
Bear et al.

(10) Patent No.: US 10,738,030 B2
(45) Date of Patent: Aug. 11, 2020

(54) MODULATORS OF CYSTIC FIBROSIS TRANSMEMBRANE CONDUCTANCE REGULATOR

(71) Applicant: Vertex Pharmaceuticals Incorporated, Boston, MA (US)

(72) Inventors: Brian Bear, Carlsbad, CA (US); Jeremy Clemens, San Diego, CA (US); Thomas Cleveland, San Diego, CA (US); Timothy Richard Coon, Carlsbad, CA (US); Peter Diederik Jan Grootenhuis, San Diego, CA (US); Bryan A. Frieman, La Jolla, CA (US); Sara S. Hadida Ruah, Del Mar, CA (US); Haripada Khatuya, San Diego, CA (US); Paul J. Krenitsky, San Diego, CA (US); Mark Thomas Miller, San Diego, CA (US); Alina Silina, San Diego, CA (US); Johnny Uy, San Diego, CA (US); Jinglan Zhou, San Diego, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 16/089,703

(22) PCT Filed: Mar. 31, 2017

(86) PCT No.: PCT/US2017/025381
§ 371 (c)(1),
(2) Date: Sep. 28, 2018

(87) PCT Pub. No.: WO2017/173274
PCT Pub. Date: Oct. 5, 2017

(65) Prior Publication Data
US 2019/0055220 A1 Feb. 21, 2019

Related U.S. Application Data

(60) Provisional application No. 62/316,043, filed on Mar. 31, 2016.

(51) Int. Cl.
| | | |
|---|---|---|
| *C07D 401/14* | (2006.01) | |
| *C07D 213/82* | (2006.01) | |
| *A61P 11/00* | (2006.01) | |
| *C07D 401/12* | (2006.01) | |
| *C07D 471/04* | (2006.01) | |

(52) U.S. Cl.
CPC ........... *C07D 401/14* (2013.01); *A61P 11/00* (2018.01); *C07D 213/82* (2013.01); *C07D 401/12* (2013.01); *C07D 471/04* (2013.01)

(58) Field of Classification Search
CPC .................. A61K 31/506; C07D 401/14
See application file for complete search history.

(56) References Cited

U.S. PATENT DOCUMENTS

| | | |
|---|---|---|
| 5,410,061 A | 4/1995 | Gilmore et al. |
| 6,441,004 B1 | 8/2002 | Faull et al. |
| 6,787,651 B2 | 9/2004 | Stolle et al. |
| 6,949,572 B2 | 9/2005 | Bertinato et al. |
| 6,979,692 B2 | 12/2005 | Bertinato et al. |
| 7,368,573 B2 | 5/2008 | Bertinato et al. |
| 8,058,299 B2 | 11/2011 | Bolin et al. |
| 9,782,408 B2 * | 10/2017 | Miller .................. A61K 31/506 |
| 10,258,624 B2 | 4/2019 | Miller et al. |
| 2002/0055631 A1 | 5/2002 | Augeri et al. |
| 2002/0086887 A1 | 7/2002 | Augeri et al. |
| 2005/0171185 A1 | 8/2005 | Yamasaki et al. |
| 2005/0197376 A1 | 9/2005 | Kayakiri et al. |
| 2011/0165118 A1 | 7/2011 | Chan et al. |
| 2013/0267493 A1 | 10/2013 | Bhattacharya et al. |
| 2015/0322002 A1 * | 11/2015 | Dehnhardt .......... C07D 401/12 514/210.01 |
| 2016/0095858 A1 * | 4/2016 | Miller .................. A61K 31/506 514/253.09 |

(Continued)

FOREIGN PATENT DOCUMENTS

| | | |
|---|---|---|
| CA | 2145473 A1 | 9/1995 |
| EP | 0 194 599 A2 | 9/1986 |
| EP | 0 673 930 A1 | 9/1995 |

(Continued)

OTHER PUBLICATIONS

Ellis's CAS: 143: 186789, 2005.*
Anilkumar, G.N. et al. (2011) "II. Novel HCV NS5B polymerase inhibitors: Discovery of indole C2 acyl sulfonamides" *Biogranic & Medicinal Chemistry Letters*, 22(1):713-717.
Borhade, S.R. et al. (2013) "Synthesis of Novel Aryl and Heteroaryl Acyl Sulfonimidamides via Pd-Catalyzed Carbonylation Using a Nongaseous Precursor" *Organic Lett*, 15(5):1056-1059.
Chen, Y. (Jan. 26, 2016) "N-Monoacylation of Sulfonimidamides" *Synthesis*, 48(7):1019-1028.
Database Caplus, Accession No. 1965:51408. Abstract of French Patent No. FR M2868, filed Nov. 23, 1964, by Roussel-UCLAF [online]. Retrieved Jan. 6, 2017 (1 page).

(Continued)

*Primary Examiner* — Rei Tsang Shiao
(74) *Attorney, Agent, or Firm* — Finnegan, Henderson, Farabow, Garrett & Dunner, LLP

(57) ABSTRACT

The present disclosure features a compound of formula I: or a pharmaceutically acceptable salt thereof, where $R_1$, $R_2$, W, X, Z, n, p, and Rings A and B are defined herein, for the treatment of CFTR mediated diseases, such as cystic fibrosis. The present disclosure also features pharmaceutical compositions, method of treating, and kits thereof.

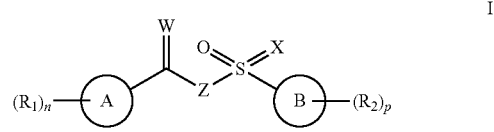

48 Claims, 8 Drawing Sheets

(56) References Cited

U.S. PATENT DOCUMENTS

| | | |
|---|---|---|
| 2018/0093969 A1 | 4/2018 | Alcacio et al. |
| 2018/0162839 A1 | 6/2018 | Abela et al. |

FOREIGN PATENT DOCUMENTS

| | | |
|---|---|---|
| EP | 1 318 978 B1 | 2/2006 |
| JP | 10-114654 A | 5/1998 |
| WO | WO 96/03380 A1 | 2/1996 |
| WO | WO 96/22022 A1 | 7/1996 |
| WO | WO 97/18712 A1 | 5/1997 |
| WO | WO 97/22586 A1 | 6/1997 |
| WO | WO 98/31226 A1 | 7/1998 |
| WO | WO 99/16744 A1 | 4/1999 |
| WO | WO 99/37153 A1 | 7/1999 |
| WO | WO 99/41238 A1 | 8/1999 |
| WO | WO 00/76969 A1 | 12/2000 |
| WO | WO 01/08487 A1 | 2/2001 |
| WO | WO 01/15533 A1 | 3/2001 |
| WO | WO 01/39597 A2 | 6/2001 |
| WO | WO 02/15902 A1 | 2/2002 |
| WO | WO 02/24636 A2 | 3/2002 |
| WO | WO 02/30895 A1 | 4/2002 |
| WO | WO 02/085120 A2 | 10/2002 |
| WO | WO 02/096883 A1 | 12/2002 |
| WO | WO 03/002533 A1 | 1/2003 |
| WO | WO 03/022050 A1 | 3/2003 |
| WO | WO 03/028458 A1 | 4/2003 |
| WO | WO 03/043423 A1 | 5/2003 |
| WO | WO 03/043655 A1 | 5/2003 |
| WO | WO 03/101959 A1 | 12/2003 |
| WO | WO 03/103394 A2 | 12/2003 |
| WO | WO 2004/021788 A1 | 3/2004 |
| WO | WO 2004/021987 A2 | 3/2004 |
| WO | WO 2004/037798 A1 | 5/2004 |
| WO | WO 2004/039753 A2 | 5/2004 |
| WO | WO 2004/043939 A1 | 5/2004 |
| WO | WO 2004/046141 A1 | 6/2004 |
| WO | WO 2004/056775 A1 | 7/2004 |
| WO | WO 2004/056777 A1 | 7/2004 |
| WO | WO 2004/078114 A2 | 9/2004 |
| WO | WO 2004/085420 A1 | 10/2004 |
| WO | WO 2005/054191 A1 | 6/2005 |
| WO | WO 2005/070006 A2 | 8/2005 |
| WO | WO 2005/080373 A1 | 9/2005 |
| WO | WO 2005/085216 A1 | 9/2005 |
| WO | WO 2005/099705 A2 | 10/2005 |
| WO | WO 2005/108369 A1 | 11/2005 |
| WO | WO 2006/030807 A1 | 3/2006 |
| WO | WO 2006/039212 A2 | 4/2006 |
| WO | WO 2006/065204 A1 | 6/2006 |
| WO | WO 2006/066968 A1 | 6/2006 |
| WO | WO 2006/067392 A2 | 6/2006 |
| WO | WO 2007/019397 A2 | 2/2007 |
| WO | WO 2007/021982 A2 | 2/2007 |
| WO | WO 2007/113327 A2 | 10/2007 |
| WO | WO 2008/005457 A2 | 1/2008 |
| WO | WO 2008/100867 A2 | 8/2008 |
| WO | WO 2008/141385 A1 | 11/2008 |
| WO | WO 2009/027730 A1 | 3/2009 |
| WO | WO 2009/032116 A1 | 3/2009 |
| WO | WO 2009/064848 A1 | 5/2009 |
| WO | WO 2009/071947 A2 | 6/2009 |
| WO | WO 2009/127822 A2 | 10/2009 |
| WO | WO 2009/138758 A2 | 11/2009 |
| WO | WO 2010/003444 A1 | 1/2010 |
| WO | WO 2010/007116 A2 | 1/2010 |
| WO | WO 2010/022307 A2 | 2/2010 |
| WO | WO 2010/025295 A2 | 3/2010 |
| WO | WO 2010/065824 A2 | 6/2010 |
| WO | WO 2010/083441 A2 | 7/2010 |
| WO | WO 2010/102758 A2 | 9/2010 |
| WO | WO 2010/110231 A1 | 9/2010 |
| WO | WO 2010/123822 A1 | 10/2010 |
| WO | WO 2010/138588 A2 | 12/2010 |
| WO | WO 2011/068560 A1 | 6/2011 |
| WO | WO 2011/102514 A1 | 8/2011 |
| WO | WO 2011/128251 A1 | 10/2011 |
| WO | WO 2011/150016 A1 | 12/2011 |
| WO | WO 2012/052540 A1 | 4/2012 |
| WO | WO 2012/087938 A1 | 6/2012 |
| WO | WO 2012/089721 A1 | 7/2012 |
| WO | WO 2012/089722 A2 | 7/2012 |
| WO | WO 2012/102297 A1 | 8/2012 |
| WO | WO 2012/110519 A1 | 8/2012 |
| WO | WO 2012/116960 A1 | 9/2012 |
| WO | WO 2012/139891 A1 | 10/2012 |
| WO | WO 2012/166415 A1 | 12/2012 |
| WO | WO 2013/033068 A1 | 3/2013 |
| WO | WO 2013/037955 A1 | 3/2013 |
| WO | WO 2013/038373 A1 | 3/2013 |
| WO | WO 2013/041602 A1 | 3/2013 |
| WO | WO 2013/082102 A1 | 6/2013 |
| WO | WO 2013/118805 A1 | 8/2013 |
| WO | WO 2013/177224 A1 | 11/2013 |
| WO | WO 2013/185202 A1 | 12/2013 |
| WO | WO 2014/008458 A2 | 1/2014 |
| WO | WO 2014/014841 A1 | 1/2014 |
| WO | WO 2014/017093 A1 | 1/2014 |
| WO | WO 2014/028381 A1 | 2/2014 |
| WO | WO 2014/028968 A1 | 2/2014 |
| WO | WO 2014/039714 A2 | 3/2014 |
| WO | WO 2014/047427 A2 | 3/2014 |
| WO | WO 2014/071122 A1 | 5/2014 |
| WO | WO 2014/071247 A1 | 5/2014 |
| WO | WO 2014/071378 A1 | 5/2014 |
| WO | WO 2014/086723 A1 | 6/2014 |
| WO | WO 2014/086739 A1 | 6/2014 |
| WO | WO 2014/086751 A1 | 6/2014 |
| WO | WO 2014/096388 A2 | 6/2014 |
| WO | WO 2014/109858 A1 | 7/2014 |
| WO | WO 2014/144100 A2 | 9/2014 |
| WO | WO 2014/152013 A1 | 9/2014 |
| WO | WO 2014/152018 A1 | 9/2014 |
| WO | WO 2014/180562 A1 | 11/2014 |
| WO | WO 2014/181287 A1 | 11/2014 |
| WO | WO 2014/190199 A1 | 11/2014 |
| WO | WO 2015/010832 A1 | 1/2015 |
| WO | WO 2015/031608 A1 | 3/2015 |
| WO | WO 2015/069287 A1 | 5/2015 |
| WO | WO 2015/160787 A1 | 10/2015 |
| WO | WO 2016/057572 A1 | 4/2016 |
| WO | WO 2016/105484 A1 | 6/2016 |
| WO | WO 2016/105485 A2 | 6/2016 |
| WO | WO 2016/160945 A1 | 10/2016 |
| WO | WO 2017/053455 A1 | 3/2017 |
| WO | WO 2017/173274 A1 | 10/2017 |
| WO | WO 2018/064632 A1 | 4/2018 |
| WO | WO 2018/107100 A1 | 6/2018 |

OTHER PUBLICATIONS

Database Caplus, Accession No. 1965:51409. Abstract of German Patent No. DE 1182243, filed Nov. 26, 1964, by Badische Anilin & Soda-Fabrik A.G. [online]. Retrieved Jan. 6, 2017 (2 pages).

Database Pubchem, CID: 2545578. Compound Summary, T5339296. NIH, U.S. National Library of Medicine, National Center for Biotechnology Information; Modify Date: Jan. 16, 2016. [online]. Retrieved from https://pubchem.ncbi.nlm.nih.gov/compound/2545578, on Jan. 22, 2016 (9 pages).

Database Pubchem, CID: 44419393. Compound Summary, CHEMBL374189. NIH, U.S. National Library of Medicine, National Center for Biotechnology Information; Modify Date: Jan. 16, 2016. [online]. Retrieved from https://pubchem.ncbi.nlm.nih.gov/compound/44419393, on Jan. 22, 2016 (11 pages).

Database Pubchem, CID: 49774135. Compound Summary, SCHEMBL13395127. NIH, U.S. National Library of Medicine, National Center for Biotechnology Information; Modify Date: Jan. 16, 2016 [online]. Retrieved from https://pubchem.ncbi.nlm.nih.gov/compound/49774135, on Jan. 22, 2016 (10 pages).

Database Pubchem, CID: 58132855. Compound Summary, SCHEMBL831192. NIH, U.S. National Library of Medicine, National

(56) References Cited

OTHER PUBLICATIONS

Center for Biotechnology Information, PubChem Open Chemistry Database; Modify Date: Jan. 16, 2016 [online]. Retrieved from: https://pubchem.ncbi.nlm.nih.gov/compound/58132855, on Jan. 22, 2016 (10 pages).

Hopkins, C.R. et al. (2006) "Design and synthesis of novel N-sulfonyl-2-indole carboxamides as potent PPAR-gamma binding agents with potential application to the treatment of osteoporosis" Bioorganic & Medicinal Chemistry Letters, 16(21):5659-5663.

International Patent Application No. PCT/US2015/54316: International Search Report and Written Opinion, dated Feb. 5, 2016 (11 pages).

International Patent Application No. PCT/US2017/025381: International Search Report and Written Opinion, dated Jun. 6, 2017 (11 pages).

International Patent Application No. PCT/US2017/054611: International Search Report and Written Opinion, dated Jan. 3, 2018 (10 pages).

International Patent Application No. PCT/US2017/065425: International Search Report and Written Opinion, dated Feb. 27, 2018 (10 pages).

International Patent Application No. PCT/US2018/036610: International Search Report and Written Opinion, dated Sep. 19, 2018 (9 pages).

International Patent Application No. PCT/US2018/040427: International Search Report and Written Opinion, dated Oct. 9, 2018 (15 pages).

International Patent Application No. PCT/US2018/042415: International Search Report and Written Opinion, dated Oct. 31, 2018 (12 pages).

International Patent Application No. PCT/US2018/042486: International Search Report and Written Opinion, dated Nov. 7, 2018 (13 pages).

International Patent Application No. PCT/US2018/044963: International Search Report and Written Opinion, dated Sep. 25, 2018 (15 pages).

International Patent Application No. PCT/US2018/056772: International Search Report and Written Opinion, dated Jan. 29, 2019 (13 pages).

Jain, B.C. et al. (1947) "Studies in Sulphanilamides. Part XIII. Reaction With Dicarboxylic Acids. Some New N1- and N4-Acyl and Heterocycic Derivatives" *Journal of the Indian Chemical Society*, 24:173-176.

Kettle, J.G. et al. (2004) "N-Benzylindole-2-carboxylic acids: potent functional antagonists of the CCR2b chemokine receptor" *Bioorganic & Medicinal Chemistry Letters*, 14(2): 405-408.

Lai, J.T. et al. (1980) "Rearrangement of 2,2,6,6-tetramethyl-4-piperidone in phase-transfer catalyzed reactions," *Journal of Organic Chemistry*, 45(8):1513-1514.

Matter, H. et al. (2002) "Design and Quantitative Structure-Activity Relationship of 3-Amidinobenzyl-1H-indole-2-carboxamides as Potent, Nonchiral, and Selective Inhibitors of Blood Coagulation Factor Xa" *Journal of Medicinal Chemistry*, 45(13):2749-2769.

Norman, P. (2014) "Novel picolinamide-based cystic fibrosis transmembrane regulator modulators: evaluation of WO2013038373, WO2013038376, WO2013038381, WO2013038386, and WO2013038390," *Expert Opinion on Therapeutic Patents*, 24(7):829-837.

Passarella, D. et al. (2001) "Cyclodimerization of indol-2-ylacetylenes. An example of intermolecular enyne-alkyne cycloaddition" *Journal of the Chemical Society, Perkin Transactions 1*, 127-129.

Rosebraugh, C.J. (2015) "Highlights of Presecribing Information for Orkambi," [online] Retrieved from the Internet: https://www.accessdata.fda.gov/drugsatfda_docs/label/2015/206038Orig1s000lbl.pdf, on Aug. 24, 2017.

Silverman, R. (2004) The Organic Chemistry of Drug Design and Drug Action, Elsevier, pp. 29-32.

Soloducho, J. (1989) "Synthesis of Some Pyrido [2,3-c][1,2,6]triazinone Derivatives" *Journal für Pracktische Chemie*, 331(3):503-506.

Tullis, E. et al. (2018) "Preliminary safety and efficacy of triple-combination CFTR modulator regimens," *Respirology*, 23(51):33.

U.S. Appl. No. 16/089,703, filed Sep. 28, 2018, by Bear et al.
U.S. Appl. No. 16/258,024, filed Jan. 25, 2019, by Miller et al.
U.S. Appl. No. 16/165,849, filed Oct. 19, 2018, by Dhamankar et al.
U.S. Appl. No. 16/267,222, filed Feb. 4, 2019, by Chu et al.
U.S. Appl. No. 16/267,350, filed Feb. 14, 2019, by Clemens et al.

Uttamsingh, V. et al. (2016) "WS13.6 CTP-656 tablet confirmed superiority of pharmacokinetic profile relative to Kalydeco in Phase I clinical studies" *Journal of Cystic Fibrosis*, 15:S22.

Wainwright, C.E. et al. (2015) "Lumacaftor-Ivacaftor in Patients with Cystic Fibrosis Homozygous for Phe508del CFTR," *The New England Journal of Medicine*, 373(3):220-231.

Winn, M. et al. (1993) "2-(Alkylamino)nicotinic Acid and Analogs. Potent Angiotensin II Antagonists" *Journal of Medicinal Chemistry*, 36(18):2676-2688.

Verardo, G. et al. (1999) "Reductive One Batch Synthesis of N-Substituted Pyrrolidines from Primary Amines and 2,5-Dimethoxytetrahydrofuran" *Synthesis*, (1):74-79.

Vertex Pharmaceuticals, Inc. (Mar. 28, 2017) "Two Phase 3 Studies of the Tezacaftor/Ivacaftor Combination Treatment Met Primary Endpoints with Statistically Significant Improvements in Lung Function (FEV1) in People With Cystic Fibrosis" [online] Retrieved from the Internet: http://investors.vrtx.com/static-files/f15217ac-4a8b-436a-9215-79144ec2e59b, on Oct. 10, 2019.

\* cited by examiner

Figure 1

| Mutation cDNA Name | Mutation Protein Name | Mutation Legacy Name |
|---|---|---|
| c.1A>G | p.? (unknown) | M1V |
| c.54-5940_273+10250del21kb | p.Ser18ArgfsX16 | CFTRdele2,3 |
| c.91C>T | p.Arg31Cys | R31C |
| c.115C>T | p.Gln39X | Q39X |
| c.137C>A | p.Ala46Asp | A46D |
| c.165-1G>A | No protein name | 297-1G->A |
| c.166G>A | p.Glu56Lys | E56K |
| c.174_175insA | p.Arg59LysfsX10 | 306insA |
| c.178G>T | p.Glu60X | E60X |
| c.200C>T | p.Pro67Leu | P67L |
| c.220C>T | p.Arg74Trp | R74W |
| c.223C>T | p.Arg75X | R75X |
| c.224G>A | p.Arg75Gln | R75Q |
| c.254G>A | p.Gly85Glu | G85E |
| c.262_263delTT | p.Leu88IlefsX22 | 394delTT |
| c.273+1G>A | No protein name | 405+1G->A |
| c.274-1G>A | No protein name | 406-1G->A |
| c.274G>A | p.Glu92Lys | E92K |
| c.274G>T | p.Glu92X | E92X |
| c.292C>T | p.Gln98X | Q98X |
| c.313delA | p.Ile105SerfsX2 | 444delA |
| c.325_327delTATinsG | p.Tyr109GlyfsX4 | 457TAT->G |
| c.328G>C | p.Asp110His | D110H |
| c.349C>T | p.Arg117Cys | R117C |
| c.350G>A | p.Arg117His | R117H |
| c.366T>A | p.Tyr122X | Y122X |
| c.442delA | p.Ile148LeufsX5 | 574delA |
| c.443T>C | p.Ile148Thr | I148T |
| c.489+1G>T | No protein name | 621+1G->T |

Figure 1 Continued

| Mutation cDNA Name | Mutation Protein Name | Mutation Legacy Name |
|---|---|---|
| c.531delT | p.Ile177MetfsX12 | 663delT |
| c.532G>A | p.Gly178Glu | G178R |
| c.543_546delTAGT | p.Leu183PhefsX5 | 675del4 |
| c.579+1G>T | No protein name | 711+1G->T |
| c.579+3A>G | No protein name | 711+3A->G |
| c.579+5G>A | No protein name | 711+5G->A |
| c.580-1G>T | No protein name | 712-1G->T |
| c.595C>T | p.His199Tyr | H199Y |
| c.613C>T | p.Pro205Ser | P205S |
| c.617T>G | p.Leu206Trp | L206W |
| c.658C>T | p.Gln220X | Q220X |
| c.680T>G | p.Leu227Arg | L227R |
| c.720_741delAGGGAGAATGATGATGAAGTAC | p.Gly241GlufsX13 | 852del22 |
| c.828C>A | p.Cys276X | C276X |
| c.948delT | p.Phe316LeufsX12 | 1078delT |
| c.988G>T | p.Gly330X | G330X |
| c.1000C>T | p.Arg334Trp | R334W |
| c.1007T>A | p.Ile336Lys | I336K |
| c.1013C>T | p.Thr338Ile | T338I |
| c.1021T>C | p.Ser341Pro | S341P |
| c.1022_1023insTC | p.Phe342HisfsX28 | 1154insTC |
| c.1040G>A | p.Arg347His | R347H |
| c.1040G>C | p.Arg347Pro | R347P |
| c.1055G>A | p.Arg352Gln | R352Q |
| c.[1075C>A;1079C>A] | p.[Gln359Lys;Thr360Lys] | Q359K/T360K |

Figure 1 Continued

| Mutation cDNA Name | Mutation Protein Name | Mutation Legacy Name |
|---|---|---|
| c.1081delT | p.Trp361GlyfsX8 | 1213delT |
| c.1116+1G>A | No protein name | 1248+1G->A |
| c.1127_1128insA | p.Gln378AlafsX4 | 1259insA |
| c.1153_1154insAT | p.Asn386IlefsX3 | 1288insTA |
| c.1202G>A or c.1203G>A | p.Trp401X | W401X |
| c.1209+1G>A | No protein name | 1341+1G->A |
| c.1210-12[5] | No protein name | 5T |
| c.1210-12[7] | No protein name | 7T |
| c.1240C>T | p.Gln414X | Q414X |
| c.1329_1330insAGAT | p.Ile444ArgfsX3 | 1461ins4 |
| c.1340delA | p.Lys447ArgfsX2 | 1471delA |
| c.1364C>A | p.Ala455Glu | A455E |
| c.1393-1G>A | No protein name | 1525-1G->A |
| c.1397C>A or c.1397C>G | p.Ser466X | S466X |
| c.1400T>C | p.Leu467Pro | L467P |
| c.1408A>G | p.Met470Val | M470V |
| c.1418delG | p.Gly473GlufsX54 | 1548delG |
| c.1466C>A | p.Ser489X | S489X |
| c.1475C>T | p.Ser492Phe | S492F |
| c.1477C>T | p.Gln493X | Q493X |
| c.1519_1521delATC | p.Ile507del | I507del |
| c.1521_1523delCTT | p.Phe508del | F508del |
| c.1545_1546delTA | p.Tyr515X | 1677delTA |
| c.1558G>T | p.Val520Phe | V520F |
| c.1573C>T | p.Gln525X | Q525X |
| c.1585-8G>A | No protein name | 1717-8G->A |
| c.1585-1G>A | No protein name | 1717-1G->A |
| c.1624G>T | p.Gly542X | G542X |
| c.1645A>C or c.1647T>G | p.Ser549Arg | S549R |

Figure 1 Continued

| Mutation cDNA Name | Mutation Protein Name | Mutation Legacy Name |
|---|---|---|
| c.1646G>A | p.Ser549Asn | S549N |
| c.1650delA | p.Gly551ValfsX8 | 1782delA |
| c.1651G>A | p.Gly551Ser | G551S |
| c.1652G>A | p.Gly551Asp | G551D |
| c.1654C>T | p.Gln552X | Q552X |
| c.1657C>T | p.Arg553X | R553X |
| c.1673T>C | p.Leu558Ser | L558S |
| c.1675G>A | p.Ala559Thr | A559T |
| c.1679G>A | p.Arg560Lys | R560K |
| c.1679G>C | p.Arg560Thr | R560T |
| c.1679+1G>C | No protein name | 1811+1G->C |
| c.1679+1.6kbA>G | No protein name | 1811+1.6kbA->G |
| c.1680-1G>A | No protein name | 1812-1G->A |
| c.1682C>A | p.Ala561Glu | A561E |
| c.1692delA | p.Asp565MetfsX7 | 1824delA |
| c.1705T>G | p.Tyr569Asp | Y569D |
| c.1727G>C | p.Gly576Ala | G576A |
| c.1736A>G | p.Asp579Gly | D579G |
| c.1753G>T | p.Glu585X | E585X |
| c.1766+1G>A | No protein name | 1898+1G->A |
| c.1766+1G>C | No protein name | 1898+1G->C |
| c.1766+3A>G | No protein name | 1898+3A->G |
| c.1841A>G | p.Asp614Gly | D614G |
| c.1923_1931del9insA | p.Ser641ArgfsX5 | 2055del9->A |

Figure 1 Continued

| Mutation cDNA Name | Mutation Protein Name | Mutation Legacy Name |
|---|---|---|
| c.1973_1985del13insAGAAA | p.Arg658LysfsX4 | 2105-2117del13insAGAAA |
| c.1986_1989delAACT | p.Thr663ArgfsX8 | 2118del4 |
| c.2002C>T | p.Arg668Cys | R668C |
| c.2012delT | p.Leu671X | 2143delT |
| c.2051_2052delAAinsG | p.Lys684SerfsX38 | 2183AA->G* |
| c.2051_2052delAAinsG | p.Lys684SerfsX38 | 2183delAA->G* |
| c.2052_2053insA | p.Gln685ThrfsX4 | 2184insA |
| c.2052delA | p.Lys684AsnfsX38 | 2184delA |
| c.2125C>T | p.Arg709X | R709X |
| c.2128A>T | p.Lys710X | K710X |
| c.2175_2176insA | p.Glu726ArgfsX4 | 2307insA |
| c.2195T>G | p.Leu732X | L732X |
| c.2215delG | p.Val739TyrfsX16 | 2347delG |
| c.2260G>A | p.Val754Met | V754M |
| c.2290C>T | p.Arg764X | R764X |
| c.2353C>T | p.Arg785X | R785X |
| c.2374C>T | p.Arg792X | R792X |
| c.2424_2425insAT | p.Ser809IlefsX13 | 2556insAT |
| c.2453delT | p.Leu818TrpfsX3 | 2585delT |
| c.2462_2463delGT | p.Ser821ArgfsX4 | No legacy name |
| c.2464G>T | p.Glu822X | E822X |
| c.2490+1G>A | No protein name | 2622+1G->A |
| c.2491G>T | p.Glu831X | E831X |
| c.2537G>A or c.2538G>A | p.Trp846X | W846X |
| c.2547C>A | p.Tyr849X | Y849X |
| c.2551C>T | p.Arg851X | R851X |
| c.2583delT | p.Phe861LeufsX3 | 2711delT |

Figure 1 Continued

| Mutation cDNA Name | Mutation Protein Name | Mutation Legacy Name |
|---|---|---|
| c.2657+2_2657+3insA | No protein name | 2789+2insA |
| c.2657+5G>A | No protein name | 2789+5G->A |
| c.2658-1G>C | No protein name | 2790-1G->C |
| c.2668C>T | p.Gln890X | Q890X |
| c.2735C>A | p.Ser912X | S912X |
| c.2737_2738insG | | 2869insG |
| c.2739T>A | p.Tyr913X | Y913X |
| c.2764_2765insAG | p.Val922GlufsX2 | 2896insAG |
| c.2780T>C | p.Leu927Pro | L927P |
| c.2834C>T | p.Ser945Leu | S945L |
| c.2875delG | p.Ala959HisfsX9 | 3007delG |
| c.2908G>C | p.Gly970Arg | G970R |
| c.2930C>T | p.Ser977Phe | S977F |
| c.2988G>A | No protein name | 3120G->A |
| c.2988+1G>A | No protein name | 3120+1G->A |
| c.2989-977_3367+248del | No protein name | 3121-977_3499+248del2515 |
| c.2989-1G>A | No protein name | 3121-1G->A |
| c.2991G>C | p.Leu997Phe | L997F |
| c.3002_3003delTG | p.Val1001AspfsX4 | 3132delTG |
| c.3080T>C | p.Ile1027Thr | I1027T |
| c.3140-26A>G | No protein name | 3272-26A->G |
| c.3154T>G | p.Phe1052Val | F1052V |
| c.3160C>G | p.His1054Asp | H1054D |
| c.3181G>C | p.Gly1061Arg | G1061R |
| c.3194T>C | p.Leu1065Pro | L1065P |
| c.3196C>T | p.Arg1066Cys | R1066C |
| c.3197G>A | p.Arg1066His | R1066H |

Figure 1 Continued

| Mutation cDNA Name | Mutation Protein Name | Mutation Legacy Name |
|---|---|---|
| c.3205G>A | p.Gly1069Arg | G1069R |
| c.3208C>T | p.Arg1070Trp | R1070W |
| c.3209G>A | p.Arg1070Gln | R1070Q |
| c.3222T>A | p.Phe1074Leu | F1074L |
| c.3230T>C | p.Leu1077Pro | L1077P |
| c.3266G>A | p.Trp1089X | W1089X |
| c.3276C>A or c.3276C>G | p.Tyr1092X | Y1092X |
| c.3302T>A | p.Met1101Lys | M1101K |
| c.3310G>T | p.Glu1104X | E1104X |
| c.3454G>C | p.Asp1152His | D1152H |
| c.3472C>T | p.Arg1158X | R1158X |
| c.3484C>T | p.Arg1162X | R1162X |
| c.3485G>T | p.Arg1162Leu | R1162L |
| c.3528delC | p.Lys1177SerfsX15 | 3659delC |
| c.3535_3536insTCAA | p.Thr1179IlefsX17 | 3667ins4 |
| c.3587C>G | p.Ser1196X | S1196X |
| c.3605delA | p.Asp1202AlafsX9 | 3737delA |
| c.3611G>A or c.3612G>A | p.Trp1204X | W1204X |
| c.3659delC | p.Thr1220LysfsX8 | 3791delC |
| c.3691delT | p.Ser1231ProfsX4 | 3821delT |
| c.3700A>G | p.Ile1234Val | I1234V |
| c.3705T>G | p.Ser1235Arg | S1235R |
| c.3717+12191C>T | No protein name | 3849+10kbC>T |

Figure 1 Continued

| Mutation cDNA Name | Mutation Protein Name | Mutation Legacy Name |
|---|---|---|
| c.3718-1G>A | No protein name | 3850-1G->A |
| c.3731G>A | p.Gly1244Glu | G1244E |
| c.3744delA | p.Lys1250ArgfsX9 | 3876delA |
| c.3752G>A | p.Ser1251Asn | S1251N |
| c.3763T>C | p.Ser1255Pro | S1255P |
| c.3764C>A | p.Ser1255X | S1255X |
| c.3773_3774insT | p.Leu1258PhefsX7 | 3905insT |
| c.3808G>A | p.Asp1270Asn | D1270N |
| c.3846G>A | p.Trp1282X | W1282X |
| c.3873+1G>A | No protein name | 4005+1G->A |
| c.3883delA | p.Ile1295PhefsX3 | 4015delA |
| c.3884_3885insT | p.Ser1297PhefsX5 | 4016insT |
| c.3909C>G | p.Asn1303Lys | N1303K |
| c.3937C>T | p.Gln1313X | Q1313X |
| c.3964-78_4242+577del | NULL | CFTRdele22,23 |
| c.4046G>A | p.Gly1349Asp | G1349D |
| c.4077_4080delTGTTinsAA | No protein name | 4209TGTT->AA |
| c.4111G>T | p.Glu1371X | E1371X |
| c.4196_4197delTC | p.Cys1400X | 4326delTC |
| c.4234C>T | p.Gln1412X | Q1412X |
| c.4242+1G>T | No protein name | 4374+1G->T |
| c.4251delA | p.Glu1418ArgfsX14 | 4382delA |
| c.4296_4297insGA | p.Ser1435GlyfsX14 | 4428insGA |

MODULATORS OF CYSTIC FIBROSIS TRANSMEMBRANE CONDUCTANCE REGULATOR

The application is a national stage application under 35 U.S.C. § 371 of international application number PCT/US2017/025381, filed Mar. 31, 2017, which designated the U.S. and claims the benefit of priority under 35 U.S.C. § 119 to U.S. provisional application Ser. No. 62/316,043, filed Mar. 31, 2016, the entire contents of which incorporated herein by reference.

The present disclosure features modulators of Cystic Fibrosis Transmembrane Conductance Regulator (CFTR), pharmaceutical compositions, methods of treatment, and kits thereof.

Cystic fibrosis (CF) is a recessive genetic disease that affects approximately 30,000 children and adults in the United States and approximately 30,000 children and adults in Europe. Despite progress in the treatment of CF, there is no cure.

In patients with CF, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245:1073-1080; Kerem, B-S et al. (1990) Proc. Natl. Acad. Sci. USA 87:8447-8451). To date, greater than 1000 disease causing mutations in the CF gene have been identified (http://cftr2.org). The most prevalent mutation is a deletion of phenylalanine at position 508 of the CFTR amino acid sequence, and is commonly referred to as F508del. This mutation occurs in approximately 70% of the cases of cystic fibrosis and is associated with a severe disease.

The deletion of residue 508 in F508del prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of F508del in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to F508del, other disease causing mutations in CFTR that result in defective trafficking, synthesis, and/or channel gating could be up- or down-regulated to alter anion secretion and modify disease progression and/or severity.

Accordingly, there is a need for novel treatments of CFTR mediated diseases.

The disclosure features a compound of formula I:

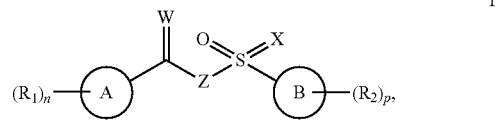

or a pharmaceutically acceptable salt thereof, wherein, independently for each occurrence:

Ring A is a $C_6$-$C_{10}$ aryl ring; a $C_3$-$C_{10}$ cycloalkyl ring; or a $C_3$-$C_{14}$ heteroaryl or heterocyclic ring wherein anywhere from 1 to 4 ring atoms are independently O, S, N, or NR;

Ring B is a $C_3$-$C_{10}$ cycloalkyl ring; a $C_6$-$C_{10}$ aryl ring; or a $C_3$-$C_{10}$ heteroaryl or $C_3$-$C_{10}$ heterocyclic ring wherein anywhere from 1 to 4 ring atoms are independently O, S, N, or NR;

W is O, S, or NR;

X is O or NR;

Z is NR or $C(R)_2$;

$R_1$ is halo; CN; NRR; $C_1$-$C_6$ alkyl or $C_1$-$C_6$ fluoroalkyl; $C_3$-$C_6$ cycloalkyl; $C_1$-$C_8$ alkoxy or $C_1$-$C_8$ fluoroalkoxy; $C_2$-$C_6$ alkenyl; $C_2$-$C_6$ alkynyl; ($C_1$-$C_9$ alkylene)-$R_3$ wherein up to four $CH_2$ units are independently replaced with O, CO, S, SO, $SO_2$ or NR; $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_2$ is halo; NRR; CN; $CO_2R$; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four $CH_2$ units are optionally and independently replaced with O, CO, S, SO, $SO_2$ or NR;

or two $R_2$ may form a $=CH_2$ or $=O$ group;

$R_3$ is H; $CF_3$; $CHF_2$; OR; C≡CH; $CO_2R$; OH; $C_6$-$C_{10}$ aryl; $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or $SO_2R$;

R is independently H; OH; $CO_2H$; $CO_2$; $C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, or N; or $C_3$-$C_{10}$ cycloalkyl;

n is 2 or 3;

p is 0, 1, 2, or 3; and

Provided that 1) when $R_1$ is adjacent to the C=W attached to Ring A, $R_1$ does not contain a ring moiety, 2) at least one $R_1$ is adjacent to the C=W attached to Ring A, and at least one $R_1$ is $C_1$-$C_6$ alkyl or $C_1$-$C_6$ fluoroalkyl, $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl; 3) when Ring A is phenyl or six-membered mono-heteroaryl wherein anywhere from 1 to 3 ring atoms are N, $R_1$ is not 4,5-dihydroisoxazole; 4) when Ring A is phenyl, $R_1$ is not

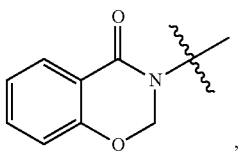 [SMILES: *N1COc2ccccc2C1=O ; ","]

ureido, or aminocarbonyl; 5) when Ring A and the at least one $R_1$ is pyridine, $R_1$ (pyridine) is not further substituted by —CONHSO$_2$—; and 6) when Ring A is pyridine or thiazole, and C=W wherein W is O in formula I is adjacent to the N on the pyridine or thiazole, $R_1$ which is adjacent to the N on the pyridine or on the thiazole is not

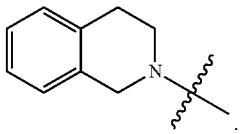 [SMILES: *N1CCc2ccccc2C1 ; "."]

The present disclosure also features pharmaceutical compositions thereof, which may include additional agents, and methods of treating CFTR mediated diseases, such as cystic fibrosis, comprising administering compounds of formula I to a subject in need thereof. The present disclosure also features kits comprising compounds of formula I.

FIG. 1 discloses a list of CFTR mutations by name, protein name, and legacy name that in one aspect of the disclosure a patient may possess and be treatable by the compounds and compositions of the present disclosure.

DEFINITIONS

As used herein, "CFTR" stands for cystic fibrosis transmembrane conductance regulator.

As used herein, "mutations" can refer to mutations in the CFTR gene or the CFTR protein. A "CFTR mutation" refers to a mutation in the CFTR gene, and a "CFTR mutation" refers to a mutation in the CFTR protein. A genetic defect or mutation, or a change in the nucleotides in a gene in general results in a mutation in the CFTR protein translated from that gene.

As used herein, a "F508del mutation" or "F508del" is a specific mutation within the CFTR protein. The mutation is a deletion of the three nucleotides that comprise the codon for amino acid phenylalanine at position 508, resulting in CFTR protein that lacks this phenylalanine residue.

The term "CFTR gating mutation" as used herein means a CFTR mutation that results in the production of a CFTR protein for which the predominant defect is a low channel open probability compared to normal CFTR (Van Goor, F., Hadida S. and Grootenhuis P., "Pharmacological Rescue of Mutant CFTR function for the Treatment of Cystic Fibrosis", Top. Med. Chem. 3: 91-120 (2008)). Gating mutations include, but are not limited to, G551D, G178R, S549N, S549R, G551S, G970R, G1244E, S1251N, S1255P, and G1349D.

As used herein, a patient who is "homozygous" for a particular mutation, e.g. F508del, has the same mutation on each allele.

As used herein, a patient who is "heterozygous" for a particular mutation, e.g. F508del, has this mutation on one allele, and a different mutation on the other allele.

As used herein, the term "modulator" refers to a compound that increases the activity of a biological compound such as a protein. For example, a CFTR modulator is a compound that increases the activity of CFTR. The increase in activity resulting from a CFTR modulator includes but is not limited to compounds that correct, potentiate, stabilize and/or amplify CFTR.

As used herein, the term "CFTR corrector" refers to a compound that increases the amount of functional CFTR protein to the cell surface, resulting in enhanced ion transport.

As used herein, the term "CFTR potentiator" refers to a compound that increases the channel activity of CFTR protein located at the cell surface, resulting in enhanced ion transport.

As used herein, the term "stabilize" or "stabilizer," as in a CFTR stabilizer, results in an elongated presence of CFTR in the epithelial cell membrane.

As used herein, the term "amplify" or "amplifier," as in a CFTR amplifier, enhances the effect of other CFTR modulators such as potentiators, correctors, or stabilizer.

As used herein, the term "active pharmaceutical ingredient" or "API" refers to a biologically active compound.

A "patient," "subject" or "individual" are used interchangeably and refer to either a human or non-human animal. The term includes mammals such as humans.

The terms "effective dose" or "effective amount" are used interchangeably herein and refer to that amount that produces the desired effect for which it is administered (e.g., improvement in CF or a symptom of CF or lessening the severity of CF or a symptom of CF). The exact amount will depend on the purpose of the treatment, and will be ascertainable by one skilled in the art using known techniques (see, e.g., Lloyd (1999) The Art, Science and Technology of Pharmaceutical Compounding).

As used herein, the terms "treatment," "treating," and the like generally mean the improvement of CF or its symptoms or lessening the severity of CF or its symptoms in a subject. "Treatment," as used herein, includes, but is not limited to, the following: increased growth of the subject, increased weight gain, reduction of mucus in the lungs, improved pancreatic and/or liver function, reduced cases of chest infections, and/or reduced instances of coughing or shortness of breath. Improvements in or lessening the severity of any of these conditions can be readily assessed according to standard methods and techniques known in the art.

As used herein, the term "in combination with" when referring to two or more compounds or agents means that the order of administration includes the compounds or agents being administered prior to, concurrent with, or subsequent to each other to the patient.

As used herein, the phrase "optionally substituted" is used interchangeably with the phrase "substituted or unsubstituted."

As described herein, compounds within the compositions of the disclosure can optionally be substituted with one or more substituents, such as are illustrated generally above, or as exemplified by particular classes, subclasses, and species of the disclosure (such as the compounds listed in Table 1). As described herein in formulas I to IIa-ii-2, the variables $R_1$ to $R_3$ in formulas I to IIa-ii-2 encompass specific groups, such as, for example, alkyl, alkenyl, alkynyl, alkoxy, heteroaryl, heterocyclic, cycloalkyl, and aryl, etc. Unless otherwise noted, each of the specific groups for the variables $R_1$ to $R_3$ can be optionally substituted with one or more groups selected from halo, phospho, OH, cycloalkyl, heterocycloalkyl, aryl, heteroaryl, fluoroalkyl, alkyl, alkenyl, alkynyl, nitro, CN, hydroxyl, and ($C_1$-$C_9$ alkylene)-E wherein up to 4 $CH_2$ units are independently replaced with O, S, $SO_2$, SO, CO, NH, N-alkyl, N-alkenyl, or N-alkynyl, and E is H, aryl, cycloalkyl, heterocycloalkyl, heteroaryl, alkoxy, CN, or $CF_3$, further wherein each of the aryl, cycloalkyl, heterocycloalkyl, and heteroaryl is optionally substituted with one or more group selected from halo, alkyl, amino, CN, alkenyl, alkynyl, and alkoxy.

In some embodiments, each of the specific groups for the variables $R_1$ to $R_3$ can be optionally substituted with one or more groups selected from halo, phospho, OH, $C_3$-$C_6$ cycloalkyl, 3-6-membered heterocycloalkyl, phenyl, 5-6-membered heteroaryl, $C_1$-$C_6$ fluoroalkyl, $C_1$-$C_6$ alkyl, $C_2$-$C_6$ alkenyl, $C_2$-$C_6$ alkynyl, nitro, CN, hydroxyl, and ($C_1$-$C_9$ alkylene)-E wherein up to 4 $CH_2$ units are independently replaced with O, S, $SO_2$, SO, CO, NH, N—$C_1$-$C_4$ alkyl, N—$C_2$-$C_4$ alkenyl, or N—$C_2$-$C_4$ alkynyl, and wherein E is H, phenyl, $C_3$-$C_6$ cycloalkyl, 3-6-membered heterocycloalkyl, 5-6-membered heteroaryl, $C_1$-$C_6$ alkoxy, CN, or $CF_3$, further wherein each of the phenyl, cycloalkyl, heterocycloalkyl, and heteroaryl is optionally substituted with one or more group selected from halo, $C_1$-$C_6$ alkyl, amino, CN, $C_2$-$C_6$ alkenyl, $C_2$-$C_6$ alkynyl, and $C_1$-$C_6$ alkoxy.

As used herein, the phrase "formulas I to IIa-ii-2" includes any one of formula I, I-i, Ia, Ia-i, Ia-i-1, Ia-i-2, Ia-ii, Ia-ii-1, Ia-ii-2, II, II-i, IIa, IIa-i, IIa-i-1, IIa-i-2, IIa-ii, IIa-ii-1, and IIa-ii-2, or any combinations thereof.

In some embodiments, each of the specific groups for the variables $R_1$ to $R_3$ can be optionally substituted with one or more groups selected from halo, $C_3$-$C_6$ cycloalkyl, 3-6-membered heterocycloalkyl, phenyl, 5-6-membered heteroaryl, $C_1$-$C_6$ fluoroalkyl, $C_1$-$C_6$ alkyl, $C_2$-$C_6$ alkenyl, $C_2$-$C_6$ alkynyl, CN, hydroxyl, and ($C_1$-$C_9$ alkylene)-E wherein up to 4 $CH_2$ units are independently replaced with O, S, $SO_2$, SO, CO, NH, N—$C_1$-$C_4$ alkyl, N—$C_2$-$C_4$ alkenyl, or N—$C_2$-$C_4$ alkynyl, and wherein E is H, phenyl, $C_3$-$C_6$ cycloalkyl, 3-6-membered heterocycloalkyl, 5-6-membered heteroaryl, $C_1$-$C_6$ alkoxy, CN, or $CF_3$, further wherein each of the phenyl, cycloalkyl, heterocycloalkyl, and heteroaryl is optionally substituted with one or more group selected from halo, $C_1$-$C_4$ alkyl, —$NH_2$, CN, $C_2$-$C_4$ alkenyl, $C_2$-$C_4$ alkynyl, and $C_1$-$C_4$ alkoxy.

In some embodiments, each of the specific groups for the variables $R_1$ to $R_3$ can be optionally substituted with one or more groups selected from halo, $C_1$-$C_6$ fluoroalkyl, $C_1$-$C_6$ alkyl, $C_2$-$C_6$ alkenyl, $C_2$-$C_6$ alkynyl, CN, hydroxyl, and ($C_1$-$C_9$ alkylene)-E wherein up to 4 $CH_2$ units are independently replaced with O, S, $SO_2$, SO, CO, NH, N—$C_1$-$C_4$ alkyl, N—$C_2$-$C_4$ alkenyl, or N—$C_2$-$C_4$ alkynyl, and wherein E is H, phenyl, $C_3$-$C_6$ cycloalkyl, 3-6-membered heterocycloalkyl, 5-6-membered heteroaryl, $C_1$-$C_6$ alkoxy, CN, or $CF_3$, further wherein each of the phenyl, cycloalkyl, heterocycloalkyl, and heteroaryl is optionally substituted with one or more group selected from halo, $C_1$-$C_4$ alkyl, —$NH_2$, CN, $C_2$-$C_4$ alkenyl, $C_2$-$C_4$ alkynyl, and $C_1$-$C_4$ alkoxy.

In some embodiments, each of the specific groups for the variables $R_1$ to $R_3$ can be optionally substituted with one or more groups selected from halo, $C_1$-$C_6$ fluoroalkyl, $C_1$-$C_6$ alkyl, $C_2$-$C_6$ alkenyl, $C_2$-$C_6$ alkynyl, CN, hydroxyl, and ($C_1$-$C_9$ alkylene)-E wherein up to 4 $CH_2$ units are independently replaced with O, S, $SO_2$, SO, CO, NH, N—$C_1$-$C_4$ alkyl, N—$C_2$-$C_4$ alkenyl, or N—$C_2$-$C_4$ alkynyl, and wherein E is H, CN, or $CF_3$.

In some embodiments, each of the specific groups for the variables $R_1$ to $R_3$ can be optionally substituted with one or more groups selected from halo, $C_1$-$C_6$ fluoroalkyl, $C_1$-$C_6$ alkyl, $C_2$-$C_6$ alkenyl, $C_2$-$C_6$ alkynyl, CN, hydroxyl, —$NH_2$, —$NH(C_1$-$C_6$ alkyl), —$N(C_1$-$C_6$ alkyl), and $C_1$-$C_6$ alkoxy.

In some embodiments, each of the specific groups for the variables $R_1$ to $R_3$ can be optionally substituted with one or more groups selected from halo, $C_1$-$C_6$ fluoroalkyl, $C_1$-$C_6$ alkyl, $C_2$-$C_6$ alkenyl, $C_2$-$C_6$ alkynyl, CN, hydroxyl, and $C_1$-$C_6$ alkoxy.

In some embodiments, each of the specific groups for the variables $R_1$ to $R_3$ can be optionally substituted with one or more groups selected from halo, $C_1$-$C_6$ fluoroalkyl, $C_1$-$C_6$ alkyl, $C_2$-$C_6$ alkenyl, $C_2$-$C_6$ alkynyl, and $C_1$-$C_6$ alkoxy.

In some embodiments, each of the specific groups for the variables $R_1$ and $R_3$ can be optionally substituted with one or more groups selected from halo, $C_1$-$C_6$ fluoroalkyl, $C_1$-$C_6$ alkyl, $C_2$-$C_6$ alkenyl, $C_2$-$C_6$ alkynyl, and $C_1$-$C_6$ alkoxy.

As one of ordinary skill in the art will recognize, combinations of substituents envisioned by this disclosure are those combinations that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week. When two alkoxy groups are bound to the same atom or adjacent atoms, the two alkoxy groups can form a ring together with the atom(s) to which they are bound.

As disclosed herein, substituents or variables (such as $R_1$ to $R_3$ in formula I to IIa-ii-2) can be selected from more than one specific group. To the extent that one specific group for a variable may include or overlap with another specific group for the same variable, the narrower specific group is provisoed out from the broader specific group. In other words, double inclusion cannot exist.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. As one of ordinary skill in the art will recognize, combinations of substituents envisioned by this disclosure are those combinations that result in the formation of stable or chemically feasible compounds.

The phrase "up to", as used herein, refers to zero or any integer number that is equal or less than the number following the phrase. For example, "up to 3" means any one of 0, 1, 2, and 3.

The terms "about" and "approximately", when used in connection with doses, amounts, or weight percent of ingredients of a composition or a dosage form, mean a dose, amount, or weight percent that is recognized by one of ordinary skill in the art to provide a pharmacological effect equivalent to that obtained from the specified dose, amount, or weight percent. Specifically the term "about" or "approximately" means an acceptable error for a particular value as determined by one of ordinary skill in the art, which depends in part on how the value is measured or determined. In certain embodiments, the term "about" or "approximately"

means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range.

The term "adjacent" as used herein refers to positions on the ring wherein the two ring atoms are bonded to each other. Two ring atoms with an intervening ring atom are not considered adjacent even when that intervening atom does not allow substitution due to valency.

The term "aliphatic", "aliphatic group," as used herein, means a straight-chain (i.e., unbranched) or branched hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Suitable aliphatic groups include, but are not limited to, linear or branched, substituted or unsubstituted alkyl, alkenyl, alkynyl groups.

The term "spiro" as used herein, means a two-ring system wherein both rings share only one common atom.

The term "cycloaliphatic" or "cycloalkyl" mean a monocyclic, bicyclic (fused or spiro), tricyclic (fused or spiro), or propellane hydrocarbon that has a single point of attachment to the rest of the molecule, and that is completely saturated or contains one or more units of unsaturation, but none of the individual rings in the monocyclic, bicyclic, or tricyclic hydrocarbon is aromatic. The single point of attachment can be on the saturated or unsaturated carbon. In some embodiments, "cycloaliphatic" or "cycloalkyl" refers to a monocyclic $C_3$-$C_8$ hydrocarbon or bicyclic $C_8$-$C_{12}$ hydrocarbon that is completely saturated or that contains one or more units of unsaturation, but none of the individual ring in the monocyclic $C_3$-$C_8$ hydrocarbon or fused bicyclic $C_8$-$C_{12}$ hydrocarbon is aromatic, and that has a single point of attachment to the rest of the molecule wherein any individual ring in said bicyclic ring system has 3-7 members.

As used herein, an "alkyl" group refers to a saturated hydrocarbon group containing 1-20 (e.g., 1-6 or 1-12) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl.

As used herein, an "alkenyl" group refers to a hydrocarbon group that contains 2-20 (e.g., 2-12, 2-6, or 2-4) carbon atoms and at least one double bond. Like an alkyl group, an alkenyl group can be straight or branched. The point of attachment can be on a saturated carbon or unsaturated carbon. Examples of an alkenyl group include, but are not limited to allyl, isoprenyl, 2-butenyl, and 2-hexenyl.

As used herein, an "alkynyl" group refers to a hydrocarbon group that contains 2-20 (e.g., 2-12, 2-6, or 2-4) carbon atoms and has at least one triple bond. An alkynyl group can be straight or branched. The point of attachment can be on a saturated carbon or unsaturated carbon. Examples of an alkynyl group include, but are not limited to, propargyl and butynyl.

As used herein, an "alkoxy" group refers to —O-alkyl, O-alkenyl, or O-alknyl, wherein alkyl, alkenyl, and alkynyl are as defined above.

As used herein, "fluoroalkyl" or "fluoroalkoxy" refers to alkyl or alkoxy wherein one or more hydrogen is substituted with a fluoro.

As used herein, an "amino" refers to $NH_2$ which is optionally substituted with one or two groups independently selected from alkyl, cycloalkyl, and heterocycloalkyl.

The term "electron withdrawing group", as used herein means an atom or a group that is electronegative relative to hydrogen. See, e.g., "Advanced Organic Chemistry: Reactions, Mechanisms, and Structure," Jerry March, 4th Ed., John Wiley & Sons (1992), e.g., pp. 14-16, 18-19, etc. Exemplary such substituents include halo such as Cl, Br, or F, CN, COOH, $CF_3$, etc.

Unless otherwise specified, the term "heterocycle", "heterocyclyl", "heterocycloaliphatic", "heterocycloalkyl" or "heterocyclic" as used herein means monocyclic, bicyclic (fused or spiro), tricyclic (fused or spiro), or propellane ring systems in which one or more ring atoms in one or more ring members is an independently selected heteroatom and none of the individual rings in the system is aromatic. Heterocyclic rings can be saturated or can contain one or more unsaturated bonds. In some embodiments, the "heterocycle", "heterocyclyl", "heterocycloaliphatic", "heterocycloalkyl" or "heterocyclic" group has three to fourteen ring members in which one or more ring members is a heteroatom independently selected from oxygen, sulfur, nitrogen, or phosphorus, and each ring in the ring system contains 3 to 7 ring members. The point of attachment can be on the carbon or heteroatom.

The term "heteroatom" means oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation but is not aromatic.

The term "alkoxy", or "thioalkyl", as used herein, refers to an alkyl group, as previously defined, attached to the principal carbon chain through an oxygen ("alkoxy") or sulfur ("thioalkyl") atom.

The term "aryl" used alone or as part of a larger moiety as in "aralkyl", "aralkoxy", or "aryloxyalkyl", refers to monocyclic, bicyclic (fused), and tricyclic (fused or spiro) hydrocarbon ring systems having a total of five to fourteen ring carbon atoms, wherein at least one ring in the system is aromatic and wherein each ring in the system contains 3 to 7 ring carbon atoms. The term "aryl" may be used interchangeably with the term "aryl ring".

The term "heteroaryl", used alone or as part of a larger moiety as in "heteroaralkyl" or "heteroarylalkoxy", refers to monocyclic, bicyclic (fused), and tricyclic (fused or spiro) ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

The term "alkylene" refers to a straight or branched hydrocarbon chain that may be fully saturated or have one or more units of unsaturation and has two points of attachment to the rest of the molecule.

The term "prodrug," as used herein, represents a compound that is transformed in vivo into a compound according to any one of the formulae listed herein. Such a transformation can be affected, for example, by hydrolysis in blood or enzymatic transformation of the prodrug form to the parent form in blood or tissue. Prodrugs of the compounds of the disclosure may be, for example, amides. Amides that may be utilized as prodrugs in the present disclosure are phenyl amides, aliphatic ($C_1$-$C_{24}$) amides, acyloxymethyl amides, ureas, carbamates, and amino acid amides. For example, a compound of the disclosure that contains an NH group may be acylated at this position in its prodrug form. Other prodrug forms include esters, such as, for example phenyl esters, aliphatic ($C_1$-$C_{24}$) esters, acyloxymethyl esters, carbonates, carbamates, and amino acid esters. A thorough discussion of prodrugs is provided in T. Higuchi and V. Stella, *Pro-drugs as Novel Delivery Systems*, Vol. 14 of the A.C.S. Symposium Series, Edward B. Roche, ed., *Bioreversible Carriers in Drug Design*, American Pharmaceutical Association and Pergamon Press, 1987, and Judkins et al., *Synthetic Communications* 26(23):4351-4367, 1996, each of which is incorporated in its entirety herein by reference. In some embodiments, the present disclosure features a prodrug of any one of the formulas or compounds listed herein.

The term "isosteres" or "bioisosteres," as used herein, refers to compounds resulting from the exchange of an atom or group of atoms to create a new compound with similar biological properties to the parent compound. The bioisosteric replacement may be physicochemically or topologically based. For example, an isosteric replacement for a carboxylic acid is $CONHSO_2$(alkyl or aryl)) such as $CONHSO_2Me$. A further discussion of isosterism is provided in R. Silverman, *The Organic Chemistry of Drug Design and Drug Action*, second edition, Elsevier Academic Press, 2004, incorporated in its entirety herein by reference. In some embodiments, the present disclosure features a isostere of any one of the formulas or compounds listed herein.

In the formulas and drawings, a line transversing a ring and bonded to an R group such as, for example, $R_1$ or $R_2$ in the following formula

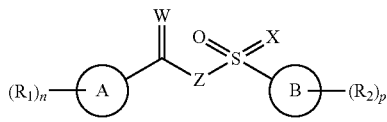

means that the R group can be bonded to any carbon, or if applicable, heteroatom such as N, of that ring, including any fused ring, as valency allows.

Within a term definition as, for example, $R_1$ to $R_3$ when a $CH_2$ unit or, interchangeably, a methylene unit may be replaced by O, CO, S, SO, $SO_2$, or NR; it is meant to include any $CH_2$ unit, including a $CH_2$ within a terminal methyl or methylene group. For example, —$CH_2CH_2CH_2SH$ is within the definition of $C_1$-$C_9$ alkylene-$R_3$ wherein up to four $CH_2$ units are independently replaced by O, CO, S, SO, $SO_2$, or NR because the $CH_2$ unit of the terminal methyl group has been replaced by S. The analogous applies to such definitions as —$CH_2CH_2OH$, —$CH_2CH_2CN$, or —$CH_2CH_2NH_2$.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the disclosure. Where the enantiomers of a racemic mixture have been separated, but the absolute chemistry has not yet been determined, the compound's structure is depicted with a wavy line.

Unless otherwise stated, all tautomeric forms of the compounds of the disclosure are within the scope of the disclosure. Thus, included within the scope of the disclosure are tautomers of compounds of formulas I to IIa-ii-2.

To the extent that a definition in the present application differs from any definition in an application incorporated by reference, the definition in the present application supercedes.

CFTR is a cAMP/ATP-mediated anion channel that is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

In patients with cystic fibrosis, mutations in endogenously expressed CFTR lead to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea-perhaps explaining the relatively high frequency of the CF gene within the population.

Sequence analysis of the CFTR gene of CF chromosomes has revealed a variety of disease-causing mutations (Cutting, G. R. et al. (1990) Nature 346:366-369; Dean, M. et al. (1990) Cell 61:863:870; and Kerem, B-S. et al. (1989) Science 245:1073-1080; Kerem, B-S et al. (1990) Proc. Natl. Acad. Sci. USA 87:8447-8451). To date, greater than 1000 disease-causing mutations in the CF gene have been identified as reported by the scientific and medical literature. The most prevalent mutation is a deletion of phenylalanine at position 508 of the CFTR amino acid sequence, and is commonly referred to as F508del. This mutation occurs in approximately 70 percent of the cases of cystic fibrosis and is associated with a severe disease. A more complete list of identified mutations can be found at www.cftr2.org.

These elements work together to achieve directional transport across the epithelium via their selective expression and localization within the cell. Chloride absorption takes place by the coordinated activity of ENaC and CFTR present on the apical membrane and the $Na^+$—$K^+$-ATPase pump and Cl– channels expressed on the basolateral surface of the cell. Secondary active transport of chloride from the luminal side leads to the accumulation of intracellular chloride, which can then passively leave the cell via $Cl^-$ channels, resulting in a vectorial transport. Arrangement of $Na^+/2Cl^-/K^+$ co-transporter, $Na^+$—$K^+$-ATPase pump and the basolateral membrane K⁺ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

Compounds of Formula I

Disclosed is a compound of formula I:

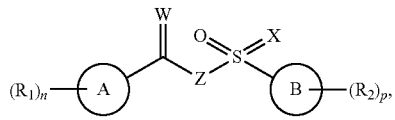

or a pharmaceutically acceptable salt thereof, wherein, independently for each occurrence:

Ring A is a $C_6$-$C_{10}$ aryl ring; a $C_3$-$C_{10}$ cycloalkyl ring; or a $C_3$-$C_{14}$ heteroaryl or heterocyclic ring wherein anywhere from 1 to 4 ring atoms are independently O, S, N, or NR;

Ring B is a $C_3$-$C_{10}$ cycloalkyl ring; a $C_6$-$C_{10}$ aryl ring; or a $C_3$-$C_{10}$ heteroaryl or $C_3$-$C_{10}$ heterocyclic ring wherein anywhere from 1 to 4 ring atoms are independently O, S, N, or NR;

W is O, S, or NR;

X is O or NR;

Z is NR or $C(R)_2$;

$R_1$ is halo; CN; NRR; $C_1$-$C_6$ alkyl or $C_1$-$C_6$ fluoroalkyl; $C_3$-$C_6$ cycloalkyl; $C_1$-$C_8$ alkoxy or $C_1$-$C_8$ fluoroalkoxy; $C_2$-$C_6$ alkenyl; $C_2$-$C_6$ alkynyl; ($C_1$-$C_9$ alkylene)-$R_3$ wherein up to four $CH_2$ units are independently replaced with O, CO, S, SO, $SO_2$ or NR; $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_2$ is halo; NRR; CN; $CO_2R$; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four $CH_2$ units are optionally and independently replaced with O, CO, S, SO, $SO_2$ or NR;

or two $R_2$ may form a =$CH_2$ or =O group;

$R_3$ is H; $CF_3$; $CHF_2$; OR; C≡CH; $CO_2R$; OH; $C_6$-$C_{10}$ aryl; $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or $SO_2R$;

R is independently H; OH; $CO_2H$; $CO_2$; $C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, or N; or $C_3$-$C_{10}$ cycloalkyl;

n is 2 or 3;

p is 0, 1, 2, or 3; and

Provided that 1) when $R_1$ is adjacent to the C=W attached to Ring A, $R_1$ does not contain a ring moiety, 2) at least one $R_1$ is adjacent to the C=W attached to Ring A, and at least one $R_1$ is $C_1$-$C_6$ alkyl or $C_1$-$C_6$ fluoroalkyl, $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl; 3) when Ring A is phenyl or six-membered mono-heteroaryl wherein anywhere from 1 to 3 ring atoms are N, $R_1$ is not 4,5-dihydroisoxazole; 4) when Ring A is phenyl, $R_1$ is not

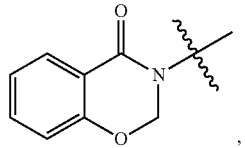 [SMILES: *N1COc2ccccc2C1=O ; ","]

ureido, or aminocarbonyl; 5) when Ring A and the at least one $R_1$ is pyridine, $R_1$ (pyridine) is not further substituted by —CONHSO$_2$—; and 6) when Ring A is pyridine or thiazole, and C=W wherein W is O in formula I is adjacent to the N on the pyridine or thiazole, $R_1$ which is adjacent to the N on the pyridine or on the thiazole is not

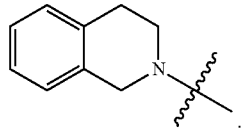 [SMILES: *N1CCc2ccccc2C1 ; "."]

In some embodiments, Ring A is a $C_3$-$C_{10}$ cycloalkyl ring, such as cyclopentane, cyclopentene, cyclohexane, or cyclohexene. In some embodiments, Ring A is a $C_6$-$C_{10}$ aryl ring, such as a phenyl, indane, 1,2,3,4-tetrahydronaphthalene, or naphthalene. In some embodiments, Ring A is a C3-C11 heteroaryl or heterocyclic ring wherein anywhere from 1 to 4 ring atoms are independently O, S, N, or NR, such as pyridyl, indole, indoline, isoindoline, pyrazole, pyrimidine, 1,2,3,4-tetrahydroquinoline, quinoline, 5,6,7,8-tetrahydroquinoline, 1,2,3,4-tetrahydroisoquinoline, pyrrolodine, azaindole, pyrrole, thiophene, oxazole, pyrazine, triazole, thiazole, indazole, 2,3,4,5-tetrahydro-1H-benzo[d]azepine, 1H-benzo[d]imidazole, imidazo[1,2-a]pyridine, or imidazole ring.

In some embodiments, Ring A is

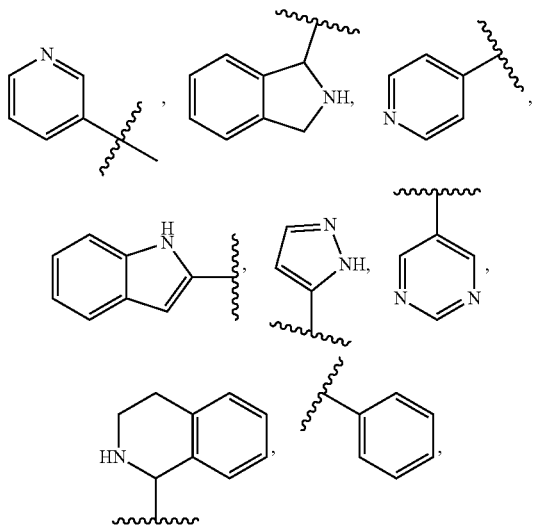

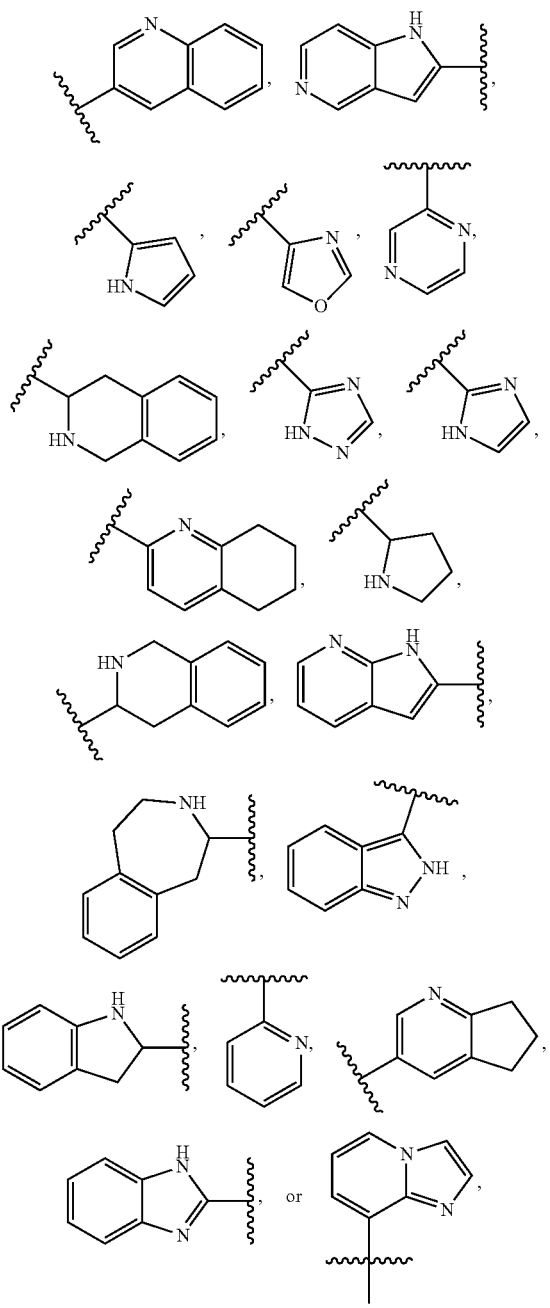

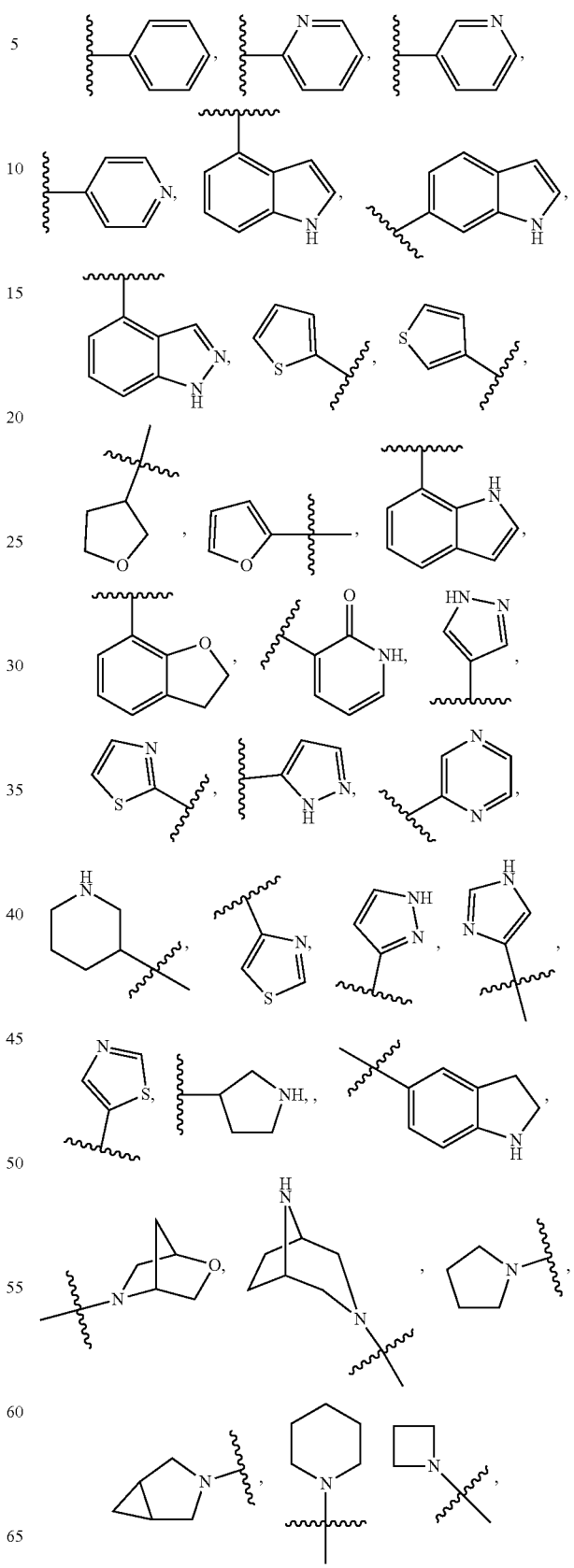

wherein the wavy line ~ indicates point of attachment of Ring A to the C=W.

In some embodiments, Ring B is a cycloalkyl ring, such as a cyclopropane, cyclobutane, cyclopentane, or cyclohexane. In some embodiments, Ring B is a $C_6$-$C_{10}$ aryl ring, such as a phenyl or naphthalene. In some embodiments, ring B is a heroaryl or heterocyclic ring wherein anywhere from 1 to 4 ring atoms are independently O, S, N, or NR, such as pyridyl, pyridine-2(1H)-one, pyrazole, indole, pyrrole, indoline, thiophene, dihydrobenzofuran, tetrahydrofuran, furan, pyrazine, indazole, thiazole, pyridine-4(1H)-one, pyrrolidinone, 3-azabicyclo[3.1.0]hexane, (1R,4R)-2-oxa-5-azabicyclo[2.2.1]heptane, pyrrolidine, azetidine, piperidine, piperazine, imidazo[1,2-a]pyridine, or quinoline.

In some embodiments, Ring B is

-continued

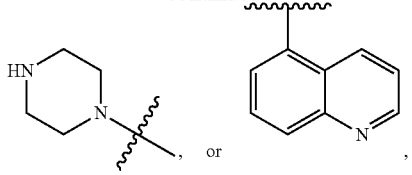
, or wherein the wavy line indicates point of attachment of Ring B to the group of (X═)S(═O) of formula I.

In some embodiments, X is O. In some embodiments, Z is NH.

In some embodiments, $R_1$ is independently halo, amino, OH, $C_2$-$C_6$ alkenyl; $C_2$-$C_6$ alkynyl, $C_1$-$C_6$ fluoroalkyl, CN, $C_1$-$C_6$ alkyl, $C_1$-$C_8$ alkoxy or $C_1$-$C_8$ fluoroalkoxy, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring, or a ($C_1$-$C_9$ alkylene)-$R_3$ wherein up to four $CH_2$ units are independently replaced with O, CO, S, SO, $SO_2$ or NR.

In some embodiments, $R_1$ is $CHF_2CH_2(CH_3)N$—, $(CH_3)_2CHCH_2CH_2O$—, $(CH_3)_3CCH_2CH_2O$—, $(CH_3)_3COCH_2CH_2O$—, $(CH_3)_2CHO$—, $CHF_2CHF_2CH(CH_3)O$—, —$CF_3$, $(CH_3CH_2)_2N$—, $CF_3CH_2CH(CH_3)O$—, $CH_3O$—, $CH_3(CH_2)_4O$—, $CH_3CH_2CH(CH_3)CH(CH_3)O$—, $CH_3CH_2OCH_2CH_2O$—, $CH_3CH_2NCH(CH_3)_2$, $(CH_3)_3CH_2O$—, (R)—$CH_3NCH(CH_3)(CF_3)$, $CH_3OCH_2CH(CH_2CH_3)O$—, $(CH_3)_2N$—, (S)—$CH_3OCH_2CH(CH_3)O$—, $CH_3O(CH_2)_3O$—, $CH_3OC(CH_3)_2(CH_2)_2O$—, $CH_3OCH_2CH(CH_3)O$—, $CH_3CH(CH_3)CH_2CH(CH_3)O$—, $(CH_3)_3CCH(CH_3)O$—, $((CH_3)_2CH)_2CHO$—, $CH_3CH_2CH_2O$—, $CH_3CH═CHCH_2O$—, (S)—$CH_3CH_2CH(CH_3)O$—, $CH_3CH_2O$—, $(CH_3)_2CHNCH_3$, $(CH_3)_3CCH_2O$—, $(CF_3)_2CHO$—, $(CH_3)_3CCH(CH_2CH_3)O$—, $CH_3C≡CCH_2CH_2O$—, $(CH_3)_3CCH_2CH(CH_3)O$—, $(CH_3)_2C═C(CH_3)$, $CHF_2CH_2O$—, $CH_3CH_2CH_2NH$, $(CH_3)_2CHCH(CH_2CH_3)O$—, $((CH_3)_2CH)_2N$, $CH_2═CHCH(CH_3)O$—, $CH_2═CHCH_2O$—, $CH_3CH_2C(CH_3)_2O$—, $(CH_3CH_2)_2CHO$—, $CF_3CH_2O$, $CH_3C(═CH_2)CH_2O$, $(CH_3)_3CCH_2CH_2NH$, $CH_3OCH_2C(CH_3)_2O$, $(CH_3)_3CCH_2N(CH_3)$, $(CH_3)_2CHCH(CH_3)NH$, $(CH_3)_2CHO(CH_2)_2O$, $CH_3CH_2CH_2CH(CH_3)O$, $CH_3CF_2CH_2O$, $(CH_3)_3CNH$, (R)—$CH_3CH_2CH(CH_3)O$, $CH_3OCH_2CH_2O$, $(CH_3)_2CHCH_2N(CH_3)$, $CH_3CH_2CH_2CH(CH_3)CH(CH_3)O$, $CH_3CH_2CH_2CH_2O$, $CH_3CH_2CH_2N(CH_3)$, (R)—$CH_3OCH_2CH(CH_3)O$, $CF_3CH_2N(CH_3)$, $CH_3CH_2N(CH_3)$, $((CH_3)_3C)_2CHO$, $(CH_3CH_2)_2CHN(CH_3)$, $(CH_3)_2CHN(CH_3)$, $CH_3CH_2OCH_2CH(CH_3)O$, $(CH_3)_3CCH_2NH$, $CF_3CH(CH_3)O$, $CH_3CH_2NCH(CH_3)_2$, $(R)$—$CF_3CH(CH_3)N(CH_3)$, $(CH_3)_2CHCH(CH_3)$, $CH_3CH_2(CH_3)_2CHCH_2CH_2O$, (S)—$CH_3OCH(CH_3)CH_2O$, $HOCH(CH_3)_2CH_2CH_2NH$, $CF_3CH_2CH_2O$, $CF_3CH_2CH_2CH_2O$, $CF_3CH═CHCH_2O$, $CH_3CH_2CH_2CH_2CH_2NH$, or $(CH_3)_3C$.

In some embodiments, $R_1$ is $CH_3$, Cl, F, CN, $CH_2CH_3$, $CH(CH_3)_2$, $OCH_2CH_2OCH_2CH_3$,

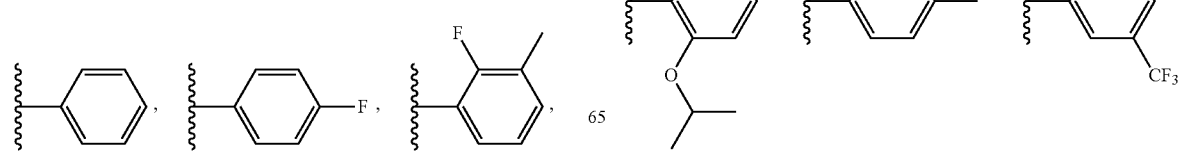

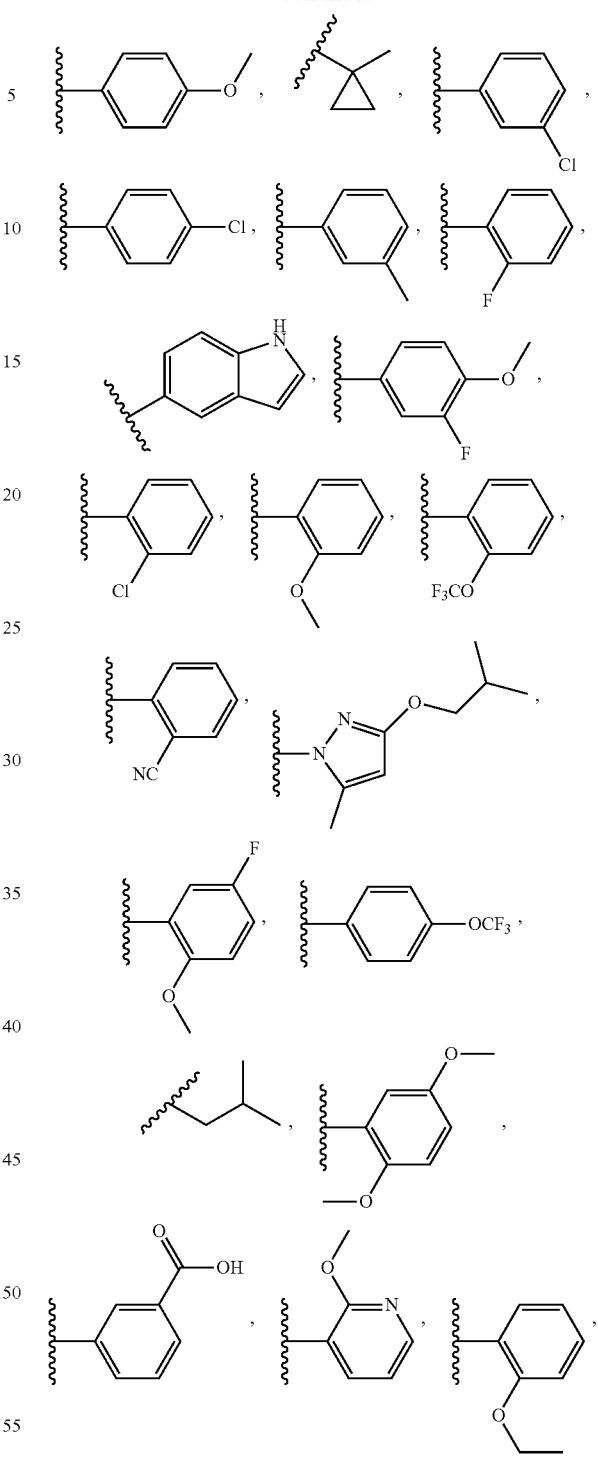

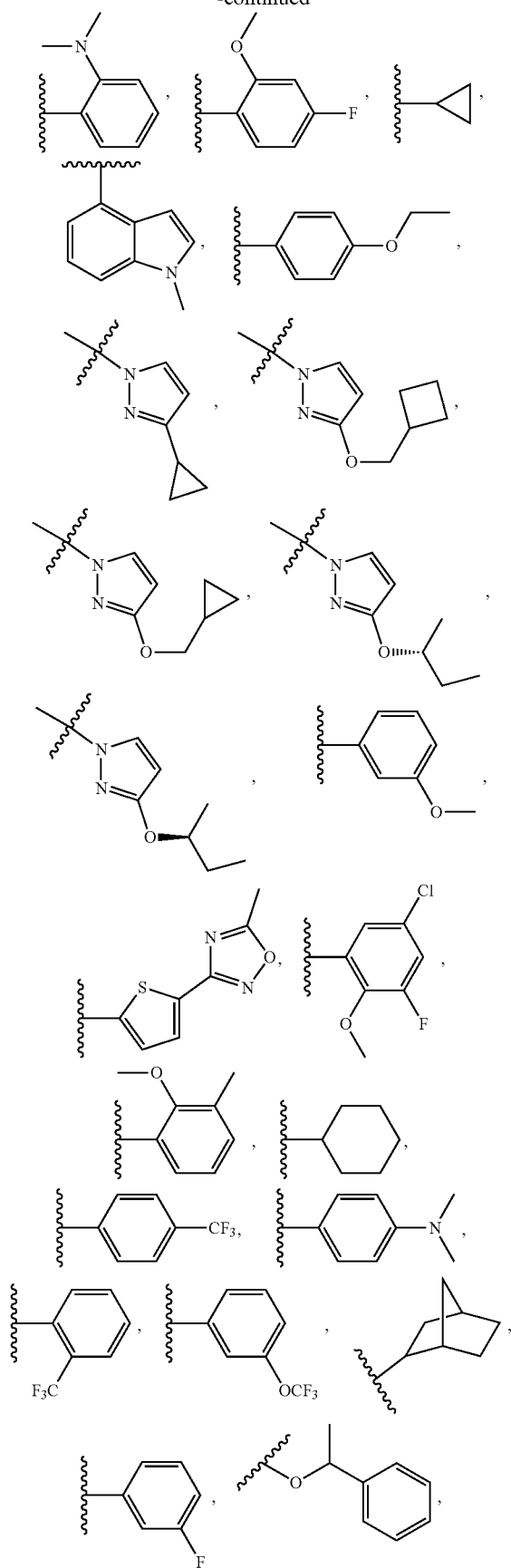
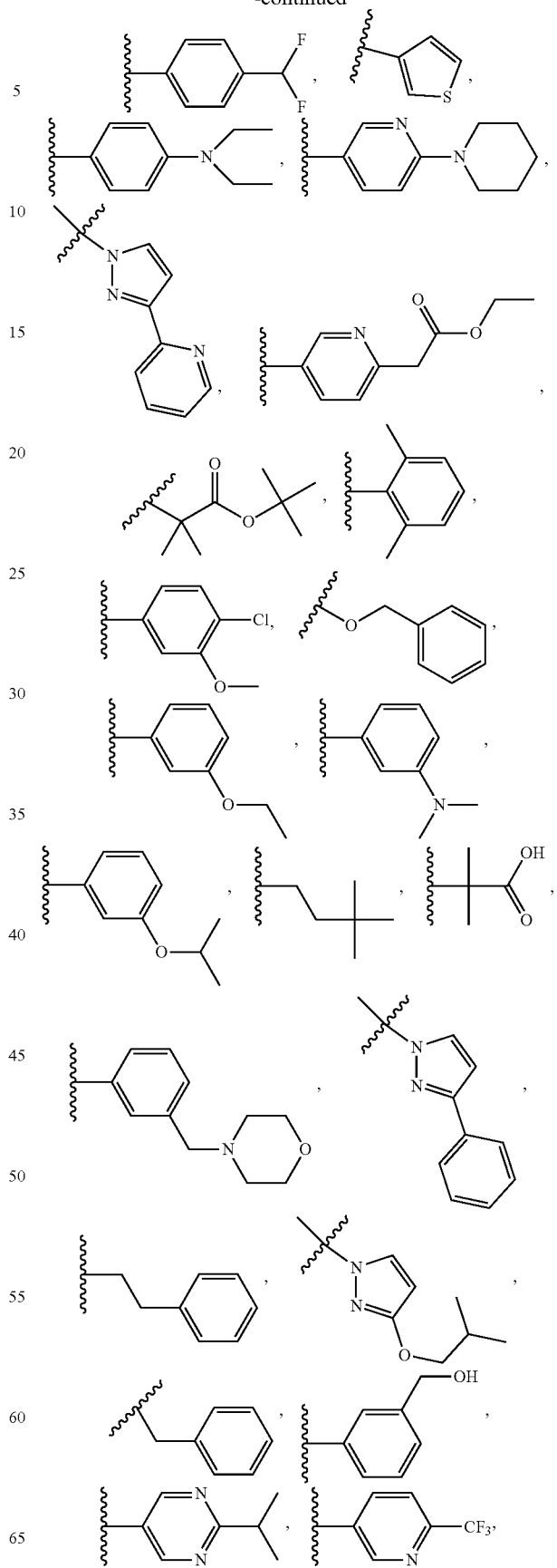

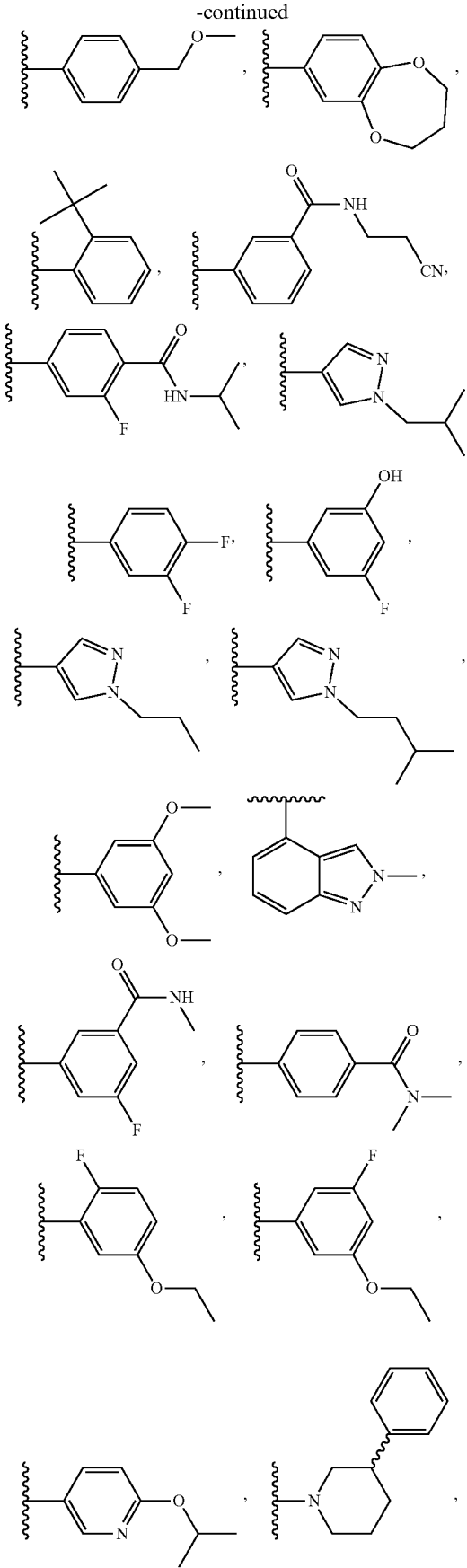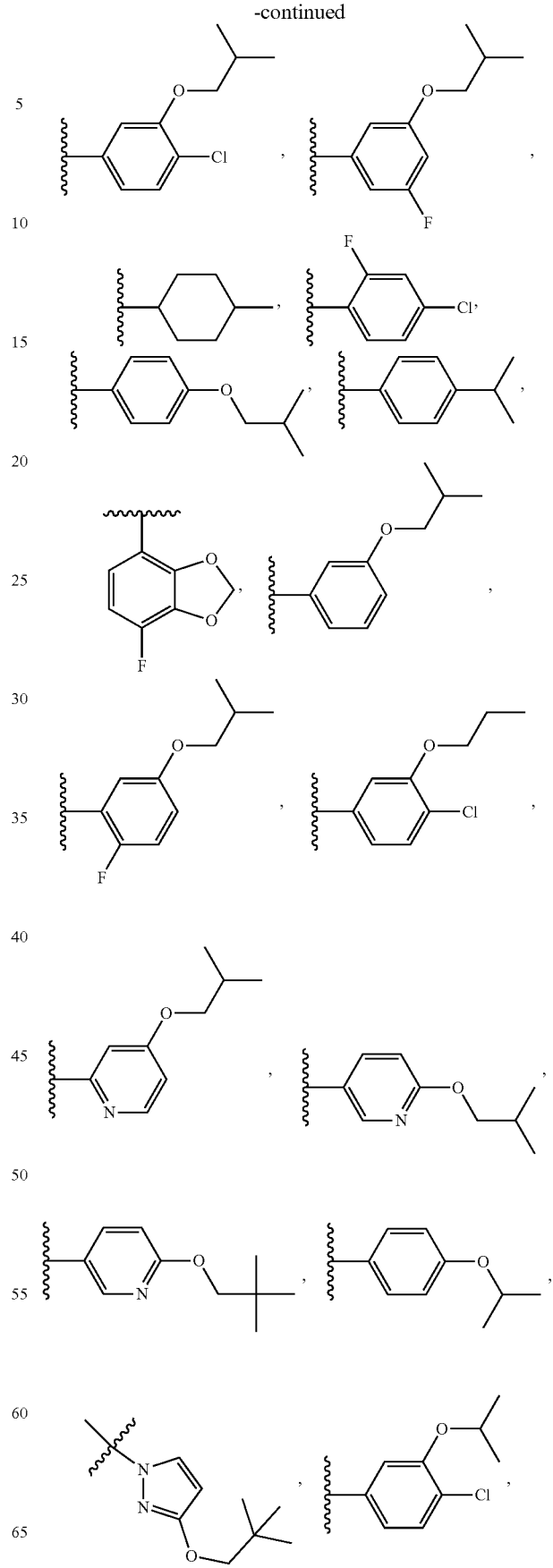

-continued

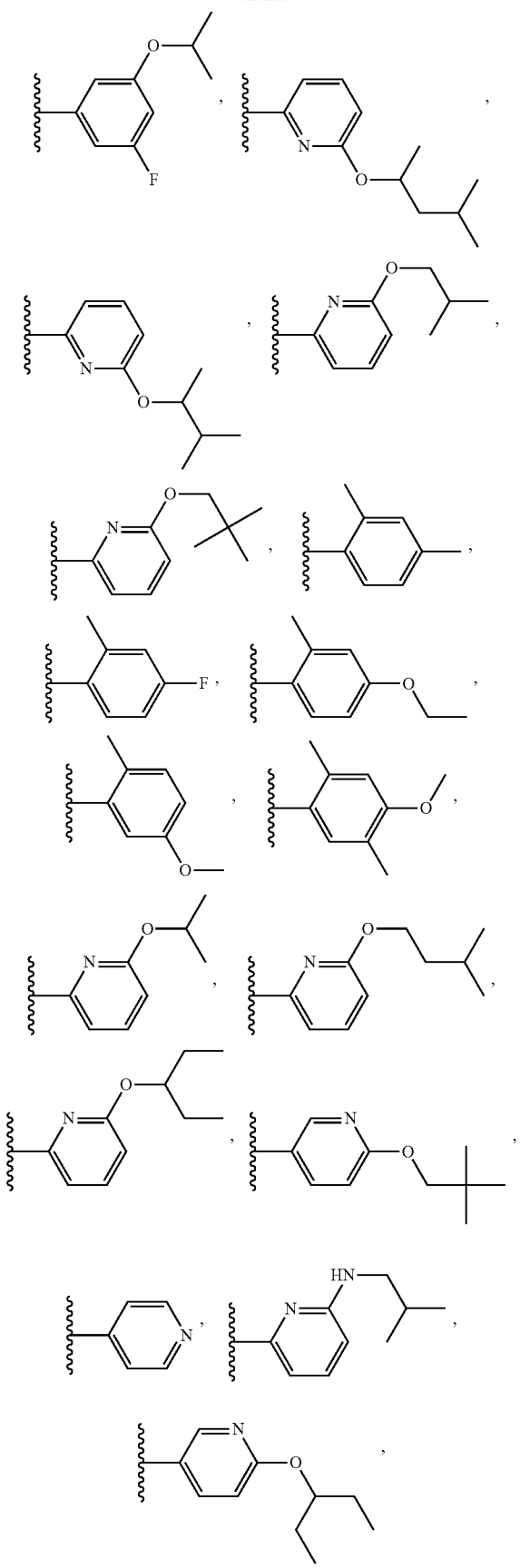

-continued

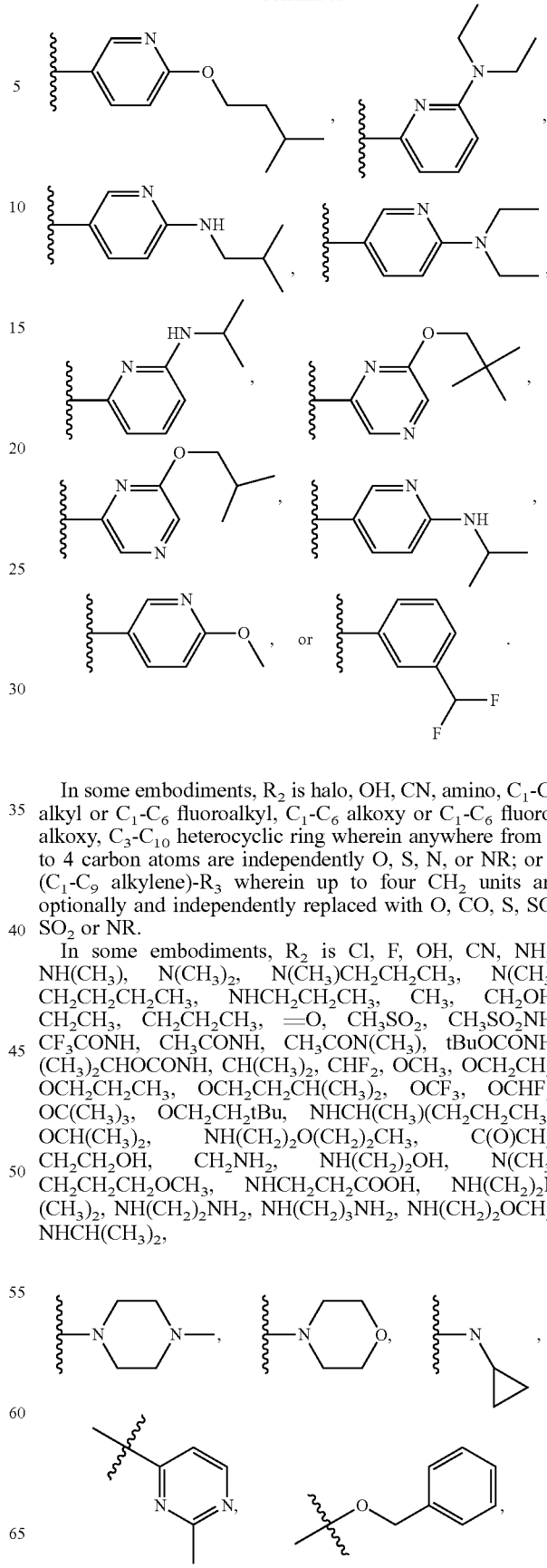

In some embodiments, $R_2$ is halo, OH, CN, amino, $C_1$-$C_6$ alkyl or $C_1$-$C_6$ fluoroalkyl, $C_1$-$C_6$ alkoxy or $C_1$-$C_6$ fluoroalkoxy, $C_3$-$C_{10}$ heterocyclic ring wherein anywhere from 1 to 4 carbon atoms are independently O, S, N, or NR; or a ($C_1$-$C_9$ alkylene)-$R_3$ wherein up to four $CH_2$ units are optionally and independently replaced with O, CO, S, SO, $SO_2$ or NR.

In some embodiments, $R_2$ is Cl, F, OH, CN, $NH_2$, $NH(CH_3)$, $N(CH_3)_2$, $N(CH_3)CH_2CH_2CH_3$, $N(CH_3)CH_2CH_2CH_2CH_3$, $NHCH_2CH_2CH_3$, $CH_3$, $CH_2OH$, $CH_2CH_3$, $CH_2CH_2CH_3$, =O, $CH_3SO_2$, $CH_3SO_2NH$, $CF_3CONH$, $CH_3CONH$, $CH_3CON(CH_3)$, tBuOCONH, $(CH_3)_2CHOCONH$, $CH(CH_3)_2$, $CHF_2$, $OCH_3$, $OCH_2CH_3$, $OCH_2CH_2CH_3$, $OCH_2CH_2CH(CH_3)_2$, $OCF_3$, $OCHF_2$, $OC(CH_3)_3$, $OCH_2CH_2tBu$, $NHCH(CH_3)(CH_2CH_2CH_3)$, $OCH(CH_3)_2$, $NH(CH_2)_2O(CH_2)_2CH_3$, $C(O)CH_3$, $CH_2CH_2OH$, $CH_2NH_2$, $NH(CH_2)_2OH$, $N(CH_3)CH_2CH_2CH_2OCH_3$, $NHCH_2CH_2COOH$, $NH(CH_2)_2N(CH_3)_2$, $NH(CH_2)_2NH_2$, $NH(CH_2)_3NH_2$, $NH(CH_2)_2OCH_3$, $NHCH(CH_3)_2$, -continued

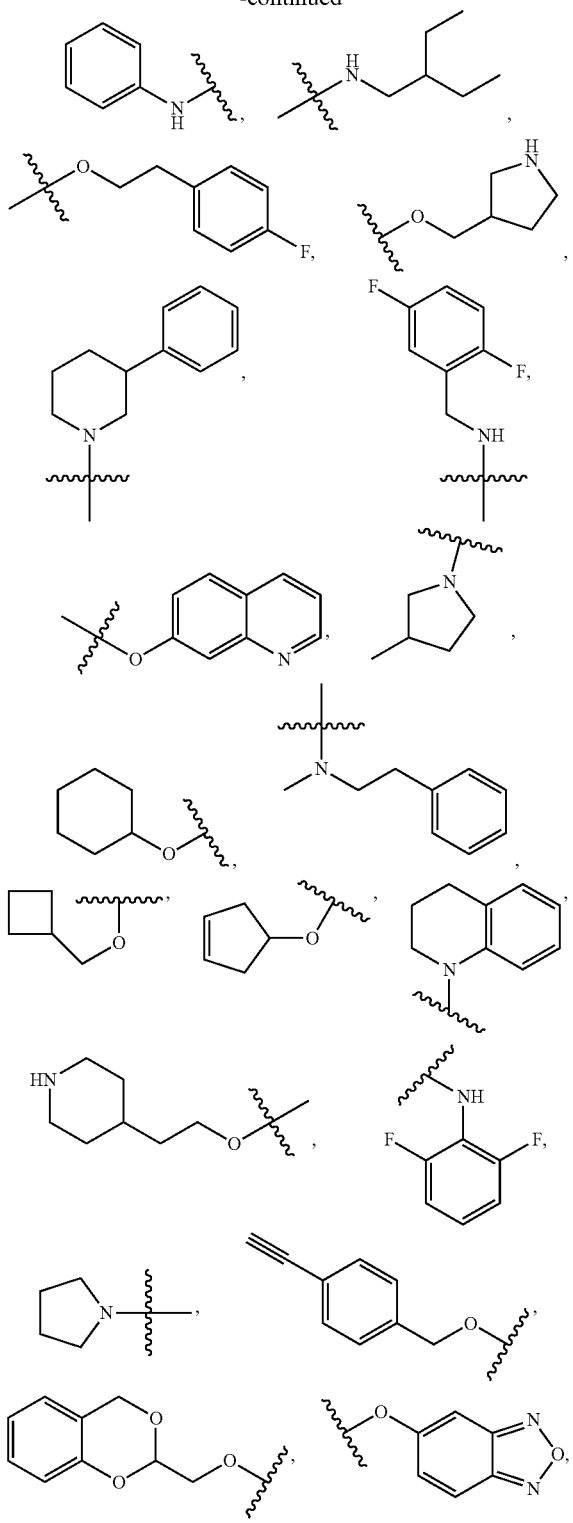

or CO$_2$H.

In some embodiments, R$_2$ is NH$_2$, or NHCH$_2$CH$_2$CH$_3$.

In some embodiments, n is 2. In some embodiments, p is 0. In some embodiments, p is 1.

In some embodiments, W is O. In some embodiments, Z is NH. In some embodiments, X is O In some embodiments, Ring A is and n is 2. In some embodiments, Ring A is and n is 2. In some embodiments, Ring A is and at least one R$_1$ is phenyl. In some embodiments, Ring A is and at least one R$_1$ is tert-butyl. In some embodiments, Ring A is and at least one R$_1$ is pyridinyl. In some embodiments, Ring A is one R$_1$ is phenyl, and one R$_1$ is alkenyl, amino, or C$_1$-C$_8$ alkoxy or C$_1$-C8 fluoroalkoxy. In some embodiments, Ring A is

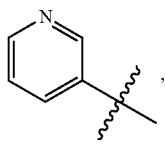 [SMILES: *c1cccnc1]

and Ring B is

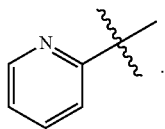

In some embodiments, Ring A is

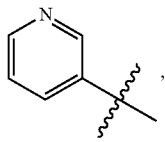 [SMILES: *c1cccnc1]

and Ring B is

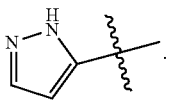

In some embodiments, Ring A is

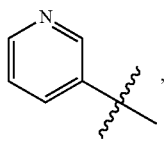

Ring B is

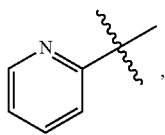

one $R_1$ is phenyl, and one $R_1$ is alkenyl, amino, or $C_1$-C8 alkoxy or $C_1$-C8 fluoroalkoxy.

In some embodiments, in the compound of formula I, one or more hydrogen atoms may be replaced by a deuterium atom.

In some embodiments of formula I, the compound of formula I or a pharmaceutically acceptable salt thereof is a compound of formula I-i:

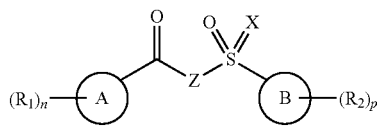

or a pharmaceutically acceptable salt thereof, wherein, independently for each occurrence:

Ring A is a $C_3$-$C_{14}$ heteroaryl or heterocyclic ring wherein anywhere from 1 to 4 ring atoms are independently O, S, N, or NR;

Ring B is a $C_3$-$C_{10}$ heteroaryl or $C_3$-$C_{10}$ heterocyclic ring wherein anywhere from 1 to 4 ring atoms are independently O, S, N, or NR;

X is O or NR;

Z is NR;

$R_1$ is halo; CN; NRR; $C_1$-$C_6$ alkyl or $C_1$-$C_6$ fluoroalkyl; $C_3$-$C_6$ cycloalkyl; $C_1$-$C_8$ alkoxy or $C_1$-$C_8$ fluoroalkoxy; $C_2$-$C_6$ alkenyl; $C_2$-$C_6$ alkynyl; ($C_1$-$C_9$ alkylene)-$R_3$ wherein up to four $CH_2$ units are independently replaced with O, CO, S, SO, $SO_2$ or NR; $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_2$ is halo; NRR; CN; $CO_2R$; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four $CH_2$ units are optionally and independently replaced with O, CO, S, SO, $SO_2$ or NR;

or two $R_2$ may form a $=CH_2$ or $=O$ group;

$R_3$ is H; $CF_3$; $CHF_2$; OR; C≡CH; $CO_2R$; OH; $C_6$-$C_{10}$ aryl; $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or $SO_2R$;

R is independently H; OH; $CO_2H$; $CO_2C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, or N; or $C_3$-$C_{10}$ cycloalkyl;

n is 2 or 3; and p is 0, 1, 2, or 3.

In some embodiments, ring A is a pyridyl, indole, indoline, isoindoline, pyrazole, pyrimidine, quinoline, 5,6,7,8-tetrahydroquinoline, 1,2,3,4-tetrahydroisoquinoline, pyrrolodine, aza-indole, pyrrole, oxazole, pyrazine, triazole, indazole, imidazo[1,2-a]pyridine, or imidazole ring.

In some embodiments, Ring A is

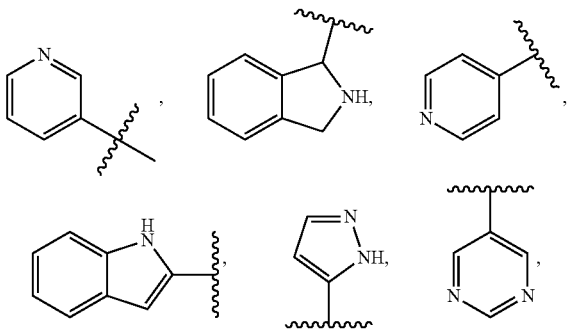

-continued
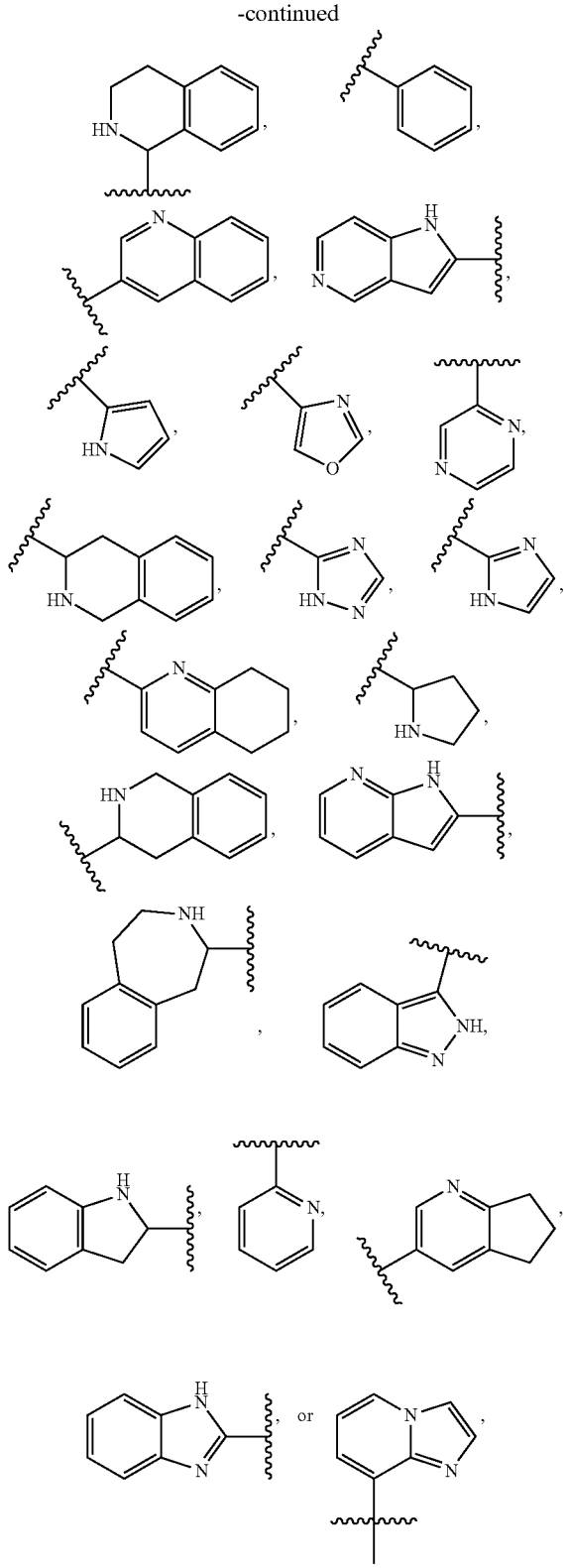
wherein the wavy line indicates point of attachment of Ring A to the carbonyl (CO).
In some embodiments, Ring B is pyridyl, pyridine-2(1H)-one, pyrazole, indole, aza-indole, thiophene, dihydrobenzofuran, thiazole, pyrrolidinone, or quinoline.
In some embodiments, Ring B is
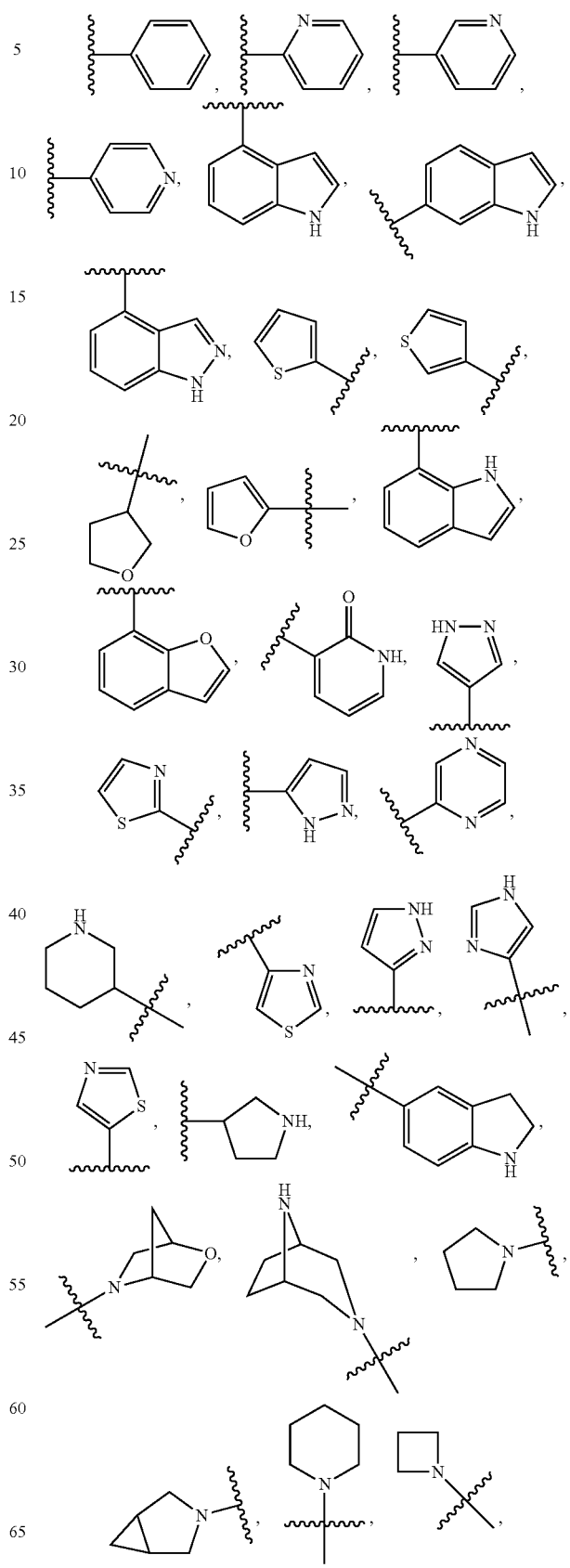

wherein the wavy line ∿ indicates point of attachment of Ring B to the sulfonyl ($SO_2$).

In some embodiments, X is O. In some embodiments, Z is NH.

In some embodiments, $R_1$ is independently halo, amino, OH, $C_1$-$C_6$ fluoroalkyl, CN, $C_1$-C6 alkyl, $C_2$-$C_6$ alkenyl; $C_2$-$C_6$ alkynyl, $C_1$-C8 alkoxy or $C_1$-$C_8$ fluoroalkoxy, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring, or a ($C_1$-$C_9$ alkylene)-$R_3$ wherein up to four $CH_2$ units are independently replaced with O, CO, S, SO, $SO_2$ or NR.

In some embodiments, $R_1$ is $CHF_2CH_2(CH_3)N$—, $(CH_3)_2CHCH_2CH2O$—, $(CH_3)_3CCH_2CH_2O$—, $(CH_3)_3COCH_2CH_2O$—, $(CH_3)_2CHO$—, $CHF_2CHF_2CH(CH_3)O$—, —$CF_3$, $(CH_3CH_2)_2N$—, $CF_3CH_2CH(CH_3)O$—, $CH_3O$—, $CH_3(CH_2)_4O$—, $CH_3CH_2CH(CH_3)CH(CH_3)O$—, $CH_3CH_2OCH_2CH_2O$—, $CH_3CH_2NCH(CH_3)_2$, $(CH_3)_3CH_2O$—, (R)—$CH_3NCH(CH_3)(CF_3)$, $CH_3OCH_2CH(CH_2CH_3)O$—, $(CH_3)_2N$—, (S)—$CH_3OCH_2CH(CH_3)O$—, $CH_3O(CH_2)_3O$—, $CH_3OC(CH_3)_2(CH_2)_2O$, $CH_3OCH_2CH(CH_3)O$, $CH_3CH(CH_3)CH_2CH(CH_3)O$—, $(CH_3)_3CCH(CH_3)O$, $((CH_3)_2CH)_2CHO$—, $CH_3CH_2CH_2O$, $CH_3CH$=$CHCH_2O$—, (S)—$CH_3CH_2CH(CH_3)O$—, $CH_3CH_2O$, $(CH_3)_2CHNCH_3$, $(CH_3)_3CCH_2O$, $(CF_3)_2CHO$—, $(CH_3)_3CCH(CH_2CH_3)O$, $CH_3C$≡$CCH_2CH_2O$, $(CH_3)_3CCH_2CH(CH_3)O$—, $(CH_3)_2C$=$C(CH_3)$, $CHF_2CH_2O$—, $CH_3CH_2CH_2NH$, $(CH_3)_2CHCH(CH_2CH_3)O$, $((CH_3)_2CH)_2N$, $CH_2$=$CHCH(CH_3)O$, $CH_2$=$CHCH_2O$—, $CH_3CH_2C(CH_3)_2O$, $(CH_3CH_2)_2CHO$, $CF_3CH_2O$, $CH_3C$(=$CH_2$)$CH_2O$, $(CH_3)_3CCH_2CH_2NH$, $CH_3OCH_2C(CH_3)_2O$, $(CH_3)_3CCH_2N(CH_3)$, $(CH_3)_2CHCH(CH_3)NH$, $(CH_3)_2CHO(CH_2)_2O$, $CH_3CH_2CH_2CH(CH_3)O$, $CH_3CF_2CH_2O$, $(CH_3)_3CNH$, (R)—$CH_3CH_2CH(CH_3)O$, $CH_3OCH_2CH_2O$, $(CH_3)_2CHCH_2N(CH_3)$, $CH_3CH_2CH_2CH(CH_3)CH(CH_3)O$, $CH_3CH_2CH_2CH_2O$, $CH_3CH_2CH_2N(CH_3)$, (R)—$CH_3OCH_2CH(CH_3)O$, $CF_3CH_2N(CH_3)$, $CH_3CH_2N(CH_3)$, $((CH_3)_3C)_2CHO$, $(CH_3CH_2)_2CHN(CH_3)$, $(CH_3)_2CHN(CH_3)$, $CH_3CH_2OCH_2CH(CH_3)O$, $(CH_3)_3CCH_2NH$, $CF_3CH(CH_3)O$, $CH_3CH_2NCH(CH_3)_2$, (R)—$CF_3CH(CH_3)N(CH_3)$, $(CH_3)_2CHCH(CH_3)$, $CH_3CH_2(CH_3)_2CHCH_2CH_2O$, (S)—$CH_3OCH(CH_3)CH_2O$, $HOCH(CH_3)_2CH_2CH_2NH$, $CF_3CH_2CH_2O$, $CF_3CH_2CH_2CH_2O$, $CF_3CH$=$CHCH_2O$, $CH_3CH_2CH_2CH_2CH_2NH$, or $(CH_3)_3C$.

In some embodiments, $R_1$ is $CH_3$, Cl, F, CN, $CH_2CH_3$, $CH(CH_3)_2$, $OCH_2CH_2OCH_2CH_3$,

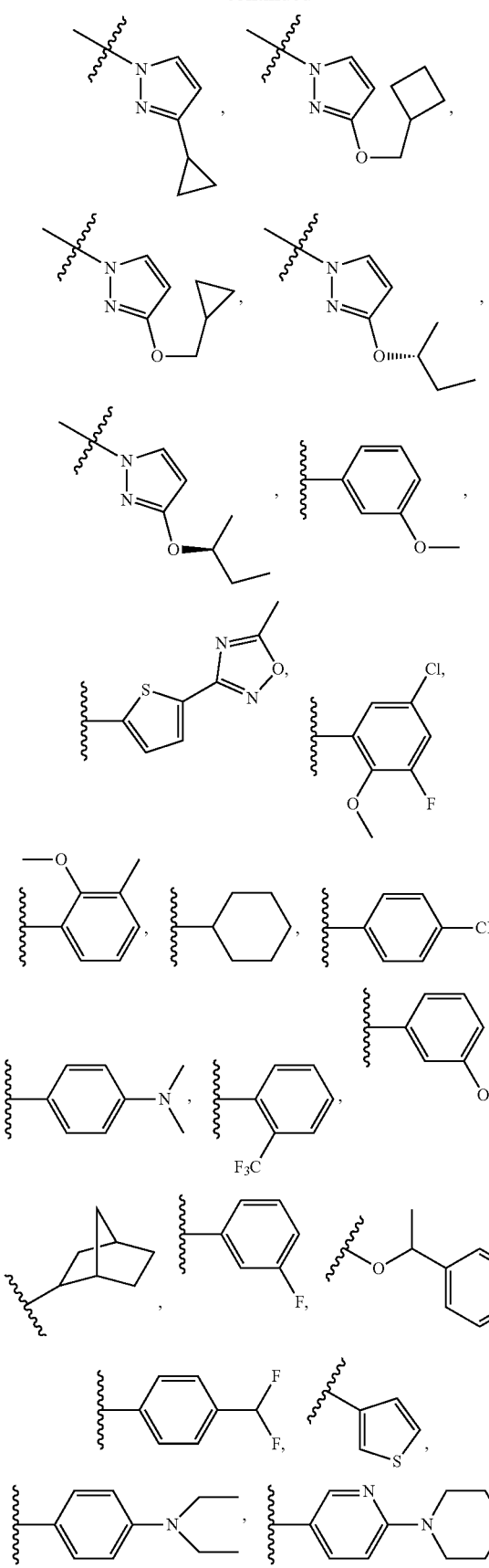
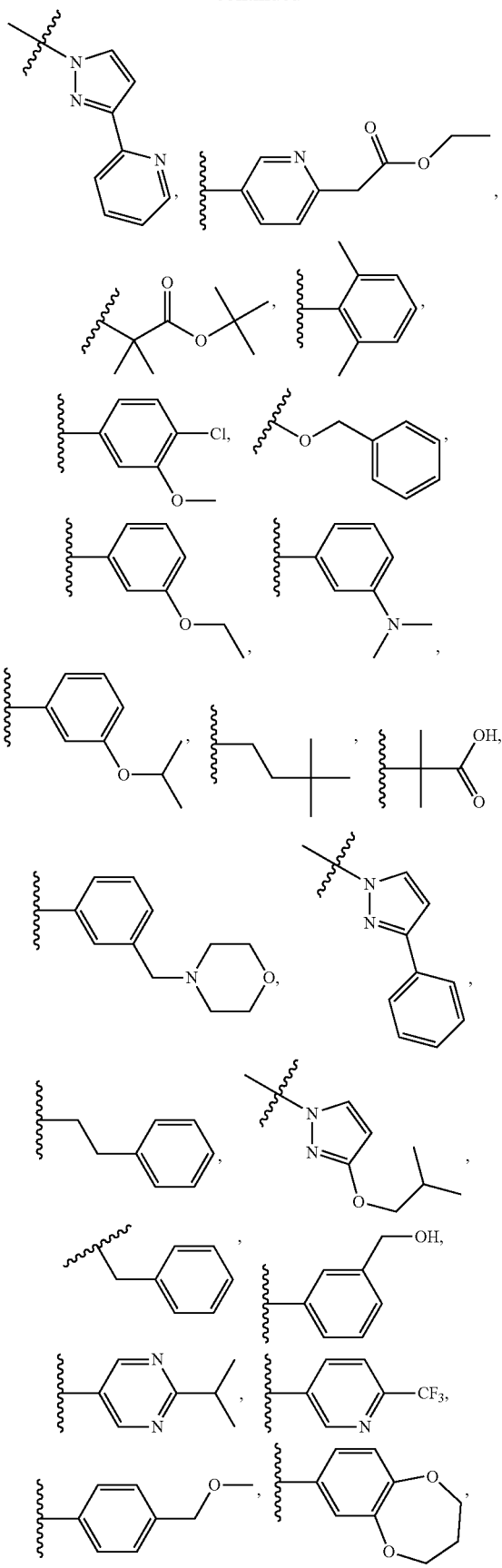

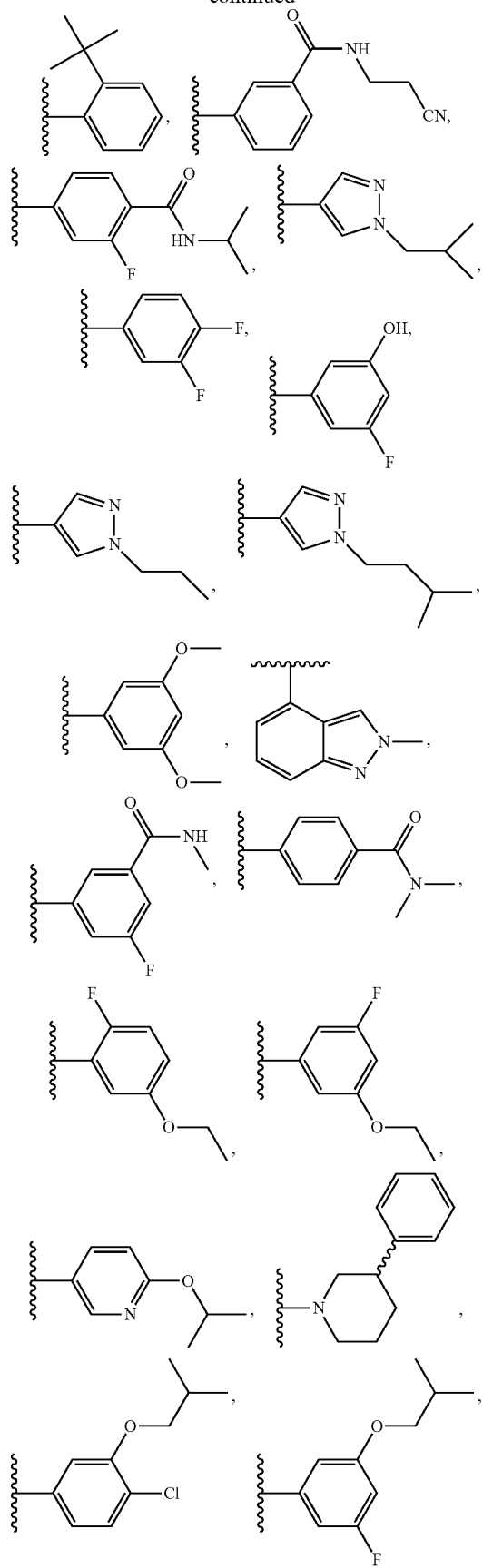
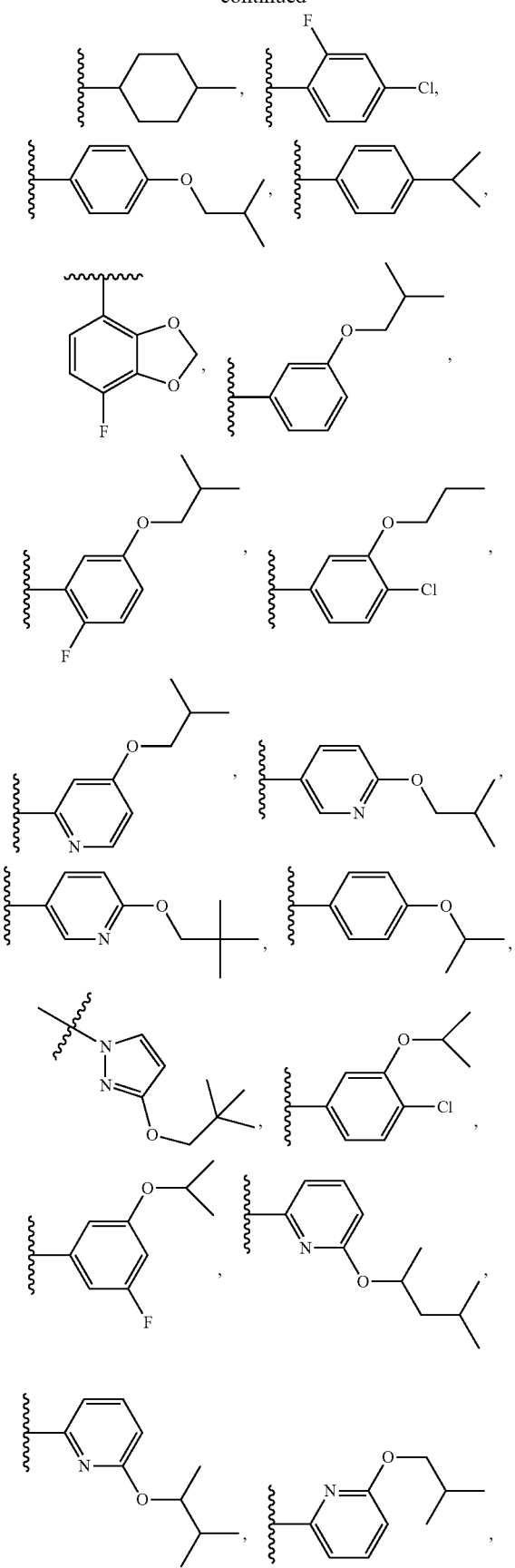

-continued

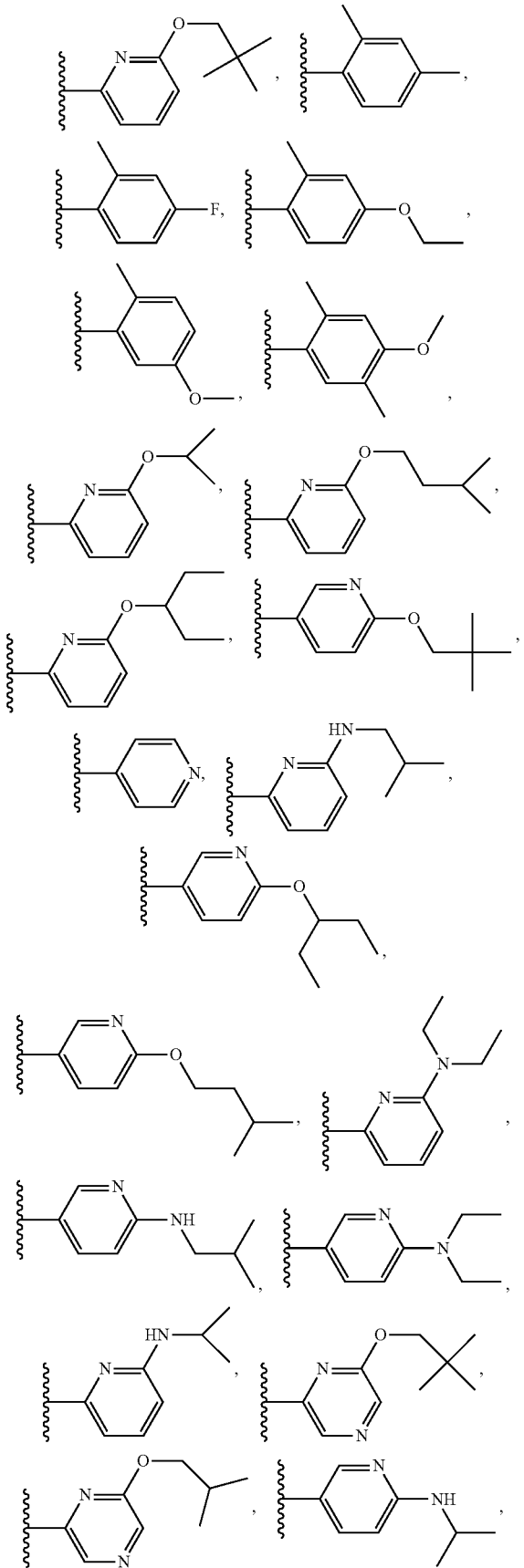

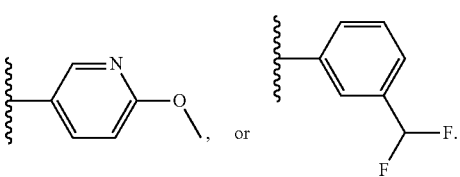

In some embodiments, $R_2$ is halo, CN, OH, amino, $C_1$-$C_6$ alkyl or $C_1$-$C_6$ fluoroalkyl, $C_1$-$C_6$ alkoxy or $C_1$-$C_6$ fluoroalkoxy, $C_3$-$C_{10}$ heterocyclic ring wherein anywhere from 1 to 4 carbon atoms are independently O, S, N, or NR; or a ($C_1$-$C_9$ alkylene)-$R_3$ wherein up to four $CH_2$ units are optionally and independently replaced with O, CO, S, SO, $SO_2$ or NR.

In some embodiments, $R_2$ is Cl, F, OH, CN, $NH_2$, $NH(CH_3)$, $N(CH_3)_2$, $N(CH_3)CH_2CH_2CH_3$, $N(CH_3)CH_2CH_2CH_2CH_3$, $NHCH_2CH_2CH_3$, $CH_3$, $CH_2OH$, $CH_2CH_3$, $CH_2CH_2CH_3$, =O, $CH_3SO_2$, $CH_3SO_2NH$, $CF_3CONH$, $CH_3CONH$, $CH_3CON(CH_3)$, tBuOCONH, $(CH_3)_2CHOCONH$, $CH(CH_3)_2$, $CHF_2$, $OCH_3$, $OCH_2CH_3$, $OCH_2CH_2CH_3$, $OCH_2CH(CH_3)_2$, $OCF_3$, $OCHF_2$, $OC(CH_3)_3$, $OCH_2CH_2tBu$, $NHCH(CH_3)(CH_2CH_2CH_3)$, $OCH(CH_3)_2$, $NH(CH_2)_2O(CH_2)_2CH_3$, $C(O)CH_3$, $CH_2CH_2OH$, $CH_2NH_2$, $NH(CH_2)_2OH$, $N(CH_3)CH_2CH_2CH_2OCH_3$, $NHCH_2CH_2COOH$, $NH(CH_2)_2N(CH_3)_2$, $NH(CH_2)_2NH_2$, $NH(CH_2)_3NH_2$, $NH(CH_2)_2OCH_3$, $NHCH(CH_3)_2$,

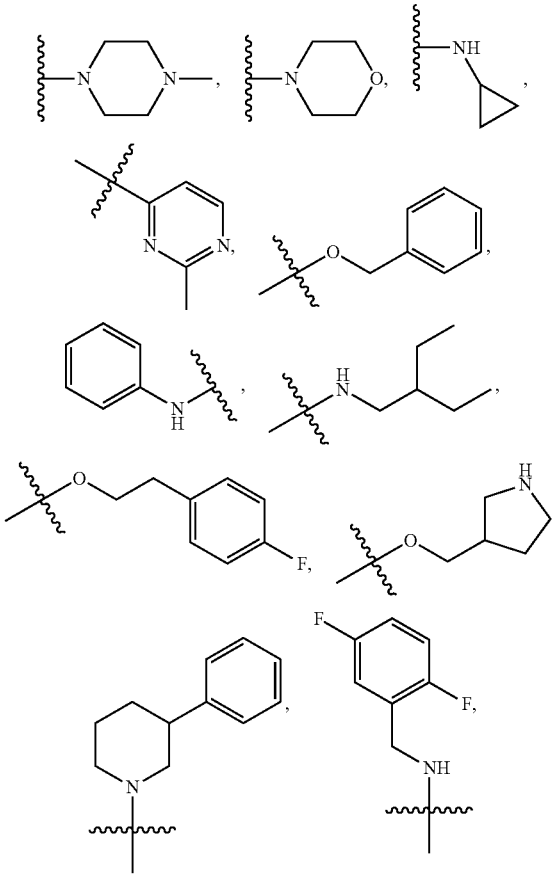

37
-continued

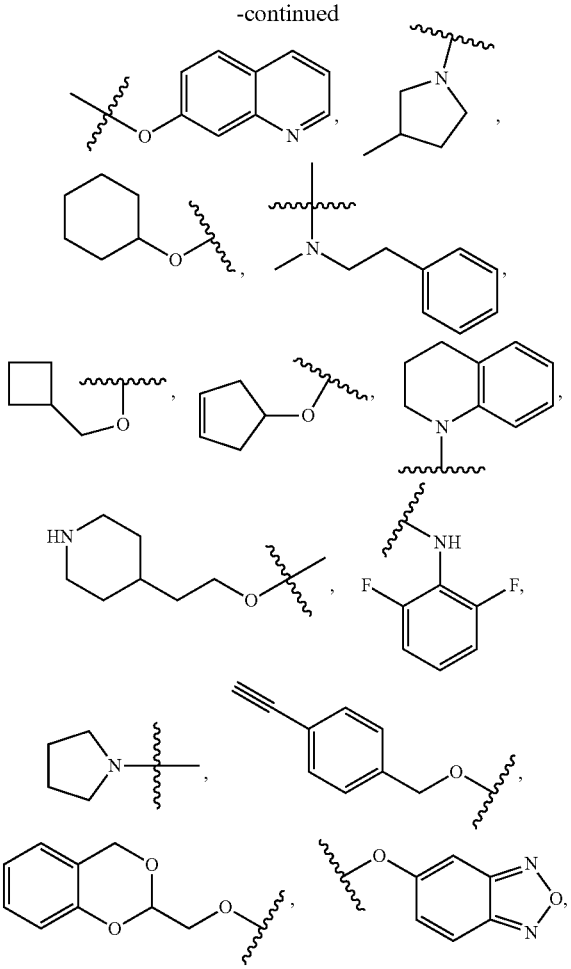

or CO$_2$H.

In some embodiments, R$_2$ is NH$_2$, or NHCH$_2$CH$_2$CH$_3$.

In some embodiments, n is 2. In some embodiments, p is 0. In some embodiments, p is 1.

In some embodiments, in the compound of formula I-i, one or more hydrogen atoms may be replaced by a deuterium atom.

In some embodiments, disclosed is a compound of formula Ia:

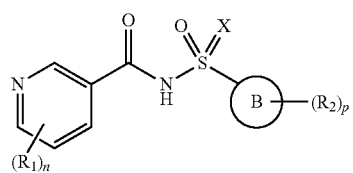

Ia or a pharmaceutically acceptable salt thereof, wherein, independently for each occurrence:
Ring B is a C$_3$-C$_{10}$ cycloalkyl ring; a C$_6$-C$_{10}$ aryl ring; or a C$_3$-C$_{10}$ heteroaryl or C$_3$-C$_{10}$ heterocyclic ring wherein anywhere from 1 to 4 ring atoms are independently O, S, N, or NR;
X is O or NR;
R$_1$ is halo; CN; NRR; C$_1$-C$_6$ alkyl or C$_1$-C$_6$ fluoroalkyl; C$_3$-C$_6$ cycloalkyl; C$_1$-C$_8$ alkoxy or C$_1$-C$_8$ fluoroalkoxy; C$_2$-C$_6$ alkenyl; C$_2$-C$_6$ alkynyl; (C$_1$-C9 alkylene)-R$_3$ wherein up to four CH$_2$ units are independently replaced with O, CO, S, SO, SO$_2$ or NR; C$_6$-C$_{10}$ aryl; C$_3$-C$_{10}$ heteroaryl or C$_3$-C$_{10}$ heterocyclic ring wherein anywhere from 1 to 4 ring atoms are independently O, S, N, or NR; or C$_3$-C$_{10}$ cycloalkyl;

R$_2$ is halo; NRR; CN; CO$_2$R; C$_1$-C$_6$ alkyl or C$_1$-C$_6$ fluoroalkyl; C$_1$-C$_6$ alkoxy or C$_1$-C$_6$ fluoroalkoxy; C$_2$-C$_6$ alkenyl; C$_2$-C$_6$ alkynyl; C$_6$-C$_{10}$ aryl; C$_3$-C$_{13}$ heteroaryl or heterocyclic ring wherein anywhere from 1 to 4 ring atoms are independently O, S, N, or NR; C$_3$-C$_{10}$ cycloalkyl; or a (C$_1$-C$_9$ alkylene)-R$_3$ wherein up to four CH$_2$ units are optionally and independently replaced with O, CO, S, SO, SO$_2$ or NR;

or two R$_2$ may form a =CH$_2$ or =O group;

R$_3$ is H; CF$_3$; CHF$_2$; OR; C≡CH; CO$_2$R; OH; C$_6$-C$_{10}$ aryl, C$_3$-C$_{10}$ heteroaryl or heterocycloalkyl wherein anywhere from 1 to 4 ring atoms are independently O, S, N, or NR; C$_3$-C$_{10}$ cycloalkyl; NRR, NRCOR, CONRR, CN, halo, or SO$_2$R;

R is independently H; OH; CO$_2$H; CO$_2$; C$_1$-C$_6$ alkyl; C$_1$-C6 alkyl; C$_2$-C$_6$ alkenyl; C$_2$-C$_6$ alkynyl; C$_6$-C$_{10}$ aryl; C$_3$-C$_{10}$ heteroaryl or heterocycloalkyl wherein anywhere from 1 to 4 ring atoms are independently O, S, or N; or C$_3$-C$_{10}$ cycloalkyl;

n is 2 or 3;
p is 0, 1, 2, or 3; and

Provided that 1) when R$_1$ is adjacent to the carbonyl attached to Ring A, R$_1$ does not contain a ring moiety, 2) at least one R$_1$ is adjacent to the C=W attached to Ring A, and at least one R$_1$ is C$_1$-C6 alkyl or C$_1$-C6 fluoroalkyl, C$_6$-C$_{10}$ aryl; C$_3$-C$_{10}$ heteroaryl or C$_3$-C$_{10}$ heterocyclic ring wherein anywhere from 1 to 4 ring atoms are independently O, S, N, or NR; or C$_3$-C$_{10}$ cycloalkyl; 3) R$_1$ is not 4,5-dihydroisoxazole; and 4) when the at least one R$_1$ is pyridine, R$_1$ is not further substituted by —CONHSO$_2$—.

In some embodiments, Ring B is pyridyl, pyridine-2(1H)-one, pyrazole, indole, aza-indole, thiophene, dihydrobenzofuran, thiazole, pyrrolidinone, or quinoline.

In some embodiments, Ring B is

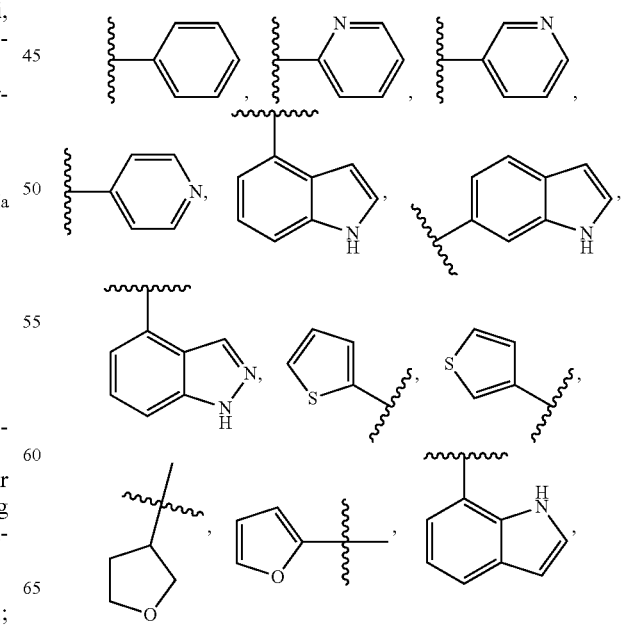

-continued

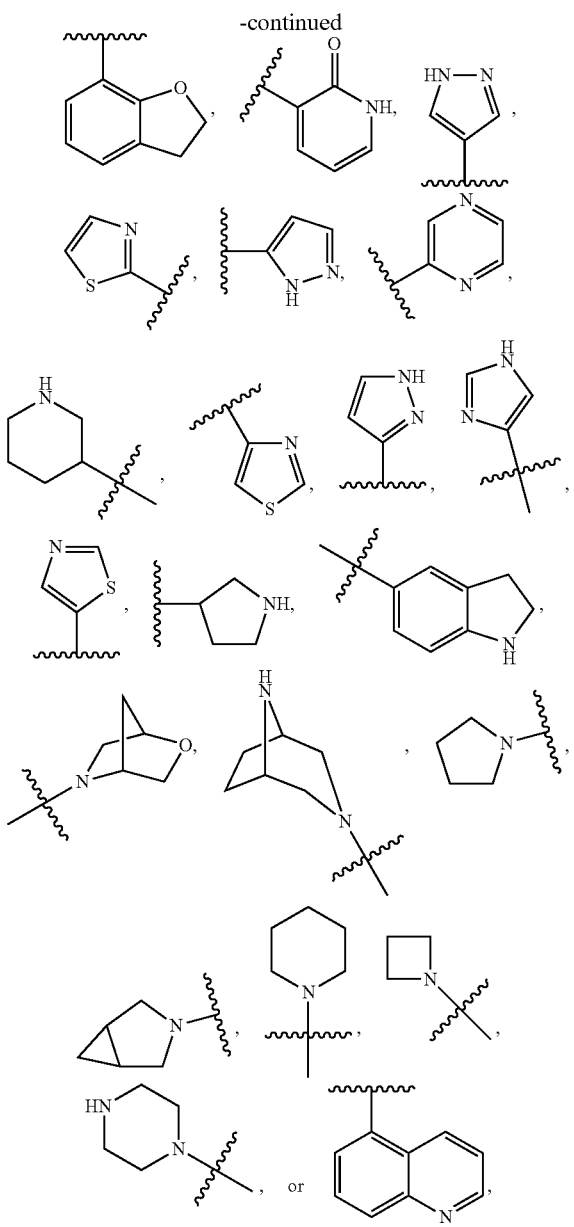

wherein the wavy line ~ indicates point of attachment of Ring B to the group of (X=)S(=O) of formula Ia.

In some embodiments, X is O.

In some embodiments, $R_1$ is independently halo, amino, OH, $C_1$-C6 fluoroalkyl, CN, $C_1$-C6 alkyl, $C_2$-$C_6$ alkenyl, $C_2$-$C_6C_2$-$C_6$ alkynyl, $C_1$-$C_8$ alkoxy or $C_1$-$C_8$ fluoroalkoxy, a phenyl, $C_3$-$C_6C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring, or a ($C_1$-$C_9$ alkylene)-$R_3$ wherein up to four $CH_2$ units are independently replaced with O, CO, S, SO, $SO_2$ or NR.

In some embodiments, $R_1$ is $CHF_2CH_2(CH_3)N$—, $(CH_3)_2CHCH_2CH2O$—, $(CH_3)_3CCH_2CH_2O$—, $(CH_3)_3COCH_2CH_2O$—, $(CH_3)_2CHO$—, $CHF_2CHF_2CH(CH_3)O$—, —$CF_3$, $(CH_3CH_2)_2N$—, $CF_3CH_2CH(CH_3)O$—, $CH_3O$—, $CH_3(CH_2)_4O$—, $CH_3CH_2CH(CH_3)CH(CH_3)O$—, $CH_3CH_2OCH_2CH_2O$—, $CH_3CH_2NCH(CH_3)_2$, $(CH_3)_3CH_2O$—, (R)—$CH_3NCH(CH_3)(CF_3)$, $CH_3OCH_2CH(CH_2CH_3)O$—, $(CH_3)_2N$—, (S)—$CH_3OCH_2CH(CH_3)O$—, $CH_3O(CH_2)_3O$—, $CH_3OC(CH_3)_2(CH_2)_2O$, $CH_3OCH_2CH(CH_3)O$, $CH_3CH(CH_3)CH_2CH(CH_3)O$—, $(CH_3)_3CCH(CH_3)O$, $((CH_3)_2CH)_2CHO$—, $CH_3CH_2CH_2O$, $CH_3CH$=$CHCH_2O$—, (S)—$CH_3CH_2CH(CH_3)O$—, $CH_3CH_2O$, $(CH_3)_2CHNCH_3$, $(CH_3)_3CCH_2O$, $(CF_3)_2CHO$—, $(CH_3)_3CCH(CH_2CH_3)O$, $CH_3C$≡$CCH_2CH_2O$, $(CH_3)_3CCH_2CH(CH_3)O$—, $(CH_3)_2C$=$C(CH_3)$, $CHF_2CH_2O$—, $CH_3CH_2CH_2NH$, $(CH_3)_2CHCH(CH_2CH_3)O$, $((CH_3)_2CH)_2N$, $CH_2$=$CHCH(CH_3)O$, $CH_2$=$CHCH_2O$—, $CH_3CH_2C(CH_3)_2O$, $(CH_3CH_2)_2CHO$, $CF_3CH_2O$, $CH_3C$(=$CH_2$)$CH_2O$, $(CH_3)_3CCH_2CH_2NH$, $CH_3OCH_2C(CH_3)_2O$, $(CH_3)_3CCH_2N(CH_3)$, $(CH_3)_2CHCH(CH_3)NH$, $(CH_3)_2CHO(CH_2)_2O$, $CH_3CH_2CH_2CH(CH_3)O$, $CH_3CF_2CH_2O$, $(CH_3)_3CNH$, (R)—$CH_3CH_2CH(CH_3)O$, $CH_3OCH_2CH_2O$, $(CH_3)_2CHCH_2N(CH_3)$, $CH_3CH_2CH_2CH(CH_3)CH(CH_3)O$, $CH_3CH_2CH_2O$, $CH_3CH_2CH_2N(CH_3)$, (R)—$CH_3OCH_2CH(CH_3)O$, $CF_3CH_2N(CH_3)$, $CH_3CH_2N(CH_3)$, $((CH_3)_3C)_2CHO$, $(CH_3CH_2)_2CHN(CH_3)$, $(CH_3)_2CHN(CH_3)$, $CH_3CH_2OCH_2CH(CH_3)O$, $(CH_3)_3CCH_2NH$, $CF_3CH(CH_3)O$, $CH_3CH_2NCH(CH_3)_2$, (R)—$CF_3CH(CH_3)N(CH_3)$, $(CH_3)_2CHCH(CH_3)$, $CH_3CH_2(CH_3)_2CHCH_2CH_2O$, (S)—$CH_3OCH(CH_3)CH_2O$, $HOCH(CH_3)_2CH_2CH_2NH$, $CF_3CH_2CH_2O$, $CF_3CH_2CH_2CH_2O$, $CF_3CH$=$CHCH_2O$, $CH_3CH_2CH_2CH_2CH_2NH$, or $(CH_3)_3C$.

In some embodiments, $R_1$ is $CH_3$, Cl, F, CN, $CH_2CH_3$, $CH(CH_3)_2$, $OCH_2CH_2OCH_2CH_3$,

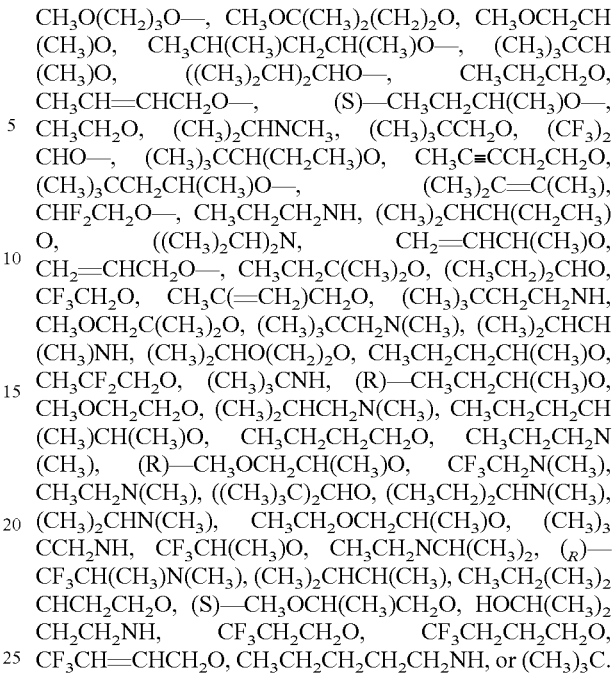

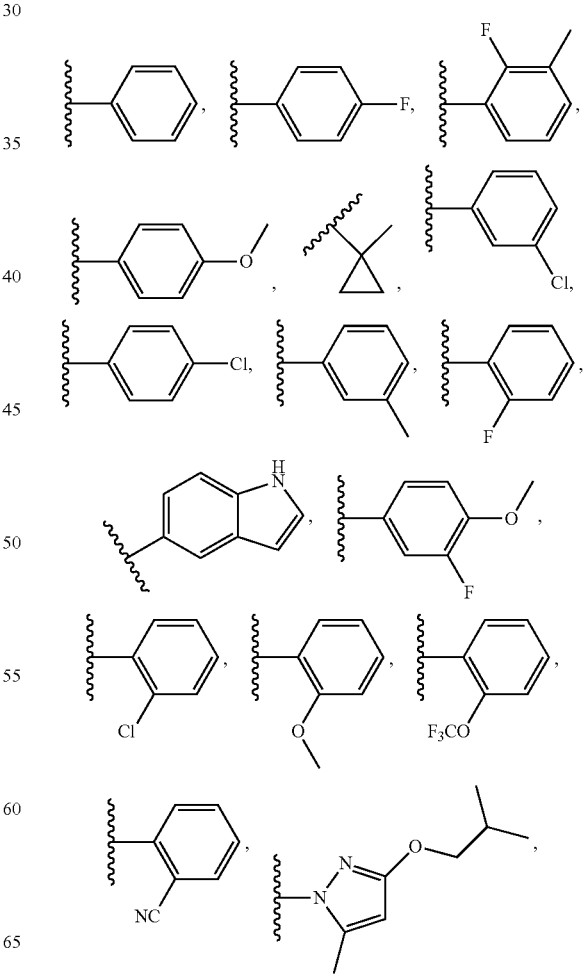

-continued
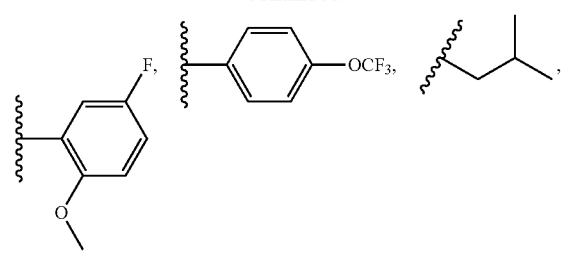
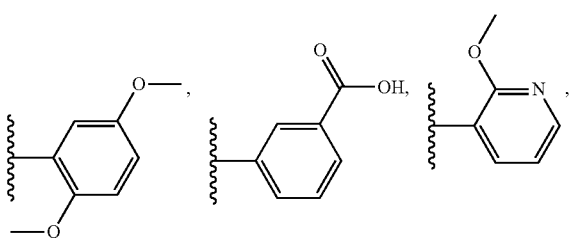
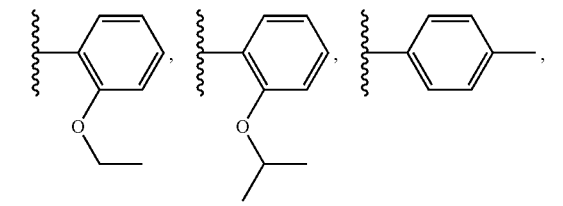
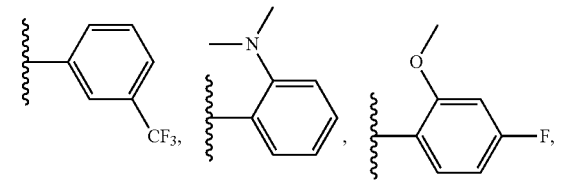
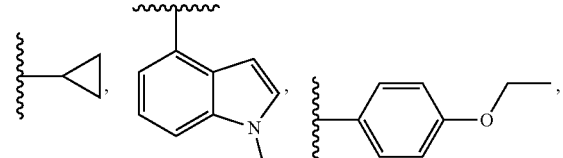
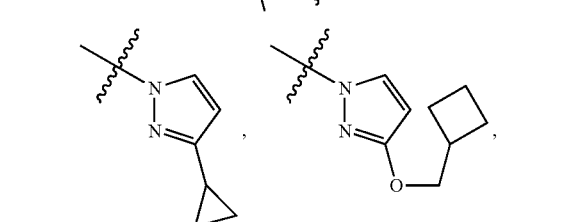
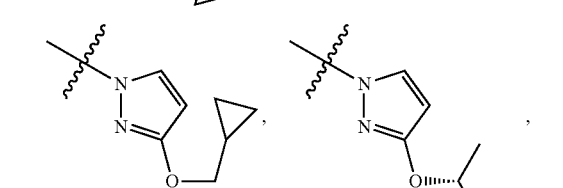
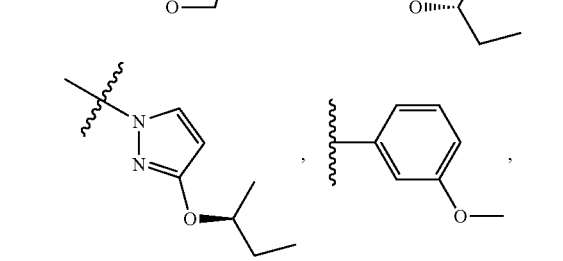
-continued
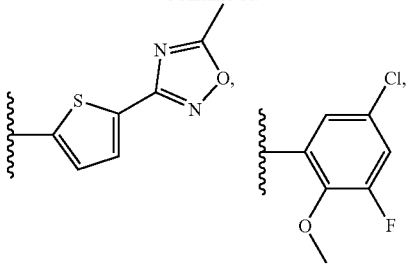
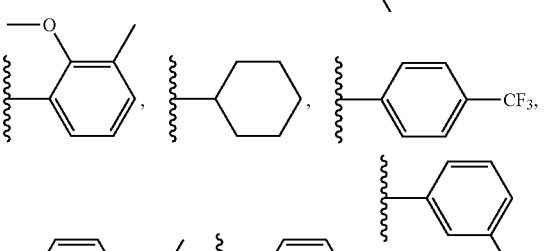

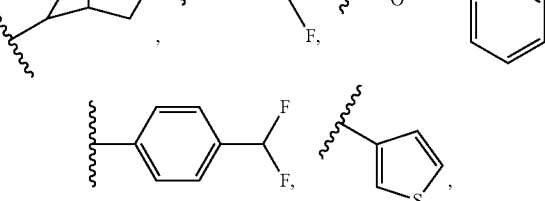
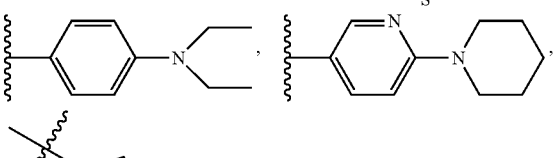
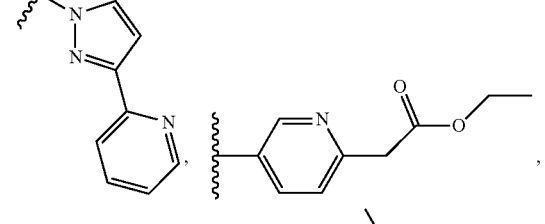
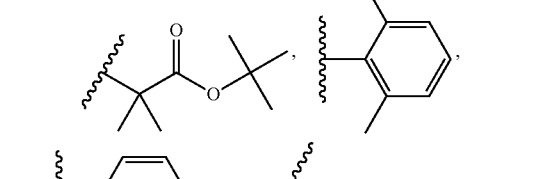
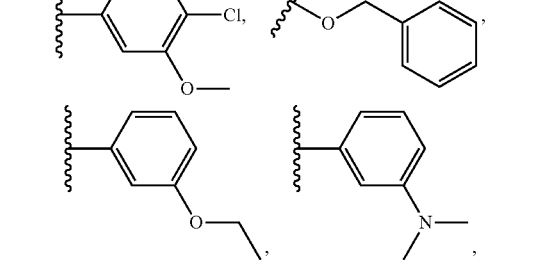

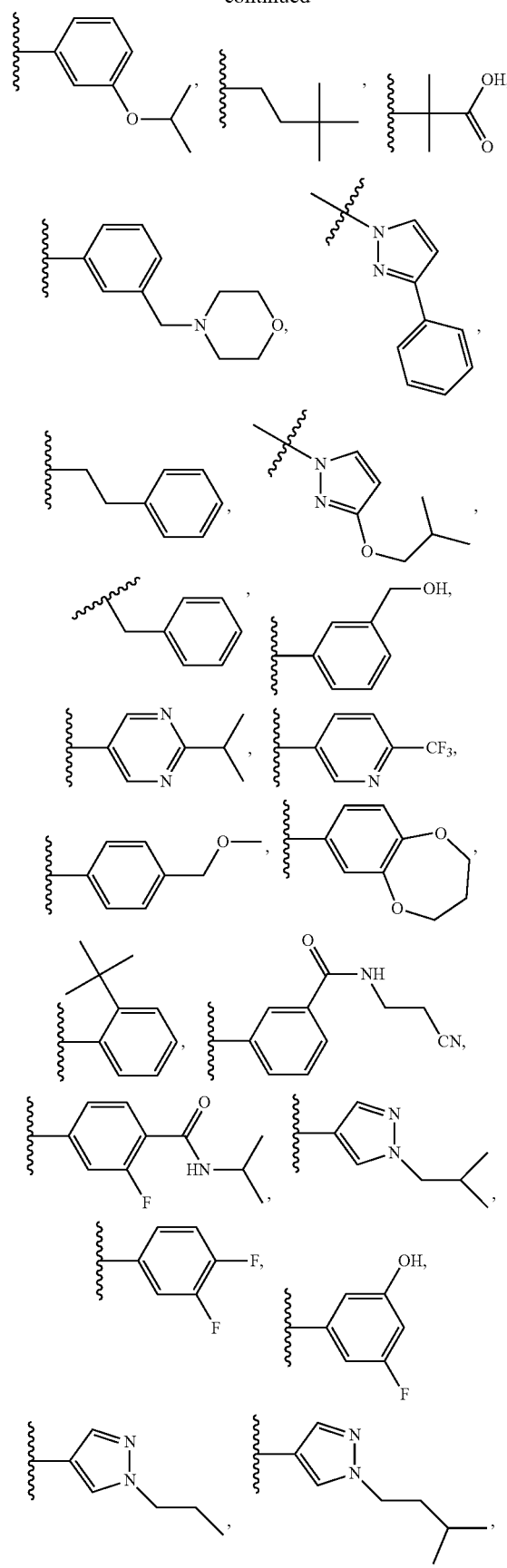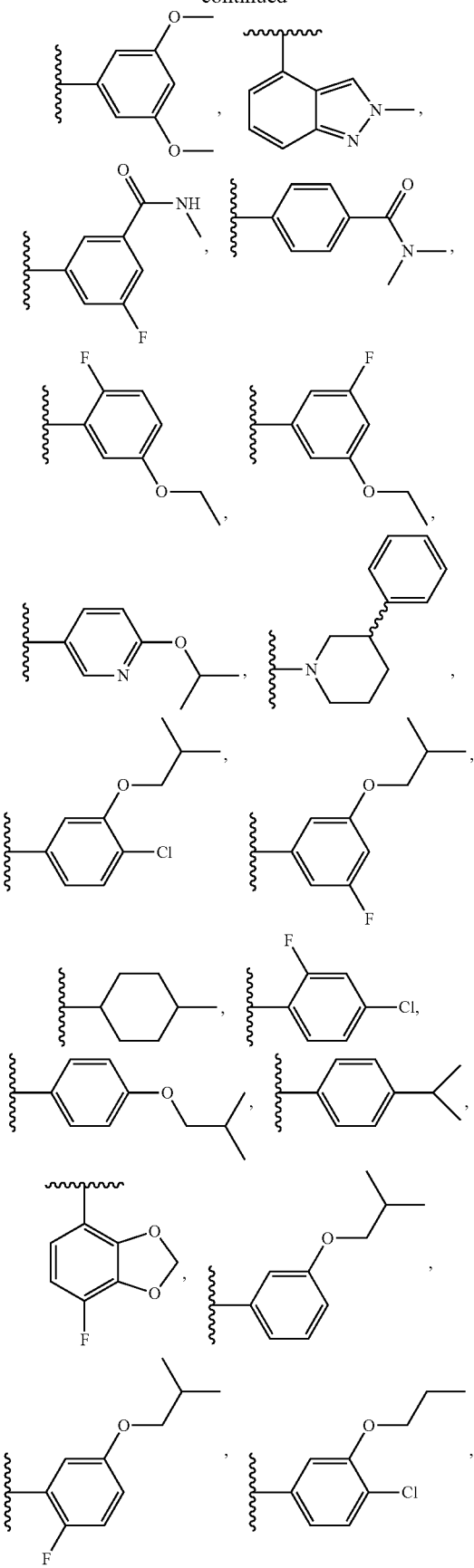

-continued

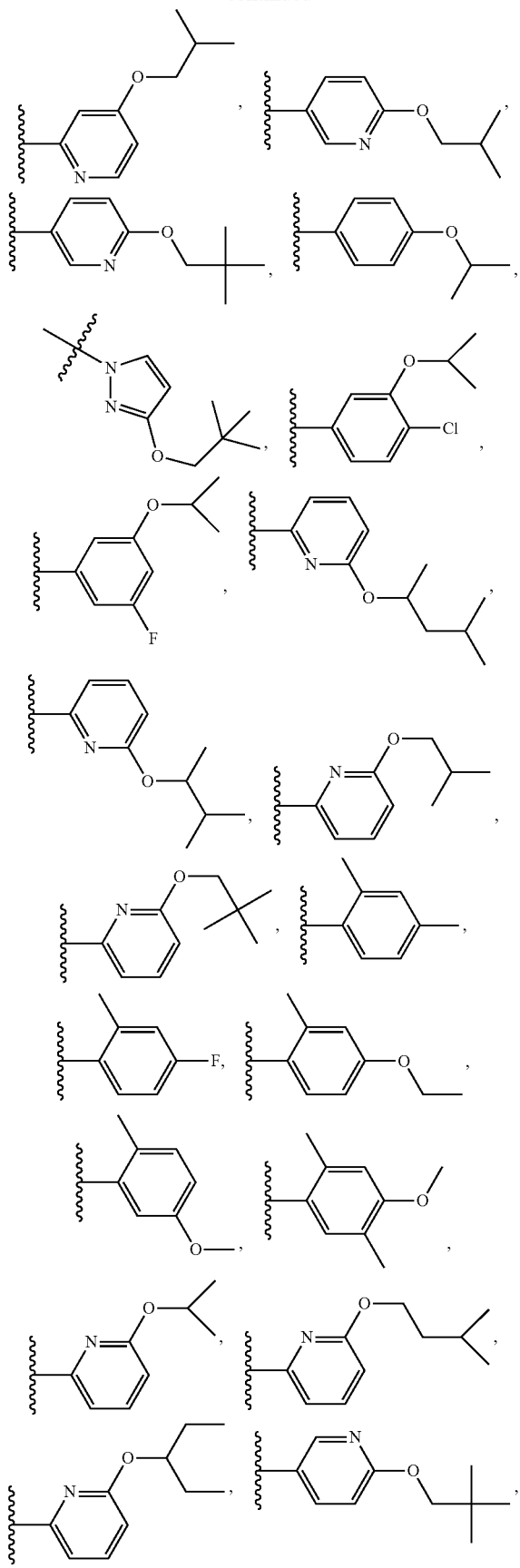
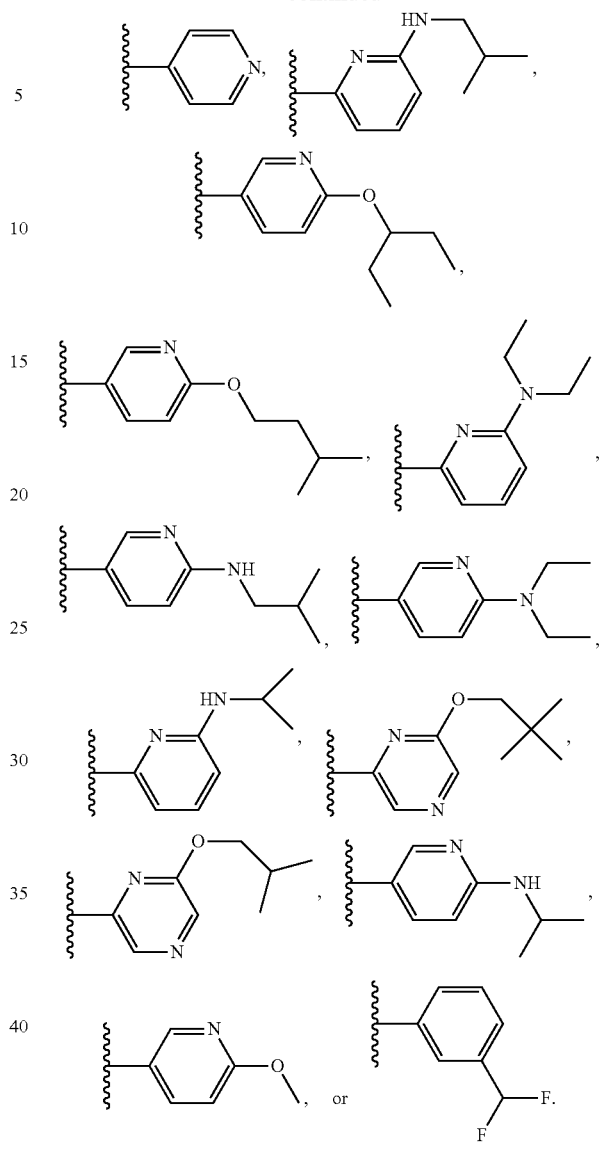

In some embodiments, $R_2$ is halo, CN, amino, OH, $C_1$-$C_6$ alkyl or $C_1$-$C_6$ fluoroalkyl, $C_1$-$C_6$ alkoxy or $C_1$-$C_6$ fluoroalkoxy, $C_3$-$C_{10}$ heterocyclic ring wherein anywhere from 1 to 4 carbon atoms are independently O, S, N, or NR; or a ($C_1$-$C_9$ alkylene)-$R_3$ wherein up to four $CH_2$ units are optionally and independently replaced with O, CO, S, SO, $SO_2$ or NR.

In some embodiments, $R_2$ is Cl, F, OH, CN, $NH_2$, $NH(CH_3)$, $N(CH_3)_2$, $N(CH_3)CH_2CH_2CH_3$, $N(CH_3)CH_2CH_2CH_2CH_3$, $NHCH_2CH_2CH_3$, $CH_3$, $CH_2OH$, $CH_2CH_3$, $CH_2CH_2CH_3$, =O, $CH_3SO_2$, $CH_3SO_2NH$, $CF_3CONH$, $CH_3CONH$, $CH_3CON(CH_3)$, tBuOCONH, $(CH_3)_2CHOCONH$, $CH(CH_3)_2$, $CHF_2$, $OCH_3$, $OCH_2CH_3$, $OCH_2CH_2CH_3$, $OCH_2CH_2CH(CH_3)_2$, $OCF_3$, $OCHF_2$, $OC(CH_3)_3$, $OCH_2CH_2tBu$, $NHCH(CH_3)(CH_2CH_2CH_3)$, $OCH(CH_3)_2$, $NH(CH_2)_2O(CH_2)_2CH_3$, $C(O)CH_3$, $CH_2CH_2OH$, $CH_2NH_2$, $NH(CH_2)_2OH$, $N(CH_3)CH_2CH_2CH_2OCH_3$, $NHCH_2CH_2COOH$, $NH(CH_2)_2N(CH_3)_2$, $NH(CH_2)_2NH_2$, $NH(CH_2)_3NH_2$, $NH(CH_2)_2OCH_3$, $NHCH(CH_3)_2$,

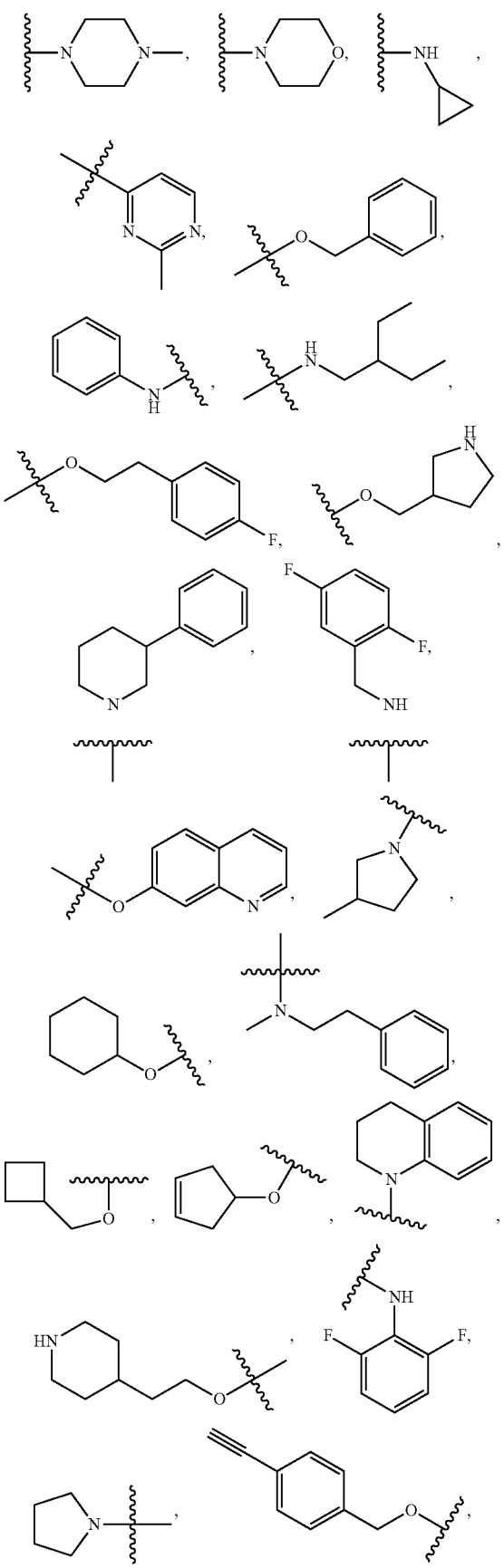

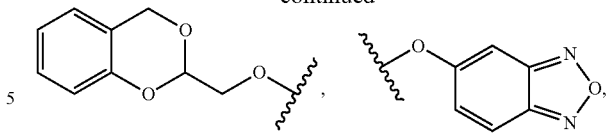

or CO₂H.

In some embodiments, $R_2$ is $NH_2$, or $NHCH_2CH_2CH_3$.

In some embodiments, n is 2. In some embodiments, p is 0. In some embodiments, p is 1.

In some embodiments, in the compound of formula Ia, one or more hydrogen atoms may be replaced by a deuterium atom.

In some embodiments, the compounds of formula Ia or a pharmaceutically acceptable salt thereof is a compound of formula Ia-i

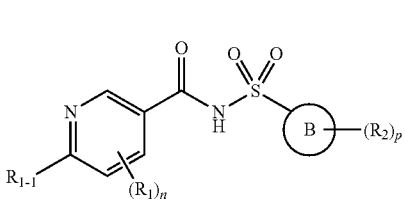

Ia-i or a pharmaceutically acceptable salt thereof, wherein, independently for each occurrence:

Ring B is a $C_3$-$C_{10}$ cycloalkyl ring; a $C_6$-$C_{10}$ aryl ring; or a $C_3$-$C_{10}$ heteroaryl or $C_3$-$C_{10}C_3$-$C_{10}$ heterocyclic ring wherein anywhere from 1 to 4 ring atoms are independently O, S, N, or NR;

$R_1$ is halo; CN; NRR; $C_1$-$C_6$ alkyl or $C_1$-$C_6$ fluoroalkyl; $C_3$-$C_6C_3$-$C_6$ cycloalkyl; $C_1$-$C_8$ alkoxy or $C_1$-$C_8$ fluoroalkoxy; $C_2$-$C_6C_2$-$C_6$ alkenyl; $C_2$-$C_6C_2$-$C_6$ alkynyl; ($C_1$-$C_9$ alkylene)-$R_3$ wherein up to four $CH_2$ units are independently replaced with O, CO, S, SO, $SO_2$ or NR; $C_6$-$C_{10}$ aryl; $C_3$-$C_{10}C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_{1-1}$ is $C_1$-$C_6$ alkyl or $C_1$-$C_6$ fluoroalkyl, $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_2$ is halo; NRR; CN; $CO_2R$; $C_1$-$C_6$ alkyl or $C_1$-$C_6$ fluoroalkyl; $C_1$-$C_6$ alkoxy or $C_1$-$C_6$ fluoroalkoxy; $C_2$-$C_6C_2$-$C_6$ alkenyl; $C_2$-$C_6C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four $CH_2$ units are optionally and independently replaced with O, CO, S, SO, $SO_2$ or NR;

or two $R_2$ may form a =$CH_2$ or =O group;

$R_3$ is H; $CF_3$; $CHF_2$; OR; C≡CH; $CO_2R$; OH; $C_6$-$C_{10}$ aryl, $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or $SO_2R$;

R is independently H; OH; $CO_2H$; $CO_2C_1$-$C_6$ alkyl; $C_1$-$C_6$ alkyl; $C_2$-$C_6C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, or N; or $C_3$-$C_{10}$ cycloalkyl;

n is 1 or 2; and p is 0, 1, 2, or 3.

In some embodiments, Ring B is pyridyl, pyridine-2(1H)-one, pyrazole, indole, aza-indole, thiophene, dihydrobenzofuran, thiazole, pyrrolidinone, or quinoline.

In some embodiments, Ring B is

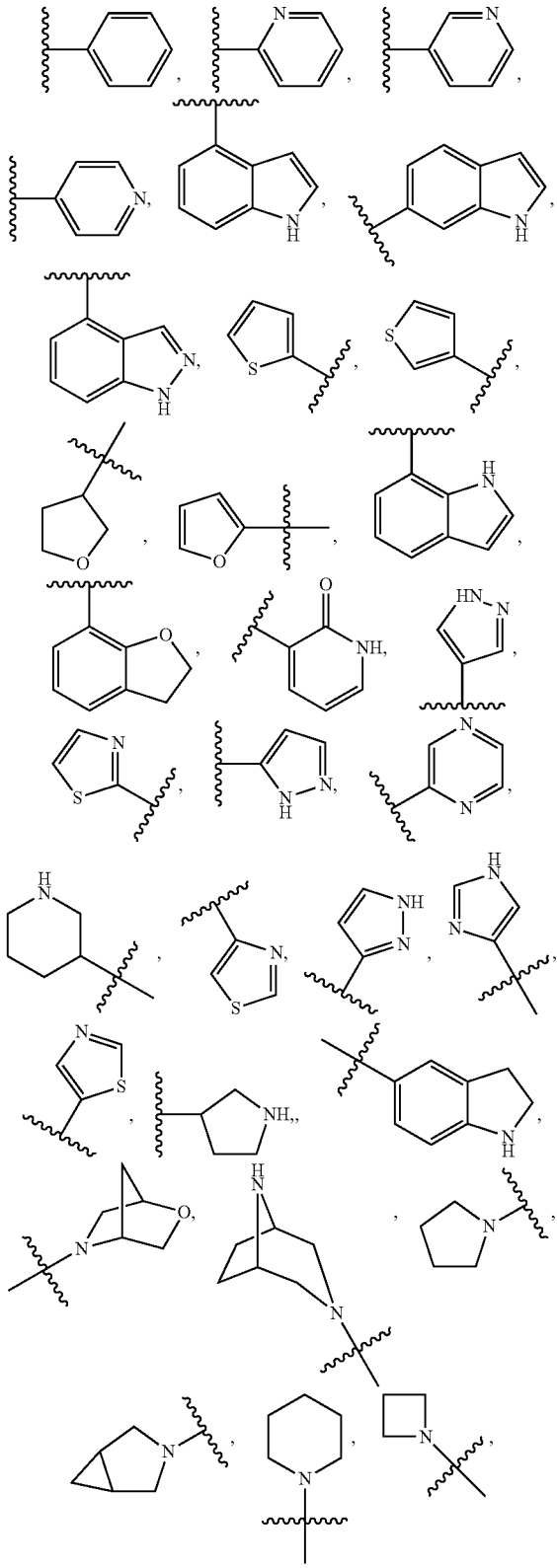


wherein the wavy line ~ indicates point of attachment of Ring B to the sulfonyl.

In some embodiments, $R_1$ is independently halo, amino, OH, $C_1$-$C_6$ fluoroalkyl, CN, $C_1$-$C_6$ alkyl, $C_2$-$C_6$ alkenyl, $C_2$-$C_6$ alkynyl, $C_1$-$C_8$ alkoxy or $C_1$-$C_8$ fluoroalkoxy, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring, or a ($C_1$-$C_9$ alkylene)-$R_3$ wherein up to four $CH_2$ units are independently replaced with O, CO, S, SO, $SO_2$ or NR.

In some embodiments, $R_{1-1}$ is $C_1$-$C_6$ alkyl or $C_1$-$C_6$ fluoroalkyl, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring.

In some embodiments, $R_{1-1}$ is tert-butyl,

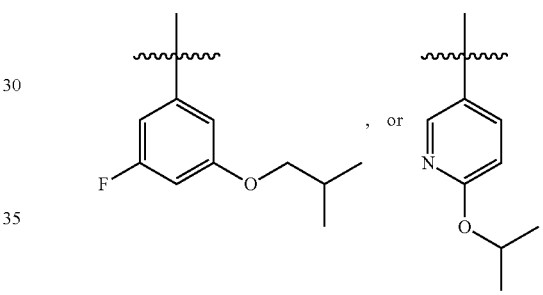

In some embodiments, $R_1$ is $CHF_2CH_2(CH_3)N$—, $(CH_3)_2CHCH_2CH2O$—, $(CH_3)_3CCH_2CH_2O$—, $(CH_3)_3COCH_2CH_2O$—, $(CH_3)_2CHO$—, $CHF_2CHF_2CH(CH_3)O$—, —$CF_3$, $(CH_3CH_2)_2N$—, $CF_3CH_2CH(CH_3)O$—, $CH_3O$—, $CH_3(CH_2)_4O$—, $CH_3CH_2CH(CH_3)CH(CH_3)O$—, $CH_3CH_2OCH_2CH_2O$—, $CH_3CH_2NCH(CH_3)_2$, $(CH_3)_3CH_2O$—, (R)—$CH_3NCH(CH_3)(CF_3)$, $CH_3OCH_2CH(CH_2CH_3)O$—, $(CH_3)_2N$—, (S)—$CH_3OCH_2CH(CH_3)O$—, $CH_3O(CH_2)_3O$—, $CH_3OC(CH_3)_2(CH_2)_2O$, $CH_3OCH_2CH(CH_3)O$, $CH_3CH(CH_3)CH_2CH(CH_3)O$—, $(CH_3)_3CCH(CH_3)O$, $((CH_3)_2CH)_2CHO$—, $CH_3CH_2CH_2O$, $CH_3CH=CHCH_2O$—, (S)—$CH_3CH_2CH(CH_3)O$—, $CH_3CH_2O$, $(CH_3)_2CHNCH_3$, $(CH_3)_3CCH_2O$, $(CF_3)_2CHO$—, $(CH_3)_3CCH(CH_2CH_3)O$, $CH_3C≡CCH_2CH_2O$, $(CH_3)_3CCH_2CH(CH_3)O$—, $(CH_3)_2C=C(CH_3)$, $CHF_2CH_2O$—, $CH_3CH_2CH_2NH$, $(CH_3)_2CHCH(CH_2CH_3)O$, $((CH_3)_2CH)_2N$, $CH_2=CHCH(CH_3)O$, $CH_2=CHCH_2O$—, $CH_3CH_2C(CH_3)_2O$, $(CH_3CH_2)_2CHO$, $CF_3CH_2O$, $CH_3C(=CH_2)CH_2O$, $(CH_3)_3CCH_2CH_2NH$, $CH_3OCH_2C(CH_3)_2O$, $(CH_3)_3CCH_2N(CH_3)$, $(CH_3)_2CHCH(CH_3)NH$, $(CH_3)_2CHO(CH_2)_2O$, $CH_3CH_2CH_2CH(CH_3)O$, $CH_3CF_2CH_2O$, $(CH_3)_3CNH$, (R)—$CH_3CH_2CH(CH_3)O$, $CH_3OCH_2CH_2O$, $(CH_3)_2CHCH_2N(CH_3)$, $CH_3CH_2CH_2CH(CH_3)CH(CH_3)O$, $CH_3CH_2CH_2O$, $CH_3CH_2CH_2N(CH_3)$, (R)—$CH_3OCH_2CH(CH_3)O$, $CF_3CH_2N(CH_3)$, $CH_3CH_2N(CH_3)$, $((CH_3)_3C)_2CHO$, $(CH_3CH_2)_2CHN(CH_3)$, $(CH_3)_2CHN(CH_3)$, $CH_3CH_2OCH_2CH(CH_3)O$, $(CH_3)_3CCH_2NH$, $CF_3CH(CH_3)O$, $CH_3CH_2NCH(CH_3)_2$, (R)—

CF₃CH(CH₃)N(CH₃), (CH₃)₂CHCH(CH₃), CH₃CH₂(CH₃)₂CHCH₂CH₂O, (S)—CH₃OCH(CH₃)CH₂O, HOCH(CH₃)₂CH₂CH₂NH, CF₃CH₂CH₂O, CF₃CH₂CH₂CH₂O, CF₃CH=CHCH₂O, or CH₃CH₂CH₂CH₂CH₂NH.

In some embodiments, R₂ is halo, CN, amino, OH, $C_1$-$C_6$ alkyl or $C_1$-$C_6$ fluoroalkyl, $C_1$-$C_6$ alkoxy or $C_1$-$C_6$ fluoroalkoxy, $C_3$-$C_{10}$ heterocyclic ring wherein anywhere from 1 to 4 carbon atoms are independently O, S, N, or NR; or a ($C_1$-$C_9$ alkylene)-R₃ wherein up to four CH₂ units are optionally and independently replaced with O, CO, S, SO, SO₂ or NR.

In some embodiments, R₂ is Cl, F, OH, CN, NH₂, NH(CH₃), N(CH₃)₂, N(CH₃)CH₂CH₂CH₃, N(CH₃)CH₂CH₂CH₂CH₃, NHCH₂CH₂CH₃, CH₃, CH₂OH, CH₂CH₃, CH₂CH₂CH₃, =O, CH₃SO₂, CH₃SO₂NH, CF₃CONH, CH₃CONH, CH₃CON(CH₃), tBuOCONH, (CH₃)₂CHOCONH, CH(CH₃)₂, CHF₂, OCH₃, OCH₂CH₃, OCH₂CH₂CH₃, OCH₂CH₂CH(CH₃)₂, OCF₃, OCHF₂, OC(CH₃)₃, OCH₂CH₂tBu, NHCH(CH₃)(CH₂CH₂CH₃), OCH(CH₃)₂, NH(CH₂)₂O(CH₂)₂CH₃, C(O)CH₃, CH₂CH₂OH, CH₂NH₂, NH(CH₂)₂OH, N(CH₃)CH₂CH₂CH₂OCH₃, NHCH₂CH₂COOH, NH(CH₂)₂N(CH₃)₂, NH(CH₂)₂NH₂, NH(CH₂)₃NH₂, NH(CH₂)₂OCH₃, NHCH(CH₃)₂,

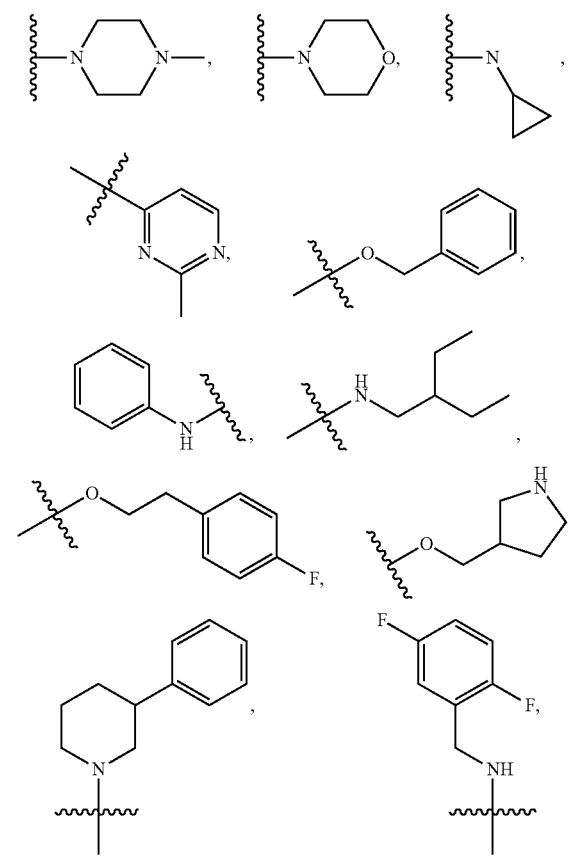

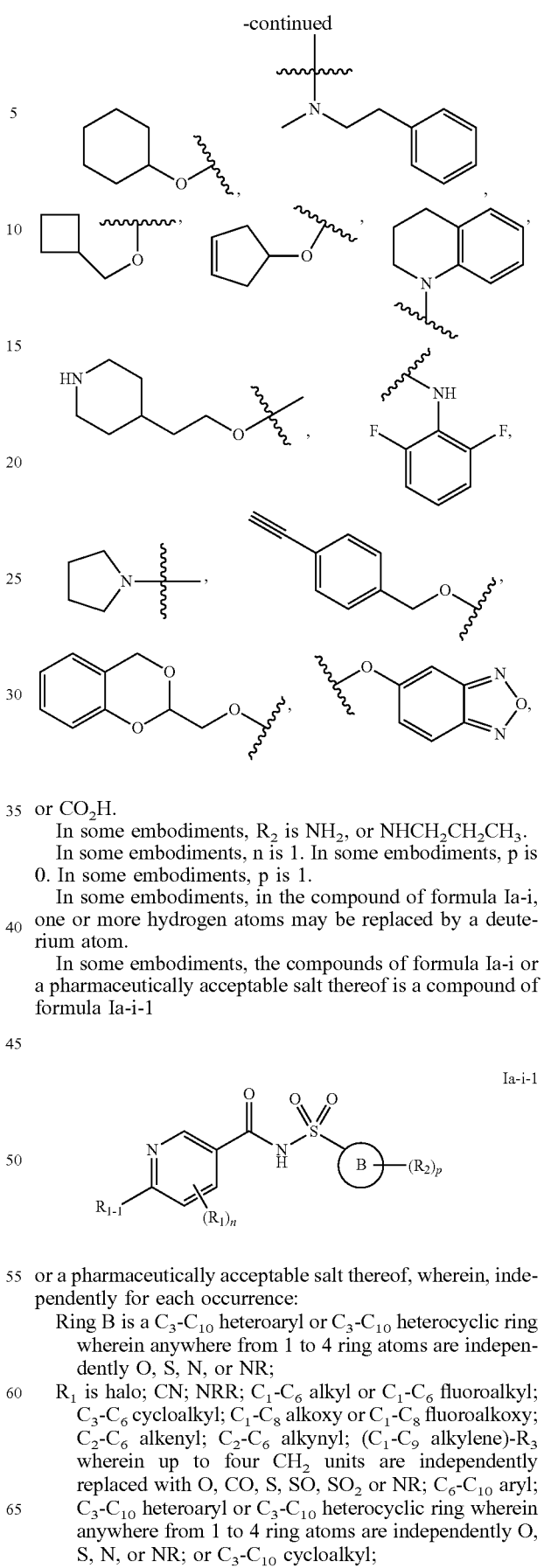

or CO₂H.

In some embodiments, R₂ is NH₂, or NHCH₂CH₂CH₃.
In some embodiments, n is 1. In some embodiments, p is 0. In some embodiments, p is 1.
In some embodiments, in the compound of formula Ia-i, one or more hydrogen atoms may be replaced by a deuterium atom.
In some embodiments, the compounds of formula Ia-i or a pharmaceutically acceptable salt thereof is a compound of formula Ia-i-1

Ia-i-1


or a pharmaceutically acceptable salt thereof, wherein, independently for each occurrence:
Ring B is a $C_3$-$C_{10}$ heteroaryl or $C_3$-$C_{10}$ heterocyclic ring wherein anywhere from 1 to 4 ring atoms are independently O, S, N, or NR;
R₁ is halo; CN; NRR; $C_1$-$C_6$ alkyl or $C_1$-$C_6$ fluoroalkyl; $C_3$-$C_6$ cycloalkyl; $C_1$-$C_8$ alkoxy or $C_1$-$C_8$ fluoroalkoxy; $C_2$-$C_6$ alkenyl; $C_2$-$C_6$ alkynyl; ($C_1$-$C_9$ alkylene)-R₃ wherein up to four CH₂ units are independently replaced with O, CO, S, SO, SO₂ or NR; $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_{1-1}$ is $C_1$-$C_6$ alkyl or $C_1$-$C_6$ fluoroalkyl, $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_2$ is halo; NRR; CN; $CO_2R$; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four $CH_2$ units are optionally and independently replaced with O, CO, S, SO, $SO_2$ or NR;

or two $R_2$ may form a $=CH_2$ or $=O$ group;

$R_3$ is H; $CF_3$; $CHF_2$; OR; C≡CH; $CO_2R$; OH; $C_6$-$C_{10}$ aryl, $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or $SO_2R$;

R is independently H; OH; $CO_2H$; $CO_2$; $C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, or N; or $C_3$-$C_{10}$ cycloalkyl;

n is 1 or 2; and p is 0, 1, 2, or 3.

In some embodiments, Ring B is pyridyl, pyridine-2(1H)-one, pyrazole, indole, aza-indole, thiophene, dihydrobenzofuran, thiazole, pyrrolidinone, or quinoline.

In some embodiments, Ring B is wherein the wavy line indicates point of attachment of Ring B to the sulfonyl.

In some embodiments, $R_1$ is independently halo, amino, OH, $C_1$-$C_6$ fluoroalkyl, CN, $C_1$-$C_6$ alkyl, $C_2$-$C_6$ alkenyl, $C_2$-$C_6$ alkynyl, $C_1$-$C_8$ alkoxy or $C_1$-$C_8$fluoroalkoxy, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring, or a ($C_1$-$C_9$ alkylene)-$R_3$ wherein up to four $CH_2$ units are independently replaced with O, CO, S, SO, $SO_2$ or NR.

In some embodiments, $R_{1-1}$ is $C_1$-$C_6$ alkyl or $C_1$-$C_6$ fluoroalkyl, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring.

In some embodiments, $R_{1-1}$ is tert-butyl,

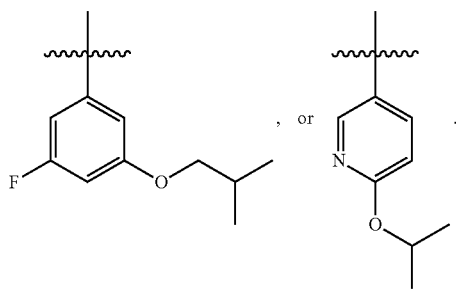 [SMILES: *c1cc(F)cc(OCC(C)C)c1 ; *c1ccc(OC(C)C)nc1]

, or .

In some embodiments, $R_1$ is $CHF_2CH_2CH(CH_3)N—$, $(CH_3)_2CHCH_2CH2O—$, $(CH_3)_3CCH_2CH_2O—$, $(CH_3)_3COCH_2CH_2O—$, $(CH_3)_2CHO—$, $CHF_2CHF_2CH(CH_3)O—$, $—CF_3$, $(CH_3CH_2)_2N—$, $CF_3CH_2CH(CH_3)O—$, $CH_3O—$, $CH_3(CH_2)_4O—$, $CH_3CH_2CH(CH_3)CH(CH_3)O—$, $CH_3CH_2OCH_2CH_2O—$, $CH_3CH_2NCH(CH_3)_2$, $(CH_3)_3CH_2O—$, (R)—$CH_3NCH(CH_3)(CF_3)$, $CH_3OCH_2CH(CH_2CH_3)O—$, $(CH_3)_2N—$, (S)—$CH_3OCH_2CH(CH_3)O—$, $CH_3O(CH_2)_3O—$, $CH_3OC(CH_3)_2(CH_2)_2O$, $CH_3OCH_2CH(CH_3)O$, $CH_3CH(CH_3)CH_2CH(CH_3)O—$, $(CH_3)_3CCH(CH_3)O$, $((CH_3)_2CH)_2CHO—$, $CH_3CH_2CH_2O$, $CH_3CH=CHCH_2O—$, (S)—$CH_3CH_2CH(CH_3)O—$, $CH_3CH_2O$, $(CH_3)_2CHNCH_3$, $(CH_3)_3CCH_2O$, $(CF_3)_2CHO—$, $(CH_3)_3CCH(CH_2CH_3)O$, $CH_3C≡CCH_2CH_2O$, $(CH_3)_3CCH_2CH(CH_3)O—$, $(CH_3)_2C=C(CH_3)$, $CHF_2CH_2O—$, $CH_3CH_2CH_2NH$, $(CH_3)_2CHCH(CH_2CH_3)O$, $((CH_3)_2CH)_2N$, $CH_2=CHCH(CH_3)O$, $CH_2=CHCH_2O—$, $CH_3CH_2C(CH_3)_2O$, $(CH_3CH_2)_2CHO—$, $CF_3CH_2O$, $CH_3C(=CH_2)CH_2O$, $(CH_3)_3CCH_2CH_2NH$, $CH_3OCH_2C(CH_3)_2O$, $(CH_3)_3CCH_2N(CH_3)$, $(CH_3)_2CHCH(CH_3)NH$, $(CH_3)_2CHO(CH_2)_2O$, $CH_3CH_2CH_2CH(CH_3)O$, $CH_3CF_2CH_2O$, $(CH_3)_3CNH$, (R)—$CH_3CH_2CH(CH_3)O$, $CH_3OCH_2CH_2O$, $(CH_3)_2CHCH_2N(CH_3)$, $CH_3CH_2CH_2CH(CH_3)CH(CH_3)O$, $CH_3CH_2CH_2O$, $CH_3CH_2CH_2N(CH_3)$, (R)—$CH_3OCH_2CH(CH_3)O$, $CF_3CH_2N(CH_3)$, $CH_3CH_2N(CH_3)$, $((CH_3)_3C)_2CHO$, $(CH_3CH_2)_2CHN(CH_3)$, $(CH_3)_2CHN(CH_3)$, $CH_3CH_2OCH_2CH(CH_3)O$, $(CH_3)_3CCH_2NH$, $CF_3CH(CH_3)O$, $CH_3CH_2NCH(CH_3)_2$, $(R)$—$CF_3CH(CH_3)N(CH_3)$, $(CH_3)_2CHCH(CH_3)$, $CH_3CH_2(CH_3)_2CHCH(CH_3)_2$, (S)—$CH_3OCH(CH_3)CH_2O$, $HOCH(CH_3)_2CH_2CH_2NH$, $CF_3CH_2CH_2O$, $CF_3CH_2CH_2CH_2O$, $CF_3CH=CHCH_2O$, or $CH_3CH_2CH_2CH_2CH_2NH$.

In some embodiments, $R_2$ is halo, CN, amino, OH, $C_1$-$C_6$ alkyl or $C_1$-$C_6$ fluoroalkyl, $C_1$-$C_6$ alkoxy or $C_1$-$C_6$ fluoroalkoxy, $C_3$-$C_{10}$ heterocyclic ring wherein anywhere from 1 to 4 carbon atoms are independently O, S, N, or NR; or a ($C_1$-$C_9$ alkylene)-$R_3$ wherein up to four $CH_2$ units are optionally and independently replaced with O, CO, S, SO, $SO_2$ or NR.

In some embodiments, $R_2$ is Cl, F, OH, CN, $NH_2$, $NH(CH_3)$, $N(CH_3)_2$, $N(CH_3)CH_2CH_2CH_3$, $N(CH_3)CH_2CH_2CH_2CH_3$, $NHCH_2CH_2CH_3$, $CH_3$, $CH_2OH$, $CH_2CH_3$, $CH_2CH_2CH_3$, $=O$, $CH_3SO_2$, $CH_3SO_2NH$, $CF_3CONH$, $CH_3CONH$, $CH_3CON(CH_3)$, $tBuOCONH$, $(CH_3)_2CHOCONH$, $CH(CH_3)_2$, $CHF_2$, $OCH_3$, $OCH_2CH_3$, $OCH_2CH_2CH_3$, $OCH_2CH_2CH(CH_3)_2$, $OCF_3$, $OCHF_2$, $OC(CH_3)_3$, $OCH_2CH_2tBu$, $NHCH(CH_3)(CH_2CH_2CH_3)$, $OCH(CH_3)_2$, $NH(CH_2)_2O(CH_2)_2CH_3$, $C(O)CH_3$, $CH_2CH_2OH$, $CH_2NH_2$, $NH(CH_2)_2OH$, $N(CH_3)CH_2CH_2CH_2OCH_3$, $NHCH_2CH_2COOH$, $NH(CH_2)_2N(CH_3)_2$, $NH(CH_2)_2NH_2$, $NH(CH_2)_3NH_2$, $NH(CH_2)_2OCH_3$, $NHCH(CH_3)_2$,

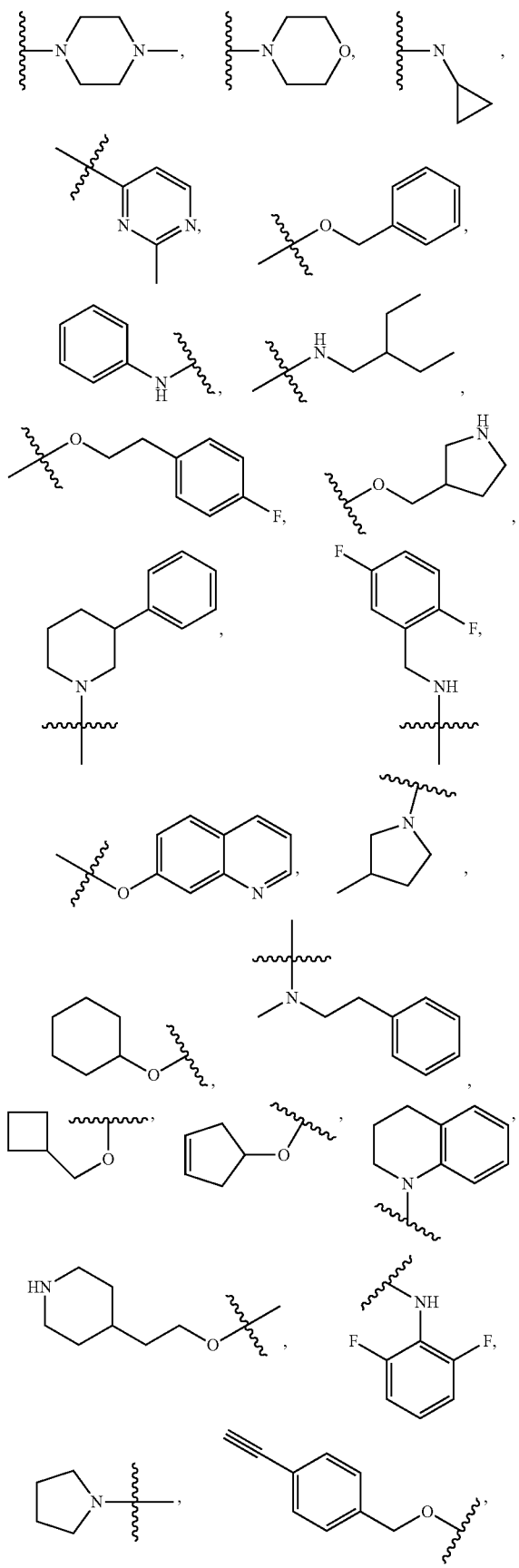

-continued

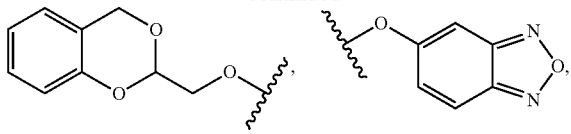 [SMILES: *OCC1OCc2ccccc2O1 ; *Oc1ccc2nonc2c1]

or CO₂H.

In some embodiments, R₂ is NH₂, or NHCH₂CH₂CH₃.

In some embodiments, n is 1. In some embodiments, p is 0. In some embodiments, p is 1.

In some embodiments, in the compound of formula Ia-i-1, one or more hydrogen atoms may be replaced by a deuterium atom.

In some embodiments, the compounds of formula Ia-i-1 or a pharmaceutically acceptable salt thereof is a compound of formula Ia-i-2

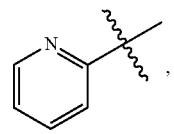

Ia-i-2 or a pharmaceutically acceptable salt thereof, wherein, independently for each occurrence:

Ring B is a pyridinyl;

R₁ is halo; CN; NRR; $C_1$-$C_6$ alkyl or $C_1$-$C_6$ fluoroalkyl; $C_3$-$C_6$ cycloalkyl; $C_1$-$C_8$ alkoxy or $C_1$-$C_8$ fluoroalkoxy; $C_2$-$C_6$ alkenyl; $C_2$-$C_6$ alkynyl; ($C_1$-$C_9$ alkylene)-R₃ wherein up to four CH₂ units are independently replaced with O, CO, S, SO, SO₂ or NR; $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

R$_{1-1}$ is $C_1$-$C_6$ alkyl or $C_1$-$C_6$ fluoroalkyl; $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

R₂ is halo; NRR; CN; CO₂R; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-R₃ wherein up to four CH₂ units are optionally and independently replaced with O, CO, S, SO, SO₂ or NR;

or two R₂ may form a =CH₂ or =O group;

R₃ is H; CF₃; CHF₂; OR; C≡CH; CO₂R; OH; $C_6$-$C_{10}$ aryl, $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or SO₂R;

R is independently H; OH; CO₂H; CO₂$C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, or N; or $C_3$-$C_{10}$ cycloalkyl;

n is 1 or 2; and p is 0, 1, 2, or 3.

In some embodiments, Ring B is

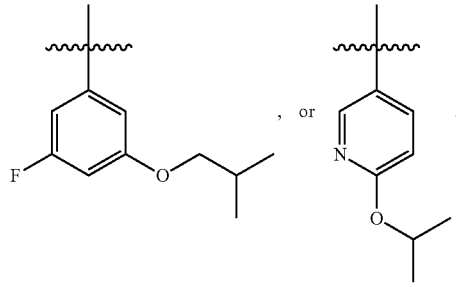

wherein the wavy line ∿ indicates point of attachment of Ring B to the sulfonyl.

In some embodiments, R₁ is independently halo, amino, OH, $C_1$-$C_6$ fluoroalkyl, CN, $C_1$-$C_6$ alkyl, $C_2$-$C_6$ alkenyl, $C_2$-$C_6$ alkynyl, $C_1$-$C_8$ alkoxy or $C_1$-$C_8$ fluoroalkoxy, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring, or a ($C_1$-$C_9$ alkylene)-R₃ wherein up to four CH₂ units are independently replaced with O, CO, S, SO, SO₂ or NR.

In some embodiments, R$_{1-1}$ is $C_1$-$C_6$ alkyl or $C_1$-$C_6$ fluoroalkyl, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring.

In some embodiments, R$_{1-1}$ is tert-butyl,

, or .

In some embodiments, R₁ is CHF₂CH₂(CH₃)N—, (CH₃)₂CHCH₂CH2O—, (CH₃)₃CCH₂CH₂O—, (CH₃)₃COCH₂CH₂O—, (CH₃)₂CHO—, CHF₂CHF₂CH(CH₃)O—, —CF₃, (CH₃CH₂)₂N—, CF₃CH₂CH(CH₃)O—, CH₃O—, CH₃(CH₂)₄O—, CH₃CH₂CH(CH₃)CH(CH₃)O—, CH₃CH₂OCH₂CH₂O—, CH₃CH₂NCH(CH₃)₂, (CH₃)₃CH₂O—, (R)—CH₃NCH(CH₃)(CF₃), CH₃OCH₂CH(CH₂CH₃)O—, (CH₃)₂N—, (S)—CH₃OCH₂CH(CH₃)O—, CH₃O(CH₂)₃O—, CH₃OC(CH₃)₂(CH₂)₂O, CH₃OCH₂CH(CH₃)O, CH₃CH(CH₃)CH₂CH(CH₃)O—, (CH₃)₃CCH(CH₃)O, ((CH₃)₂CH)₂CHO—, CH₃CH₂CH₂O, CH₃CH=CHCH₂O—, (S)—CH₃CH₂CH(CH₃)O—, CH₃CH₂O, (CH₃)₂CHNCH₃, (CH₃)₃CCH₂O, (CF₃)₂CHO—, (CH₃)₃CCH(CH₂CH₃)O—, CH₃C≡CCH₂CH₂O, (CH₃)₃CCH₂CH(CH₃)O—, (CH₃)₂C=C(CH₃), CHF₂CH₂O—, CH₃CH₂CH₂NH, (CH₃)₂CHCH(CH₂CH₃)O, ((CH₃)₂CH)₂N, CH₂=CHCH(CH₃)O, CH₂=CHCH₂O—, CH₃CH₂C(CH₃)₂O, (CH₃CH₂)₂CHO, CF₃CH₂O, CH₃C(=CH₂)CH₂O, (CH₃)₃CCH₂CH₂NH, CH₃OCH₂C(CH₃)₂O, (CH₃)₃CCH₂N(CH₃), (CH₃)₂CHCH(CH₃)NH, (CH₃)₂CHO(CH₂)₂O, CH₃CH₂CH₂CH(CH₃)O, CH₃CF₂CH₂O, (CH₃)₃CNH, (R)—CH₃CH₂CH(CH₃)O, CH₃OCH₂CH₂O, (CH₃)₂CHCH₂N(CH₃), CH₃CH₂CH₂CH(CH₃)CH(CH₃)O, CH₃CH₂CH₂O, CH₃CH₂CH₂N(CH₃), (R)—CH₃OCH₂CH(CH₃)O, CF₃CH₂N(CH₃), CH₃CH₂N(CH₃), ((CH₃)₃C)₂CHO, (CH₃CH₂)₂CHN(CH₃), (CH₃)₂CHN(CH₃), CH₃CH₂OCH₂CH(CH₃)O, (CH₃)₃

CCH$_2$NH, CF$_3$CH(CH$_3$)O, CH$_3$CH$_2$NCH(CH$_3$)$_2$, $_{(R)}$—CF$_3$CH(CH$_3$)N(CH$_3$), (CH$_3$)$_2$CHCH(CH$_3$), CH$_3$CH$_2$(CH$_3$)$_2$CHCH$_2$CH$_2$O, (S)—CH$_3$OCH(CH$_3$)CH$_2$O, HOCH(CH$_3$)$_2$CH$_2$CH$_2$NH, CF$_3$CH$_2$CH$_2$O, CF$_3$CH$_2$CH$_2$CH$_2$O, CF$_3$CH═CHCH$_2$O, or CH$_3$CH$_2$CH$_2$CH$_2$CH$_2$NH.

In some embodiments, R$_2$ is halo, CN, amino, OH, C$_1$-C$_6$ alkyl or C$_1$-C$_6$ fluoroalkyl, C$_1$-C$_6$ alkoxy or C$_1$-C$_6$ fluoroalkoxy, C$_3$-C$_{10}$ heterocyclic ring wherein anywhere from 1 to 4 carbon atoms are independently O, S, N, or NR; or a (C$_1$-C$_9$ alkylene)-R$_3$ wherein up to four CH$_2$ units are optionally and independently replaced with O, CO, S, SO, SO$_2$ or NR.

In some embodiments, R$_2$ is Cl, F, OH, CN, NH$_2$, NH(CH$_3$), N(CH$_3$)$_2$, N(CH$_3$)CH$_2$CH$_2$CH$_3$, N(CH$_3$)CH$_2$CH$_2$CH$_2$CH$_3$, NHCH$_2$CH$_2$CH$_3$, CH$_3$, CH$_2$OH, CH$_2$CH$_3$, CH$_2$CH$_2$CH$_3$, ═O, CH$_3$SO$_2$, CH$_3$SO$_2$NH, CF$_3$CONH, CH$_3$CONH, CH$_3$CON(CH$_3$), tBuOCONH, (CH$_3$)$_2$CHOCONH, CH(CH$_3$)$_2$, CHF$_2$, OCH$_3$, OCH$_2$CH$_3$, OCH$_2$CH$_2$CH$_3$, OCH$_2$CH$_2$CH(CH$_3$)$_2$, OCF$_3$, OCHF$_2$, OC(CH$_3$)$_3$, OCH$_2$CH$_2$tBu, NHCH(CH$_3$)(CH$_2$CH$_2$CH$_3$), OCH(CH$_3$)$_2$, NH(CH$_2$)$_2$O(CH$_2$)$_2$CH$_3$, C(O)CH$_3$, CH$_2$CH$_2$OH, CH$_2$NH$_2$, NH(CH$_2$)$_2$OH, N(CH$_3$)CH$_2$CH$_2$CH$_2$OCH$_3$, NHCH$_2$CH$_2$COOH, NH(CH$_2$)$_2$N(CH$_3$)$_2$, NH(CH$_2$)$_2$NH$_2$, NH(CH$_2$)$_3$NH$_2$, NH(CH$_2$)$_2$OCH$_3$, NHCH(CH$_3$)$_2$,

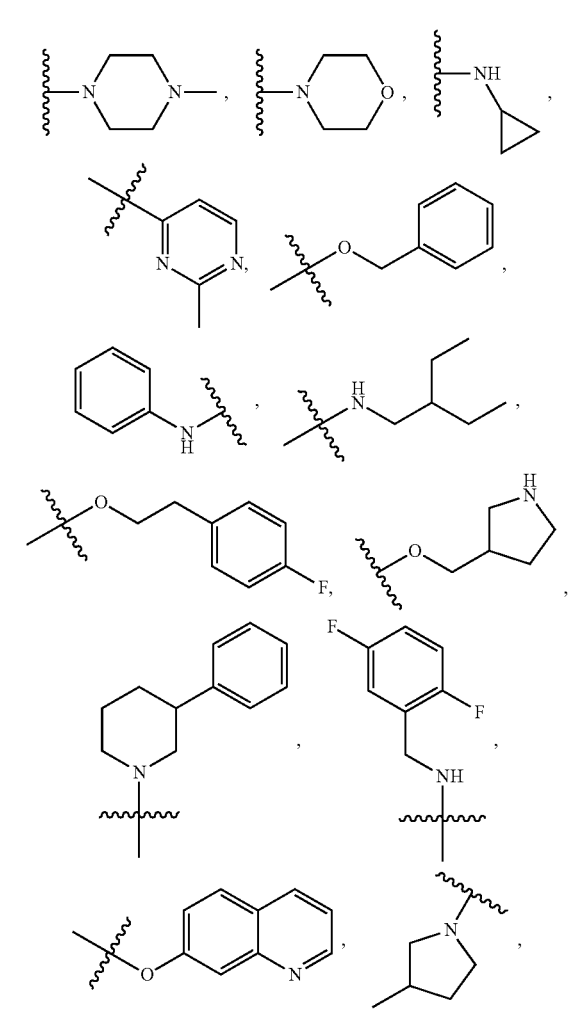

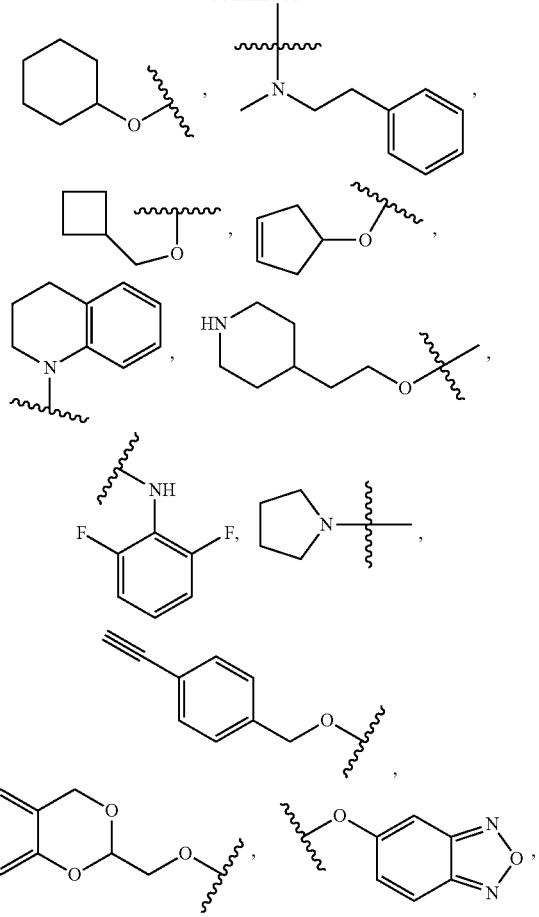

or CO$_2$H.

In some embodiments, R$_2$ is NH$_2$, or NHCH$_2$CH$_2$CH$_3$.

In some embodiments, n is 1. In some embodiments, p is 0. In some embodiments, p is 1.

In some embodiments, in the compound of formula Ia-i-2, one or more hydrogen atoms may be replaced by a deuterium atom In some embodiments, the compounds of formula Ia or a pharmaceutically acceptable salt thereof is a compound of formula Ia-ii

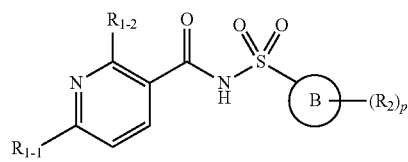

Ia-ii or a pharmaceutically acceptable salt thereof, wherein, independently for each occurrence:
Ring B is a C$_3$-C$_{10}$ cycloalkyl ring; a C$_6$-C$_{10}$ aryl ring; or a C$_3$-C$_{10}$ heteroaryl or C$_3$-C$_{10}$ heterocyclic ring wherein anywhere from 1 to 4 ring atoms are independently O, S, N, or NR;
R$_{1-2}$ is halo; CN; NRR; C$_1$-C$_6$ alkyl or C$_1$-C$_6$ fluoroalkyl; C$_1$-C$_8$ alkoxy or C$_1$-C$_8$ fluoroalkoxy; C$_2$-C$_6$ alkenyl; C$_2$-C$_6$ alkynyl; or (C$_1$-C$_9$ alkylene)-R$_3$ wherein up to four CH$_2$ units are independently replaced with O, CO, S, SO, SO$_2$ or NR;

$R_{1-1}$ is $C_1$-$C_6$ alkyl or $C_1$-$C_6$ fluoroalkyl, $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_2$ is halo; NRR; CN; $CO_2R$; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four $CH_2$ units are optionally and independently replaced with O, CO, S, SO, $SO_2$ or NR;

or two $R_2$ may form a $=CH_2$ or $=O$ group;

$R_3$ is H; $CF_3$; $CHF_2$; OR; C≡CH; $CO_2R$; OH; $C_6$-$C_{10}$ aryl, $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or $SO_2R$;

R is independently H; OH; $CO_2H$; $CO_2C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, or N; or $C_3$-$C_{10}$ cycloalkyl; and p is 0, 1, 2, or 3.

In some embodiments, Ring B is pyridyl, pyridine-2(1H)-one, pyrazole, indole, aza-indole, thiophene, dihydrobenzofuran, thiazole, pyrrolidinone, or quinoline.

In some embodiments, Ring B is

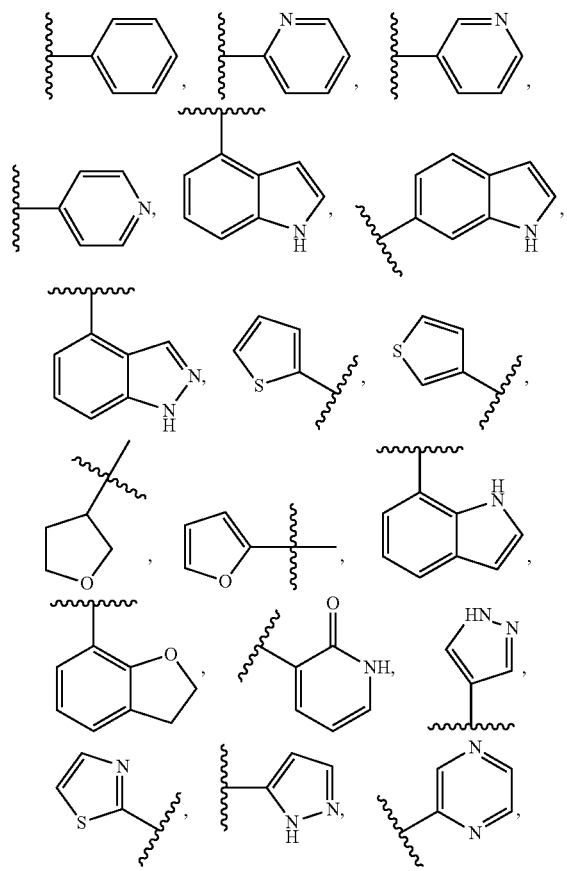

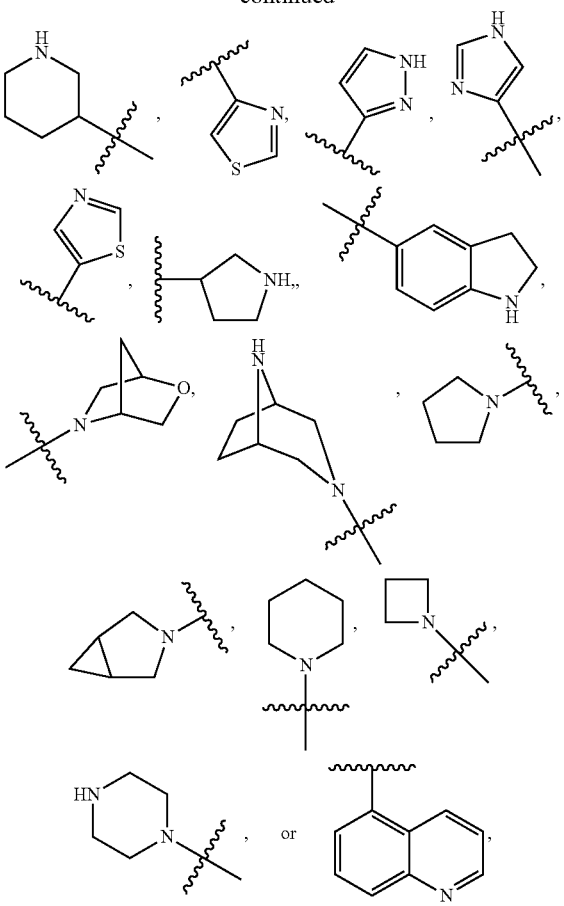

wherein the wavy line indicates point of attachment of Ring B to the sulfonyl ($SO_2$).

In some embodiments, $R_{1-2}$ is independently halo, amino, OH, $C_1$-$C_6$ fluoroalkyl, CN, $C_1$-$C_6$ alkyl, $C_2$-$C_6$ alkenyl, $C_2$-$C_6$ alkynyl, $C_1$-$C_8$ alkoxy or $C_1$-$C_8$ fluoroalkoxy, or a ($C_1$-$C_9$ alkylene)-$R_3$ wherein up to four $CH_2$ units are independently replaced with O, CO, S, SO, $SO_2$ or NR.

In some embodiments, $R_{1-1}$ is $C_1$-$C_6$ alkyl or $C_1$-$C_6$ fluoroalkyl, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring.

In some embodiments, $R_{1-1}$ is tert-butyl,

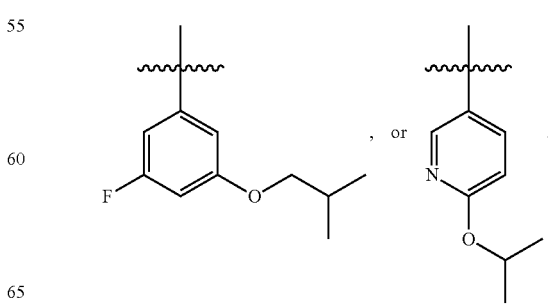

In some embodiments, $R_{1-1}$ is

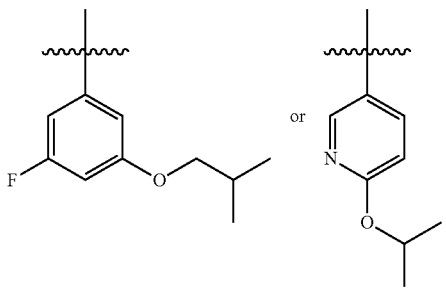

or

In some embodiments, $R_1$-2 is $CHF_2CH_2(CH_3)N—$, $(CH_3)_2CHCH_2CH2O—$, $(CH_3)_3CCH_2CH_2O—$, $(CH_3)_3COCH_2CH_2O—$, $(CH_3)_2CHO—$, $CHF_2CHF_2CH(CH_3)O—$, $—CF_3$, $(CH_3CH_2)_2N—$, $CF_3CH_2CH(CH_3)O—$, $CH_3O—$, $CH_3(CH_2)_4O—$, $CH_3CH_2CH(CH_3)CH(CH_3)O—$, $CH_3CH_2OCH_2CH_2O—$, $CH_3CH_2NCH(CH_3)_2$, $(CH_3)_3CH_2O—$, $(R)—CH_3NCH(CH_3)(CF_3)$, $CH_3OCH_2CH(CH_2CH_3)O—$, $(CH_3)_2N—$, $(S)—CH_3OCH_2CH(CH_3)O—$, $CH_3O(CH_2)_3O—$, $CH_3OC(CH_3)_2(CH_2)_2O$, $CH_3OCH_2CH(CH_3)O$, $CH_3CH(CH_3)CH_2CH(CH_3)O—$, $(CH_3)_3CCH(CH_3)O$, $((CH_3)_2CH)_2CHO—$, $CH_3CH_2CH_2O$, $CH_3CH=CHCH_2O—$, $(S)—CH_3CH_2CH(CH_3)O—$, $CH_3CH_2O$, $(CH_3)_2CHNCH_3$, $(CH_3)_3CCH_2O$, $(CF_3)_2CHO—$, $(CH_3)_3CCH(CH_2CH_3)O$, $CH_3C≡CCH_2CH_2O$, $(CH_3)_3CCH(CH_3)O—$, $(CH_3)_2C=C(CH_3)$, $CHF_2CH_2O—$, $CH_3CH_2CH_2NH$, $(CH_3)_2CHCH(CH_2CH_3)O$, $((CH_3)_2CH)_2N$, $CH_2=CHCH(CH_3)O$, $CH_2=CHCH_2O—$, $CH_3CH_2C(CH_3)_2O$, $(CH_3CH_2)_2CHO—$, $CF_3CH_2O$, $CH_3C(=CH_2)CH_2O$, $(CH_3)_3CCH_2CH_2NH$, $CH_3OCH_2C(CH_3)_2O$, $(CH_3)_3CCH_2N(CH_3)$, $(CH_3)_2CHCH(CH_3)NH$, $(CH_3)_2CHO(CH_2)_2O$, $CH_3CH_2CH_2CH(CH_3)O$, $CH_3CF_2CH_2O$, $(CH_3)_3CNH$, $(R)—CH_3CH_2CH(CH_3)O$, $CH_3OCH_2CH_2O$, $(CH_3)_2CHCH_2N(CH_3)$, $CH_3CH_2CH_2CH(CH_3)CH(CH_3)O$, $CH_3CH_2CH_2O$, $CH_3CH_2CH_2N(CH_3)$, $(R)—CH_3OCH_2CH(CH_3)O$, $CF_3CH_2N(CH_3)$, $CH_3CH_2N(CH_3)$, $((CH_3)_3C)_2CHO$, $(CH_3CH_2)_2CHN(CH_3)$, $(CH_3)_2CHN(CH_3)$, $CH_3CH_2OCH_2CH(CH_3)O$, $(CH_3)_3CCH_2NH$, $CF_3CH(CH_3)O$, $CH_3CH_2NCH(CH_3)_2$, $(R)—CF_3CH(CH_3)N(CH_3)$, $(CH_3)_2CHCH(CH_3)$, $CH_3CH_2(CH_3)_2CHCH_2CH_3$, $(S)—CH_3OCH(CH_3)CH_2O$, $HOCH(CH_3)_2CH_2CH_2NH$, $CF_3CH_2CH_2O$, $CF_3CH_2CH_2CH_2O$, $CF_3CH=CHCH_2O$, or $CH_3CH_2CH_2CH_2CH_2NH$.

In some embodiments, $R_2$ is halo, CN, amino, OH, $C_1-C_6$ alkyl or $C_1-C_6$ fluoroalkyl, $C_1-C_6$ alkoxy or $C_1-C_6$ fluoroalkoxy, $C_3-C_{10}$ heterocyclic ring wherein anywhere from 1 to 4 carbon atoms are independently O, S, N, or NR; or a $(C_1-C_9$ alkylene$)-R_3$ wherein up to four $CH_2$ units are optionally and independently replaced with O, CO, S, SO, $SO_2$ or NR.

In some embodiments, $R_2$ is Cl, F, OH, CN, $NH_2$, $NH(CH_3)$, $N(CH_3)_2$, $N(CH_3)CH_2CH_2CH_3$, $N(CH_3)CH_2CH_2CH_2CH_3$, $NHCH_2CH_2CH_3$, $CH_3$, $CH_2OH$, $CH_2CH_3$, $CH_2CH_2CH_3$, $=O$, $CH_3SO_2$, $CH_3SO_2NH$, $CF_3CONH$, $CH_3CONH$, $CH_3CON(CH_3)$, $tBuOCONH$, $(CH_3)_2CHOCONH$, $CH(CH_3)_2$, $CHF_2$, $OCH_3$, $OCH_2CH_3$, $OCH_2CH_2CH_3$, $OCH_2CH_2CH(CH_3)_2$, $OCF_3$, $OCHF_2$, $OC(CH_3)_3$, $OCH_2CH_2tBu$, $NHCH(CH_3)(CH_2CH_2CH_3)$, $OCH(CH_3)_2$, $NH(CH_2)_2O(CH_2)_2CH_3$, $C(O)CH_3$, $CH_2CH_2OH$, $CH_2NH_2$, $NH(CH_2)_2OH$, $N(CH_3)CH_2CH_2CH_2OCH_3$, $NHCH_2CH_2COOH$, $NH(CH_2)_2N(CH_3)_2$, $NH(CH_2)_2NH_2$, $NH(CH_2)_3NH_2$, $NH(CH_2)_2OCH_3$, $NHCH(CH_3)_2$,

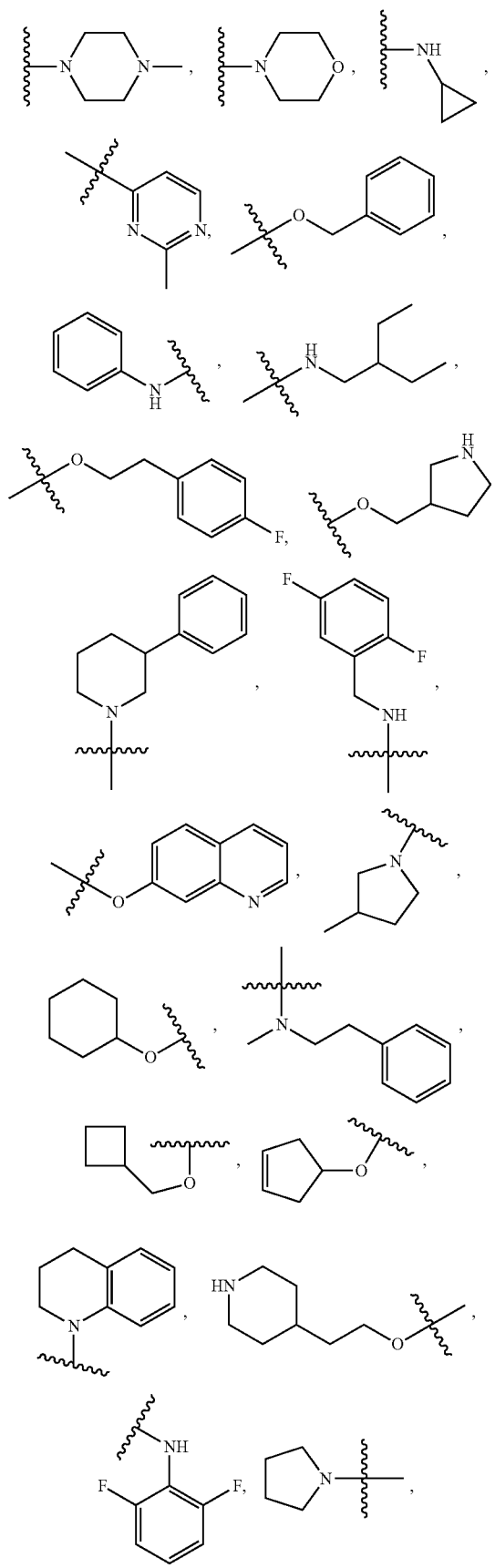

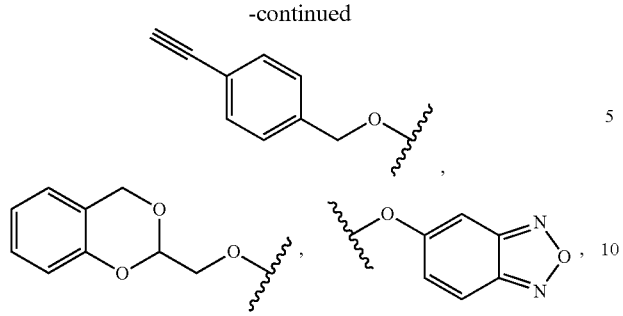

or CO₂H.

In some embodiments, $R_2$ is $NH_2$, or $NHCH_2CH_2CH_3$.

In some embodiments, p is 0. In some embodiments, p is 1.

In some embodiments, in the compound of formula Ia-ii, one or more hydrogen atoms may be replaced by a deuterium atom.

In some embodiments, the compounds of formula Ia-ii or a pharmaceutically acceptable salt thereof is a compound of formula Ia-ii-1

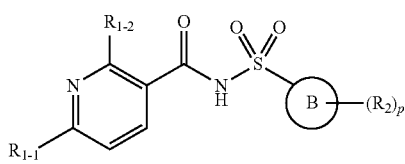

Ia-ii-1 or a pharmaceutically acceptable salt thereof, wherein, independently for each occurrence:

Ring B is a $C_3$-$C_{10}$ heteroaryl or $C_3$-$C_{10}$ heterocyclic ring wherein anywhere from 1 to 4 ring atoms are independently O, S, N, or NR;

$R_{1-2}$ is halo; CN; NRR; $C_1$-$C_6$ alkyl or $C_1$-$C_6$ fluoroalkyl; $C_1$-$C_8$ alkoxy or $C_1$-$C_8$ fluoroalkoxy; $C_2$-$C_6$ alkenyl; $C_2$-$C_6$ alkynyl; or ($C_1$-$C_9$ alkylene)-$R_3$ wherein up to four $CH_2$ units are independently replaced with O, CO, S, SO, $SO_2$ or NR;

$R_{1-1}$ is $C_1$-$C_6$ alkyl or $C_1$-$C_6$ fluoroalkyl, $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_2$ is halo; NRR; CN; $CO_2R$; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four $CH_2$ units are optionally and independently replaced with O, CO, S, SO, $SO_2$ or NR;

or two $R_2$ may form a $=CH_2$ or $=O$ group;

$R_3$ is H; $CF_3$; $CHF_2$; OR; C≡CH; $CO_2R$; OH; $C_6$-$C_{10}$ aryl; $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or $SO_2R$;

R is independently H; OH; $CO_2H$; $CO_2C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, N; or $C_3$-$C_{10}$ cycloalkyl; and p is 0, 1, 2, or 3.

In some embodiments, Ring B is pyridyl, pyridine-2(1H)-one, pyrazole, indole, aza-indole, thiophene, dihydrobenzofuran, thiazole, pyrrolidinone, or quinoline.

In some embodiments, Ring B is

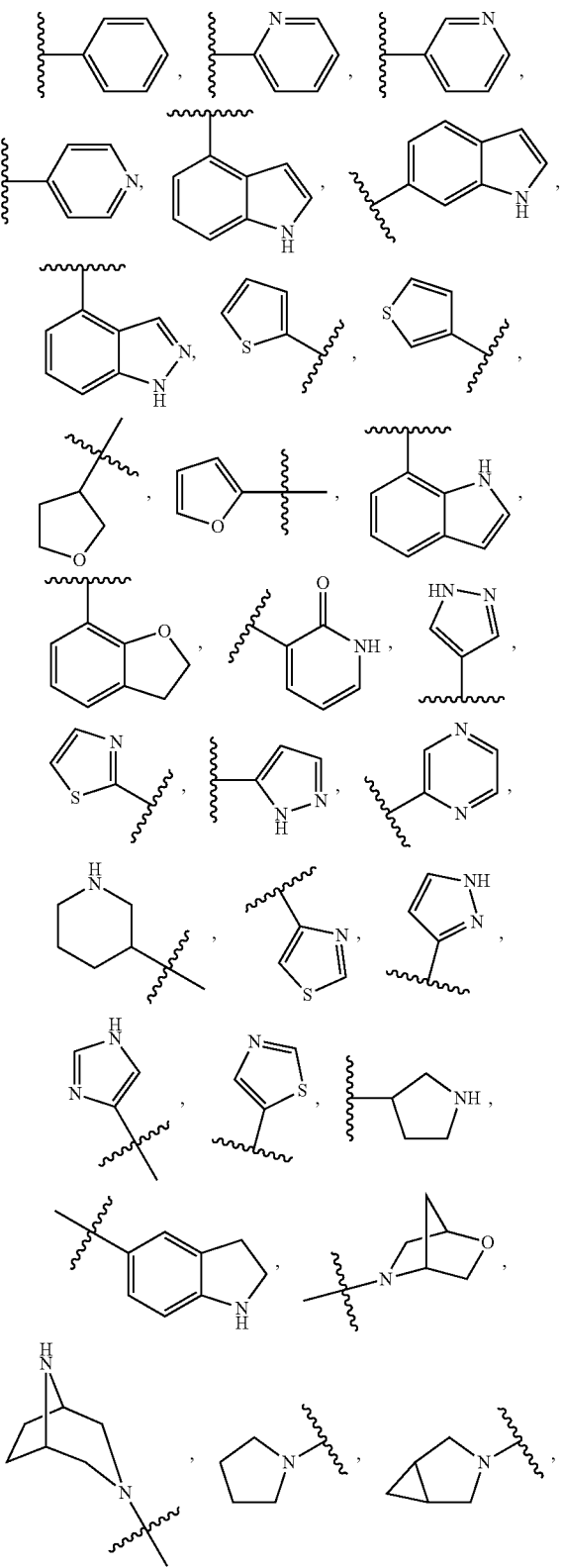

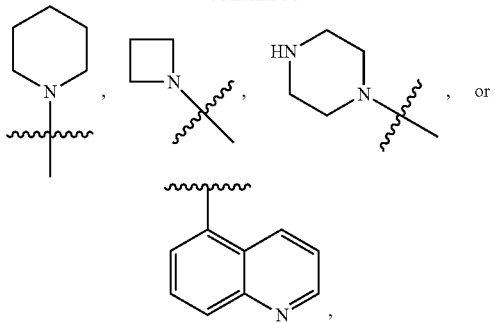

wherein the wavy line ⁓ indicates point of attachment of Ring B to the sulfonyl (SO$_2$).

In some embodiments, R$_{1-2}$ is independently halo, amino, OH, C$_1$-C$_6$ fluoroalkyl, CN, C$_1$-C$_6$ alkyl, C$_2$-C$_6$ alkenyl, C$_2$-C$_6$ alkynyl, C$_1$-C$_8$ alkoxy or C$_1$-C$_5$ fluoroalkoxy, or a (C$_1$-C$_9$ alkylene)-R$_3$ wherein up to four CH$_2$ units are independently replaced with O, CO, SO, SO$_2$ or NR.

In some embodiments, R$_{1-1}$ is C$_1$-C$_6$ alkyl or C$_1$-C$_6$ fluoroalkyl, a phenyl, C$_3$-C$_6$ mono-cycloalkly, mono-C$_4$-C$_6$ heterocyclic ring, 1,2,3,4-tetrahydroisoquinoline, pyridyl, pyrimidine, indole, aza-indole, pyrazole, pyrrole, or thiophene ring.

In some embodiments, R$_{1-1}$ is tert-butyl,

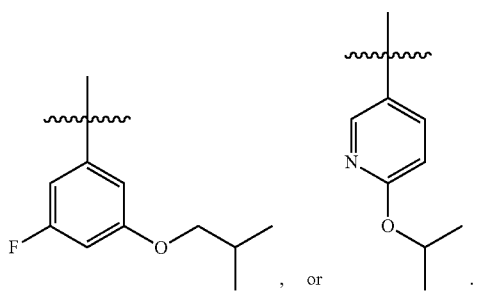 [SMILES: *c1cc(F)cc(OCC(C)C)c1 ; *c1ccc(OC(C)C)nc1]

, or .

In some embodiments, R$_{1-1}$ is

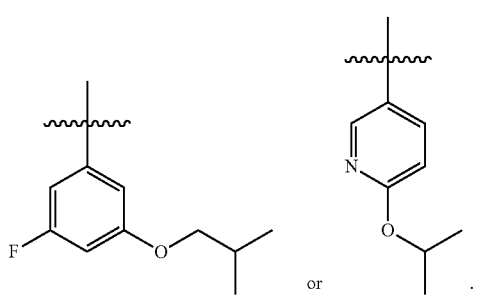 [SMILES: *c1cc(F)cc(OCC(C)C)c1 ; *c1ccc(OC(C)C)nc1]

or .

In some embodiments, R$_{1-2}$ is CHF$_2$CH$_2$(CH$_3$)N—, (CH$_3$)$_2$CHCH$_2$CH2O—, (CH$_3$)$_3$CCH$_2$CH$_2$O—, (CH$_3$)$_3$COCH$_2$CH$_2$O—, (CH$_3$)$_2$CHO—, CHF$_2$CHF$_2$CH(CH$_3$)O—, —CF$_3$, (CH$_3$CH$_2$)$_2$N—, CF$_3$CH$_2$CH(CH$_3$)O—, CH$_3$O—, CH$_3$(CH$_2$)$_4$O—, CH$_3$CH$_2$CH(CH$_3$)CH(CH$_3$)O—, CH$_3$CH$_2$OCH$_2$CH$_2$O—, CH$_3$CH$_2$NCH(CH$_3$)$_2$, (CH$_3$)$_3$CH$_2$O—, (R)—CH$_3$NCH(CH$_3$)(CF$_3$), CH$_3$OCH$_2$CH(CH$_2$CH$_3$)O—, (CH$_3$)$_2$N—, (S)—CH$_3$OCH$_2$CH(CH$_3$)O—, CH$_3$O(CH$_2$)$_3$O—, CH$_3$OC(CH$_3$)$_2$(CH$_2$)$_2$O, CH$_3$OCH$_2$CH(CH$_3$)O, CH$_3$CH(CH$_3$)CH$_2$CH(CH$_3$)O—, (CH$_3$)$_3$CCH (CH$_3$)O, ((CH$_3$)$_2$CH)$_2$CHO—, CH$_3$CH$_2$CH$_2$O, CH$_3$CH═CHCH$_2$O—, (S)—CH$_3$CH$_2$CH(CH$_3$)O—, CH$_3$CH$_2$O, (CH$_3$)$_2$CHNCH$_3$, (CH$_3$)$_3$CCH$_2$O, (CF$_3$)$_2$CHO—, (CH$_3$)$_3$CCH(CH$_2$CH$_3$)O, CH$_3$C≡CCH$_2$CH$_2$O, (CH$_3$)$_3$CCH$_2$CH(CH$_3$)O—, (CH$_3$)$_2$C═C(CH$_3$), CHF$_2$CH$_2$O—, CH$_3$CH$_2$CH$_2$NH, (CH$_3$)$_2$CHCH(CH$_2$CH$_3$)O, ((CH$_3$)$_2$CH)$_2$N, CH$_2$═CHCH(CH$_3$)O, CH$_2$═CHCH$_2$O—, CH$_3$CH$_2$C(CH$_3$)$_2$O, (CH$_3$CH$_2$)$_2$CHO, CF$_3$CH$_2$O, CH$_3$C(═CH$_2$)CH$_2$O, (CH$_3$)$_3$CCH$_2$CH$_2$NH, CH$_3$OCH$_2$C(CH$_3$)$_2$O, (CH$_3$)$_3$CCH$_2$N(CH$_3$), (CH$_3$)$_2$CHCH(CH$_3$)NH, (CH$_3$)$_2$CHO(CH$_2$)$_2$O, CH$_3$CH$_2$CH$_2$CH(CH$_3$)O, CH$_3$CF$_2$CH$_2$O, (CH$_3$)$_3$CNH, (R)—CH$_3$CH$_2$CH(CH$_3$)O, CH$_3$OCH$_2$CH$_2$O, (CH$_3$)$_2$CHCH$_2$N(CH$_3$), CH$_3$CH$_2$CH$_2$CH(CH$_3$)CH(CH$_3$)O, CH$_3$CH$_2$CH$_2$O, CH$_3$CH$_2$CH$_2$N(CH$_3$), (R)—CH$_3$OCH$_2$CH(CH$_3$)O, CF$_3$CH$_2$N(CH$_3$), CH$_3$CH$_2$N(CH$_3$), ((CH$_3$)$_3$C)$_2$CHO, (CH$_3$CH$_2$)$_2$CHN(CH$_3$), (CH$_3$)$_2$CHN(CH$_3$), CH$_3$CH$_2$OCH$_2$CH(CH$_3$)O, (CH$_3$)$_3$CCH$_2$NH, CF$_3$CH(CH$_3$)O, CH$_3$CH$_2$NCH(CH$_3$)$_2$, (R)—CF$_3$CH(CH$_3$)N(CH$_3$), (CH$_3$)$_2$CHCH(CH$_3$), CH$_3$CH$_2$(CH$_3$)$_2$CHCH$_2$CH$_2$O, (S)—CH$_3$OCH(CH$_3$)CH$_2$O, HOCH(CH$_3$)$_2$CH$_2$CH$_2$NH, CF$_3$CH$_2$CH$_2$O, CF$_3$CH$_2$CH$_2$CH$_2$O, CF$_3$CH═CHCH$_2$O, or CH$_3$CH$_2$CH$_2$CH$_2$NH.

In some embodiments, R$_2$ is halo, CN, amino, OH, C$_1$-C$_6$ alkyl or C$_1$-C$_6$ fluoroalkyl, C$_1$-C$_6$ alkoxy or C$_1$-C$_6$ fluoroalkoxy, C$_3$-C$_{10}$ heterocyclic ring wherein anywhere from 1 to 4 carbon atoms are independently O, S, N, or NR; or a (C$_1$-C$_9$ alkylene)-R$_3$ wherein up to four CH$_2$ units are optionally and independently replaced with O, CO, S, SO, SO$_2$ or NR.

In some embodiments, R$_2$ is Cl, F, OH, CN, NH$_2$, NH(CH$_3$), N(CH$_3$)$_2$, N(CH$_3$)CH$_2$CH$_2$CH$_3$, N(CH$_3$)CH$_2$CH$_2$CH$_2$CH$_3$, NHCH$_2$CH$_2$CH$_3$, CH$_3$, CH$_2$OH, CH$_2$CH$_3$, CH$_2$CH$_2$CH$_3$, ═O, CH$_3$SO$_2$, CH$_3$SO$_2$NH, CF$_3$CONH, CH$_3$CONH, CH$_3$CON(CH$_3$), tBuOCONH, (CH$_3$)$_2$CHOCONH, CH(CH$_3$)$_2$, CHF$_2$, OCH$_3$, OCH$_2$CH$_3$, OCH$_2$CH$_2$CH$_3$, OCH$_2$CH$_2$CH(CH$_3$)$_2$, OCF$_3$, OCHF$_2$, OC(CH$_3$)$_3$, OCH$_2$CH$_2$tBu, NHCH(CH$_3$)(CH$_2$CH$_2$CH$_3$), OCH(CH$_3$)$_2$, NH(CH$_2$)$_2$O(CH$_2$)$_2$CH$_3$, C(O)CH$_3$, CH$_2$CH$_2$OH, CH$_2$NH$_2$, NH(CH$_2$)$_2$OH, N(CH$_3$)CH$_2$CH$_2$CH$_2$OCH$_3$, NHCH$_2$CH$_2$COOH, NH(CH$_2$)$_2$N(CH$_3$)$_2$, NH(CH$_2$)$_2$NH$_2$, NH(CH$_2$)$_3$NH$_2$, NH(CH$_2$)$_2$OCH$_3$, NHCH(CH$_3$)$_2$,

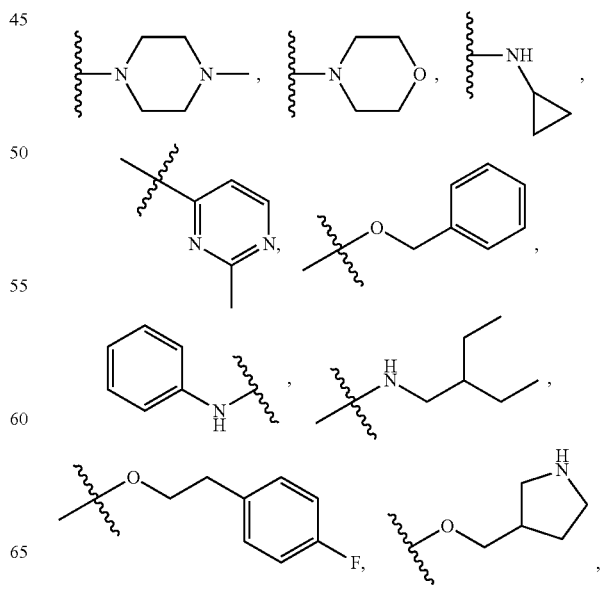

-continued

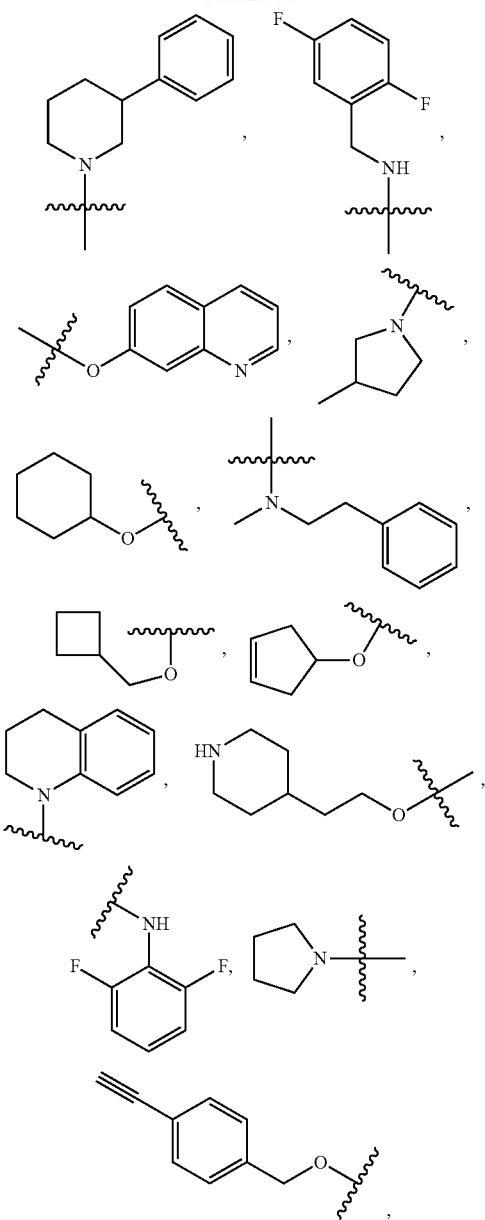

or CO₂H.

In some embodiments, R₂ is NH₂, or NHCH₂CH₂CH₃.

In some embodiments, p is 0. In some embodiments, p is 1.

In some embodiments, in the compound of formula Ia-ii-1, one or more hydrogen atoms may be replaced by a deuterium atom.

In some embodiments, the compounds of formula Ia-ii-1 or a pharmaceutically acceptable salt thereof is a compound of formula Ia-ii-2

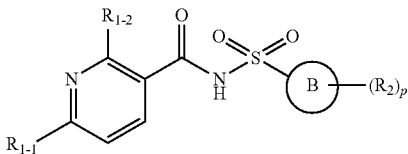
Ia-ii-2 or a pharmaceutically acceptable salt thereof, wherein, independently for each occurrence:

Ring B is a pyridinyl;

$R_{1-2}$ is halo; CN; NRR; $C_1$-$C_6$ alkyl or $C_1$-$C_6$ fluoroalkyl; $C_1$-$C_8$ alkoxy or $C_1$-$C_8$ fluoroalkoxy; $C_2$-$C_6$ alkenyl; $C_2$-$C_6$ alkynyl; or ($C_1$-$C_9$ alkylene)-$R_3$ wherein up to four CH₂ units are independently replaced with O, CO, S, SO, SO₂ or NR;

$R_{1-1}$ is $C_1$-$C_6$ alkyl or $C_1$-$C_6$ fluoroalkyl, $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_2$ is halo; NRR; CN; CO₂R; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four CH₂ units are optionally and independently replaced with O, CO, S, SO, SO₂ or NR;

or two $R_2$ may form a =CH₂ or =O group;

$R_3$ is H; CF₃; CHF₂; OR; C≡CH; CO₂R; OH; $C_6$-$C_{10}$ aryl, $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or SO₂R;

R is independently H; OH; CO₂H; CO₂$C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, or N; or $C_3$-$C_{10}$ cycloalkyl; and p is 0, 1, 2, or 3.

In some embodiments, Ring B is

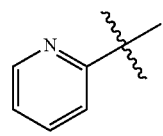

wherein the wavy line indicates point of attachment of Ring B to the sulfonyl (SO₂).

In some embodiments, $R_{1-2}$ is independently halo, amino, OH, $C_1$-$C_6$ fluoroalkyl, CN, $C_1$-$C_6$ alkyl, $C_2$-$C_6$ alkenyl, $C_2$-$C_6$ alkynyl, $C_1$-$C_8$ alkoxy or $C_1$-$C_8$ fluoroalkoxy, or a ($C_1$-$C_9$ alkylene)-$R_3$ wherein up to four CH₂ units are independently replaced with O, CO, S, SO, SO₂ or NR.

In some embodiments, $R_{1-1}$ is $C_1$-$C_6$ alkyl or $C_1$-$C_6$ fluoroalkyl, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring.

In some embodiments, $R_{1-1}$ is tert-butyl,

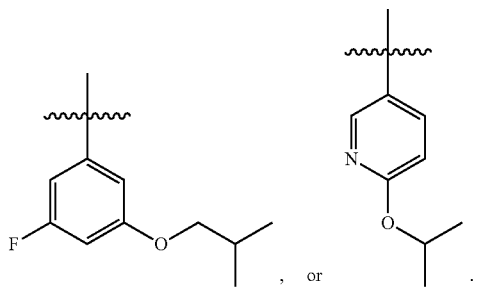 [SMILES: *c1cc(F)cc(OCC(C)C)c1 ; *c1ccc(OC(C)C)nc1]

, or .

In some embodiments, $R_{1-1}$ is

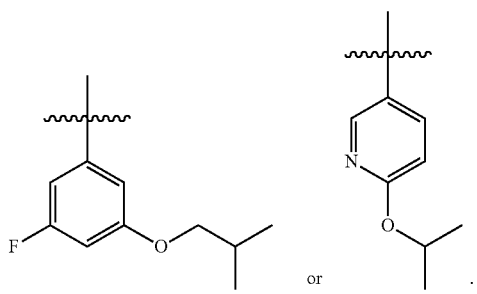 [SMILES: *c1cc(F)cc(OCC(C)C)c1 ; *c1ccc(OC(C)C)nc1]

or .

In some embodiments, $R_{1-2}$ is $CHF_2CH_2(CH_3)N—$, $(CH_3)_2CHCH_2CH_2O—$, $(CH_3)_3CCH_2CH_2O—$, $(CH_3)_3COCH_2CH_2O—$, $(CH_3)_2CHO—$, $CHF_2CHF_2CH(CH_3)O—$, $—CF_3$, $(CH_3CH_2)_2N—$, $CF_3CH_2CH(CH_3)O—$, $CH_3O—$, $CH_3(CH_2)_4O—$, $CH_3CH_2CH(CH_3)CH(CH_3)O—$, $CH_3CH_2OCH_2CH_2O—$, $CH_3CH_2NCH(CH_3)_2$, $(CH_3)_3CH_2O—$, $(R)—CH_3NCH(CH_3)(CF_3)$, $CH_3OCH_2CH(CH_2CH_3)O—$, $(CH_3)_2N—$, $(S)—CH_3OCH_2CH(CH_3)O—$, $CH_3O(CH_2)_3O—$, $CH_3OC(CH_3)_2(CH_2)_2O$, $CH_3OCH_2CH(CH_3)O$, $CH_3CH(CH_3)CH_2CH(CH_3)O—$, $(CH_3)_3CCH(CH_3)O$, $((CH_3)_2CH)_2CHO—$, $CH_3CH_2CH_2O$, $CH_3CH=CHCH_2O—$, $(S)—CH_3CH_2CH(CH_3)O—$, $CH_3CH_2O$, $(CH_3)_2CHNCH_3$, $(CH_3)_3CCH_2O$, $(CF_3)_2CHO—$, $(CH_3)_3CCH(CH_2CH_3)O$, $CH_3C≡CCH_2CH_2O$, $(CH_3)_3CCH_2CH(CH_3)O—$, $(CH_3)_2C=C(CH_3)$, $CHF_2CH_2O—$, $CH_3CH_2CH_2NH$, $(CH_3)_2CHCH(CH_2CH_3)O$, $((CH_3)_2CH)_2N$, $CH_2=CHCH(CH_3)O$, $CH_2=CHCH_2O—$, $CH_3CH_2C(CH_3)_2O$, $(CH_3CH_2)_2CHO$, $CF_3CH_2O$, $CH_3C(=CH_2)CH_2O$, $(CH_3)_3CCH_2CH_2NH$, $CH_3OCH_2C(CH_3)_2O$, $(CH_3)_3CCH_2N(CH_3)$, $(CH_3)_2CHCH(CH_3)NH$, $(CH_3)_2CHO(CH_2)_2O$, $CH_3CH_2CH_2CH(CH_3)O$, $CH_3CF_2CH_2O$, $(CH_3)_3CNH$, $(R)—CH_3CH_2CH(CH_3)O$, $CH_3OCH_2CH_2O$, $(CH_3)_2CHCH_2N(CH_3)$, $CH_3CH_2CH_2CH(CH_3)CH(CH_3)O$, $CH_3CH_2CH_2CH_2O$, $CH_3CH_2CH_2N(CH_3)$, $(R)—CH_3OCH_2CH(CH_3)O$, $CF_3CH_2N(CH_3)$, $CH_3CH_2N(CH_3)$, $((CH_3)_3C)_2CHO$, $(CH_3CH_2)_2CHN(CH_3)$, $(CH_3)_2CHN(CH_3)$, $CH_3CH_2OCH_2CH(CH_3)O$, $(CH_3)_3CCH_2NH$, $CF_3CH(CH_3)O$, $CH_3CH_2NCH(CH_3)_2$, $(R)—CF_3CH(CH_3)N(CH_3)$, $(CH_3)_2CHCH(CH_3)$, $CH_3CH_2(CH_2)_2CHCH_2CH_2O$, $(S)—CH_3OCH(CH_3)CH_2O$, $HOCH(CH_3)_2CH_2CH_2NH$, $CF_3CH_2CH_2O$, $CF_3CH_2CH_2CH_2O$, $CF_3CH=CHCH_2O$, or $CH_3CH_2CH_2CH_2NH$.

In some embodiments, $R_2$ is halo, CN, amino, OH, $C_1$-$C_6$ alkyl or $C_1$-$C_6$ fluoroalkyl, $C_1$-$C_6$ alkoxy or $C_1$-$C_6$ fluoroalkoxy, $C_3$-$C_{10}$ heterocyclic ring wherein anywhere from 1 to 4 carbon atoms are independently O, S, N, or NR; or a ($C_1$-$C_9$ alkylene)-$R_3$ wherein up to four $CH_2$ units are optionally and independently replaced with O, CO, S, SO, $SO_2$ or NR.

In some embodiments, $R_2$ is Cl, F, OH, CN, $NH_2$, $NH(CH_3)$, $N(CH_3)_2$, $N(CH_3)CH_2CH_2CH_3$, $N(CH_3)CH_2CH_2CH_2CH_3$, $NHCH_2CH_2CH_3$, $CH_3$, $CH_2OH$, $CH_2CH_3$, $CH_2CH_2CH_3$, =O, $CH_3SO_2$, $CH_3SO_2NH$, $CF_3CONH$, $CH_3CONH$, $CH_3CON(CH_3)$, tBuOCONH, $(CH_3)_2CHOCONH$, $CH(CH_3)_2$, $CHF_2$, $OCH_3$, $OCH_2CH_3$, $OCH_2CH_2CH_3$, $OCH_2CH(CH_3)_2$, $OCF_3$, $OCHF_2$, $OC(CH_3)_3$, $OCH_2CH_2tBu$, $NHCH(CH_3)(CH_2CH_2CH_3)$, $OCH(CH_3)_2$, $NH(CH_2)_2O(CH_2)_2CH_3$, $C(O)CH_3$, $CH_2CH_2OH$, $CH_2NH_2$, $NH(CH_2)_2OH$, $N(CH_3)CH_2CH_2CH_2OCH_3$, $NHCH_2CH_2COOH$, $NH(CH_2)_2N(CH_3)_2$, $NH(CH_2)_2NH_2$, $NH(CH_2)_3NH_2$, $NH(CH_2)_2OCH_3$, $NHCH(CH_3)_2$,

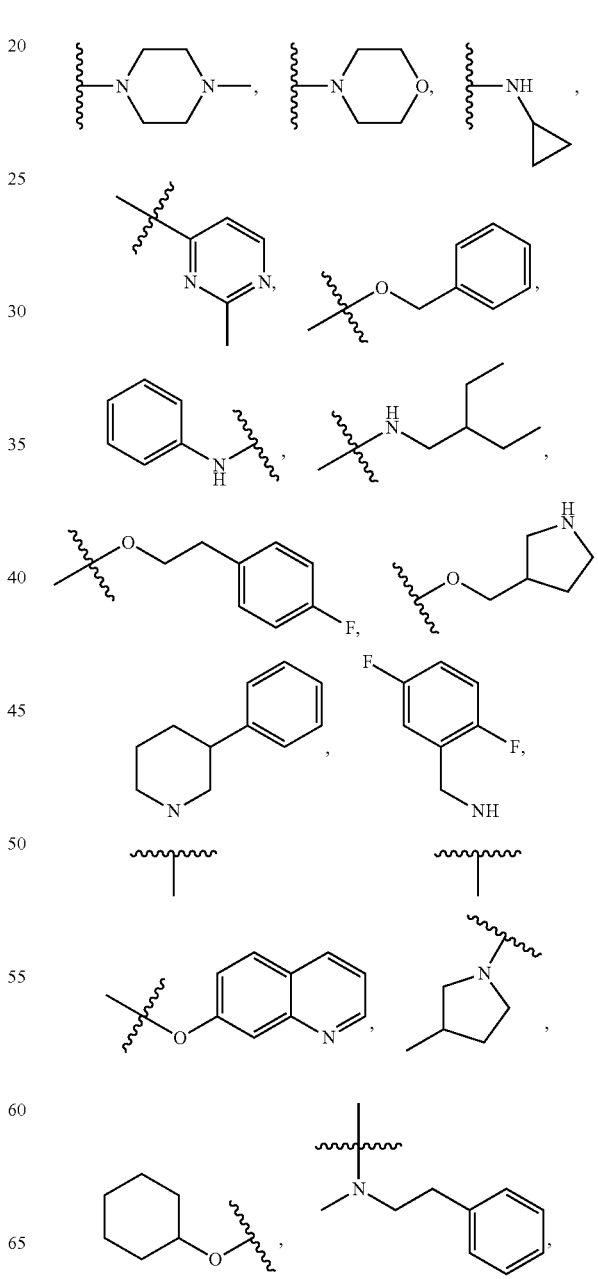

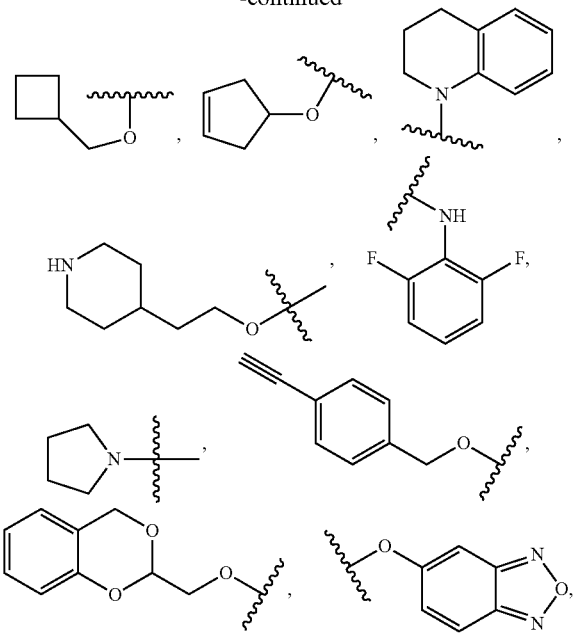

or CO$_2$H.

In some embodiments, R$_2$ is NH$_2$, or NHCH$_2$CH$_2$CH$_3$.

In some embodiments, p is 0. In some embodiments, p is 1.

In some embodiments, in the compound of formula Ia-ii-2, one or more hydrogen atoms may be replaced by a deuterium atom.

In another embodiment, the present disclosure provides compounds of formulas I to IIa-ii-2 that contain isotope-labelled forms thereof. An isotope-labelled form of a compound of formulas I to IIa-ii-2 is identical to this compound apart from the fact that one or more atoms of the compound have been replaced by an atom or atoms having an atomic mass or mass number which differs from the atomic mass or mass number of the atom which usually occurs in greater natural abundance. Examples of isotopes which are readily commercially available and which can be incorporated into a compound of formulas I to IIa-ii-2 by well-known methods include isotopes of hydrogen, carbon, nitrogen, oxygen, phosphorus, fluorine and chlorine, for example $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl, respectively. A compound of formulas I to IIa-ii-2, a prodrug thereof, or a pharmaceutically acceptable salt of either which contains one or more of the above-mentioned isotopes and/or other iso-topes of other atoms is intended to be part of the present disclosure. An isotope-labelled compound of formulas I to IIa-ii-2 can be used in a number of beneficial ways. For example, an isotope-labelled compound of formula I to IIa-ii-2 into which, for example, a radioisotope, such as $^3$H or $^{14}$C, has been incorporated is suitable for medicament and/or substrate tissue distribution assays. These radioisotopes, i.e. tritium ($^3$H) and carbon-14 ($^{14}$C), are particularly preferred owing to simple preparation and excellent detectability. Incorporation of heavier isotopes, for example deuterium ($^2$H), into a compound of formulas I to IIa-ii-2 has therapeutic advantages owing to the higher metabolic stability of this isotope-labelled compound. Higher metabolic stability translates directly into an increased in vivo half-life or lower dosages, which under most circumstances would represent a preferred embodiment of the present disclosure.

An isotope-labelled compound of formulas I to IIa-ii-2 can usually be prepared by carrying out the procedures disclosed in the synthesis schemes and the related description, in the example part and in the preparation part in the present text, replacing a non-isotope-labelled reactant by a readily available isotope-labelled reactant.

Deuterium ($^2$H) can also be incorporated into a compound of formulas I to IIa-ii-2 for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. If this rate difference is successfully applied to a compound of formulas I to IIa-ii-2 that is susceptible to oxidation, the profile of this compound in vivo can be drastically modified and result in improved pharmacokinetic properties. For a further discussion, see S. L. Harbeson and R. D. Tung, *Deuterium In Drug Discovery and Development*, Ann. Rep. Med. Chem. 2011, 46, 403-417, incorporated in its entirety herein by reference.

The concentration of the isotope(s) (e.g., deuterium) incorporated into the isotope-labelled compounds of the invention may be defined by the isotopic enrichment factor. The term "isotopic enrichment factor" as used herein means the ratio between the isotopic abundance and the natural abundance of a specified isotope. In some embodiments, if a substituent in a compound of the invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In some embodiments, the isotope-labelled compounds of the invention are deuterium ($^2$H)-labelled compounds. In some specific embodiments, the isotope-labelled compounds of Formula I to IIa-ii-2 or pharmaceutically acceptable salts thereof are deuterium ($^2$H)-labelled, wherein one or more hydrogen atoms therein have been replaced by deuterium.

When discovering and developing therapeutic agents, the person skilled in the art attempts to improve pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of formulas I to IIa-ii-2 with improved stability through resistance to such oxidative metabolism. Significant improvements in the pharmacokinetic profiles of compounds of formulas I to IIa-ii-2 are thereby obtained, and can be expressed quantitatively in terms of increases in the in vivo half-life ($t_{1/2}$), concentration at maximum therapeutic effect ($C_{max}$), area under the dose response curve (AUC), and bioavailability; and in terms of reduced clearance, dose and materials costs.

The following is intended to illustrate the above: a compound of formulas I to IIa-ii-2 which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of formulas I to IIa-ii-2 can also be used to achieve a favorable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

In some embodiments, the compound of formula I is selected from Table 1:

TABLE 1

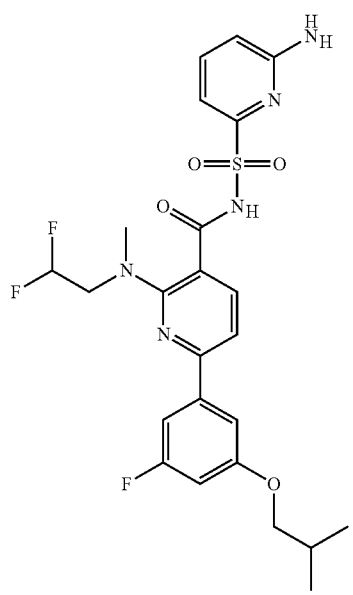

1

TABLE 1-continued

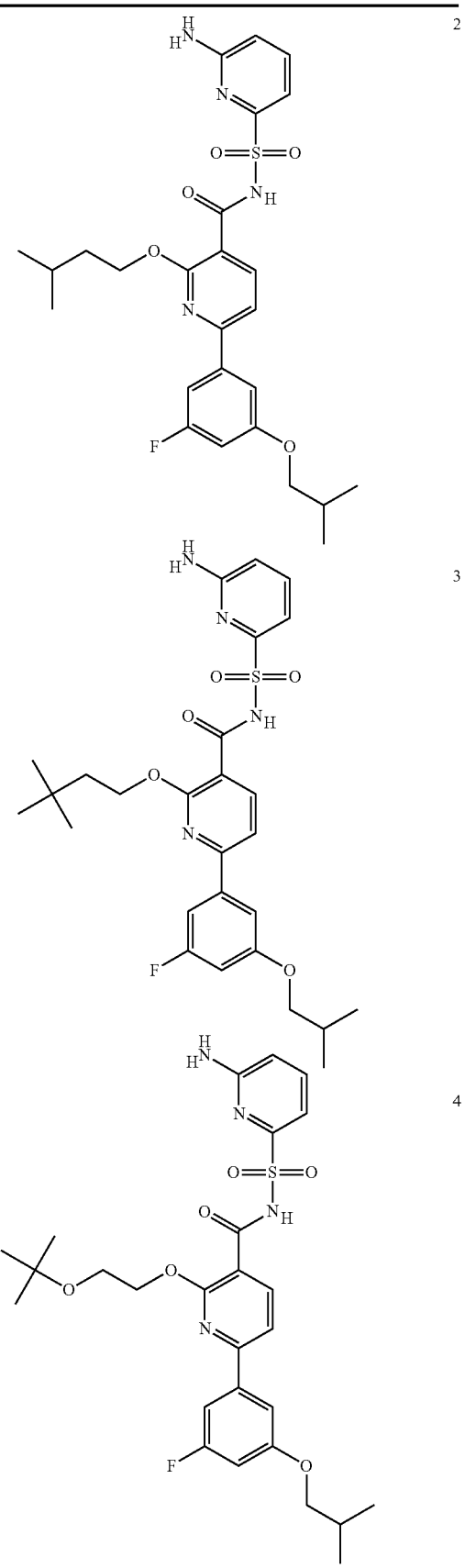

2

3

4

TABLE 1-continued
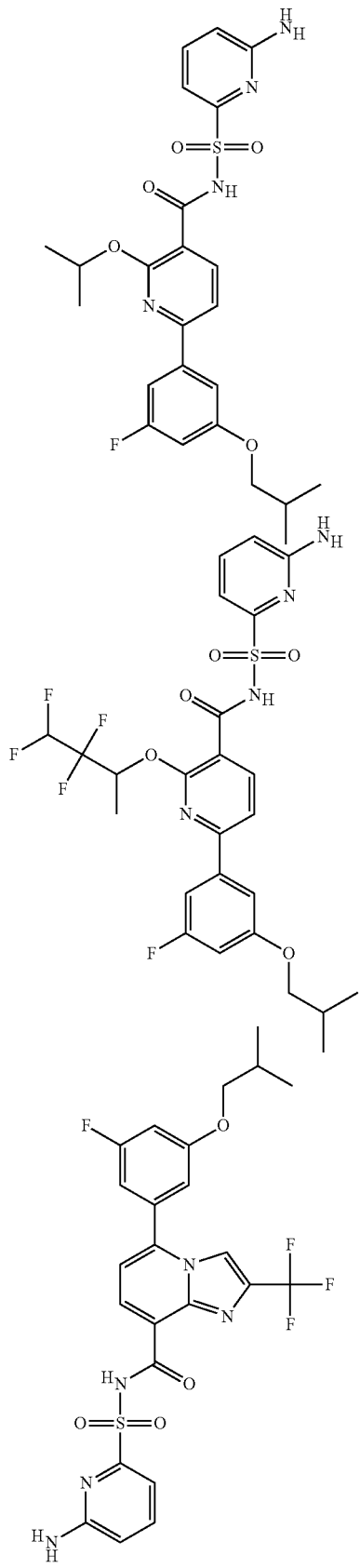
TABLE 1-continued
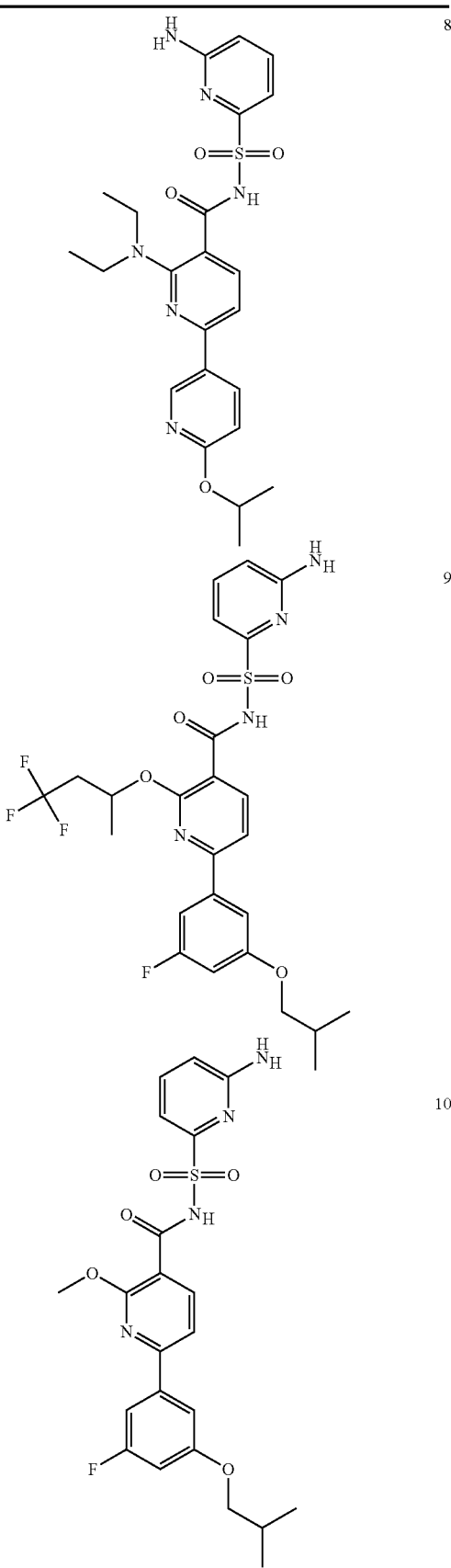

TABLE 1-continued
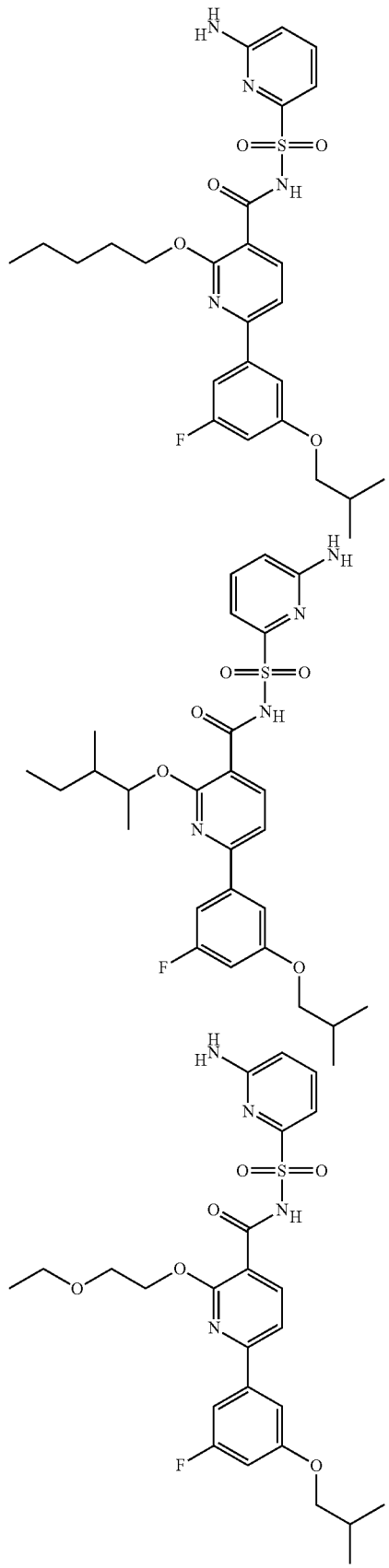
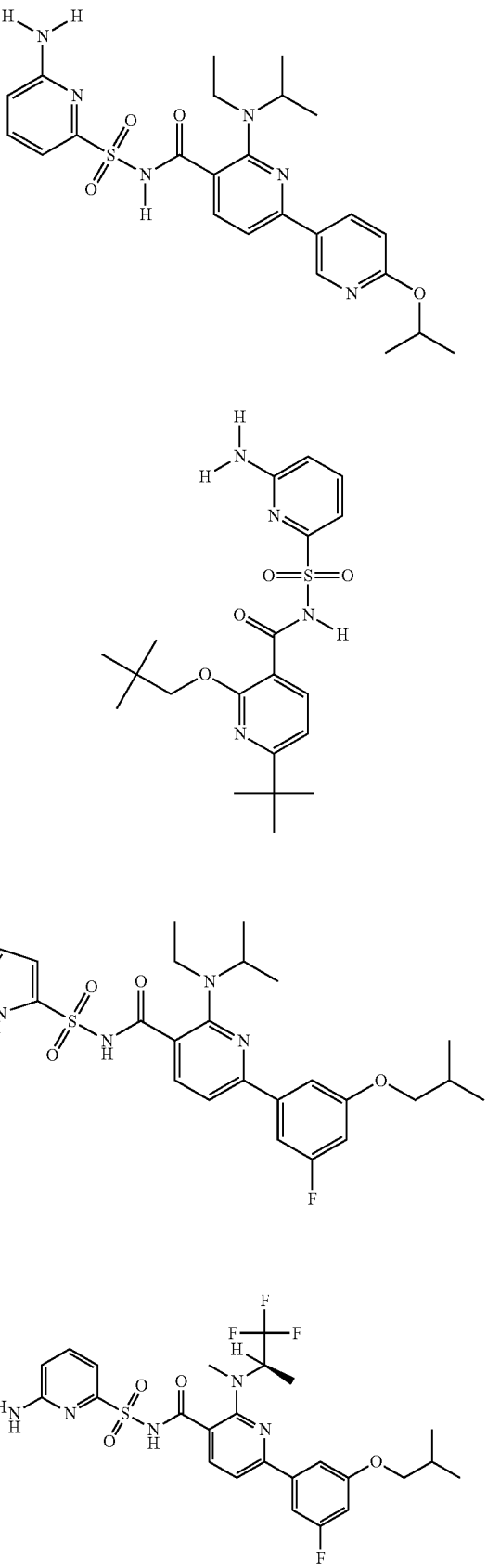

TABLE 1-continued
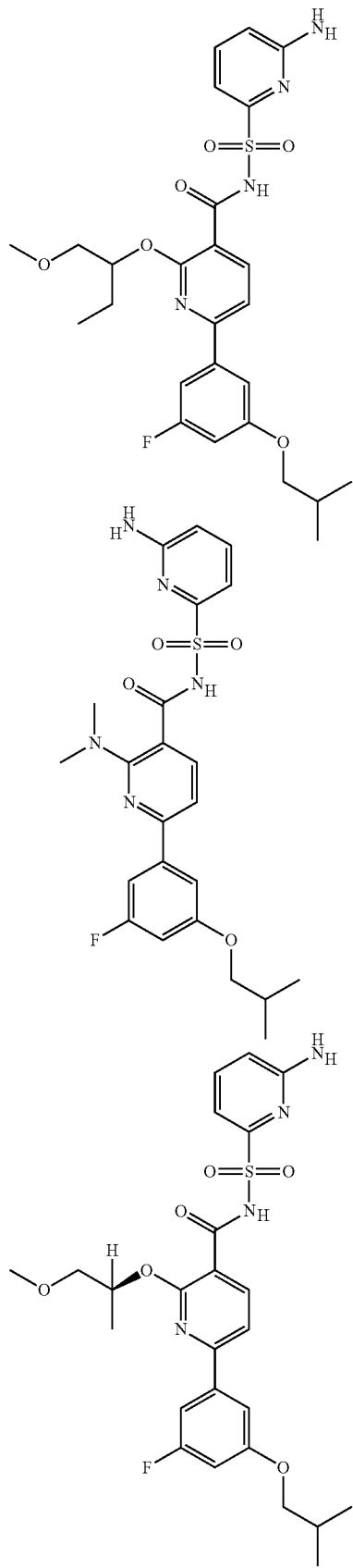
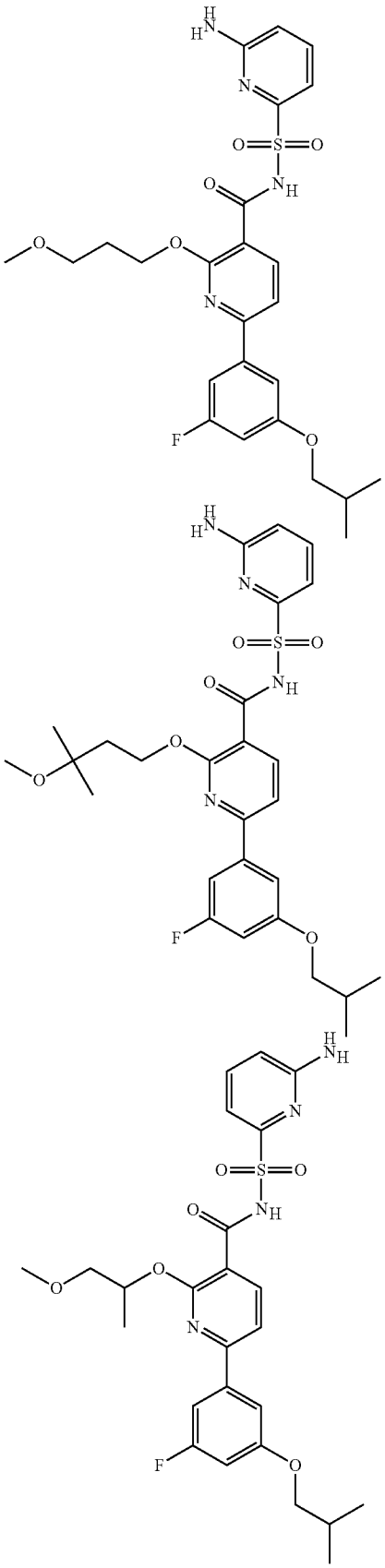

TABLE 1-continued
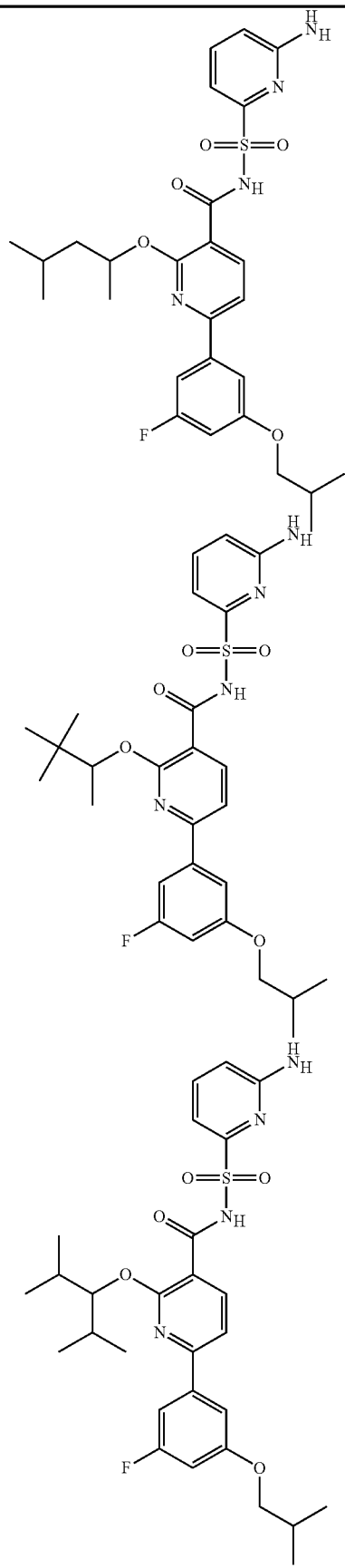
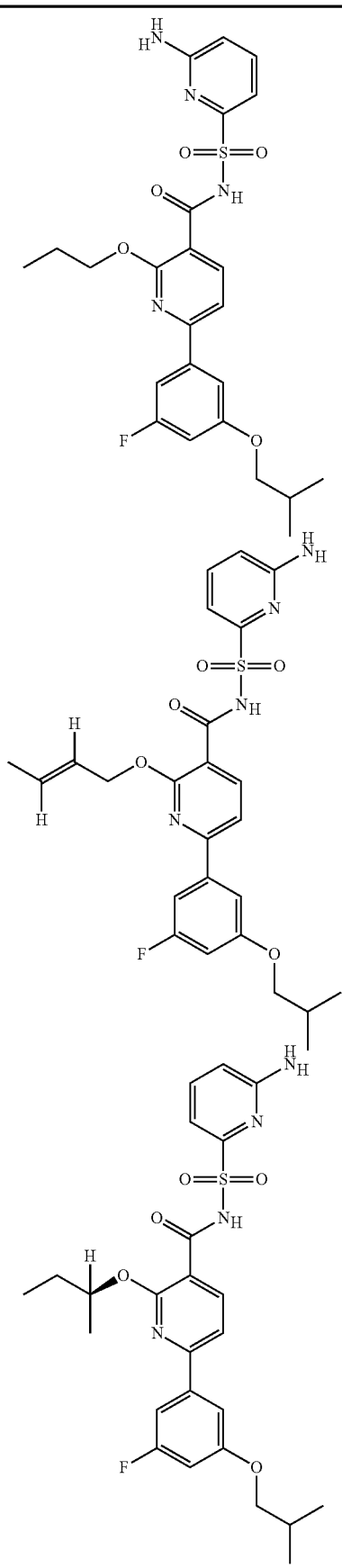

TABLE 1-continued
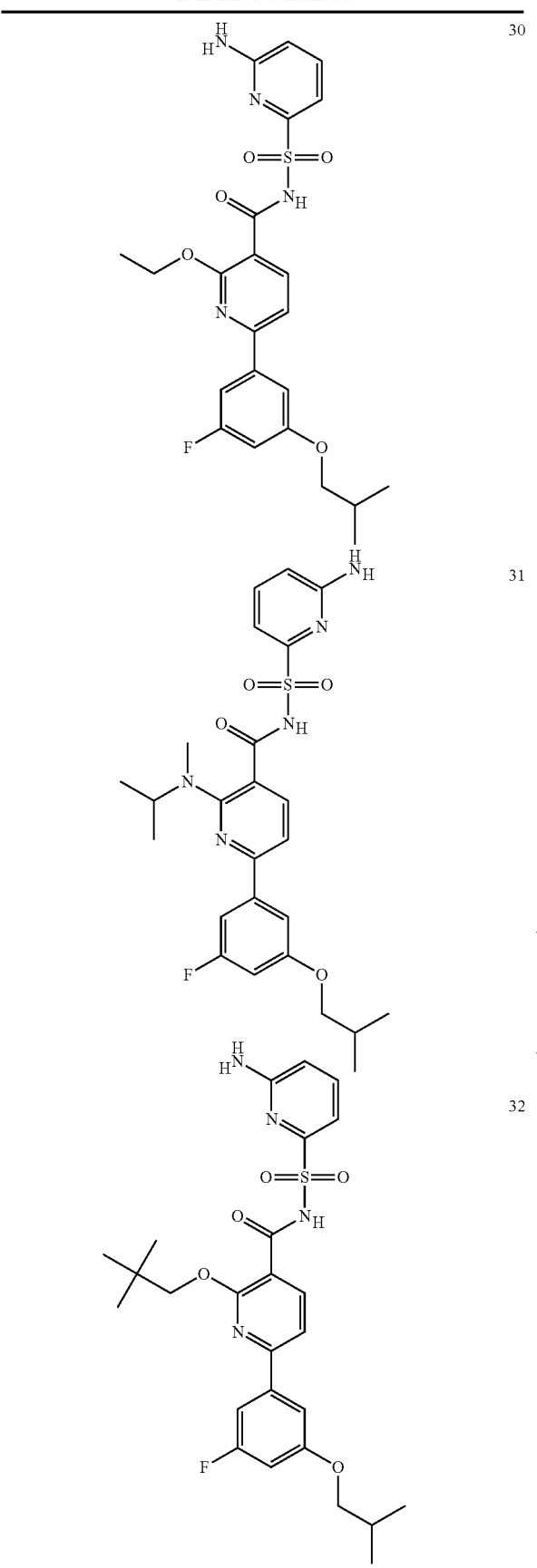
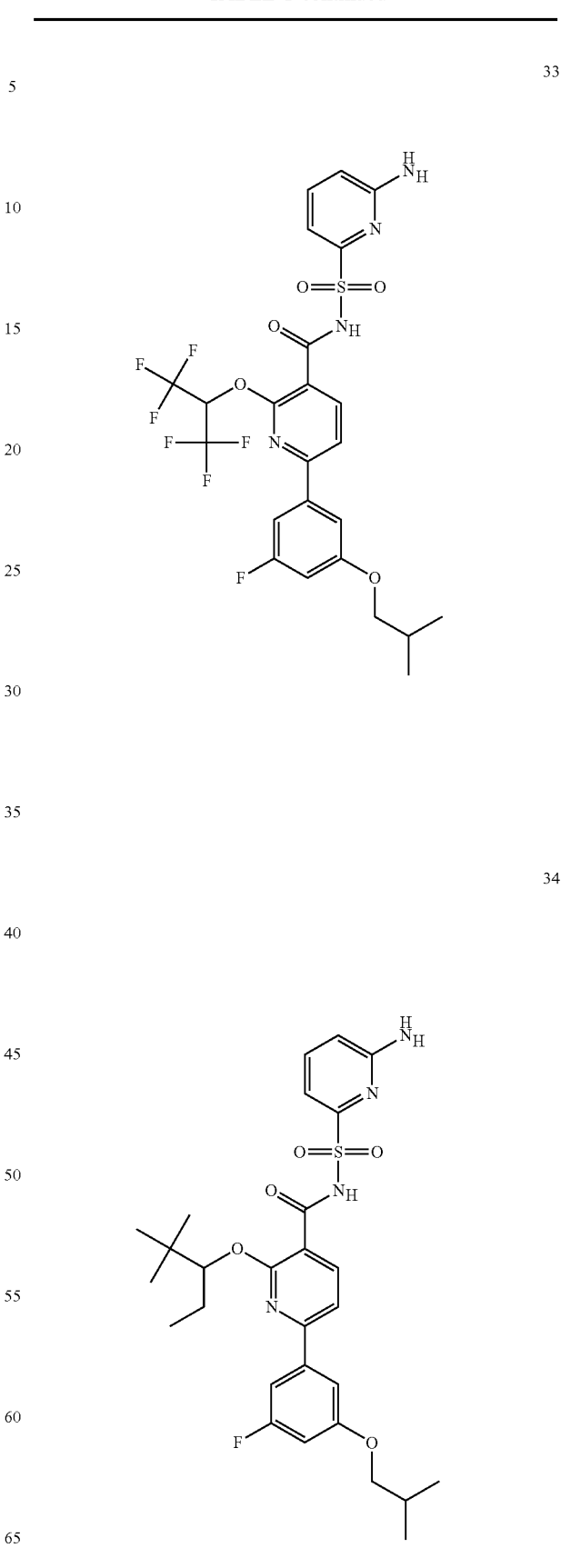

TABLE 1-continued
35
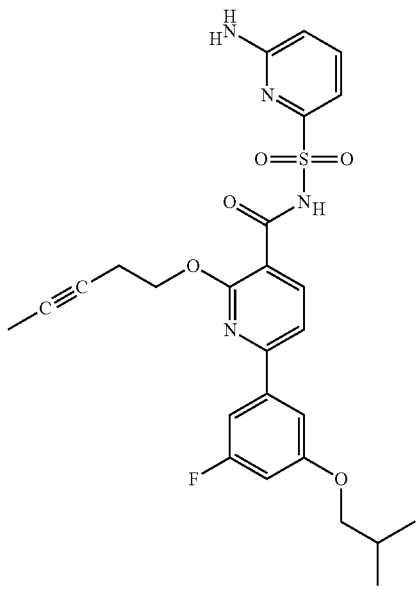
37
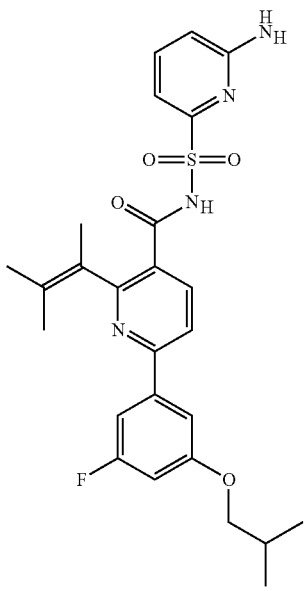
36
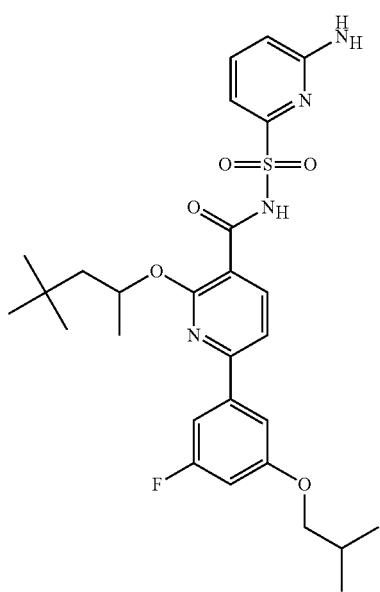
38
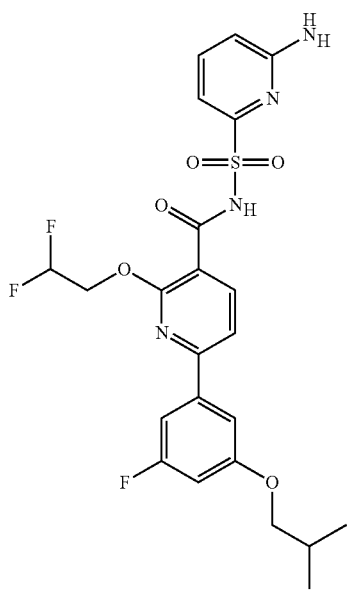

TABLE 1-continued
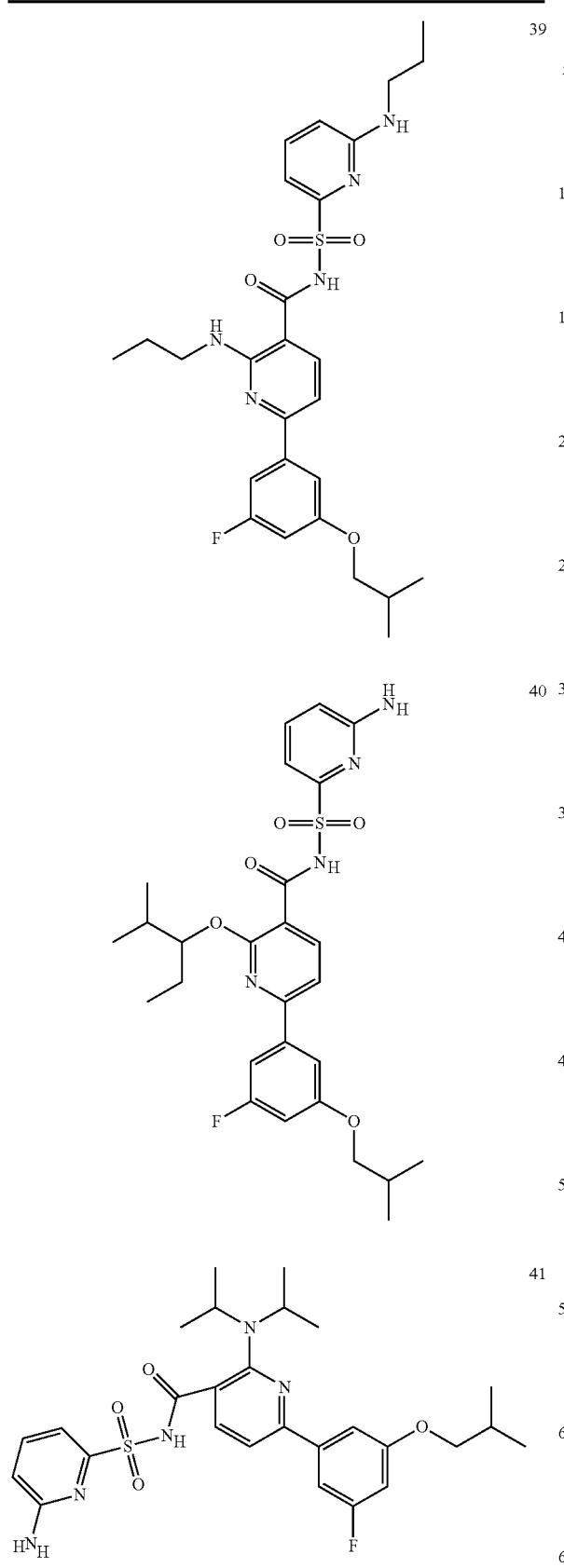
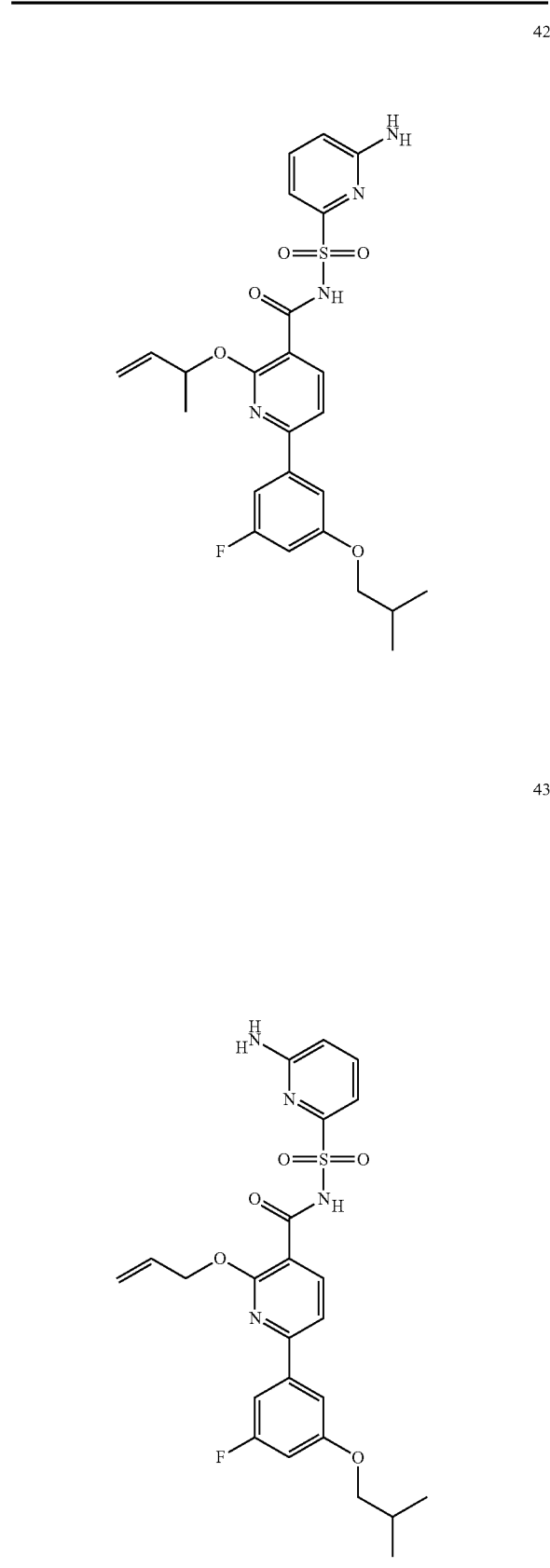

TABLE 1-continued
44
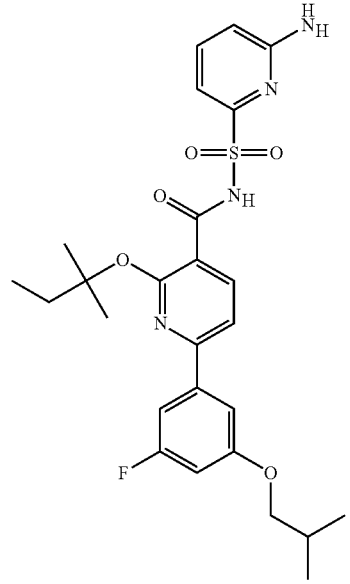
45
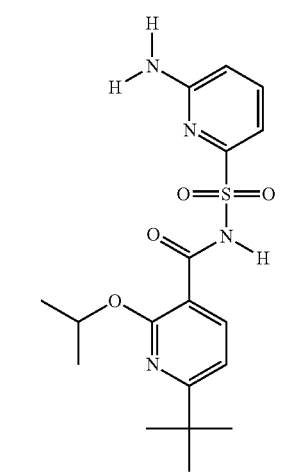 [SMILES: CC(C)Oc1nc(C(C)(C)C)ccc1C(=O)NS(=O)(=O)c1cccc(N)n1]
46
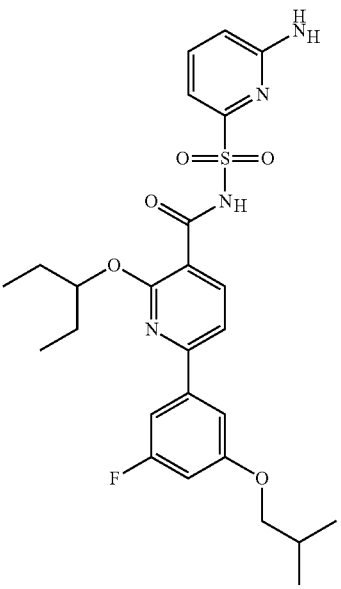
TABLE 1-continued
47
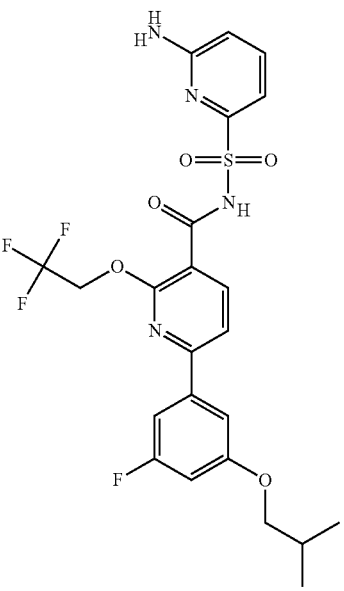
48

TABLE 1-continued
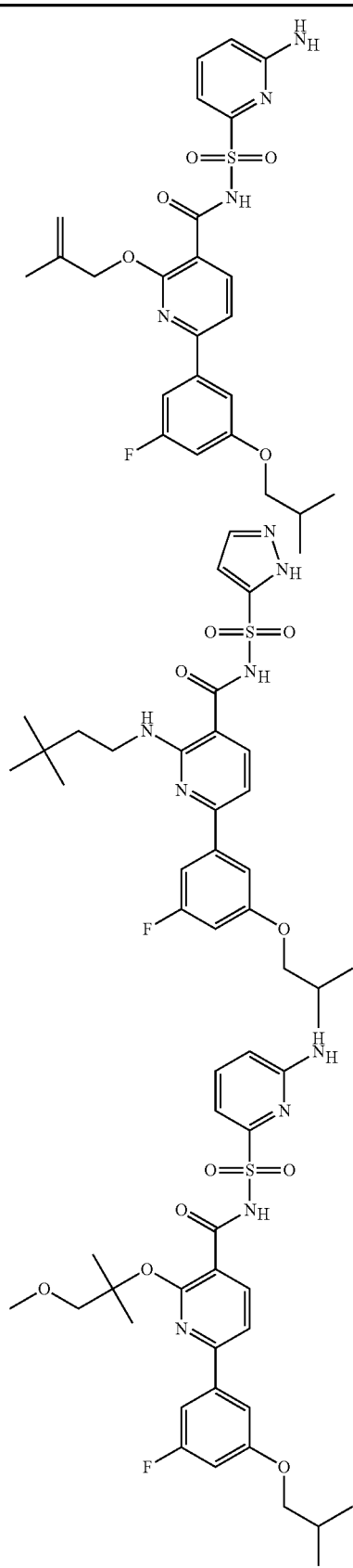
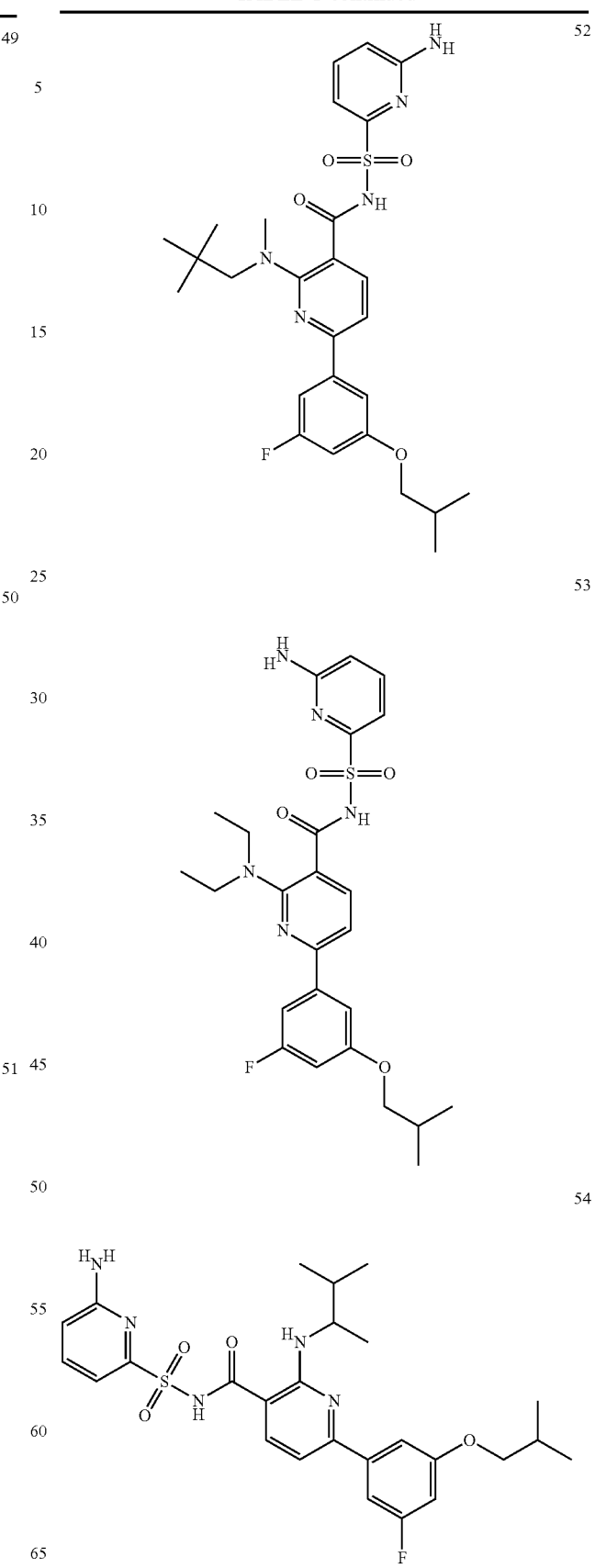

TABLE 1-continued
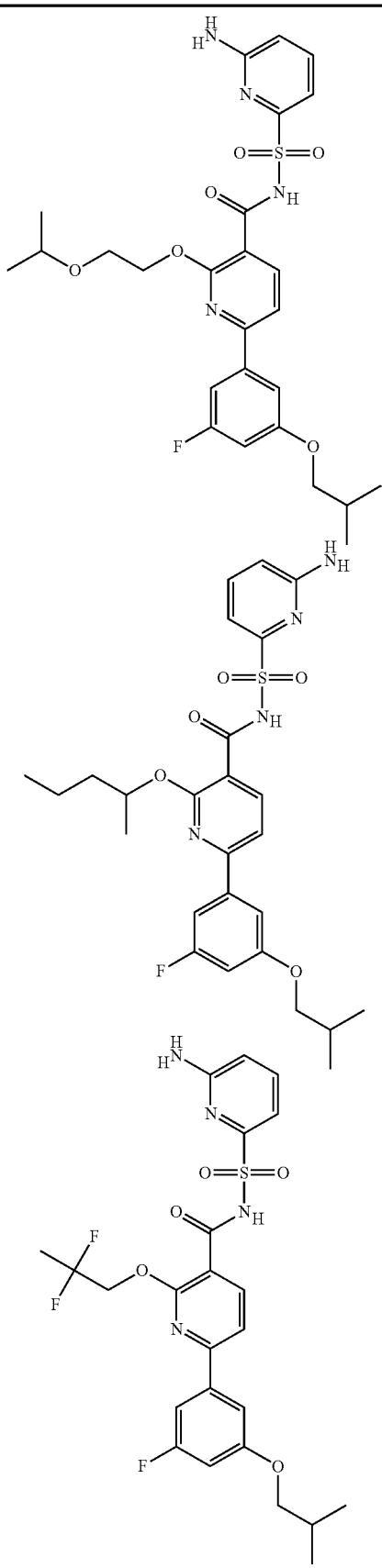
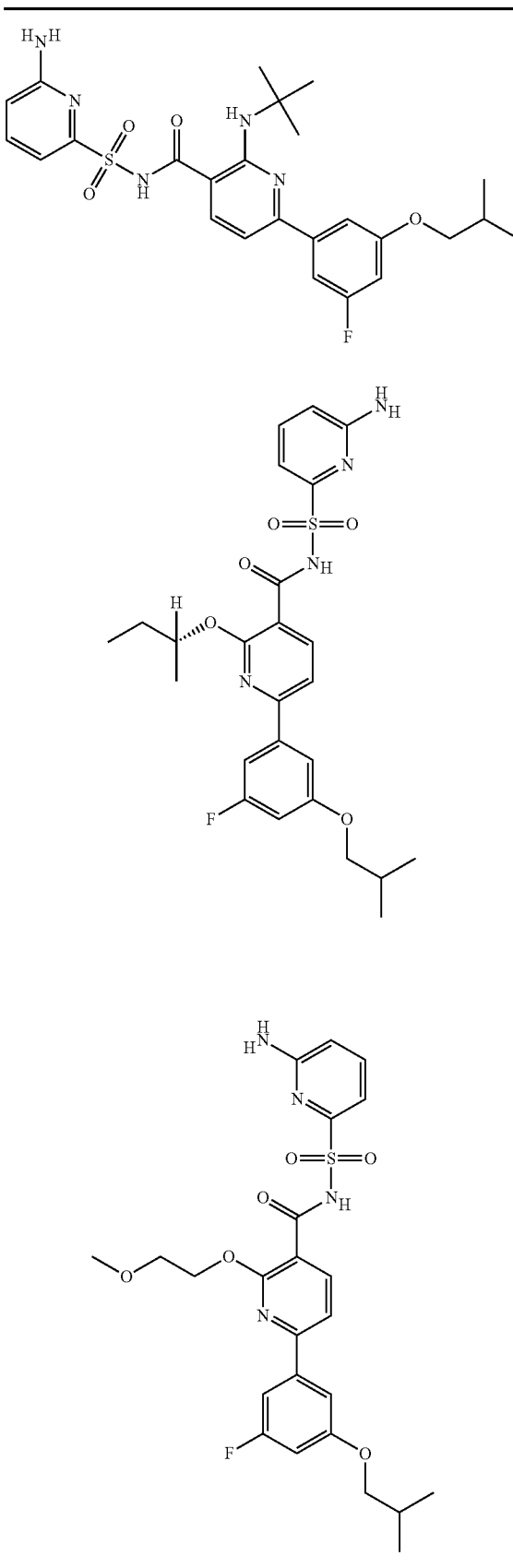

TABLE 1-continued
61
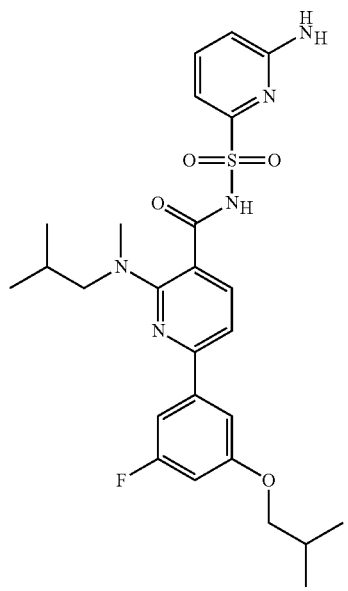
62
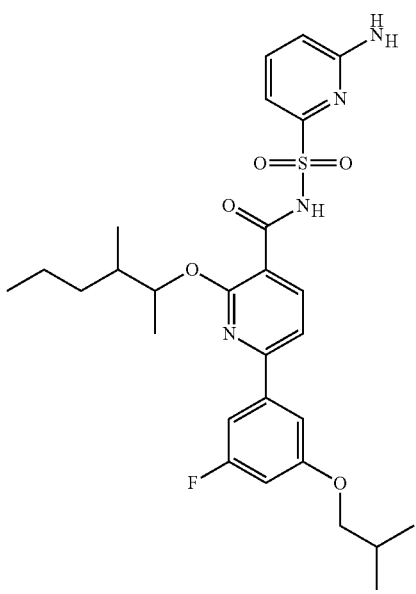
TABLE 1-continued
63
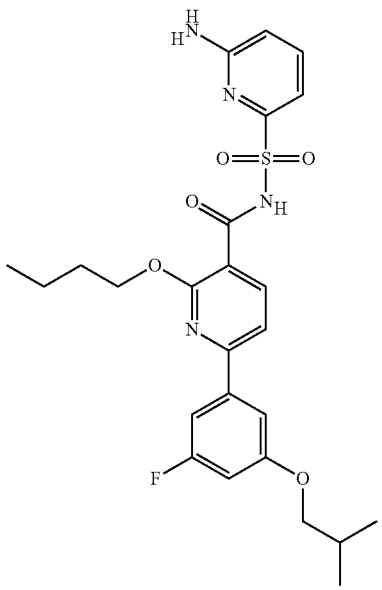
64
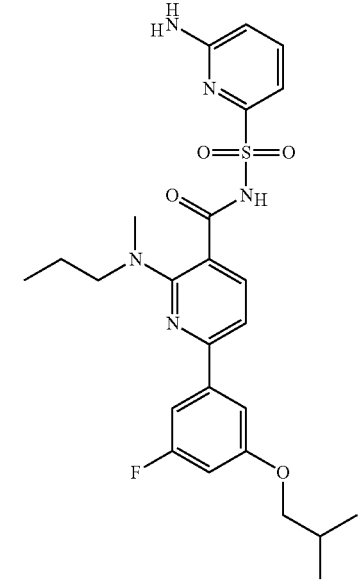

TABLE 1-continued
65
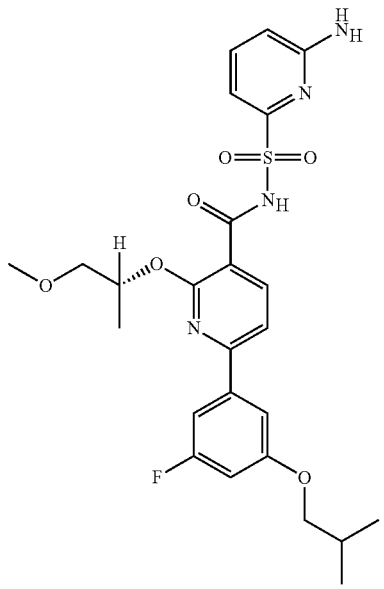
66
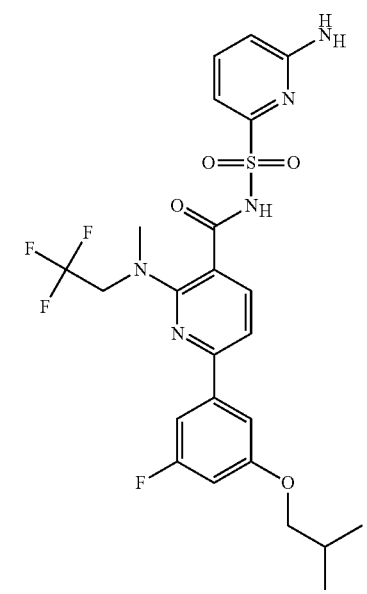
67
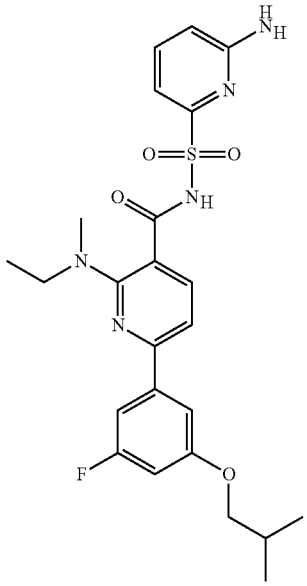
68
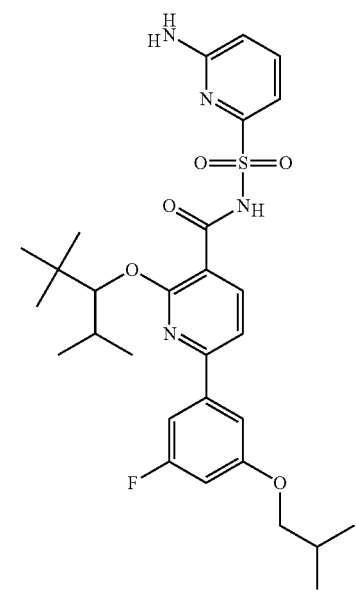
69
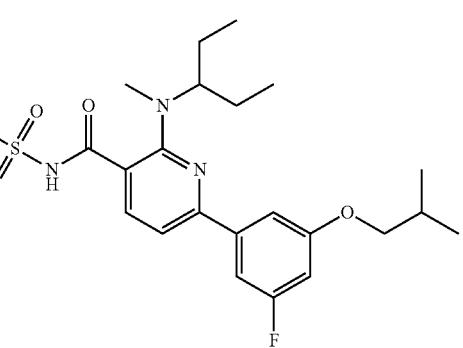

TABLE 1-continued
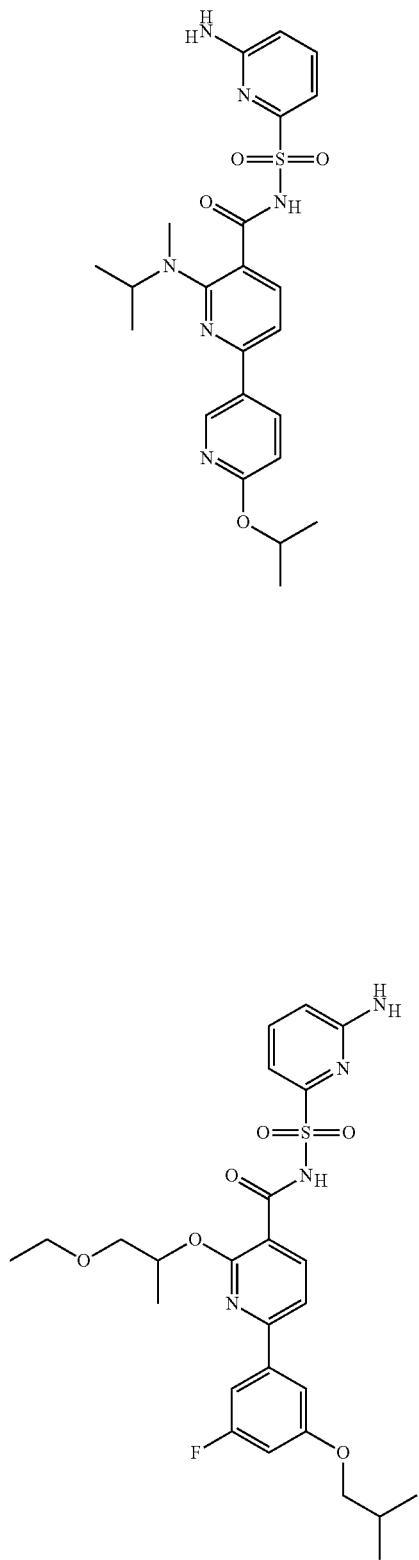
70
71
TABLE 1-continued
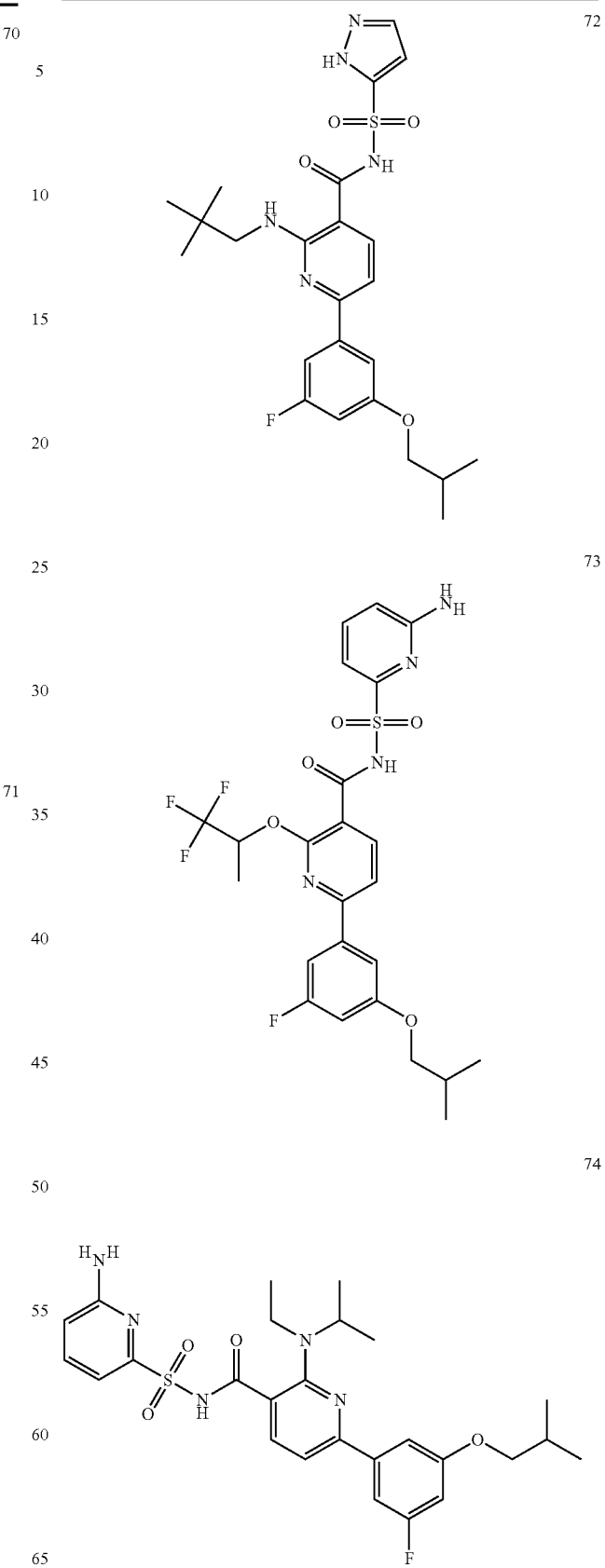
72
73
74

TABLE 1-continued
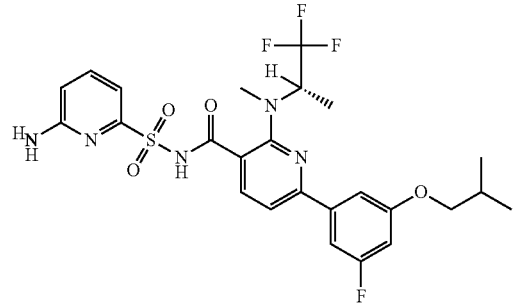
75
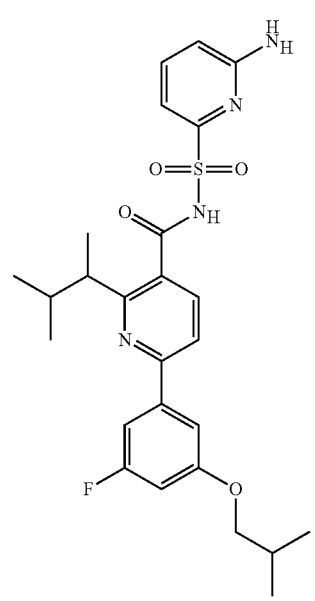
76
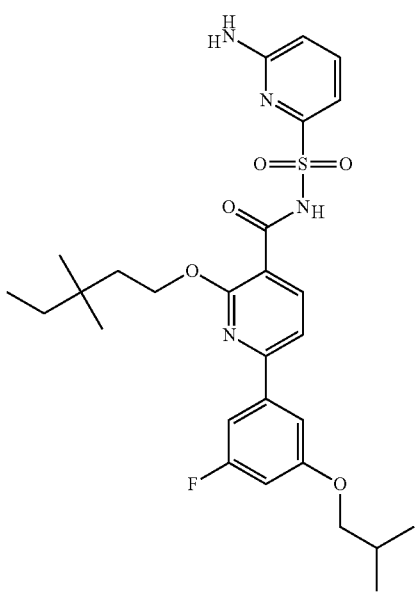
77
TABLE 1-continued
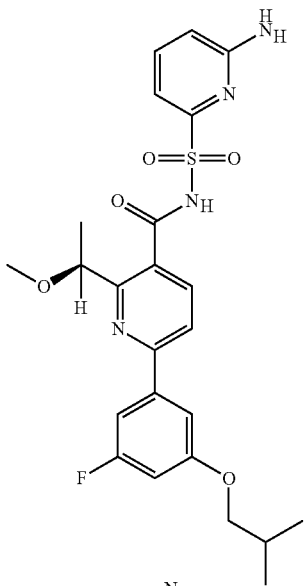
78
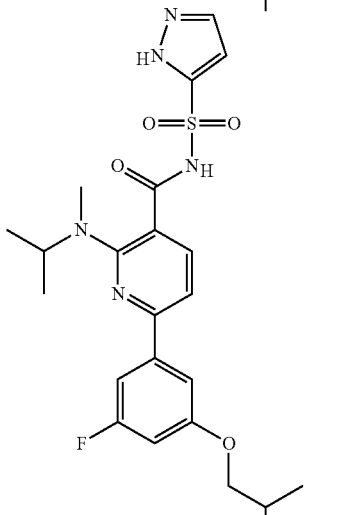
79
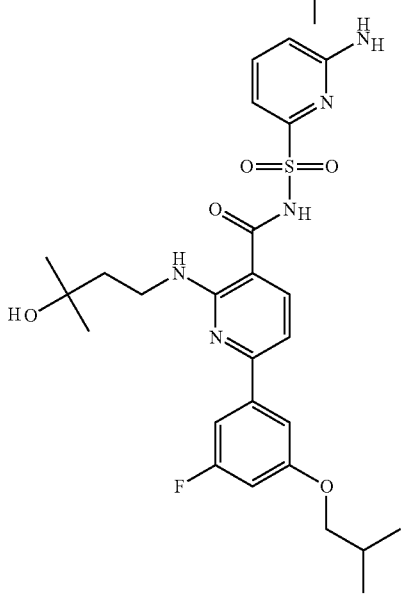
80

TABLE 1-continued
81
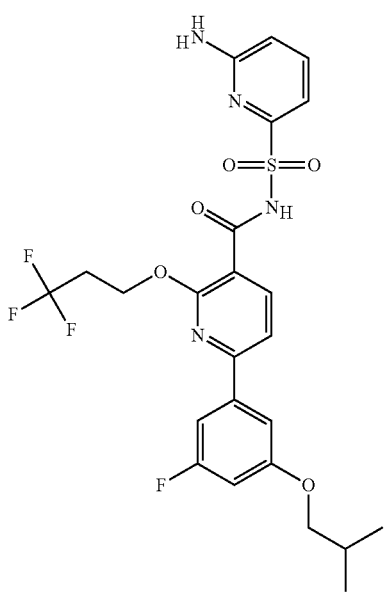
82
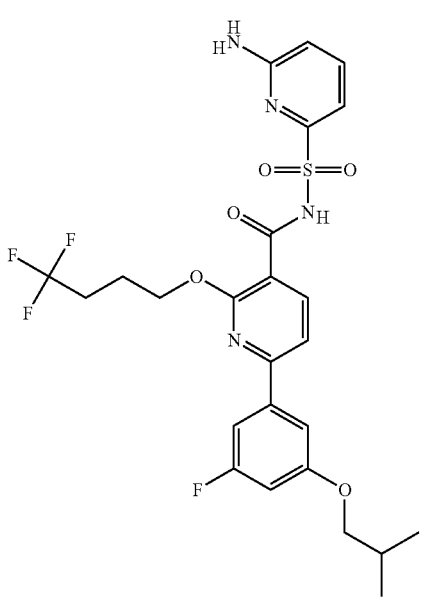
TABLE 1-continued
83
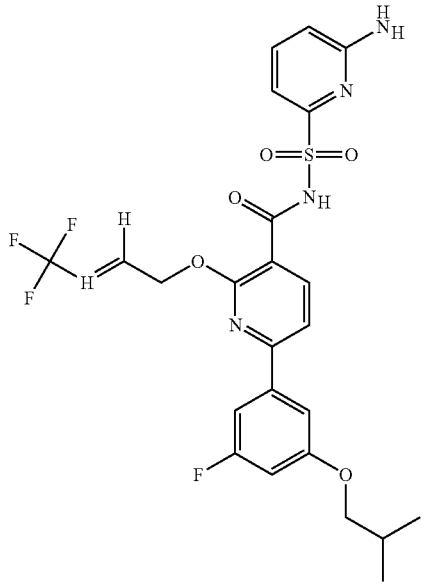
84
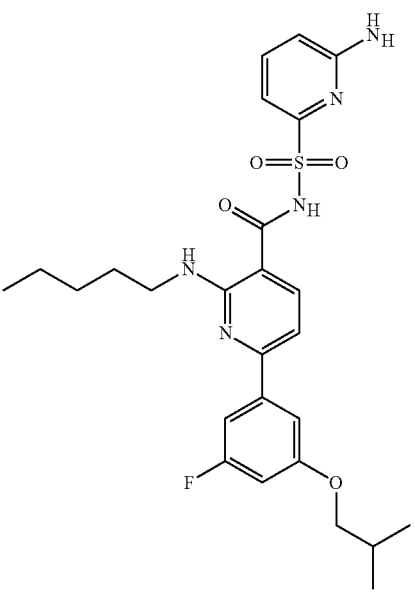
In some embodiments, the compound of formula I is a pharmaceutical salt of a compound selected from Table 1.
In some embodiments, the compound of formula I is selected from the group consisting of Compounds 1, 16, 17, 31, 42, 61, 63, 64, 66, 67, 69, 74, and 75:

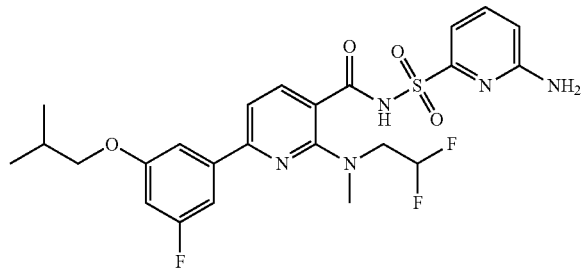
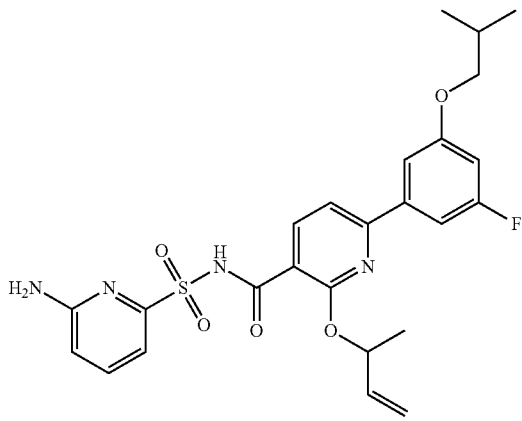
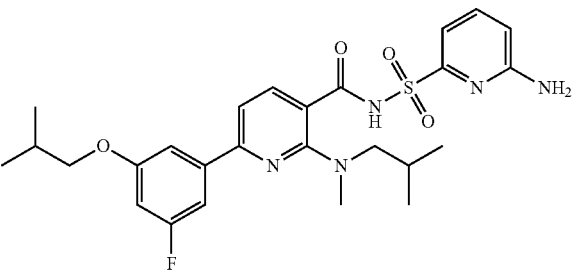
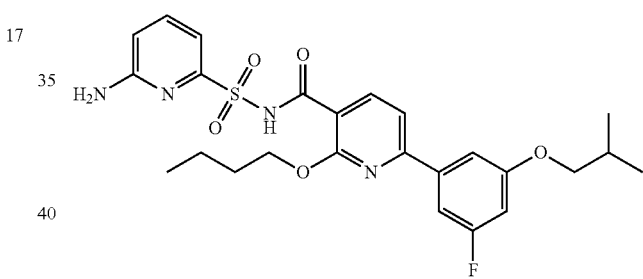
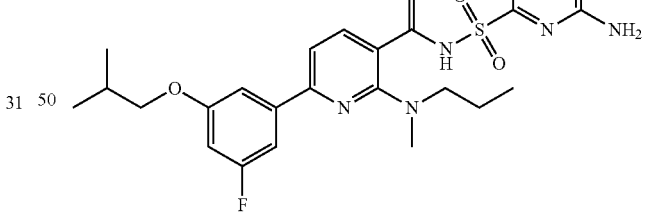
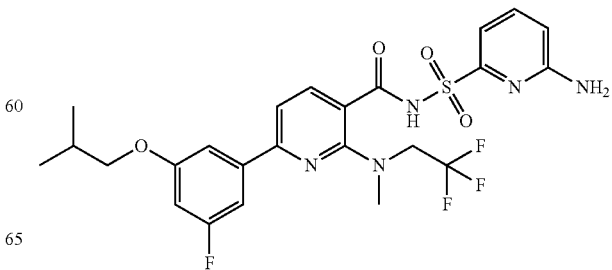

67

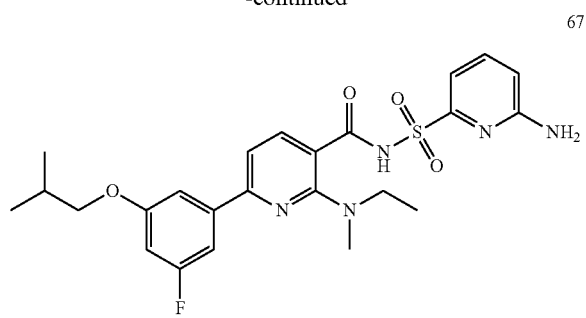

69

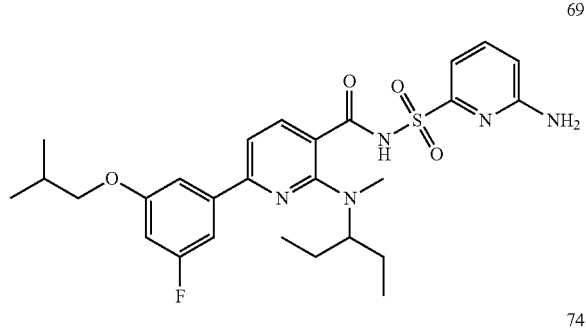

74

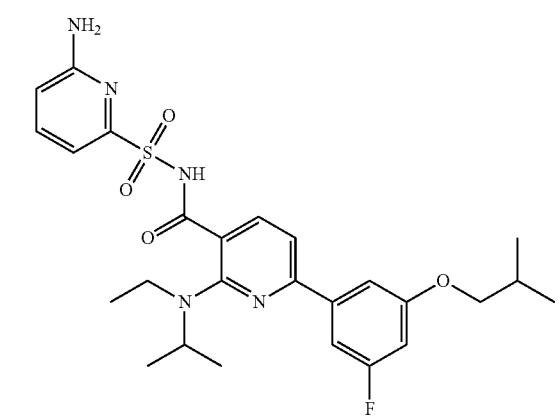

75

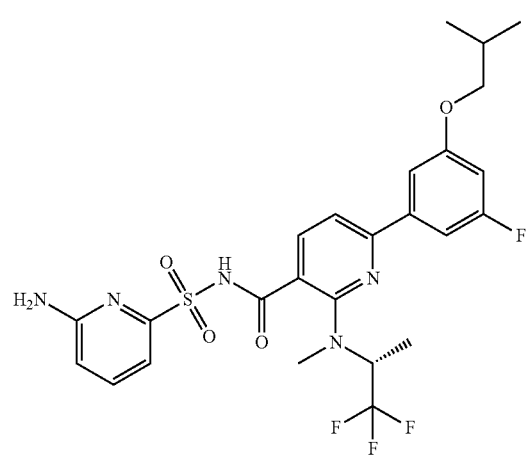

In some embodiments, the compound of formula I is a pharmaceutical salt of a compound selected from the group consisting of Compounds 1, 16, 17, 31, 42, 61, 63, 64, 66, 67, 69, 74, and 75.

In some embodiments, the compound of formula I is selected from the group consisting of Compounds 85 and 86:

85

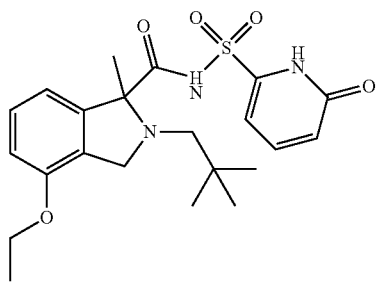

86

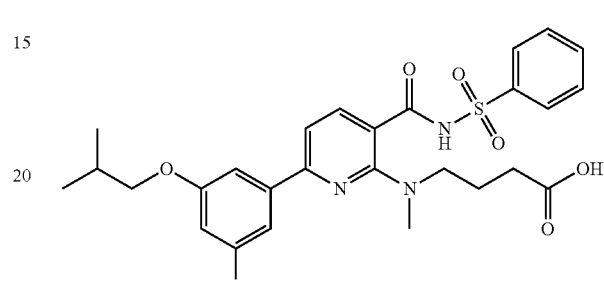

In some embodiments, the compound of formula I is a pharmaceutical salt of a compound selected from the group consisting of Compounds 85 and 86.

Disclosed is a method of treating cystic fibrosis in a patient comprising administering to the patient in need thereof an effective amount of 1) a compound of formula II or a pharmaceutically acceptable salt thereof, or 2) a pharmaceutical composition comprising a pharmaceutically acceptable excipient and a compound of formula II or a pharmaceutically acceptable salt thereof:

II

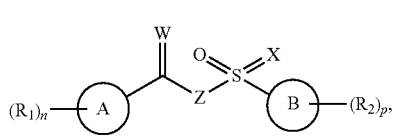

wherein, independently for each occurrence:

Ring A is a $C_6$-$C_{10}$ aryl ring; $C_3$-$C_{10}$ cycloalkyl ring; or a $C_3$-$C_{14}$ heteroaryl or heterocyclic ring wherein anywhere from 1 to 4 ring atoms are independently O, S, N, or NR;

Ring B is a $C_3$-$C_{10}$ cycloalkyl ring; a $C_6$-$C_{10}$ aryl ring; or a $C_3$-$C_{10}$ heteroaryl or $C_3$-$C_{10}$ heterocyclic ring wherein anywhere from 1 to 4 ring atoms are independently O, S, N, or NR;

W is O, S, or NR;

X is O or NR;

Z is NR;

$R_1$ is halo; CN; NRR; $C_1$-$C_6$ alkyl or $C_1$-$C_6$ fluoroalkyl; $C_3$-$C_6$ cycloalkyl; $C_1$-$C_8$ alkoxy or $C_1$-$C_8$ fluoroalkoxy; $C_2$-$C_6$ alkenyl; $C_2$-$C_6$ alkynyl; ($C_1$-$C_9$ alkylene)-$R_3$ wherein up to four $CH_2$ units are independently replaced with O, CO, S, SO, $SO_2$ or NR; $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_2$ is halo; NRR; CN; $CO_2R$; $C_1$-$C_6$ alkyl or $C_1$-$C_6$ fluoroalkyl; $C_1$-$C_6$ alkoxy or $C_1$-$C_6$ fluoroalkoxy;

$C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four $CH_2$ units are optionally and independently replaced with O, CO, S, SO, $SO_2$ or NR;

or two $R_2$ may form a $=CH_2$ or $=O$ group;

$R_3$ is H; $CF_3$; $CHF_2$; OR; C≡CH; $CO_2R$; OH; $C_6$-$C_{10}$ aryl, $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or $SO_2R$;

R is independently H; OH; $CO_2H$; $CO_2C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, or N; or $C_3$-$C_{10}$ cycloalkyl;

n is 2 or 3;

p is 0, 1, 2, or 3; and

Provided that 1) when $R_1$ is adjacent to C=W attached to Ring A, $R_1$ does not contain a ring moiety, and 2) at least one $R_1$ is adjacent to the C=W attached to Ring A.

In some embodiments, Ring A is a $C_3$-$C_{10}$ cycloalkyl ring, such as cyclopentane, cyclopentene, cyclohexane, or cyclohexene. In some embodiments, Ring A is a $C_6$-$C_{10}$ aryl ring, such as a phenyl, indane, 1,2,3,4-tetrahydronaphthalene, or naphthalene. In some embodiments, Ring A is a $C_3$-$C_{11}$ heteroaryl or heterocyclic ring wherein anywhere from 1 to 4 ring atoms are independently O, S, N, or NR, such as pyridyl, indole, indoline, isoindoline, pyrazole, pyrimidine, 1,2,3,4-tetrahydroquinoline, quinoline, 5,6,7,8-tetrahydroquinoline, 1,2,3,4-tetrahydroisoquinoline, pyrrolodine, azaindole, pyrrole, thiophene, oxazole, pyrazine, triazole, thiazole, indazole, 2,3,4,5-tetrahydro-1H-benzo[d]azepine, 1H-benzo[d]imidazole, imidazo[1,2-a]pyridine, or imidazole ring.

In some embodiments, Ring A is

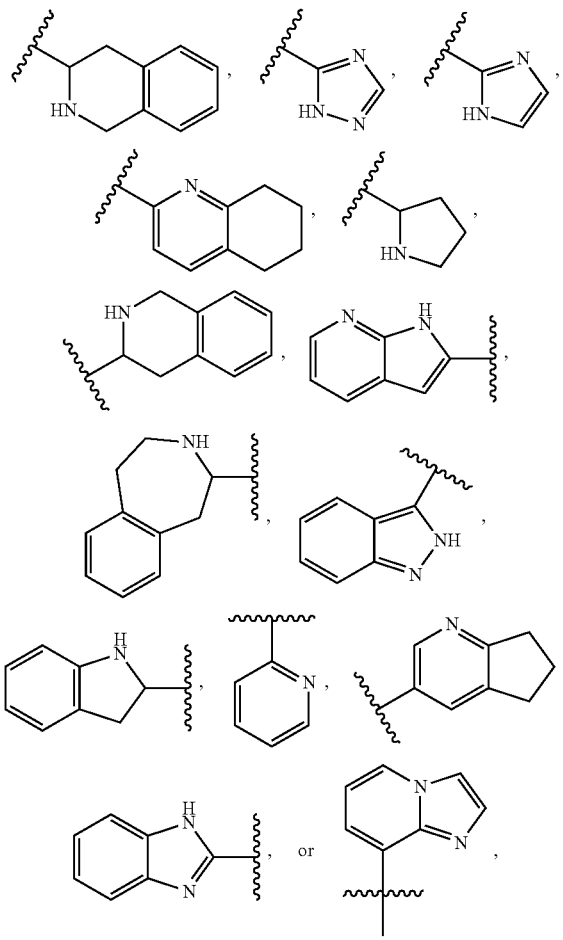

wherein the wavy line indicates point of attachment of Ring A to C=W.

In some embodiments, Ring B is a cycloalkyl ring, such as a cyclopropane, cyclobutane, cyclopentane, or cyclohexane. In some embodiments, Ring B is a $C_6$-$C_{10}$ aryl ring, such as a phenyl or naphthalene. In some embodiments, ring B is a heroaryl or heterocyclic ring wherein anywhere from 1 to 4 ring atoms are independently O, S, N, or NR, such as pyridyl, pyridine-2(1H)-one, pyrazole, indole, pyrrole, indoline, thiophene, dihydrobenzofuran, tetrahydrofuran, furan, pyrazine, indazole, thiazole, pyridine-4(1H)-one, pyrrolidinone, 3-azabicyclo[3.1.0]hexane, (1R,4R)-2-oxa-5-azabicyclo[2.2.1]heptane, pyrrolidine, azetidine, piperidine, piperazine, imidazo[1,2-a]pyridine, or quinoline.

In some embodiments, Ring B is

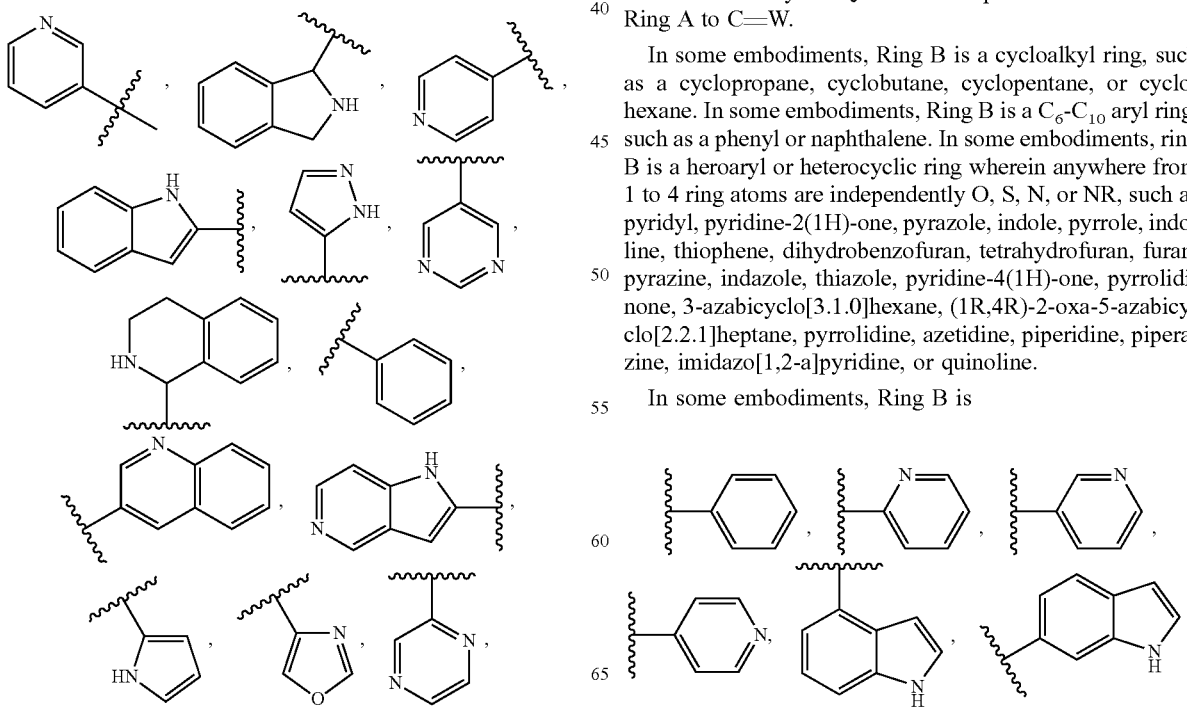

-continued

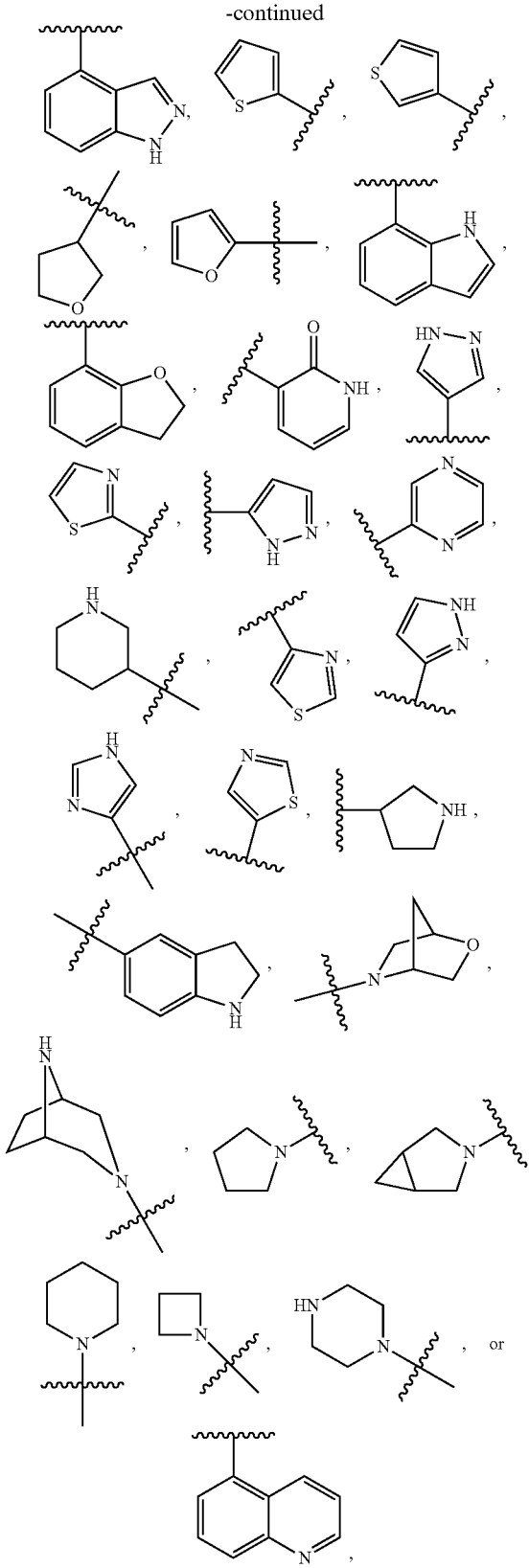

wherein the wavy line ⁓ indicates point of attachment of Ring B to the (X═)S(═O) group of formula II.

In some embodiments, X is O. In some embodiments, Z is NH.

In some embodiments, $R_1$ is independently halo, amino, OH, $C_2$-$C_6$ alkenyl; $C_2$-$C_6$ alkynyl, $C_1$-$C_6$ fluoroalkyl, CN, $C_1$-$C_6$ alkyl, $C_1$-$C_8$ alkoxy or $C_1$-$C_8$ fluoroalkoxy, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring, or a ($C_1$-$C_9$ alkylene)-$R_3$ wherein up to four $CH_2$ units are independently replaced with O, CO, S, SO, $SO_2$ or NR.

In some embodiments, $R_1$ is $CHF_2CH_2(CH_3)N$—, $(CH_3)_2CHCH_2CH2O$—, $(CH_3)_3CCH_2CH_2O$—, $(CH_3)_3COCH_2CH_2O$—, $(CH_3)_2CHO$—, $CHF_2CHF_2CH(CH_3)O$—, —$CF_3$, $(CH_3CH_2)_2N$—, $CF_3CH_2CH(CH_3)O$—, $CH_3O$—, $CH_3(CH_2)_4O$—, $CH_3CH_2CH(CH_3)CH(CH_3)O$—, $CH_3CH_2OCH_2CH_2O$—, $CH_3CH_2NCH(CH_3)_2$, $(CH_3)_3CH_2O$—, (R)—$CH_3NCH(CH_3)(CF_3)$, $CH_3OCH_2CH(CH_2CH_3)O$—, $(CH_3)_2N$—, (S)—$CH_3OCH_2CH(CH_3)O$—, $CH_3O(CH_2)_3O$—, $CH_3OC(CH_3)_2(CH_2)_2O$, $CH_3OCH_2CH(CH_3)O$, $CH_3CH(CH_3)CH_2CH(CH_3)O$—, $(CH_3)_3CCH(CH_3)O$, $((CH_3)_2CH)_2CHO$—, $CH_3CH_2CH_2O$, $CH_3CH$═$CHCH_2O$—, (S)—$CH_3CH_2CH(CH_3)O$—, $CH_3CH_2O$, $(CH_3)_2CHNCH_3$, $(CH_3)_3CCH_2O$, $(CF_3)_2CHO$—, $(CH_3)_3CCH(CH_2CH_3)O$, $CH_3C$≡$CCH_2CH_2O$, $(CH_3)_3CCH_2CH(CH_3)O$—, $(CH_3)_2C$═$C(CH_3)$, $CHF_2CH_2O$—, $CH_3CH_2CH_2NH$, $(CH_3)_2CHCH(CH_2CH_3)O$, $((CH_3)_2CH)_2N$, $CH_2$═$CHCH(CH_3)O$, $CH_2$═$CHCH_2O$—, $CH_3CH_2C(CH_3)_2O$, $(CH_3CH_2)_2CHO$, $CF_3CH_2O$, $CH_3C(═CH_2)CH_2O$, $(CH_3)_3CCH_2CH_2NH$, $CH_3OCH_2C(CH_3)_2O$, $(CH_3)_3CCH_2N(CH_3)$, $(CH_3)_2CHCH(CH_3)NH$, $(CH_3)_2CHO(CH_2)_2O$, $CH_3CH_2CH_2CH(CH_3)O$, $CH_3CF_2CH_2O$, $(CH_3)_3CNH$, (R)—$CH_3CH_2CH(CH_3)O$, $CH_3OCH_2CH_2O$, $(CH_3)_2CHCH_2N(CH_3)$, $CH_3CH_2CH_2CH(CH_3)CH(CH_3)O$, $CH_3CH_2CH_2CH_2O$, $CH_3CH_2CH_2N(CH_3)$, (R)—$CH_3OCH_2CH(CH_3)O$, $CF_3CH_2N(CH_3)$, $CH_3CH_2N(CH_3)$, $((CH_3)_3C)_2CHO$, $(CH_3CH_2)_2CHN(CH_3)$, $(CH_3)_2CHN(CH_3)$, $CH_3CH_2OCH_2CH(CH_3)O$, $(CH_3)_3CCH_2NH$, $CF_3CH(CH_3)O$, $CH_3CH_2NCH(CH_3)_2$, $(R)$—$CF_3CH(CH_3)N(CH_3)$, $(CH_3)_2CHCH(CH_3)$, $CH_3CH_2(CH_3)_2CHCH_2CH_2O$, (S)—$CH_3OCH(CH_3)CH_2O$, $HOCH(CH_3)_2CH_2CH_2NH$, $CF_3CH_2CH_2O$, $CF_3CH_2CH_2CH_2O$, $CF_3CH$═$CHCH_2O$, $CH_3CH_2CH_2CH_2CH_2NH$, or $(CH_3)_3C$.

In some embodiments, $R_1$ is $CH_3$, Cl, F, CN, $CH_2CH_3$, $CH(CH_3)_2$, $OCH_2CH_2OCH_2CH_3$,

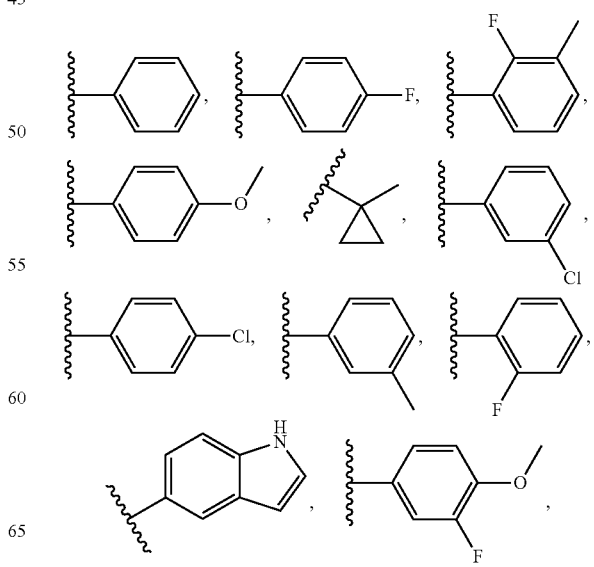

115
-continued
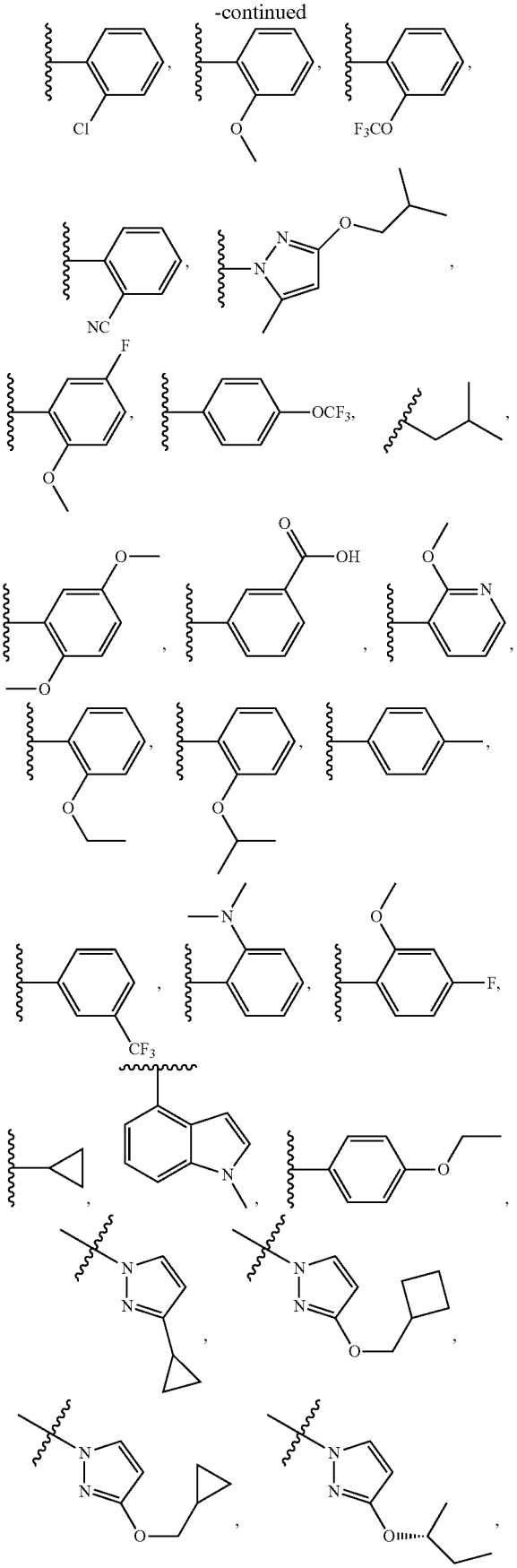
116
-continued
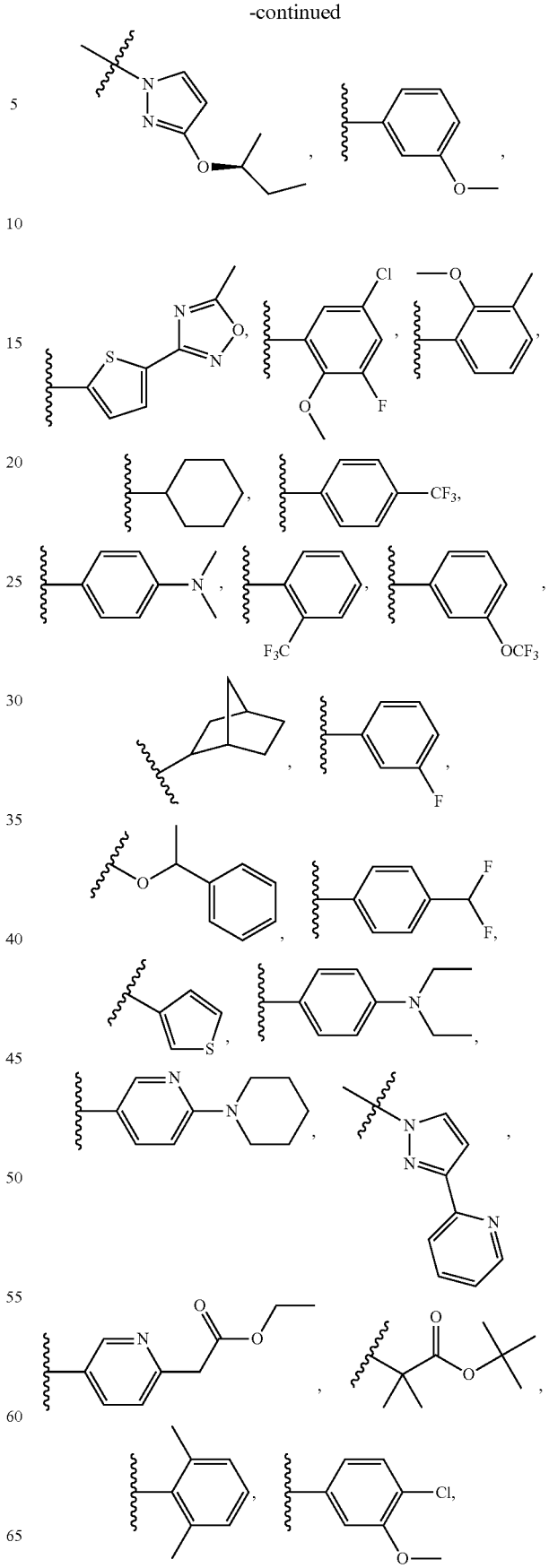

117
-continued
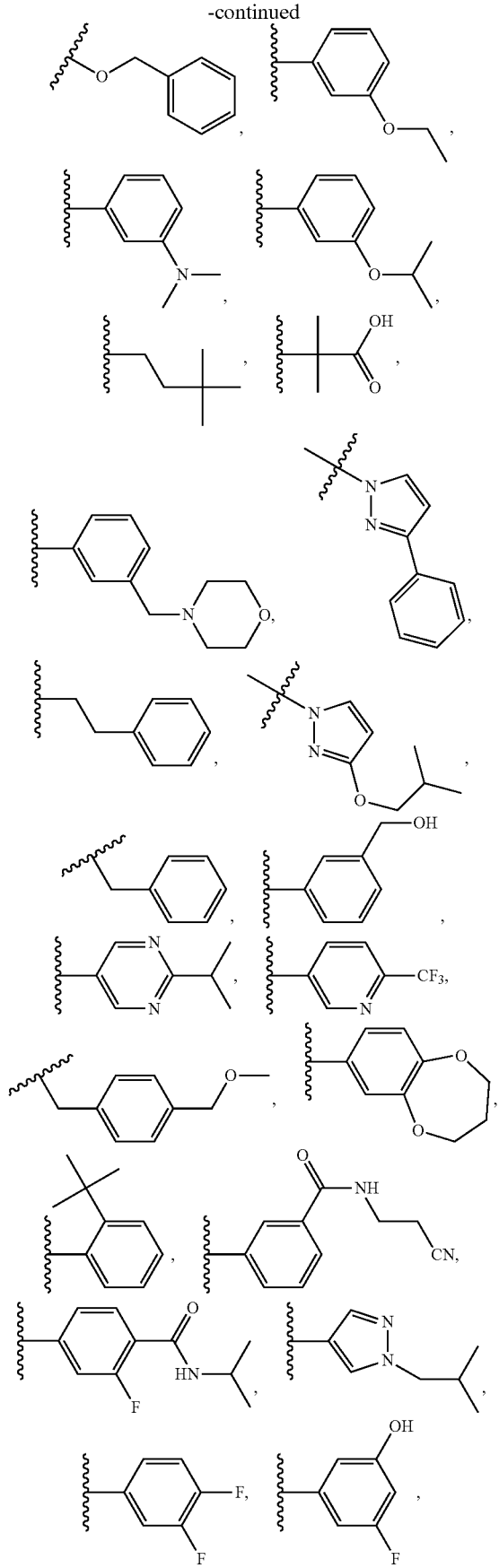
118
-continued
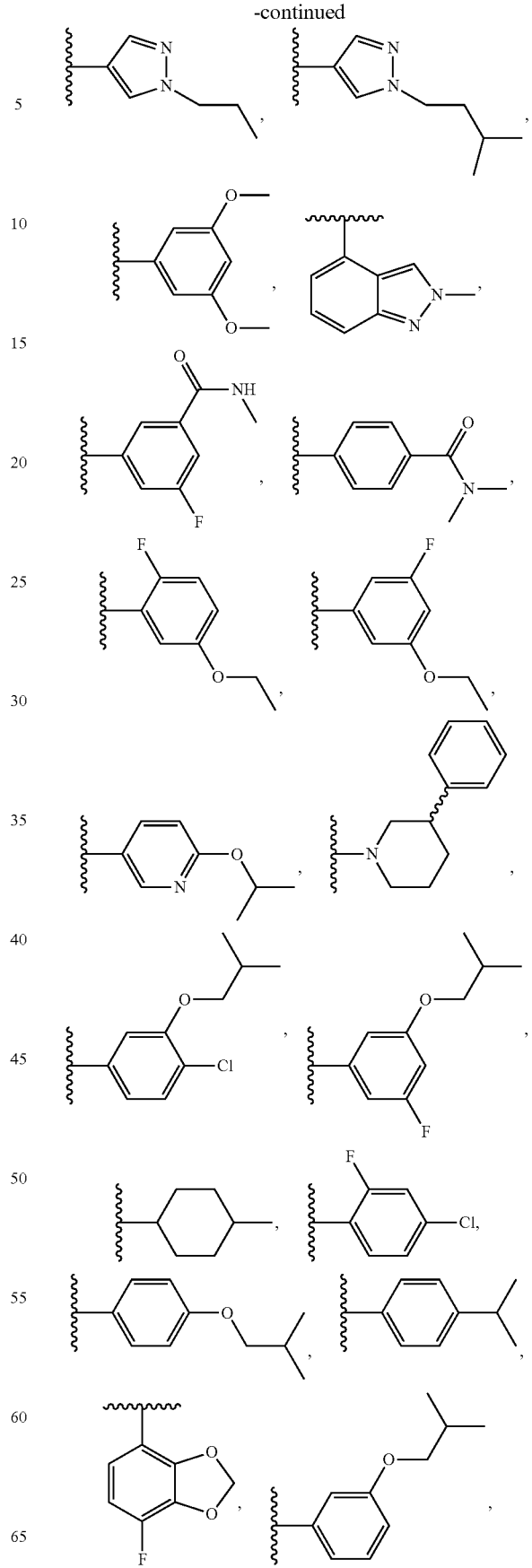

-continued

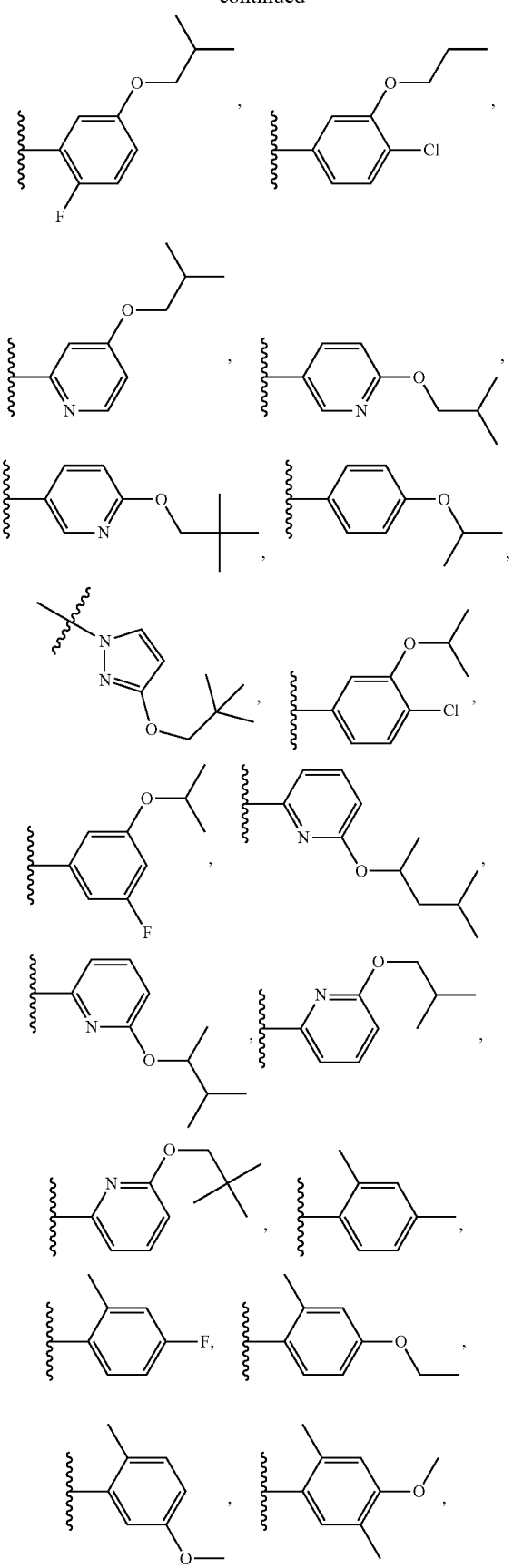

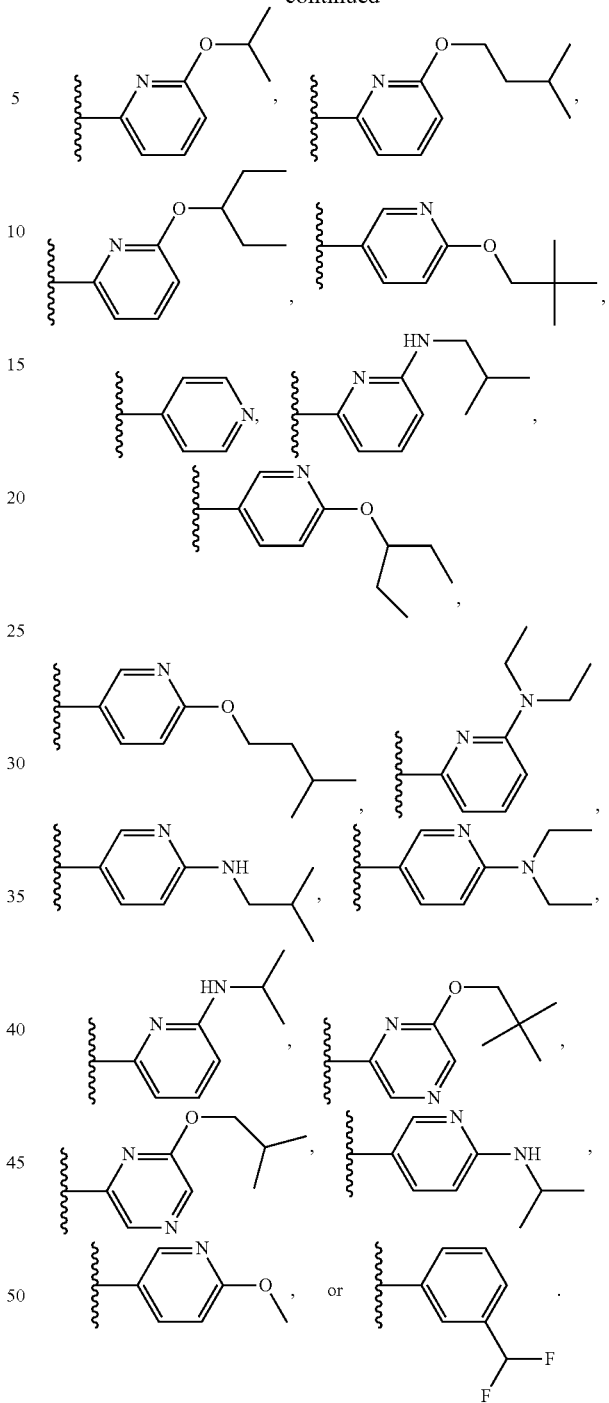

In some embodiments, R₂ is halo, CN, amino, OH, $C_1$-$C_6$ alkyl or $C_1$-$C_6$ fluoroalkyl, $C_1$-$C_6$ alkoxy or $C_1$-$C_6$ fluoroalkoxy, $C_3$-$C_{10}$ heterocyclic ring wherein anywhere from 1 to 4 carbon atoms are independently O, S, N, or NR; or a ($C_1$-$C_9$ alkylene)-R₃ wherein up to four $CH_2$ units are optionally and independently replaced with O, CO, S, SO, $SO_2$ or NR.

In some embodiments, R₂ is Cl, F, OH, CN, $NH_2$, $NH(CH_3)$, $N(CH_3)_2$, $N(CH_3)CH_2CH_2CH_3$, $N(CH_3)CH_2CH_2CH_2CH_3$, $NHCH_2CH_2CH_3$, $CH_3$, $CH_2OH$, $CH_2CH_3$, $CH_2CH_2CH_3$, =O, $CH_3SO_2$, $CH_3SO_2NH$, $CF_3CONH$, $CH_3CONH$, $CH_3CON(CH_3)$, tBuOCONH, (CH$_3$)$_2$CHOCONH, CH(CH$_3$)$_2$, CHF$_2$, OCH$_3$, OCH$_2$CH$_3$, OCH$_2$CH$_2$CH$_3$, OCH$_2$CH$_2$CH(CH$_3$)$_2$, OCF$_3$, OCHF$_2$, OC(CH$_3$)$_3$, OCH$_2$CH$_2$tBu, NHCH(CH$_3$)(CH$_2$CH$_2$CH$_3$), OCH(CH$_3$)$_2$, NH(CH$_2$)$_2$O(CH$_2$)$_2$CH$_3$, C(O)CH$_3$, CH$_2$CH$_2$OH, CH$_2$NH$_2$, NH(CH$_2$)$_2$OH, N(CH$_3$)CH$_2$CH$_2$CH$_2$OCH$_3$, NHCH$_2$CH$_2$COOH, NH(CH$_2$)$_2$N(CH$_3$)$_2$, NH(CH$_2$)$_2$NH$_2$, NH(CH$_2$)$_3$NH$_2$, NH(CH$_2$)$_2$OCH$_3$, NHCH(CH$_3$)$_2$,

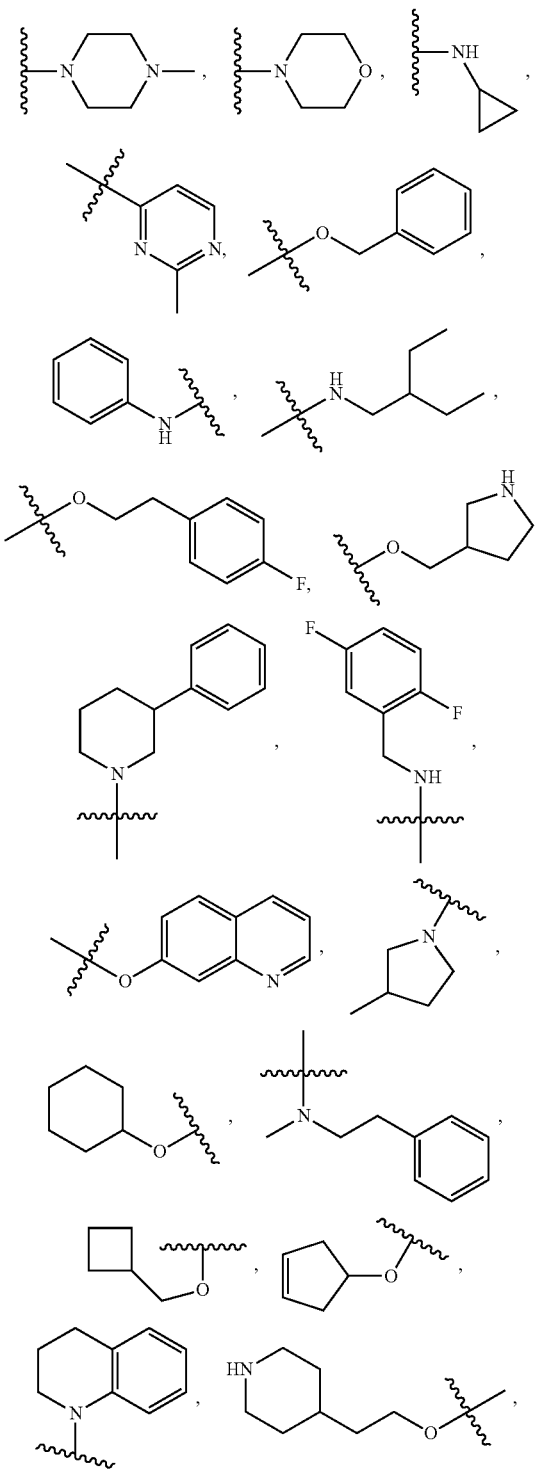

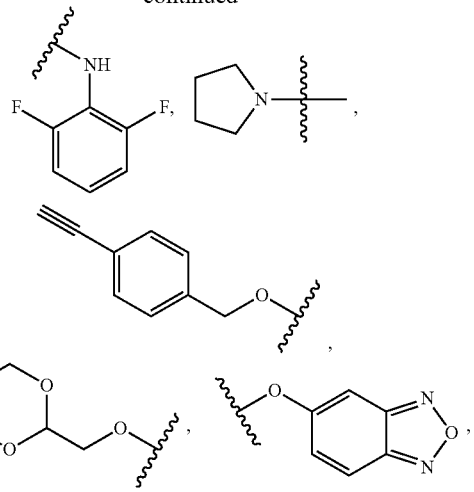

or CO$_2$H.

In some embodiments, R$_2$ is NH$_2$, or NHCH$_2$CH$_2$CH$_3$.

In some embodiments, n is 2. In some embodiments, p is 0. In some embodiments, p is 1.

In some embodiments, W is O. In some embodiments, Z is NH. In some embodiments, X is O In some embodiments, Ring A is

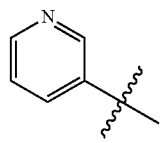 [SMILES: *c1cccnc1]

and n is 2. In some embodiments, Ring A is

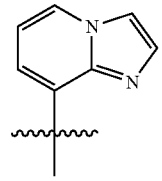 [SMILES: *c1cccn2ccnc12]

and n is 2. In some embodiments, Ring A is

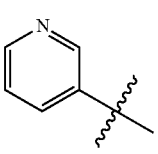

and at least one $R_1$ is phenyl. In some embodiments, Ring A is

[pyridin-3-yl structure]

, and at least one $R_1$ is tert-butyl. In some embodiments, Ring A is

[pyridin-3-yl structure]

, and at least one $R_1$ is pyridinyl. In some embodiments, Ring A is

[pyridin-3-yl structure]

, one $R_1$ is phenyl, and one $R_1$ is alkenyl, amino, or $C_1$-$C_8$ alkoxy or $C_1$-$C_8$ fluoroalkoxy. In some embodiments, Ring A is

[pyridin-3-yl structure]

, and Ring B is

[pyridin-2-yl structure]

.

In some embodiments, Ring A is

[pyridin-3-yl structure]

, and Ring B is

[1H-pyrazol-5-yl structure]

.

In some embodiments, Ring A is

[pyridin-3-yl structure]

,

Ring B is

[pyridin-2-yl structure]

, one $R_1$ is phenyl, and one $R_1$ is alkenyl, amino, or $C_1$-$C_8$ alkoxy or $C_1$-$C_8$ fluoroalkoxy.

In some embodiments, in the compound of formula II, one or more hydrogen atoms may be replaced by a deuterium atom.

In some embodiments of formula II, the compound of formula II or a pharmaceutically acceptable salt thereof is a compound of formula II-i:

II-i

[structure: $(R_1)_n$—A—C(O)—S(=O)(=X)—Z—B—$(R_2)_p$]

or a pharmaceutically acceptable salt thereof, wherein, independently for each occurrence:

Ring A is a $C_3$-$C_{14}$ heteroaryl or heterocyclic ring wherein anywhere from 1 to 4 ring atoms are independently O, S, N, or NR;

Ring B is a $C_3$-$C_{10}$ heteroaryl or $C_3$-$C_{10}$ heterocyclic ring wherein anywhere from 1 to 4 ring atoms are independently O, S, N, or NR;

X is O or NR;

Z is NR;

$R_1$ is halo; CN; NRR; $C_1$-$C_6$ alkyl or $C_1$-$C_6$ fluoroalkyl; $C_3$-$C_6$ cycloalkyl; $C_1$-$C_8$ alkoxy or $C_1$-$C_8$ fluoroalkoxy; $C_2$-$C_6$ alkenyl; $C_2$-$C_6$ alkynyl; ($C_1$-$C_9$ alkylene)-$R_3$ wherein up to four $CH_2$ units are independently replaced with O, CO, S, SO, $SO_2$ or NR; $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_2$ is halo; NRR; CN; $CO_2R$; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four CH$_2$ units are optionally and independently replaced with O, CO, S, SO, SO$_2$ or NR;

or two R$_2$ may form a =CH$_2$ or =O group;

R$_3$ is H; CF$_3$; CHF$_2$; OR; C≡CH; CO$_2$R; OH; C$_6$-C$_{10}$ aryl, C$_3$-C$_{10}$ heteroaryl or heterocycloalkyl wherein anywhere from 1 to 4 ring atoms are independently O, S, N, or NR; C$_3$-C$_{10}$ cycloalkyl; NRR, NRCOR, CONRR, CN, halo, or SO$_2$R;

R is independently H; OH; CO$_2$H; CO$_2$C$_1$-C$_6$ alkyl; C$_1$-C$_6$ alkyl; C$_2$-C$_6$ alkenyl; C$_2$-C$_6$ alkynyl; C$_6$-C$_{10}$ aryl; C$_3$-C$_{10}$ heteroaryl or heterocycloalkyl wherein anywhere from 1 to 4 ring atoms are independently O, S, or N; or C$_3$-C$_{10}$ cycloalkyl;

n is 2 or 3; and p is 0, 1, 2, or 3.

In some embodiments, ring A is a pyridyl, indole, indoline, isoindoline, pyrazole, pyrimidine, quinoline, 5,6,7,8-tetrahydroquinoline, 1,2,3,4-tetrahydroisoquinoline, pyrrolodine, aza-indole, pyrrole, oxazole, pyrazine, triazole, indazole, imidazo[1,2-a]pyridine, or imidazole ring.

In some embodiments, Ring A is

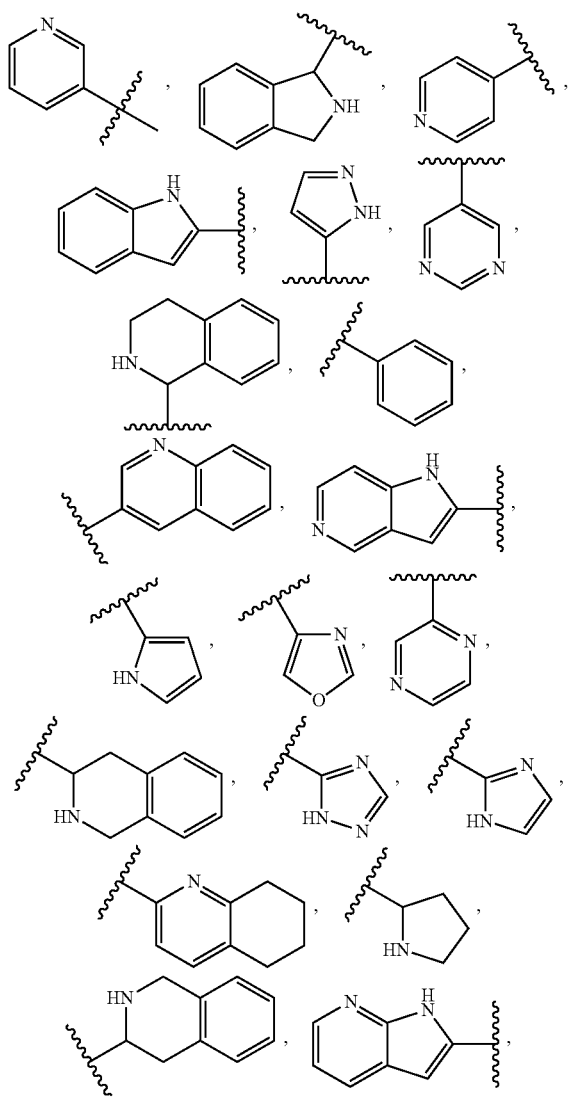

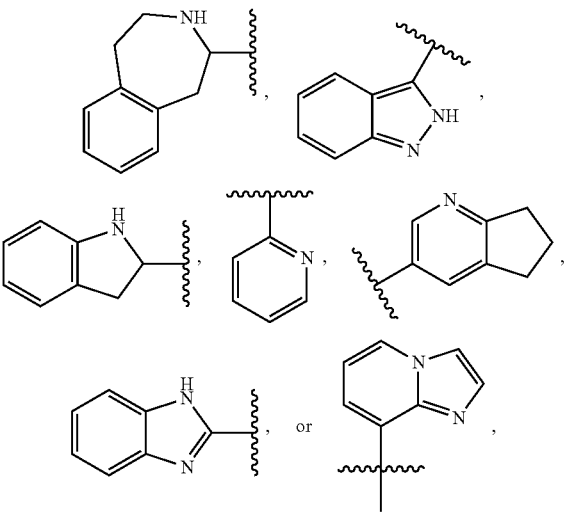

wherein the wavy line indicates point of attachment of Ring A to the carbonyl (CO).

In some embodiments, Ring B is pyridyl, pyridine-2(1H)-one, pyrazole, indole, aza-indole, thiophene, dihydrobenzofuran, thiazole, pyrrolidinone, or quinoline.

In some embodiments, Ring B is

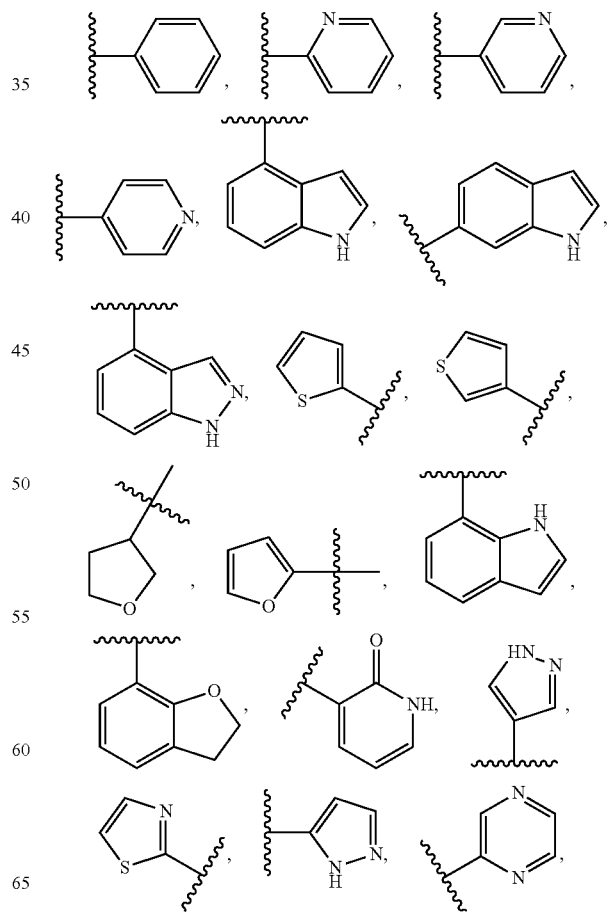

-continued

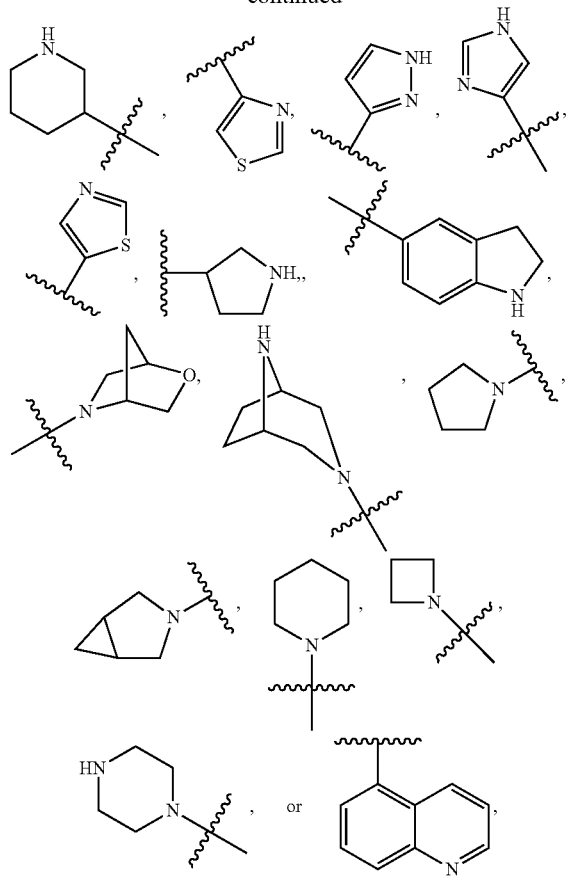

wherein the wavy line 〰 indicates point of attachment of Ring B to the sulfonyl (SO₂).

In some embodiments, X is O. In some embodiments, Z is NH.

In some embodiments, R₁ is independently halo, amino, OH, C₁-C₆ fluoroalkyl, CN, C₁-C₆ alkyl, C₂-C₆ alkenyl; C₂-C₆ alkynyl, C₁-C₈ alkoxy or C₁-C₈ fluoroalkoxy, a phenyl, C₃-C₆ mono-cycloalkly, mono-C₄-C₆ heterocyclic ring, 1,2,3,4-tetrahydroisoquinoline, pyridyl, pyrimidine, indole, aza-indole, pyrazole, pyrrole, or thiophene ring, or a (C₁-C₉ alkylene)-R₃ wherein up to four CH₂ units are independently replaced with O, CO, S, SO, SO₂ or NR.

In some embodiments, R₁ is CHF₂CH₂(CH₃)N—, (CH₃)₂CHCH₂CH2O—, (CH₃)₃CCH₂CH₂O—, (CH₃)₃COCH₂CH₂O—, (CH₃)₂CHO—, CHF₂CHF₂CH(CH₃)O—, —CF₃, (CH₃CH₂)₂N—, CF₃CH₂CH(CH₃)O—, CH₃O—, CH₃(CH₂)₄O—, CH₃CH₂CH(CH₃)CH(CH₃)O—, CH₃CH₂OCH₂CH₂O—, CH₃CH₂NCH(CH₃)₂, (CH₃)₃CH₂O—, (R)—CH₃NCH(CH₃)(CF₃), CH₃OCH₂CH(CH₂CH₃)O—, (CH₃)₂N—, (S)—CH₃OCH₂CH(CH₃)O—, CH₃O(CH₂)₃O—, CH₃OC(CH₃)₂(CH₂)₂O, CH₃OCH₂CH(CH₃)O, CH₃CH(CH₃)CH₂CH(CH₃)O—, (CH₃)₃CCH(CH₃)O, ((CH₃)₂CH)₂CHO—, CH₃CH₂CH₂O, CH₃CH=CHCH₂O—, (S)—CH₃CH₂CH(CH₃)O—, CH₃CH₂O, (CH₃)₂CHNCH₃, (CH₃)₃CCH₂O, (CF₃)₂CHO—, (CH₃)₃CCH(CH₂CH₃)O, CH₃C≡CCH₂CH₂O, (CH₃)₃CCH₂CH(CH₃)O—, (CH₃)₂C=C(CH₃), CHF₂CH₂O—, CH₃CH₂CH₂NH, (CH₃)₂CHCH(CH₂CH₃)O, ((CH₃)₂CH)₂N, CH₂=CHCH(CH₃)O, CH₂=CHCH₂O—, CH₃CH₂C(CH₃)₂O, (CH₃CH₂)₂CHO, CF₃CH₂O, CH₃C(=CH₂)CH₂O, (CH₃)₃CCH₂CH₂NH, CH₃OCH₂C(CH₃)₂O, (CH₃)₃CCH₂N(CH₃), (CH₃)₂CHCH(CH₃)NH, (CH₃)₂CHO(CH₂)₂O, CH₃CH₂CH₂CH(CH₃)O, CH₃CF₂CH₂O, (CH₃)₃CNH, (R)—CH₃CH₂CH(CH₃)O, CH₃OCH₂CH₂O, (CH₃)₂CHCH₂N(CH₃), CH₃CH₂CH₂CH(CH₃)CH(CH₃)O, CH₃CH₂CH₂O, CH₃CH₂CH₂N(CH₃), (R)—CH₃OCH₂CH(CH₃)O, CF₃CH₂N(CH₃), CH₃CH₂N(CH₃), ((CH₃)₃C)₂CHO, (CH₃CH₂)₂CHN(CH₃), (CH₃)₂CHN(CH₃), CH₃CH₂OCH₂CH(CH₃)O, (CH₃)₃CCH₂NH, CF₃CH(CH₃)O, CH₃CH₂NCH(CH₃)₂, (R)—CF₃CH(CH₃)N(CH₃), (CH₃)₂CHCH(CH₃), CH₃CH₂(CH₃)₂CHCH₂CH₂O, (S)—CH₃OCH(CH₃)CH₂O, HOCH(CH₃)₂CH₂CH₂NH, CF₃CH₂CH₂O, CF₃CH₂CH₂CH₂O, CF₃CH=CHCH₂O, CH₃CH₂CH₂CH₂CH₂NH, or (CH₃)₃C.

In some embodiments, R₁ is CH₃, Cl, F, CN, CH₂CH₃, CH(CH₃)₂, OCH₂CH₂OCH₂CH₃,

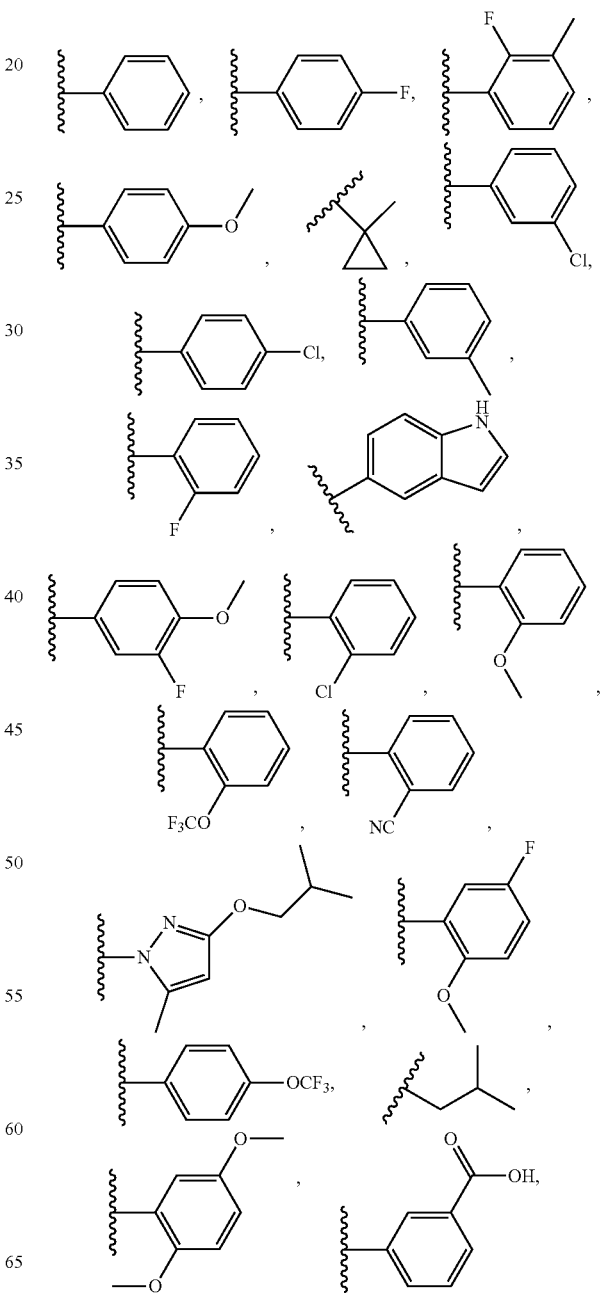

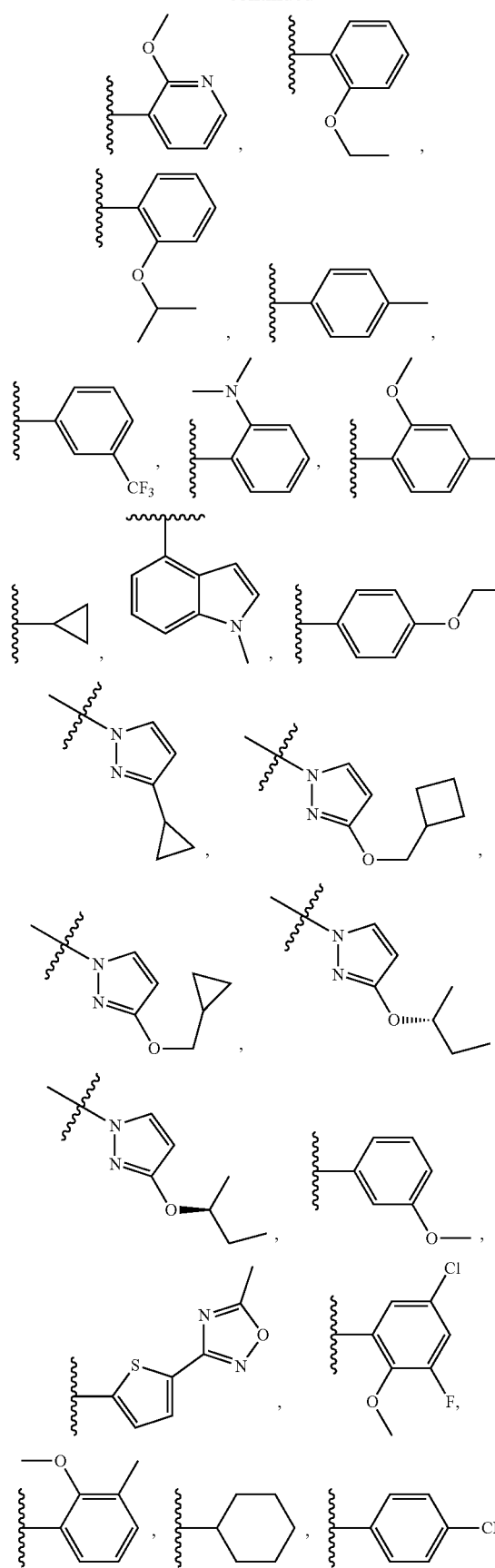
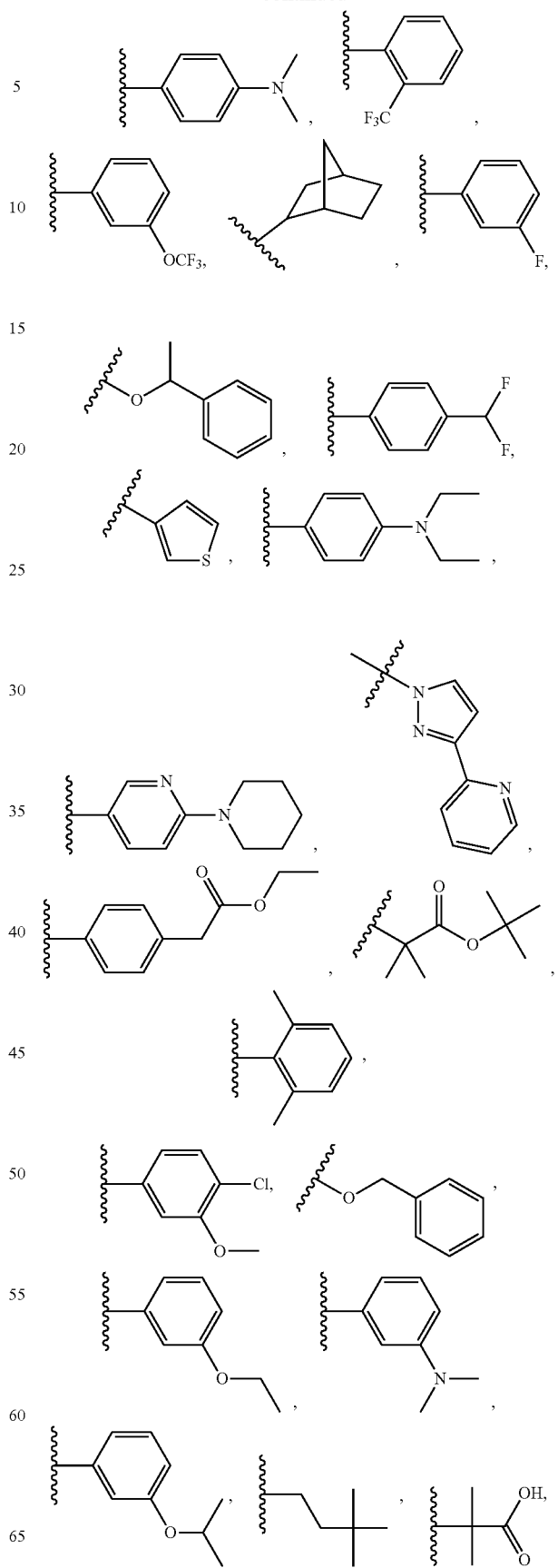

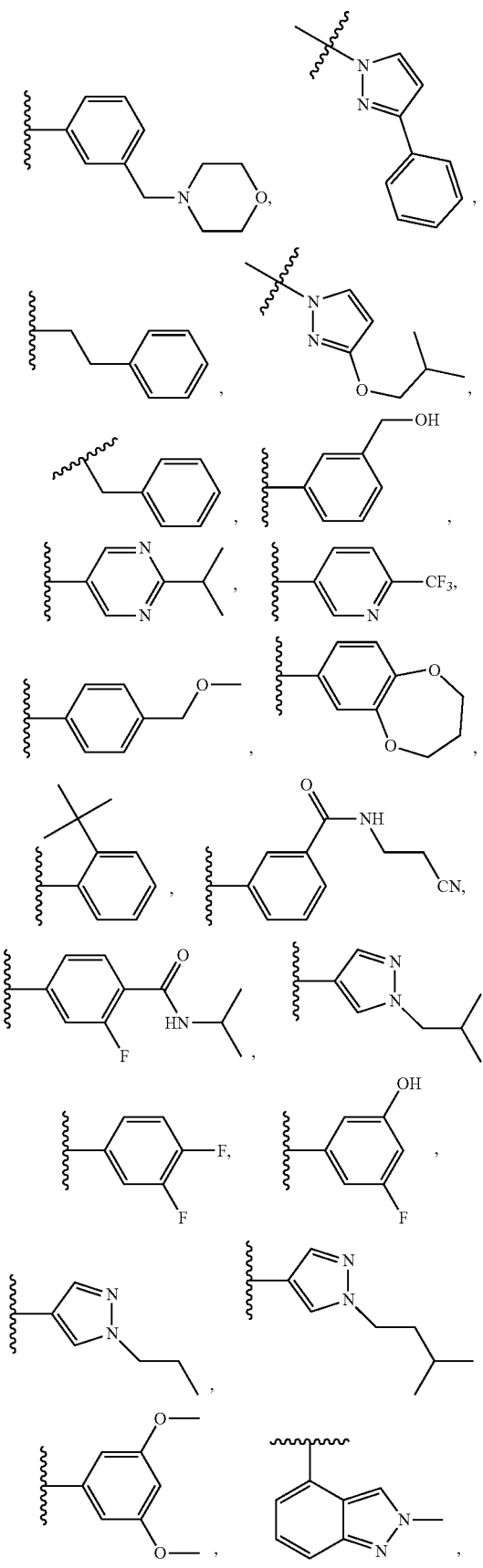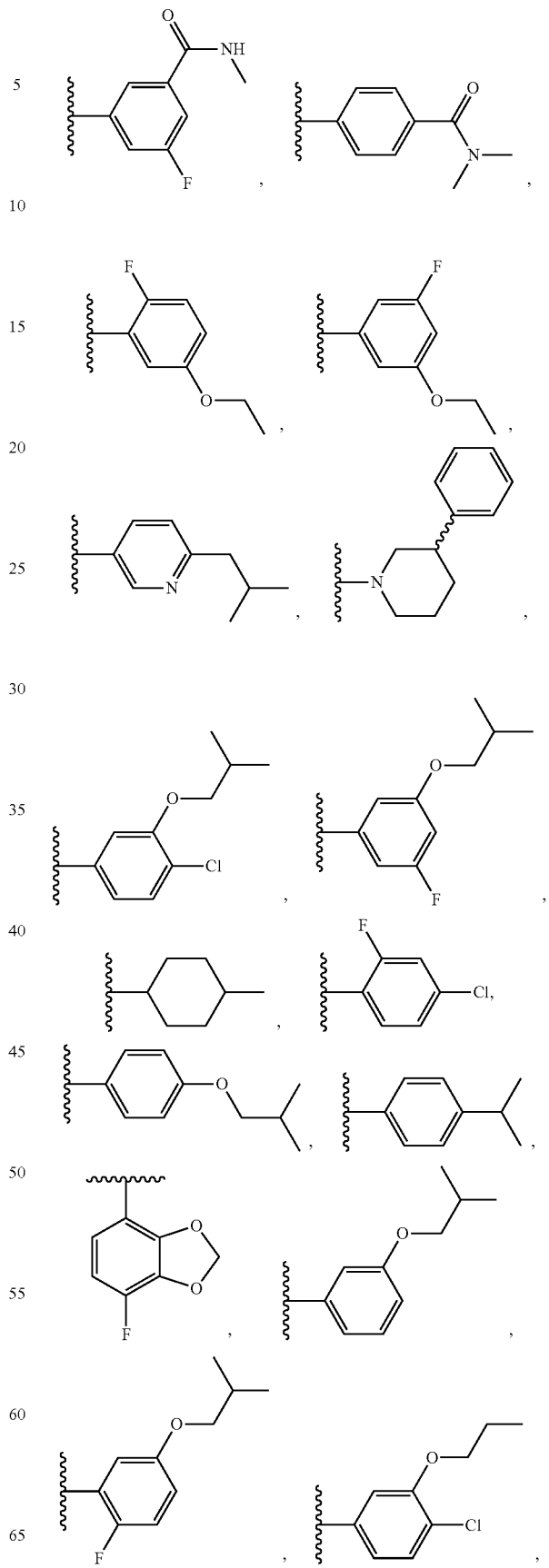

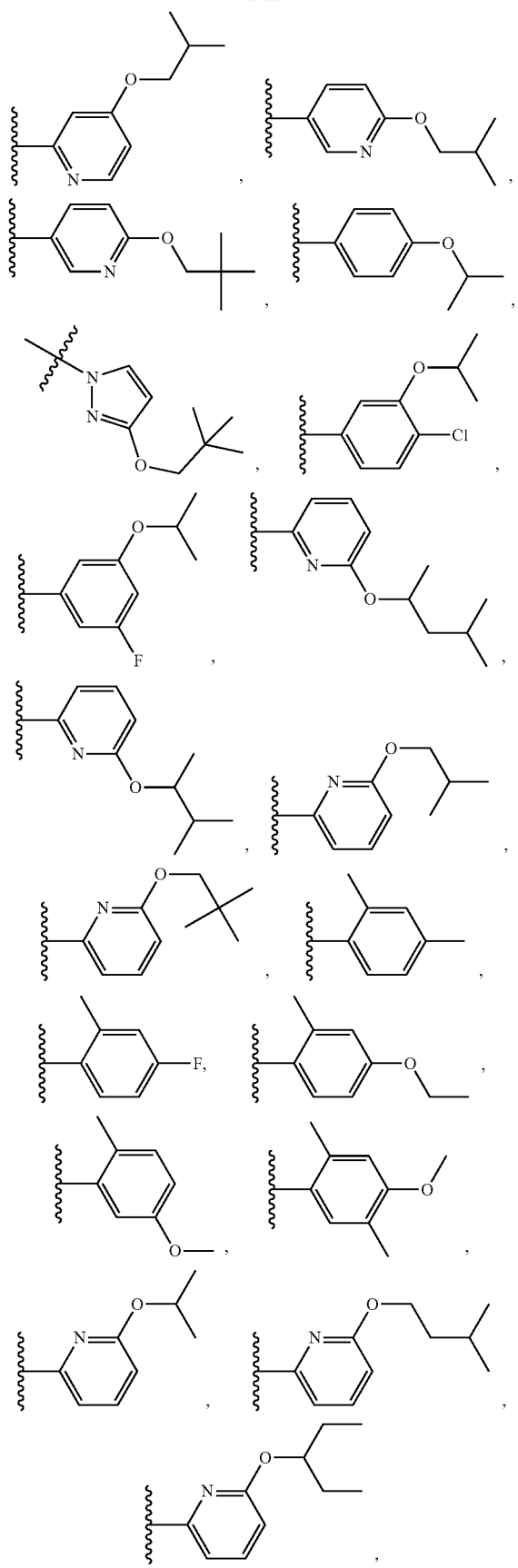
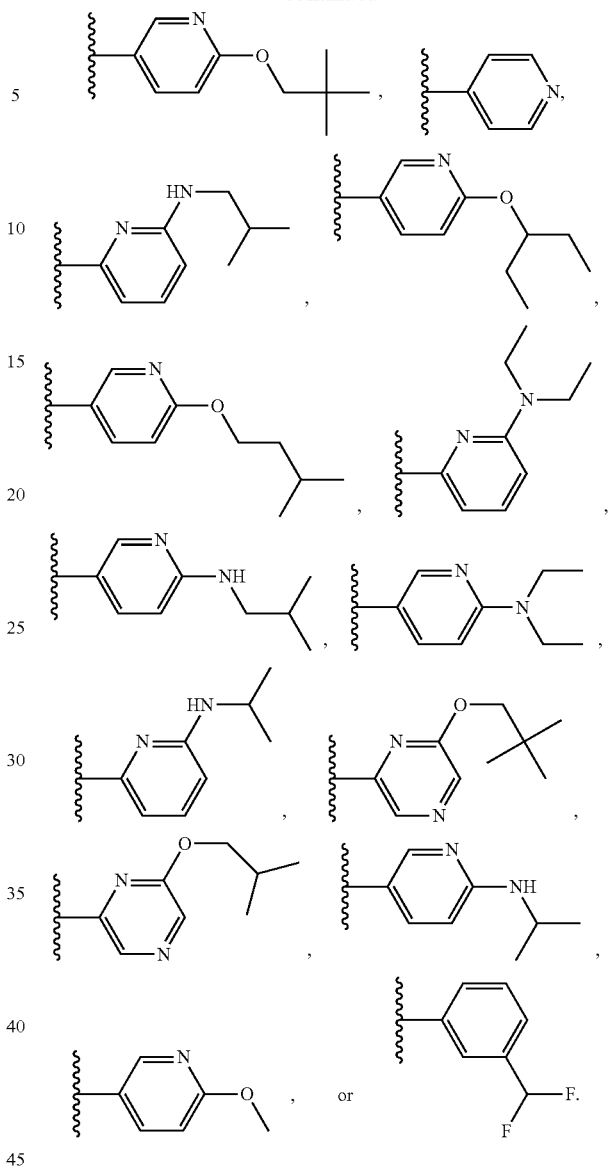

In some embodiments, $R_2$ is halo, CN, OH, amino, $C_1$-$C_6$ alkyl or $C_1$-$C_6$ fluoroalkyl, $C_1$-$C_6$ alkoxy or $C_1$-$C_6$ fluoroalkoxy, $C_3$-$C_{10}$ heterocyclic ring wherein anywhere from 1 to 4 carbon atoms are independently O, S, N, or NR; or a ($C_1$-$C_9$ alkylene)-$R_3$ wherein up to four $CH_2$ units are optionally and independently replaced with O, CO, S, SO, $SO_2$ or NR.

In some embodiments, $R_2$ is Cl, F, OH, CN, $NH_2$, $NH(CH_3)$, $N(CH_3)_2$, $N(CH_3)CH_2CH_2CH_3$, $N(CH_3)CH_2CH_2CH_2CH_3$, $NHCH_2CH_2CH_3$, $CH_3$, $CH_2OH$, $CH_2CH_3$, $CH_2CH_2CH_3$, =O, $CH_3SO_2$, $CH_3SO_2NH$, $CF_3CONH$, $CH_3CONH$, $CH_3CON(CH_3)$, tBuOCONH, $(CH_3)_2CHOCONH$, $CH(CH_3)_2$, $CHF_2$, $OCH_3$, $OCH_2CH_3$, $OCH_2CH_2CH_3$, $OCH_2CH(CH_3)_2$, $OCF_3$, $OCHF_2$, $OC(CH_3)_3$, $OCH_2CH_2tBu$, $NHCH(CH_3)(CH_2CH_2CH_3)$, $OCH(CH_3)_2$, $NH(CH_2)_2O(CH_2)_2CH_3$, $C(O)CH_3$, $CH_2CH_2OH$, $CH_2NH_2$, $NH(CH_2)_2OH$, $N(CH_3)CH_2CH_2CH_2OCH_3$, $NHCH_2CH_2COOH$, $NH(CH_2)_2N(CH_3)_2$, $NH(CH_2)_2NH_2$, $NH(CH_2)_3NH_2$, $NH(CH_2)_2OCH_3$, $NHCH(CH_3)_2$,

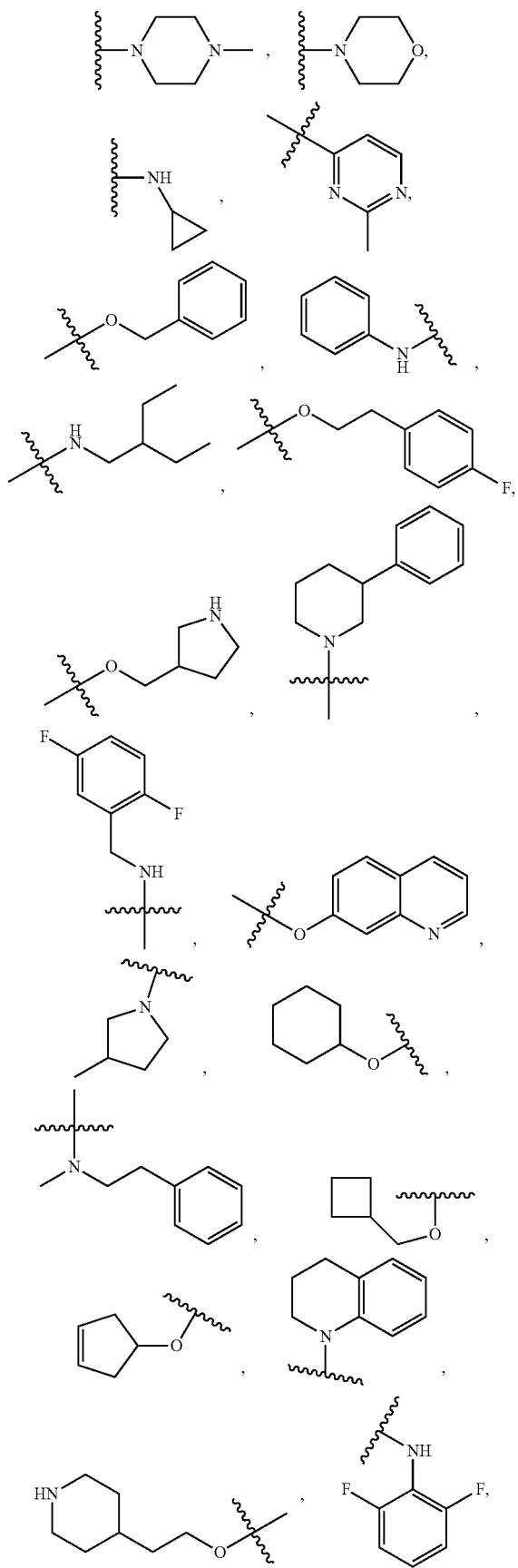

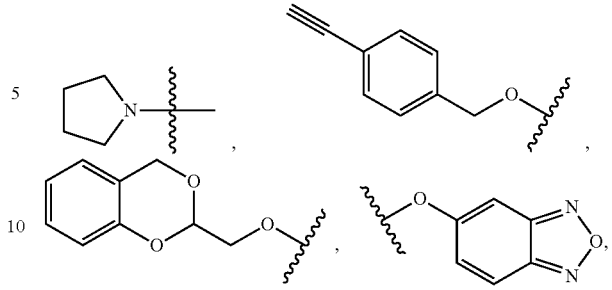

or CO$_2$H.

In some embodiments, R$_2$ is NH$_2$, or NHCH$_2$CH$_2$CH$_3$.

In some embodiments, n is 2. In some embodiments, p is 0. In some embodiments, p is 1.

In some embodiments, in the compound of formula II-i, one or more hydrogen atoms may be replaced by a deuterium atom.

In some embodiments, the compound of formula II or a pharmaceutically acceptable salt thereof is a compound of formula IIa:

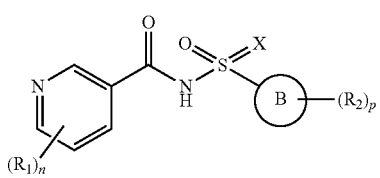

IIa or a pharmaceutically acceptable salt thereof, wherein, independently for each occurrence:

Ring B is a C$_3$-C$_{10}$ cycloalkyl ring; a C$_6$-C$_{10}$ aryl ring; or a C$_3$-C$_{10}$ heteroaryl or C$_3$-C$_{10}$ heterocyclic ring wherein anywhere from 1 to 4 ring atoms are independently O, S, N, or NR;

X is O or NR;

R$_1$ is halo; CN; NRR; C$_1$-C$_6$ alkyl or C$_1$-C$_6$ fluoroalkyl; C$_3$-C$_6$ cycloalkyl; C$_1$-C$_8$ alkoxy or C$_1$-C$_8$ fluoroalkoxy; C$_2$-C$_6$ alkenyl; C$_2$-C$_6$ alkynyl; (C$_1$-C$_9$ alkylene)-R$_3$ wherein up to four CH$_2$ units are independently replaced with O, CO, S, SO, SO$_2$ or NR; C$_6$-C$_{10}$ aryl; C$_3$-C$_{10}$ heteroaryl or C$_3$-C$_{10}$ heterocyclic ring wherein anywhere from 1 to 4 ring atoms are independently O, S, N, or NR; or C$_3$-C$_{10}$ cycloalkyl;

R$_2$ is halo; NRR; CN; CO$_2$R; C$_1$-C$_6$ alkyl or C$_1$-C$_6$ fluoroalkyl; C$_1$-C$_6$ alkoxy or C$_1$-C$_6$ fluoroalkoxy; C$_2$-C$_6$ alkenyl; C$_2$-C$_6$ alkynyl; C$_6$-C$_{10}$ aryl; C$_3$-C$_{13}$ heteroaryl or heterocyclic ring wherein anywhere from 1 to 4 ring atoms are independently O, S, N, or NR; C$_3$-C$_{10}$ cycloalkyl; or a (C$_1$-C$_9$ alkylene)-R$_3$ wherein up to four CH$_2$ units are optionally and independently replaced with O, CO, S, SO, SO$_2$ or NR;

or two R$_2$ may form a =CH$_2$ or =O group;

R$_3$ is H; CF$_3$; CHF$_2$; OR; C≡CH; CO$_2$R; OH; C$_6$-C$_{10}$ aryl; C$_3$-C$_{10}$ heteroaryl or heterocycloalkyl wherein anywhere from 1 to 4 ring atoms are independently O, S, N, or NR; C$_3$-C$_{10}$ cycloalkyl; NRR, NRCOR, CONRR, CN, halo, or SO$_2$R;

R is independently H; OH; CO$_2$H; CO$_2$C$_1$-C$_6$ alkyl; C$_1$-C$_6$ alkyl; C$_2$-C$_6$ alkenyl; C$_2$-C$_6$ alkynyl; C$_6$-C$_{10}$ aryl; C$_3$-C$_{10}$ heteroaryl or heterocycloalkyl wherein anywhere from 1 to 4 ring atoms are independently O, S, or N; or $C_3$-$C_{10}$ cycloalkyl;

n is 2 or 3;

p is 0, 1, 2, or 3; and

Provided that 1) when $R_1$ is adjacent to the carbonyl attached to Ring A, $R_1$ does not contain a ring moiety, 2) at least one $R_1$ is adjacent to the carbonyl attached to Ring A, and 3) at least one $R_1$ is $C_1$-$C_6$ alkyl or $C_1$-$C_6$ fluoroalkyl, $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl.

In some embodiments, Ring B is pyridyl, pyridine-2(1H)-one, pyrazole, indole, aza-indole, thiophene, dihydrobenzofuran, thiazole, pyrrolidinone, or quinoline.

In some embodiments, Ring B is

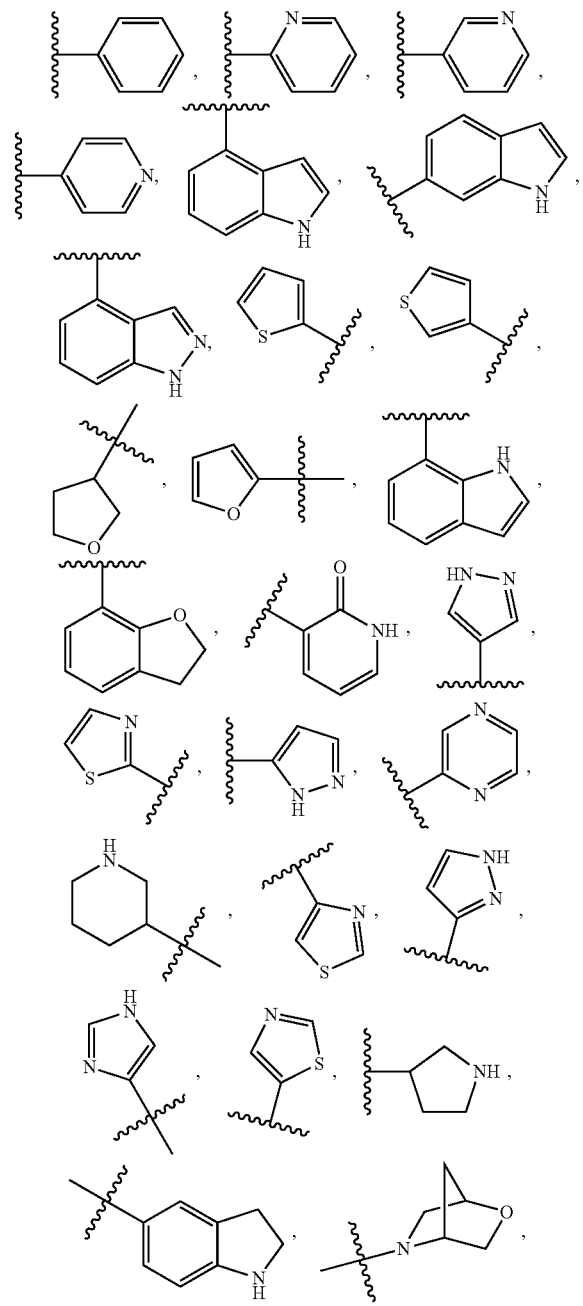

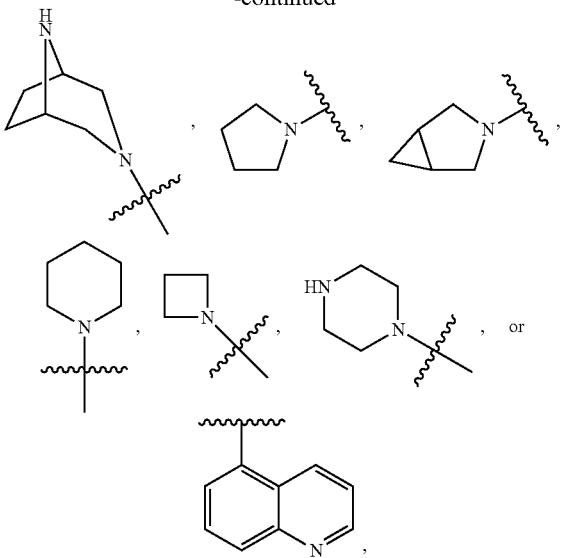

wherein the wavy line ∿ indicates point of attachment of

In some embodiments, X is O.

In some embodiments, $R_1$ is independently halo, amino, OH, $C_1$-$C_6$ fluoroalkyl, CN, $C_1$-$C_6$ alkyl, $C_2$-$C_6$ alkenyl, $C_2$-$C_6$ alkynyl, $C_1$-$C_8$ alkoxy or $C_1$-$C_8$ fluoroalkoxy, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring, or a ($C_1$-$C_9$ alkylene)-$R_3$ wherein up to four $CH_2$ units are independently replaced with O, CO, S, SO, $SO_2$ or NR.

In some embodiments, $R_1$ is $CHF_2CH_2(CH_3)N—$, $(CH_3)_2CHCH_2CH_2O—$, $(CH_3)_3CCH_2CH_2O—$, $(CH_3)_3COCH_2CH_2O—$, $(CH_3)_2CHO—$, $CHF_2CHF_2CH(CH_3)O—$, $—CF_3$, $(CH_3CH_2)_2N—$, $CF_3CH_2CH(CH_3)O—$, $CH_3O—$, $CH_3(CH_2)_4O—$, $CH_3CH_2CH(CH_3)CH(CH_3)O—$, $CH_3CH_2OCH_2CH_2O—$, $CH_3CH_2NCH(CH_3)_2$, $(CH_3)_3CH_2O—$, (R)—$CH_3NCH(CH_3)(CF_3)$, $CH_3OCH_2CH(CH_2CH_3)O—$, $(CH_3)_2N—$, (S)—$CH_3OCH_2CH(CH_3)O—$, $CH_3O(CH_2)_3O—$, $CH_3OC(CH_3)_2(CH_2)_2O$, $CH_3OCH_2CH(CH_3)O$, $CH_3CH(CH_3)CH_2CH(CH_3)O—$, $(CH_3)_3CCH(CH_3)O$, $((CH_3)_2CH)_2CHO—$, $CH_3CH_2CH_2O$, $CH_3CH=CHCH_2O—$, (S)—$CH_3CH_2CH(CH_3)O—$, $CH_3CH_2O$, $(CH_3)_2CHNCH_3$, $(CH_3)_3CCH_2O$, $(CF_3)_2CHO—$, $(CH_3)_3CCH(CH_2CH_3)O$, $CH_3C≡CCH_2CH_2O$, $(CH_3)_3CCH_2CH(CH_3)O—$, $(CH_3)_2C=C(CH_3)$, $CHF_2CH_2O—$, $CH_3CH_2CH_2NH$, $(CH_3)_2CHCH(CH_2CH_3)O$, $((CH_3)_2CH)_2N$, $CH_2=CHCH(CH_3)O$, $CH_2=CHCH_2O—$, $CH_3CH_2C(CH_3)_2O$, $(CH_3CH_2)_2CHO$, $CF_3CH_2O$, $CH_3C(=CH_2)CH_2O$, $(CH_3)_3CCH_2NH$, $CH_3OCH_2C(CH_3)_2O$, $(CH_3)_3CCH_2N(CH_3)$, $(CH_3)_2CHCH(CH_3)NH$, $(CH_3)_2CHO(CH_2)_2O$, $CH_3CH_2CH_2CH(CH_3)O$, $CH_3CF_2CH_2O$, $(CH_3)_3CNH$, (R)—$CH_3CH_2CH(CH_3)O$, $CH_3OCH_2CH_2O$, $(CH_3)_2CHCH_2N(CH_3)$, $CH_3CH_2CH_2CH(CH_3)CH(CH_3)O$, $CH_3CH_2CH_2O$, $CH_3CH_2CH_2N(CH_3)$, (R)—$CH_3OCH_2CH(CH_3)O$, $CF_3CH_2N(CH_3)$, $CH_3CH_2N(CH_3)$, $((CH_3)_3C)_2CHO$, $(CH_3CH_2)_2CHN(CH_3)$, $(CH_3)_2CHN(CH_3)$, $CH_3CH_2OCH_2CH(CH_3)O$, $(CH_3)_3CCH_2NH$, $CF_3CH(CH_3)O$, $CH_3CH_2NCH(CH_3)_2$, (R)—$CF_3CH(CH_3)N(CH_3)$, $(CH_3)_2CHCH(CH_3)$, $CH_3CH_2(CH_3)_2CHCH_2CH_2O$, (S)—$CH_3OCH(CH_3)CH_2O$, $HOCH(CH_3)_2CH_2CH_2NH$, $CF_3CH_2CH_2O$, $CF_3CH_2CH_2O$, $CF_3CH=CHCH_2O$, $CH_3CH_2CH_2CH_2CH_2NH$, or $(CH_3)_3C$.

In some embodiments, R₁ is CH₃, Cl, F, CN, CH₂CH₃, CH(CH₃)₂, OCH₂CH₂OCH₂CH₃,
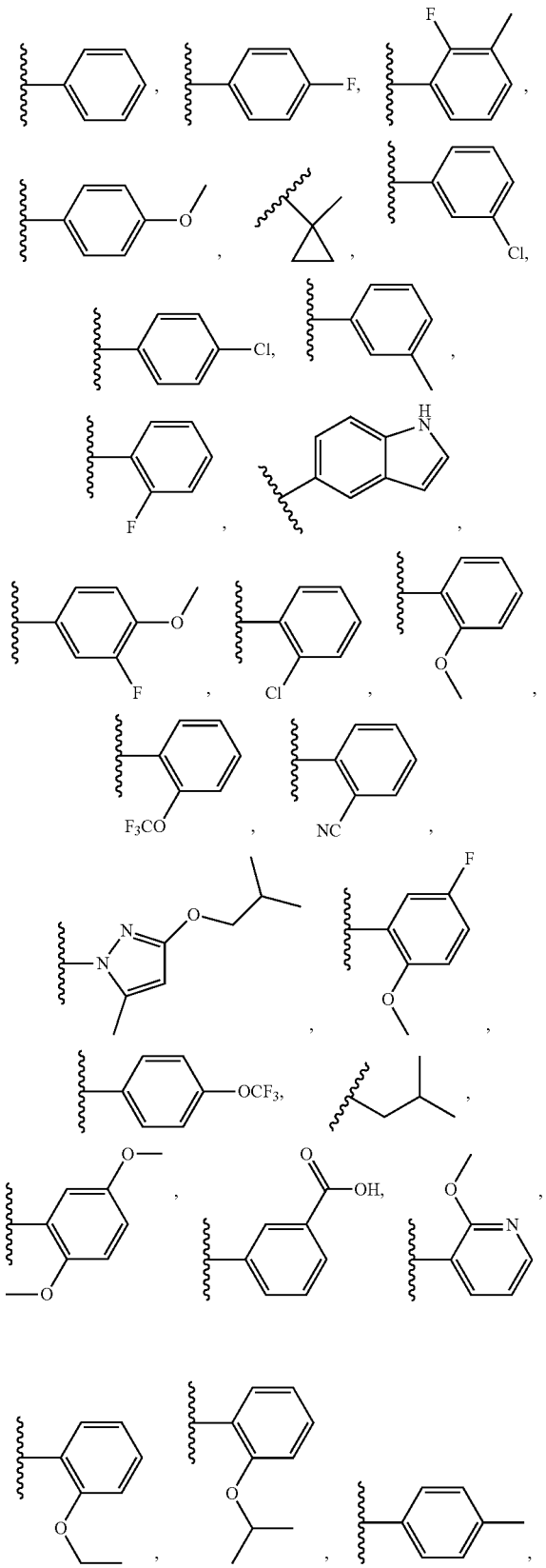
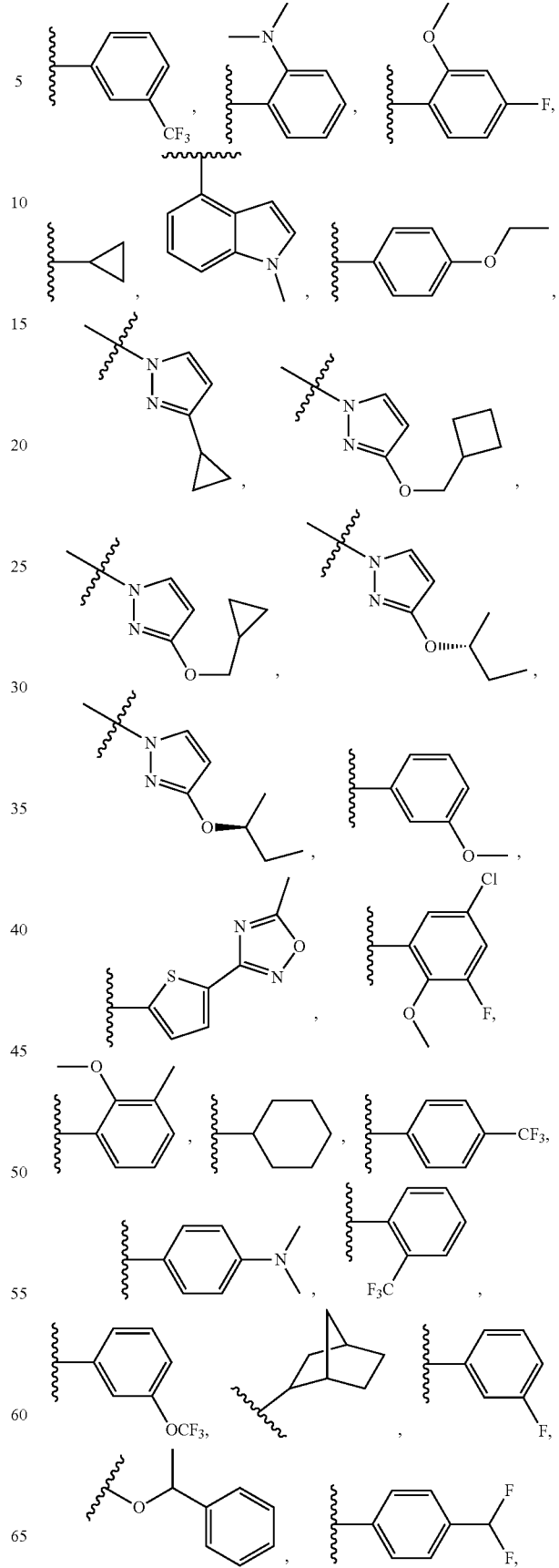

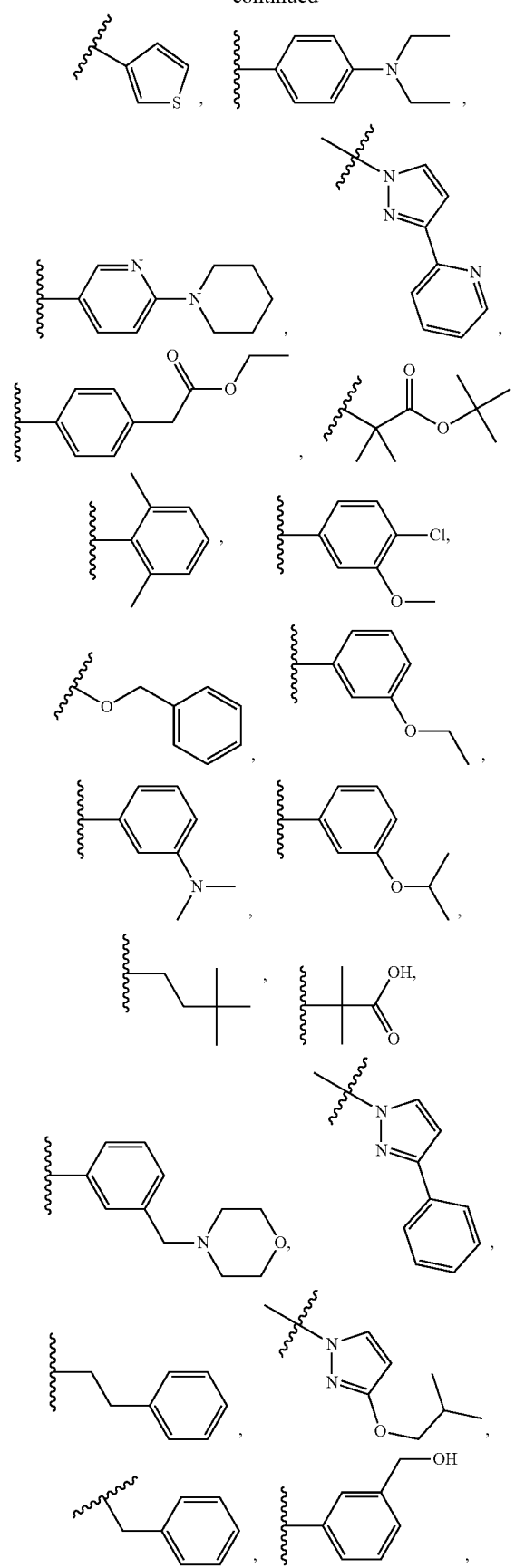
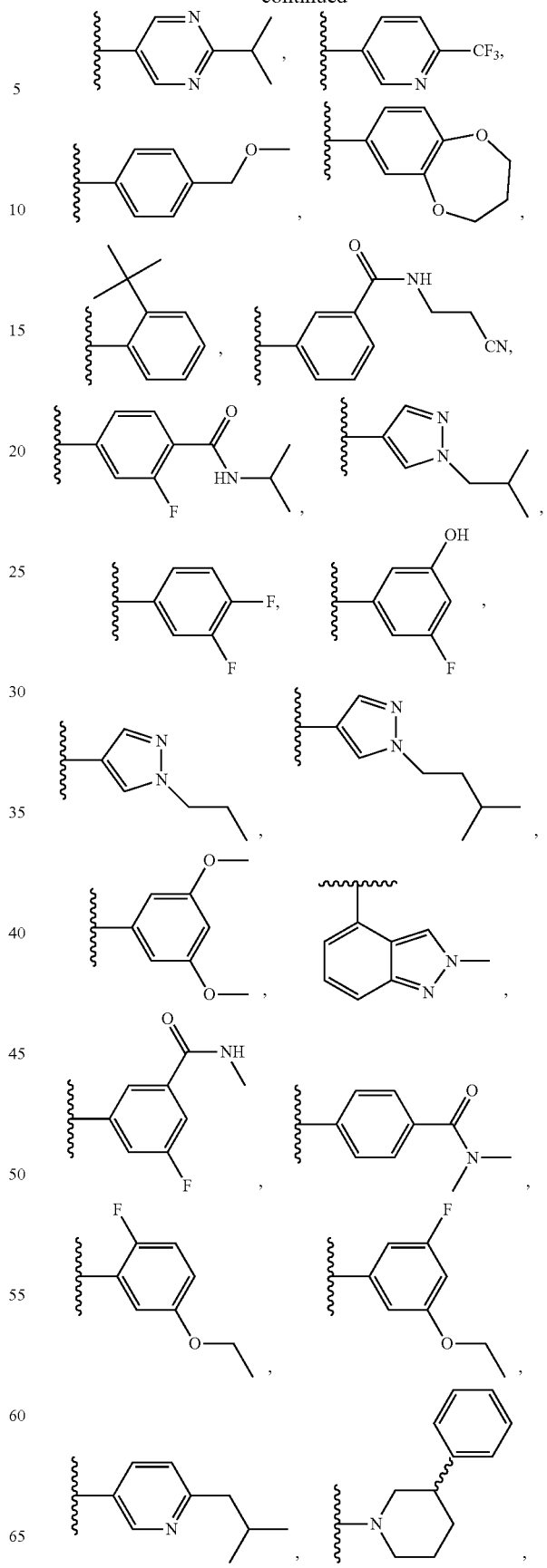

143
-continued
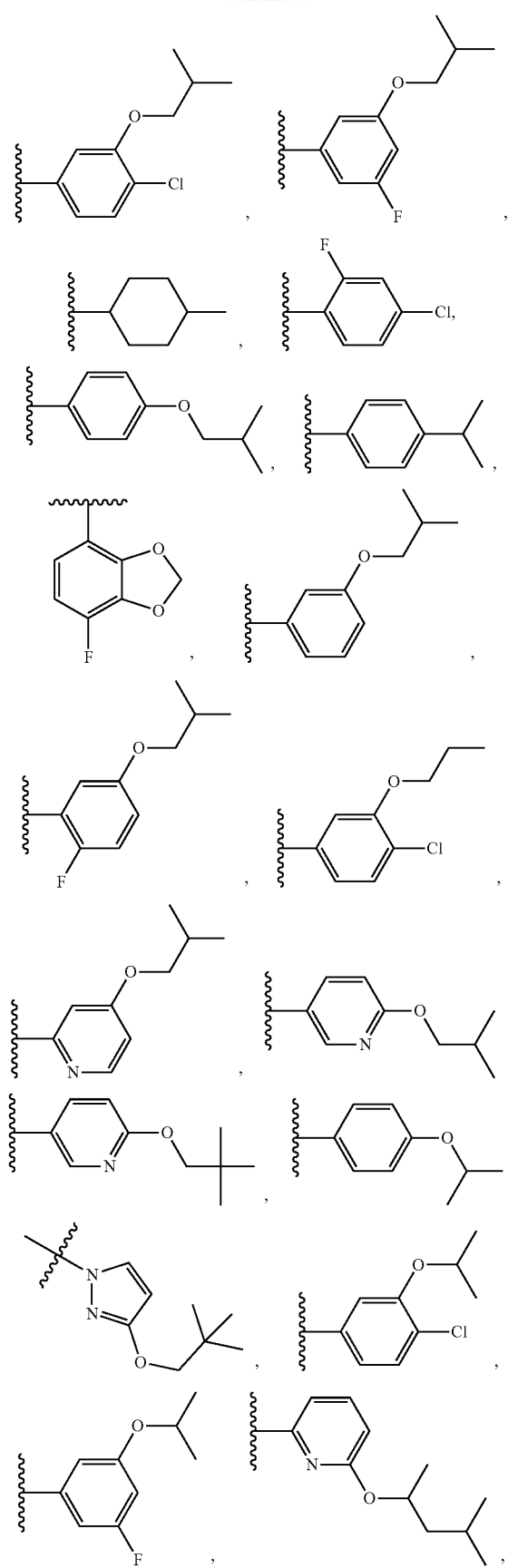
144
-continued
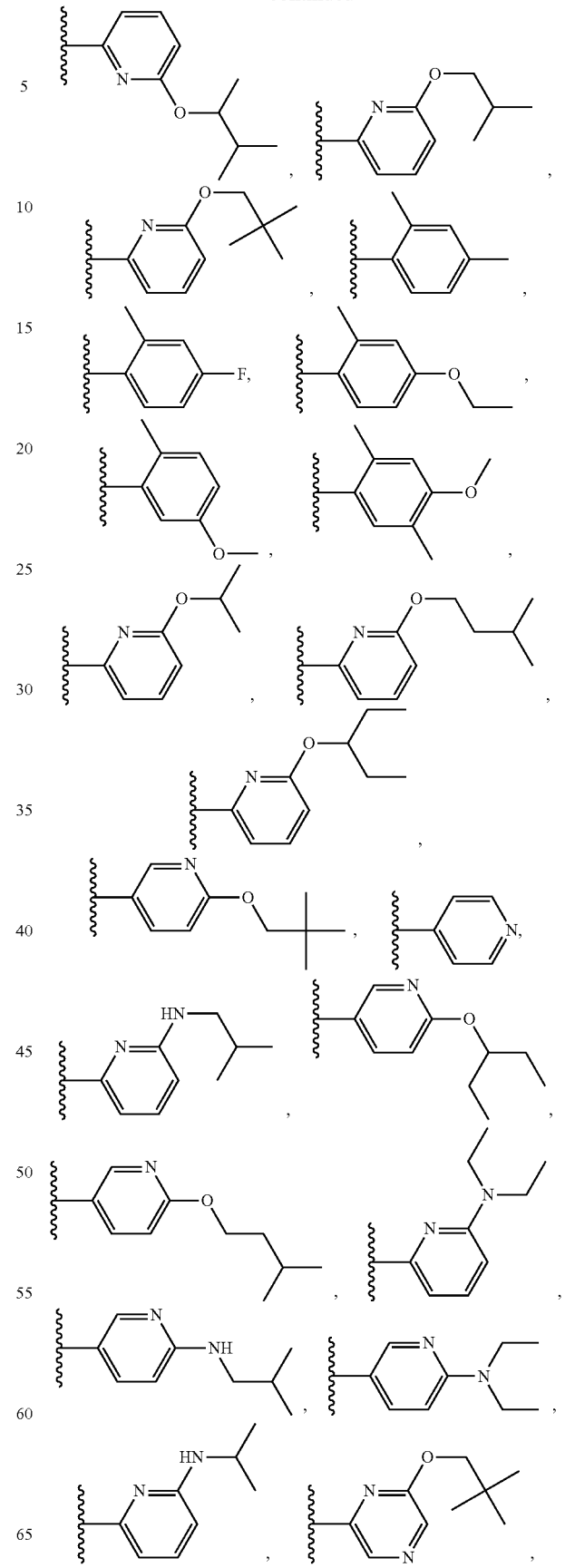

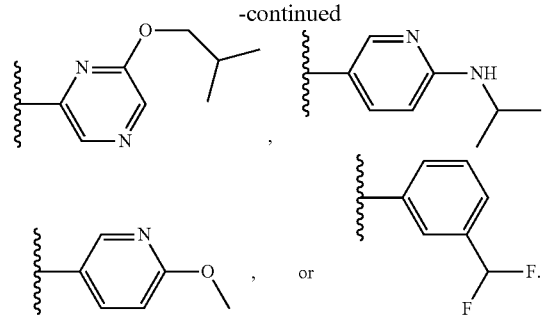

In some embodiments, $R_2$ is halo, CN, amino, OH, $C_1$-$C_6$ alkyl or $C_1$-$C_6$ fluoroalkyl, $C_1$-$C_6$ alkoxy or $C_1$-$C_6$ fluoroalkoxy, $C_3$-$C_{10}$ heterocyclic ring wherein anywhere from 1 to 4 carbon atoms are independently O, S, N, or NR; or a ($C_1$-$C_9$ alkylene)-$R_3$ wherein up to four $CH_2$ units are optionally and independently replaced with O, CO, S, SO, $SO_2$, or NR.

In some embodiments, $R_2$ is Cl, F, OH, CN, $NH_2$, $NH(CH_3)$, $N(CH_3)_2$, $N(CH_3)CH_2CH_2CH_3$, $N(CH_3)CH_2CH_2CH_2CH_3$, $NHCH_2CH_2CH_3$, CH, $CH_2H$, $CH_2CH_3$, $CH_2CH_2CH_3$, =O, $CH_3SO_2$, $CH_3SO_2NH$, $CF_3CONH$, $CH_3CONH$, $CH_3CON(CH_3)$, tBuOCONH, $(CH_3)_2CHOCONH$, $CH(CH_3)_2$, $CHF_2$, $OCH_3$, $OCH_2CH_3$, $OCH_2CH_2CH_3$, $OCH_2CH_2CH(CH_3)_2$, $OCF_3$, $OCHF_2$, $OC(CH_3)_3$, $OCH_2CH_2tBu$, $NHCH(CH_3)(CH_2CH_2CH_3)$, $OCH(CH_3)_2$, $NH(CH_2)_2O(CH_2)_2CH_3$, $C(O)CH_3$, $CH_2CH_2OH$, $CH_2NH_2$, $NH(CH_2)_2OH$, $N(CH_3)CH_2CH_2CH_2OCH_3$, $NHCH_2CH_2COOH$, $NH(CH_2)_2N(CH_3)_2$, $NH(CH_2)_2NH_2$, $NH(CH_2)_3NH_2$, $NH(CH_2)_2OCH_3$, $NHCH(CH_3)_2$,

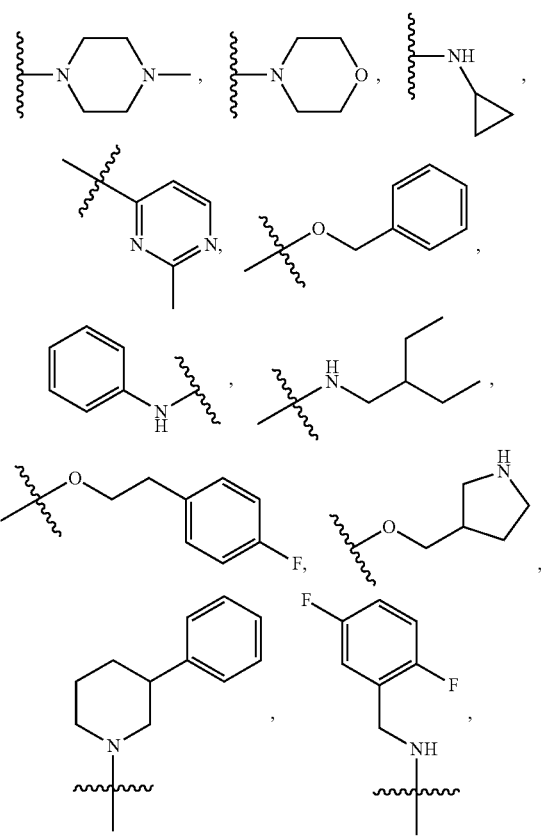

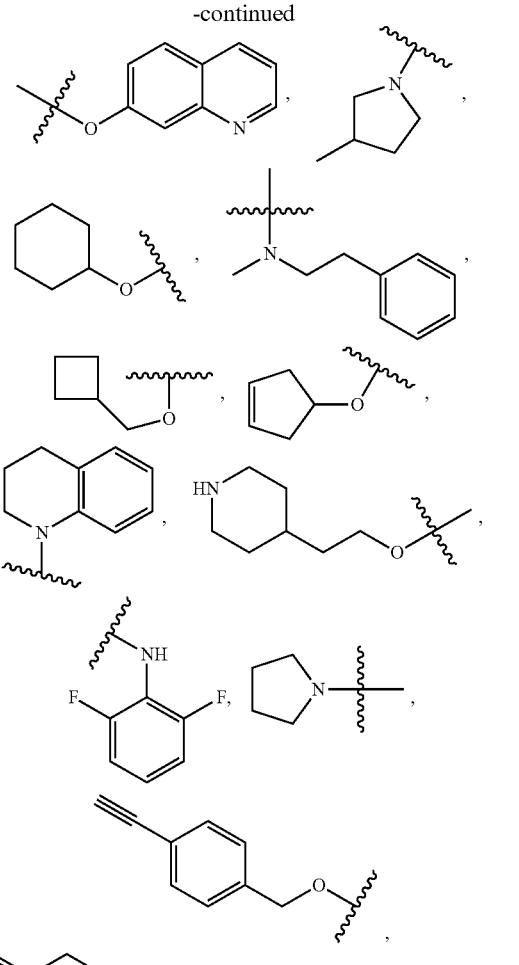

or $CO_2H$.

In some embodiments, $R_2$ is $NH_2$, or $NHCH_2CH_2CH_3$.

In some embodiments, n is 2. In some embodiments, p is 0. In some embodiments, p is 1.

In some embodiments, in the compound of formula IIa, one or more hydrogen atoms may be replaced by a deuterium atom.

In some embodiments, the compounds of formula IIa or a pharmaceutically acceptable salt thereof is a compound of formula IIa-i IIa-i

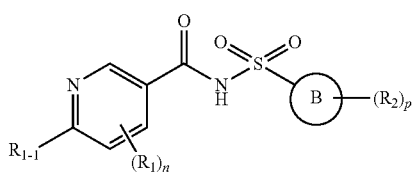

or a pharmaceutically acceptable salt thereof, wherein, independently for each occurrence:

Ring B is a $C_3$-$C_{10}$ cycloalkyl ring; a $C_6$-$C_{10}$ aryl ring; or a $C_3$-$C_{10}$ heteroaryl or $C_3$-$C_{10}$ heterocyclic ring wherein anywhere from 1 to 4 ring atoms are independently O, S, N, or NR;

$R_1$ is halo; CN; NRR; $C_1$-$C_6$ alkyl or $C_1$-$C_6$ fluoroalkyl; $C_3$-$C_6$ cycloalkyl; $C_1$-$C_8$ alkoxy or $C_1$-$C_8$ fluoroalkoxy; $C_2$-$C_6$ alkenyl; $C_2$-$C_6$ alkynyl; ($C_1$-$C_9$ alkylene)-$R_3$ wherein up to four $CH_2$ units are independently replaced with O, CO, S, SO, $SO_2$ or NR; $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_{1-1}$ is $C_1$-$C_6$ alkyl or $C_1$-$C_6$ fluoroalkyl, $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_2$ is halo; NRR; CN; $CO_2R$; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four $CH_2$ units are optionally and independently replaced with O, CO, S, SO, $SO_2$ or NR;

or two $R_2$ may form a $=CH_2$ or $=O$ group;

$R_3$ is H; $CF_3$; $CHF_2$; OR; C≡CH; $CO_2R$; OH; $C_6$-$C_{10}$ aryl, $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or $SO_2R$;

R is independently H; OH; $CO_2H$; $CO_2C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, or N; or $C_3$-$C_{10}$ cycloalkyl;

n is 1 or 2; and p is 0, 1, 2, or 3.

In some embodiments, Ring B is pyridyl, pyridine-2(1H)-one, pyrazole, indole, aza-indole, thiophene, dihydrobenzofuran, thiazole, pyrrolidinone, or quinoline.

In some embodiments, Ring B is

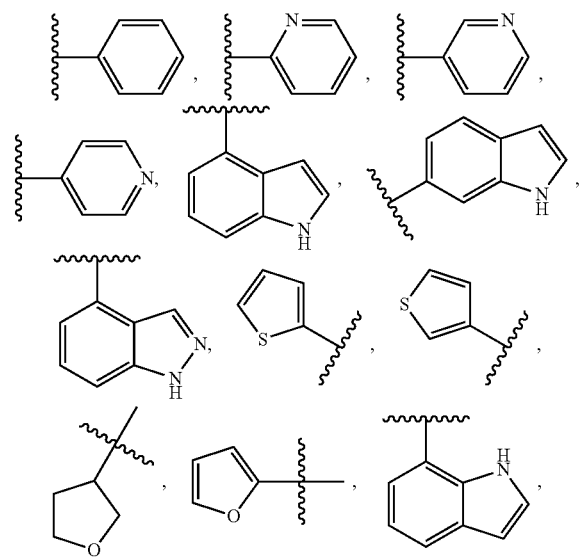

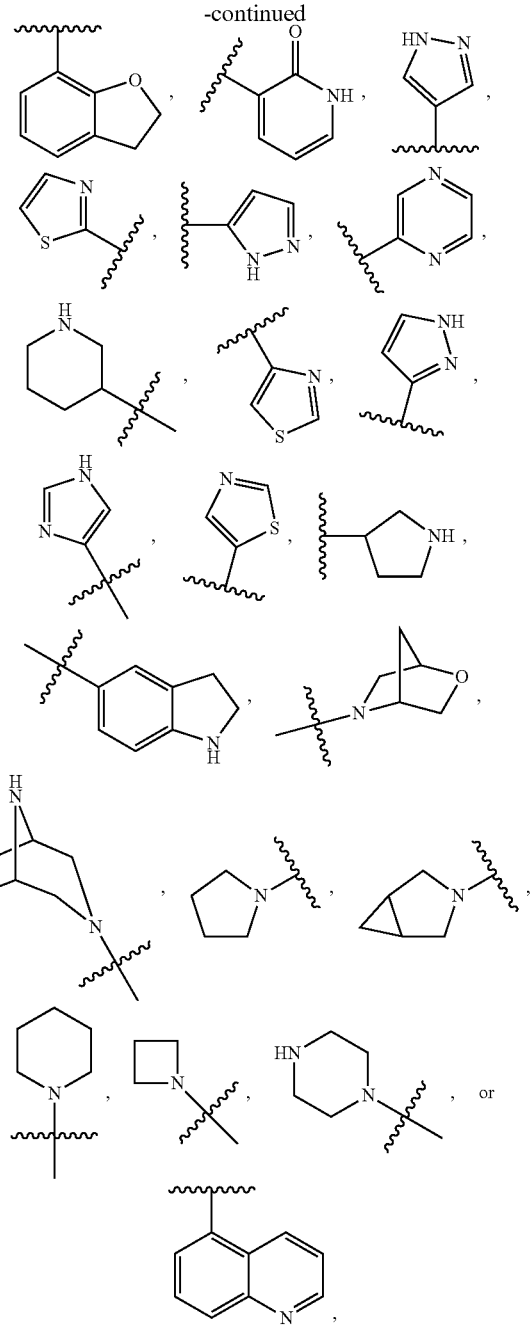

wherein the wavy line indicates point of attachment of Ring B to the sulfonyl.

In some embodiments, $R_1$ is independently halo, amino, OH, $C_1$-$C_6$ fluoroalkyl, CN, $C_1$-$C_6$ alkyl, $C_2$-$C_6$ alkenyl, $C_2$-$C_6$ alkynyl, $C_1$-$C_8$ alkoxy or $C_1$-$C_8$ fluoroalkoxy, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring, or a ($C_1$-$C_9$ alkylene)-$R_3$ wherein up to four $CH_2$ units are independently replaced with O, CO, S, SO, $SO_2$ or NR.

In some embodiments, $R_{1-1}$ is $C_1$-$C_6$ alkyl or $C_1$-$C_6$ fluoroalkyl, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring.

In some embodiments, $R_{1-1}$ is tert-butyl,

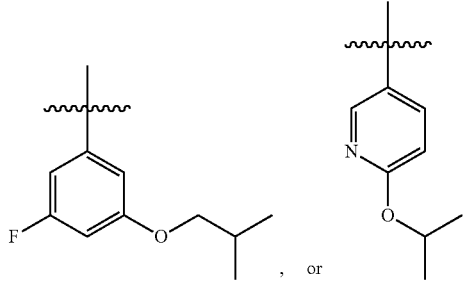

, or

In some embodiments, $R_1$ is $CHF_2CH_2(CH_3)N—$, $(CH_3)_2CHCH_2CH2O—$, $(CH_3)_3CCH_2CH_2O—$, $(CH_3)_3COCH_2CH_2O—$, $(CH_3)_2CHO—$, $CHF_2CHF_2CH(CH_3)O—$, $—CF_3$, $(CH_3CH_2)_2N—$, $CF_3CH_2CH(CH_3)O—$, $CH_3O—$, $CH_3(CH_2)_4O—$, $CH_3CH_2CH(CH_3)CH(CH_3)O—$, $CH_3CH_2OCH_2CH_2O—$, $CH_3CH_2NCH(CH_3)_2$, $(CH_3)_3CH_2O—$, $(R)—CH_3NCH(CH_3)(CF_3)$, $CH_3OCH_2CH(CH_2CH_3)O—$, $(CH_3)_2N—$, $(S)—CH_3OCH_2CH(CH_3)O—$, $CH_3O(CH_2)_3O—$, $CH_3OC(CH_3)_2(CH_2)_2O$, $CH_3OCH_2CH(CH_3)O$, $CH_3CH(CH_3)CH_2CH(CH_3)O—$, $(CH_3)_3CCH(CH_3)O$, $((CH_3)_2CH)_2CHO—$, $CH_3CH_2CH_2O$, $CH_3CH=CHCH_2O—$, $(S)—CH_3CH_2CH(CH_3)O—$, $CH_3CH_2O$, $(CH_3)_2CHNCH_3$, $(CH_3)_3CCH_2O$, $(CF_3)_2CHO—$, $(CH_3)_3CCH(CH_2CH_3)O$, $CH_3C\equiv CCH_2CH_2O$, $(CH_3)_3CCH_2CH(CH_3)O—$, $(CH_3)_2C=C(CH_3)$, $CHF_2CH_2O—$, $CH_3CH_2CH_2NH$, $(CH_3)_2CHCH(CH_2CH_3)O$, $((CH_3)_2CH)_2N$, $CH_2=CHCH(CH_3)O$, $CH_2=CHCH_2O—$, $CH_3CH_2C(CH_3)_2O$, $(CH_3CH_2)_2CHO—$, $CF_3CH_2O$, $CH_3C(=CH_2)CH_2O$, $(CH_3)_3CCH_2CH_2NH$, $CH_3OCH_2C(CH_3)_2O$, $(CH_3)_3CCH_2N(CH_3)$, $(CH_3)_2CHCH(CH_3)NH$, $(CH_3)_2CHO(CH_2)_2O$, $CH_3CH_2CH_2CH(CH_3)O$, $CH_3CF_2CH_2O$, $(CH_3)_3CNH$, $(R)—CH_3CH_2CH(CH_3)O$, $CH_3OCH_2CH_2O$, $(CH_3)_2CHCH_2N(CH_3)$, $CH_3CH_2CH_2CH(CH_3)CH(CH_3)O$, $CH_3CH_2CH_2CH_2O$, $CH_3CH_2CH_2N(CH_3)$, $(R)—CH_3OCH_2CH(CH_3)O$, $CF_3CH_2N(CH_3)$, $CH_3CH_2N(CH_3)$, $((CH_3)_3C)_2CHO$, $(CH_3CH_2)_2CHN(CH_3)$, $(CH_3)_2CHN(CH_3)$, $CH_3CH_2OCH_2CH(CH_3)O$, $(CH_3)_3CCH_2NH$, $CF_3CH(CH_3)O$, $CH_3CH_2NCH(CH_3)_2$, $(R)—CF_3CH(CH_3)N(CH_3)$, $(CH_3)_2CHCH(CH_3)$, $CH_3CH_2(CH_3)_2CHCH(CH_3)_2$, $(S)—CH_3OCH(CH_3)CH_2O$, $HOCH(CH_3)_2CH_2CH_2NH$, $CF_3CH_2CH_2O$, $CF_3CH_2CH_2CH_2O$, $CF_3CH=CHCH_2O$, or $CH_3CH_2CH_2CH_2CH_2NH$.

In some embodiments, $R_2$ is halo, CN, amino, OH, $C_1$-$C_6$ alkyl or $C_1$-$C_6$ fluoroalkyl, $C_1$-$C_6$ alkoxy or $C_1$-$C_6$ fluoroalkoxy, $C_3$-$C_{10}$ heterocyclic ring wherein anywhere from 1 to 4 carbon atoms are independently O, S, N, or NR; or a ($C_1$-$C_9$ alkylene)-$R_3$ wherein up to four $CH_2$ units are optionally and independently replaced with O, CO, S, SO, $SO_2$ or NR.

In some embodiments, $R_2$ is Cl, F, OH, CN, $NH_2$, $NH(CH_3)$, $N(CH_3)_2$, $N(CH_3)CH_2CH_2CH_3$, $N(CH_3)CH_2CH_2CH_2CH_3$, $NHCH_2CH_2CH_3$, $CH_3$, $CH_2OH$, $CH_2CH_3$, $CH_2CH_2CH_3$, $=O$, $CH_3SO_2$, $CH_3SO_2NH$, $CF_3CONH$, $CH_3CONH$, $CH_3CON(CH_3)$, $tBuOCONH$, $(CH_3)_2CHOCONH$, $CH(CH_3)_2$, $CHF_2$, $OCH_3$, $OCH_2CH_3$, $OCH_2CH_2CH_3$, $OCH_2CH_2CH(CH_3)_2$, $OCF_3$, $OCHF_2$, $OC(CH_3)_3$, $OCH_2CH_2tBu$, $NHCH(CH_3)(CH_2CH_2CH_3)$, $OCH(CH_3)_2$, $NH(CH_2)_2O(CH_2)_2CH_3$, $C(O)CH_3$, $CH_2CH_2OH$, $CH_2NH_2$, $NH(CH_2)_2OH$, $N(CH_3)CH_2CH_2CH_2OCH_3$, $NHCH_2CH_2COOH$, $NH(CH_2)_2N(CH_3)_2$, $NH(CH_2)_2NH_2$, $NH(CH_2)_3NH_2$, $NH(CH_2)_2OCH_3$, $NHCH(CH_3)_2$,

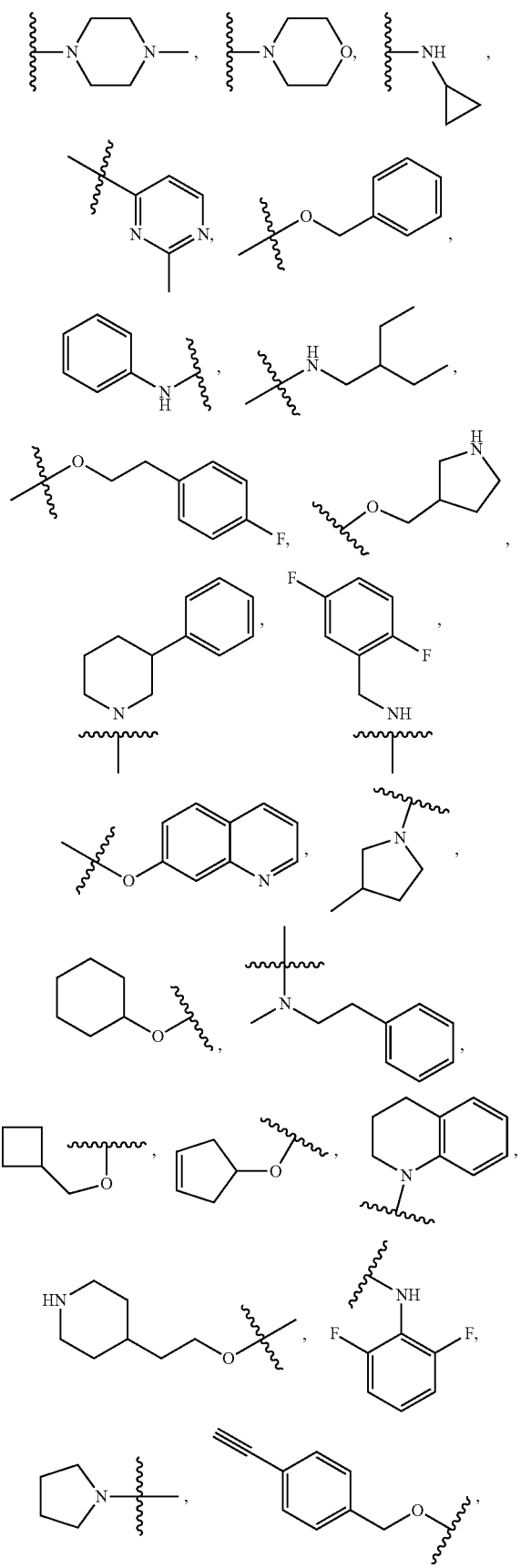

-continued

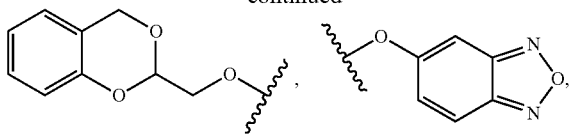

or CO₂H.

In some embodiments, R₂ is NH₂, or NHCH₂CH₂CH₃.

In some embodiments, n is 1. In some embodiments, p is 0. In some embodiments, p is 1.

In some embodiments, in the compound of formula IIa-i, one or more hydrogen atoms may be replaced by a deuterium atom.

In some embodiments, the compounds of formula IIa-i or a pharmaceutically acceptable salt thereof is a compound of formula IIa-i-1

IIa-i-1

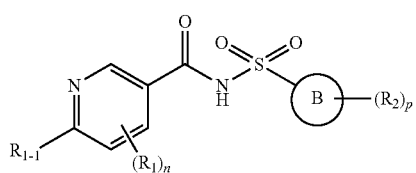

or a pharmaceutically acceptable salt thereof, wherein, independently for each occurrence:

Ring B is a $C_3$-$C_{10}$ heteroaryl or $C_3$-$C_{10}$ heterocyclic ring wherein anywhere from 1 to 4 ring atoms are independently O, S, N, or NR;

$R_1$ is halo; CN; NRR; $C_1$-$C_6$ alkyl or $C_1$-$C_6$ fluoroalkyl; $C_3$-$C_6$ cycloalkyl; $C_1$-$C_8$ alkoxy or $C_1$-$C_8$ fluoroalkoxy; $C_2$-$C_6$ alkenyl; $C_2$-$C_6$ alkynyl; ($C_1$-$C_9$ alkylene)-$R_3$ wherein up to four CH₂ units are independently replaced with O, CO, S, SO, SO₂ or NR; $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_{1-1}$ is $C_1$-$C_6$ alkyl or $C_1$-$C_6$ fluoroalkyl, $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_2$ is halo; NRR; CN; CO₂R; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four CH₂ units are optionally and independently replaced with O, CO, S, SO, SO₂ or NR;

or two $R_2$ may form a =CH₂ or =O group;

$R_3$ is H; CF₃; CHF₂; OR; C≡CH; CO₂R; OH; $C_6$-$C_{10}$ aryl, $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or SO₂R;

R is independently H; OH; CO₂H; CO₂$C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, or N; or $C_3$-$C_{10}$ cycloalkyl;

n is 1 or 2; and p is 0, 1, 2, or 3.

In some embodiments, Ring B is pyridyl, pyridine-2(1H)-one, pyrazole, indole, aza-indole, thiophene, dihydrobenzofuran, thiazole, pyrrolidinone, or quinoline.

In some embodiments, Ring B is

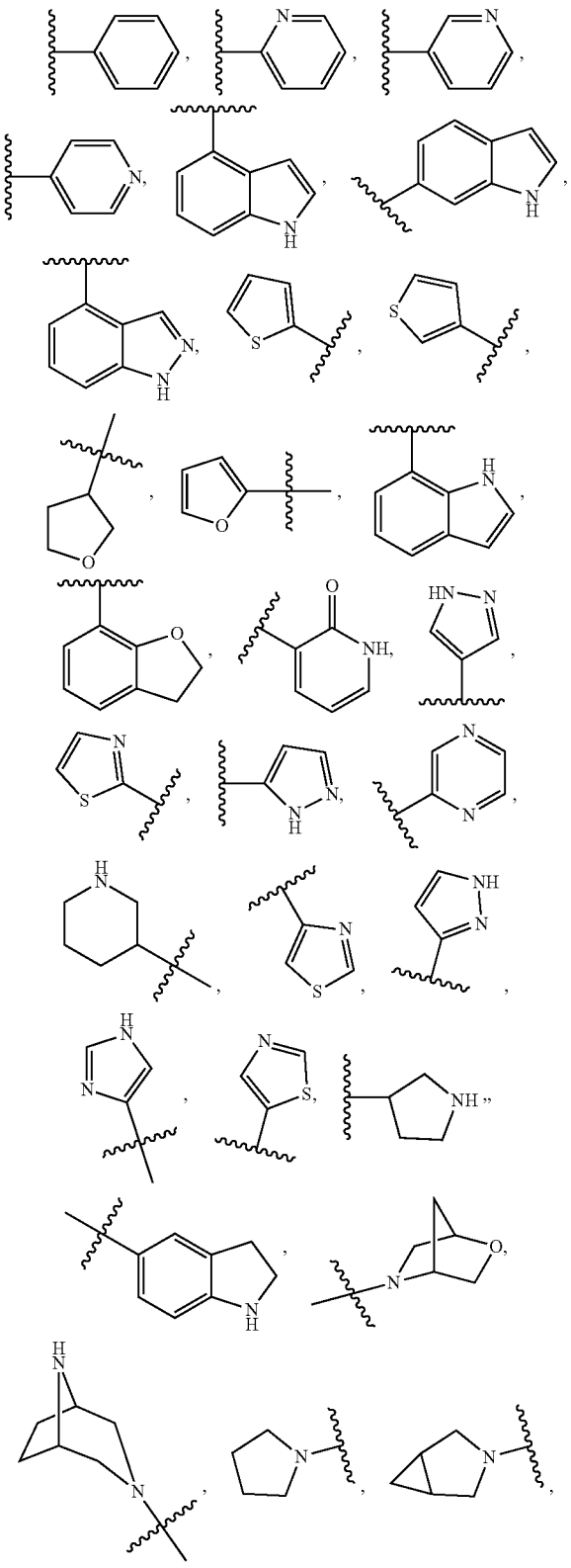

-continued

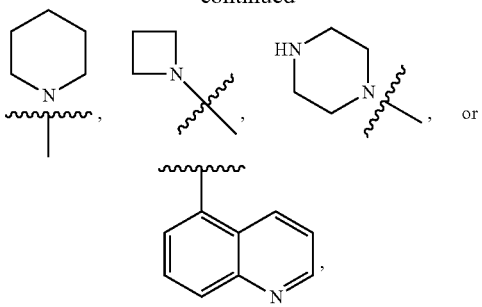

wherein the wavy line ⌇ indicates point of attachment of Ring B to the sulfonyl.

In some embodiments, $R_1$ is independently halo, amino, OH, $C_1$-$C_6$ fluoroalkyl, CN, $C_1$-$C_6$ alkyl, $C_2$-$C_6$ alkenyl, $C_2$-$C_6$ alkynyl, $C_1$-$C_8$ alkoxy or $C_1$-$C_8$fluoroalkoxy, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring, or a ($C_1$-$C_9$ alkylene)-$R_3$ wherein up to four $CH_2$ units are independently replaced with O, CO, S, SO, $SO_2$ or NR.

In some embodiments, $R_{1-1}$ is $C_1$-$C_6$ alkyl or $C_1$-$C_6$ fluoroalkyl, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring.

In some embodiments, $R_{1-1}$ is tert-butyl,

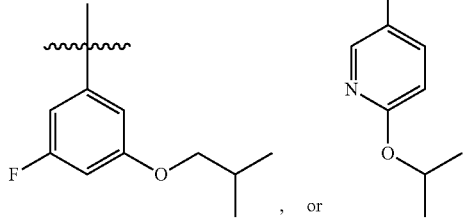

, or

In some embodiments, $R_1$ is $CHF_2CH_2(CH_3)N-$, $(CH_3)_2CHCH_2CH2O-$, $(CH_3)_3CCH_2CH_2O-$, $(CH_3)_3COCH_2CH_2O-$, $(CH_3)_2CHO-$, $CHF_2CHF_2CH(CH_3)O-$, $-CF_3$, $(CH_3CH_2)_2N-$, $CF_3CH_2CH(CH_3)O-$, $CH_3O-$, $CH_3(CH_2)_4O-$, $CH_3CH_2CH(CH_3)CH(CH_3)O-$, $CH_3CH_2OCH_2CH_2O-$, $CH_3CH_2NCH(CH_3)_2$, $(CH_3)_3CH_2O-$, (R)-$CH_3NCH(CH_3)(CF_3)$, $CH_3OCH_2CH(CH_2CH_3)O-$, $(CH_3)_2N-$, (S)-$CH_3OCH_2CH(CH_3)O-$, $CH_3O(CH_2)_3O-$, $CH_3OC(CH_3)_2(CH_2)_2O$, $CH_3OCH_2CH(CH_3)O$, $CH_3CH(CH_3)CH_2CH(CH_3)O-$, $(CH_3)_3CCH(CH_3)O$, $((CH_3)_2CH)_2CHO-$, $CH_3CH_2CH_2O$, $CH_3CH=CHCH_2O-$, (S)-$CH_3CH_2CH(CH_3)O-$, $CH_3CH_2O$, $(CH_3)_2CHNCH_3$, $(CH_3)_3CCH_2O$, $(CF_3)_2CHO-$, $(CH_3)_3CCH(CH_2CH_3)O$, $CH_3C\equiv CCH_2CH_2O$, $(CH_3)_3CCH_2CH(CH_3)O-$, $(CH_3)_2C=C(CH_3)$, $CHF_2CH_2O-$, $CH_3CH_2CH_2NH$, $(CH_3)_2CHCH(CH_2CH_3)O$, $((CH_3)_2CH)_2N$, $CH_2=CHCH(CH_3)O$, $CH_2=CHCH_2O-$, $CH_3CH_2C(CH_3)_2O$, $(CH_3CH_2)_2CHO$, $CF_3CH_2O$, $CH_3C(=CH_2)CH_2O$, $(CH_3)_3CCH_2CH_2NH$, $CH_3OCH_2C(CH_3)_2O$, $(CH_3)_3CCH_2N(CH_3)$, $(CH_3)_2CHCH(CH_3)NH$, $(CH_3)_2CHO(CH_2)_2O$, $CH_3CH_2CH(CH_3)O$, $CH_3CF_2CH_2O$, $(CH_3)_3CNH$, (R)-$CH_3CH_2CH(CH_3)O$, $CH_3OCH_2CH_2O$, $(CH_3)_2CHCH_2N(CH_3)$, $CH_3CH_2CH_2CH$ $(CH_3)CH(CH_3)O$, $CH_3CH_2CH_2CH_2O$, $CH_3CH_2CH_2N$ $(CH_3)$, (R)-$CH_3OCH_2CH(CH_3)O$, $CF_3CH_2N(CH_3)$, $CH_3CH_2N(CH_3)$, $((CH_3)_3C)_2CHO$, $(CH_3CH_2)_2CHN(CH_3)$, $(CH_3)_2CHN(CH_3)$, $CH_3CH_2OCH_2CH(CH_3)O$, $(CH_3)_3CCH_2NH$, $CF_3CH(CH_3)O$, $CH_3CH_2NCH(CH_3)_2$, $(R)-CF_3CH(CH_3)N(CH_3)$, $(CH_3)_2CHCH(CH_3)$, $CH_3CH_2(CH_3)_2CHCH_2CH_2O$, (S)-$CH_3OCH(CH_3)CH_2O$, $HOCH(CH_3)_2CH_2CH_2NH$, $CF_3CH_2CH_2O$, $CF_3CH_2CH_2CH_2O$, $CF_3CH=CHCH_2O$, or $CH_3CH_2CH_2CH_2CH_2NH$.

In some embodiments, $R_2$ is halo, CN, amino, OH, $C_1$-$C_6$ alkyl or $C_1$-$C_6$ fluoroalkyl, $C_1$-$C_6$ alkoxy or $C_1$-$C_6$ fluoroalkoxy, $C_3$-$C_{10}$ heterocyclic ring wherein anywhere from 1 to 4 carbon atoms are independently O, S, N, or NR; or a ($C_1$-$C_9$ alkylene)-$R_3$ wherein up to four $CH_2$ units are optionally and independently replaced with O, CO, S, SO, $SO_2$ or NR.

In some embodiments, $R_2$ is Cl, F, OH, CN, $NH_2$, $NH(CH_3)$, $N(CH_3)_2$, $N(CH_3)CH_2CH_2CH_3$, $N(CH_3)CH_2CH_2CH_2CH_3$, $NHCH_2CH_2CH_3$, $CH_3$, $CH_2OH$, $CH_2CH_3$, $CH_2CH_2CH_3$, =O, $CH_3SO_2$, $CH_3SO_2NH$, $CF_3CONH$, $CH_3CONH$, $CH_3CON(CH_3)$, tBuOCONH, $(CH_3)_2CHOCONH$, $CH(CH_3)_2$, $CHF_2$, $OCH_3$, $OCH_2CH_3$, $OCH_2CH_2CH_3$, $OCH_2CH_2CH(CH_3)_2$, $OCF_3$, $OCHF_2$, $OC(CH_3)_3$, $OCH_2CH_2tBu$, $NHCH(CH_3)(CH_2CH_2CH_3)$, $OCH(CH_3)_2$, $NH(CH_2)_2O(CH_2)_2CH_3$, $C(O)CH_3$, $CH_2CH_2OH$, $CH_2NH_2$, $NH(CH_2)_2OH$, $N(CH_3)CH_2CH_2CH_2OCH_3$, $NHCH_2CH_2COOH$, $NH(CH_2)_2N(CH_3)_2$, $NH(CH_2)_2NH_2$, $NH(CH_2)_3NH_2$, $NH(CH_2)_2OCH_3$, $NHCH(CH_3)_2$,

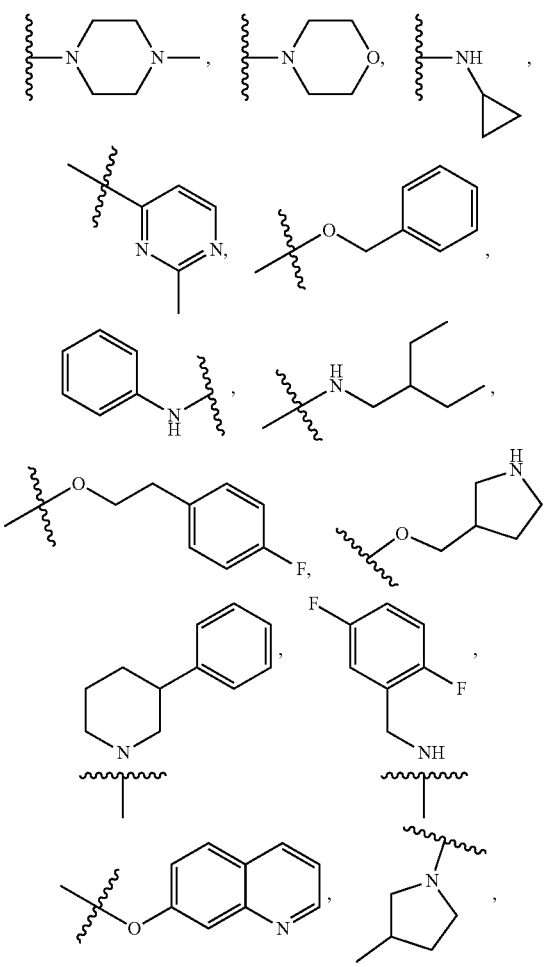

-continued

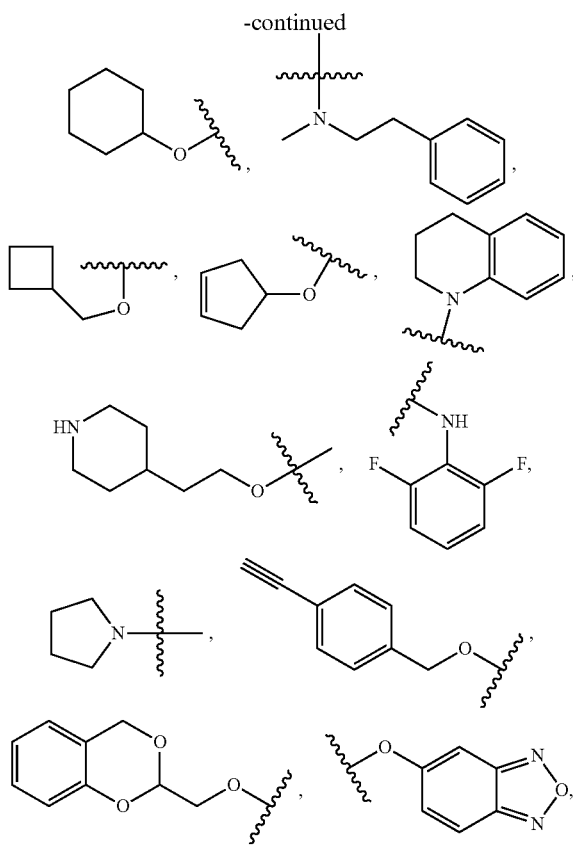

or CO₂H.

In some embodiments, R₂ is NH₂, or NHCH₂CH₂CH₃.

In some embodiments, n is 1. In some embodiments, p is 0. In some embodiments, p is 1.

In some embodiments, in the compound of formula IIa-i-1, one or more hydrogen atoms may be replaced by a deuterium atom.

In some embodiments, the compounds of formula IIa-i-1 or a pharmaceutically acceptable salt thereof is a compound of formula IIa-i-2

IIa-i-2

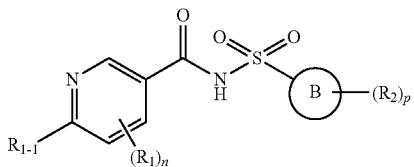

or a pharmaceutically acceptable salt thereof, wherein, independently for each occurrence:
Ring B is a pyridinyl;
R₁ is halo; CN; NRR; $C_1$-$C_6$ alkyl or $C_1$-$C_6$ fluoroalkyl; $C_3$-$C_6$ cycloalkyl; $C_1$-$C_8$ alkoxy or $C_1$-$C_8$ fluoroalkoxy; $C_2$-$C_6$ alkenyl; $C_2$-$C_6$ alkynyl; ($C_1$-$C_9$ alkylene)-$R_3$ wherein up to four CH₂ units are independently replaced with O, CO, S, SO, SO₂ or NR; $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;
$R_{1-1}$ is $C_1$-$C_6$ alkyl or $C_1$-$C_6$ fluoroalkyl, $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;
R₂ is halo; NRR; CN; CO₂R; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four CH₂ units are optionally and independently replaced with O, CO, S, SO, SO₂ or NR;
or two R₂ may form a =CH₂ or =O group;
$R_3$ is H; CF₃; CHF₂; OR; C≡CH; CO₂R; OH; $C_6$-$C_{10}$ aryl, $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or SO₂R;
R is independently H; OH; CO₂H; CO₂$C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, or N; or $C_3$-$C_{10}$ cycloalkyl;
n is 1 or 2; and
p is 0, 1, 2, or 3.

In some embodiments, Ring B is

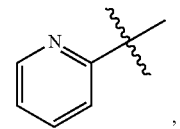 [SMILES: *c1ccccn1]

wherein the wavy line ⁓ indicates point of attachment of Ring B to the sulfonyl.

In some embodiments, R₁ is independently halo, amino, OH, $C_1$-$C_6$ fluoroalkyl, CN, $C_1$-$C_6$ alkyl, $C_2$-$C_6$ alkenyl, $C_2$-$C_6$ alkynyl, $C_1$-$C_8$ alkoxy or $C_1$-$C_8$ fluoroalkoxy, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring, or a ($C_1$-$C_9$ alkylene)-$R_3$ wherein up to four CH₂ units are independently replaced with O, CO, S, SO, SO₂ or NR.

In some embodiments, $R_{1-1}$ is $C_1$-$C_6$ alkyl or $C_1$-$C_6$ fluoroalkyl, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring.

In some embodiments, $R_{1-1}$ is tert-butyl,

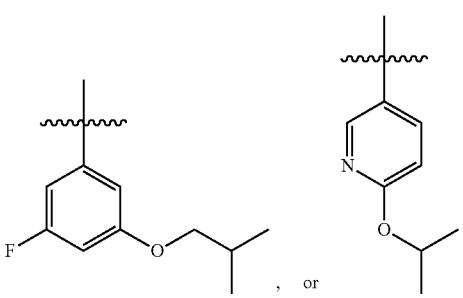

In some embodiments, R₁ is CHF₂CH₂(CH₃)N—, (CH₃)₂CHCH₂CH₂O—, (CH₃)₃CCH₂CH₂O—, (CH₃)₃COCH₂CH₂O—, (CH₃)₂CHO—, CHF₂CHF₂CH(CH₃)O—, —CF₃, (CH₃CH₂)₂N—, CF₃CH₂CH(CH₃)O—, CH₃O—, CH₃(CH₂)₄O—, CH₃CH₂CH(CH₃)CH(CH₃)O—, CH₃CH₂OCH₂CH₂O—, CH₃CH₂NCH(CH₃)₂, (CH₃)₃CH₂O—, (R)—CH₃NCH(CH₃)(CF₃), CH₃OCH₂CH(CH₂CH₃)O—, (CH₃)₂N—, (S)—CH₃OCH₂CH(CH₃)O—, CH₃O(CH₂)₃O—, CH₃OC(CH₃)₂(CH₂)₂O, CH₃OCH₂CH(CH₃)O, CH₃CH(CH₃)CH₂CH(CH₃)O—, (CH₃)₃CCH(CH₃)O, ((CH₃)₂CH)₂CHO—, CH₃CH₂CH₂O, CH₃CH=CHCH₂O—, (S)—CH₃CH₂CH(CH₃)O—, CH₃CH₂O, (CH₃)₂CHNCH₃, (CH₃)₃CCH₂O, (CF₃)₂CHO—, (CH₃)₃CCH(CH₂CH₃)O, CH₃C≡CCH₂CH₂O, (CH₃)₃CCH₂CH(CH₃)O—, (CH₃)₂C=C(CH₃), CHF₂CH₂O—, CH₃CH₂CH₂NH, (CH₃)₂CHCH(CH₂CH₃)O, ((CH₃)₂CH)₂N, CH₂=CHCH(CH₃)O, CH₂=CHCH₂O—, CH₃CH₂C(CH₃)₂O, (CH₃CH₂)₂CHO, CF₃CH₂O, CH₃C(=CH₂)CH₂O, (CH₃)₃CCH₂CH₂NH, CH₃OCH₂C(CH₃)₂O, (CH₃)₃CCH₂N(CH₃), (CH₃)₂CHCH(CH₃)NH, (CH₃)₂CHO(CH₂)₂O, CH₃CH₂CH₂CH(CH₃)O, CH₃CF₂CH₂O, (CH₃)₃CNH, (R)—CH₃CH₂CH(CH₃)O, CH₃OCH₂CH₂O, (CH₃)₂CHCH₂N(CH₃), CH₃CH₂CH₂CH(CH₃)CH(CH₃)O, CH₃CH₂CH₂CH₂O, CH₃CH₂CH₂N(CH₃), (R)—CH₃OCH₂CH(CH₃)O, CF₃CH₂N(CH₃), CH₃CH₂N(CH₃), ((CH₃)₃C)₂CHO, (CH₃CH₂)₂CHN(CH₃), (CH₃)₂CHN(CH₃), CH₃CH₂OCH₂CH(CH₃)O, (CH₃)₃CCH₂NH, CF₃CH(CH₃)O, CH₃CH₂NCH(CH₃)₂, (R)—CF₃CH(CH₃)N(CH₃), (CH₃)₂CHCH(CH₃), CH₃CH₂(CH₃)₂CHCH₂CH₂O, (S)—CH₃OCH(CH₃)CH₂O, HOCH(CH₃)₂CH₂CH₂NH, CF₃CH₂CH₂O, CF₃CH₂CH₂CH₂O, CF₃CH=CHCH₂O, or CH₃CH₂CH₂CH₂CH₂NH.

In some embodiments, R₂ is halo, CN, amino, OH, C₁-C₆ alkyl or C₁-C₆ fluoroalkyl, C₁-C₆ alkoxy or C₁-C₆ fluoroalkoxy, C₃-C₁₀ heterocyclic ring wherein anywhere from 1 to 4 carbon atoms are independently O, S, N, or NR; or a (C₁-C₉ alkylene)-R₃ wherein up to four CH₂ units are optionally and independently replaced with O, CO, S, SO, SO₂ or NR.

In some embodiments, R₂ is Cl, F, OH, CN, NH₂, NH(CH₃), N(CH₃)₂, N(CH₃)CH₂CH₂CH₃, N(CH₃)CH₂CH₂CH₂CH₃, NHCH₂CH₂CH₃, CH₃, CH₂OH, CH₂CH₃, CH₂CH₂CH₃, =O, CH₃SO₂, CH₃SO₂NH, CF₃CONH, CH₃CONH, CH₃CON(CH₃), tBuOCONH, (CH₃)₂CHOCONH, CH(CH₃)₂, CHF₂, OCH₃, OCH₂CH₃, OCH₂CH₂CH₃, OCH₂CH₂CH(CH₃)₂, OCF₃, OCHF₂, OC(CH₃)₃, OCH₂CH₂tBu, NHCH(CH₃)(CH₂CH₂CH₃), OCH(CH₃)₂, NH(CH₂)₂O(CH₂)₂CH₃, C(O)CH₃, CH₂CH₂OH, CH₂NH₂, NH(CH₂)₂OH, N(CH₃)CH₂CH₂CH₂OCH₃, NHCH₂CH₂COOH, NH(CH₂)₂N(CH₃)₂, NH(CH₂)₂NH₂, NH(CH₂)₃NH₂, NH(CH₂)₂OCH₃, NHCH(CH₃)₂,

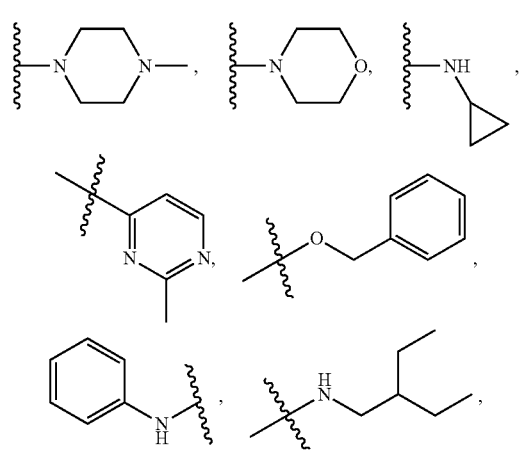

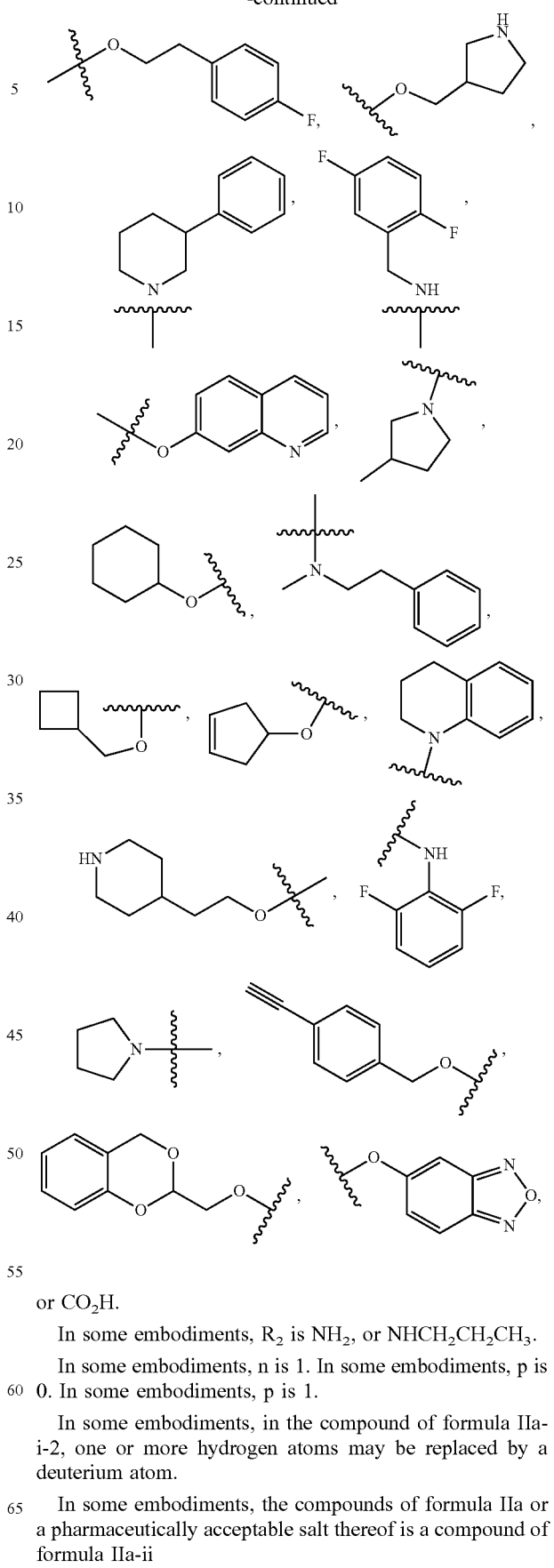

or CO₂H.

In some embodiments, R₂ is NH₂, or NHCH₂CH₂CH₃.

In some embodiments, n is 1. In some embodiments, p is 0. In some embodiments, p is 1.

In some embodiments, in the compound of formula IIa-i-2, one or more hydrogen atoms may be replaced by a deuterium atom.

In some embodiments, the compounds of formula IIa or a pharmaceutically acceptable salt thereof is a compound of formula IIa-ii

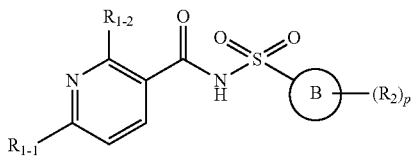

IIa-ii or a pharmaceutically acceptable salt thereof, wherein, independently for each occurrence:

Ring B is a $C_3$-$C_{10}$ cycloalkyl ring; a $C_6$-$C_{10}$ aryl ring; or a $C_3$-$C_{10}$ heteroaryl or $C_3$-$C_{10}$ heterocyclic ring wherein anywhere from 1 to 4 ring atoms are independently O, S, N, or NR;

$R_{1-2}$ is halo; CN; NRR; $C_1$-$C_6$ alkyl or $C_1$-$C_6$ fluoroalkyl; $C_1$-$C_8$ alkoxy or $C_1$-$C_8$ fluoroalkoxy; $C_2$-$C_6$ alkenyl; $C_2$-$C_6$ alkynyl; or ($C_1$-$C_9$ alkylene)-$R_3$ wherein up to four $CH_2$ units are independently replaced with O, CO, S, SO, $SO_2$ or NR;

$R_{1-1}$ is $C_1$-$C_6$ alkyl or $C_1$-$C_6$ fluoroalkyl, $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_2$ is halo; NRR; CN; $CO_2R$; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four $CH_2$ units are optionally and independently replaced with O, CO, S, SO, $SO_2$ or NR;

or two $R_2$ may form a $=CH_2$ or $=O$ group;

$R_3$ is H; $CF_3$; $CHF_2$; OR; C≡CH; $CO_2R$; OH; $C_6$-$C_{10}$ aryl, $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or $SO_2R$;

R is independently H; OH; $CO_2H$; $CO_2C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, or N; or $C_3$-$C_{10}$ cycloalkyl; and p is 0, 1, 2, or 3.

In some embodiments, Ring B is pyridyl, pyridine-2(1H)-one, pyrazole, indole, aza-indole, thiophene, dihydrobenzofuran, thiazole, pyrrolidinone, or quinoline.

In some embodiments, Ring B is

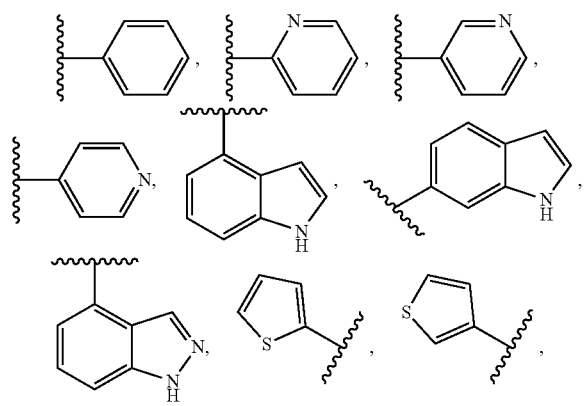

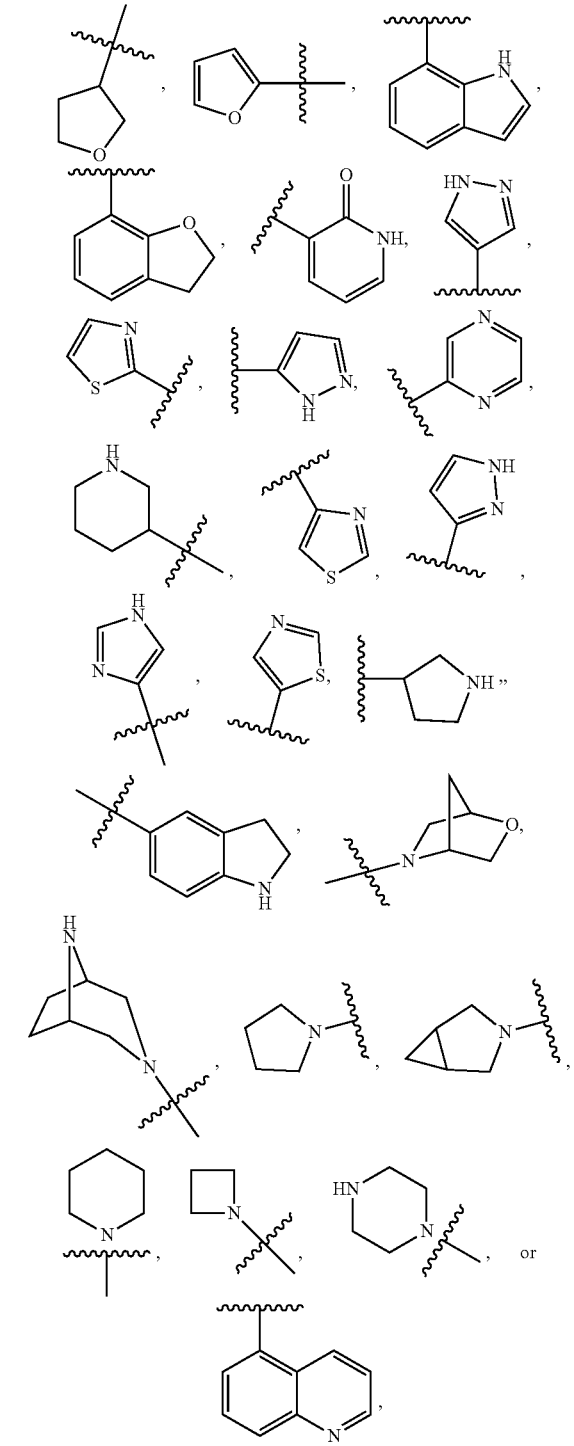

wherein the wavy line ⁓ indicates point of attachment of Ring B to the sulfonyl ($SO_2$).

In some embodiments, $R_{1-2}$ is independently halo, amino, OH, $C_1$-$C_6$ fluoroalkyl, CN, $C_1$-$C_6$ alkyl, $C_2$-$C_6$ alkenyl, $C_2$-$C_6$ alkynyl, $C_1$-$C_8$ alkoxy or $C_1$-$C_8$ fluoroalkoxy, or a ($C_1$-$C_9$ alkylene)-$R_3$ wherein up to four $CH_2$ units are independently replaced with O, CO, S, SO, $SO_2$ or NR.

In some embodiments, $R_{1-1}$ is $C_1$-$C_6$ alkyl or $C_1$-$C_6$ fluoroalkyl, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring.

In some embodiments, $R_{1-1}$ is tert-butyl,

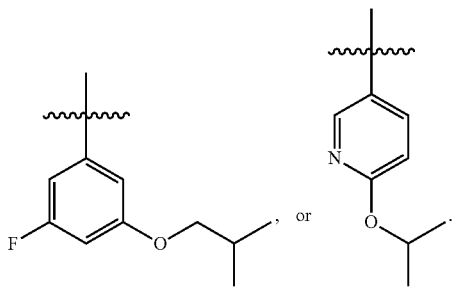 [SMILES: *c1cc(F)cc(OCC(C)C)c1 ; *c1ccc(OC(C)C)nc1]

In some embodiments, $R_{1-1}$ is

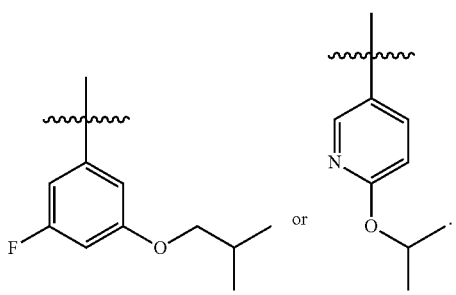 [SMILES: *c1cc(F)cc(OCC(C)C)c1 ; *c1ccc(OC(C)C)nc1]

In some embodiments, $R_{1-2}$ is $CHF_2CH_2(CH_3)N—$, $(CH_3)_2CHCH_2CH2O—$, $(CH_3)_3CCH_2CH_2O—$, $(CH_3)_3COCH_2CH_2O—$, $(CH_3)_2CHO—$, $CHF_2CHF_2CH(CH_3)O—$, $—CF_3$, $(CH_3CH_2)_2N—$, $CF_3CH_2CH(CH_3)O—$, $CH_3O—$, $CH_3(CH_2)_4O—$, $CH_3CH_2CH(CH_3)CH(CH_3)O—$, $CH_3CH_2OCH_2CH_2O—$, $CH_3CH_2NCH(CH_3)_2$, $(CH_3)_3CH_2O—$, $(R)—CH_3NCH(CH_3)(CF_3)$, $CH_3OCH_2CH(CH_2CH_3)O—$, $(CH_3)_2N—$, $(S)—CH_3OCH_2CH(CH_3)O—$, $CH_3O(CH_2)_3O—$, $CH_3OC(CH_3)_2(CH_2)_2O$, $CH_3OCH_2CH(CH_3)O$, $CH_3CH(CH_3)CH_2CH(CH_3)O—$, $(CH_3)_3CCH(CH_3)O$, $((CH_3)_2CH)_2CHO—$, $CH_3CH_2CH_2O$, $CH_3CH=CHCH_2O—$, $(S)—CH_3CH_2CH(CH_3)O—$, $CH_3CH_2O$, $(CH_3)_2CHNCH_3$, $(CH_3)_3CCH_2O$, $(CF_3)_2CHO—$, $(CH_3)_3CCH(CH_2CH_3)O$, $CH_3C≡CCH_2CH_2O$, $(CH_3)_3CCH_2CH(CH_3)O—$, $(CH_3)_2C=C(CH_3)$, $CHF_2CH_2O—$, $CH_3CH_2CH_2NH$, $(CH_3)_2CHCH(CH_2CH_3)$ $O$, $((CH_3)_2CH)_2N$, $CH_2=CHCH(CH_3)O$, $CH_2=CHCH_2O—$, $CH_3CH_2C(CH_3)_2O$, $(CH_3CH_2)_2CHO$, $CF_3CH_2O$, $CH_3C(=CH_2)CH_2O$, $(CH_3)_3CCH_2CH_2NH$, $CH_3OCH_2C(CH_3)_2O$, $(CH_3)_3CCH_2N(CH_3)$, $(CH_3)_2CHCH(CH_3)NH$, $(CH_3)_2CHO(CH_2)_2O$, $CH_3CH_2CH_2CH(CH_3)O$, $CH_3CF_2CH_2O$, $(CH_3)_3CNH$, $(R)—CH_3CH_2CH(CH_3)O$, $CH_3OCH_2CH_2O$, $(CH_3)_2CHCH_2N(CH_3)$, $CH_3CH_2CH_2CH(CH_3)CH(CH_3)O$, $CH_3CH_2CH_2CH_2O$, $CH_3CH_2CH_2N(CH_3)$, $(R)—CH_3OCH_2CH(CH_3)O$, $CF_3CH_2N(CH_3)$, $CH_3CH_2N(CH_3)$, $((CH_3)_3C)_2CHO$, $(CH_3CH_2)_2CHN(CH_3)$, $(CH_3)_2CHN(CH_3)$, $CH_3CH_2OCH_2CH(CH_3)O$, $(CH_3)_3CCH_2NH$, $CF_3CH(CH_3)O$, $CH_3CH_2NCH(CH_3)_2$, $(R)—CF_3CH(CH_3)N(CH_3)$, $(CH_3)_2CHCH(CH_3)$, $CH_3CH_2(CH_3)_2CHCH_2CH_2O$, $(S)—CH_3OCH(CH_3)CH_2O$, $HOCH(CH_3)_2CH_2CH_2NH$, $CF_3CH_2CH_2O$, $CF_3CH_2CH_2CH_2O$, $CF_3CH=CHCH_2O$, or $CH_3CH_2CH_2CH_2CH_2NH$.

In some embodiments, $R_2$ is halo, CN, amino, OH, $C_1$-$C_6$ alkyl or $C_1$-$C_6$ fluoroalkyl, $C_1$-$C_6$ alkoxy or $C_1$-$C_6$ fluoroalkoxy, $C_3$-$C_{10}$ heterocyclic ring wherein anywhere from 1 to 4 carbon atoms are independently O, S, N, or NR; or a ($C_1$-$C_9$ alkylene)-$R_3$ wherein up to four $CH_2$ units are optionally and independently replaced with O, CO, S, SO, $SO_2$ or NR.

In some embodiments, $R_2$ is Cl, F, OH, CN, $NH_2$, $NH(CH_3)$, $N(CH_3)_2$, $N(CH_3)CH_2CH_2CH_3$, $N(CH_3)CH_2CH_2CH_2CH_3$, $NHCH_2CH_2CH_3$, $CH_3$, $CH_2OH$, $CH_2CH_3$, $CH_2CH_2CH_3$, $=O$, $CH_3SO_2$, $CH_3SO_2NH$, $CF_3CONH$, $CH_3CONH$, $CH_3CON(CH_3)$, tBuOCONH, $(CH_3)_2CHOCONH$, $CH(CH_3)_2$, $CHF_2$, $OCH_3$, $OCH_2CH_3$, $OCH_2CH_2CH_3$, $OCH_2CH_2CH(CH_3)_2$, $OCF_3$, $OCHF_2$, $OC(CH_3)_3$, $OCH_2CH_2tBu$, $NHCH(CH_3)(CH_2CH_2CH_3)$, $OCH(CH_3)_2$, $NH(CH_2)_2O(CH_2)_2CH_3$, $C(O)CH_3$, $CH_2CH_2OH$, $CH_2NH_2$, $NH(CH_2)_2OH$, $N(CH_3)CH_2CH_2CH_2OCH_3$, $NHCH_2CH_2COOH$, $NH(CH_2)_2N(CH_3)_2$, $NH(CH_2)_2NH_2$, $NH(CH_2)_3NH_2$, $NH(CH_2)_2OCH_3$, $NHCH(CH_3)_2$,

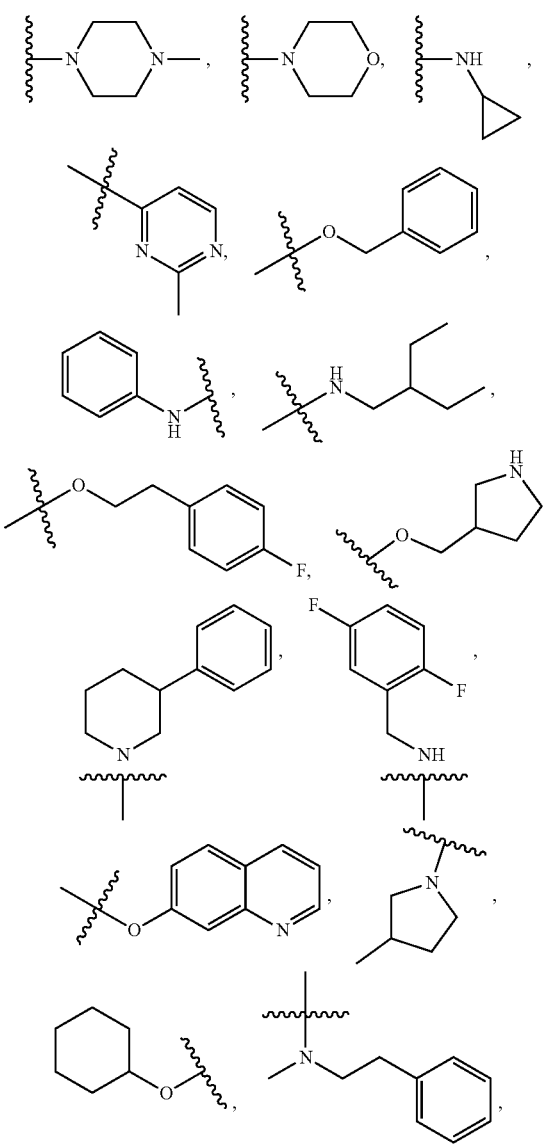

-continued

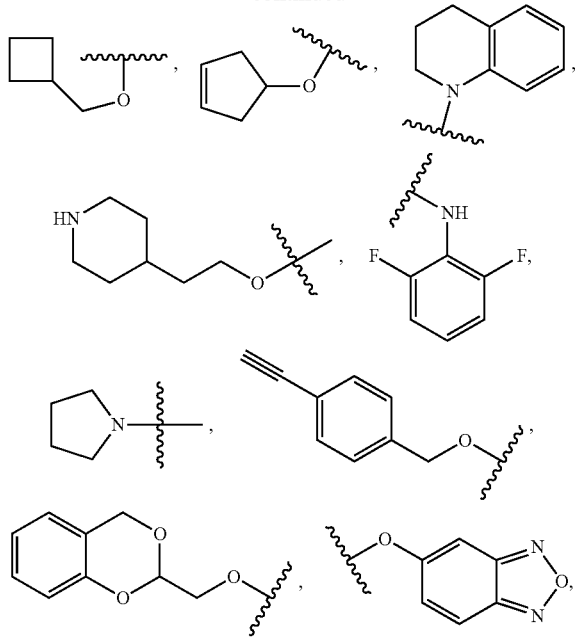

or CO₂H.

In some embodiments, R₂ is NH₂, or NHCH₂CH₂CH₃.

In some embodiments, p is 0. In some embodiments, p is 1.

In some embodiments, in the compound of formula IIa-ii, one or more hydrogen atoms may be replaced by a deuterium atom.

In some embodiments, the compounds of formula IIa-ii or a pharmaceutically acceptable salt thereof is a compound of formula IIa-ii-1

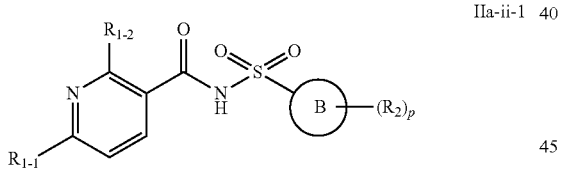

IIa-ii-1 or a pharmaceutically acceptable salt thereof, wherein, independently for each occurrence:

Ring B is a $C_3$-$C_{10}$ heteroaryl or $C_3$-$C_{10}$ heterocyclic ring wherein anywhere from 1 to 4 ring atoms are independently O, S, N, or NR;

$R_{1-2}$ is halo; CN; NRR; $C_1$-$C_6$ alkyl or $C_1$-$C_6$ fluoroalkyl; $C_1$-$C_8$ alkoxy or $C_1$-$C_8$ fluoroalkoxy; $C_2$-$C_6$ alkenyl; $C_2$-$C_6$ alkynyl; or ($C_1$-$C_9$ alkylene)-$R_3$ wherein up to four CH₂ units are independently replaced with O, CO, S, SO, SO₂ or NR;

$R_{1-1}$ is $C_1$-$C_6$ alkyl or $C_1$-$C_6$ fluoroalkyl, $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_2$ is halo; NRR; CN; CO₂R; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four CH₂ units are optionally and independently replaced with O, CO, S, SO, SO₂ or NR;

or two R₂ may form a =CH₂ or =O group;

$R_3$ is H; CF₃; CHF₂; OR; C≡CH; CO₂R; OH; $C_6$-$C_{10}$ aryl, $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or SO₂R;

R is independently H; OH; CO₂H; CO₂$C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, or N; or $C_3$-$C_{10}$ cycloalkyl; and p is 0, 1, 2, or 3.

In some embodiments, Ring B is pyridyl, pyridine-2(1H)-one, pyrazole, indole, aza-indole, thiophene, dihydrobenzofuran, thiazole, pyrrolidinone, or quinoline.

In some embodiments, Ring B is

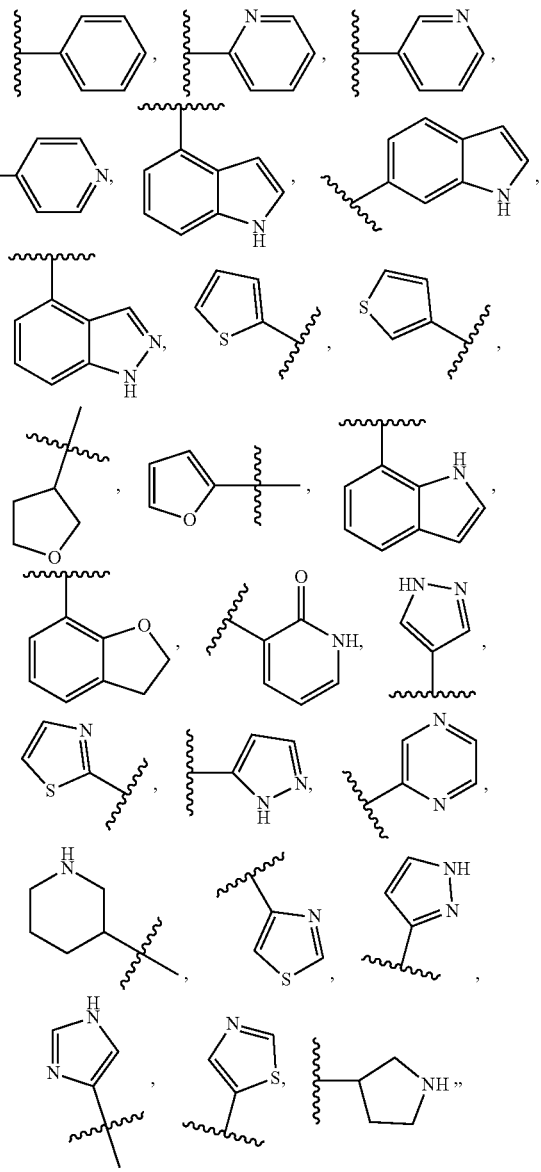

-continued

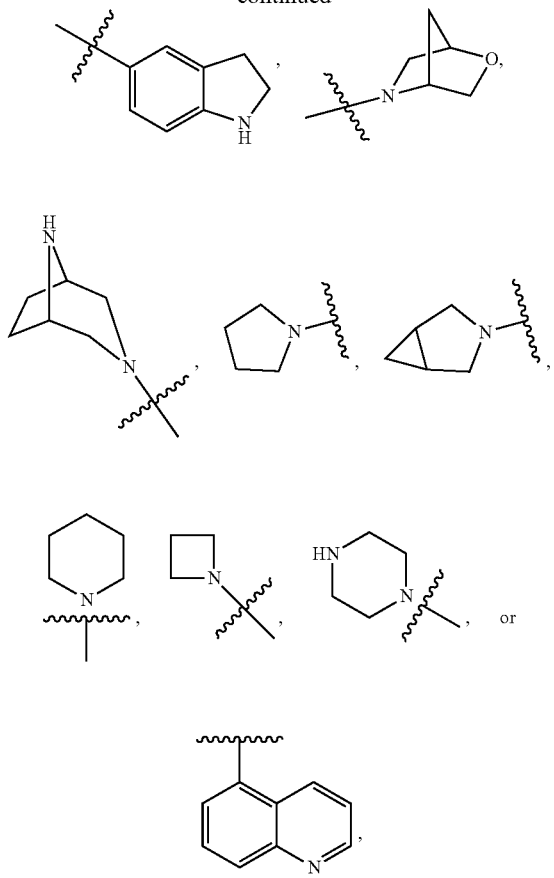

wherein the wavy line ⌇ indicates point of attachment of Ring B to the sulfonyl (SO₂).

In some embodiments, $R_{1-2}$ is independently halo, amino, OH, $C_1$-$C_6$ fluoroalkyl, CN, $C_1$-$C_6$ alkyl, $C_2$-$C_6$ alkenyl, $C_2$-$C_6$ alkynyl, $C_1$-$C_8$ alkoxy or $C_1$-$C_8$ fluoroalkoxy, or a ($C_1$-$C_9$ alkylene)-$R_3$ wherein up to four $CH_2$ units are independently replaced with O, CO, S, SO, $SO_2$ or NR.

In some embodiments, $R_{1-1}$ is $C_1$-$C_6$ alkyl or $C_1$-$C_6$ fluoroalkyl, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring.

In some embodiments, $R_{1-1}$ is tert-butyl,

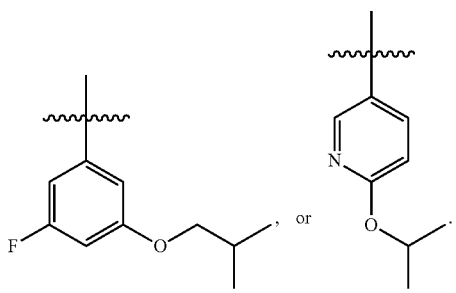 [SMILES: *c1cc(F)cc(OCC(C)C)c1 ; *c1ccc(OC(C)C)nc1], or

In some embodiments, $R_{1-1}$ is

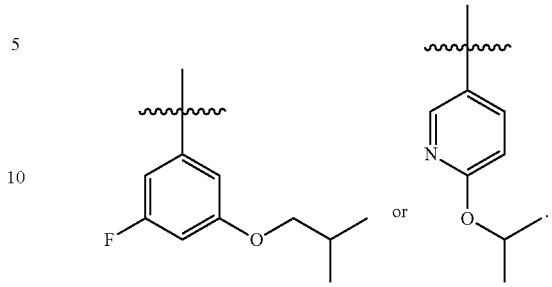

In some embodiments, $R_{1-2}$ is $CHF_2CH_2(CH_3)N—$, $(CH_3)_2CHCH_2CH_2O—$, $(CH_3)_3CCH_2CH_2O—$, $(CH_3)_3COCH_2CH_2O—$, $(CH_3)_2CHO—$, $CHF_2CHF_2CH(CH_3)O—$, $—CF_3$, $(CH_3CH_2)_2N—$, $CF_3CH_2CH(CH_3)O—$, $CH_3O—$, $CH_3(CH_2)_4O—$, $CH_3CH_2CH(CH_3)CH(CH_3)O—$, $CH_3CH_2OCH_2CH_2O—$, $CH_3CH_2NCH(CH_3)_2$, $(CH_3)_3CH_2O—$, (R)—$CH_3NCH(CH_3)(CF_3)$, $CH_3OCH_2CH(CH_2CH_3)O—$, $(CH_3)_2N—$, (S)—$CH_3OCH_2CH(CH_3)O—$, $CH_3O(CH_2)_3O—$, $CH_3OC(CH_3)_2(CH_2)_2O$, $CH_3OCH_2CH(CH_3)O$, $CH_3CH(CH_3)CH_2CH(CH_3)O—$, $(CH_3)_3CCH(CH_3)O$, $((CH_3)_2CH)_2CHO—$, $CH_3CH_2CH_2O$, $CH_3CH=CHCH_2O—$, (S)—$CH_3CH_2CH(CH_3)O—$, $CH_3CH_2O$, $(CH_3)_2CHNCH_3$, $(CH_3)_3CCH_2O$, $(CF_3)_2CHO—$, $(CH_3)_3CCH(CH_2CH_3)O$, $CH_3C≡CCH_2CH_2O$, $(CH_3)_3CCH_2CH(CH_3)O—$, $(CH_3)_2C=C(CH_3)$, $CHF_2CH_2O—$, $CH_3CH_2CH_2NH$, $(CH_3)_2CHCH(CH_2CH_3)O$, $((CH_3)_2CH)_2N$, $CH_2=CHCH(CH_3)O$, $CH_2=CHCH_2O—$, $CH_3CH_2C(CH_3)_2O$, $(CH_3CH_2)_2CHO$, $CF_3CH_2O$, $CH_3C(=CH_2)CH_2O$, $(CH_3)_3CCH_2CH_2NH$, $CH_3OCH_2C(CH_3)_2O$, $(CH_3)_3CCH_2N(CH_3)$, $(CH_3)_2CHCH(CH_3)NH$, $(CH_3)_2CHO(CH_2)_2O$, $CH_3CH_2CH_2CH(CH_3)O$, $CH_3CF_2CH_2O$, $(CH_3)_3CNH$, (R)—$CH_3CH_2CH(CH_3)O$, $CH_3OCH_2CH_2O$, $(CH_3)_2CHCH_2N(CH_3)$, $CH_3CH_2CH_2CH(CH_3)CH(CH_3)O$, $CH_3CH_2CH_2CH_2O$, $CH_3CH_2CH_2N(CH_3)$, (R)—$CH_3OCH_2CH(CH_3)O$, $CF_3CH_2N(CH_3)$, $CH_3CH_2N(CH_3)$, $((CH_3)_3C)_2CHO$, $(CH_3CH_2)_2CHN(CH_3)$, $(CH_3)_2CHN(CH_3)$, $CH_3CH_2OCH_2CH(CH_3)O$, $(CH_3)_3CCH_2NH$, $CF_3CH(CH_3)O$, $CH_3CH_2NCH(CH_3)_2$, $(R)—CF_3CH(CH_3)N(CH_3)$, $(CH_3)_2CHCH(CH_3)$, $CH_3CH_2(CH_3)_2CHCH_2CH_2O$, (S)—$CH_3OCH(CH_3)CH_2O$, $HOCH(CH_3)_2CH_2CH_2NH$, $CF_3CH_2CH_2O$, $CF_3CH_2CH_2CH_2O$, $CF_3CH=CHCH_2O$, or $CH_3CH_2CH_2CH_2CH_2NH$.

In some embodiments, $R_2$ is halo, CN, amino, OH, $C_1$-$C_6$ alkyl or $C_1$-$C_6$ fluoroalkyl, $C_1$-$C_6$ alkoxy or $C_1$-$C_6$ fluoroalkoxy, $C_3$-$C_{10}$ heterocyclic ring wherein anywhere from 1 to 4 carbon atoms are independently O, S, N, or NR; or a ($C_1$-$C_9$ alkylene)-$R_3$ wherein up to four $CH_2$ units are optionally and independently replaced with O, CO, S, SO, $SO_2$ or NR.

In some embodiments, $R_2$ is Cl, F, OH, CN, $NH_2$, $NH(CH_3)$, $N(CH_3)_2$, $N(CH_3)CH_2CH_2CH_3$, $N(CH_3)CH_2CH_2CH_2CH_3$, $NHCH_2CH_2CH_3$, $CH_3$, $CH_2OH$, $CH_2CH_3$, $CH_2CH_2CH_3$, =O, $CH_3SO_2$, $CH_3SO_2NH$, $CF_3CONH$, $CH_3CONH$, $CH_3CON(CH_3)$, tBuOCONH, $(CH_3)_2CHOCONH$, $CH(CH_3)_2$, $CHF_2$, $OCH_3$, $OCH_2CH_3$, $OCH_2CH_2CH_3$, $OCH_2CH(CH_3)_2$, $OCF_3$, $OCHF_2$, $OC(CH_3)_3$, $OCH_2CH_2tBu$, $NHCH(CH_3)(CH_2CH_2CH_3)$, $OCH(CH_3)_2$, $NH(CH_2)_2O(CH_2)_2CH_3$, $C(O)CH_3$, $CH_2CH_2OH$, $CH_2NH_2$, $NH(CH_2)_2OH$, $N(CH_3)CH_2CH_2CH_2OCH_3$, $NHCH_2CH_2COOH$, $NH(CH_2)_2N(CH_3)_2$, $NH(CH_2)_2NH_2$, $NH(CH_2)_3NH_2$, $NH(CH_2)_2OCH_3$, $NHCH(CH_3)_2$,

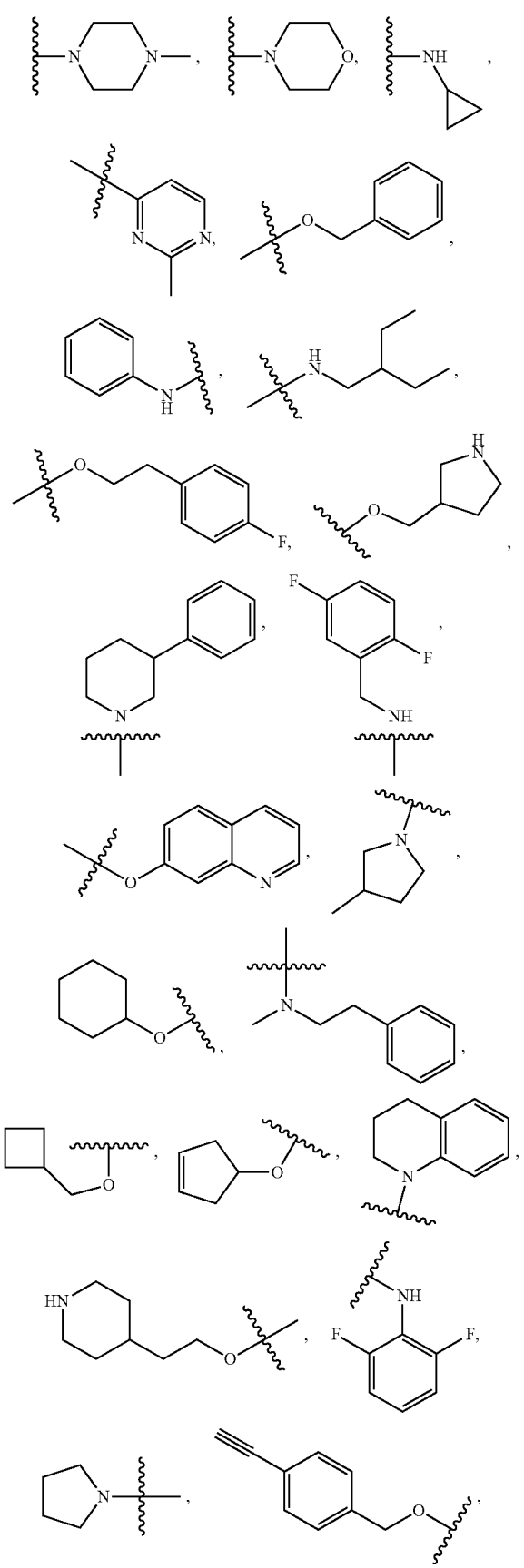

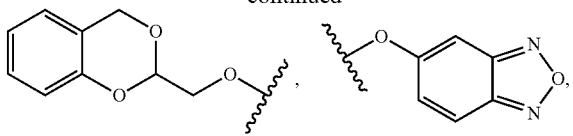

or CO$_2$H.

In some embodiments, R$_2$ is NH$_2$, or NHCH$_2$CH$_2$CH$_3$.

In some embodiments, p is 0. In some embodiments, p is 1.

In some embodiments, in the compound of formula IIa-ii-1, one or more hydrogen atoms may be replaced by a deuterium atom.

In some embodiments, the compounds of formula IIa-ii-1 or a pharmaceutically acceptable salt thereof is a compound of formula IIa-ii-2

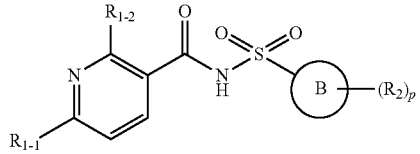

IIa-ii-2 or a pharmaceutically acceptable salt thereof, wherein, independently for each occurrence:

Ring B is a pyridinyl;

R$_{1-2}$ is halo; CN; NRR; C$_1$-C$_6$ alkyl or C$_1$-C$_6$ fluoroalkyl; C$_1$-C$_8$ alkoxy or C$_1$-C$_8$ fluoroalkoxy; C$_2$-C$_6$ alkenyl; C$_2$-C$_6$ alkynyl; or (C$_1$-C$_9$ alkylene)-R$_3$ wherein up to four CH$_2$ units are independently replaced with O, CO, S, SO, SO$_2$ or NR;

R$_{1-1}$ is C$_1$-C$_6$ alkyl or C$_1$-C$_6$ fluoroalkyl, C$_6$-C$_{10}$ aryl; C$_3$-C$_{10}$ heteroaryl or C$_3$-C$_{10}$ heterocyclic ring wherein anywhere from 1 to 4 ring atoms are independently O, S, N, or NR; or C$_3$-C$_{10}$ cycloalkyl;

R$_2$ is halo; NRR; CN; CO$_2$R; C$_1$-C$_6$ alkyl or C$_1$-C$_6$ fluoroalkyl; C$_1$-C$_6$ alkoxy or C$_1$-C$_6$ fluoroalkoxy; C$_2$-C$_6$ alkenyl; C$_2$-C$_6$ alkynyl; C$_6$-C$_{10}$ aryl; C$_3$-C$_{13}$ heteroaryl or heterocyclic ring wherein anywhere from 1 to 4 ring atoms are independently O, S, N, or NR; C$_3$-C$_{10}$ cycloalkyl; or a (C$_1$-C$_9$ alkylene)-R$_3$ wherein up to four CH$_2$ units are optionally and independently replaced with O, CO, S, SO, SO$_2$ or NR;

or two R$_2$ may form a =CH$_2$ or =O group;

R$_3$ is H; CF$_3$; CHF$_2$; OR; C≡CH; CO$_2$R; OH; C$_6$-C$_{10}$ aryl, C$_3$-C$_{10}$ heteroaryl or heterocycloalkyl wherein anywhere from 1 to 4 ring atoms are independently O, S, N, or NR; C$_3$-C$_{10}$ cycloalkyl; NRR, NRCOR, CONRR, CN, halo, or SO$_2$R;

R is independently H; OH; CO$_2$H; CO$_2$C$_1$-C$_6$ alkyl; C$_1$-C$_6$ alkyl; C$_2$-C$_6$ alkenyl; C$_2$-C$_6$ alkynyl; C$_6$-C$_{10}$ aryl; C$_3$-C$_{10}$ heteroaryl or heterocycloalkyl wherein anywhere from 1 to 4 ring atoms are independently O, S, or N; or C$_3$-C$_{10}$ cycloalkyl; and p is 0, 1, 2, or 3.

In some embodiments, Ring B is

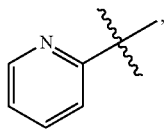

wherein the wavy line ⌇ indicates point of attachment of Ring B to the sulfonyl (SO$_2$).

In some embodiments, R$_{1-2}$ is independently halo, amino, OH, C$_1$-C$_6$ fluoroalkyl, CN, C$_1$-C$_6$ alkyl, C$_2$-C$_6$ alkenyl, C$_2$-C$_6$ alkynyl, C$_1$-C$_8$ alkoxy or C$_1$-C$_8$ fluoroalkoxy, or a (C$_1$-C$_9$ alkylene)-R$_3$ wherein up to four CH$_2$ units are independently replaced with O, CO, S, SO, SO$_2$ or NR.

In some embodiments, R$_{1-1}$ is C$_1$-C$_6$ alkyl or C$_1$-C$_6$ fluoroalkyl, a phenyl, C$_3$-C$_6$ mono-cycloalkly, mono-C$_4$-C$_6$ heterocyclic ring, 1,2,3,4-tetrahydroisoquinoline, pyridyl, pyrimidine, indole, aza-indole, pyrazole, pyrrole, or thiophene ring.

In some embodiments, R$_{1-1}$ is tert-butyl,

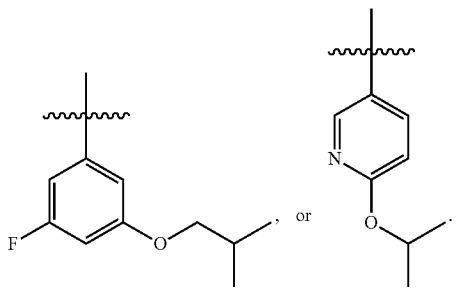 [SMILES: *c1cc(F)cc(OCC(C)C)c1 ; *c1ccc(OC(C)C)nc1]

In some embodiments, R$_{1-1}$ is or

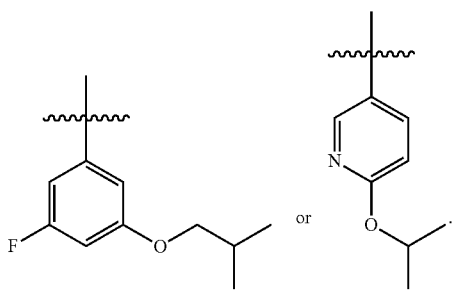 [SMILES: *c1cc(F)cc(OCC(C)C)c1 ; *c1ccc(OC(C)C)nc1]

In some embodiments, R$_{1-2}$ is CHF$_2$CH$_2$(CH$_3$)N—, (CH$_3$)$_2$CHCH$_2$CH$_2$O—, (CH$_3$)$_3$CCH$_2$CH$_2$O—, (CH$_3$)$_3$COCH$_2$CH$_2$O—, (CH$_3$)$_2$CHO—, CHF$_2$CHF$_2$CH(CH$_3$)O—, —CF$_3$, (CH$_3$CH$_2$)$_2$N—, CF$_3$CH$_2$CH(CH$_3$)O—, CH$_3$O—, CH$_3$(CH$_2$)$_4$O—, CH$_3$CH$_2$CH(CH$_3$)CH(CH$_3$)O—, CH$_3$CH$_2$OCH$_2$CH$_2$O—, CH$_3$CH$_2$NCH(CH$_3$)$_2$, (CH$_3$)$_3$CH$_2$O—, (R)—CH$_3$NCH(CH$_3$)(CF$_3$), CH$_3$OCH$_2$CH(CH$_2$CH$_3$)O—, (CH$_3$)$_2$N—, (S)—CH$_3$OCH$_2$CH(CH$_3$)O—, CH$_3$O(CH$_2$)$_3$O—, CH$_3$OC(CH$_3$)$_2$(CH$_2$)$_2$O, CH$_3$OCH$_2$CH(CH$_3$)O, CH$_3$CH(CH$_3$)CH$_2$CH(CH$_3$)O—, (CH$_3$)$_3$CCH(CH$_3$)O, ((CH$_3$)$_2$CH)$_2$CHO—, CH$_3$CH$_2$CH$_2$O, CH$_3$CH=CHCH$_2$O—, (S)—CH$_3$CH$_2$CH(CH$_3$)O—, CH$_3$CH$_2$O, (CH$_3$)$_2$CHNCH$_3$, (CH$_3$)$_2$CCH$_2$O, (CF$_3$)$_2$CHO—, (CH$_3$)$_3$CCH(CH$_2$CH$_3$)O, CH$_3$C≡CCH$_2$CH$_2$O, (CH$_3$)$_3$CCH$_2$CH(CH$_3$)O—, (CH$_3$)$_2$C=C(CH$_3$), CHF$_2$CH$_2$O—, CH$_3$CH$_2$CH$_2$NH, (CH$_3$)$_2$CHCH(CH$_2$CH$_3$)O, ((CH$_3$)$_2$CH)$_2$N, CH$_2$=CHCH(CH$_3$)O, CH$_2$=CHCH$_2$O—, CH$_3$CH$_2$C(CH$_3$)$_2$O, (CH$_3$CH$_2$)$_2$CHO, CF$_3$CH$_2$O, CH$_3$C(=CH$_2$)CH$_2$O, (CH$_3$)$_3$CCH$_2$CH$_2$NH, CH$_3$OCH$_2$C(CH$_3$)$_2$O, (CH$_3$)$_3$CCH$_2$N(CH$_3$), (CH$_3$)$_2$CHCH(CH$_3$)NH, (CH$_3$)$_2$CHO(CH$_2$)$_2$O, CH$_3$CH$_2$CH$_2$CH(CH$_3$)O, CH$_3$CF$_2$CH$_2$O, (CH$_3$)$_3$CNH, (R)—CH$_3$CH$_2$CH(CH$_3$)O, CH$_3$OCH$_2$CH$_2$O, (CH$_3$)$_2$CHCH$_2$N(CH$_3$), CH$_3$CH$_2$CH$_2$CH(CH$_3$)CH(CH$_3$)O, CH$_3$CH$_2$CH$_2$CH$_2$O, CH$_3$CH$_2$CH$_2$N(CH$_3$), (R)—CH$_3$OCH$_2$CH(CH$_3$)O, CF$_3$CH$_2$N(CH$_3$), CH$_3$CH$_2$N(CH$_3$), ((CH$_3$)$_3$C)$_2$CHO, (CH$_3$CH$_2$)$_2$CHN(CH$_3$), (CH$_3$)$_2$CHN(CH$_3$), CH$_3$CH$_2$OCH$_2$CH(CH$_3$)O, (CH$_3$)$_3$CCH$_2$NH, CF$_3$CH(CH$_3$)O, CH$_3$CH$_2$NCH(CH$_3$)$_2$, (R)—CF$_3$CH(CH$_3$)N(CH$_3$), (CH$_3$)$_2$CHCH(CH$_3$), CH$_3$CH$_2$(CH$_3$)$_2$CHCH$_2$CH$_2$O, (S)—CH$_3$OCH(CH$_3$)CH$_2$O, HOCH(CH$_3$)$_2$CH$_2$CH$_2$NH, CF$_3$CH$_2$CH$_2$O, CF$_3$CH$_2$CH$_2$CH$_2$O, CF$_3$CH=CHCH$_2$O, or CH$_3$CH$_2$CH$_2$CH$_2$CH$_2$NH.

In some embodiments, R$_2$ is halo, CN, amino, OH, C$_1$-C$_6$ alkyl or C$_1$-C$_6$ fluoroalkyl, C$_1$-C$_6$ alkoxy or C$_1$-C$_6$ fluoroalkoxy, C$_3$-C$_{10}$ heterocyclic ring wherein anywhere from 1 to 4 carbon atoms are independently O, S, N, or NR; or a (C$_1$-C$_9$ alkylene)-R$_3$ wherein up to four CH$_2$ units are optionally and independently replaced with O, CO, S, SO, SO$_2$ or NR.

In some embodiments, R$_2$ is Cl, F, OH, CN, NH$_2$, NH(CH$_3$), N(CH$_3$)$_2$, N(CH$_3$)CH$_2$CH$_2$CH$_3$, N(CH$_3$)CH$_2$CH$_2$CH$_2$CH$_3$, NHCH$_2$CH$_2$CH$_3$, CH$_3$, CH$_2$OH, CH$_2$CH$_3$, CH$_2$CH$_2$CH$_3$, =O, CH$_3$SO$_2$, CH$_3$SO$_2$NH, CF$_3$CONH, CH$_3$CONH, CH$_3$CON(CH$_3$), tBuOCONH, (CH$_3$)$_2$CHOCONH, CH(CH$_3$)$_2$, CHF$_2$, OCH$_3$, OCH$_2$CH$_3$, OCH$_2$CH$_2$CH$_3$, OCH$_2$CH$_2$CH(CH$_3$)$_2$, OCF$_3$, OCHF$_2$, OC(CH$_3$)$_3$, OCH$_2$CH$_2$tBu, NHCH(CH$_3$)(CH$_2$CH$_2$CH$_3$), OCH(CH$_3$)$_2$, NH(CH$_2$)$_2$O(CH$_2$)$_2$CH$_3$, C(O)CH$_3$, CH$_2$CH$_2$OH, CH$_2$NH$_2$, NH(CH$_2$)$_2$OH, N(CH$_3$)CH$_2$CH$_2$CH$_2$OCH$_3$, NHCH$_2$CH$_2$COOH, NH(CH$_2$)$_2$N(CH$_3$)$_2$, NH(CH$_2$)$_2$NH$_2$, NH(CH$_2$)$_3$NH$_2$, NH(CH$_2$)$_2$OCH$_3$, NHCH(CH$_3$)$_2$,

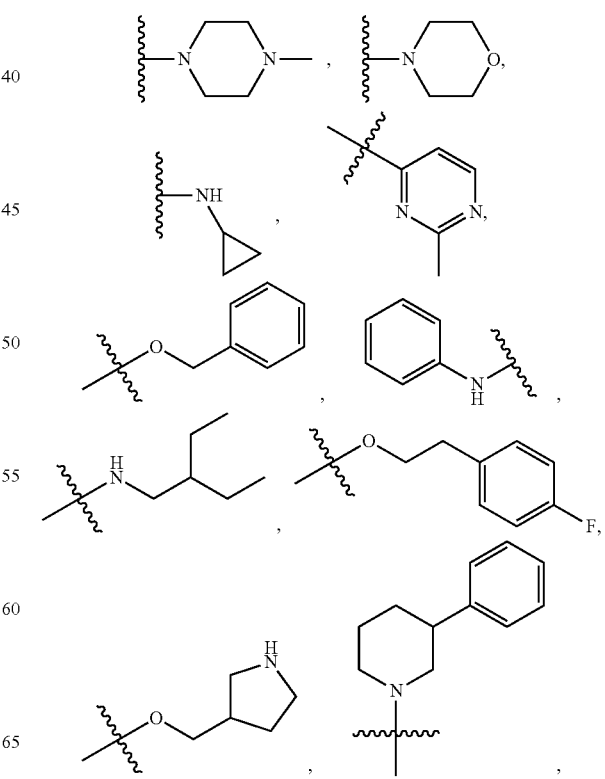

-continued

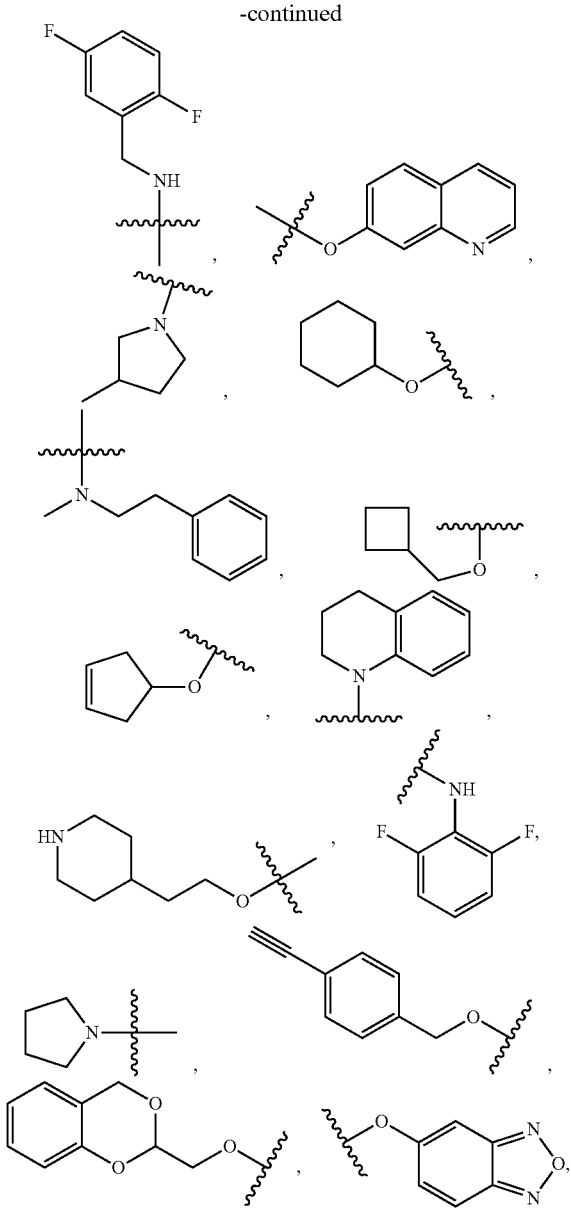

or CO₂H.

In some embodiments, R₂ is NH₂, or NHCH₂CH₂CH₃.

In some embodiments, p is 0. In some embodiments, p is 1.

In some embodiments, in the compound of formula IIa-ii-2, one or more hydrogen atoms may be replaced by a deuterium atom.

Disclosed is a method of treating cystic fibrosis in a patient comprising administering to the patient in need thereof an effective amount of 1) a compound of any of formulas I, I-i, Ia, Ia-i and Ia-ii, including all embodiments disclosed herein, or a pharmaceutically acceptable salt thereof, or 2) a pharmaceutical composition comprising a pharmaceutically acceptable excipient and a compound of formulae any of formulas I, I-i, Ia, Ia-i and Ia-ii, including all embodiments disclosed herein, or a pharmaceutically acceptable salt thereof.

In one embodiment, the present disclosure features any of the below numerated embodiments.

1. In one embodiment, the present disclosure features a compound of formula I:

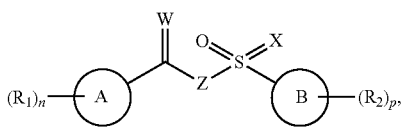

or a pharmaceutically acceptable salt thereof, wherein, independently for each occurrence:

Ring A is a $C_6$-$C_{10}$ aryl ring; a $C_3$-$C_{10}$ cycloalkyl ring; or a $C_3$-$C_{14}$ heteroaryl or heterocyclic ring wherein anywhere from 1 to 4 ring atoms are independently O, S, N, or NR;

Ring B is a $C_3$-$C_{10}$ cycloalkyl ring; a $C_6$-$C_{10}$ aryl ring; or a $C_3$-$C_{10}$ heteroaryl or $C_3$-$C_{10}$ heterocyclic ring wherein anywhere from 1 to 4 ring atoms are independently O, S, N, or NR;

W is O, S, or NR;

X is O or NR;

Z is NR or $C(R)_2$;

R₁ is halo; CN; NRR; $C_1$-$C_6$ alkyl or $C_1$-$C_6$ fluoroalkyl; $C_3$-$C_6$ cycloalkyl; $C_1$-$C_8$ alkoxy or $C_1$-$C_8$ fluoroalkoxy; $C_2$-$C_6$ alkenyl; $C_2$-$C_6$ alkynyl; ($C_1$-$C_9$ alkylene)-R₃ wherein up to four $CH_2$ units are independently replaced with O, CO, S, SO, $SO_2$ or NR; $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

R₂ is halo; NRR; CN; $CO_2R$; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-R₃ wherein up to four $CH_2$ units are optionally and independently replaced with O, CO, S, SO, $SO_2$ or NR;

or two R₂ may form a $=CH_2$ or $=O$ group;

R₃ is H; $CF_3$; $CHF_2$; OR; $C\equiv CH$; $CO_2R$; OH; $C_6$-$C_{10}$ aryl, $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or $SO_2R$;

R is independently H; OH; $CO_2H$; $CO_2C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, or N; or $C_3$-$C_{10}$ cycloalkyl;

n is 2 or 3;

p is 0, 1, 2, or 3; and

Provided that 1) when R₁ is adjacent to the C=W attached to Ring A, R₁ does not contain a ring moiety, 2) at least one R₁ is adjacent to the C=W attached to Ring A, and at least one R₁ is $C_1$-$C_6$ alkyl or $C_1$-$C_6$ fluoroalkyl, $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl; 3) when Ring A is phenyl or six-membered mono-heteroaryl wherein anywhere from 1 to 3 ring atoms are N, R₁ is not 4,5-dihydroisoxazole; 4) when Ring A is phenyl, R₁ is not

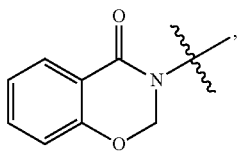 [SMILES: *N1COc2ccccc2C1=O]

ureido, or aminocarbonyl; 5) when Ring A and the at least one $R_1$ is pyridine, $R_1$ (pyridine) is not further substituted by —$CONHSO_2$—; and 6) when Ring A is pyridine or thiazole, and C=W wherein W is O in formula I is adjacent to the N on the pyridine or thiazole, $R_1$ which is adjacent to the N on the pyridine or on the thiazole is not

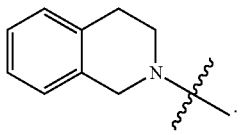 [SMILES: *N1CCc2ccccc2C1]

2. In another embodiment, the present disclosure features the compound of embodiment 1 or a pharmaceutically acceptable salt thereof, wherein Ring A is pyridyl, indole, indoline, isoindoline, pyrazole, pyrimidine, 1,2,3,4-tetrahydroquinoline, quinoline, 5,6,7,8-tetrahydroquinoline, 1,2,3,4-tetrahydroisoquinoline, pyrrolodine, aza-indole, pyrrole, thiophene, oxazole, pyrazine, triazole, thiazole, indazole, 2,3,4,5-tetrahydro-1H-benzo[d]azepine, 1H-benzo[d]imidazole, imidazo[1,2-a]pyridine, or imidazole ring.

3. In another embodiment, the present disclosure features the compound of embodiment 1 or 2 or a pharmaceutically acceptable salt thereof, wherein Ring A is

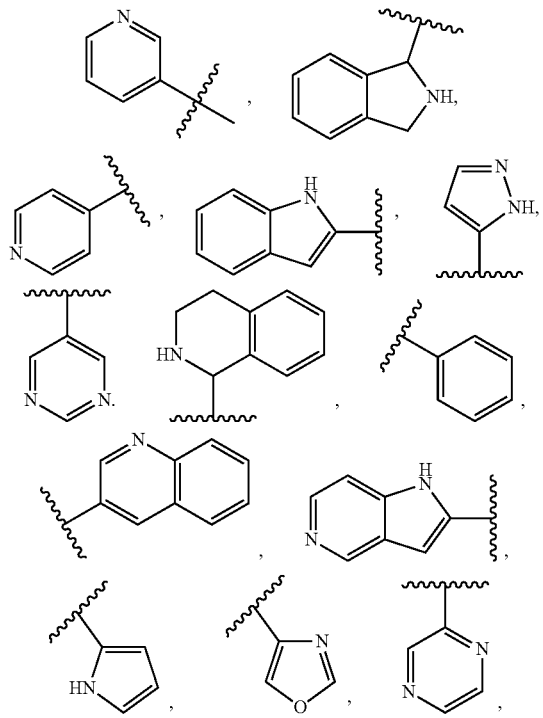

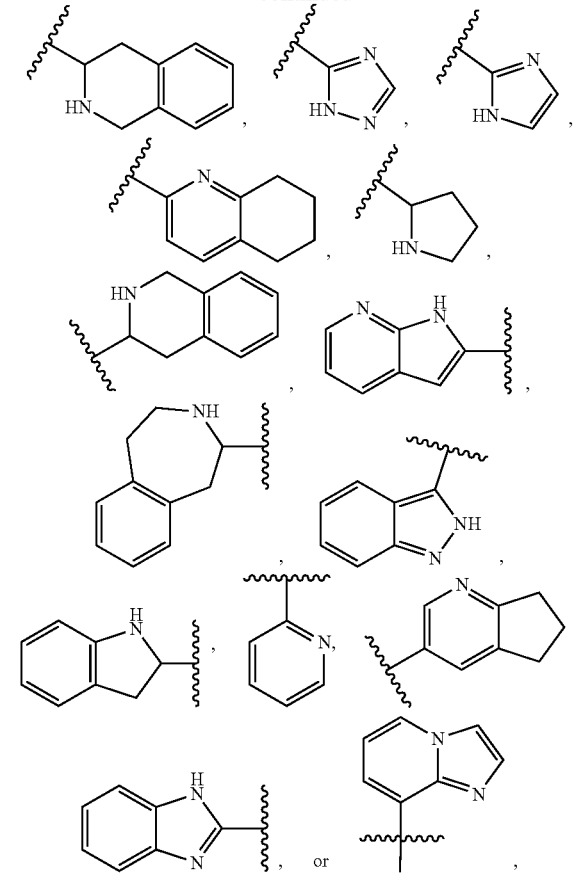

wherein the wavy line  indicates point of attachment of Ring A to the C=W.

4. In another embodiment, the present disclosure features the compound of any one of embodiments 1 to 3 or a pharmaceutically acceptable salt thereof, wherein Ring B is a pyridyl, pyridine-2(1H)-one, pyrazole, indole, pyrrole, indoline, thiophene, dihydrobenzofuran, tetrahydrofuran, furan, pyrazine, indazole, thiazole, pyridine-4(1H)-one, pyrrolidinone, 3-azabicyclo[3.1.0]hexane, (1R,4R)-2-oxa-5-azabicyclo[2.2.1]heptane, pyrrolidine, azetidine, piperidine, piperazine, imidazo[1,2-a]pyridine, or quinoline.

5. In another embodiment, the present disclosure features the compound of any one of embodiments 1 to 4 or a pharmaceutically acceptable salt thereof, wherein Ring B is

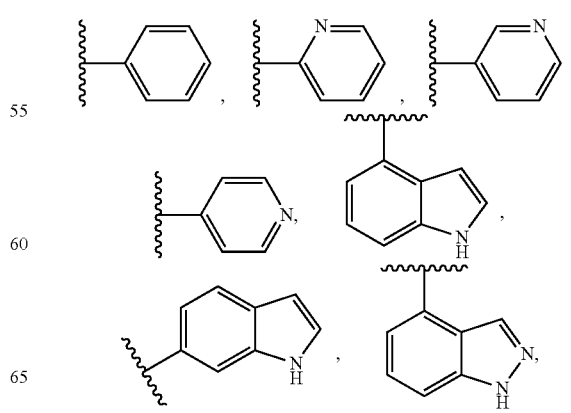

-continued

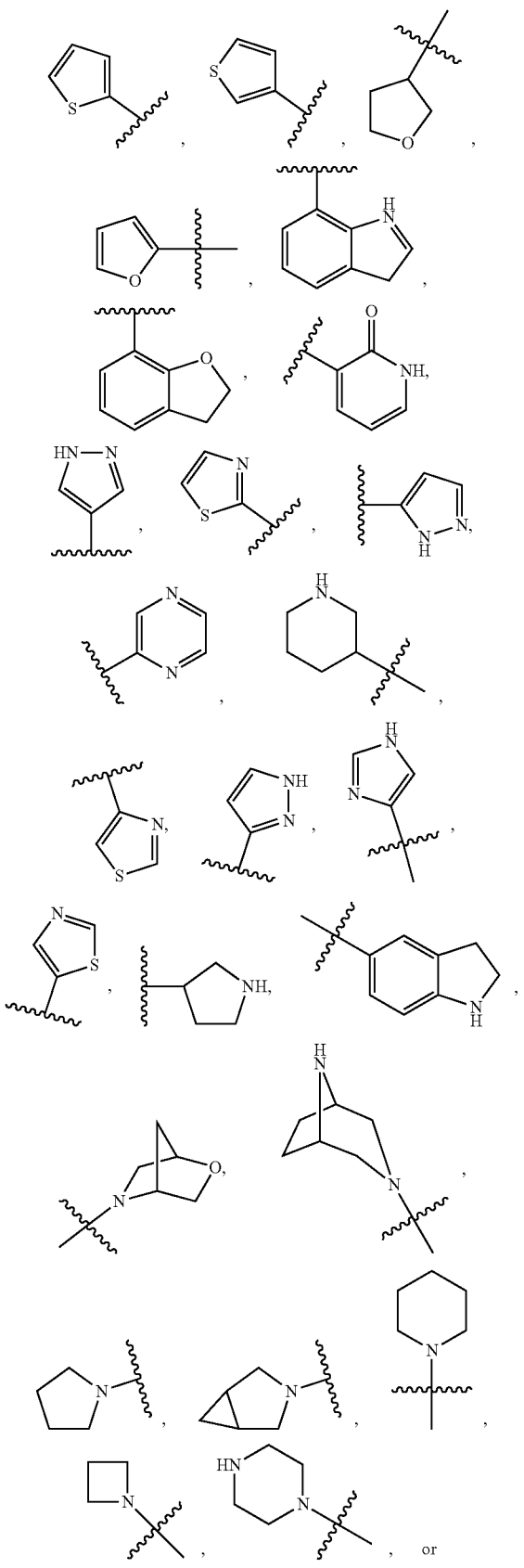

-continued

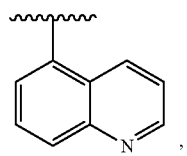

wherein the wavy line  indicates point of attachment of Ring B to the X=S=O.

6. In another embodiment, the present disclosure features the compound of any one of embodiments 1 to 5 or a pharmaceutically acceptable salt thereof, wherein $R_1$ is independently halo, amino, OH, $C_2$-$C_6$ alkenyl; $C_2$-$C_6$ alkynyl, $C_1$-$C_6$ fluoroalkyl, CN, $C_1$-$C_6$ alkyl, $C_1$-$C_8$ alkoxy or $C_1$-$C_8$ fluoroalkoxy, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring, or a ($C_1$-$C_9$ alkylene)-$R_3$ wherein up to four $CH_2$ units are independently replaced with O, CO, S, SO, $SO_2$ or NR.

7. In another embodiment, the present disclosure features the compound of any one of embodiments 1 to 6 or a pharmaceutically acceptable salt thereof, wherein $R_1$ is $CHF_2CH_2$ $(CH_3)N$—, $(CH_3)_2CHCH_2CH2O$—, $(CH_3)_3CCH_2CH_2O$—, $(CH_3)_3COCH_2CH_2O$—, $(CH_3)_2CHO$—, $CHF_2CHF_2CH$ $(CH_3)O$—, —$CF_3$, $(CH_3CH_2)_2N$—, $CF_3CH_2CH(CH_3)O$—, $CH_3O$—, $CH_3(CH_2)_4O$—, $CH_3CH_2CH(CH_3)CH(CH_3)O$—, $CH_3CH_2OCH_2CH_2O$—, $CH_3CH_2NCH(CH_3)_2$, $(CH_3)_3CH_2O$—, (R)—$CH_3NCH(CH_3)(CF_3)$, $CH_3OCH_2CH$ $(CH_2CH_3)O$—, $(CH_3)_2N$—, (S)—$CH_3OCH_2CH(CH_3)O$—, $CH_3O(CH_2)_3O$—, $CH_3OC(CH_3)_2(CH_2)_2O$, $CH_3OCH_2CH$ $(CH_3)O$, $CH_3CH(CH_3)CH_2CH(CH_3)O$—, $(CH_3)_3CCH$ $(CH_3)O$, $((CH_3)_2CH)_2CHO$—, $CH_3CH_2CH_2O$, $CH_3CH=CHCH_2O$—, (S)—$CH_3CH_2CH(CH_3)O$—, $CH_3CH_2O$, $(CH_3)_2CHNCH_3$, $(CH_3)_3CCH_2O$, $(CF_3)_2$ $CHO$—, $(CH_3)_3CCH(CH_2CH_3)O$, $CH_3C≡CCH_2CH_2O$, $(CH_3)_3CCH_2CH(CH_3)O$—, $(CH_3)_2C=C(CH_3)$, $CHF_2CH_2O$—, $CH_3CH_2CH_2NH$, $(CH_3)_2CHCH(CH_2CH_3)$ O, $((CH_3)_2CH)_2N$, $CH_2=CHCH(CH_3)O$, $CH_2=CHCH_2O$—, $CH_3CH_2C(CH_3)_2O$, $(CH_3CH_2)_2CHO$, $CF_3CH_2O$, $CH_3C(=CH_2)CH_2O$, $(CH_3)_3CCH_2CH_2NH$, $CH_3OCH_2C(CH_3)_2O$, $(CH_3)_3CCH_2N(CH_3)$, $(CH_3)_2CHCH$ $(CH_3)NH$, $(CH_3)_2CHO(CH_2)_2O$, $CH_3CH_2CH_2CH(CH_3)O$, $CH_3CF_2CH_2O$, $(CH_3)_3CNH$, (R)—$CH_3CH_2CH(CH_3)O$, $CH_3OCH_2CH_2O$, $(CH_3)_2CHCH_2N(CH_3)$, $CH_3CH_2CH_2CH$ $(CH_3)CH(CH_3)O$, $CH_3CH_2CH_2CH_2O$, $CH_3CH_2CH_2N$ $(CH_3)$, (R)—$CH_3OCH_2CH(CH_3)O$, $CF_3CH_2N(CH_3)$, $CH_3CH_2N(CH_3)$, $((CH_3)_3C)_2CHO$, $(CH_3CH_2)_2CHN(CH_3)$, $(CH_3)_2CHN(CH_3)$, $CH_3CH_2OCH_2CH(CH_3)O$, $(CH_3)_3$ $CCH_2NH$, $CF_3CH(CH_3)O$, $CH_3CH_2NCH(CH_3)_2$, (R)—$CF_3CH(CH_3)N(CH_3)$, $(CH_3)_2CHCH(CH_3)$, $CH_3CH_2(CH_3)_2$ $CHCH_2CH_2O$, (S)—$CH_3OCH(CH_3)CH_2O$, $HOCH(CH_3)_2$ $CH_2CH_2NH$, $CF_3CH_2CH_2O$, $CF_3CH_2CH_2CH_2O$, $CF_3CH=CHCH_2O$, $CH_3CH_2CH_2CH_2CH_2NH$,

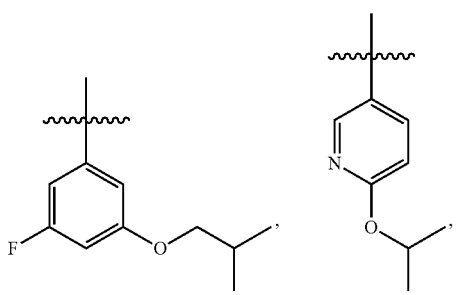 [SMILES: *c1cc(F)cc(OCC(C)C)c1 ; *c1ccc(OC(C)C)nc1]

or (CH₃)₃C.

8. In another embodiment, the present disclosure features the compound of any one of embodiments 1 to 7 or a pharmaceutically acceptable salt thereof, wherein $R_2$ is halo, OH, CN, amino, $C_1$-$C_6$ alkyl or $C_1$-$C_6$ fluoroalkyl, $C_1$-$C_6$ alkoxy or $C_1$-$C_6$ fluoroalkoxy, $C_3$-$C_{10}$ heterocyclic ring wherein anywhere from 1 to 4 carbon atoms are independently O, S, N, or NR; or a ($C_1$-$C_9$ alkylene)-$R_3$ wherein up to four $CH_2$ units are optionally and independently replaced with O, CO, S, SO, $SO_2$ or NR.

9. In another embodiment, the present disclosure features the compound of any one of embodiments 1 to 8 or a pharmaceutically acceptable salt thereof, wherein $R_2$ is $NH_2$, or $NHCH_2CH_2CH_3$.

10. In another embodiment, the present disclosure features the compound of any one of embodiments 1 to 9 or a pharmaceutically acceptable salt thereof, wherein n is 2.

11. In another embodiment, the present disclosure features the compound of any one of embodiments 1 to 10 or a pharmaceutically acceptable salt thereof, wherein p is 0.

12. In another embodiment, the present disclosure features the compound of any one of embodiments 1 to 10 or a pharmaceutically acceptable salt thereof, wherein p is 1.

13. In another embodiment, the present disclosure features the compound of any one of embodiments 1 to 12 or a pharmaceutically acceptable salt thereof, wherein W is O.

14. In another embodiment, the present disclosure features the compound of any one of embodiments 1 to 13 or a pharmaceutically acceptable salt thereof, wherein Z is NH.

15. In another embodiment, the present disclosure features the compound of any one of embodiments 1 to 14 or a pharmaceutically acceptable salt thereof, wherein X is O.

16. In another embodiment, the present disclosure features the compound of any one of embodiments 1 to 15 or a pharmaceutically acceptable salt thereof, wherein Ring A is

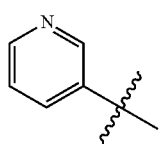

and n is 2.

17. In another embodiment, the present disclosure features the compound of any one of embodiments 1 to 15 or a pharmaceutically acceptable salt thereof, wherein Ring A is

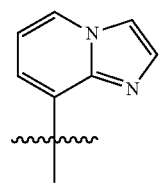 [SMILES: *c1cccn2ccnc12]

and n is 2.

18. In another embodiment, the present disclosure features the compound of any one of embodiments 1 to 15 or a pharmaceutically acceptable salt thereof, wherein Ring A is

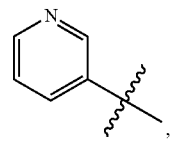

and at least one $R_1$ is phenyl.

19. In another embodiment, the present disclosure features the compound of any one of embodiments 1 to 15 or a pharmaceutically acceptable salt thereof, wherein Ring A is

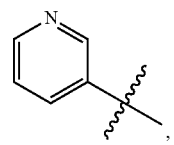

and at least one $R_1$ is tert-butyl.

20. In another embodiment, the present disclosure features the compound of any one of embodiments 1 to 19 or a pharmaceutically acceptable salt thereof, wherein Ring A is

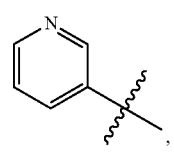

and at least one $R_1$ is pyridinyl. In some embodiments, Ring A is

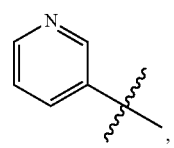

one $R_1$ is phenyl, and one $R_1$ is alkenyl, amino, or $C_1$-$C_8$ alkoxy or $C_1$-$C_8$ fluoroalkoxy. In some embodiments, Ring A is

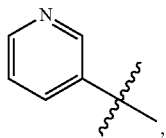

and Ring B is

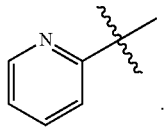

In some embodiments, Ring A is

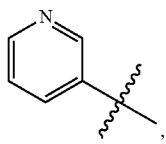

and Ring B is

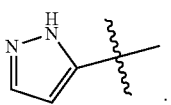

In some embodiments, Ring A is

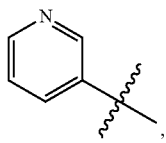

Ring B is

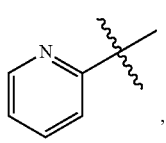

one $R_1$ is phenyl, and one $R_1$ is alkenyl, amino, or $C_1$-$C_8$ alkoxy or $C_1$-$C_8$ fluoroalkoxy.

21. In another embodiment, the present disclosure features the compound of any one of embodiments 1 to 20 or a pharmaceutically acceptable salt thereof, wherein one or more hydrogen atoms is replaced by a deuterium atom.

22. In another embodiment, the present disclosure features the compound of embodiment 1 or a pharmaceutically acceptable salt thereof, wherein the compound of formula I or a pharmaceutically acceptable salt thereof is a compound of formula I-i:

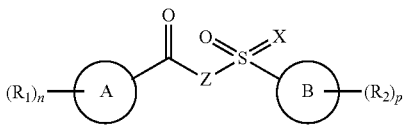

I-i or a pharmaceutically acceptable salt thereof, wherein, independently for each occurrence:

Ring A is a $C_3$-$C_{14}$ heteroaryl or heterocyclic ring wherein anywhere from 1 to 4 ring atoms are independently O, S, N, or NR;

Ring B is a $C_3$-$C_{10}$ heteroaryl or $C_3$-$C_{10}$ heterocyclic ring wherein anywhere from 1 to 4 ring atoms are independently O, S, N, or NR;

X is O or NR;

Z is NR;

$R_1$ is halo; CN; NRR; $C_1$-$C_6$ alkyl or $C_1$-$C_6$ fluoroalkyl; $C_3$-$C_6$ cycloalkyl; $C_1$-$C_8$ alkoxy or $C_1$-$C_8$ fluoroalkoxy; $C_2$-$C_6$ alkenyl; $C_2$-$C_6$ alkynyl; ($C_1$-$C_9$ alkylene)-$R_3$ wherein up to four $CH_2$ units are independently replaced with O, CO, S, SO, $SO_2$ or NR; $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_2$ is halo; NRR; CN; $CO_2R$; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four $CH_2$ units are optionally and independently replaced with O, CO, S, SO, $SO_2$ or NR;

or two $R_2$ may form a $=CH_2$ or $=O$ group;

$R_3$ is H; $CF_3$; $CHF_2$; OR; C≡CH; $CO_2R$; OH; $C_6$-$C_{10}$ aryl, $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or $SO_2R$;

R is independently H; OH; $CO_2H$; $CO_2C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, or N; or $C_3$-$C_{10}$ cycloalkyl;

n is 2 or 3; and p is 0, 1, 2, or 3.

23. In another embodiment, the present disclosure features the compound of embodiment 22 or a pharmaceutically acceptable salt thereof, wherein ring A is a pyridyl, indole, indoline, isoindoline, pyrazole, pyrimidine, quinoline, 5,6,7,8-tetrahydroquinoline, 1,2,3,4-tetrahydroisoquinoline, pyrrolodine, aza-indole, pyrrole, oxazole, pyrazine, triazole, indazole, imidazo[1,2-a]pyridine, or imidazole ring.

24. In another embodiment, the present disclosure features the compound of embodiment 22 or 23 or a pharmaceutically acceptable salt thereof, wherein Ring A is

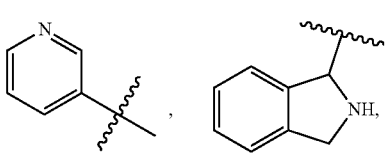

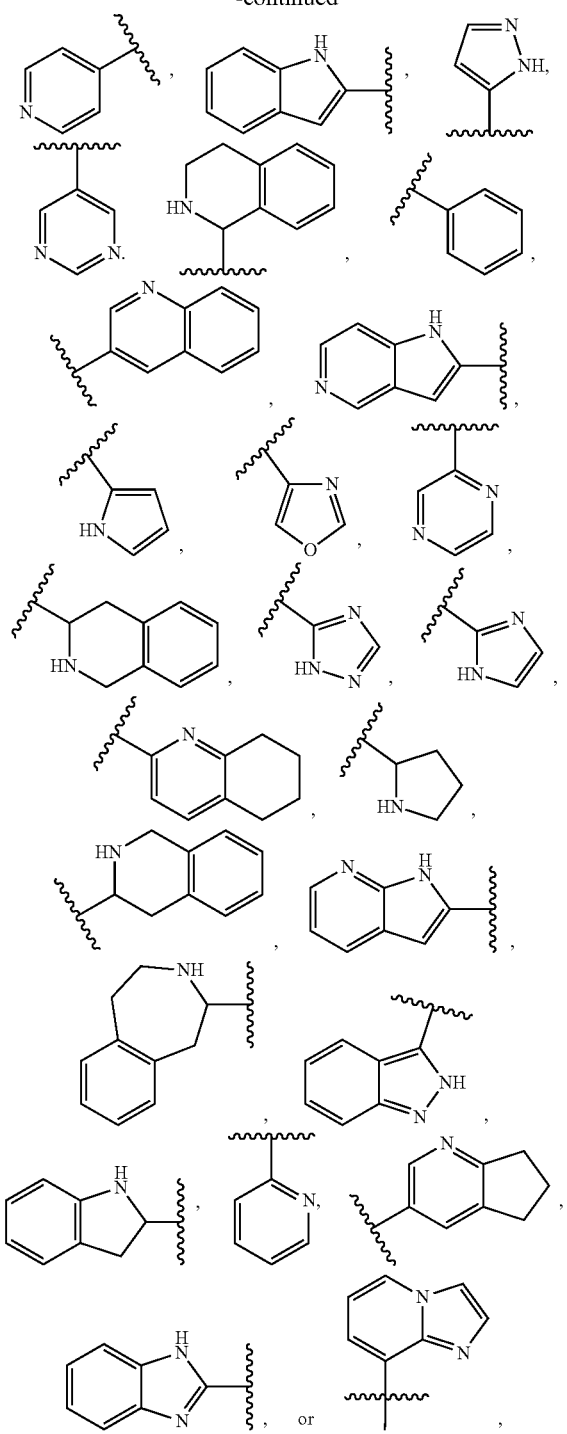
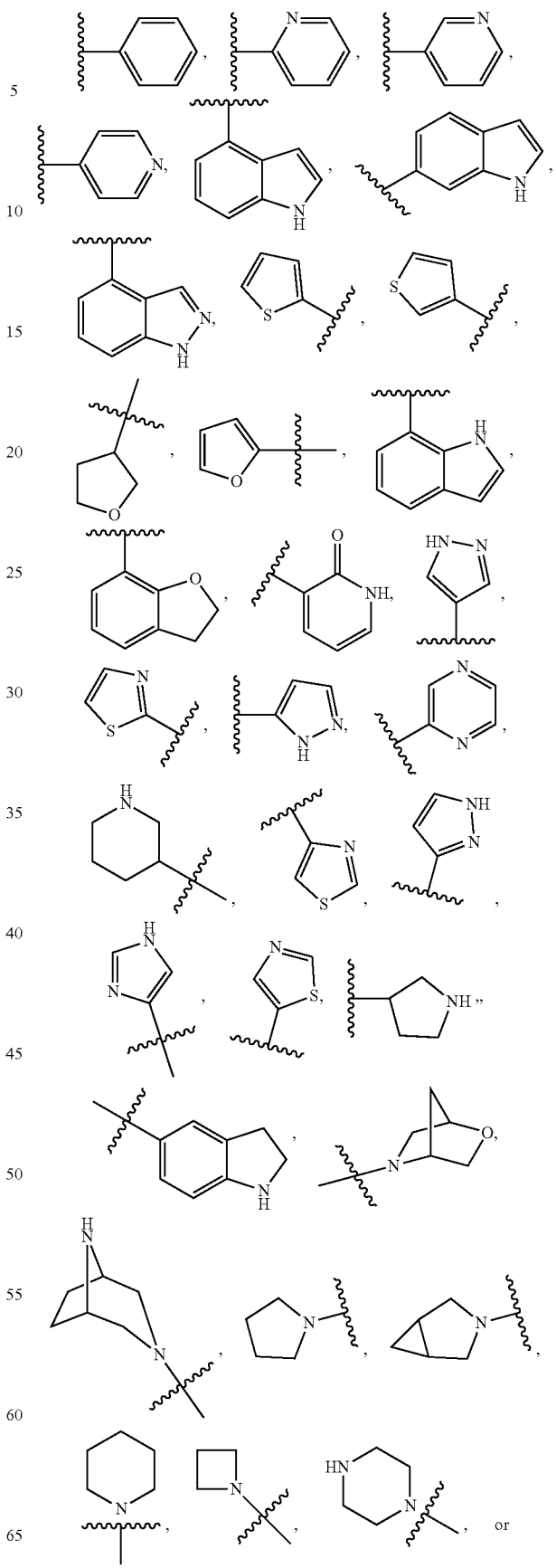

wherein the wavy line ⌇ indicates point of attachment of Ring A to the carbonyl (CO).

25. In another embodiment, the present disclosure features the compound of any one of embodiments 22 to 24 or a pharmaceutically acceptable salt thereof, wherein Ring B is pyridyl, pyridine-2(1H)-one, pyrazole, indole, aza-indole, thiophene, dihydrobenzofuran, thiazole, pyrrolidinone, or quinoline.

26. In another embodiment, the present disclosure features the compound of any one of embodiments 22 to 25 or a pharmaceutically acceptable salt thereof, wherein Ring B

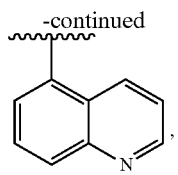

wherein the wavy line ⌇ indicates point of attachment of Ring B to X=S=O.

27. In another embodiment, the present disclosure features the compound of any one of embodiments 22 to 26 or a pharmaceutically acceptable salt thereof, wherein X is O.

28. In another embodiment, the present disclosure features the compound of any one of embodiments 22 to 27 or a pharmaceutically acceptable salt thereof, wherein Z is NH.

29. In another embodiment, the present disclosure features the compound of any one of embodiments 22 to 28 or a pharmaceutically acceptable salt thereof, wherein $R_1$ is independently halo, amino, OH, $C_1$-$C_6$ fluoroalkyl, CN, $C_1$-$C_6$ alkyl, $C_2$-$C_6$ alkenyl; $C_2$-$C_6$ alkynyl, $C_1$-$C_8$ alkoxy or $C_1$-$C_8$fluoroalkoxy, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring, or a ($C_1$-$C_9$ alkylene)-$R_3$ wherein up to four $CH_2$ units are independently replaced with O, CO, S, SO, $SO_2$ or NR.

30. In another embodiment, the present disclosure features the compound of any one of embodiments 22 to 29 or a pharmaceutically acceptable salt thereof, wherein $R_1$ is $CHF_2CH_2(CH_3)N$—, $(CH_3)_2CHCH_2CH2O$—, $(CH_3)_3CCH_2CH_2O$—, $(CH_3)_3COCH_2CH_2O$—, $(CH_3)_2CHO$—, $CHF_2CHF_2CH(CH_3)O$—, —$CF_3$, $(CH_3CH_2)_2N$—, $CF_3CH_2CH(CH_3)O$—, $CH_3O$—, $CH_3(CH_2)_4O$—, $CH_3CH_2CH(CH_3)CH(CH_3)O$—, $CH_3CH_2OCH_2CH_2O$—, $CH_3CH_2NCH(CH_3)_2$, $(CH_3)_3CH_2O$—, (R)—$CH_3NCH(CH_3)(CF_3)$, $CH_3OCH_2CH(CH_2CH_3)O$—, $(CH_3)_2N$—, (S)—$CH_3OCH_2CH(CH_3)O$—, $CH_3O(CH_2)_3O$—, $CH_3OC(CH_3)_2(CH_2)_2O$, $CH_3OCH_2CH(CH_3)O$, $CH_3CH(CH_3)CH_2CH(CH_3)O$—, $(CH_3)_3CCH(CH_3)O$, $((CH_3)_2CH)_2CHO$—, $CH_3CH_2CH_2O$, $CH_3CH=CHCH_2O$—, (S)—$CH_3CH_2CH(CH_3)O$—, $CH_3CH_2O$, $(CH_3)_2CHNCH_3$, $(CH_3)_3$ $CCH_2O$, $(CF_3)_2CHO$—, $(CH_3)_3CCH(CH_2CH_3)O$, $CH_3C\equiv CCH_2CH_2O$, $(CH_3)_3CCH_2CH(CH_3)O$—, $(CH_3)_2C=C(CH_3)$, $CHF_2CH_2O$—, $CH_3CH_2CH_2NH$, $(CH_3)_2CHCH(CH_2CH_3)O$, $((CH_3)_2CH)_2N$, $CH_2=CHCH(CH_3)O$, $CH_2=CHCH_2O$—, $CH_3CH_2C(CH_3)_2O$, $(CH_3CH_2)_2CHO$, $CF_3CH_2O$, $CH_3C(=CH_2)CH_2O$, $(CH_3)_3CCH_2CH_2NH$, $CH_3OCH_2C(CH_3)_2O$, $(CH_3)_3CCH_2N(CH_3)$, $(CH_3)_2CHCH(CH_3)NH$, $(CH_3)_2CHO(CH_2)_2O$, $CH_3CH_2CH_2CH(CH_3)O$, $CH_3CF_2CH_2O$, $(CH_3)_3CNH$, (R)—$CH_3CH_2CH(CH_3)O$, $CH_3OCH_2CH_2O$, $(CH_3)_2CHCH_2N(CH_3)$, $CH_3CH_2CH_2CH(CH_3)CH(CH_3)O$, $CH_3CH_2CH_2CH_2O$, $CH_3CH_2CH_2N(CH_3)$, (R)—$CH_3OCH_2CH(CH_3)O$, $CF_3CH_2N(CH_3)$, $CH_3CH_2N(CH_3)$, $((CH_3)_3C)_2CHO$, $(CH_3CH_2)_2CHN(CH_3)$, $(CH_3)_2CHN(CH_3)$, $CH_3CH_2OCH_2CH(CH_3)O$, $(CH_3)_3CCH_2NH$, $CF_3CH(CH_3)O$, $CH_3CH_2NCH(CH_3)_2$, $(R)$—$CF_3CH(CH_3)N(CH_3)$, $(CH_3)_2CHCH(CH_3)$, $CH_3CH_2(CH_3)_2CHCH_2CH_2O$, (S)—$CH_3OCH(CH_3)CH_2O$, $HOCH(CH_3)_2CH_2CH_2NH$, $CF_3CH_2CH_2O$, $CF_3CH_2CH_2CH_2O$, $CF_3CH=CHCH_2O$, $CH_3CH_2CH_2CH_2CH_2NH$,

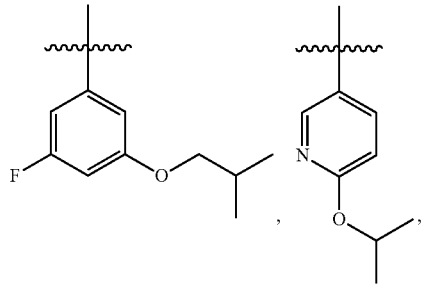

or $(CH_3)_3C$.

31. In another embodiment, the present disclosure features the compound of any one of embodiments 22 to 30 or a pharmaceutically acceptable salt thereof, wherein $R_2$ is halo, CN, OH, amino, $C_1$-$C_6$ alkyl or $C_1$-$C_6$ fluoroalkyl, $C_1$-$C_6$ alkoxy or $C_1$-$C_6$ fluoroalkoxy, $C_3$-$C_{10}$ heterocyclic ring wherein anywhere from 1 to 4 carbon atoms are independently O, S, N, or NR; or a ($C_1$-$C_9$ alkylene)-$R_3$ wherein up to four $CH_2$ units are optionally and independently replaced with O, CO, S, SO, $SO_2$ or NR.

32. In another embodiment, the present disclosure features the compound of any one of embodiments 22 to 31 or a pharmaceutically acceptable salt thereof, wherein $R_2$ is $NH_2$, or $NHCH_2CH_2CH_3$.

33. In another embodiment, the present disclosure features the compound of any one of embodiments 22 to 32 or a pharmaceutically acceptable salt thereof, wherein n is 2.

34. In another embodiment, the present disclosure features the compound of any one of embodiments 22 to 33 or a pharmaceutically acceptable salt thereof, wherein p is 0.

35. In another embodiment, the present disclosure features the compound of any one of embodiments 22 to 33 or a pharmaceutically acceptable salt thereof, wherein p is 1.

36. In another embodiment, the present disclosure features the compound of any one of embodiments 22 to 35 or a pharmaceutically acceptable salt thereof, wherein one or more hydrogen atoms are replaced by a deuterium atom.

37. In another embodiment, the present disclosure features the compound of embodiment 1 or a pharmaceutically acceptable salt thereof, wherein the compound of formula I or a pharmaceutically acceptable salt thereof is a compound of formula Ia:

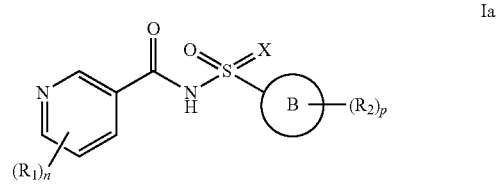

Ia or a pharmaceutically acceptable salt thereof, wherein, independently for each occurrence:

Ring B is a $C_3$-$C_{10}$ cycloalkyl ring; a $C_6$-$C_{10}$ aryl ring; or a $C_3$-$C_{10}$ heteroaryl or $C_3$-$C_{10}$ heterocyclic ring wherein anywhere from 1 to 4 ring atoms are independently O, S, N, or NR;

X is O or NR;

$R_1$ is halo; CN; NRR; $C_1$-$C_6$ alkyl or $C_1$-$C_6$ fluoroalkyl; $C_3$-$C_6$ cycloalkyl; $C_1$-$C_8$ alkoxy or $C_1$-$C_8$ fluoroalkoxy; $C_2$-$C_6$ alkenyl; $C_2$-$C_6$ alkynyl; ($C_1$-$C_9$ alkylene)-$R_3$ wherein up to four $CH_2$ units are independently replaced with O, CO, S, SO, SO₂ or NR; $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_2$ is halo; NRR; CN; $CO_2R$; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four $CH_2$ units are optionally and independently replaced with O, CO, S, SO, SO₂ or NR;

or two $R_2$ may form a =$CH_2$ or =O group;

$R_3$ is H; $CF_3$; $CHF_2$; OR; C≡CH; $CO_2R$; OH; $C_6$-$C_{10}$ aryl, $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or $SO_2R$;

R is independently H; OH; $CO_2H$; $CO_2C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, or N; or $C_3$-$C_{10}$ cycloalkyl;

n is 2 or 3; and p is 0, 1, 2, or 3.

38. In another embodiment, the present disclosure features the compound of embodiment 37 or a pharmaceutically acceptable salt thereof, wherein Ring B is pyridyl, pyridine-2(1H)-one, pyrazole, indole, aza-indole, thiophene, dihydrobenzofuran, thiazole, pyrrolidinone, or quinoline.

39. In another embodiment, the present disclosure features the compound of embodiment 37 or 38 or a pharmaceutically acceptable salt thereof, wherein Ring B is

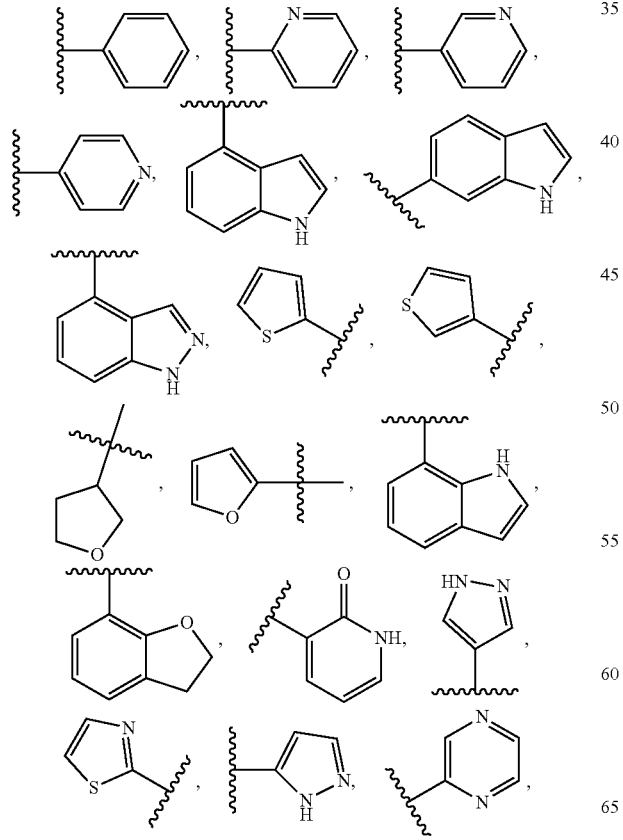

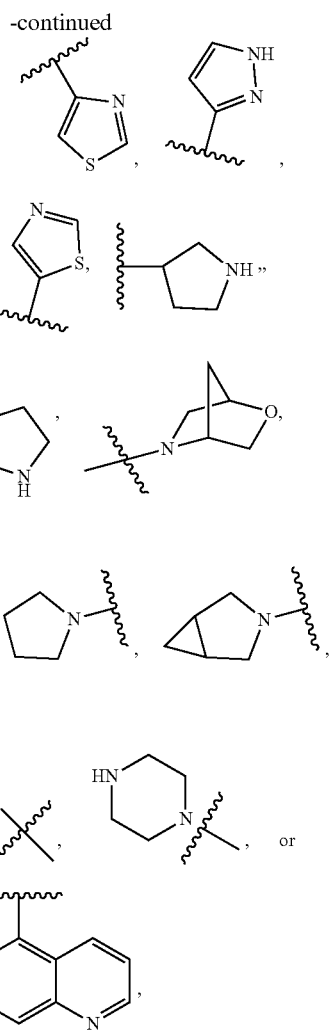

wherein the wavy line ⁓ indicates point of attachment of Ring B to X=S=O.

40. In another embodiment, the present disclosure features the compound of any one of embodiments 37 to 39 or a pharmaceutically acceptable salt thereof, wherein X is O.

41. In another embodiment, the present disclosure features the compound of any one of embodiments 37 to 40 or a pharmaceutically acceptable salt thereof, wherein $R_1$ is independently halo, amino, OH, $C_1$-$C_6$ fluoroalkyl, CN, $C_1$-$C_6$ alkyl, $C_2$-$C_6$ alkenyl, $C_2$-$C_6$ alkynyl, $C_1$-$C_8$ alkoxy or $C_1$-$C_8$ fluoroalkoxy, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring, or a ($C_1$-$C_9$ alkylene)-$R_3$ wherein up to four $CH_2$ units are independently replaced with O, CO, S, SO, $SO_2$ or NR.

42. In another embodiment, the present disclosure features the compound of any one of embodiments 37 to 41 or a pharmaceutically acceptable salt thereof, wherein $R_1$ is $CHF_2CH_2(CH_3)N$—, $(CH_3)_2CHCH_2CH2O$—, $(CH_3)_3CCH_2CH_2O$—, $(CH_3)_3COCH_2CH_2O$—, $(CH_3)_2CHO$—, $CHF_2CHF_2CH(CH_3)O$—, —$CF_3$, $(CH_3CH_2)_2N$—, $CF_3CH_2CH(CH_3)O$—, $CH_3O$—, $CH_3(CH_2)_4O$—, $CH_3CH_2CH(CH_3)CH(CH_3)O$—, $CH_3CH_2OCH_2CH_2O$—, $CH_3CH_2NCH(CH_3)_2$, $(CH_3)_3CH_2O$—, (R)—$CH_3NCH(CH_3)(CF_3)$, $CH_3OCH_2CH(CH_2CH_3)O$—, $(CH_3)_2N$—, (S)—CH₃OCH₂CH(CH₃)O—, CH₃O(CH₂)₃O—, CH₃OC(CH₃)₂(CH₂)₂O, CH₃OCH₂CH(CH₃)O, CH₃CH(CH₃)CH₂CH(CH₃)O—, (CH₃)₃CCH(CH₃)O, ((CH₃)₂CH)₂CHO—, CH₃CH₂CH₂O, CH₃CH=CHCH₂O—, (S)—CH₃CH₂CH(CH₃)O—, CH₃CH₂O, (CH₃)₂CHNCH₃, (CH₃)₃CCH₂O, (CF₃)₂CHO—, (CH₃)₃CCH(CH₂CH₃)O, CH₃C≡CCH₂CH₂O, (CH₃)₃CCH₂CH(CH₃)O—, (CH₃)₂C=C(CH₃), CHF₂CH₂O—, CH₃CH₂CH₂NH, (CH₃)₂CHCH(CH₂CH₃)O, ((CH₃)₂CH)₂N, CH₂=CHCH(CH₃)O, CH₂=CHCH₂O—, CH₃CH₂C(CH₃)₂O, (CH₃CH₂)₂CHO, CF₃CH₂O, CH₃C(=CH₂)CH₂O, (CH₃)₃CCH₂CH₂NH, CH₃OCH₂C(CH₃)₂O, (CH₃)₃CCH₂N(CH₃), (CH₃)₂CHCH(CH₃)NH, (CH₃)₂CHO(CH₂)₂O, CH₃CH₂CH₂CH(CH₃)O, CH₃CF₂CH₂O, (CH₃)₃CNH, (R)—CH₃CH₂CH(CH₃)O, CH₃OCH₂CH₂O, (CH₃)₂CHCH₂N(CH₃), CH₃CH₂CH₂CH(CH₃)CH(CH₃)O, CH₃CH₂CH₂CH₂O, CH₃CH₂CH₂N(CH₃), (R)—CH₃OCH₂CH(CH₃)O, CF₃CH₂N(CH₃), CH₃CH₂N(CH₃), ((CH₃)₃C)₂CHO, (CH₃CH₂)₂CHN(CH₃), (CH₃)₂CHN(CH₃), CH₃CH₂OCH₂CH(CH₃)O, (CH₃)₃CCH₂NH, CF₃CH(CH₃)O, CH₃CH₂NCH(CH₃)₂, (R)—CF₃CH(CH₃)N(CH₃), (CH₃)₂CHCH(CH₃), CH₃CH₂(CH₃)₂CHCH₂CH₂O, (S)—CH₃OCH(CH₃)CH₂O, HOCH(CH₃)₂CH₂CH₂NH, CF₃CH₂CH₂O, CF₃CH₂CH₂CH₂O, CF₃CH=CHCH₂O, CH₃CH₂CH₂CH₂CH₂NH,

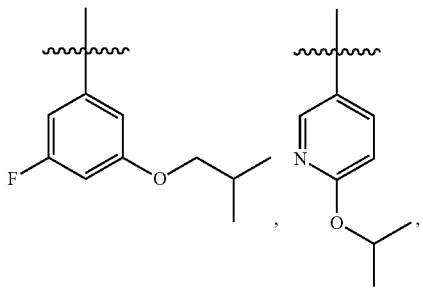

or (CH₃)₃C.

43. In another embodiment, the present disclosure features the compound of any one of embodiments 37 to 42 or a pharmaceutically acceptable salt thereof, wherein R₂ is halo, CN, amino, OH, C₁-C₆ alkyl or C₁-C₆ fluoroalkyl, C₁-C₆ alkoxy or C₁-C₆ fluoroalkoxy, C₃-C₁₀ heterocyclic ring wherein anywhere from 1 to 4 carbon atoms are independently O, S, N, or NR; or a (C₁-C₉ alkylene)-R₃ wherein up to four CH₂ units are optionally and independently replaced with O, CO, S, SO, SO₂ or NR.

44. In another embodiment, the present disclosure features the compound of any one of embodiments 37 to 43 or a pharmaceutically acceptable salt thereof, wherein R₂ is NH₂, or NHCH₂CH₂CH₃.

45. In another embodiment, the present disclosure features the compound of any one of embodiments 37 to 44 or a pharmaceutically acceptable salt thereof, wherein n is 2.

46. In another embodiment, the present disclosure features the compound of any one of embodiments 37 to 45 or a pharmaceutically acceptable salt thereof, wherein p is 0.

47. In another embodiment, the present disclosure features the compound of any one of embodiments 37 to 45 or a pharmaceutically acceptable salt thereof, wherein p is 1.

48. In another embodiment, the present disclosure features the compound of any one of embodiments 37 to 47 or a pharmaceutically acceptable salt thereof, wherein one or more hydrogen atoms are replaced by a deuterium atom.

49. In another embodiment, the present disclosure features the compound of embodiment 37 or a pharmaceutically acceptable salt thereof, wherein the compounds of formula Ia or a pharmaceutically acceptable salt thereof is a compound of formula Ia-i

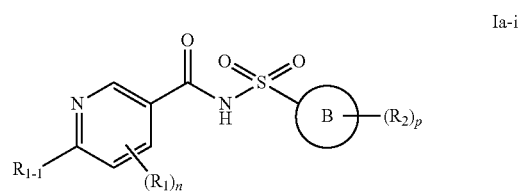

or a pharmaceutically acceptable salt thereof, wherein, independently for each occurrence:

Ring B is a C₃-C₁₀ cycloalkyl ring; a C₆-C₁₀ aryl ring; or a C₃-C₁₀ heteroaryl or C₃-C₁₀ heterocyclic ring wherein anywhere from 1 to 4 ring atoms are independently O, S, N, or NR;

R₁ is halo; CN; NRR; C₁-C₆ alkyl or C₁-C₆ fluoroalkyl; C₃-C₆ cycloalkyl; C₁-C₈ alkoxy or C₁-C₈ fluoroalkoxy; C₂-C₆ alkenyl; C₂-C₆ alkynyl; (C₁-C₉ alkylene)-R₃ wherein up to four CH₂ units are independently replaced with O, CO, S, SO, SO₂ or NR; C₆-C₁₀ aryl; C₃-C₁₀ heteroaryl or C₃-C₁₀ heterocyclic ring wherein anywhere from 1 to 4 ring atoms are independently O, S, N, or NR; or C₃-C₁₀ cycloalkyl;

R₁₋₁ is C₁-C₆ alkyl or C₁-C₆ fluoroalkyl, C₆-C₁₀ aryl; C₃-C₁₀ heteroaryl or C₃-C₁₀ heterocyclic ring wherein anywhere from 1 to 4 ring atoms are independently O, S, N, or NR; or C₃-C₁₀ cycloalkyl;

R₂ is halo; NRR; CN; CO₂R; C₁-C₆ alkyl or C₁-C₆ fluoroalkyl; C₁-C₆ alkoxy or C₁-C₆ fluoroalkoxy; C₂-C₆ alkenyl; C₂-C₆ alkynyl; C₆-C₁₀ aryl; C₃-C₁₃ heteroaryl or heterocyclic ring wherein anywhere from 1 to 4 ring atoms are independently O, S, N, or NR; C₃-C₁₀ cycloalkyl; or a (C₁-C₉ alkylene)-R₃ wherein up to four CH₂ units are optionally and independently replaced with O, CO, S, SO, SO₂ or NR;

or two R₂ may form a =CH₂ or =O group;

R₃ is H; CF₃; CHF₂; OR; C≡CH; CO₂R; OH; C₆-C₁₀ aryl, C₃-C₁₀ heteroaryl or heterocycloalkyl wherein anywhere from 1 to 4 ring atoms are independently O, S, N, or NR; C₃-C₁₀ cycloalkyl; NRR, NRCOR, CONRR, CN, halo, or SO₂R;

R is independently H; OH; CO₂H; CO₂C₁-C₆ alkyl; C₁-C₆ alkyl; C₂-C₆ alkenyl; C₂-C₆ alkynyl; C₆-C₁₀ aryl; C₃-C₁₀ heteroaryl or heterocycloalkyl wherein anywhere from 1 to 4 ring atoms are independently O, S, or N; or C₃-C₁₀ cycloalkyl;

n is 1 or 2; and p is 0, 1, 2, or 3.

50. In another embodiment, the present disclosure features the compound of embodiment 49 or a pharmaceutically acceptable salt thereof, wherein Ring B is pyridyl, pyridine-2(1H)-one, pyrazole, indole, aza-indole, thiophene, dihydrobenzofuran, thiazole, pyrrolidinone, or quinoline.

51. In another embodiment, the present disclosure features the compound of embodiment 49 or 50 or a pharmaceutically acceptable salt thereof, wherein Ring B is

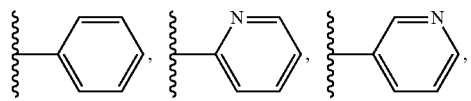

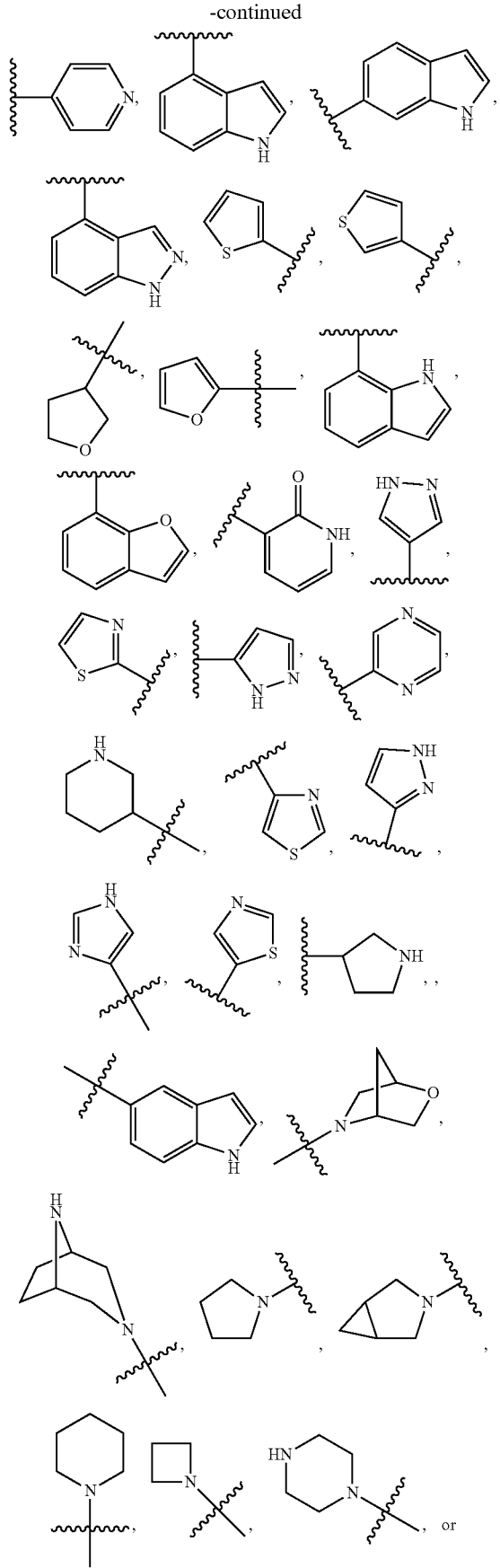

wherein the wavy line  indicates point of attachment of Ring B to the sulfonyl.

52. In another embodiment, the present disclosure features the compound of any one of embodiments 49 to 51 or a pharmaceutically acceptable salt thereof, wherein $R_1$ is independently halo, amino, OH, $C_1$-$C_6$ fluoroalkyl, CN, $C_1$-$C_6$ alkyl, $C_2$-$C_6$ alkenyl, $C_2$-$C_6$ alkynyl, $C_1$-$C_8$ alkoxy or $C_1$-$C_8$fluoroalkoxy, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring, or a ($C_1$-$C_9$ alkylene)-$R_3$ wherein up to four $CH_2$ units are independently replaced with O, CO, S, SO, $SO_2$ or NR.

53. In another embodiment, the present disclosure features the compound of any one of embodiments 49 to 52 or a pharmaceutically acceptable salt thereof, wherein $R_{1-1}$ is $C_1$-$C_6$ alkyl or $C_1$-$C_6$ fluoroalkyl, a phenyl, mono-$C_4$-$C_6$ heterocyclic ring, 1,2,3,4-tetrahydroisoquinoline, pyridyl, pyrimidine, indole, aza-indole, pyrazole, pyrrole, or thiophene ring.

54. In another embodiment, the present disclosure features the compound of any one of embodiments 49 to 53 or a pharmaceutically acceptable salt thereof, wherein $R_{1-1}$ is tert-butyl,

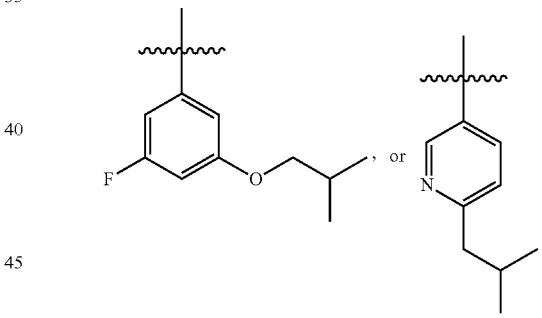

55. In another embodiment, the present disclosure features the compound of any one of embodiments 49 to 54 or a pharmaceutically acceptable salt thereof, wherein $R_1$ is $CHF_2CH_2(CH_3)N$—, $(CH_3)_2CHCH_2CH2O$—, $(CH_3)_3CCH_2CH_2O$—, $(CH_3)_3COCH_2CH_2O$—, $(CH_3)_2CHO$—, $CHF_2CHF_2CH(CH_3)O$—, —$CF_3$, $(CH_3CH_2)_2N$—, $CF_3CH_2CH(CH_3)O$—, $CH_3O$—, $CH_3(CH_2)_4O$—, $CH_3CH_2CH(CH_3)CH(CH_3)O$—, $CH_3CH_2OCH_2CH_2O$—, $CH_3CH_2NCH(CH_3)_2$, $(CH_3)_3CH_2O$—, (R)—$CH_3NCH(CH_3)(CF_3)$, $CH_3OCH_2CH(CH_2CH_3)O$—, $(CH_3)_2N$—, (S)—$CH_3OCH_2CH(CH_3)O$—, $CH_3O(CH_2)_3O$—, $CH_3OC(CH_3)_2(CH_2)_2O$, $CH_3OCH_2CH(CH_3)O$, $CH_3CH(CH_3)CH_2CH(CH_3)O$—, $(CH_3)_3CCH(CH_3)O$, $((CH_3)_2CH)_2CHO$—, $CH_3CH_2CH_2O$, $CH_3CH=CHCH_2O$—, (S)—$CH_3CH_2CH(CH_3)O$—, $CH_3CH_2O$, $(CH_3)_2CHNCH_3$, $(CH_3)_3CCH_2O$, $(CF_3)_2CHO$—, $(CH_3)_3CCH(CH_2CH_3)O$, $CH_3C\equiv CCH_2CH_2O$, $(CH_3)_3CCH_2CH(CH_3)O$—, $(CH_3)_2C=C(CH_3)$, $CHF_2CH_2O$—, $CH_3CH_2CH_2NH$, $(CH_3)_2CHCH(CH_2CH_3)O$, $((CH_3)_2CH)_2N$, $CH_2=CHCH(CH_3)O$, CH$_2$=CHCH$_2$O—, CH$_3$CH$_2$C(CH$_3$)$_2$O, (CH$_3$CH$_2$)$_2$CHO, CF$_3$CH$_2$O, CH$_3$C(=CH$_2$)CH$_2$O, (CH$_3$)$_3$CCH$_2$CH$_2$NH, CH$_3$OCH$_2$C(CH$_3$)$_2$O, (CH$_3$)$_3$CCH$_2$N(CH$_3$), (CH$_3$)$_2$CHCH(CH$_3$)NH, (CH$_3$)$_2$CHO(CH$_2$)$_2$O, CH$_3$CH$_2$CH$_2$CH(CH$_3$)O, CH$_3$CF$_2$CH$_2$O, (CH$_3$)$_3$CNH, (R)—CH$_3$CH$_2$CH(CH$_3$)O, CH$_3$OCH$_2$CH$_2$O, (CH$_3$)$_2$CHCH$_2$N(CH$_3$), CH$_3$CH$_2$CH$_2$CH(CH$_3$)CH(CH$_3$)O, CH$_3$CH$_2$CH$_2$CH$_2$O, CH$_3$CH$_2$CH$_2$N(CH$_3$), (R)—CH$_3$OCH$_2$CH(CH$_3$)O, CF$_3$CH$_2$N(CH$_3$), CH$_3$CH$_2$N(CH$_3$), ((CH$_3$)$_3$C)$_2$CHO, (CH$_3$CH$_2$)$_2$CHN(CH$_3$), (CH$_3$)$_2$CHN(CH$_3$), CH$_3$CH$_2$OCH$_2$CH(CH$_3$)O, (CH$_3$)$_3$CCH$_2$NH, CF$_3$CH(CH$_3$)O, CH$_3$CH$_2$NCH(CH$_3$)$_2$, $(_R)$—CF$_3$CH(CH$_3$)N(CH$_3$), (CH$_3$)$_2$CHCH(CH$_3$), CH$_3$CH$_2$(CH$_3$)$_2$CHCH$_2$CH$_2$O, (S)—CH$_3$OCH(CH$_3$)CH$_2$O, HOCH(CH$_3$)$_2$CH$_2$CH$_2$NH, CF$_3$CH$_2$CH$_2$O, CF$_3$CH$_2$CH$_2$CH$_2$O, CF$_3$CH=CHCH$_2$O, or CH$_3$CH$_2$CH$_2$CH$_2$CH$_2$NH.

56. In another embodiment, the present disclosure features the compound of any one of embodiments 49 to 55 or a pharmaceutically acceptable salt thereof, wherein R$_2$ is halo, CN, amino, OH, C$_1$-C$_6$ alkyl or C$_1$-C$_6$ fluoroalkyl, C$_1$-C$_6$ alkoxy or C$_1$-C$_6$ fluoroalkoxy, C$_3$-C$_{10}$ heterocyclic ring wherein anywhere from 1 to 4 carbon atoms are independently O, S, N, or NR; or a (C$_1$-C$_9$ alkylene)-R$_3$ wherein up to four CH$_2$ units are optionally and independently replaced with O, CO, S, SO, SO$_2$ or NR.

57. In another embodiment, the present disclosure features the compound of any one of embodiments 49 to 56 or a pharmaceutically acceptable salt thereof, wherein R$_2$ is NH$_2$, or NHCH$_2$CH$_2$CH$_3$.

58. In another embodiment, the present disclosure features the compound of any one of embodiments 49 to 57 or a pharmaceutically acceptable salt thereof, wherein n is 1.

59. In another embodiment, the present disclosure features the compound of any one of embodiments 49 to 58 or a pharmaceutically acceptable salt thereof, wherein p is 0.

60. In another embodiment, the present disclosure features the compound of any one of embodiments 49 to 58 or a pharmaceutically acceptable salt thereof, wherein p is 1.

61. In another embodiment, the present disclosure features the compound of any one of embodiments 49 to 60 or a pharmaceutically acceptable salt thereof, wherein one or more hydrogen atoms are replaced by a deuterium atom.

62. In another embodiment, the present disclosure features the compound of embodiment 49 or a pharmaceutically acceptable salt thereof, wherein the compounds of formula Ia-i or a pharmaceutically acceptable salt thereof is a compound of formula Ia-i-1

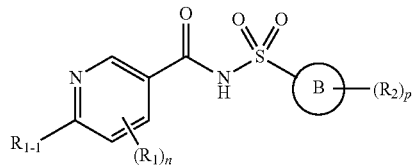

Ia-i-1 or a pharmaceutically acceptable salt thereof, wherein, independently for each occurrence:

Ring B is a C$_3$-C$_{10}$ heteroaryl or C$_3$-C$_{10}$ heterocyclic ring wherein anywhere from 1 to 4 ring atoms are independently O, S, N, or NR;

R$_1$ is halo; CN; NRR; C$_1$-C$_6$ alkyl or C$_1$-C$_6$ fluoroalkyl; C$_3$-C$_6$ cycloalkyl; C$_1$-C$_8$ alkoxy or C$_1$-C$_8$ fluoroalkoxy; C$_2$-C$_6$ alkenyl; C$_2$-C$_6$ alkynyl; (C$_1$-C$_9$ alkylene)-R$_3$ wherein up to four CH$_2$ units are independently replaced with O, CO, S, SO, SO$_2$ or NR; C$_6$-C$_{10}$ aryl; C$_3$-C$_{10}$ heteroaryl or C$_3$-C$_{10}$ heterocyclic ring wherein anywhere from 1 to 4 ring atoms are independently O, S, N, or NR; or C$_3$-C$_{10}$ cycloalkyl;

R$_{1\text{-}1}$ is C$_1$-C$_6$ alkyl or C$_1$-C$_6$ fluoroalkyl, C$_6$-C$_{10}$ aryl; C$_3$-C$_{10}$ heteroaryl or C$_3$-C$_{10}$ heterocyclic ring wherein anywhere from 1 to 4 ring atoms are independently O, S, N, or NR; or C$_3$-C$_{10}$ cycloalkyl;

R$_2$ is halo; NRR; CN; CO$_2$R; C$_1$-C$_6$ alkyl or C$_1$-C$_6$ fluoroalkyl; C$_1$-C$_6$ alkoxy or C$_1$-C$_6$ fluoroalkoxy; C$_2$-C$_6$ alkenyl; C$_2$-C$_6$ alkynyl; C$_6$-C$_{10}$ aryl; C$_3$-C$_{13}$ heteroaryl or heterocyclic ring wherein anywhere from 1 to 4 ring atoms are independently O, S, N, or NR; C$_3$-C$_{10}$ cycloalkyl; or a (C$_1$-C$_9$ alkylene)-R$_3$ wherein up to four CH$_2$ units are optionally and independently replaced with O, CO, S, SO, SO$_2$ or NR;

or two R$_2$ may form a =CH$_2$ or =O group;

R$_3$ is H; CF$_3$; CHF$_2$; OR; C≡CH; CO$_2$R; OH; C$_6$-C$_{10}$ aryl, C$_3$-C$_{10}$ heteroaryl or heterocycloalkyl wherein anywhere from 1 to 4 ring atoms are independently O, S, N, or NR; C$_3$-C$_{10}$ cycloalkyl; NRR, NRCOR, CONRR, CN, halo, or SO$_2$R;

R is independently H; OH; CO$_2$H; CO$_2$C$_1$-C$_6$ alkyl; C$_1$-C$_6$ alkyl; C$_2$-C$_6$ alkenyl; C$_2$-C$_6$ alkynyl; C$_6$-C$_{10}$ aryl; C$_3$-C$_{10}$ heteroaryl or heterocycloalkyl wherein anywhere from 1 to 4 ring atoms are independently O, S, or N; or C$_3$-C$_{10}$ cycloalkyl;

n is 1 or 2; and p is 0, 1, 2, or 3.

63. In another embodiment, the present disclosure features the compound of embodiment 62 or a pharmaceutically acceptable salt thereof, wherein Ring B is pyridyl, pyridine-2(1H)-one, pyrazole, indole, aza-indole, thiophene, dihydrobenzofuran, thiazole, pyrrolidinone, or quinoline.

64. In another embodiment, the present disclosure features the compound of embodiment 62 or 63 or a pharmaceutically acceptable salt thereof, wherein Ring B is

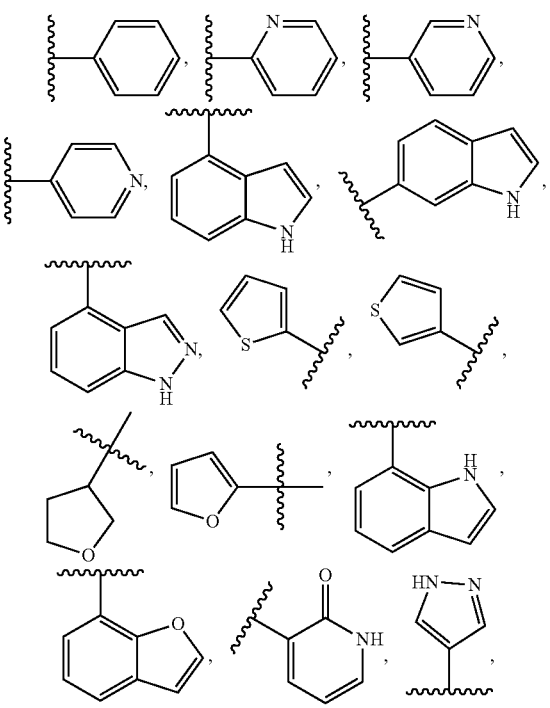

193
-continued

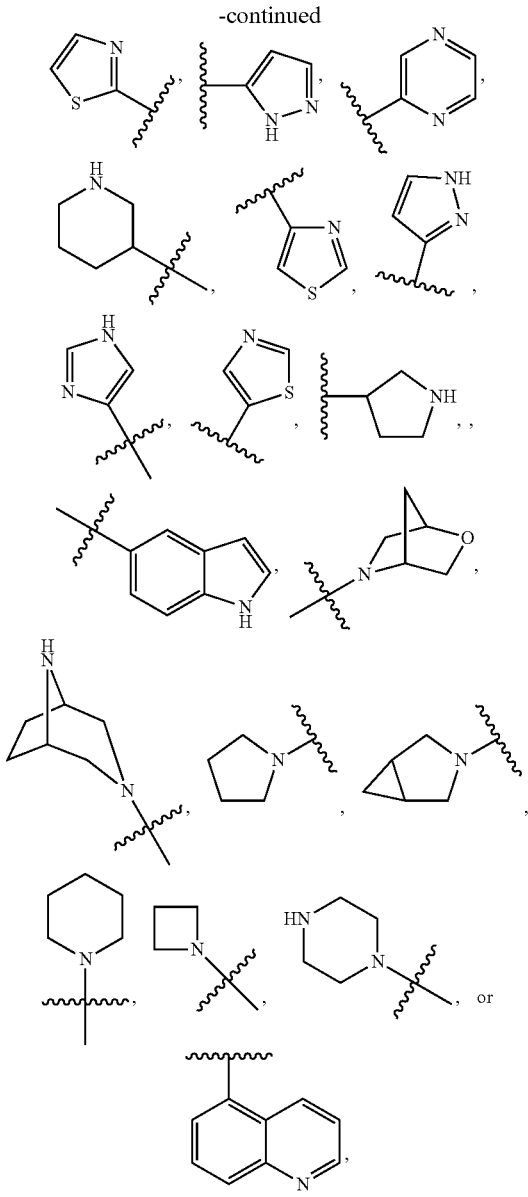

wherein the wavy line ⌇ indicates point of attachment of Ring B to the sulfonyl.

65. In another embodiment, the present disclosure features the compound of any one of embodiments 62 to 64 or a pharmaceutically acceptable salt thereof, wherein $R_1$ is independently halo, amino, OH, $C_1$-$C_6$ fluoroalkyl, CN, $C_1$-$C_6$ alkyl, $C_2$-$C_6$ alkenyl, $C_2$-$C_6$ alkynyl, $C_1$-$C_8$ alkoxy or $C_1$-$C_8$fluoroalkoxy, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring, or a ($C_1$-$C_9$ alkylene)-$R_3$ wherein up to four $CH_2$ units are independently replaced with O, CO, S, SO, $SO_2$ or NR.

66. In another embodiment, the present disclosure features the compound of any one of embodiments 62 to 65 or a pharmaceutically acceptable salt thereof, wherein $R_1$ is $C_1$-$C_6$ alkyl or $C_1$-$C_6$ fluoroalkyl, a phenyl, mono-$C_4$-$C_6$ heterocyclic ring, 1,2,3,4-tetrahydroisoquinoline, pyridyl, pyrimidine, indole, aza-indole, pyrazole, pyrrole, or thiophene ring.

194

67. In another embodiment, the present disclosure features the compound of any one of embodiments 62 to 66 or a pharmaceutically acceptable salt thereof, wherein $R_{1-1}$ is tert-butyl,

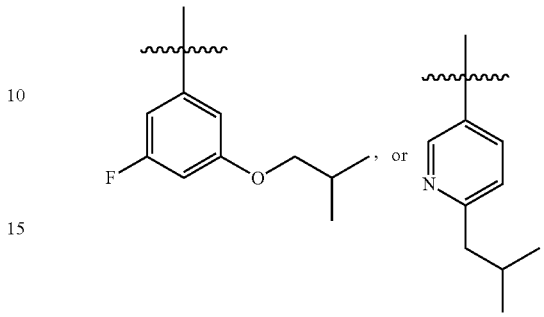

68. In another embodiment, the present disclosure features the compound of any one of embodiments 62 to 67 or a pharmaceutically acceptable salt thereof, wherein $R_1$ is $CHF_2CH_2(CH_3)N$—, $(CH_3)_2CHCH_2CH_2O$—, $(CH_3)_3CCH_2CH_2O$—, $(CH_3)_3COCH_2CH_2O$—, $(CH_3)_2CHO$—, $CHF_2CHF_2CH(CH_3)O$—, —$CF_3$, $(CH_3CH_2)_2N$—, $CF_3CH_2CH(CH_3)O$—, $CH_3O$—, $CH_3(CH_2)_4O$—, $CH_3CH_2CH(CH_3)CH(CH_3)O$—, $CH_3CH_2OCH_2CH_2O$—, $CH_3CH_2NCH(CH_3)_2$, $(CH_3)_3CH_2O$—, (R)—$CH_3NCH$ $(CH_3)(CF_3)$, $CH_3OCH_2CH(CH_2CH_3)O$—, $(CH_3)_2N$—, (S)—$CH_3OCH_2CH(CH_3)O$—, $CH_3O(CH_2)_3O$—, $CH_3OC$ $(CH_3)_2(CH_2)_2O$, $CH_3OCH_2CH(CH_3)O$, $CH_3CH(CH_3)$ $CH_2CH(CH_3)O$—, $(CH_3)_3CCH(CH_3)O$, $((CH_3)_2CH)_2$ $CHO$—, $CH_3CH_2CH_2O$, $CH_3CH=CHCH_2O$—, (S)—$CH_3CH_2CH(CH_3)O$—, $CH_3CH_2O$, $(CH_3)_2CHNCH_3$, $(CH_3)_3$ $CCH_2O$, $(CF_3)_2CHO$—, $(CH_3)_3CCH(CH_2CH_3)O$, $CH_3C\equiv CCH_2CH_2O$, $(CH_3)_3CCH_2CH(CH_3)O$—, $(CH_3)_2$ $C=C(CH_3)$, $CHF_2CH_2O$—, $CH_3CH_2CH_2NH$, $(CH_3)_2$ $CHCH(CH_2CH_3)O$, $((CH_3)_2CH)_2N$, $CH_2=CHCH(CH_3)O$, $CH_2=CHCH_2O$—, $CH_3CH_2C(CH_3)_2O$, $(CH_3CH_2)_2CHO$, $CF_3CH_2O$, $CH_3C(=CH_2)CH_2O$, $(CH_3)_3CCH_2CH_2NH$, $CH_3OCH_2C(CH_3)_2O$, $(CH_3)_3CCH_2N(CH_3)$, $(CH_3)_2CHCH$ $(CH_3)NH$, $(CH_3)_2CHO(CH_2)_2O$, $CH_3CH_2CH_2CH(CH_3)O$, $CH_3CF_2CH_2O$, $(CH_3)_3CNH$, (R)—$CH_3CH_2CH(CH_3)O$, $CH_3OCH_2CH_2O$, $(CH_3)_2CHCH_2N(CH_3)$, $CH_3CH_2CH_2CH$ $(CH_3)CH(CH_3)O$, $CH_3CH_2CH_2CH_2O$, $CH_3CH_2CH_2N$ $(CH_3)$, (R)—$CH_3OCH_2CH(CH_3)O$, $CF_3CH_2N(CH_3)$, $CH_3CH_2N(CH_3)$, $((CH_3)_3C)_2CHO$, $(CH_3CH_2)_2CHN(CH_3)$, $(CH_3)_2CHN(CH_3)$, $CH_3CH_2OCH_2CH(CH_3)O$, $(CH_3)_3$ $CCH_2NH$, $CF_3CH(CH_3)O$, $CH_3CH_2NCH(CH_3)_2$, $(R)$—$CF_3CH(CH_3)N(CH_3)$, $(CH_3)_2CHCH(CH_3)$, $CH_3CH_2(CH_3)_2$ $CHCH_2CH_2O$, (S)—$CH_3OCH(CH_3)CH_2O$, $HOCH(CH_3)_2$ $CH_2CH_2NH$, $CF_3CH_2CH_2O$, $CF_3CH_2CH_2CH_2O$, $CF_3CH=CHCH_2O$, or $CH_3CH_2CH_2CH_2CH_2NH$.

69. In another embodiment, the present disclosure features the compound of any one of embodiments 62 to 68 or a pharmaceutically acceptable salt thereof, wherein $R_2$ is halo, CN, amino, OH, $C_1$-$C_6$ alkyl or $C_1$-$C_6$ fluoroalkyl, $C_1$-$C_6$ alkoxy or $C_1$-$C_6$ fluoroalkoxy, $C_3$-$C_{10}$ heterocyclic ring wherein anywhere from 1 to 4 carbon atoms are independently O, S, N, or NR; or a ($C_1$-$C_9$ alkylene)-$R_3$ wherein up to four $CH_2$ units are optionally and independently replaced with O, CO, S, SO, $SO_2$ or NR.

70. In another embodiment, the present disclosure features the compound of any one of embodiments 62 to 69 or a pharmaceutically acceptable salt thereof, wherein $R_2$ is $NH_2$, or $NHCH_2CH_2CH_3$.

71. In another embodiment, the present disclosure features the compound of any one of embodiments 62 to 70 or a pharmaceutically acceptable salt thereof, wherein n is 1.

72. In another embodiment, the present disclosure features the compound of any one of embodiments 62 to 71 or a pharmaceutically acceptable salt thereof, wherein p is 0.

73. In another embodiment, the present disclosure features the compound of any one of embodiments 62 to 71 or a pharmaceutically acceptable salt thereof, wherein p is 1.

74. In another embodiment, the present disclosure features the compound of any one of embodiments 62 to 73 or a pharmaceutically acceptable salt thereof, wherein one or more hydrogen atoms are replaced by a deuterium atom.

75. In another embodiment, the present disclosure features the compound of embodiment 62 or a pharmaceutically acceptable salt thereof, wherein the compound of formula Ia-i-1 or a pharmaceutically acceptable salt thereof is a compound of formula Ia-i-2

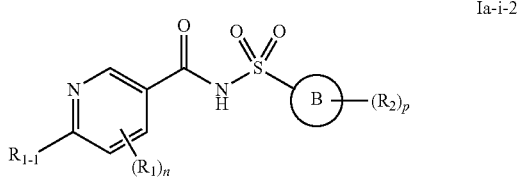

Ia-i-2 or a pharmaceutically acceptable salt thereof, wherein, independently for each occurrence:

Ring B is a pyridinyl;

$R_1$ is halo; CN; NRR; $C_1$-$C_6$ alkyl or $C_1$-$C_6$ fluoroalkyl; $C_3$-$C_6$ cycloalkyl; $C_1$-$C_8$ alkoxy or $C_1$-$C_8$ fluoroalkoxy; $C_2$-$C_6$ alkenyl; $C_2$-$C_6$ alkynyl; ($C_1$-$C_9$ alkylene)-$R_3$ wherein up to four $CH_2$ units are independently replaced with O, CO, S, SO, $SO_2$ or NR; $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_{1-1}$ is $C_1$-$C_6$ alkyl or $C_1$-$C_6$ fluoroalkyl, $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_2$ is halo; NRR; CN; $CO_2R$; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four $CH_2$ units are optionally and independently replaced with O, CO, S, SO, $SO_2$ or NR;

or two $R_2$ may form a =$CH_2$ or =O group;

$R_3$ is H; $CF_3$; $CHF_2$; OR; C≡CH; $CO_2R$; OH; $C_6$-$C_{10}$ aryl; $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or $SO_2R$;

R is independently H; OH; $CO_2H$; $CO_2C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocyloalkyl wherein anywhere from 1 to 4 ring atoms are independently O, S, or N; or $C_3$-$C_{10}$ cycloalkyl;

n is 1 or 2; and p is 0, 1, 2, or 3.

76. In another embodiment, the present disclosure features the compound of embodiment 75 or a pharmaceutically acceptable salt thereof, wherein Ring B is

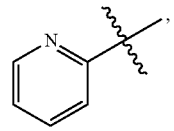

wherein the wavy line ⌇ indicates point of attachment of Ring B to the sulfonyl.

77. In another embodiment, the present disclosure features the compound of embodiment 75 or 76 or a pharmaceutically acceptable salt thereof, wherein $R_1$ is independently halo, amino, OH, $C_1$-$C_6$ fluoroalkyl, CN, $C_1$-$C_6$ alkyl, $C_2$-$C_6$ alkenyl, $C_2$-$C_6$ alkynyl, $C_1$-$C_8$ alkoxy or $C_1$-$C_8$fluoroalkoxy, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring, or a ($C_1$-$C_9$ alkylene)-$R_3$ wherein up to four $CH_2$ units are independently replaced with O, CO, S, SO, $SO_2$ or NR.

78. In another embodiment, the present disclosure features the compound of any one of embodiments 75 to 77 or a pharmaceutically acceptable salt thereof, wherein $R_{1-1}$ is $C_1$-$C_6$ alkyl or $C_1$-$C_6$ fluoroalkyl, a phenyl, mono-$C_4$-$C_6$ heterocyclic ring, 1,2,3,4-tetrahydroisoquinoline, pyridyl, pyrimidine, indole, aza-indole, pyrazole, pyrrole, or thiophene ring.

79. In another embodiment, the present disclosure features the compound of any one of embodiments 75 to 78 or a pharmaceutically acceptable salt thereof, wherein $R_{1-1}$ is tert-butyl,

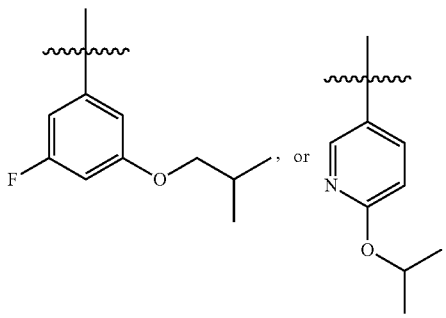

80. In another embodiment, the present disclosure features the compound of any one of embodiments 75 to 79 or a pharmaceutically acceptable salt thereof, wherein $R_1$ is $CHF_2CH_2(CH_3)N$—, $(CH_3)_2CHCH_2CH2O$—, $(CH_3)_3CCH_2CH_2O$—, $(CH_3)_3COCH_2CH_2O$—, $(CH_3)_2CHO$—, $CHF_2CHF_2CH(CH_3)O$—, —$CF_3$, $(CH_3CH_2)_2N$—, $CF_3CH_2CH(CH_3)O$—, $CH_3O$—, $CH_3(CH_2)_4O$—, $CH_3CH_2CH(CH_3)CH(CH_3)O$—, $CH_3CH_2OCH_2CH_2O$—, $CH_3CH_2NCH(CH_3)_2$, $(CH_3)_3CH_2O$—, (R)—$CH_3NCH(CH_3)(CF_3)$, $CH_3OCH_2CH(CH_2CH_3)O$—, $(CH_3)_2N$—, (S)—$CH_3OCH_2CH(CH_3)O$—, $CH_3O(CH_2)_3O$—, $CH_3OC(CH_3)_2(CH_2)_2O$, $CH_3OCH_2CH(CH_3)O$, $CH_3CH(CH_3)CH_2CH(CH_3)O$—, $(CH_3)_3CCH(CH_3)O$, $((CH_3)_2CH)_2CHO$—, $CH_3CH_2CH_2O$, $CH_3CH$=$CHCH_2O$—, (S)—$CH_3CH_2CH(CH_3)O$—, $CH_3CH_2O$, $(CH_3)_2CHNCH_3$, $(CH_3)_3$ $CCH_2O$, $(CF_3)_2CHO$—, $(CH_3)_3CCH(CH_2CH_3)O$, CH₃C≡CCH₂CH₂O, (CH₃)₃CCH₂CH(CH₃)O—, (CH₃)₂C=C(CH₃), CHF₂CH₂O—, CH₃CH₂CH₂NH, (CH₃)₂CHCH(CH₂CH₃)O, ((CH₃)₂CH)₂N, CH₂=CHCH(CH₃)O, CH₂=CHCH₂O—, CH₃CH₂C(CH₃)₂O, (CH₃CH₂)₂CHO, CF₃CH₂O, CH₃C(=CH₂)CH₂O, (CH₃)₃CCH₂CH₂NH, CH₃OCH₂C(CH₃)₂O, (CH₃)₃CCH₂N(CH₃), (CH₃)₂CHCH(CH₃)NH, (CH₃)₂CHO(CH₂)₂O, CH₃CH₂CH₂CH(CH₃)O, CH₃CF₂CH₂O, (CH₃)₃CNH, (R)—CH₃CH₂CH(CH₃)O, CH₃OCH₂CH₂O, (CH₃)₂CHCH₂N(CH₃), CH₃CH₂CH₂CH(CH₃)CH(CH₃)O, CH₃CH₂CH₂CH₂O, CH₃CH₂CH₂N(CH₃), (R)—CH₃OCH₂CH(CH₃)O, CF₃CH₂N(CH₃), CH₃CH₂N(CH₃), ((CH₃)₃C)₂CHO, (CH₃CH₂)₂CHN(CH₃), (CH₃)₂CHN(CH₃), CH₃CH₂OCH₂CH(CH₃)O, (CH₃)₃CCH₂NH, CF₃CH(CH₃)O, CH₃CH₂NCH(CH₃)₂, (R)—CF₃CH(CH₃)N(CH₃), (CH₃)₂CHCH(CH₃), CH₃CH₂(CH₃)₂CHCH₂CH₂O, (S)—CH₃OCH(CH₃)CH₂O, HOCH(CH₃)₂CH₂CH₂NH, CF₃CH₂CH₂O, CF₃CH₂CH₂CH₂O, CF₃CH=CHCH₂O, or CH₃CH₂CH₂CH₂CH₂NH.

81. In another embodiment, the present disclosure features the compound of any one of embodiments 75 to 80 or a pharmaceutically acceptable salt thereof, wherein R₂ is halo, CN, amino, OH, C₁-C₆ alkyl or C₁-C₆ fluoroalkyl, C₁-C₆ alkoxy or C₁-C₆ fluoroalkoxy, C₃-C₁₀ heterocyclic ring wherein anywhere from 1 to 4 carbon atoms are independently O, S, N, or NR; or a (C₁-C₉ alkylene)-R₃ wherein up to four CH₂ units are optionally and independently replaced with O, CO, S, SO, SO₂ or NR.

82. In another embodiment, the present disclosure features the compound of any one of embodiments 75 to 81 or a pharmaceutically acceptable salt thereof, wherein R₂ is NH₂, or NHCH₂CH₂CH₃.

83. In another embodiment, the present disclosure features the compound of any one of embodiments 75 to 82 or a pharmaceutically acceptable salt thereof, wherein n is 1.

84. In another embodiment, the present disclosure features the compound of any one of embodiments 75 to 83 or a pharmaceutically acceptable salt thereof, wherein p is 0.

85. In another embodiment, the present disclosure features the compound of any one of embodiments 75 to 83 or a pharmaceutically acceptable salt thereof, wherein p is 1.

86. In another embodiment, the present disclosure features the compound of any one of embodiments 75 to 85 or a pharmaceutically acceptable salt thereof, wherein one or more hydrogen atoms are replaced by a deuterium atom 87. In another embodiment, the present disclosure features the compound of embodiment 37 or a pharmaceutically acceptable salt thereof, wherein the compounds of formula Ia or a pharmaceutically acceptable salt thereof is a compound of formula Ia-ii Ia-ii

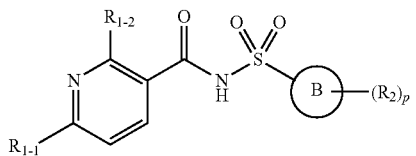

or a pharmaceutically acceptable salt thereof, wherein, independently for each occurrence:

Ring B is a $C_3$-$C_{10}$ cycloalkyl ring; a $C_6$-$C_{10}$ aryl ring; or a $C_3$-$C_{10}$ heteroaryl or $C_3$-$C_{10}$ heterocyclic ring wherein anywhere from 1 to 4 ring atoms are independently O, S, N, or NR;

$R_{1-2}$ is halo; CN; NRR; $C_1$-$C_6$ alkyl or $C_1$-$C_6$ fluoroalkyl; $C_1$-$C_8$ alkoxy or $C_1$-$C_8$ fluoroalkoxy; $C_2$-$C_6$ alkenyl; $C_2$-$C_6$ alkynyl; or ($C_1$-$C_9$ alkylene)-$R_3$ wherein up to four CH₂ units are independently replaced with O, CO, S, SO, SO₂ or NR;

$R_{1-1}$ is $C_1$-$C_6$ alkyl or $C_1$-$C_6$ fluoroalkyl, $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_2$ is halo; NRR; CN; CO₂R; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four CH₂ units are optionally and independently replaced with O, CO, S, SO, SO₂ or NR;

or two $R_2$ may form a =CH₂ or =O group;

$R_3$ is H; CF₃; CHF₂; OR; C≡CH; CO₂R; OH; $C_6$-$C_{10}$ aryl, $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or SO₂R;

R is independently H; OH; CO₂H; CO₂$C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, or N; or $C_3$-$C_{10}$ cycloalkyl; and p is 0, 1, 2, or 3.

88. In another embodiment, the present disclosure features the compound of embodiment 87 or a pharmaceutically acceptable salt thereof, wherein Ring B is pyridyl, pyridine-2(1H)-one, pyrazole, indole, aza-indole, thiophene, dihydrobenzofuran, thiazole, pyrrolidinone, or quinoline.

89. In another embodiment, the present disclosure features the compound of embodiment 87 or 88 or a pharmaceutically acceptable salt thereof, wherein Ring B is

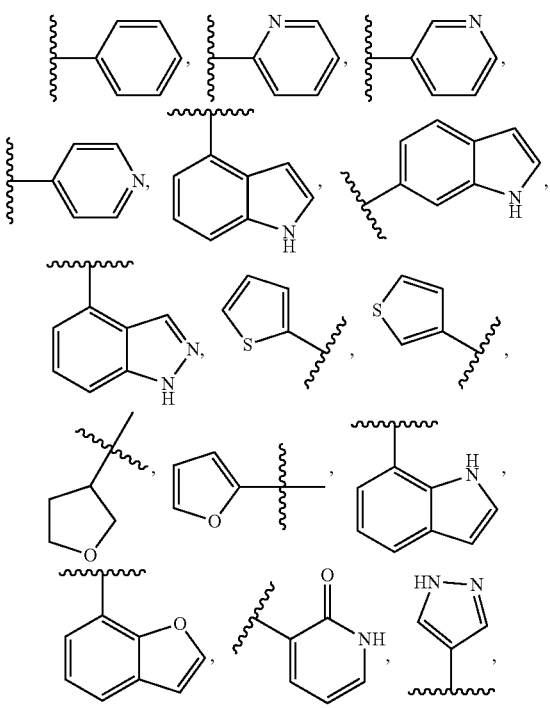

-continued

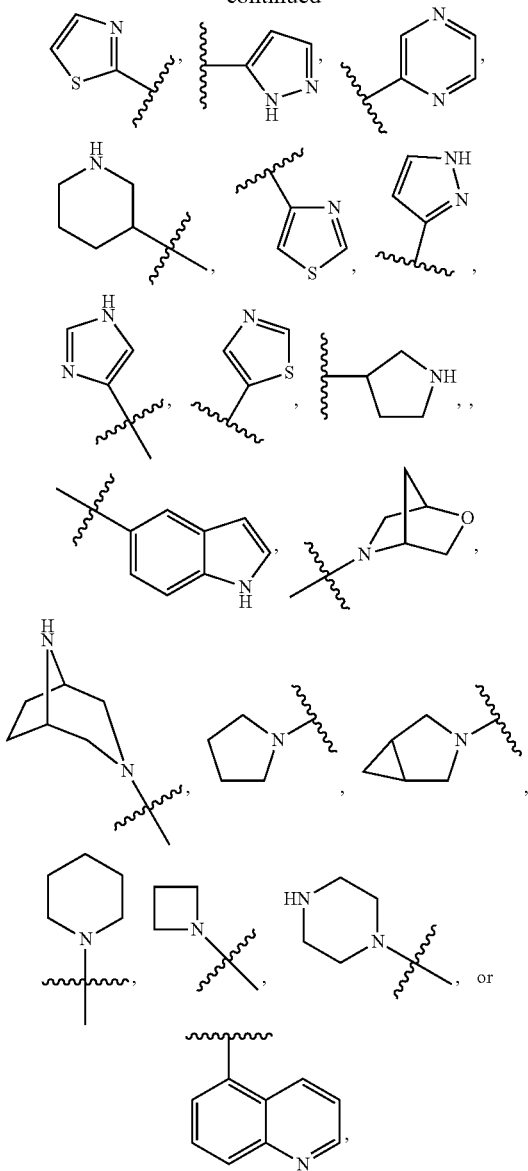

wherein the wavy line ～ indicates point of attachment of Ring B to the sulfonyl (SO$_2$).

90. In another embodiment, the present disclosure features the compound of any one of embodiments 87 to 89 or a pharmaceutically acceptable salt thereof, wherein R$_{1-2}$ is independently halo, amino, OH, C$_1$-C$_6$ fluoroalkyl, CN, C$_1$-C$_6$ alkyl, C$_2$-C$_6$ alkenyl, C$_2$-C$_6$ alkynyl, C$_1$-C$_8$ alkoxy or C$_1$-C$_8$ fluoroalkoxy, or a (C$_1$-C$_9$ alkylene)-R$_3$ wherein up to four CH$_2$ units are independently replaced with O, CO, S, SO, SO$_2$ or NR.

91. In another embodiment, the present disclosure features the compound of any one of embodiments 87 to 90 or a pharmaceutically acceptable salt thereof, wherein R$_{1-1}$ is C$_1$-C$_6$ alkyl or C$_1$-C$_6$ fluoroalkyl, a phenyl, mono-C$_4$-C$_6$ heterocyclic ring, 1,2,3,4-tetrahydroisoquinoline, pyridyl, pyrimidine, indole, aza-indole, pyrazole, pyrrole, or thiophene ring.

92. In another embodiment, the present disclosure features the compound of any one of embodiments 87 to 91 or a pharmaceutically acceptable salt thereof, wherein R$_{1-1}$ is tert-butyl,

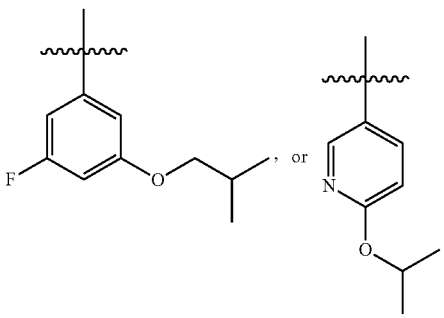

93. In another embodiment, the present disclosure features the compound of any one of embodiments 87 to 92 or a pharmaceutically acceptable salt thereof, wherein R$_{1-1}$ is

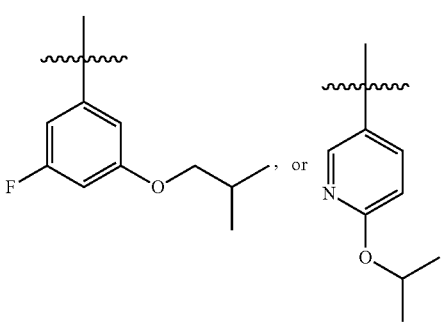

94. In another embodiment, the present disclosure features the compound of any one of embodiments 87 to 93 or a pharmaceutically acceptable salt thereof, wherein R$_{1-2}$ is CHF$_2$CH$_2$(CH$_3$)N—, (CH$_3$)$_2$CHCH$_2$CH2O—, (CH$_3$)$_3$CCH$_2$CH$_2$O—, (CH$_3$)$_3$COCH$_2$CH$_2$O—, (CH$_3$)$_2$CHO—, CHF$_2$CHF$_2$CH(CH$_3$)O—, —CF$_3$, (CH$_3$CH$_2$)$_2$N—, CF$_3$CH$_2$CH(CH$_3$)O—, CH$_3$O—, CH$_3$(CH$_2$)$_4$O—, CH$_3$CH$_2$CH(CH$_3$)CH(CH$_3$)O—, CH$_3$CH$_2$OCH$_2$CH$_2$O—, CH$_3$CH$_2$NCH(CH$_3$)$_2$, (CH$_3$)$_3$CH$_2$O—, (R)—CH$_3$NCH(CH$_3$)(CF$_3$), CH$_3$OCH$_2$CH(CH$_2$CH$_3$)O—, (CH$_3$)$_2$N—, (S)—CH$_3$OCH$_2$CH(CH$_3$)O—, CH$_3$O(CH$_2$)$_3$O—, CH$_3$OC(CH$_3$)$_2$(CH$_2$)$_2$O, CH$_3$OCH$_2$CH(CH$_3$)O, CH$_3$CH(CH$_3$)CH$_2$CH(CH$_3$)O—, (CH$_3$)$_3$CCH(CH$_3$)O, ((CH$_3$)$_2$CH)$_2$CHO—, CH$_3$CH$_2$CH$_2$O, CH$_3$CH═CHCH$_2$O—, (S)—CH$_3$CH$_2$CH(CH$_3$)O—, CH$_3$CH$_2$O, (CH$_3$)$_2$CHNCH$_3$, (CH$_3$)$_3$CCH$_2$O, (CF$_3$)$_2$CHO—, (CH$_3$)$_3$CCH(CH$_2$CH$_3$)O, CH$_3$C≡CCH$_2$CH$_2$O, (CH$_3$)$_3$CCH$_2$CH(CH$_3$)O—, (CH$_3$)$_2$C═C(CH$_3$), CHF$_2$CH$_2$O—, CH$_3$CH$_2$CH$_2$NH, (CH$_3$)$_2$CHCH(CH$_2$CH$_3$)O, ((CH$_3$)$_2$CH)$_2$N, CH$_2$═CHCH(CH$_3$)O, CH$_2$═CHCH$_2$O—, CH$_3$CH$_2$C(CH$_3$)$_2$O, (CH$_3$CH$_2$)$_2$CHO, CF$_3$CH$_2$O, CH$_3$C(═CH$_2$)CH$_2$O, (CH$_3$)$_3$CCH$_2$CH$_2$NH, CH$_3$OCH$_2$C(CH$_3$)$_2$O, (CH$_3$)$_3$CCH$_2$N(CH$_3$), (CH$_3$)$_2$CHCH(CH$_3$)NH, (CH$_3$)$_2$CHO(CH$_2$)$_2$O, CH$_3$CH$_2$CH$_2$CH(CH$_3$)O, CH$_3$CF$_2$CH$_2$O, (CH$_3$)$_3$CNH, (R)—CH$_3$CH$_2$CH(CH$_3$)O, CH$_3$OCH$_2$CH$_2$O, (CH$_3$)$_2$CHCH$_2$N(CH$_3$), CH$_3$CH$_2$CH$_2$CH(CH$_3$)CH(CH$_3$)O, CH$_3$CH$_2$CH$_2$CH$_2$O, CH$_3$CH$_2$CH$_2$N(CH$_3$), (R)—CH$_3$OCH$_2$CH(CH$_3$)O, CF$_3$CH$_2$N(CH$_3$), CH$_3$CH$_2$N(CH$_3$), ((CH$_3$)$_3$C)$_2$CHO, (CH$_3$CH$_2$)$_2$CHN(CH$_3$), (CH$_3$)$_2$CHN(CH$_3$), CH$_3$CH$_2$OCH$_2$CH(CH$_3$)O, (CH$_3$)$_3$CCH$_2$NH, CF$_3$CH(CH$_3$)O, CH$_3$CH$_2$NCH(CH$_3$)$_2$, (R)—CF$_3$CH(CH$_3$)N(CH$_3$), (CH$_3$)$_2$CHCH(CH$_3$), CH$_3$CH$_2$(CH$_3$)$_2$CHCH$_2$CH$_2$O, (S)—CH$_3$OCH(CH$_3$)CH$_2$O, HOCH(CH$_3$)$_2$CH$_2$CH$_2$NH, CF$_3$CH$_2$CH$_2$O, CF$_3$CH$_2$CH$_2$CH$_2$O, CF$_3$CH═CHCH$_2$O, or CH$_3$CH$_2$CH$_2$CH$_2$CH$_2$NH.

95. In another embodiment, the present disclosure features the compound of any one of embodiments 87 to 94 or a pharmaceutically acceptable salt thereof, wherein $R_2$ is halo, CN, amino, OH, $C_1$-$C_6$ alkyl or $C_1$-$C_6$ fluoroalkyl, $C_1$-$C_6$ alkoxy or $C_1$-$C_6$ fluoroalkoxy, $C_3$-$C_{10}$ heterocyclic ring wherein anywhere from 1 to 4 carbon atoms are independently O, S, N, or NR; or a ($C_1$-$C_9$ alkylene)-$R_3$ wherein up to four $CH_2$ units are optionally and independently replaced with O, CO, S, SO, $SO_2$ or NR.

96. In another embodiment, the present disclosure features the compound of any one of embodiments 87 to 95 or a pharmaceutically acceptable salt thereof, wherein $R_2$ is $NH_2$, or $NHCH_2CH_2CH_3$.

97. In another embodiment, the present disclosure features the compound of any one of embodiments 87 to 96 or a pharmaceutically acceptable salt thereof, wherein p is 0. In some embodiments, p is 1.

98. In another embodiment, the present disclosure features the compound of any one of embodiments 87 to 97 or a pharmaceutically acceptable salt thereof, wherein one or more hydrogen atoms are replaced by a deuterium atom.

99. In another embodiment, the present disclosure features the compound of embodiment 87 or a pharmaceutically acceptable salt thereof, wherein the compounds of formula Ia-ii or a pharmaceutically acceptable salt thereof is a compound of formula Ia-ii-1

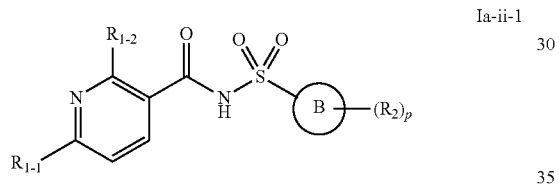

or a pharmaceutically acceptable salt thereof, wherein, independently for each occurrence:

Ring B is a $C_3$-$C_{10}$ heteroaryl or $C_3$-$C_{10}$ heterocyclic ring wherein anywhere from 1 to 4 ring atoms are independently O, S, N, or NR;

$R_{1-2}$ is halo; CN; NRR; $C_1$-$C_6$ alkyl or $C_1$-$C_6$ fluoroalkyl; $C_1$-$C_8$ alkoxy or $C_1$-$C_8$ fluoroalkoxy; $C_2$-$C_6$ alkenyl; $C_2$-$C_6$ alkynyl; or ($C_1$-$C_9$ alkylene)-$R_3$ wherein up to four $CH_2$ units are independently replaced with O, CO, S, SO, $SO_2$ or NR;

$R_{1-1}$ is $C_1$-$C_6$ alkyl or $C_1$-$C_6$ fluoroalkyl, $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_2$ is halo; NRR; CN; $CO_2R$; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four $CH_2$ units are optionally and independently replaced with O, CO, S, SO, $SO_2$ or NR;

or two $R_2$ may form a $=CH_2$ or $=O$ group;

$R_3$ is H; $CF_3$; $CHF_2$; OR; C≡CH; $CO_2R$; OH; $C_6$-$C_{10}$ aryl; $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or $SO_2R$;

R is independently H; OH; $CO_2H$; $CO_2C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, or N; or $C_3$-$C_{10}$ cycloalkyl; and p is 0, 1, 2, or 3.

100. In another embodiment, the present disclosure features the compound of embodiment 99 or a pharmaceutically acceptable salt thereof, wherein Ring B is pyridyl, pyridine-2(1H)-one, pyrazole, indole, aza-indole, thiophene, dihydrobenzofuran, thiazole, pyrrolidinone, or quinoline.

101. In another embodiment, the present disclosure features the compound of embodiment 99 or 100 or a pharmaceutically acceptable salt thereof, wherein Ring B is

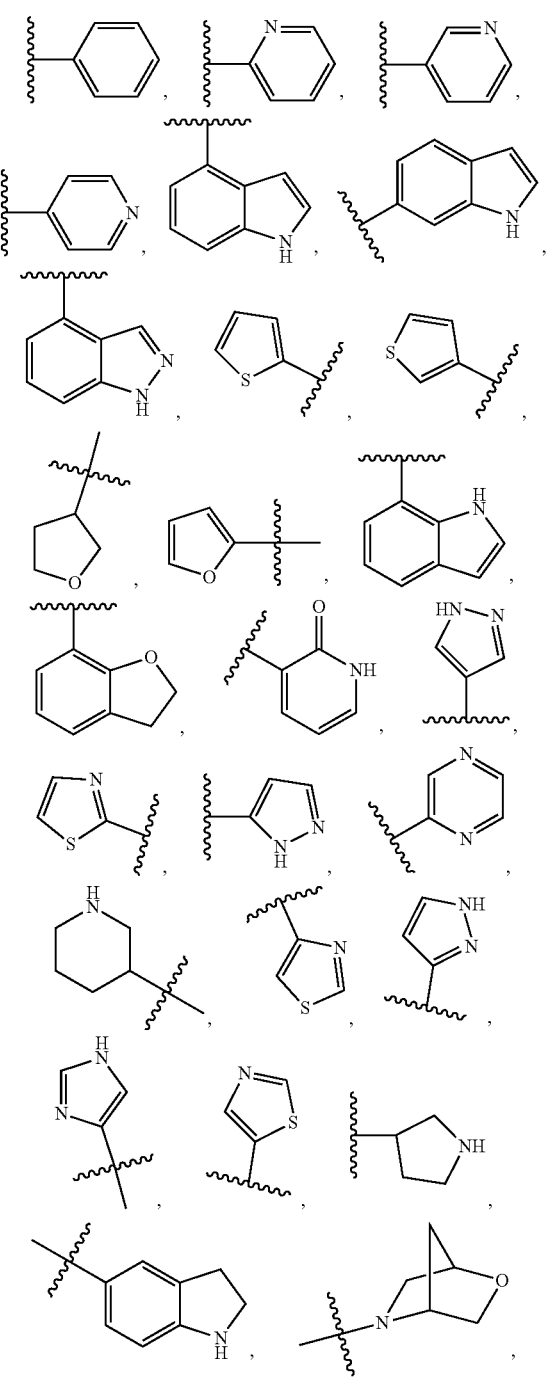

-continued

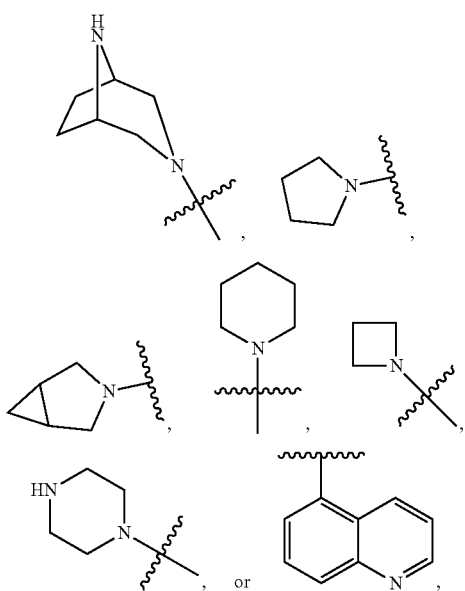

wherein the wavy line ⌇ indicates point of attachment of Ring B to the sulfonyl (SO$_2$).

102. In another embodiment, the present disclosure features the compound of any one of embodiments 99 to 101 or a pharmaceutically acceptable salt thereof, wherein R$_{1-2}$ is independently halo, amino, OH, C$_1$-C$_6$ fluoroalkyl, CN, C$_1$-C$_6$ alkyl, C$_2$-C$_6$ alkenyl, C$_2$-C$_6$ alkynyl, C$_1$-C$_8$ alkoxy or C$_1$-C$_8$ fluoroalkoxy, or a (C$_1$-C$_9$ alkylene)-R$_3$ wherein up to four CH$_2$ units are independently replaced with O, CO, S, SO, SO$_2$ or NR.

103. In another embodiment, the present disclosure features the compound of any one of embodiments 99 to 102 or a pharmaceutically acceptable salt thereof, wherein R$_{1-1}$ is C$_1$-C$_6$ alkyl or C$_1$-C$_6$ fluoroalkyl, a phenyl, mono-C$_4$-C$_6$ heterocyclic ring, 1,2,3,4-tetrahydroisoquinoline, pyridyl, pyrimidine, indole, aza-indole, pyrazole, pyrrole, or thiophene ring.

104. In another embodiment, the present disclosure features the compound of any one of embodiments 99 to 103 or a pharmaceutically acceptable salt thereof, wherein R$_{1-1}$ is tert-butyl,

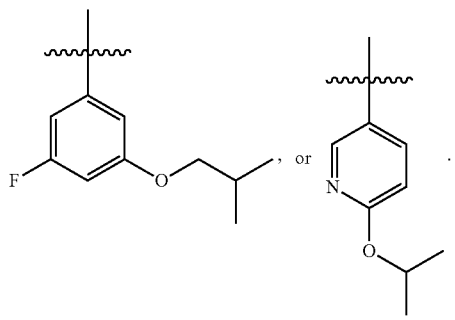 [SMILES: *c1cc(F)cc(OCC(C)C)c1 ; "," ; "or" ; *c1ccc(OC(C)C)nc1 ; "."]

105. In another embodiment, the present disclosure features the compound of any one of embodiments 99 to 104 or a pharmaceutically acceptable salt thereof, wherein R$_{1-1}$ is

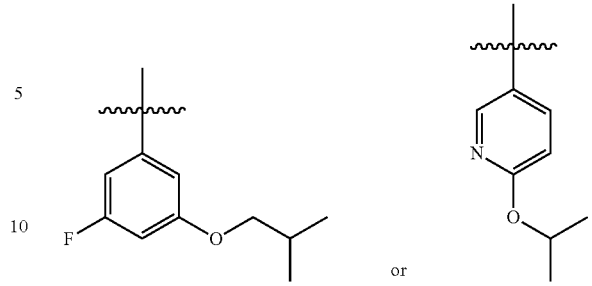

106. In another embodiment, the present disclosure features the compound of any one of embodiments 99 to 105 or a pharmaceutically acceptable salt thereof, wherein R$_{1-2}$ is CHF$_2$CH$_2$(CH$_3$)N—, (CH$_3$)$_2$CHCH$_2$CH2O—, (CH$_3$)$_3$CCH$_2$CH$_2$O—, (CH$_3$)$_3$COCH$_2$CH$_2$O—, (CH$_3$)$_2$CHO—, CHF$_2$CHF$_2$CH(CH$_3$)O—, —CF$_3$, (CH$_3$CH$_2$)$_2$N—, CF$_3$CH$_2$CH(CH$_3$)O—, CH$_3$O—, CH$_3$(CH$_2$)$_4$O—, CH$_3$CH$_2$CH(CH$_3$)CH(CH$_3$)O—, CH$_3$CH$_2$OCH$_2$CH$_2$O—, CH$_3$CH$_2$NCH(CH$_3$)$_2$, (CH$_3$)$_3$CH$_2$O—, (R)—CH$_3$NCH(CH$_3$)(CF$_3$), CH$_3$OCH$_2$CH(CH$_2$CH$_3$)O—, (CH$_3$)$_2$N—, (S)—CH$_3$OCH$_2$CH(CH$_3$)O—, CH$_3$O(CH$_2$)$_3$O—, CH$_3$OC(CH$_3$)$_2$(CH$_2$)$_2$O, CH$_3$OCH$_2$CH(CH$_3$)O, CH$_3$CH(CH$_3$)CH$_2$CH(CH$_3$)O—, (CH$_3$)$_3$CCH(CH$_3$)O, ((CH$_3$)$_2$CH)$_2$CHO—, CH$_3$CH$_2$CH$_2$O, CH$_3$CH=CHCH$_2$O—, (S)—CH$_3$CH$_2$CH(CH$_3$)O—, CH$_3$CH$_2$O, (CH$_3$)$_2$CHNCH$_3$, (CH$_3$)$_3$CCH$_2$O, (CF$_3$)$_2$CHO—, (CH$_3$)$_3$CCH(CH$_2$CH$_3$)O, CH$_3$C≡CCH$_2$CH$_2$O, (CH$_3$)$_3$CCH$_2$CH(CH$_3$)O—, (CH$_3$)$_2$C=C(CH$_3$), CHF$_2$CH$_2$O—, CH$_3$CH$_2$CH$_2$NH, (CH$_3$)$_2$CHCH(CH$_2$CH$_3$)O, ((CH$_3$)$_2$CH)$_2$N, CH$_2$=CHCH(CH$_3$)O, CH$_2$=CHCH$_2$O—, CH$_3$CH$_2$C(CH$_3$)$_2$O, (CH$_3$CH$_2$)$_2$CHO, CF$_3$CH$_2$O, CH$_3$C(=CH$_2$)CH$_2$O, (CH$_3$)$_3$CCH$_2$CH$_2$NH, CH$_3$OCH$_2$C(CH$_3$)$_2$O, (CH$_3$)$_3$CCH$_2$N(CH$_3$), (CH$_3$)$_2$CHCH(CH$_3$)NH, (CH$_3$)$_2$CHO(CH$_2$)$_2$O, CH$_3$CH$_2$CH$_2$CH(CH$_3$)O, CH$_3$CF$_2$CH$_2$O, (CH$_3$)$_3$CNH, (R)—CH$_3$CH$_2$CH(CH$_3$)O, CH$_3$OCH$_2$CH$_2$O, (CH$_3$)$_2$CHCH$_2$N(CH$_3$), CH$_3$CH$_2$CH$_2$CH(CH$_3$)CH(CH$_3$)O, CH$_3$CH$_2$CH$_2$CH$_2$O, CH$_3$CH$_2$CH$_2$N(CH$_3$), (R)—CH$_3$OCH$_2$CH(CH$_3$)O, CF$_3$CH$_2$N(CH$_3$), CH$_3$CH$_2$N(CH$_3$), ((CH$_3$)$_3$C)$_2$CHO, (CH$_3$CH$_2$)$_2$CHN(CH$_3$), (CH$_3$)$_2$CHN(CH$_3$), CH$_3$CH$_2$OCH$_2$CH(CH$_3$)O, (CH$_3$)$_3$CCH$_2$NH, CF$_3$CH(CH$_3$)O, CH$_3$CH$_2$NCH(CH$_3$)$_2$, $_{(R)}$—CF$_3$CH(CH$_3$)N(CH$_3$), (CH$_3$)$_2$CHCH(CH$_3$), CH$_3$CH$_2$(CH$_3$)$_2$CHCH$_2$CH$_2$O, (S)—CH$_3$OCH(CH$_3$)CH$_2$O, HOCH(CH$_3$)$_2$CH$_2$CH$_2$NH, CF$_3$CH$_2$CH$_2$O, CF$_3$CH$_2$CH$_2$CH$_2$O, CF$_3$CH=CHCH$_2$O, or CH$_3$CH$_2$CH$_2$CH$_2$NH.

107. In another embodiment, the present disclosure features the compound of any one of embodiments 99 to 106 or a pharmaceutically acceptable salt thereof, wherein R$_2$ is halo, CN, amino, OH, C$_1$-C$_6$ alkyl or C$_1$-C$_6$ fluoroalkyl, C$_1$-C$_6$ alkoxy or C$_1$-C$_6$ fluoroalkoxy, C$_3$-C$_{10}$ heterocyclic ring wherein anywhere from 1 to 4 carbon atoms are independently O, S, N, or NR; or a (C$_1$-C$_9$ alkylene)-R$_3$ wherein up to four CH$_2$ units are optionally and independently replaced with O, CO, S, SO, SO$_2$ or NR.

108. In another embodiment, the present disclosure features the compound of any one of embodiments 99 to 107 or a pharmaceutically acceptable salt thereof, wherein R$_2$ is NH$_2$, or NHCH$_2$CH$_2$CH$_3$.

109. In another embodiment, the present disclosure features the compound of any one of embodiments 99 to 108 or a pharmaceutically acceptable salt thereof, wherein p is 0.

110. In another embodiment, the present disclosure features the compound of any one of embodiments 99 to 108 or a pharmaceutically acceptable salt thereof, wherein p is 1.

111. In another embodiment, the present disclosure features the compound of any one of embodiments 99 to 110 or a pharmaceutically acceptable salt thereof, wherein one or more hydrogen atoms are replaced by a deuterium atom.

112. In another embodiment, the present disclosure features the compound of embodiment 99 or a pharmaceutically acceptable salt thereof, wherein the compounds of formula Ia-ii-1 or a pharmaceutically acceptable salt thereof is a compound of formula Ia-ii-2

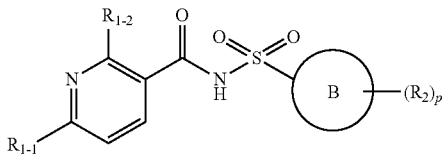

Ia-ii-2 or a pharmaceutically acceptable salt thereof, wherein, independently for each occurrence:

Ring B is a pyridinyl;

$R_{1-2}$ is halo; CN; NRR; $C_1$-$C_6$ alkyl or $C_1$-$C_6$ fluoroalkyl; $C_1$-$C_8$ alkoxy or $C_1$-$C_8$ fluoroalkoxy; $C_2$-$C_6$ alkenyl; $C_2$-$C_6$ alkynyl; or ($C_1$-$C_9$ alkylene)-$R_3$ wherein up to four $CH_2$ units are independently replaced with O, CO, S, SO, $SO_2$ or NR;

$R_{1-1}$ is $C_1$-$C_6$ alkyl or $C_1$-$C_6$ fluoroalkyl, $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_2$ is halo; NRR; CN; $CO_2R$; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four $CH_2$ units are optionally and independently replaced with O, CO, S, SO, $SO_2$ or NR;

or two $R_2$ may form a =$CH_2$ or =O group;

$R_3$ is H; $CF_3$; $CHF_2$; OR; C≡CH; $CO_2R$; OH; $C_6$-$C_{10}$ aryl, $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or $SO_2R$;

R is independently H; OH; $CO_2H$; $CO_2C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, or N; or $C_3$-$C_{10}$ cycloalkyl; and p is 0, 1, 2, or 3.

113. In another embodiment, the present disclosure features the compound of embodiment 112 or a pharmaceutically acceptable salt thereof, wherein Ring B is

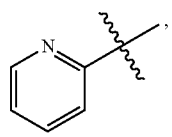 [SMILES: *c1ccccn1]

wherein the wavy line ⌇ indicates point of attachment of Ring B to the sulfonyl ($SO_2$).

114. In another embodiment, the present disclosure features the compound of embodiment 112 or 113 or a pharmaceutically acceptable salt thereof, wherein $R_{1-2}$ is independently halo, amino, OH, $C_1$-$C_6$ fluoroalkyl, CN, $C_1$-$C_6$ alkyl, $C_2$-$C_6$ alkenyl, $C_2$-$C_6$ alkynyl, $C_1$-$C_8$ alkoxy or $C_1$-$C_8$ fluoroalkoxy, or a ($C_1$-$C_9$ alkylene)-$R_3$ wherein up to four $CH_2$ units are independently replaced with O, CO, S, SO, $SO_2$ or NR.

115. In another embodiment, the present disclosure features the compound of any one of embodiments 112 to 114 or a pharmaceutically acceptable salt thereof, wherein $R_{1-1}$ is $C_1$-$C_6$ alkyl or $C_1$-$C_6$ fluoroalkyl, a phenyl, mono-$C_4$-$C_6$ heterocyclic ring, 1,2,3,4-tetrahydroisoquinoline, pyridyl, pyrimidine, indole, aza-indole, pyrazole, pyrrole, or thiophene ring.

116. In another embodiment, the present disclosure features the compound of any one of embodiments 112 to 115 or a pharmaceutically acceptable salt thereof, wherein $R_{1-1}$ is tert-butyl,

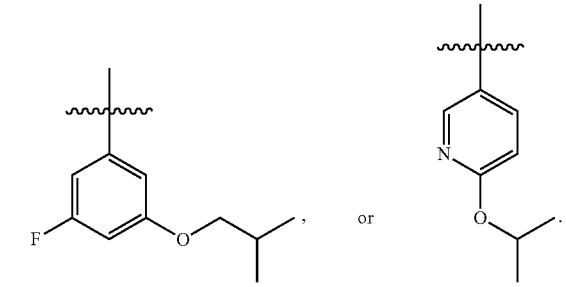 [SMILES: *c1cc(F)cc(OCC(C)C)c1 ; *c1ccc(OC(C)C)nc1]

117. In another embodiment, the present disclosure features the compound of any one of embodiments 112 to 116 or a pharmaceutically acceptable salt thereof, wherein $R_{1-1}$ is

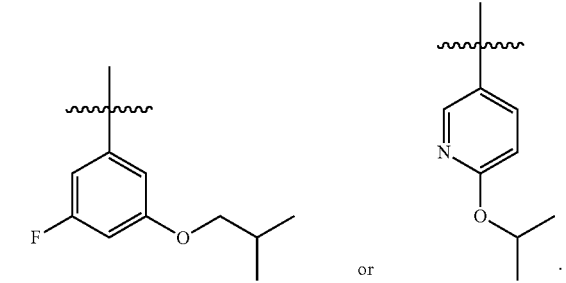 [SMILES: *c1cc(F)cc(OCC(C)C)c1 ; *c1ccc(OC(C)C)nc1]

118. In another embodiment, the present disclosure features the compound of any one of embodiments 112 to 117 or a pharmaceutically acceptable salt thereof, wherein $R_{1-2}$ is $CHF_2CH_2(CH_3)N$—, $(CH_3)_2CHCH_2CH_2O$—, $(CH_3)_3CCH_2CH_2O$—, $(CH_3)_3COCH_2CH_2O$—, $(CH_3)_2CHO$—, $CHF_2CHF_2CH(CH_3)O$—, —$CF_3$, $(CH_3CH_2)_2N$—, $CF_3CH_2CH(CH_3)O$—, $CH_3O$—, $CH_3(CH_2)_4O$—, $CH_3CH_2CH(CH_3)CH(CH_3)O$—, $CH_3CH_2OCH_2CH_2O$—, $CH_3CH_2NCH(CH_3)_2$, $(CH_3)_3CH_2O$—, (R)—$CH_3NCH(CH_3)(CF_3)$, $CH_3OCH_2CH(CH_2CH_3)O$—, $(CH_3)_2N$—, (S)—$CH_3OCH_2CH(CH_3)O$—, $CH_3O(CH_2)_3O$—, $CH_3OC(CH_3)_2(CH_2)_2O$, $CH_3OCH_2CH(CH_3)O$, $CH_3CH(CH_3)CH_2CH(CH_3)O$—, $(CH_3)_3CCH(CH_3)O$, $((CH_3)_2CH)_2CHO$—, $CH_3CH_2CH_2O$, $CH_3CH$=$CHCH_2O$—, (S)—$CH_3CH_2CH(CH_3)O$—, $CH_3CH_2O$, $(CH_3)_2CHNCH_3$, $(CH_3)_3CCH_2O$, $(CF_3)_2CHO$—, $(CH_3)_3CCH(CH_2CH_3)O$, $CH_3C$≡$CCH_2CH_2O$, $(CH_3)_3CCH(CH_3)O$—, $(CH_3)_2C$=$C(CH_3)$, $CHF_2CH_2O$—, $CH_3CH_2CH_2NH$, $(CH_3)_2CHCH(CH_2CH_3)O$, $((CH_3)_2CH)_2N$, $CH_2$=$CHCH(CH_3)O$, CH$_2$=CHCH$_2$O—, CH$_3$CH$_2$C(CH$_3$)$_2$O, (CH$_3$CH$_2$)$_2$CHO, CF$_3$CH$_2$O, CH$_3$C(=CH$_2$)CH$_2$O, (CH$_3$)$_3$CCH$_2$CH$_2$NH, CH$_3$OCH$_2$C(CH$_3$)$_2$O, (CH$_3$)$_3$CCH$_2$N(CH$_3$), (CH$_3$)$_2$CHCH (CH$_3$)NH, (CH$_3$)$_2$CHO(CH$_2$)$_2$O, CH$_3$CH$_2$CH$_2$CH(CH$_3$)O, CH$_3$CF$_2$CH$_2$O, (CH$_3$)$_3$CNH, (R)—CH$_3$CH$_2$CH(CH$_3$)O, CH$_3$OCH$_2$CH$_2$O, (CH$_3$)$_2$CHCH$_2$N(CH$_3$), CH$_3$CH$_2$CH$_2$CH (CH$_3$)CH(CH$_3$)O, CH$_3$CH$_2$CH$_2$CH$_2$O, CH$_3$CH$_2$CH$_2$N (CH$_3$), (R)—CH$_3$OCH$_2$CH(CH$_3$)O, CF$_3$CH$_2$N(CH$_3$), CH$_3$CH$_2$N(CH$_3$), ((CH$_3$)$_3$C)$_2$CHO, (CH$_3$CH$_2$)$_2$CHN(CH$_3$), (CH$_3$)$_2$CHN(CH$_3$), CH$_3$CH$_2$OCH$_2$CH(CH$_3$)O, (CH$_3$)$_3$CCH$_2$NH, CF$_3$CH(CH$_3$)O, CH$_3$CH$_2$NCH(CH$_3$)$_2$, $_{(R)}$—CF$_3$CH(CH$_3$)N(CH$_3$), (CH$_3$)$_2$CHCH(CH$_3$), CH$_3$CH$_2$(CH$_3$)$_2$ CHCH$_2$CH$_2$O, (S)—CH$_3$OCH(CH$_3$)CH$_2$O, HOCH(CH$_3$)$_2$ CH$_2$CH$_2$NH, CF$_3$CH$_2$CH$_2$O, CF$_3$CH$_2$CH$_2$CH$_2$O, CF$_3$CH=CHCH$_2$O, or CH$_3$CH$_2$CH$_2$CH$_2$CH$_2$NH.

119. In another embodiment, the present disclosure features the compound of any one of embodiments 112 to 118 or a pharmaceutically acceptable salt thereof, wherein R$_2$ is halo, CN, amino, OH, C$_1$-C$_6$ alkyl or C$_1$-C$_6$ fluoroalkyl, C$_1$-C$_6$ alkoxy or C$_1$-C$_6$ fluoroalkoxy, C$_3$-C$_{10}$ heterocyclic ring wherein anywhere from 1 to 4 carbon atoms are independently O, S, N, or NR; or a (C$_1$-C$_9$ alkylene)-R$_3$ wherein up to four CH$_2$ units are optionally and independently replaced with O, CO, S, SO, SO$_2$ or NR.

120. In another embodiment, the present disclosure features the compound of any one of embodiments 112 to 119 or a pharmaceutically acceptable salt thereof, wherein R$_2$ is NH$_2$, or NHCH$_2$CH$_2$CH$_3$.

121. In another embodiment, the present disclosure features the compound of any one of embodiments 112 to 120 or a pharmaceutically acceptable salt thereof, wherein p is 0.

122. In another embodiment, the present disclosure features the compound of any one of embodiments 112 to 121 or a pharmaceutically acceptable salt thereof, wherein one or more hydrogen atoms may be replaced by a deuterium atom.

123. In another embodiment, the present disclosure features a compound selected from Table 1 or a pharmaceutically acceptable salt thereof.

124. In another embodiment, the present disclosure features a pharmaceutical composition comprising the compound of any one of embodiments 1-123 or a pharmaceutically acceptable salt thereof, and a pharmaceutically acceptable carrier.

125. In another embodiment, the present disclosure features the pharmaceutical composition of embodiment 124, further comprising one or more additional therapeutic agent(s).

126. In another embodiment, the present disclosure features the pharmaceutical composition of embodiment 125, wherein the additional therapeutic agent is selected from a mucolytic agent, bronchodialator, an antibiotic, an anti-infective agent, a CFTR modulator, or an anti-inflammatory agent.

127. In another embodiment, the present disclosure features the pharmaceutical composition of embodiment 125, wherein the additional therapeutic agent is a CFTR modulator.

128. In another embodiment, the present disclosure features the pharmaceutical composition of embodiment 125, wherein the additional therapeutic agent is a CFTR corrector.

129. In another embodiment, the present disclosure features the pharmaceutical composition of embodiment 125, wherein the additional therapeutic agent is

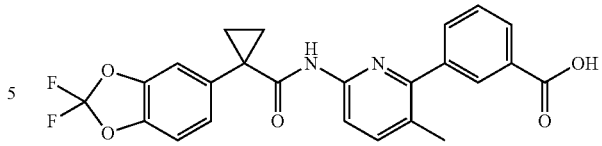

or a pharmaceutically acceptable salt thereof.

130. In another embodiment, the present disclosure features the pharmaceutical composition of embodiment 125, wherein the additional therapeutic agent is

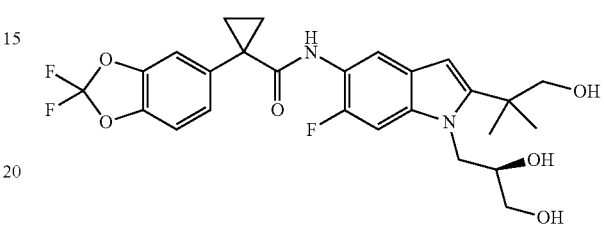

or a pharmaceutically acceptable salt thereof.

131. In another embodiment, the present disclosure features the pharmaceutical composition of embodiment 125, wherein the additional therapeutic agent is

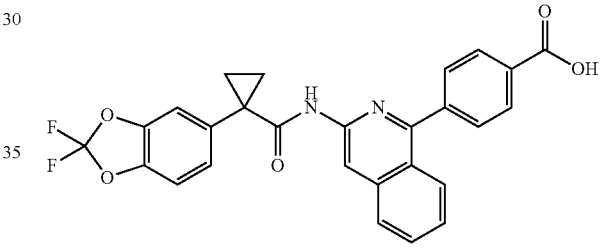

or a pharmaceutically acceptable salt thereof.

132. In another embodiment, the present disclosure features the pharmaceutical composition of embodiment 125, wherein the additional therapeutic agent is a CFTR potentiator.

133. In another embodiment, the present disclosure features the pharmaceutical composition of embodiment 125, wherein the additional therapeutic agent is

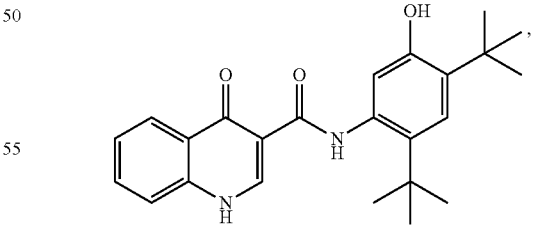

or pharmaceutically acceptable salt thereof.

134. In another embodiment, the present disclosure features the pharmaceutical composition of embodiment 125, wherein the additional therapeutic agents are a CFTR corrector and a CFTR potentiator.

135. In another embodiment, the present disclosure features the pharmaceutical composition of embodiment 125, wherein the additional therapeutic agents are

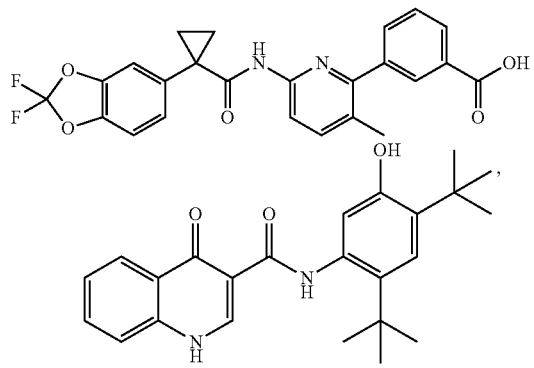

or pharmaceutically acceptable salts thereof.

136. In another embodiment, the present disclosure features the pharmaceutical composition of embodiment 125, wherein the additional therapeutic agents are

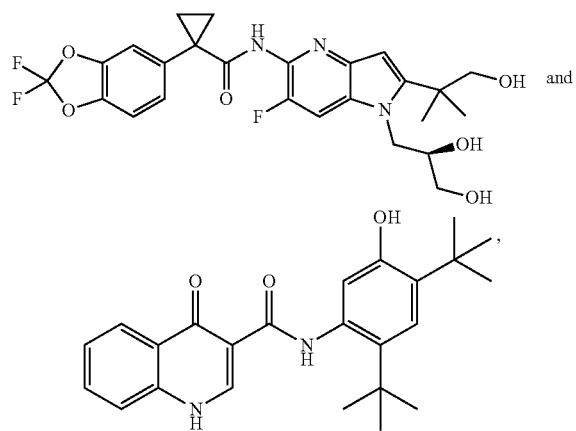

or pharmaceutically acceptable salts thereof.

137. In another embodiment, the present disclosure features the pharmaceutical composition of embodiment 125, wherein the additional therapeutic agents are

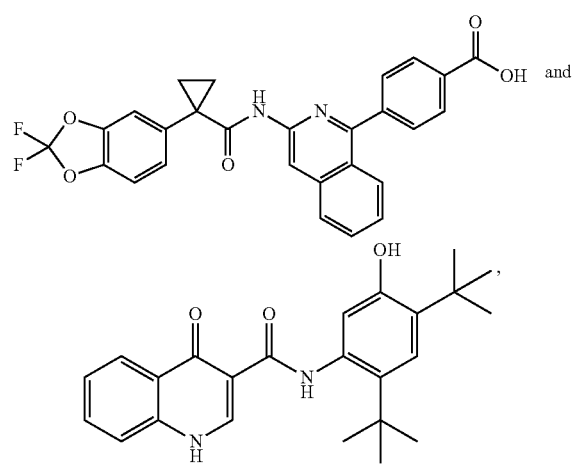

or pharmaceutically acceptable salts thereof.

138. In another embodiment, the present disclosure features a method of treating cystic fibrosis in a patient comprising administering to the patient in need thereof an effective amount of 1) a compound of formula II or a pharmaceutically acceptable salt thereof, or 2) a pharmaceutical composition comprising a pharmaceutically acceptable excipient and a compound of formula II or a pharmaceutically acceptable salt thereof:

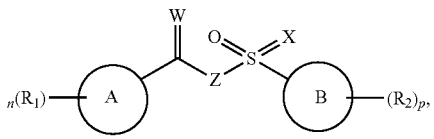

II wherein, independently for each occurrence:

Ring A is a $C_6$-$C_{10}$ aryl ring; $C_3$-$C_{10}$ cycloalkyl ring; or a $C_3$-$C_{14}$ heteroaryl or heterocyclic ring wherein anywhere from 1 to 4 ring atoms are independently O, S, N, or NR;

Ring B is a $C_3$-$C_{10}$ cycloalkyl ring; a $C_6$-$C_{10}$ aryl ring; or a $C_3$-$C_{10}$ heteroaryl or $C_3$-$C_{10}$ heterocyclic ring wherein anywhere from 1 to 4 ring atoms are independently O, S, N, or NR;

W is O, S, or NR;

X is O or NR;

Z is NR;

$R_1$ is halo; CN; NRR; $C_1$-$C_6$ alkyl or $C_1$-$C_6$ fluoroalkyl; $C_3$-$C_6$ cycloalkyl; $C_1$-$C_8$ alkoxy or $C_1$-$C_8$ fluoroalkoxy; $C_2$-$C_6$ alkenyl; $C_2$-$C_6$ alkynyl; ($C_1$-$C_9$ alkylene)-$R_3$ wherein up to four $CH_2$ units are independently replaced with O, CO, S, SO, $SO_2$ or NR; $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_2$ is halo; NRR; CN; $CO_2R$; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four $CH_2$ units are optionally and independently replaced with O, CO, S, SO, $SO_2$ or NR;

or two $R_2$ may form a =$CH_2$ or =O group;

$R_3$ is H; $CF_3$; $CHF_2$; OR; C≡CH; $CO_2R$; OH; $C_6$-$C_{10}$ aryl, $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or $SO_2R$;

R is independently H; OH; $CO_2H$; $CO_2C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, or N; or $C_3$-$C_{10}$ cycloalkyl;

n is 2 or 3;

p is 0, 1, 2, or 3; and

Provided that 1) when $R_1$ is adjacent to C=W attached to Ring A, $R_1$ does not contain a ring moiety, and 2) at least one $R_1$ is adjacent to the C=W attached to Ring A.

139. In another embodiment, the present disclosure features a method of embodiment 138, wherein Ring A is a pyridyl, indole, indoline, isoindoline, pyrazole, pyrimidine, 1,2,3,4-tetrahydroquinoline, quinoline, 5,6,7,8-tetrahydroquinoline, 1,2,3,4-tetrahydroisoquinoline, pyrrolodine, aza-indole, pyrrole, thiophene, oxazole, pyrazine, triazole, thiazole, indazole, 2,3,4,5-tetrahydro-1H-benzo[d]azepine, 1H-benzo[d]imidazole, imidazo[1,2-a]pyridine, or imidazole ring.

140. In another embodiment, the present disclosure features a method of embodiment 138 or 139, wherein Ring A is

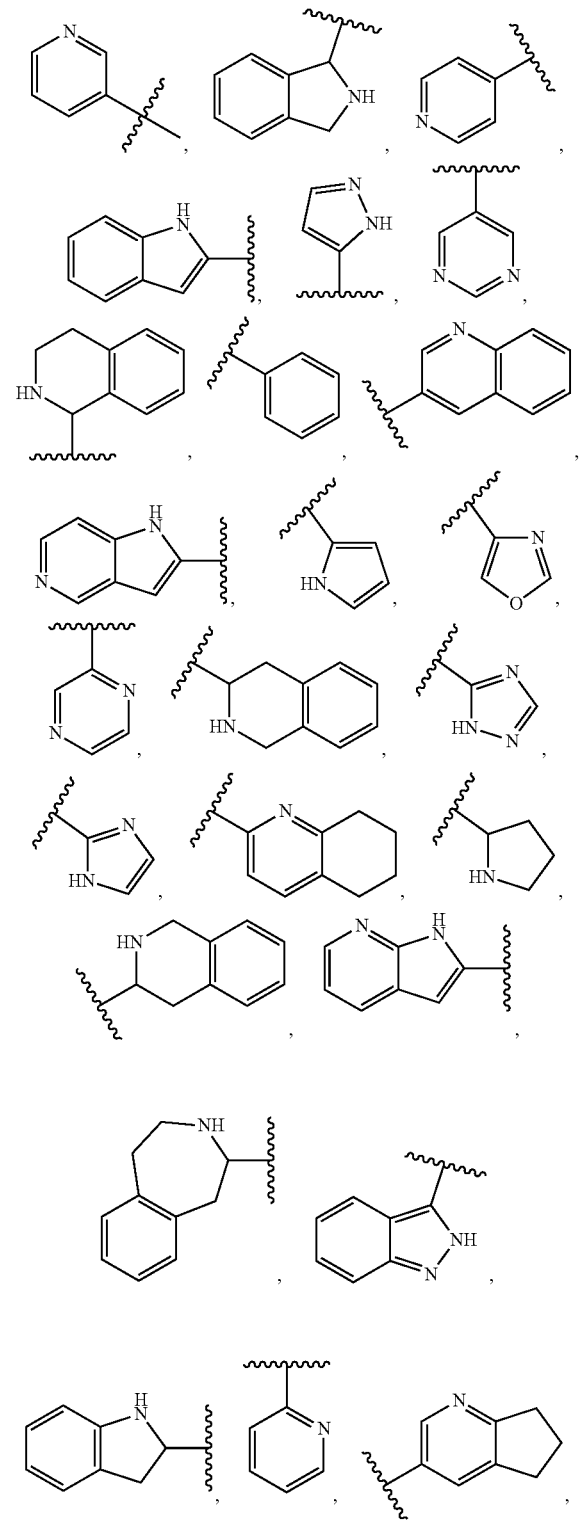

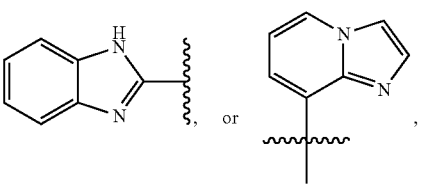

wherein the wavy line indicates point of attachment of Ring A to C=W.

141. In another embodiment, the present disclosure features a method of any one of embodiments 138 to 140, wherein Ring B is a pyridyl, pyridine-2(1H)-one, pyrazole, indole, pyrrole, indoline, thiophene, dihydrobenzofuran, tetrahydrofuran, furan, pyrazine, indazole, thiazole, pyridine-4(1H)-one, pyrrolidinone, 3-azabicyclo[3.1.0]hexane, (1R,4R)-2-oxa-5-azabicyclo[2.2.1]heptane, pyrrolidine, azetidine, piperidine, piperazine, imidazo[1,2-a]pyridine, or quinoline.

142. In another embodiment, the present disclosure features a method of any one of embodiments 138 to 141, wherein Ring B is

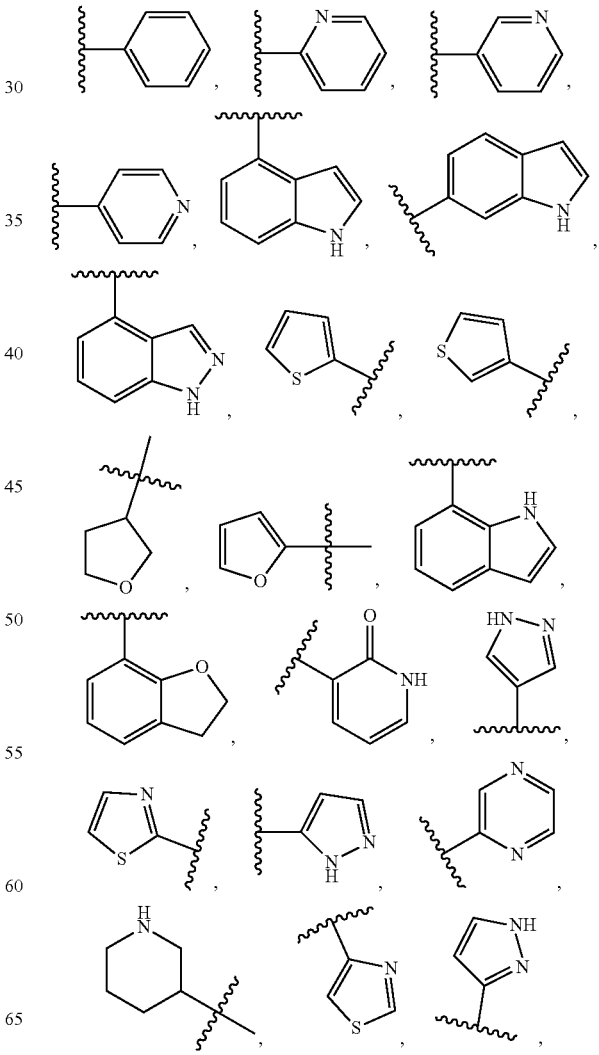

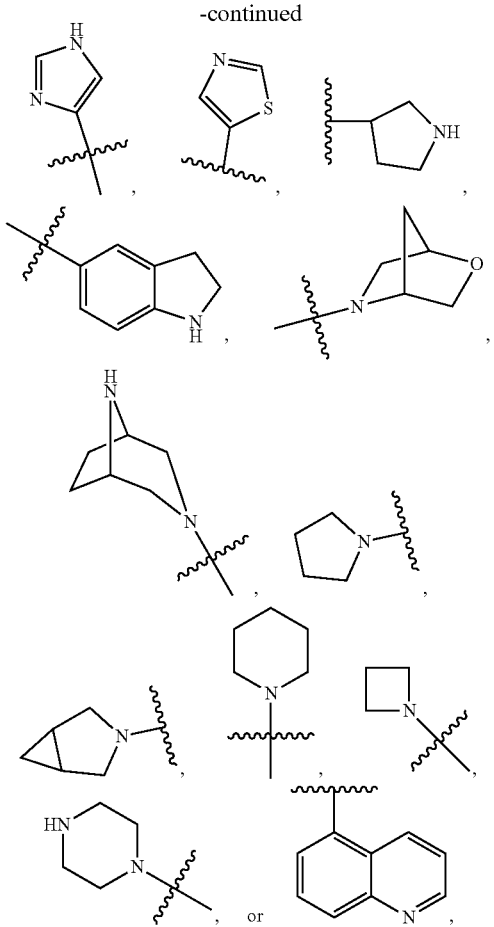

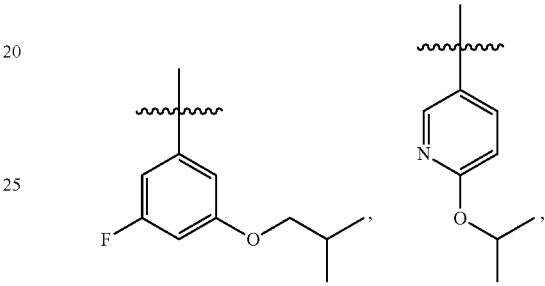

wherein the wavy line ⁓ indicates point of attachment of Ring B to X=S=O.

143. In another embodiment, the present disclosure features a method of any one of embodiments 138 to 142, wherein $R_1$ is independently halo, amino, OH, $C_2$-$C_6$ alkenyl; $C_2$-$C_6$ alkynyl, $C_1$-$C_6$ fluoroalkyl, CN, $C_1$-$C_6$ alkyl, $C_1$-$C_8$ alkoxy or $C_1$-$C_8$ fluoroalkoxy, a phenyl, $C_3$-$C_6$ mono-cycloalkyl, mono-$C_4$-$C_6$ heterocyclic ring, 1,2,3,4-tetrahydroisoquinoline, pyridyl, pyrimidine, indole, aza-indole, pyrazole, pyrrole, or thiophene ring, or a ($C_1$-$C_9$ alkylene)-$R_3$ wherein up to four $CH_2$ units are independently replaced with O, CO, S, SO, $SO_2$ or NR.

144. In another embodiment, the present disclosure features a method of any one of embodiments 138 to 143, wherein $R_1$ is $CHF_2CH_2(CH_3)N—$, $(CH_3)_2CHCH_2CH_2O—$, $(CH_3)_3CCH_2CH_2O—$, $(CH_3)_3COCH_2CH_2O—$, $(CH_3)_2CHO—$, $CHF_2CHF_2CH(CH_3)O—$, $—CF_3$, $(CH_3CH_2)_2N—$, $CF_3CH_2CH(CH_3)O—$, $CH_3O—$, $CH_3(CH_2)_4O—$, $CH_3CH_2CH(CH_3)CH(CH_3)O—$, $CH_3CH_2OCH_2CH_2O—$, $CH_3CH_2NCH(CH_3)_2$, $(CH_3)_3CH_2O—$, (R)—$CH_3NCH(CH_3)(CF_3)$, $CH_3OCH_2CH(CH_2CH_3)O—$, $(CH_3)_2N—$, (S)—$CH_3OCH_2CH(CH_3)O—$, $CH_3O(CH_2)_3O—$, $CH_3OC(CH_3)_2(CH_2)_2O$, $CH_3OCH_2CH(CH_3)O$, $CH_3CH(CH_3)CH_2CH(CH_3)O—$, $(CH_3)_3CCH(CH_3)O$, $((CH_3)_2CH)_2CHO—$, $CH_3CH_2CH_2O$, $CH_3CH=CHCH_2O—$, (S)—$CH_3CH_2CH(CH_3)O—$, $CH_3CH_2O$, $(CH_3)_2CHNCH_3$, $(CH_3)_3CCH_2O$, $(CF_3)_2CHO—$, $(CH_3)_3CCH(CH_2CH_3)O$, $CH_3C≡CCH_2CH_2O$, $(CH_3)_3CCH_2CH(CH_3)O—$, $(CH_3)_2C=C(CH_3)$, $CHF_2CH_2O—$, $CH_3CH_2CH_2NH$, $(CH_3)_2CHCH(CH_2CH_3)O$, $((CH_3)_2CH)_2N$, $CH_2=CHCH(CH_3)O$, $CH_2=CHCH_2O—$, $CH_3CH_2C(CH_3)_2O$, $(CH_3CH_2)_2CHO$, $CF_3CH_2O$, $CH_3C(=CH_2)CH_2O$, $(CH_3)_3CCH_2CH_2NH$, $CH_3OCH_2C(CH_3)_2O$, $(CH_3)_3CCH_2N(CH_3)$, $(CH_3)_2CHCH(CH_3)NH$, $(CH_3)_2CHO(CH_2)_2O$, $CH_3CH_2CH_2CH(CH_3)O$, $CH_3CF_2CH_2O$, $(CH_3)_3CNH$, (R)—$CH_3CH_2CH(CH_3)O$, $CH_3OCH_2CH_2O$, $(CH_3)_2CHCH_2N(CH_3)$, $CH_3CH_2CH_2CH(CH_3)CH(CH_3)O$, $CH_3CH_2CH_2O$, $CH_3CH_2CH_2N(CH_3)$, (R)—$CH_3OCH_2CH(CH_3)O$, $CF_3CH_2N(CH_3)$, $CH_3CH_2N(CH_3)$, $((CH_3)_3C)_2CHO$, $(CH_3CH_2)_2CHN(CH_3)$, $(CH_3)_2CHN(CH_3)$, $CH_3CH_2OCH_2CH(CH_3)O$, $(CH_3)_3CCH_2NH$, $CF_3CH(CH_3)O$, $CH_3CH_2NCH(CH_3)_2$, $_{(R)}$—$CF_3CH(CH_3)N(CH_3)$, $(CH_3)_2CHCH(CH_3)$, $CH_3CH_2(CH_3)_2CHCH_2CH_2O$, (S)—$CH_3OCH(CH_3)CH_2O$, $HOCH(CH_3)_2CH_2CH_2NH$, $CF_3CH_2CH_2O$, $CF_3CH_2CH_2CH_2O$, $CF_3CH=CHCH_2O$, $CH_3CH_2CH_2CH_2CH_2NH$, or $(CH_3)_3C$.

145. In another embodiment, the present disclosure features a method of any one of embodiments 138 to 144, wherein $R_2$ is halo, CN, amino, OH, $C_1$-$C_6$ alkyl or $C_1$-$C_6$ fluoroalkyl, $C_1$-$C_6$ alkoxy or $C_1$-$C_6$ fluoroalkoxy, $C_3$-$C_{10}$ heterocyclic ring wherein anywhere from 1 to 4 carbon atoms are independently O, S, N, or NR; or a ($C_1$-$C_9$ alkylene)-$R_3$ wherein up to four $CH_2$ units are optionally and independently replaced with O, CO, S, SO, $SO_2$ or NR.

146. In another embodiment, the present disclosure features a method of any one of embodiments 138 to 145, wherein $R_2$ is $NH_2$, or $NHCH_2CH_2CH_3$.

147. In another embodiment, the present disclosure features a method of any one of embodiments 138 to 146, wherein n is 2.

148. In another embodiment, the present disclosure features a method of any one of embodiments 138 to 147, wherein p is 0.

149. In another embodiment, the present disclosure features a method of any one of embodiments 138 to 147, wherein p is 1.

150. In another embodiment, the present disclosure features a method of any one of embodiments 138 to 149, wherein W is O.

151. In another embodiment, the present disclosure features a method of any one of embodiments 138 to 150, wherein Z is NH.

152. In another embodiment, the present disclosure features a method of any one of embodiments 138 to 151, wherein X is O.

152. In another embodiment, the present disclosure features a method of any one of embodiments 138 to 152, wherein Ring A is

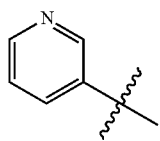

and n is 2.

154. In another embodiment, the present disclosure features a method of any one of embodiments 138 to 152, wherein Ring A is

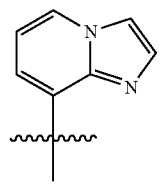 [SMILES: *c1cccn2ccnc12]

and n is 2.

155. In another embodiment, the present disclosure features a method of any one of embodiments 138 to 152, wherein Ring A is

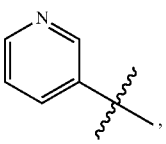

and at least one $R_1$ is phenyl.

156. In another embodiment, the present disclosure features a method of any one of embodiments 138 to 152, wherein Ring A is

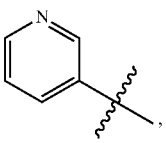

and at least one $R_1$ is tert-butyl.

157. In another embodiment, the present disclosure features a method of any one of embodiments 138 to 152, wherein Ring A is

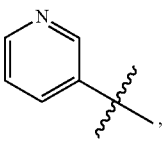

and at least one $R_1$ is pyridinyl.

158. In another embodiment, the present disclosure features a method of any one of embodiments 138 to 152, wherein Ring A is

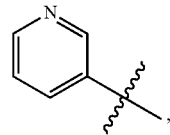 [SMILES: *c1cccnc1 ; ","]

one $R_1$ is phenyl, and one $R_1$ is alkenyl, amino, or $C_1$-$C_8$ alkoxy or $C_1$-$C_8$ fluoroalkoxy.

159. In another embodiment, the present disclosure features a method of any one of embodiments 138 to 152, wherein Ring A is

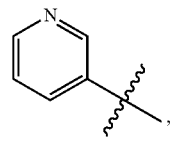 [SMILES: *c1cccnc1 ; ","]

and Ring B is

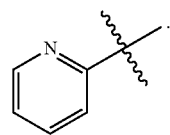

160. In another embodiment, the present disclosure features a method of embodiment 138, wherein Ring A is

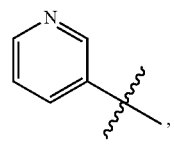 [SMILES: *c1cccnc1 ; ","]

and Ring B is

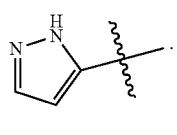

161. In another embodiment, the present disclosure features a method of any one of embodiments 138 to 152, wherein Ring A is

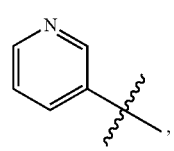 [SMILES: *c1cccnc1 ; ","]

Ring B is

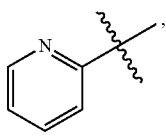

one R₁ is phenyl, and one R₁ is alkenyl, amino, or $C_1$-$C_8$ alkoxy or $C_1$-$C_8$ fluoroalkoxy.

162. In another embodiment, the present disclosure features a method of any one of embodiments 138 to 161, wherein one or more hydrogen atoms are replaced by a deuterium atom.

163. In another embodiment, the present disclosure features a method of embodiment 138, wherein the compound of formula II or a pharmaceutically acceptable salt thereof is a compound of formula II-i:

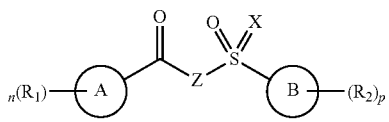

II-i or a pharmaceutically acceptable salt thereof, wherein, independently for each occurrence:
  Ring A is a $C_3$-$C_{14}$ heteroaryl or heterocyclic ring wherein anywhere from 1 to 4 ring atoms are independently O, S, N, or NR;
  Ring B is a $C_3$-$C_{10}$ heteroaryl or $C_3$-$C_{10}$ heterocyclic ring wherein anywhere from 1 to 4 ring atoms are independently O, S, N, or NR;
  X is O or NR;
  Z is NR;
  R₁ is halo; CN; NRR; $C_1$-$C_6$ alkyl or $C_1$-$C_6$ fluoroalkyl; $C_3$-$C_6$ cycloalkyl; $C_1$-$C_8$ alkoxy or $C_1$-$C_8$ fluoroalkoxy; $C_2$-$C_6$ alkenyl; $C_2$-$C_6$ alkynyl; ($C_1$-$C_9$ alkylene)-R₃ wherein up to four CH₂ units are independently replaced with O, CO, S, SO, SO₂ or NR; $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;
  R₂ is halo; NRR; CN; CO₂R; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-R₃ wherein up to four CH₂ units are optionally and independently replaced with O, CO, S, SO, SO₂ or NR;
  or two R₂ may form a =CH₂ or =O group;
  R₃ is H; CF₃; CHF₂; OR; C≡CH; CO₂R; OH; $C_6$-$C_{10}$ aryl, $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or SO₂R;
  R is independently H; OH; CO₂H; CO₂$C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, or N; or $C_3$-$C_{10}$ cycloalkyl;
  n is 2 or 3; and
  p is 0, 1, 2, or 3.

164. In another embodiment, the present disclosure features a method of embodiment 163, wherein ring A is a pyridyl, indole, indoline, isoindoline, pyrazole, pyrimidine, quinoline, 5,6,7,8-tetrahydroquinoline, 1,2,3,4-tetrahydroisoquinoline, pyrrolodine, aza-indole, pyrrole, oxazole, pyrazine, triazole, indazole, imidazo[1,2-a]pyridine, or imidazole ring.

165. In another embodiment, the present disclosure features a method of embodiment 163 or 164, wherein Ring A is

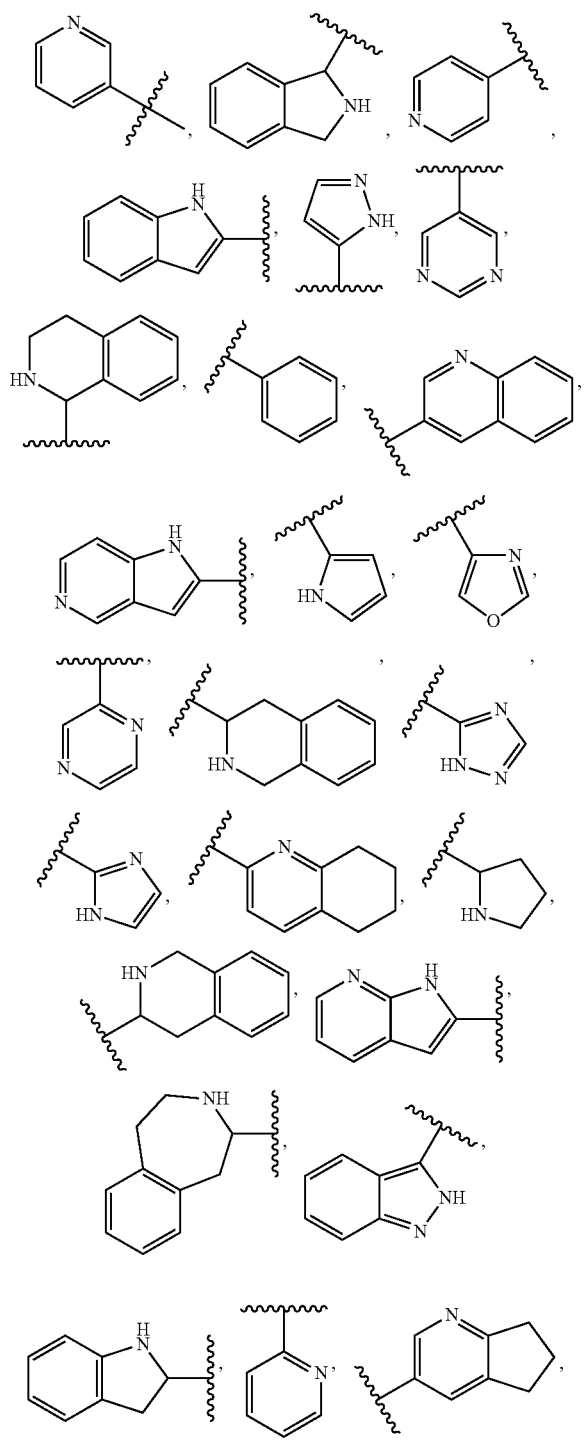

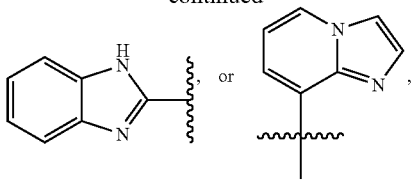

wherein the wavy line indicates point of attachment of Ring A to the carbonyl (CO).

166. In another embodiment, the present disclosure features a method of any one of embodiments 163 to 165, wherein Ring B is pyridyl, pyridine-2(1H)-one, pyrazole, indole, aza-indole, thiophene, dihydrobenzofuran, thiazole, pyrrolidinone, or quinoline.

167. In another embodiment, the present disclosure features a method of any one of embodiments 163 to 166, wherein Ring B is

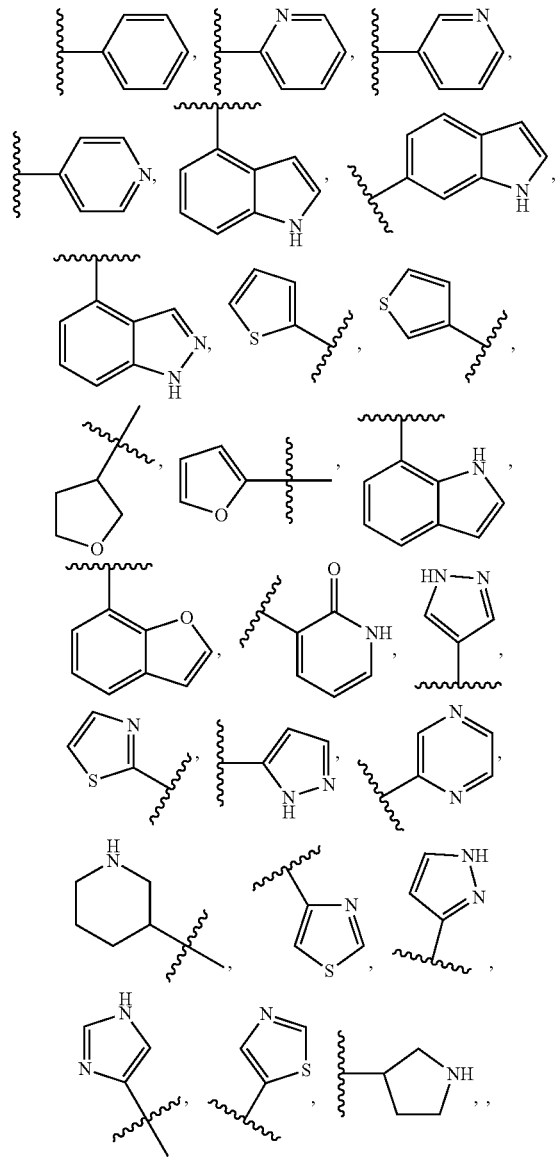

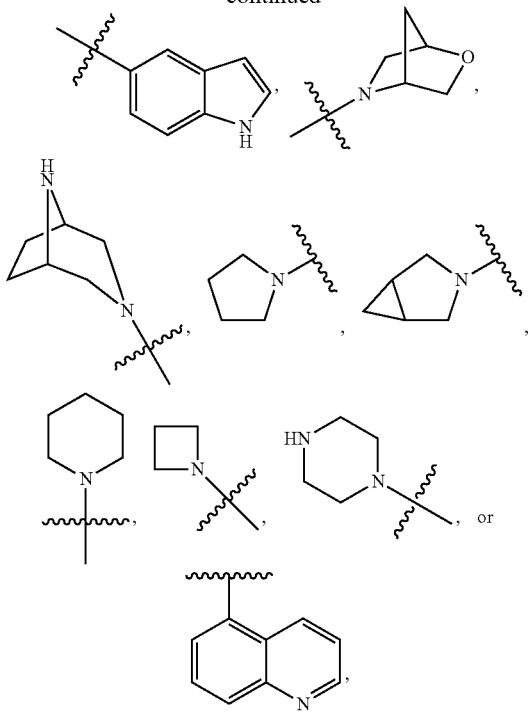

wherein the wavy line indicates point of attachment of Ring B to the X=S=O.

168. In another embodiment, the present disclosure features a method of any one of embodiments 163 to 167, wherein $R_1$ is independently halo, amino, OH, $C_1$-$C_6$ fluoroalkyl, CN, $C_1$-$C_6$ alkyl, $C_2$-$C_6$ alkenyl; $C_2$-$C_6$ alkynyl, $C_1$-$C_8$ alkoxy or $C_1$-$C_8$ fluoroalkoxy, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring, or a ($C_1$-$C_9$ alkylene)-$R_3$ wherein up to four $CH_2$ units are independently replaced with O, CO, S, SO, $SO_2$ or NR.

169. In another embodiment, the present disclosure features a method of any one of embodiments 163 to 168, wherein $R_1$ is $CF_2CH_2(CH_3)N$—, $(CH_3)_2CHCH_2CH2O$—, $(CH_3)_3CCH_2CH_2O$—, $(CH_3)_3COCH_2CH_2O$—, $(CH_3)_2CHO$—, $CHF_2CHF_2CH(CH_3)O$—, —$CF_3$, $(CH_3CH_2)_2N$—, $CF_3CH_2CH(CH_3)O$—, $CH_3O$—, $CH_3(CH_2)_4O$—, $CH_3CH_2CH(CH_3)CH(CH_3)O$—, $CH_3CH_2OCH_2CH_2O$—, $CH_3CH_2NCH(CH_3)_2$, $(CH_3)_3CH_2O$—, (R)—$CH_3NCH(CH_3)(CF_3)$, $CH_3OCH_2CH(CH_2CH_3)O$—, $(CH_3)_2N$—, (S)—$CH_3OCH_2CH(CH_3)O$—, $CH_3O(CH_2)_3O$—, $CH_3OC(CH_3)_2(CH_2)_2O$, $CH_3OCH_2CH(CH_3)O$, $CH_3CH(CH_3)CH_2CH(CH_3)O$—, $(CH_3)_3CCH(CH_3)O$, $((CH_3)_2CH)_2CHO$—, $CH_3CH_2CH_2O$, $CH_3CH=CHCH_2O$—, (S)—$CH_3CH_2CH(CH_3)O$—, $CH_3CH_2O$, $(CH_3)_2CHNCH_3$, $(CH_3)_3$ $CCH_2O$, $(CF_3)_2CHO$—, $(CH_3)_3CCH(CH_2CH_3)O$, $CH_3C\equiv CCH_2CH_2O$, $(CH_3)_3CCH_2CH(CH_3)O$—, $(CH_3)_2C=C(CH_3)$, $CHF_2CH_2O$—, $CH_3CH_2CH_2NH$, $(CH_3)_2CHCH(CH_2CH_3)O$, $((CH_3)_2CH)_2N$, $CH_2=CHCH(CH_3)O$, $CH_2=CHCH_2O$—, $CH_3CH_2C(CH_3)_2O$, $(CH_3CH_2)_2CHO$, $CF_3CH_2O$, $CH_3C(=CH_2)CH_2O$, $(CH_3)_3CCH_2CH_2NH$, $CH_3OCH_2C(CH_3)_2O$, $(CH_3)_3CCH_2N(CH_3)$, $(CH_3)_2CHCH(CH_3)NH$, $(CH_3)_2CHO(CH_2)_2O$, $CH_3CH_2CH_2CH(CH_3)O$, $CH_3CF_2CH_2O$, $(CH_3)_3CNH$, (R)—$CH_3CH_2CH(CH_3)O$, $CH_3OCH_2CH_2O$, $(CH_3)_2CHCH_2N(CH_3)$, $CH_3CH_2CH_2CH(CH_3)CH(CH_3)O$, $CH_3CH_2CH_2CH_2O$, $CH_3CH_2CH_2N$ (CH₃), (R)—CH₃OCH₂CH(CH₃)O, CF₃CH₂N(CH₃), CH₃CH₂N(CH₃), ((CH₃)₃C)₂CHO, (CH₃CH₂)₂CHN(CH₃), (CH₃)₂CHN(CH₃), CH₃CH₂OCH₂CH(CH₃)O, (CH₃)₃CCH₂NH, CF₃CH(CH₃)O, CH₃CH₂NCH(CH₃)₂, (R)—CF₃CH(CH₃)N(CH₃), (CH₃)₂CHCH(CH₃), CH₃CH₂(CH₃)₂CHCH₂CH₂O, (S)—CH₃OCH(CH₃)CH₂O, HOCH(CH₃)₂CH₂CH₂NH, CF₃CH₂CH₂O, CF₃CH₂CH₂CH₂O, CF₃CH=CHCH₂O, CH₃CH₂CH₂CH₂CH₂NH,

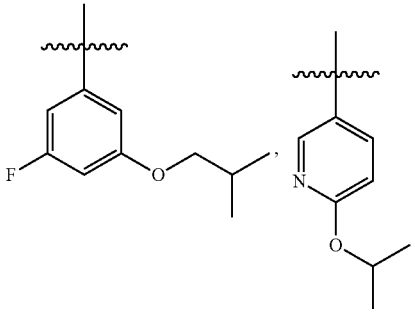

or (CH₃)₃C.

170. In another embodiment, the present disclosure features a method of any one of embodiments 163 to 169, wherein R₂ is halo, CN, OH, amino, $C_1$-$C_6$ alkyl or $C_1$-$C_6$ fluoroalkyl, $C_1$-$C_6$ alkoxy or $C_1$-$C_6$ fluoroalkoxy, $C_3$-$C_{10}$ heterocyclic ring wherein anywhere from 1 to 4 carbon atoms are independently O, S, N, or NR; or a ($C_1$-$C_9$ alkylene)-$R_3$ wherein up to four CH₂ units are optionally and independently replaced with O, CO, S, SO, SO₂ or NR.

171. In another embodiment, the present disclosure features a method of any one of embodiments 163 to 170, wherein R₂ is NH₂, or NHCH₂CH₂CH₃.

172. In another embodiment, the present disclosure features a method of any one of embodiments 163 to 171, wherein n is 2.

173. In another embodiment, the present disclosure features a method of any one of embodiments 163 to 172, wherein p is 0.

174. In another embodiment, the present disclosure features a method of any one of embodiments 163 to 172, wherein p is 1.

175. In another embodiment, the present disclosure features a method of any one of embodiments 163 to 174, wherein in the compound of formula II-i, one or more hydrogen atoms are replaced by a deuterium atom.

176. In another embodiment, the present disclosure features a method of embodiment 138, wherein the compound of formula II or a pharmaceutically acceptable salt thereof is a compound of formula IIa:

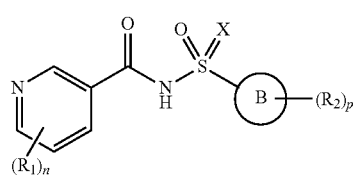

IIa or a pharmaceutically acceptable salt thereof, wherein, independently for each occurrence:
Ring B is a $C_3$-$C_{10}$ cycloalkyl ring; a $C_6$-$C_{10}$ aryl ring; or a $C_3$-$C_{10}$ heteroaryl or $C_3$-$C_{10}$ heterocyclic ring wherein anywhere from 1 to 4 ring atoms are independently O, S, N, or NR;

X is O or NR;
R₁ is halo; CN; NRR; $C_1$-$C_6$ alkyl or $C_1$-$C_6$ fluoroalkyl; $C_3$-$C_6$ cycloalkyl; $C_1$-$C_8$ alkoxy or $C_1$-$C_8$ fluoroalkoxy; $C_2$-$C_6$ alkenyl; $C_2$-$C_6$ alkynyl; ($C_1$-$C_9$ alkylene)-$R_3$ wherein up to four CH₂ units are independently replaced with O, CO, S, SO, SO₂ or NR; $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;
R₂ is halo; NRR; CN; CO₂R; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four CH₂ units are optionally and independently replaced with O, CO, S, SO, SO₂ or NR;
or two R₂ may form a =CH₂ or =O group;
R₃ is H; CF₃; CHF₂; OR; C≡CH; CO₂R; OH; $C_6$-$C_{10}$ aryl, $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or SO₂R;
R is independently H; OH; CO₂H; CO₂$C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, or N; or $C_3$-$C_{10}$ cycloalkyl;
n is 2 or 3; and
p is 0, 1, 2, or 3.

177. In another embodiment, the present disclosure features a method of embodiment 176, wherein Ring B is pyridyl, pyridine-2(1H)-one, pyrazole, indole, aza-indole, thiophene, dihydrobenzofuran, thiazole, pyrrolidinone, or quinoline.

178. In another embodiment, the present disclosure features a method of embodiment 176 or 177, wherein Ring B is

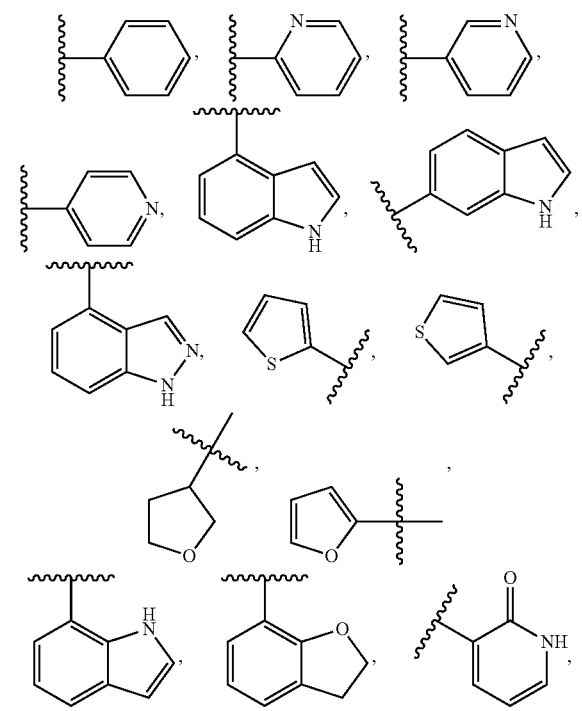

-continued

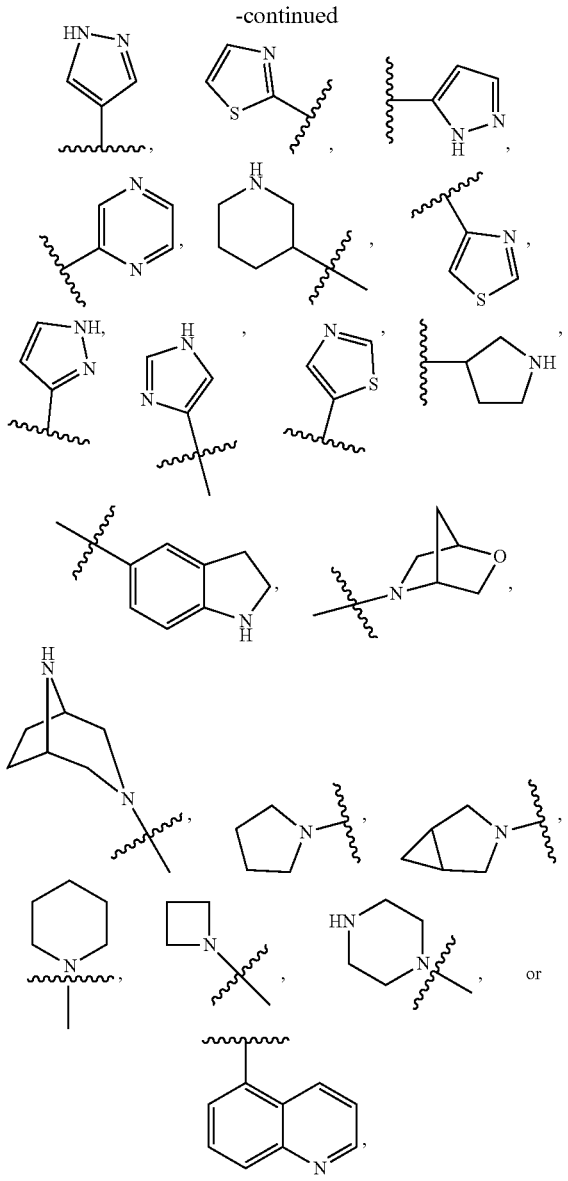

wherein the wavy line ∿ indicates point of attachment of Ring B to X=S=O.

179. In another embodiment, the present disclosure features a method of any one of embodiments 176 to 178, wherein X is O.

180. In another embodiment, the present disclosure features a method of any one of embodiments 176 to 179, wherein $R_1$ is independently halo, amino, OH, $C_1$-$C_6$ fluoroalkyl, CN, $C_1$-$C_6$ alkyl, $C_2$-$C_6$ alkenyl, $C_2$-$C_6$ alkynyl, $C_1$-$C_8$ alkoxy or $C_1$-$C_8$ fluoroalkoxy, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring, or a ($C_1$-$C_9$ alkylene)-$R_3$ wherein up to four $CH_2$ units are independently replaced with O, CO, S, SO, $SO_2$ or NR.

181. In another embodiment, the present disclosure features a method of any one of embodiments 176 to 180, wherein $R_1$ is $CHF_2CH_2CH(CH_3)N$—, $(CH_3)_2CHCH_2CH_2O$—, $(CH_3)_3CCH_2CH_2O$—, $(CH_3)_3COCH_2CH_2O$—, $(CH_3)_2CHO$—, $CHF_2CHF_2CH(CH_3)O$—, —$CF_3$, $(CH_3CH_2)_2N$—, $CF_3CH_2CH(CH_3)O$—, $CH_3O$—, $CH_3(CH_2)_4O$—, $CH_3CH_2CH(CH_3)CH(CH_3)O$—, $CH_3CH_2OCH_2CH_2O$—, $CH_3CH_2NCH(CH_3)_2$, $(CH_3)_3CH_2O$—, (R)—$CH_3NCH(CH_3)(CF_3)$, $CH_3OCH_2CH(CH_2CH_3)O$—, $(CH_3)_2N$—, (S)—$CH_3OCH_2CH(CH_3)O$—, $CH_3O(CH_2)_3O$—, $CH_3OC(CH_3)_2(CH_2)_2O$, $CH_3OCH_2CH(CH_3)O$, $CH_3CH(CH_3)CH_2CH(CH_3)O$—, $(CH_3)_3CCH(CH_3)O$, $((CH_3)_2CH)_2CHO$—, $CH_3CH_2CH_2O$, $CH_3CH$=$CHCH_2O$—, (S)—$CH_3CH_2CH(CH_3)O$—, $CH_3CH_2O$, $(CH_3)_2CHNCH_3$, $(CH_3)_3CCH_2O$, $(CF_3)_2CHO$—, $(CH_3)_3CCH(CH_2CH_3)O$, $CH_3C$≡$CCH_2CH_2O$, $(CH_3)_3CCH_2CH(CH_3)O$—, $(CH_3)_2C$=$C(CH_3)$, $CHF_2CH_2O$—, $CH_3CH_2CH_2NH$, $(CH_3)_2CHCH(CH_2CH_3)O$, $((CH_3)_2CH)_2N$, $CH_2$=$CHCH(CH_3)O$, $CH_2$=$CHCH_2O$—, $CH_3CH_2C(CH_3)_2O$, $(CH_3CH_2)_2CHO$, $CF_3CH_2O$, $CH_3C$(=$CH_2)CH_2O$, $(CH_3)_3CCH_2CH_2NH$, $CH_3OCH_2C(CH_3)_2O$, $(CH_3)_3CCH_2N(CH_3)$, $(CH_3)_2CHCH(CH_3)NH$, $(CH_3)_2CHO(CH_2)_2O$, $CH_3CH_2CH_2CH(CH_3)O$, $CH_3CF_2CH_2O$, $(CH_3)_3CNH$, (R)—$CH_3CH_2CH(CH_3)O$, $CH_3OCH_2CH_2O$, $(CH_3)_2CHCH_2N(CH_3)$, $CH_3CH_2CH_2CH(CH_3)CH(CH_3)O$, $CH_3CH_2CH_2CH_2O$, $CH_3CH_2CH_2N(CH_3)$, (R)—$CH_3OCH_2CH(CH_3)O$, $CF_3CH_2N(CH_3)$, $CH_3CH_2N(CH_3)$, $((CH_3)_3C)_2CHO$, $(CH_3CH_2)_2CHN(CH_3)$, $(CH_3)_2CHN(CH_3)$, $CH_3CH_2OCH_2CH(CH_3)O$, $(CH_3)_3CCH_2NH$, $CF_3CH(CH_3)O$, $CH_3CH_2NCH(CH_3)_2$, (R)—$CF_3CH(CH_3)N(CH_3)$, $(CH_3)_2CHCH(CH_3)$, $CH_3CH_2(CH_3)_2CHCH_2CH_2O$, (S)—$CH_3OCH(CH_3)CH_2O$, $HOCH(CH_3)_2CH_2CH_2NH$, $CF_3CH_2CH_2O$, $CF_3CH_2CH_2CH_2O$, $CF_3CH$=$CHCH_2O$, $CH_3CH_2CH_2CH_2CH_2NH$,

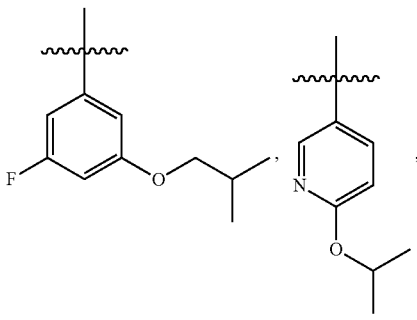

or $(CH_3)_3C$.

182. In another embodiment, the present disclosure features a method of any one of embodiments 176 to 181, wherein $R_2$ is halo, CN, amino, OH, $C_1$-$C_6$ alkyl or $C_1$-$C_6$ fluoroalkyl, $C_1$-$C_6$ alkoxy or $C_1$-$C_6$ fluoroalkoxy, $C_3$-$C_{10}$ heterocyclic ring wherein anywhere from 1 to 4 carbon atoms are independently O, S, N, or NR; or a ($C_1$-$C_9$ alkylene)-$R_3$ wherein up to four $CH_2$ units are optionally and independently replaced with O, CO, S, SO, $SO_2$ or NR.

183. In another embodiment, the present disclosure features a method of any one of embodiments 176 to 182, wherein $R_2$ is $NH_2$, or $NHCH_2CH_2CH_3$.

184. In another embodiment, the present disclosure features a method of any one of embodiments 176 to 183, wherein n is 2.

185. In another embodiment, the present disclosure features a method of any one of embodiments 176 to 184, wherein p is 0.

186. In another embodiment, the present disclosure features a method of any one of embodiments 176 to 184, wherein p is 1.

187. In another embodiment, the present disclosure features a method of any one of embodiments 176 to 186, wherein in the compound of formula IIa, one or more hydrogen atoms are replaced by a deuterium atom.
188. In another embodiment, the present disclosure features a method of embodiment 176, wherein the compounds of formula IIa or a pharmaceutically acceptable salt thereof is a compound of formula IIa-i

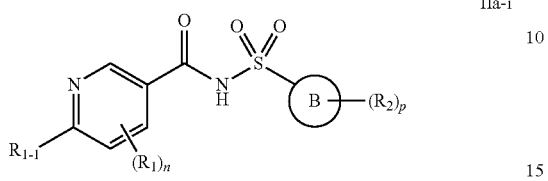

IIa-i or a pharmaceutically acceptable salt thereof, wherein, independently for each occurrence:
  Ring B is a $C_3$-$C_{10}$ cycloalkyl ring; a $C_6$-$C_{10}$ aryl ring; or a $C_3$-$C_{10}$ heteroaryl or $C_3$-$C_{10}$ heterocyclic ring wherein anywhere from 1 to 4 ring atoms are independently O, S, N, or NR;
  $R_1$ is halo; CN; NRR; $C_1$-$C_6$ alkyl or $C_1$-$C_6$ fluoroalkyl; $C_3$-$C_6$ cycloalkyl; $C_1$-$C_8$ alkoxy or $C_1$-$C_8$ fluoroalkoxy; $C_2$-$C_6$ alkenyl; $C_2$-$C_6$ alkynyl; ($C_1$-$C_9$ alkylene)-$R_3$ wherein up to four $CH_2$ units are independently replaced with O, CO, S, SO, $SO_2$ or NR; $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;
  $R_{1-1}$ is $C_1$-$C_6$ alkyl or $C_1$-$C_6$ fluoroalkyl, $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;
  $R_2$ is halo; NRR; CN; $CO_2R$; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four $CH_2$ units are optionally and independently replaced with O, CO, S, SO, $SO_2$ or NR;
  or two $R_2$ may form a =$CH_2$ or =O group;
  $R_3$ is H; $CF_3$; $CHF_2$; OR; C≡CH; $CO_2R$; OH; $C_6$-$C_{10}$ aryl, $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or $SO_2R$;
  R is independently H; OH; $CO_2H$; $CO_2C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, or N; or $C_3$-$C_{10}$ cycloalkyl;
  n is 1 or 2; and
  p is 0, 1, 2, or 3.
189. In another embodiment, the present disclosure features a method of embodiment 188, wherein Ring B is pyridyl, pyridine-2(1H)-one, pyrazole, indole, aza-indole, thiophene, dihydrobenzofuran, thiazole, pyrrolidinone, or quinoline.
190. In another embodiment, the present disclosure features a method of embodiment 188 or 189, wherein Ring B is

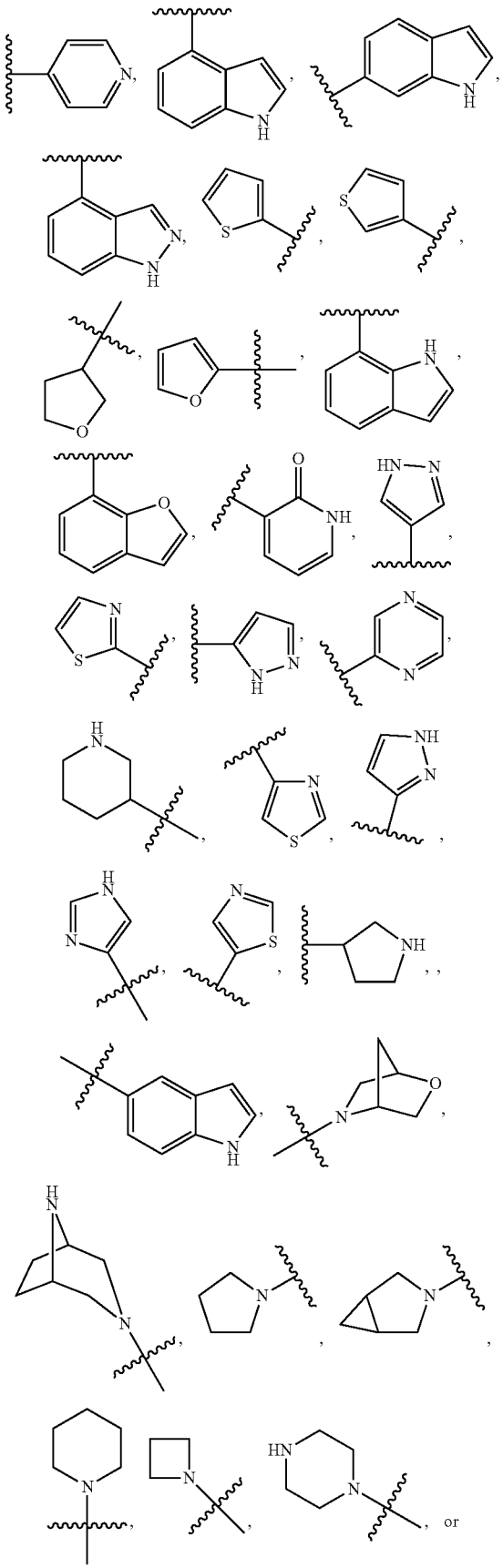

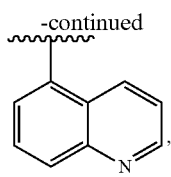

wherein the wavy line ∿ indicates point of attachment of Ring B to the sulfonyl.

191. In another embodiment, the present disclosure features a method of any one of embodiments 188 to 190, wherein $R_1$ is independently halo, amino, OH, $C_1$-$C_6$ fluoroalkyl, CN, $C_1$-$C_6$ alkyl, $C_2$-$C_6$ alkenyl, $C_2$-$C_6$ alkynyl, $C_1$-$C_8$ alkoxy or $C_1$-$C_8$ fluoroalkoxy, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring, or a ($C_1$-$C_9$ alkylene)-$R_3$ wherein up to four $CH_2$ units are independently replaced with O, CO, S, SO, $SO_2$ or NR.

192. In another embodiment, the present disclosure features a method of any one of embodiments 188 to 191, wherein $R_{1-1}$ is $C_1$-$C_6$ alkyl or $C_1$-$C_6$ fluoroalkyl, a phenyl, mono-$C_4$-$C_6$ heterocyclic ring, 1,2,3,4-tetrahydroisoquinoline, pyridyl, pyrimidine, indole, aza-indole, pyrazole, pyrrole, or thiophene ring.

193. In another embodiment, the present disclosure features a method of any one of embodiments 188 to 192, wherein $R_{1-1}$ is tert-butyl,

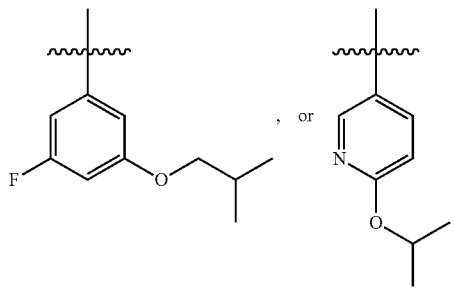

194. In another embodiment, the present disclosure features a method of any one of embodiments 188 to 193, wherein $R_1$ is $CHF_2CH_2(CH_3)N$—, $(CH_3)_2CHCH_2CH_2O$—, $(CH_3)_3CCH_2CH_2O$—, $(CH_3)_3COCH_2CH_2O$—, $(CH_3)_2CHO$—, $CHF_2CHF_2CH(CH_3)O$—, —$CF_3$, $(CH_3CH_2)_2N$—, $CF_3CH_2CH(CH_3)O$—, $CH_3O$—, $CH_3(CH_2)_4O$—, $CH_3CH_2CH(CH_3)CH(CH_3)O$—, $CH_3CH_2OCH_2CH_2O$—, $CH_3CH_2NCH(CH_3)_2$, $(CH_3)_3CH_2O$—, (R)—$CH_3NCH(CH_3)(CF_3)$, $CH_3OCH_2CH(CH_2CH_3)O$—, $(CH_3)_2N$—, (S)—$CH_3OCH_2CH(CH_3)O$—, $CH_3O(CH_2)_3O$—, $CH_3OC(CH_3)_2(CH_2)_2O$—, $CH_3OCH_2CH(CH_3)O$—, $CH_3CH(CH_3)CH_2CH(CH_3)O$—, $(CH_3)_3CCH(CH_3)O$—, $((CH_3)_2CH)_2CHO$—, $CH_3CH_2CH_2O$—, $CH_3CH=CHCH_2O$—, (S)—$CH_3CH_2CH(CH_3)O$—, $CH_3CH_2O$—, $(CH_3)_2CHNCH_3$, $(CH_3)_3CCH_2O$—, $(CF_3)_2CHO$—, $(CH_3)_3CCH(CH_2CH_3)O$—, $CH_3C\equiv CCH_2CH_2O$—, $(CH_3)_3CCH_2CH(CH_3)O$—, $(CH_3)_2C=C(CH_3)$, $CHF_2CH_2O$—, $CH_3CH_2CH_2NH$, $(CH_3)_2CHCH(CH_2CH_3)O$, $((CH_3)_2CH)_2N$, $CH_2=CHCH(CH_3)O$, $CH_2=CHCH_2O$—, $CH_3CH_2C(CH_3)_2O$, $(CH_3CH_2)_2CHO$—, $CF_3CH_2O$, $CH_3C(=CH_2)CH_2O$, $(CH_3)_3CCH_2CH_2NH$, $CH_3OCH_2C(CH_3)_2O$, $(CH_3)_3CCH_2N(CH_3)$, $(CH_3)_2CHCH(CH_3)NH$, $(CH_3)_2CHO(CH_2)_2O$, $(CH_3)_3CHOCH(CH_3)O$, $CH_3CF_2CH_2O$, $(CH_3)_3CNH$, (R)—$CH_3CH_2CH(CH_3)O$, $CH_3OCH_2CH_2O$, $(CH_3)_2CHCH_2N(CH_3)$, $CH_3CH_2CH_2CH(CH_3)CH(CH_3)O$, $CH_3CH_2CH_2CH_2O$, $CH_3CH_2CH_2N(CH_3)$, (R)—$CH_3OCH_2CH(CH_3)O$, $CF_3CH_2N(CH_3)$, $CH_3CH_2N(CH_3)$, $((CH_3)_3C)_2CHO$, $(CH_3CH_2)_2CHN(CH_3)$, $(CH_3)_2CHN(CH_3)$, $CH_3CH_2OCH_2CH(CH_3)O$, $(CH_3)_3CCH_2NH$, $CF_3CH(CH_3)O$, $CH_3CH_2NCH(CH_3)_2$, (R)—$CF_3CH(CH_3)N(CH_3)$, $(CH_3)_2CHCH(CH_3)$, $CH_3CH_2(CH_3)_2CHCH_2CH_2O$, (S)—$CH_3OCH(CH_3)CH_2O$, $HOCH(CH_3)_2CH_2CH_2NH$, $CF_3CH_2CH_2O$, $CF_3CH_2CH_2CH_2O$, $CF_3CH=CHCH_2O$, or $CH_3CH_2CH_2CH_2CH_2NH$.

195. In another embodiment, the present disclosure features a method of any one of embodiments 188 to 194, wherein $R_2$ is halo, CN, amino, OH, $C_1$-$C_6$ alkyl or $C_1$-$C_6$ fluoroalkyl, $C_1$-$C_6$ alkoxy or $C_1$-$C_6$ fluoroalkoxy, $C_3$-$C_{10}$ heterocyclic ring wherein anywhere from 1 to 4 carbon atoms are independently O, S, N, or NR; or a ($C_1$-$C_9$ alkylene)-$R_3$ wherein up to four $CH_2$ units are optionally and independently replaced with O, CO, S, SO, $SO_2$ or NR.

196. In another embodiment, the present disclosure features a method of any one of embodiments 188 to 195, wherein $R_2$ is $NH_2$, or $NHCH_2CH_2CH_3$.

197. In another embodiment, the present disclosure features a method of any one of embodiments 188 to 196, wherein n is 1.

198. In another embodiment, the present disclosure features a method of any one of embodiments 188 to 197, wherein p is 0.

199. In another embodiment, the present disclosure features a method of any one of embodiments 188 to 197, wherein p is 1.

200. In another embodiment, the present disclosure features a method of any one of embodiments 188 to 199, wherein in the compound of formula IIa-i, one or more hydrogen atoms are replaced by a deuterium atom.

201. In another embodiment, the present disclosure features a method of embodiment 188, wherein the compounds of formula IIa-i or a pharmaceutically acceptable salt thereof is a compound of formula IIa-i-1

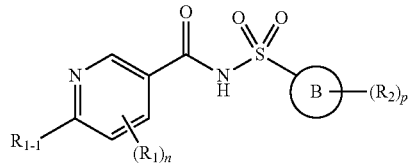

IIa-i-1 or a pharmaceutically acceptable salt thereof, wherein, independently for each occurrence:

Ring B is a $C_3$-$C_{10}$ heteroaryl or $C_3$-$C_{10}$ heterocyclic ring wherein anywhere from 1 to 4 ring atoms are independently O, S, N, or NR;

$R_1$ is halo; CN; NRR; $C_1$-$C_6$ alkyl or $C_1$-$C_6$ fluoroalkyl; $C_3$-$C_6$ cycloalkyl; $C_1$-$C_8$ alkoxy or $C_1$-$C_8$ fluoroalkoxy; $C_2$-$C_6$ alkenyl; $C_2$-$C_6$ alkynyl; ($C_1$-$C_9$ alkylene)-$R_3$ wherein up to four $CH_2$ units are independently replaced with O, CO, S, SO, $SO_2$ or NR; $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_{1-1}$ is $C_1$-$C_6$ alkyl or $C_1$-$C_6$ fluoroalkyl, $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_2$ is halo; NRR; CN; $CO_2R$; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four $CH_2$ units are optionally and independently replaced with O, CO, S, SO, $SO_2$ or NR;
or two $R_2$ may form a =$CH_2$ or =O group;
$R_3$ is H; $CF_3$; $CHF_2$; OR; C≡CH; $CO_2R$; OH; $C_6$-$C_{10}$ aryl; $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or $SO_2R$;
R is independently H; OH; $CO_2H$; $CO_2C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, or N; or $C_3$-$C_{10}$ cycloalkyl;
n is 1 or 2; and
p is 0, 1, 2, or 3.

202. In another embodiment, the present disclosure features a method of embodiment 201, wherein Ring B is pyridyl, pyridine-2(1H)-one, pyrazole, indole, aza-indole, thiophene, dihydrobenzofuran, thiazole, pyrrolidinone, or quinoline.

203. In another embodiment, the present disclosure features a method of embodiment 201 or 202, wherein Ring B is

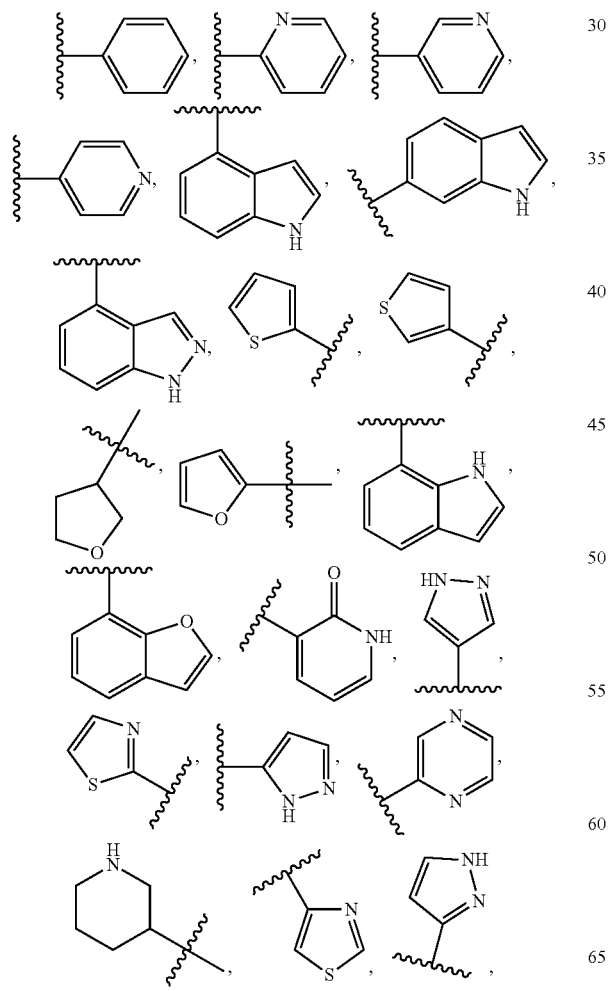

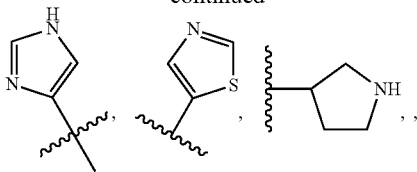

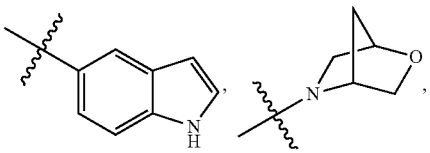

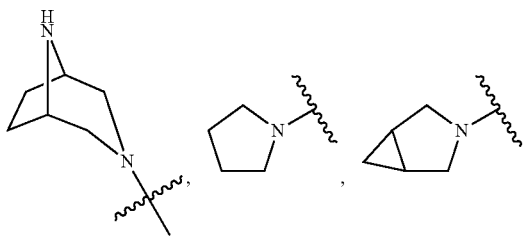

wherein the wavy line indicates point of attachment of Ring B to the sulfonyl.

204. In another embodiment, the present disclosure features a method of any one of embodiments 201 to 203, wherein $R_1$ is independently halo, amino, OH, $C_1$-$C_6$ fluoroalkyl, CN, $C_1$-$C_6$ alkyl, $C_2$-$C_6$ alkenyl, $C_2$-$C_6$ alkynyl, $C_1$-$C_8$ alkoxy or $C_1$-$C_8$fluoroalkoxy, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring, or a ($C_1$-$C_9$ alkylene)-$R_3$ wherein up to four $CH_2$ units are independently replaced with O, CO, S, SO, $SO_2$ or NR.

205. In another embodiment, the present disclosure features a method of any one of embodiments 201 to 204, wherein $R_{1-1}$ is $C_1$-$C_6$ alkyl or $C_1$-$C_6$ fluoroalkyl, a phenyl, mono-$C_4$-$C_6$ heterocyclic ring, 1,2,3,4-tetrahydroisoquinoline, pyridyl, pyrimidine, indole, aza-indole, pyrazole, pyrrole, or thiophene ring.

206. In another embodiment, the present disclosure features a method of any one of embodiments 201 to 205, wherein $R_{1-1}$ is tert-butyl,

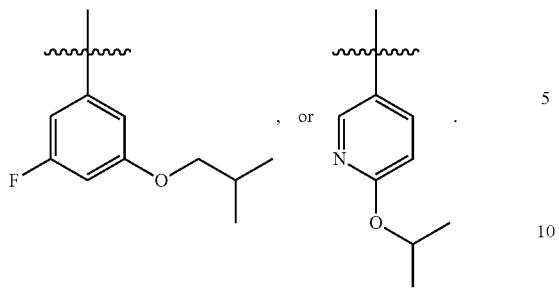

, or

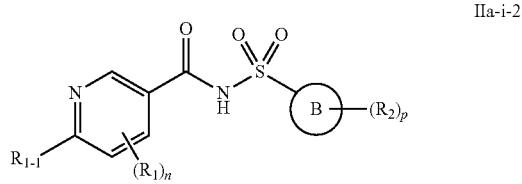

207. In another embodiment, the present disclosure features a method of any one of embodiments 201 to 206, wherein $R_1$ is $CHF_2CH_2(CH_3)N-$, $(CH_3)_2CHCH_2CH2O-$, $(CH_3)_3CCH_2CH_2O-$, $(CH_3)_3COCH_2CH_2O-$, $(CH_3)_2CHO-$, $CHF_2CHF_2CH(CH_3)O-$, $-CF_3$, $(CH_3CH_2)_2N-$, $CF_3CH_2CH(CH_3)O-$, $CH_3O-$, $CH_3(CH_2)_4O-$, $CH_3CH_2CH(CH_3)CH(CH_3)O-$, $CH_3CH_2OCH_2CH_2O-$, $CH_3CH_2NCH(CH_3)_2$, $(CH_3)_3CH_2O-$, $(R)-CH_3NCH(CH_3)(CF_3)$, $CH_3OCH_2CH(CH_2CH_3)O-$, $(CH_3)_2N-$, $(S)-CH_3OCH_2CH(CH_3)O-$, $CH_3O(CH_2)_3O-$, $CH_3OC(CH_3)_2(CH_2)_2O$, $CH_3OCH_2CH(CH_3)O$, $CH_3CH(CH_3)CH_2CH(CH_3)O-$, $(CH_3)_3CCH(CH_3)O$, $((CH_3)_2CH)_2CHO-$, $CH_3CH_2CH_2O$, $CH_3CH=CHCH_2O-$, $(S)-CH_3CH_2CH(CH_3)O-$, $CH_3CH_2O$, $(CH_3)_2CHNCH_3$, $(CH_3)_3CCH_2O$, $(CF_3)_2CHO-$, $(CH_3)_3CCH(CH_2CH_3)O$, $CH_3C\equiv CCH_2CH_2O$, $(CH_3)_3CCH_2CH(CH_3)O-$, $(CH_3)_2C=C(CH_3)$, $CHF_2CH_2O-$, $CH_3CH_2CH_2NH$, $(CH_3)_2CHCH(CH_2CH_3)O$, $((CH_3)_2CH)_2N$, $CH_2=CHCH(CH_3)O$, $CH_2=CHCH_2O-$, $CH_3CH_2C(CH_3)_2O$, $(CH_3CH_2)_2CHO-$, $CF_3CH_2O$, $CH_3C(=CH_2)CH_2O$, $(CH_3)_3CCH_2CH_2NH$, $CH_3OCH_2C(CH_3)_2O$, $(CH_3)_3CCH_2N(CH_3)$, $(CH_3)_2CHCH(CH_3)NH$, $(CH_3)_2CHO(CH_2)_2O$, $CH_3CH_2CH_2CH(CH_3)O$, $CH_3CF_2CH_2O$, $(CH_3)_3CNH$, $(R)-CH_3CH_2CH(CH_3)O-$, $CH_3OCH_2CH_2O$, $(CH_3)_2CHCH_2N(CH_3)$, $CH_3CH_2CH_2CH(CH_3)CH(CH_3)O$, $CH_3CH_2CH_2CH_2O$, $CH_3CH_2CH_2N(CH_3)$, $(R)-CH_3OCH_2CH(CH_3)O$, $CF_3CH_2N(CH_3)$, $CH_3CH_2N(CH_3)$, $((CH_3)_3C)_2CHO$, $(CH_3CH_2)_2CHN(CH_3)$, $(CH_3)_2CHN(CH_3)$, $CH_3CH_2OCH_2CH(CH_3)O$, $(CH_3)_3CCH_2NH$, $CF_3CH(CH_3)O$, $CH_3CH_2NCH(CH_3)_2$, $(R)-CF_3CH(CH_3)N(CH_3)$, $(CH_3)_2CHCH(CH_3)$, $CH_3CH_2(CH_3)_2CHCH_2CH_2O$, $(S)-CH_3OCH(CH_3)_2CH_2O$, $HOCH(CH_3)_2CH_2CH_2NH$, $CF_3CH_2CH_2O$, $CF_3CH_2CH_2CH_2O$, $CF_3CH=CHCH_2O$, or $CH_3CH_2CH_2CH_2CH_2NH$.

208. In another embodiment, the present disclosure features a method of any one of embodiments 201 to 207, wherein $R_2$ is halo, CN, amino, OH, $C_1$-$C_6$ alkyl or $C_1$-$C_6$ fluoroalkyl, $C_1$-$C_6$ alkoxy or $C_1$-$C_6$ fluoroalkoxy, $C_3$-$C_{10}$ heterocyclic ring wherein anywhere from 1 to 4 carbon atoms are independently O, S, N, or NR; or a ($C_1$-$C_9$ alkylene)-$R_3$ wherein up to four $CH_2$ units are optionally and independently replaced with O, CO, S, SO, $SO_2$ or NR.

208. In another embodiment, the present disclosure features a method of any one of embodiments 201 to 207, wherein $R_2$ is $NH_2$, or $NHCH_2CH_2CH_3$.

209. In another embodiment, the present disclosure features a method of any one of embodiments 201 to 208, wherein n is 1.

210. In another embodiment, the present disclosure features a method of any one of embodiments 201 to 209, wherein p is 0.

211. In another embodiment, the present disclosure features a method of any one of embodiments 201 to 209, wherein p is 1.

212. In another embodiment, the present disclosure features a method of any one of embodiments 201 to 211, wherein in the compound of formula IIa-i-1, one or more hydrogen atoms are replaced by a deuterium atom.

213. In another embodiment, the present disclosure features a method of embodiment 201, wherein the compound of formula IIa-i-1 or a pharmaceutically acceptable salt thereof is a compound of formula IIa-i-2

IIa-i-2

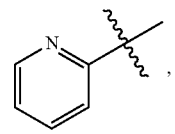

or a pharmaceutically acceptable salt thereof, wherein, independently for each occurrence:

Ring B is a pyridinyl;

$R_1$ is halo; CN; NRR; $C_1$-$C_6$ alkyl or $C_1$-$C_6$ fluoroalkyl; $C_3$-$C_6$ cycloalkyl; $C_1$-$C_8$ alkoxy or $C_1$-$C_8$ fluoroalkoxy; $C_2$-$C_6$ alkenyl; $C_2$-$C_6$ alkynyl; ($C_1$-$C_9$ alkylene)-$R_3$ wherein up to four $CH_2$ units are independently replaced with O, CO, S, SO, $SO_2$ or NR; $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_{1-1}$ is $C_1$-$C_6$ alkyl or $C_1$-$C_6$ fluoroalkyl, $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_2$ is halo; NRR; CN; $CO_2R$; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four $CH_2$ units are optionally and independently replaced with O, CO, S, SO, $SO_2$ or NR;

or two $R_2$ may form a $=CH_2$ or $=O$ group;

$R_3$ is H; $CF_3$; $CHF_2$; OR; $C\equiv CH$; $CO_2R$; OH; $C_6$-$C_{10}$ aryl, $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or $SO_2R$;

R is independently H; OH; $CO_2H$; $CO_2C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, or N; or $C_3$-$C_{10}$ cycloalkyl;

n is 1 or 2; and p is 0, 1, 2, or 3.

214. In another embodiment, the present disclosure features a method of embodiment 213, wherein Ring B is

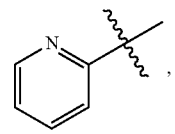

, wherein the wavy line indicates point of attachment of Ring B to the sulfonyl.

215. In another embodiment, the present disclosure features a method of embodiment 213 or 214, wherein $R_1$ is independently halo, amino, OH, $C_1$-$C_6$ fluoroalkyl, CN, $C_1$-$C_6$ alkyl, $C_2$-$C_6$ alkenyl, $C_2$-$C_6$ alkynyl, $C_1$-$C_8$alkoxy or $C_1$-$C_8$fluoroalkoxy, a phenyl, $C_3$-$C_6$ mono-cycloalkly, mono-$C_4$-$C_6$ heterocyclic ring, 1,2,3,4-tetrahydroisoquinoline, pyridyl, pyrimidine, indole, aza-indole, pyrazole, pyrrole, or thiophene ring, or a ($C_1$-$C_9$ alkylene)-$R_3$ wherein up to four $CH_2$ units are independently replaced with O, CO, S, SO, $SO_2$ or NR.

216. In another embodiment, the present disclosure features a method of any one of embodiments 213 to 215, wherein $R_{1-1}$ is $C_1$-$C_6$ alkyl or $C_1$-$C_6$ fluoroalkyl, a phenyl, mono-$C_4$-$C_6$ heterocyclic ring, 1,2,3,4-tetrahydroisoquinoline, pyridyl, pyrimidine, indole, aza-indole, pyrazole, pyrrole, or thiophene ring.

217. In another embodiment, the present disclosure features a method of any one of embodiments 213 to 216, wherein $R_{1-1}$ is tert-butyl,

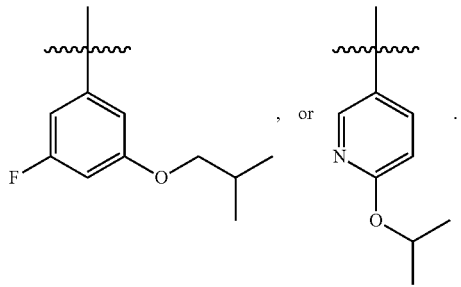 [SMILES: *c1cc(F)cc(OCC(C)C)c1 ; *c1ccc(OC(C)C)nc1]

, or

218. In another embodiment, the present disclosure features a method of any one of embodiments 213 to 217, wherein $R_1$ is $CHF_2CH_2(CH_3)N-$, $(CH_3)_2CHCH_2CH2O-$, $(CH_3)_3CCH_2CH_2O-$, $(CH_3)_3COCH_2CH_2O-$, $(CH_3)_2CHO$, $CHF_2CHF_2CH(CH_3)O-$, $-CF_3$, $(CH_3CH_2)_2N-$, $CF_3CH_2CH(CH_3)O-$, $CH_3O-$, $CH_3(CH_2)_4O-$, $CH_3CH_2CH(CH_3)CH(CH_3)O-$, $CH_3CH_2OCH_2CH_2O-$, $CH_3CH_2NCH(CH_3)_2$, $(CH_3)_3CH_2O-$, (R)—$CH_3NCH(CH_3)(CF_3)$, $CH_3OCH_2CH(CH_2CH_3)O-$, $(CH_3)_2N-$, (S)—$CH_3OCH_2CH(CH_3)O-$, $CH_3O(CH_2)_3O-$, $CH_3OC(CH_3)_2(CH_2)_2O$, $CH_3OCH_2CH(CH_3)O$, $CH_3CH(CH_3)CH_2CH(CH_3)O-$, $(CH_3)_3CCH(CH_3)O$, $((CH_3)_2CH)_2CHO-$, $CH_3CH_2CH_2O$, $CH_3CH=CHCH_2O-$, (S)—$CH_3CH_2CH(CH_3)O-$, $CH_3CH_2O$, $(CH_3)_2CHNCH_3$, $(CH_3)_3CCH_2O$, $(CF_3)_2CHO-$, $(CH_3)_3CCH(CH_2CH_3)O$, $CH_3C\equiv CCH_2CH_2O$, $(CH_3)_3CCH_2CH(CH_3)O-$, $(CH_3)_2C=C(CH_3)$, $CHF_2CH_2O-$, $CH_3CH_2CH_2NH$, $(CH_3)_2CHCH(CH_2CH_3)O$, $((CH_3)_2CH)_2N$, $CH_2=CHCH(CH_3)O$, $CH_2=CHCH_2O-$, $CH_3CH_2C(CH_3)_2O$, $(CH_3CH_2)_2CHO$, $CF_3CH_2O$, $CH_3C(=CH_2)CH_2O$, $(CH_3)_3CCH_2CH_2NH$, $CH_3OCH_2C(CH_3)_2O$, $(CH_3)_3CCH_2N(CH_3)$, $(CH_3)_2CHCH(CH_3)NH$, $(CH_3)_2CHO(CH_2)_2O$, $CH_3CH_2CH(CH_3)O$, $CH_3CF_2CH_2O$, $(CH_3)_3CNH$, (R)—$CH_3CH_2CH(CH_3)O$, $CH_3OCH_2CH_2O$, $(CH_3)_2CHCH_2N(CH_3)$, $CH_3CH_2CH_2CH(CH_3)CH(CH_3)O$, $CH_3CH_2CH_2O$, $CH_3CH_2CH_2N(CH_3)$, (R)—$CH_3OCH_2CH(CH_3)O$, $CF_3CH_2N(CH_3)$, $CH_3CH_2N(CH_3)$, $((CH_3)_3C)_2CHO$, $(CH_3CH_2)_2CHN(CH_3)$, $(CH_3)_2CHN(CH_3)$, $CH_3CH_2OCH(CH_3)O$, $(CH_3)_3CCH_2NH$, $CF_3CH(CH_3)O$, $CH_3CH_2NCH(CH_3)_2$, $(_R)$—$CF_3CH(CH_3)N(CH_3)$, $(CH_3)_2CHCH(CH_3)$, $CH_3CH_2(CH_3)_2CHCH_2CH_2O$, (S)—$CH_3OCH(CH_3)CH_2O$, $HOCH(CH_3)_2CH_2CH_2NH$, $CF_3CH_2CH_2O$, $CF_3CH_2CH_2O$, $CF_3CH=CHCH_2O$, or $CH_3CH_2CH_2CH_2NH$.

219. In another embodiment, the present disclosure features a method of any one of embodiments 213 to 218, wherein $R_2$ is halo, CN, amino, OH, $C_1$-$C_6$ alkyl or $C_1$-$C_6$ fluoroalkyl, $C_1$-$C_6$ alkoxy or $C_1$-$C_6$ fluoroalkoxy, $C_3$-$C_{10}$ heterocyclic ring wherein anywhere from 1 to 4 carbon atoms are independently O, S, N, or NR; or a ($C_1$-$C_9$ alkylene)-$R_3$ wherein up to four $CH_2$ units are optionally and independently replaced with O, CO, S, SO, $SO_2$ or NR.

220. In another embodiment, the present disclosure features a method of any one of embodiments 213 to 219, wherein $R_2$ is $NH_2$, or $NHCH_2CH_2CH_3$.

221. In another embodiment, the present disclosure features a method of any one of embodiments 213 to 220, wherein n is 1.

222. In another embodiment, the present disclosure features a method of any one of embodiments 213 to 221, wherein p is 0.

223. In another embodiment, the present disclosure features a method of embodiment 213, wherein p is 1.

224. In another embodiment, the present disclosure features a method of any one of embodiments 213 to 223, wherein in the compound of formula IIa-i-2, one or more hydrogen atoms are replaced by a deuterium atom.

225. In another embodiment, the present disclosure features a method of embodiment 176, wherein the compounds of formula IIa or a pharmaceutically acceptable salt thereof is a compound of formula IIa-ii

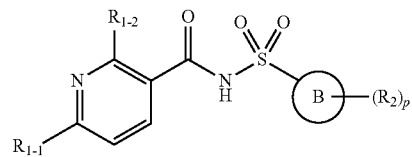

IIa-ii or a pharmaceutically acceptable salt thereof, wherein, independently for each occurrence:

Ring B is a $C_3$-$C_{10}$ cycloalkyl ring; a $C_6$-$C_{10}$ aryl ring; or a $C_3$-$C_{10}$ heteroaryl or $C_3$-$C_{10}$ heterocyclic ring wherein anywhere from 1 to 4 ring atoms are independently O, S, N, or NR;

$R_{1-2}$ is halo; CN; NRR; $C_1$-$C_6$ alkyl or $C_1$-$C_6$ fluoroalkyl; $C_1$-$C_8$ alkoxy or $C_1$-$C_8$ fluoroalkoxy; $C_2$-$C_6$ alkenyl; $C_2$-$C_6$ alkynyl; or ($C_1$-$C_9$ alkylene)-$R_3$ wherein up to four $CH_2$ units are independently replaced with O, CO, S, SO, $SO_2$ or NR;

$R_{1-1}$ is $C_1$-$C_6$ alkyl or $C_1$-$C_6$ fluoroalkyl, $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_2$ is halo; NRR; CN; $CO_2R$; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four $CH_2$ units are optionally and independently replaced with O, CO, S, SO, $SO_2$ or NR;

or two $R_2$ may form a $=CH_2$ or $=O$ group;

$R_3$ is H; $CF_3$; $CHF_2$; OR; $C\equiv CH$; $CO_2R$; OH; $C_6$-$C_{10}$ aryl, $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or $SO_2R$;

R is independently H; OH; CO₂H; CO₂C₁-C₆ alkyl; C₁-C₆ alkyl; C₂-C₆ alkenyl; C₂-C₆ alkynyl; C₆-C₁₀ aryl; C₃-C₁₀ heteroaryl or heterocycloalkyl wherein anywhere from 1 to 4 ring atoms are independently O, S, or N; or C₃-C₁₀ cycloalkyl; and p is 0, 1, 2, or 3.

226. In another embodiment, the present disclosure features a method of embodiment 225, wherein Ring B is pyridyl, pyridine-2(1H)-one, pyrazole, indole, aza-indole, thiophene, dihydrobenzofuran, thiazole, pyrrolidinone, or quinoline.

227. In another embodiment, the present disclosure features a method of embodiment 225 or 226, wherein Ring B is

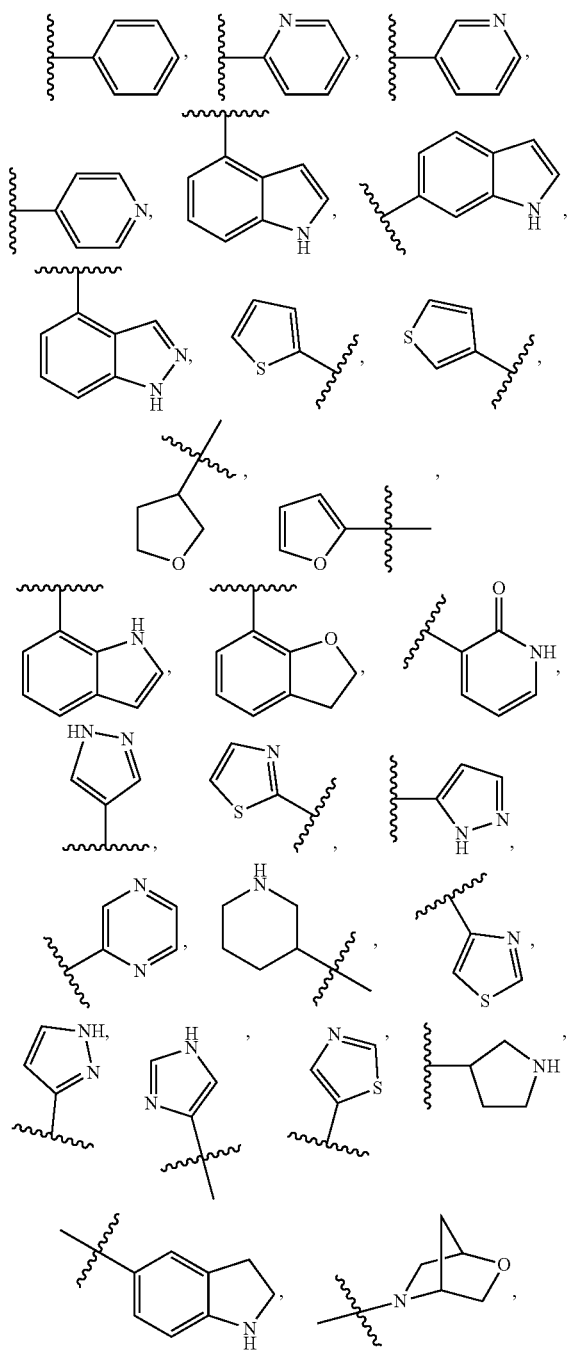

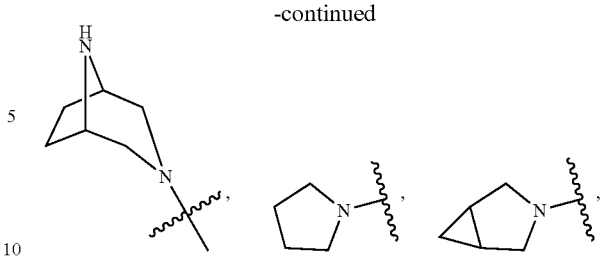

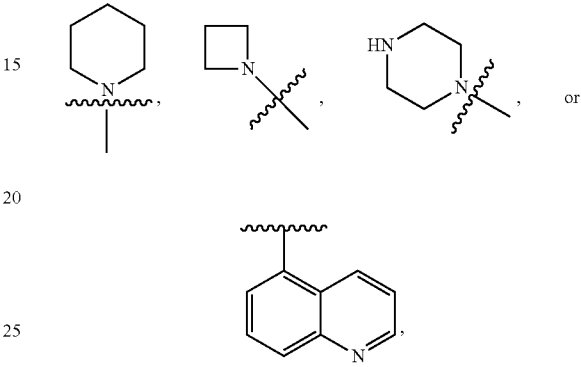

wherein the wavy line indicates point of attachment of Ring B to the sulfonyl (SO₂).

228. In another embodiment, the present disclosure features a method of any one of embodiments 225 to 227, wherein $R_{1-2}$ is independently halo, amino, OH, C₁-C₆ fluoroalkyl, CN, C₁-C₆ alkyl, C₂-C₆ alkenyl, C₂-C₆ alkynyl, C₁-C₈ alkoxy or C₁-C₈ fluoroalkoxy, or a (C₁-C₉ alkylene)-R₃ wherein up to four CH₂ units are independently replaced with O, CO, S, SO, SO₂ or NR.

229. In another embodiment, the present disclosure features a method of any one of embodiments 225 to 228, wherein $R_{1-1}$ is C₁-C₆ alkyl or C₁-C₆ fluoroalkyl, a phenyl, mono-C₄-C₆ heterocyclic ring, 1,2,3,4-tetrahydroisoquinoline, pyridyl, pyrimidine, indole, aza-indole, pyrazole, pyrrole, or thiophene ring.

230. In another embodiment, the present disclosure features a method of any one of embodiments 225 to 229, wherein $R_{1-1}$ is tert-butyl,

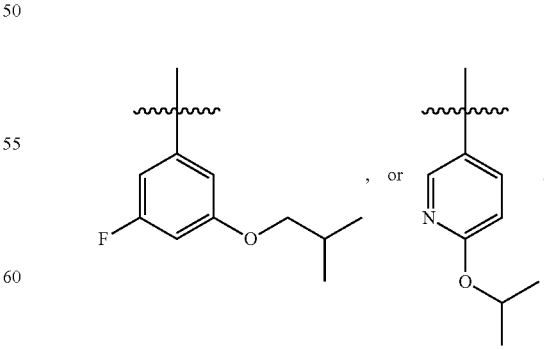

231. In another embodiment, the present disclosure features a method of any one of embodiments 225 to 230, wherein $R_{1-1}$ is

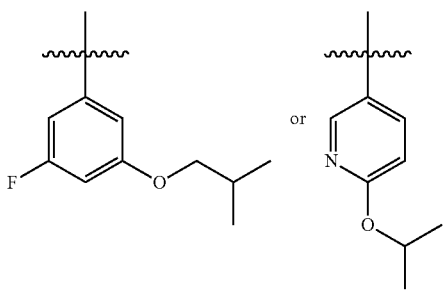

232. In another embodiment, the present disclosure features a method of any one of embodiments 225 to 231, wherein $R_{1-2}$ is $CHF_2CH_2(CH_3)N-$, $(CH_3)_2CHCH_2CH_2O-$, $(CH_3)_3CCH_2CH_2O-$, $(CH_3)_3COCH_2CH_2O-$, $(CH_3)_2CHO-$, $CHF_2CHF_2CH(CH_3)O-$, $-CF_3$, $(CH_3CH_2)_2N-$, $CF_3CH_2CH(CH_3)O-$, $CH_3O-$, $CH_3(CH_2)_4O-$, $CH_3CH_2CH(CH_3)CH(CH_3)O-$, $CH_3CH_2OCH_2CH_2O-$, $CH_3CH_2NCH(CH_3)_2$, $(CH_3)_3CH_2O-$, $(R)-CH_3NCH(CH_3)(CF_3)$, $CH_3OCH_2CH(CH_2CH_3)O-$, $(CH_3)_2N-$, $(S)-CH_3OCH_2CH(CH_3)O-$, $CH_3O(CH_2)_3O-$, $CH_3OC(CH_3)_2(CH_2)_2O$, $CH_3OCH_2CH(CH_3)O$, $CH_3CH(CH_3)CH_2CH(CH_3)O-$, $(CH_3)_3CCH(CH_3)O$, $((CH_3)_2CH)_2CHO-$, $CH_3CH_2CH_2O$, $CH_3CH=CHCH_2O-$, $(S)-CH_3CH_2CH(CH_3)O-$, $CH_3CH_2O$, $(CH_3)_2CHNCH_3$, $(CH_3)_3CCH_2O$, $(CF_3)_2CHO-$, $(CH_3)_3CCH(CH_2CH_3)O$, $CH_3C\equiv CCH_2CH_2O$, $(CH_3)_3CCH_2CH(CH_3)O-$, $(CH_3)_2C=C(CH_3)$, $CHF_2CH_2O-$, $CH_3CH_2CH_2NH$, $(CH_3)_2CHCH(CH_2CH_3)O$, $((CH_3)_2CH)_2N$, $CH_2=CHCH(CH_3)O$, $CH_2=CHCH_2O-$, $CH_3CH_2C(CH_3)_2O$, $(CH_3CH_2)_2CHO-$, $CF_3CH_2O$, $CH_3C(=CH_2)CH_2O$, $(CH_3)_3CCH_2CH_2NH$, $CH_3OCH_2C(CH_3)_2O$, $(CH_3)_3CCH_2N(CH_3)$, $(CH_3)_2CHCH(CH_3)NH$, $(CH_3)_2CHO(CH_2)_2O$, $CH_3CH_2CH_2CH(CH_3)O$, $CH_3CF_2CH_2O$, $(CH_3)_3CNH$, $(R)-CH_3CH_2CH(CH_3)O$, $CH_3OCH_2CH_2O$, $(CH_3)_2CHCH_2N(CH_3)$, $CH_3CH_2CH_2CH(CH_3)CH(CH_3)O$, $CH_3CH_2CH_2CH_2O$, $CH_3CH_2CH_2N(CH_3)$, $(R)-CH_3OCH_2CH(CH_3)O$, $CF_3CH_2N(CH_3)$, $CH_3CH_2N(CH_3)$, $((CH_3)_3C)_2CHO-$, $(CH_3CH_2)_2CHN(CH_3)$, $(CH_3)_2CHN(CH_3)$, $CH_3CH_2OCH_2CH(CH_3)O$, $(CH_3)_3CCH_2NH$, $CF_3CH(CH_3)O$, $CH_3CH_2NCH(CH_3)_2$, $_{(R)}$—$CF_3CH(CH_3)N(CH_3)$, $(CH_3)_2CHCH(CH_3)$, $CH_3CH_2(CH_3)_2CHCH_2CH_2O$, $(S)$—$CH_3OCH(CH_3)CH_2O$, $HOCH(CH_3)_2CH_2CH_2NH$, $CF_3CH_2CH_2O$, $CF_3CH_2CH_2CH_2O$, $CF_3CH=CHCH_2O$, or $CH_3CH_2CH_2CH_2CH_2NH$. 234. In another embodiment, the present disclosure features a method of any one of embodiments 225 to 233, wherein $R_2$ is halo, CN, amino, OH, $C_1-C_6$ alkyl or $C_1-C_6$ fluoroalkyl, $C_1-C_6$ alkoxy or $C_1-C_6$ fluoroalkoxy, $C_3-C_{10}$ heterocyclic ring wherein anywhere from 1 to 4 carbon atoms are independently O, S, N, or NR; or a $(C_1-C_9$ alkylene)-$R_3$ wherein up to four $CH_2$ units are optionally and independently replaced with O, CO, S, SO, $SO_2$ or NR.

235. In another embodiment, the present disclosure features a method of any one of embodiments 225 to 234, wherein $R_2$ is $NH_2$, or $NHCH_2CH_2CH_3$.

236. In another embodiment, the present disclosure features a method of any one of embodiments 225 to 235, wherein p is 0.

237. In another embodiment, the present disclosure features a method of any one of embodiments 225 to 235, wherein p is 1.

238. In another embodiment, the present disclosure features a method of any one of embodiments 225 to 237, wherein in the compound of formula IIa-ii, one or more hydrogen atoms are replaced by a deuterium atom.

239. In another embodiment, the present disclosure features a method of embodiment 225, wherein the compounds of formula IIa-ii or a pharmaceutically acceptable salt thereof is a compound of formula IIa-ii-1

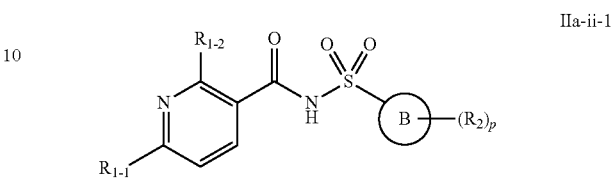

IIa-ii-1 or a pharmaceutically acceptable salt thereof, wherein, independently for each occurrence:

Ring B is a $C_3-C_{10}$ heteroaryl or $C_3-C_{10}$ heterocyclic ring wherein anywhere from 1 to 4 ring atoms are independently O, S, N, or NR;

$R_{1-2}$ is halo; CN; NRR; $C_1-C_6$ alkyl or $C_1-C_6$ fluoroalkyl; $C_1-C_8$ alkoxy or $C_1-C_8$ fluoroalkoxy; $C_2-C_6$ alkenyl; $C_2-C_6$ alkynyl; or $(C_1-C_9$ alkylene)-$R_3$ wherein up to four $CH_2$ units are independently replaced with O, CO, S, SO, $SO_2$ or NR;

$R_{1-1}$ is $C_1-C_6$ alkyl or $C_1-C_6$ fluoroalkyl, $C_6-C_{10}$ aryl; $C_3-C_{10}$ heteroaryl or $C_3-C_{10}$ heterocyclic ring wherein anywhere from 1 to 4 ring atoms are independently O, S, N, or NR; or $C_3-C_{10}$ cycloalkyl;

$R_2$ is halo; NRR; CN; $CO_2R$; $C_1-C_6$ alkyl or $C_1-C_6$ fluoroalkyl; $C_1-C_6$ alkoxy or $C_1-C_6$ fluoroalkoxy; $C_2-C_6$ alkenyl; $C_2-C_6$ alkynyl; $C_6-C_{10}$ aryl; $C_3-C_{13}$ heteroaryl or heterocyclic ring wherein anywhere from 1 to 4 ring atoms are independently O, S, N, or NR; $C_3-C_{10}$ cycloalkyl; or a $(C_1-C_9$ alkylene)-$R_3$ wherein up to four $CH_2$ units are optionally and independently replaced with O, CO, S, SO, $SO_2$ or NR;

or two $R_2$ may form a $=CH_2$ or $=O$ group;

$R_3$ is H; $CF_3$; $CHF_2$; OR; $C\equiv CH$; $CO_2R$; OH; $C_6-C_{10}$ aryl, $C_3-C_{10}$ heteroaryl or heterocycloalkyl wherein anywhere from 1 to 4 ring atoms are independently O, S, N, or NR; $C_3-C_{10}$ cycloalkyl; NRR, NRCOR, CONRR, CN, halo, or $SO_2R$;

R is independently H; OH; $CO_2H$; $CO_2C_1-C_6$ alkyl; $C_1-C_6$ alkyl; $C_2-C_6$ alkenyl; $C_2-C_6$ alkynyl; $C_6-C_{10}$ aryl; $C_3-C_{10}$ heteroaryl or heterocycloalkyl wherein anywhere from 1 to 4 ring atoms are independently O, S, or N; or $C_3-C_{10}$ cycloalkyl; and p is 0, 1, 2, or 3.

240. In another embodiment, the present disclosure features a method of embodiment 239, wherein Ring B is pyridyl, pyridine-2(1H)-one, pyrazole, indole, aza-indole, thiophene, dihydrobenzofuran, thiazole, pyrrolidinone, or quinoline.

241. In another embodiment, the present disclosure features a method of embodiment 239 or 240, wherein Ring B is

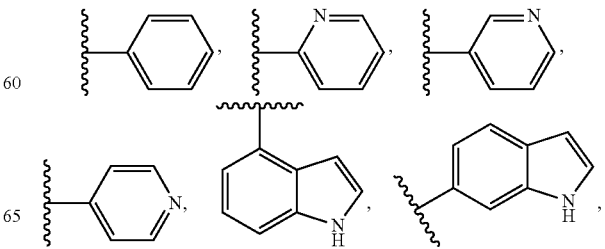

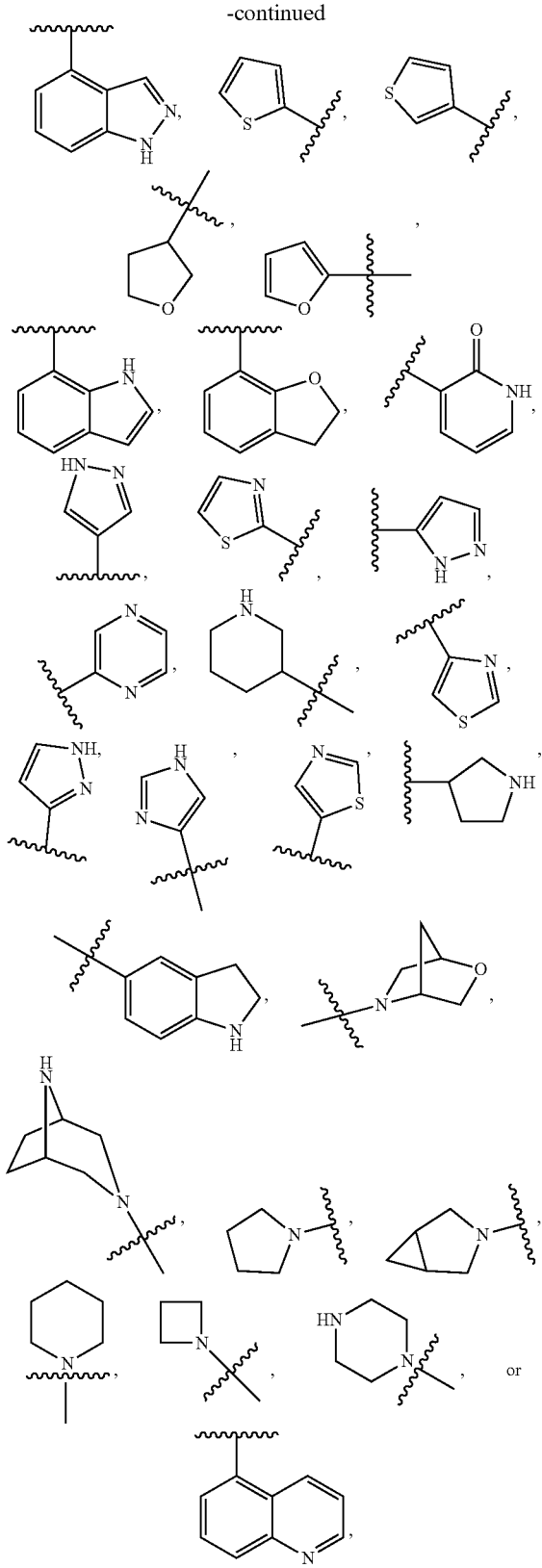

wherein the wavy line ⌇ indicates point of attachment of Ring B to the sulfonyl ($SO_2$).

242. In another embodiment, the present disclosure features a method of any one of embodiments 239 to 241, wherein $R_{1-2}$ is independently halo, amino, OH, $C_1$-$C_6$ fluoroalkyl, CN, $C_1$-$C_6$ alkyl, $C_2$-$C_6$ alkenyl, $C_2$-$C_6$ alkynyl, $C_1$-$C_8$ alkoxy or $C_1$-$C_8$ fluoroalkoxy, or a ($C_1$-$C_9$ alkylene)-$R_3$ wherein up to four $CH_2$ units are independently replaced with O, CO, S, SO, $SO_2$ or NR.

243. In another embodiment, the present disclosure features a method of any one of embodiments 239 to 242, wherein $R_{1-1}$ is $C_1$-$C_6$ alkyl or $C_1$-$C_6$ fluoroalkyl, a phenyl, mono-$C_4$-$C_6$ heterocyclic ring, 1,2,3,4-tetrahydroisoquinoline, pyridyl, pyrimidine, indole, aza-indole, pyrazole, pyrrole, or thiophene ring.

244. In another embodiment, the present disclosure features a method of any one of embodiments 239 to 243, wherein $R_{1-1}$ is tert-butyl,

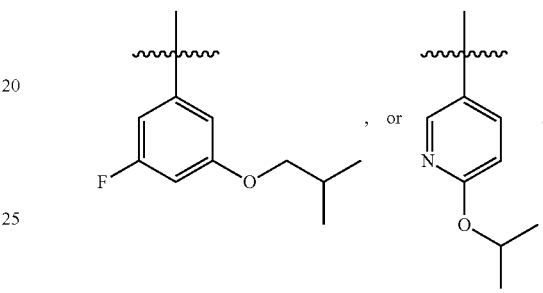

245. In another embodiment, the present disclosure features a method of any one of embodiments 239 to 244, wherein $R_{1-1}$ is

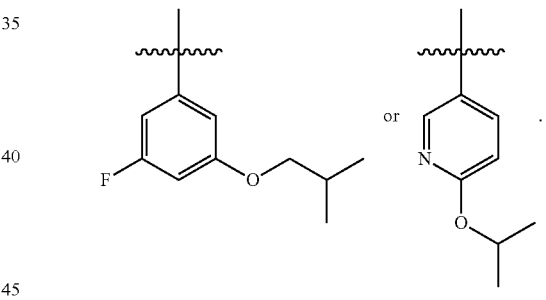

246. In another embodiment, the present disclosure features a method of any one of embodiments 239 to 245, wherein $R_{1-2}$ is $CHF_2CH_2(CH_3)N$—, $(CH_3)_2CHCH_2CH2O$—, $(CH_3)_3CCH_2CH_2O$—, $(CH_3)_3COCH_2CH_2O$—, $(CH_3)_2CHO$—, $CHF_2CHF_2CH(CH_3)O$—, —$CF_3$, $(CH_3CH_2)_2N$—, $CF_3CH_2CH(CH_3)O$—, $CH_3O$—, $CH_3(CH_2)_4O$—, $CH_3CH_2CH(CH_3)CH(CH_3)O$—, $CH_3CH_2OCH_2CH_2O$—, $CH_3CH_2NCH(CH_3)_2$, $(CH_3)_3CH_2O$—, (R)—$CH_3NCH(CH_3)(CF_3)$, $CH_3OCH_2CH(CH_2CH_3)O$—, $(CH_3)_2N$—, (S)—$CH_3OCH_2CH(CH_3)O$—, $CH_3O(CH_2)_3O$—, $CH_3OC(CH_3)_2(CH_2)_2O$, $CH_3OCH_2CH(CH_3)O$, $CH_3CH(CH_3)CH_2CH(CH_3)O$—, $(CH_3)_3CCH(CH_3)O$, $((CH_3)_2CH)_2CHO$—, $CH_3CH_2CH_2O$, $CH_3CH$=$CHCH_2O$—, (S)—$CH_3CH_2CH(CH_3)O$—, $CH_3CH_2O$, $(CH_3)_2CHNCH_3$, $(CH_3)_3CCH_2O$, $(CF_3)_2CHO$—, $(CH_3)_3CCH(CH_2CH_3)O$, $CH_3C$≡$CCH_2CH_2O$, $(CH_3)_3CCH_2CH(CH_3)O$—, $(CH_3)_2C$=$C(CH_3)$, $CHF_2CH_2O$—, $CH_3CH_2CH_2NH$, $(CH_3)_2CHCH(CH_2CH_3)O$, $((CH_3)_2CH)_2N$, $CH_2$=$CHCH(CH_3)O$, $CH_2$=$CHCH_2O$—, $CH_3CH_2C(CH_3)_2O$, $(CH_3CH_2)_2CHO$, $CF_3CH_2O$, $CH_3C$(=$CH_2$)$CH_2O$, $(CH_3)_3CCH_2CH_2NH$, $CH_3OCH_2C(CH_3)_2O$, $(CH_3)_3CCH_2N$ (CH$_3$), (CH$_3$)$_2$CHCH(CH$_3$)NH, (CH$_3$)$_2$CHO(CH$_2$)$_2$O, CH$_3$CH$_2$CH$_2$CH(CH$_3$)O, CH$_3$CF$_2$CH$_2$O, (CH$_3$)$_3$CNH, (R)—CH$_3$CH$_2$CH(CH$_3$)O, CH$_3$OCH$_2$CH$_2$O, (CH$_3$)$_2$CHCH$_2$N(CH$_3$), CH$_3$CH$_2$CH$_2$CH(CH$_3$)CH(CH$_3$)O, CH$_3$CH$_2$CH$_2$CH$_2$O, CH$_3$CH$_2$CH$_2$N(CH$_3$), (R)—CH$_3$OCH$_2$CH(CH$_3$)O, CF$_3$CH$_2$N(CH$_3$), CH$_3$CH$_2$N(CH$_3$), ((CH$_3$)$_3$C)$_2$CHO, (CH$_3$CH$_2$)$_2$CHN(CH$_3$), (CH$_3$)$_2$CHN(CH$_3$), CH$_3$CH$_2$OCH$_2$CH(CH$_3$)O, (CH$_3$)$_3$CCH$_2$NH, CF$_3$CH(CH$_3$)O, CH$_3$CH$_2$NCH(CH$_3$)$_2$, $_{(R)}$—CF$_3$CH(CH$_3$)N(CH$_3$), (CH$_3$)$_2$CHCH(CH$_3$), CH$_3$CH$_2$(CH$_3$)$_2$CHCH$_2$CH$_2$O, (S)—CH$_3$OCH(CH$_3$)CH$_2$O, HOCH(CH$_3$)$_2$CH$_2$CH$_2$NH, CF$_3$CH$_2$CH$_2$O, CF$_3$CH$_2$CH$_2$CH$_2$O, CF$_3$CH=CHCH$_2$O, or CH$_3$CH$_2$CH$_2$CH$_2$CH$_2$NH.

247. In another embodiment, the present disclosure features a method of any one of embodiments 239 to 246, wherein R$_2$ is halo, CN, amino, OH, C$_1$-C$_6$ alkyl or C$_1$-C$_6$ fluoroalkyl, C$_1$-C$_6$ alkoxy or C$_1$-C$_6$ fluoroalkoxy, C$_3$-C$_{10}$ heterocyclic ring wherein anywhere from 1 to 4 carbon atoms are independently O, S, N, or NR; or a (C$_1$-C$_9$ alkylene)-R$_3$ wherein up to four CH$_2$ units are optionally and independently replaced with O, CO, S, SO, SO$_2$ or NR.

248. In another embodiment, the present disclosure features a method of any one of embodiments 239 to 247, wherein R$_2$ is NH$_2$, or NHCH$_2$CH$_2$CH$_3$.

249. In another embodiment, the present disclosure features a method of any one of embodiments 239 to 248, wherein p is 0.

250. In another embodiment, the present disclosure features a method of any one of embodiments 239 to 248, wherein p is 1.

251. In another embodiment, the present disclosure features a method of any one of embodiments 239 to 250, wherein in the compound of formula IIa-ii-1, one or more hydrogen atoms are replaced by a deuterium atom.

252. In another embodiment, the present disclosure features a method of embodiment 239, wherein the compound of formula IIa-ii-1 or a pharmaceutically acceptable salt thereof is a compound of formula IIa-ii-2

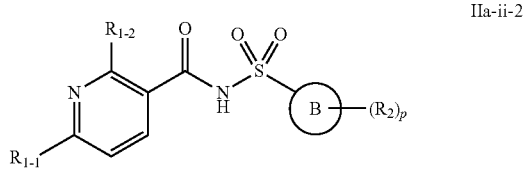
IIa-ii-2 or a pharmaceutically acceptable salt thereof, wherein, independently for each occurrence:
Ring B is a pyridinyl;
R$_{1-2}$ is halo; CN; NRR; C$_1$-C$_6$ alkyl or C$_1$-C$_6$ fluoroalkyl; C$_1$-C$_8$ alkoxy or C$_1$-C$_8$ fluoroalkoxy; C$_2$-C$_6$ alkenyl; C$_2$-C$_6$ alkynyl; or (C$_1$-C$_9$ alkylene)-R$_3$ wherein up to four CH$_2$ units are independently replaced with O, CO, S, SO, SO$_2$ or NR;
R$_{1-1}$ is C$_1$-C$_6$ alkyl or C$_1$-C$_6$ fluoroalkyl, C$_6$-C$_{10}$ aryl; C$_3$-C$_{10}$ heteroaryl or C$_3$-C$_{10}$ heterocyclic ring wherein anywhere from 1 to 4 ring atoms are independently O, S, N, or NR; or C$_3$-C$_{10}$ cycloalkyl;
R$_2$ is halo; NRR; CN; CO$_2$R; C$_1$-C$_6$ alkyl or C$_1$-C$_6$ fluoroalkyl; C$_1$-C$_6$ alkoxy or C$_1$-C$_6$ fluoroalkoxy; C$_2$-C$_6$ alkenyl; C$_2$-C$_6$ alkynyl; C$_6$-C$_{10}$ aryl; C$_3$-C$_{13}$ heteroaryl or heterocyclic ring wherein anywhere from 1 to 4 ring atoms are independently O, S, N, or NR; C$_3$-C$_{10}$ cycloalkyl; or a (C$_1$-C$_9$ alkylene)-R$_3$ wherein up to four CH$_2$ units are optionally and independently replaced with O, CO, S, SO, SO$_2$ or NR;
or two R$_2$ may form a =CH$_2$ or =O group;
R$_3$ is H; CF$_3$; CHF$_2$; OR; C≡CH; CO$_2$R; OH; C$_6$-C$_{10}$ aryl, C$_3$-C$_{10}$ heteroaryl or heterocycloalkyl wherein anywhere from 1 to 4 ring atoms are independently O, S, N, or NR; C$_3$-C$_{10}$ cycloalkyl; NRR, NRCOR, CONRR, CN, halo, or SO$_2$R;
R is independently H; OH; CO$_2$H; CO$_2$C$_1$-C$_6$ alkyl; C$_1$-C$_6$ alkyl; C$_2$-C$_6$ alkenyl; C$_2$-C$_6$ alkynyl; C$_6$-C$_{10}$ aryl; C$_3$-C$_{10}$ heteroaryl or heterocycloalkyl wherein anywhere from 1 to 4 ring atoms are independently O, S, or N; or C$_3$-C$_{10}$ cycloalkyl; and
p is 0, 1, 2, or 3.

253. In another embodiment, the present disclosure features a method of embodiment 252, wherein Ring B is

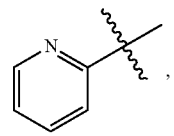

wherein the wavy line indicates point of attachment of Ring B to the sulfonyl (SO$_2$).

254. In another embodiment, the present disclosure features a method of embodiment 252 or 253, wherein R$_{1-2}$ is independently halo, amino, OH, C$_1$-C$_6$ fluoroalkyl, CN, C$_1$-C$_6$ alkyl, C$_2$-C$_6$ alkenyl, C$_2$-C$_6$ alkynyl, C$_1$-C$_8$ alkoxy or C$_1$-C$_8$ fluoroalkoxy, or a (C$_1$-C$_9$ alkylene)-R$_3$ wherein up to four CH$_2$ units are independently replaced with O, CO, S, SO, SO$_2$ or NR.

255. In another embodiment, the present disclosure features a method of any one of embodiments 252 to 254, wherein R$_{1-1}$ is C$_1$-C$_6$ alkyl or C$_1$-C$_6$ fluoroalkyl, a phenyl, mono-C$_4$-C$_6$ heterocyclic ring, 1,2,3,4-tetrahydroisoquinoline, pyridyl, pyrimidine, indole, aza-indole, pyrazole, pyrrole, or thiophene ring.

256. In another embodiment, the present disclosure features a method of any one of embodiments 252 to 255, wherein R$_{1-1}$ is tert-butyl,

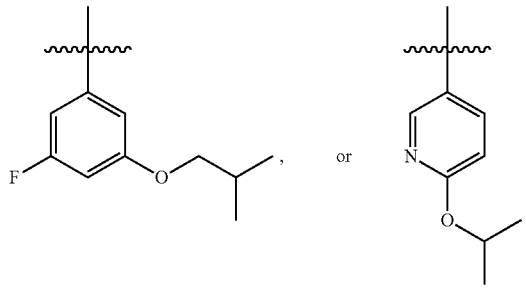

257. In another embodiment, the present disclosure features a method of any one of embodiments 252 to 256, wherein R$_{1-1}$ is

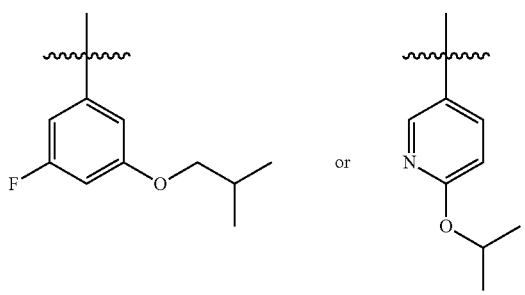

or

258. In another embodiment, the present disclosure features a method of any one of embodiments 252 to 257, wherein $R_{1-2}$ is $CHF_2CH_2(CH_3)N-$, $(CH_3)_2CHCH_2CH2O-$, $(CH_3)_3CCH_2CH_2O-$, $(CH_3)_3COCH_2CH_2O-$, $(CH_3)_2CHO-$, $CHF_2CHF_2CH(CH_3)O-$, $-CF_3$, $(CH_3CH_2)_2N-$, $CF_3CH_2CH(CH_3)O-$, $CH_3O-$, $CH_3(CH_2)_4O-$, $CH_3CH_2CH(CH_3)CH(CH_3)O-$, $CH_3CH_2OCH_2CH_2O-$, $CH_3CH_2NCH(CH_3)_2$, $(CH_3)_3CH_2O-$, (R)—$CH_3NCH(CH_3)(CF_3)$, $CH_3OCH_2CH(CH_2CH_3)O-$, $(CH_3)_2N-$, (S)—$CH_3OCH_2CH(CH_3)O-$, $CH_3O(CH_2)_3O-$, $CH_3OC(CH_3)_2(CH_2)_2O$, $CH_3OCH_2CH(CH_3)O$, $CH_3CH(CH_3)CH_2CH(CH_3)O-$, $(CH_3)_3CCH(CH_3)O$, $((CH_3)_2CH)_2CHO-$, $CH_3CH_2CH_2O$, $CH_3CH=CHCH_2O-$, (S)—$CH_3CH_2CH(CH_3)O-$, $CH_3CH_2O$, $(CH_3)_2CHNCH_3$, $(CH_3)_3CCH_2O$, $(CF_3)_2CHO-$, $(CH_3)_3CCH(CH_2CH_3)O$, $CH_3C≡CCH_2CH_2O$, $(CH_3)_3CCH_2CH(CH_3)O-$, $(CH_3)_2C=C(CH_3)$, $CHF_2CH_2O-$, $CH_3CH_2CH_2NH$, $(CH_3)_2CHCH(CH_2CH_3)O$, $((CH_3)_2CH)_2N$, $CH_2=CHCH(CH_3)O$, $CH_2=CHCH_2O-$, $CH_3CH_2C(CH_3)_2O$, $(CH_3CH_2)_2CHO-$, $CF_3CH_2O$, $CH_3C(=CH_2)CH_2O$, $(CH_3)_3CCH_2CH_2NH$, $CH_3OCH_2C(CH_3)_2O$, $(CH_3)_3CCH_2N(CH_3)$, $(CH_3)_2CHCH(CH_3)NH$, $(CH_3)_2CHO(CH_2)_2O$, $CH_3CH_2CH_2CH(CH_3)O$, $CH_3CF_2CH_2O$, $(CH_3)_3CNH$, (R)—$CH_3CH_2CH(CH_3)O$, $CH_3OCH_2CH_2O$, $(CH_3)_2CHCH_2N(CH_3)$, $CH_3CH_2CH_2CH(CH_3)CH(CH_3)O$, $CH_3CH_2CH_2CH_2O$, $CH_3CH_2CH_2N(CH_3)$, (R)—$CH_3OCH_2CH(CH_3)O$, $CF_3CH_2N(CH_3)$, $CH_3CH_2N(CH_3)$, $((CH_3)_3C)_2CHO$, $(CH_3CH_2)_2CHN(CH_3)$, $(CH_3)_2CHN(CH_3)$, $CH_3CH_2OCH_2CH(CH_3)O$, $(CH_3)_3CCH_2NH$, $CF_3CH(CH_3)O$, $CH_3CH_2NCH(CH_3)_2$, $(R)$—$CF_3CH(CH_3)N(CH_3)$, $(CH_3)_2CHCH(CH_3)$, $CH_3CH_2(CH_3)_2CHCH_2O$, (S)—$CH_3OCH(CH_3)CH_2O$, $HOCH(CH_3)_2CH_2CH_2NH$, $CF_3CH_2CH_2O$, $CF_3CH_2CH_2CH_2O$, $CF_3CH=CHCH_2O$, or $CH_3CH_2CH_2CH_2CH_2NH$.

259. In another embodiment, the present disclosure features a method of any one of embodiments 252 to 258, wherein $R_2$ is halo, CN, amino, OH, $C_1$-$C_6$ alkyl or $C_1$-$C_6$ fluoroalkyl, $C_1$-$C_6$ alkoxy or $C_1$-$C_6$ fluoroalkoxy, $C_3$-$C_{10}$ heterocyclic ring wherein anywhere from 1 to 4 carbon atoms are independently O, S, N, or NR; or a ($C_1$-$C_9$ alkylene)-$R_3$ wherein up to four $CH_2$ units are optionally and independently replaced with O, CO, S, SO, $SO_2$ or NR.

260. In another embodiment, the present disclosure features a method of any one of embodiments 252 to 259, wherein $R_2$ is $NH_2$, or $NHCH_2CH_2CH_3$.

261. In another embodiment, the present disclosure features a method of any one of embodiments 252 to 260, wherein p is 0.

262. In another embodiment, the present disclosure features a method of any one of embodiments 252 to 260, wherein p is 1.

263. In another embodiment, the present disclosure features a method of any one of embodiments 252 to 262, wherein in the compound of formula IIa-ii-2, one or more hydrogen atoms are replaced by a deuterium atom.

264. In another embodiment, the present disclosure features a method of any one of embodiments 138-263, further comprising administering to the patient one or more additional therapeutic agent(s) prior to, concurrent with, or subsequent to 1) the compound of any one of embodiments 1 to or a pharmaceutically acceptable salt thereof, or 2) the pharmaceutical composition comprising a pharmaceutically acceptable excipient and a compound of formula II or a pharmaceutically acceptable salt thereof.

265. In another embodiment, the present disclosure features a method of embodiment 264, wherein the additional therapeutic agent is selected from a mucolytic agent, bronchodilator, an antibiotic, an anti-infective agent, a CFTR modulator, or an anti-inflammatory agent.

266. In another embodiment, the present disclosure features a method of embodiment 264, wherein the additional therapeutic agent is a CFTR modulator.

267. In another embodiment, the present disclosure features a method of embodiment 264, wherein the additional therapeutic agent is a CFTR corrector.

268. In another embodiment, the present disclosure features a method of embodiment 264, wherein the additional therapeutic agent is

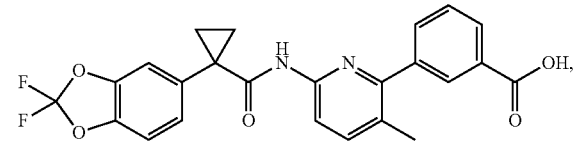 [SMILES: Cc1ccc(NC(=O)C2(c3ccc4c(c3)OC(F)(F)O4)CC2)nc1-c1cccc(C(=O)O)c1]

or a pharmaceutically acceptable salt thereof.

269. In another embodiment, the present disclosure features a method of embodiment 264, wherein the additional therapeutic agent is

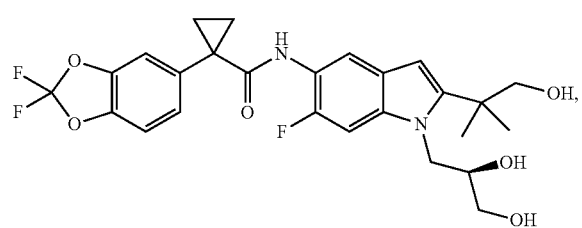 [SMILES: CC(C)(CO)c1cc2cc(NC(=O)C3(c4ccc5c(c4)OC(F)(F)O5)CC3)c(F)cc2n1C[C@@H](O)CO]

or a pharmaceutically acceptable salt thereof.

270. In another embodiment, the present disclosure features a method of embodiment 264, wherein the additional therapeutic agent is

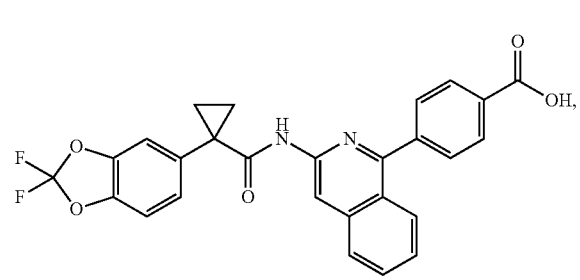 [SMILES: O=C(O)c1ccc(-c2nc(NC(=O)C3(c4ccc5c(c4)OC(F)(F)O5)CC3)cc3ccccc23)cc1]

or a pharmaceutically acceptable salt thereof.

271. In another embodiment, the present disclosure features a method of embodiment 264, wherein the additional therapeutic agent is a CFTR potentiator.
272. In another embodiment, the present disclosure features a method of embodiment 264, wherein the additional therapeutic agent is

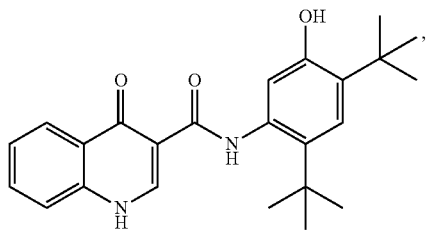

or a pharmaceutically acceptable salt thereof.
273. In another embodiment, the present disclosure features a method of any one of embodiments 138 to 272, wherein the patient is homozygous in the ΔF508 CFTR mutation.
274. In another embodiment, the present disclosure features a method of any one of embodiments 138 to 272, wherein the patient is heterozygous in the ΔF508 CFTR mutation.
275. In another embodiment, the present disclosure features a method of treating cystic fibrosis in a patient comprising administering to the patient in need thereof an effective amount of
  1) the compound of any one of embodiments 1 to 123 or a pharmaceutically acceptable salt thereof, or
  2) the pharmaceutical composition of embodiment 124.
276. In another embodiment, the present disclosure features a method of embodiment 275, further comprising administering to the patient one or more additional therapeutic agent(s) prior to, concurrent with, or subsequent to the compound of any one of embodiments 1 to 123 or the pharmaceutical composition of embodiment 124.
277. In another embodiment, the present disclosure features a method of embodiment 275, wherein the additional therapeutic agent is selected from a mucolytic agent, bronchodilator, an antibiotic, an anti-infective agent, a CFTR modulator, or an anti-inflammatory agent.
278. In another embodiment, the present disclosure features a method of embodiment 275, wherein the additional therapeutic agent is a CFTR modulator.
279. In another embodiment, the present disclosure features a method of embodiment 275, wherein the additional therapeutic agent is a CFTR corrector.
280. In another embodiment, the present disclosure features a method of embodiment 275, wherein the additional therapeutic agent is

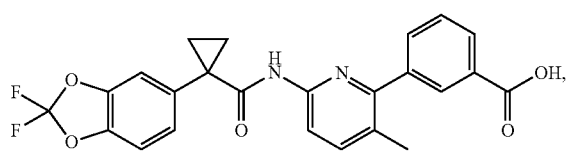 [SMILES: Cc1ccc(NC(=O)C2(c3ccc4c(c3)OC(F)(F)O4)CC2)nc1-c1cccc(C(=O)O)c1]

or a pharmaceutically acceptable salt thereof.
281. In another embodiment, the present disclosure features a method of embodiment 275, wherein the additional therapeutic agent is

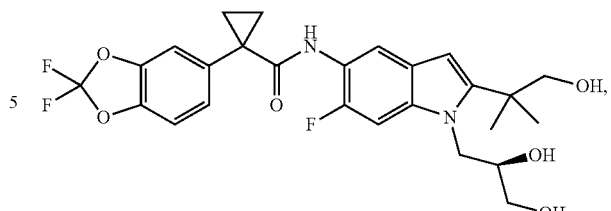

or a pharmaceutically acceptable salt thereof.
282. In another embodiment, the present disclosure features a method of embodiment 275, wherein the additional therapeutic agent is

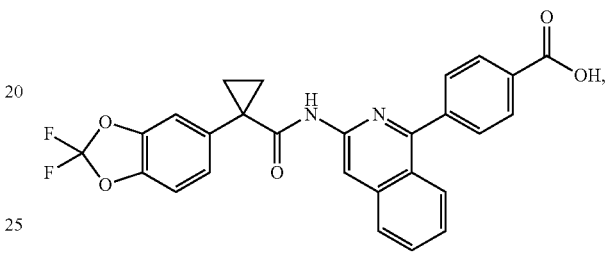

or a pharmaceutically acceptable salt thereof.
283. In another embodiment, the present disclosure features a method of embodiment 275, wherein the additional therapeutic agent is a CFTR potentiator.
284. In another embodiment, the present disclosure features a method of embodiment 275, wherein the additional therapeutic agent is

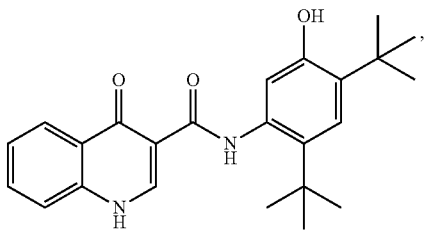

or a pharmaceutically acceptable salt thereof.
285. In another embodiment, the present disclosure features a method of any one of embodiments 275 to 284, wherein the patient is homozygous in the ΔF508 CFTR mutation.
286. In another embodiment, the present disclosure features a method of any one of embodiments 275 to 284, wherein the patient is heterozygous in the ΔF508 CFTR mutation.
289. In another embodiment, the present disclosure features a kit comprising
  1) the compound of any one of embodiments 1 to 123 or a pharmaceutically acceptable salt thereof, or
  2) the pharmaceutical composition of any one of embodiments 124 to 137, and instructions for use thereof.
290. In another embodiment, the present disclosure features the kit of embodiment 289, further comprising one or more additional therapeutic agent(s).
291. In another embodiment, the present disclosure features the kit of embodiment 290, wherein the additional therapeutic agent is selected from a mucolytic agent, bronchodilator, an antibiotic, an anti-infective agent, a CFTR modulator, or an anti-inflammatory agent.

292. In another embodiment, the present disclosure features the kit of embodiment 290, wherein the additional therapeutic agent is a CFTR modulator.

293. In another embodiment, the present disclosure features the kit of embodiment 290, wherein the additional therapeutic agent is a CFTR corrector.

294. In another embodiment, the present disclosure features the kit of embodiment 290, wherein the additional therapeutic agent is

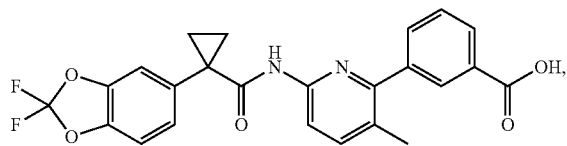 [SMILES: Cc1ccc(NC(=O)C2(c3ccc4c(c3)OC(F)(F)O4)CC2)nc1-c1cccc(C(=O)O)c1]

or a pharmaceutically acceptable salt thereof.

295. In another embodiment, the present disclosure features the kit of embodiment 290, wherein the additional therapeutic agent is

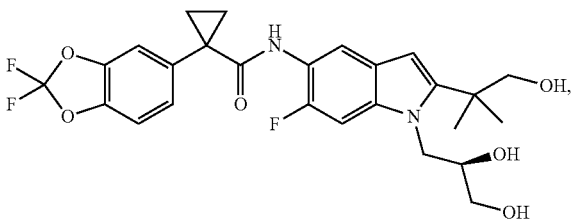 [SMILES: CC(C)(CO)c1cc2cc(NC(=O)C3(c4ccc5c(c4)OC(F)(F)O5)CC3)c(F)cc2n1C[C@@H](O)CO]

or a pharmaceutically acceptable salt thereof.

296. In another embodiment, the present disclosure features the kit of embodiment 290, wherein the additional therapeutic agent is

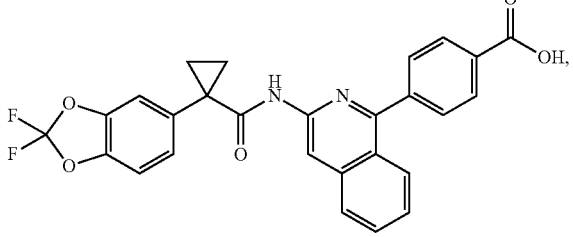

or a pharmaceutically acceptable salt thereof.

297. In another embodiment, the present disclosure features the kit of embodiment 290, wherein the additional therapeutic agent is a CFTR potentiator.

298. In another embodiment, the present disclosure features the kit of embodiment 290, wherein the additional therapeutic agent is

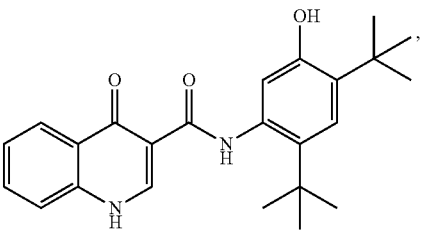

or a pharmaceutically acceptable salt thereof.

299. In another embodiment, the present disclosure features the kit of embodiment 290, wherein the additional therapeutic agents are a CFTR corrector and a CFTR potentiator.

300. In another embodiment, the present disclosure features the kit of embodiment 290, wherein the additional therapeutic agents are

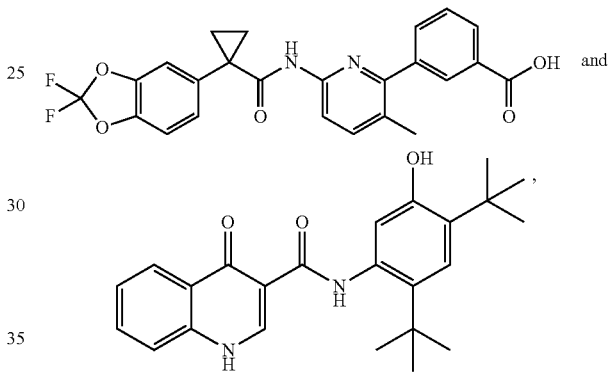

pharmaceutically acceptable salts thereof.

301. In another embodiment, the present disclosure features the kit of embodiment 290, wherein the additional therapeutic agents are

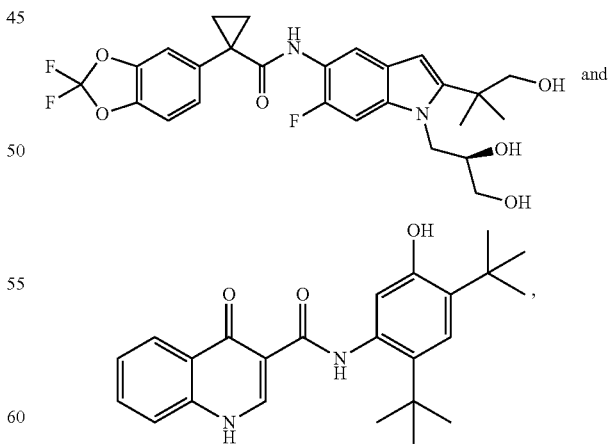

pharmaceutically acceptable salts thereof.

302. In another embodiment, the present disclosure features the kit of embodiment 290, wherein the additional therapeutic agents are

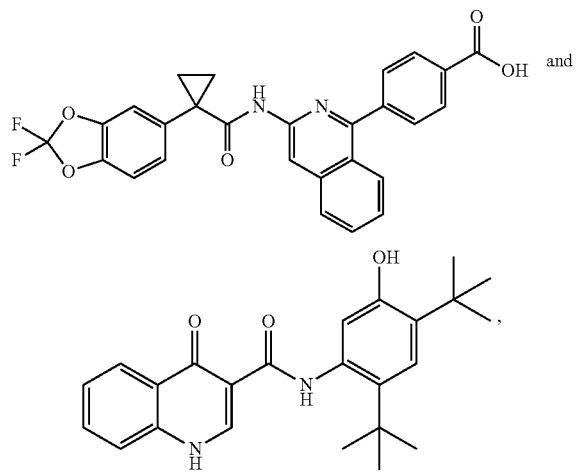

pharmaceutically acceptable salts thereof.

303. In another embodiment, the present disclosure features the kit of any one of embodiments 289 to 302, wherein the compound of any one of embodiments 1 to 123 or the pharmaceutical composition of any one of embodiments 124 to 137 and the one or more additional therapeutic agent(s) are in separate containers.

304. In another embodiment, the present disclosure features the kit of any one of embodiments 289 to 303, wherein the compound of any one of embodiments 1 to 123 or the pharmaceutical composition of any one of embodiments 124 to 137 and the one or more additional therapeutic agent(s) are in the same container.

305. In another embodiment, the present disclosure features the kit of embodiment 303 or 304, wherein the container is a bottle, vial, or blister pack, or combination thereof.

Methods of Preparing Compounds of Formula I

Compounds of the disclosure may be prepared by known methods and as illustrated in Schemes I-III. $R_1$, $R_2$, n, p, and rings A and B are as defined in the Specification unless noted otherwise below for each individual scheme.

Scheme I

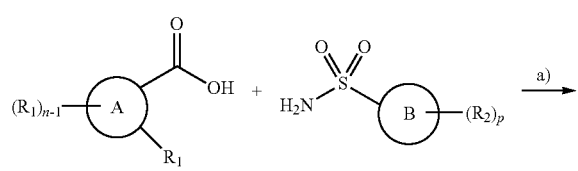

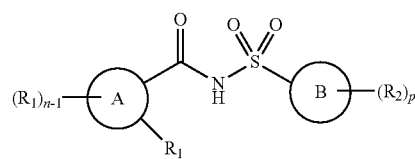

a) HATU or CDI, $Et_3N$ or $(i-Pr)_2NEt$ or $K_2CO_3$ or NaH, DMF or $CH_2Cl_2$

Scheme II

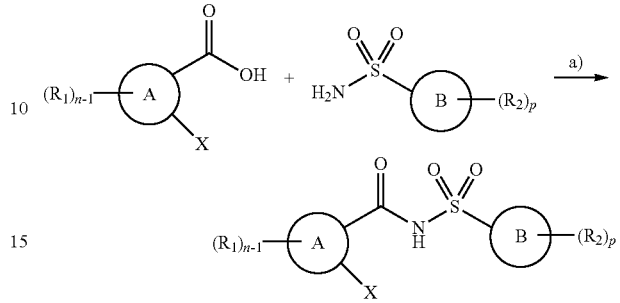

a) X=halogen (F or Cl or Br), HATU or CDI, $Et_3N$ or $(i-Pr)_2NEt$ or $K_2CO_3$ or NaH, DMF or $CH_2Cl_2$ Scheme III

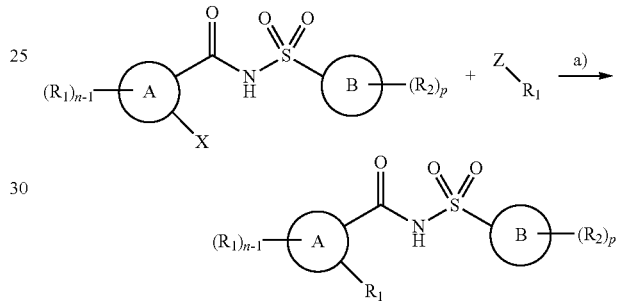

a) X=halogen (F or Cl or Br), Z=H: NaH or $Cs_2CO_3$ or $K_2CO_3$ or DIEA or $Et_3N$, CsF, DMF or DMSO or dioxane or NMP.

Pharmaceutically Acceptable Salts and Prodrugs

It will also be appreciated that certain compounds of the compositions of the present disclosure can exist in free form for treatment, or where appropriate, as a pharmaceutically acceptable derivative or a prodrug thereof. According to the present disclosure, a pharmaceutically acceptable derivative or a prodrug includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this disclosure that, upon administration to a recipient, is capable of providing, either directly or indirectly, a compound of this disclosure or an inhibitorily active metabolite or residue thereof.

Pharmaceutically acceptable salts are well known in the art. For example, S. M. Berge, et al. describe pharmaceutically acceptable salts in detail in *J. Pharmaceutical Sciences*, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_1-C_4alkyl)_4$ salts. This disclosure also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Pharmaceutical Compositions
Pharmaceutically Acceptable Vehicle, Adjuvant, or Carrier In one aspect, the present disclosure features a pharmaceutical composition comprising a compound of formulas I to IIa-ii-2 or pharmaceutically acceptable salt or prodrug thereof, and a pharmaceutically acceptable vehicle, adjuvant, or carrier.

As described above, the pharmaceutical compositions of the present disclosure additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington: *The Science and Practice of Pharmacy,* 21st edition, 2005, ed. D. B. Troy, Lippincott Williams & Wilkins, Philadelphia, and *Encyclopedia of Pharmaceutical Technology,* eds. J. Swarbrick and J. C. Boylan, 1988-1999, Marcel Dekker, New York, the contents of each of which is incorporated by reference herein, disclose various carriers used in formulating pharmaceutically acceptable compositions and known techniques for the preparation thereof. Except insofar as any conventional carrier medium is incompatible with the compounds of the disclosure, such as by producing any undesirable biological effect or otherwise interacting in a deleterious manner with any other component(s) of the pharmaceutically acceptable composition, its use is contemplated to be within the scope of this disclosure. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Additional Therapeutic Agent(s)

In another embodiment, the pharmaceutical compositions of the present disclosure further comprise one or more additional therapeutic agent(s). In one embodiment, the additional therapeutic agent is a CFTR modulator. In one embodiment, the additional therapeutic agent is a CFTR corrector. In one embodiment, the additional therapeutic agent is a CFTR potentiator. In another embodiment, the pharmaceutical composition comprises a compound of Formulas I to IIa-ii-2, or pharmaceutically acceptable salt thereof and one or more of the following additional therapeutic agents.

In another embodiment, the additional therapeutic agent is selected from:

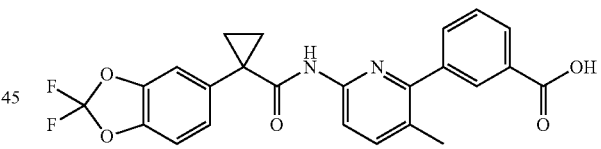

3-(6-(1-(2,2-difluorobenzo[d][1,3]dioxol-5-yl) cyclopropanecarboxamido)-3-methylpyridin-2-yl)benzoic acid, or pharmaceutically acceptable salt thereof;

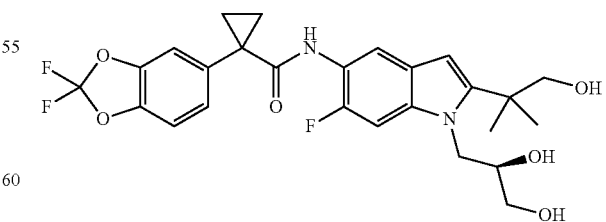

(R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-yl)cyclopropanecarboxamide, or a pharmaceutically acceptable salt thereof; or

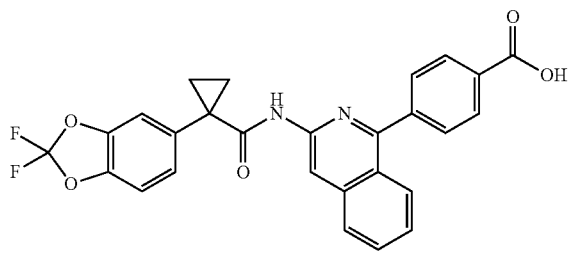 [SMILES: O=C(O)c1ccc(-c2nc(NC(=O)C3(c4ccc5c(c4)OC(F)(F)O5)CC3)cc3ccccc23)cc1]

4-(3-(1-(2,2-difluorobenzo[d][1,3]dioxol-5-yl)cyclopropanecarboxamido) isoquinolin-1-yl)benzoic acid, or pharmaceutically acceptable salt thereof.

In another embodiment, the pharmaceutical composition of the present disclosure comprises a compound of formulas I to IIa-ii-2, or pharmaceutically acceptable salt thereof and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises a compound of Table 1, or pharmaceutically acceptable salt thereof and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises a compound of formulas I to IIa-ii-2, or pharmaceutically acceptable salt thereof and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises a compound of Table 1, or pharmaceutically acceptable salt thereof and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises a compound of formulas I to IIa-ii-2, or pharmaceutically acceptable salt thereof and 4-(3-(1-(2,2-difluorobenzo[d][1,3]dioxol-5-yl)cyclopropanecarboxamido) isoquinolin-1-yl)benzoic acid, or pharmaceutically acceptable salt thereof.

In another embodiment, the pharmaceutical composition of the present disclosure comprises a compound of Table 1, or pharmaceutically acceptable salt thereof and 4-(3-(1-(2,2-difluorobenzo[d][1,3]dioxol-5-yl)cyclopropanecarboxamido) isoquinolin-1-yl)benzoic acid, or pharmaceutically acceptable salt thereof.

In another embodiment, the pharmaceutical composition of the present disclosure comprises a compound of formulas I to IIa-ii-2, or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises a compound of Table 1, or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-2-[2,2-difluoroethyl(methyl)amino]-6-(3-fluoro-5-isobutoxy-phenyl)pyridine-3-carboxamide (Compound 1), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-isopentyloxy-pyridine-3-carboxamide (Compound 2), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl) cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-2-(3,3-dimethylbutoxy)-6-(3-fluoro-5-isobutoxy-phenyl)pyridine-3-carboxamide (Compound 3), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl) cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-2-(2-tert-butoxyethoxy)-6-(3-fluoro-5-isobutoxy-phenyl)pyridine-3-carboxamide (Compound 4), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl) cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-isopropoxy-pyridine-3-carboxamide (Compound 5), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-

1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-(2,2,3,3-tetrafluoro-1-methyl-propoxy)pyridine-3-carboxamide (Compound 6), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-5-(3-fluoro-5-isobutoxy-phenyl)-2-(trifluoromethyl)imidazo[1,2-a]pyridine-8-carboxamide (Compound 7), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-(3,3,3-trifluoro-1-methyl-propoxy)pyridine-3-carboxamide (Compound 9), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-methoxy-pyridine-3-carboxamide (Compound 10), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-pentoxy-pyridine-3-carboxamide (Compound 11), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-2-(1,2-dimethylbutoxy)-6-(3-fluoro-5-isobutoxy-phenyl)pyridine-3-carboxamide (Compound 12), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-2-(2-ethoxyethoxy)-6-(3-fluoro-5-isobutoxy-phenyl)pyridine-3-carboxamide (Compound 13), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-2-[ethyl(isopropyl)amino]-6-(6-isopropoxy-3-pyridyl)pyridine-3-carboxamide (Compound 14), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-tert-butyl-2-(2,2-dimethylpropoxy)pyridine-3-carboxamide (Compound 15), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises 2-[ethyl(isopropyl)amino]-6-(3-fluoro-5-isobutoxy-phenyl)-N-(1H-pyrazol-5-ylsulfonyl)pyridine-3-carboxamide (Compound 16), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol- 5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-[methyl-[(1S)-2,2,2-trifluoro-1-methyl-ethyl]amino]pyridine-3-carboxamide (Compound 17), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-[1-(methoxymethyl)propoxy]pyridine-3-carboxamide (Compound 18), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-2-(dimethylamino)-6-(3-fluoro-5-isobutoxy-phenyl)pyridine-3-carboxamide (Compound 19), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl) cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-[(1S)-2-methoxy-1-methyl-ethoxy]pyridine-3-carboxamide (Compound 20), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-(3-methoxypropoxy)pyridine-3-carboxamide (Compound 21), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-(3-methoxy-3-methyl-butoxy)pyridine-3-carboxamide (Compound 22), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-2-(1,3-dimethylbutoxy)-6-(3-fluoro-5-isobutoxy-phenyl)pyridine-3-carboxamide (Compound 24), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-(1,2,2-trimethylpropoxy)pyridine-3-carboxamide (Compound 25), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-(1-isopropyl-2-methyl-propoxy)pyridine-3-carboxamide (Compound 26), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-propoxy-pyridine-3-carboxamide (Compound 27), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl) cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-2-[(E)-but-2-enoxy]-6-(3-fluoro-5-isobutoxy-phenyl)pyridine-3-carboxamide (Compound 28), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-[(1S)-1-methylpropoxy]pyridine-3-carboxamide (Compound 29), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-2-ethoxy-6-(3-fluoro-5-isobutoxy-phenyl)pyridine-3-carboxamide (Compound 30), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-[isopropyl(methyl)amino]pyridine-3-carboxamide (Compound 31), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-2-(2,2-dimethylpropoxy)-6-(3-fluoro-5-isobutoxy-phenyl)pyridine-3-carboxamide (Compound 32), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-[2,2,2-trifluoro-1-(trifluoromethyl)ethoxy]pyridine-3-carboxamide (Compound 33), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-2-(diethylamino)-6-(6-isopropoxy-3-pyridyl)pyridine-3-carboxamide (Compound 34), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-pent-3-ynoxy-pyridine-3-carboxamide (Compound 35), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-(1,3,3-trimethylbutoxy)pyridine-3-carboxamide (Compound 36), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-2-(1,2-dimethylprop-1-enyl)-6-(3-fluoro-5-isobutoxy-phenyl)pyridine-3-carboxamide (Compound 37), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises 6-(3-fluoro-5-isobutoxy-phenyl)-2-(propylamino)-N-[[6-(propylamino)-2-pyridyl]sulfonyl]pyridine-3-carboxamide (Compound 39), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-2-(1-ethyl-2-methyl-propoxy)-6-(3-fluoro-5-isobutoxy-phenyl)pyridine-3-carboxamide (Compound 40), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-2-(diisopropylamino)-6-(3-fluoro-5-isobutoxy-phenyl)pyridine-3-carboxamide (Compound 41), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-(1-methylallyloxy)pyridine-3-carboxamide (Compound 42), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl) cyclopropanecarboxamido) isoquinolin-1-yl)benzoic acid, or pharmaceutically acceptable salts thereof.

In another embodiment, the pharmaceutical composition of the present disclosure comprises 2-allyloxy-N-[(6-amino-2-pyridyl)sulfonyl]-6-(3-fluoro-5-isobutoxy-phenyl)pyridine-3-carboxamide (Compound 43), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl) cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-2-(1,1-dimethylpropoxy)-6-(3-fluoro-5-isobutoxy-phenyl)pyridine-3-carboxamide (Compound 44), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises 2-(diethylamino)-6-(3-fluoro-5-isobutoxy-phenyl)-N-(1H-pyrazol-5-ylsulfonyl)pyridine-3-carboxamide (Compound 46), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl) cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-2-(1-ethylpropoxy)-6-(3-fluoro-5-isobutoxy-phenyl)pyridine-3-carboxamide (Compound 47), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl) cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-(2-methylallyloxy)pyridine-3-carboxamide (Compound 49), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl) cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-(2-methoxy-1,1-dimethyl-ethoxy)pyridine-3-carboxamide (Compound 51), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-2-[2,2-dimethylpropyl(methyl)amino]-6-(3-fluoro-5-isobutoxy-phenyl)pyridine-3-carboxamide (Compound 52), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol- 5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-2-(diethylamino)-6-(3-fluoro-5-isobutoxy-phenyl)pyridine-3-carboxamide (Compound 53), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-(2-isopropoxyethoxy)pyridine-3-carboxamide (Compound 55), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-(1-methylbutoxy)pyridine-3-carboxamide (Compound 56), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-2-(2,2-difluoropropoxy)-6-(3-fluoro-5-isobutoxy-phenyl)pyridine-3-carboxamide (Compound 57), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-2-(tert-butylamino)-6-(3-fluoro-5-isobutoxy-phenyl)pyridine-3-carboxamide (Compound 58), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl) cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-[(1R)-1-methylpropoxy]pyridine-3-carboxamide (Compound 59), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-(2-methoxyethoxy)pyridine-3-carboxamide (Compound 60), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-[isobutyl(methyl)amino]pyridine-3-carboxamide (Compound 61), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-2-(1,2-dimethylpentoxy)-6-(3-fluoro-5-isobutoxy-phenyl)pyridine-3-carboxamide (Compound 62), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-2-butoxy-6-(3-fluoro-5-isobutoxy-phenyl)pyridine-3-carboxamide (Compound 63), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)

cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-[methyl(propyl)amino]pyridine-3-carboxamide (Compound 64), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-[(1R)-2-methoxy-1-methyl-ethoxy]pyridine-3-carboxamide (Compound 65), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-[methyl(2,2,2-trifluoroethyl)amino]pyridine-3-carboxamide (Compound 66), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-2-[ethyl(methyl)amino]-6-(3-fluoro-5-isobutoxy-phenyl)pyridine-3-carboxamide (Compound 67), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-(1-isopropyl-2,2-dimethyl-propoxy)pyridine-3-carboxamide (Compound 68), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-2-[1-ethylpropyl(methyl)amino]-6-(3-fluoro-5-isobutoxy-phenyl)pyridine-3-carboxamide (Compound 69), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-2-(2-ethoxy-1-methyl-ethoxy)-6-(3-fluoro-5-isobutoxy-phenyl)pyridine-3-carboxamide (Compound 71), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-(2,2,2-trifluoro-1-methyl-ethoxy)pyridine-3-carboxamide (Compound 73), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-2-[ethyl(isopropyl)amino]-6-(3-fluoro-5-isobutoxy-phenyl)pyridine-3-carboxamide (Compound 74), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-[methyl-[(1R)-2,2,2-trifluoro-1-methyl-ethyl]amino]pyridine-3-carboxamide (Compound 75), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-2-(1,2-dimethylpropyl)-6-(3-fluoro-5-isobutoxy-phenyl)pyridine-3-carboxamide (Compound 76), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-2-(3,3-dimethylpentoxy)-6-(3-fluoro-5-isobutoxy-phenyl)pyridine-3-carboxamide (Compound 77), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-[(2S)-2-methoxypropoxy]pyridine-3-carboxamide (Compound 78), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises 6-(3-fluoro-5-isobutoxy-phenyl)-2-[isopropyl(methyl)amino]-N-(1H-pyrazol-5-yl-sulfonyl)pyridine-3-carboxamide (Compound 79), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-(3,3,3-trifluoropropoxy)pyridine-3-carboxamide (Compound 81), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-(4,4,4-trifluorobutoxy)pyridine-3-carboxamide (Compound 82), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In another embodiment, the pharmaceutical composition of the present disclosure comprises N-[(6-amino-2-pyridyl)sulfonyl]-6-(3-fluoro-5-isobutoxy-phenyl)-2-[(E)-4,4,4-trifluorobut-2-enoxy]pyridine-3-carboxamide (Compound 83), or pharmaceutically acceptable salt thereof; and a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or 4-(3-(1-(2,2-difluorobenzo[d][1,3]dioxol-5-yl)cyclopropanecarboxamido) isoquinolin-1-yl)benzoic acid, or pharmaceutically acceptable salts thereof.

In one embodiment, the above recited pharmaceutical compositions contain a pharmaceutically acceptable prodrug of the compound of the present disclosure.

In another embodiment, the pharmaceutical composition of the present disclosure comprises a compound of formulas I to IIa-ii-2, or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises a compound of Table 1, or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-[2,2-difluoroethyl(methyl)amino]-6-(3-fluoro-5-isobutoxy-phenyl)pyridine-3-carboxamide (Compound 1), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-isopentyloxy-pyridine-3-carboxamide (Compound 2), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(3,3-dimethylbutoxy)-6-(3-fluoro-5-isobutoxy-phenyl)pyridine-3-carboxamide (Compound 3), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(2-tert-butoxyethoxy)-6-(3-fluoro-5-isobutoxy-phenyl)pyridine-3-carboxamide (Compound 4), or pharmaceutically acceptable salt thereof; and 3-(6-(1-(2,2-difluorobenzo[d][1,3]dioxol-5-yl)cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-isopropoxy-pyridine-3-carboxamide (Compound 5), or pharmaceutically acceptable salt thereof; and 3-(6-(1-(2,2-difluorobenzo[d][1,3]dioxol-5-yl)cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(2,2,3,3-tetrafluoro-1-methyl-propoxy)pyridine-3-carboxamide (Compound 6), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-5-(3-fluoro-5-isobutoxy-phenyl)-2-(trifluoromethyl)imidazo[1,2-a]pyridine-8-carboxamide (Compound 7), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(3,3,3-trifluoro-1-methyl-propoxy)pyridine-3-carboxamide (Compound 9), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-methoxy-pyridine-3-carboxamide (Compound 10), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-pentoxy-pyridine-3-carboxamide (Compound 11), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(1,2-dimethylbutoxy)-6-(3-fluoro-5-isobutoxy-phenyl)pyridine-3-carboxamide (Compound 12), or pharmaceutically acceptable salt thereof; and 3-(6-(1-(2,2-difluorobenzo[d][1,3]dioxol-5-yl)cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(2-ethoxyethoxy)-6-(3-fluoro-5-isobutoxy-phenyl)pyridine-3-carboxamide (Compound 13), or pharmaceutically acceptable salt thereof; and 3-(6-(1-(2,2-difluorobenzo[d][1,3]dioxol-5-yl)cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-[ethyl(isopropyl)amino]-6-(6-isopropoxy-3-pyridyl)pyridine-3-carboxamide (Compound 14), or pharmaceutically acceptable salt thereof; and 3-(6-(1-(2,2-difluorobenzo[d][1,3]dioxol-5-yl)cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-tert-butyl-2-(2,2-dimethylpropoxy)pyridine-3-carboxamide (Compound 15), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises 2-[ethyl(isopropyl)amino]-6-(3-fluoro-5-isobutoxy-phenyl)-N-(1H-pyrazol-5-ylsulfonyl)pyridine-3-carboxamide (Compound 16), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[methyl-[(1S)-2,2,2-trifluoro-1-methyl-ethyl]amino]pyridine-3-carboxamide (Compound 17), or pharmaceutically acceptable salt thereof; and 3-(6-(1-(2,2-difluorobenzo[d][1,3]dioxol-5-yl)cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[1-(methoxymethyl)propoxy]pyridine-3-carboxamide (Compound 18), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(dimethylamino)-6-(3-fluoro-5-isobutoxy-phenyl)pyridine-3-carboxamide (Compound 19), or pharmaceutically acceptable salt thereof; and 3-(6-(1-(2,2-difluorobenzo[d][1,3]dioxol-5-yl)cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[(1S)-2-methoxy-1-methyl-ethoxy]pyridine-3-carboxamide (Compound 20), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(3-methoxypropoxy)pyridine-3-carboxamide (Compound 21), or pharmaceutically acceptable salt thereof; and 3-(6-(1-(2,2-difluorobenzo[d][1,3]dioxol-5-yl)cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)

sulfonyl]-6-(3-fluoro-5-isobutoxy-phenyl)-2-(3-methoxy-3-methyl-butoxy)pyridine-3-carboxamide (Compound 22), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(1,3-dimethylbutoxy)-6-(3-fluoro-5-isobutoxy-phenyl)pyridine-3-carboxamide (Compound 24), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(1,2,2-trimethylpropoxy)pyridine-3-carboxamide (Compound 25), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(1-isopropyl-2-methyl-propoxy)pyridine-3-carboxamide (Compound 26), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-propoxy-pyridine-3-carboxamide (Compound 27), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-[(E)-but-2-enoxy]-6-(3-fluoro-5-isobutoxy-phenyl)pyridine-3-carboxamide (Compound 28), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[(1S)-1-methylpropoxy]pyridine-3-carboxamide (Compound 29), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-ethoxy-6-(3-fluoro-5-isobutoxy-phenyl)pyridine-3-carboxamide (Compound 30), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[isopropyl(methyl)amino]pyridine-3-carboxamide (Compound 31), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(2,2-dimethylpropoxy)-6-(3-fluoro-5-isobutoxy-phenyl)pyridine-3-carboxamide (Compound 32), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[2,2,2-trifluoro-1-(trifluoromethyl)ethoxy]pyridine-3-carboxamide (Compound 33), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(diethylamino)-6-(6-isopropoxy-3-pyridyl)pyridine-3-carboxamide (Compound 34), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-pent-3-ynoxy-pyridine-3-carboxamide (Compound 35), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(1,3,3-trimethylbutoxy)pyridine-3-carboxamide (Compound 36), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(1,2-dimethylprop-1-enyl)-6-(3-fluoro-5-isobutoxy-phenyl)pyridine-3-carboxamide (Compound 37), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises 6-(3-fluoro-5-isobutoxy-phenyl)-2-(propylamino)-N-[[6-(propylamino)-2-pyridyl]sulfonyl]pyridine-3-carboxamide (Compound 39), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(1-ethyl-2-methyl-propoxy)-6-(3-fluoro-5-isobutoxy-phenyl)pyridine-3-carboxamide (Compound 40), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(diisopropylamino)-6-(3-fluoro-5-isobutoxyphenyl)pyridine-3-carboxamide (Compound 41), or pharmaceutically acceptable salt thereof; and 3-(6-(1-(2,2-difluorobenzo[d][1,3]dioxol-5-yl)cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(1-methylallyloxy)pyridine-3-carboxamide (Compound 42), or pharmaceutically acceptable salt thereof; and 3-(6-(1-(2,2-difluorobenzo[d][1,3]dioxol-5-yl)cyclopropanecarboxamido)-3-methylpyridin-2-yl)benzoic acid, or pharmaceutically acceptable salt thereof.

In another embodiment, the pharmaceutical composition of the present disclosure comprises 2-allyloxy-N-[(6-amino-2-pyridyl)sulfonyl]-6-(3-fluoro-5-isobutoxy-phenyl)pyridine-3-carboxamide (Compound 43), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(1,1-dimethylpropoxy)-6-(3-fluoro-5-isobutoxy-phenyl)pyridine-3-carboxamide (Compound 44), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises 2-(diethylamino)-6-(3-fluoro-5-isobutoxy-phenyl)-N-(1H-pyrazol-5-yl sulfonyl)pyridine-3-carboxamide (Compound 46), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(1-ethylpropoxy)-6-(3-fluoro-5-isobutoxy-phenyl)pyridine-3-carboxamide (Compound 47), or pharmaceutically acceptable salt thereof; and 3-(6-(1-(2,2-difluorobenzo[d][1,3]dioxol-5-yl)cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(2-methylallyloxy)pyridine-3-carboxamide (Compound 49), or pharmaceutically acceptable salt thereof; and 3-(6-(1-(2,2-difluorobenzo[d][1,3]dioxol-5-yl)cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(2-methoxy-1,1-dimethyl-ethoxy)pyridine-3-carboxamide (Compound 51), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-[2,2-dimethylpropyl(methyl)amino]-6-(3-fluoro-5-isobutoxy-phenyl)pyridine-3-carboxamide (Compound 52), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(diethylamino)-6-(3-fluoro-5-isobutoxy-phenyl)pyridine-3-carboxamide (Compound 53), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(2-isopropoxyethoxy)pyridine-3-carboxamide (Compound 55), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(1-methylbutoxy)pyridine-3-carboxamide (Compound 56), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(2,2-difluoropropoxy)-6-(3-fluoro-5-isobutoxy-phenyl)pyridine-3-carboxamide (Compound 57), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(tert-butylamino)-6-(3-fluoro-5-isobutoxy-phenyl)pyridine-3-carboxamide (Compound 58), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[(1R)-1-methylpropoxy]pyridine-3-carboxamide (Compound 59), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(2-methoxyethoxy)pyridine-3-carboxamide (Compound 60), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[isobutyl(methyl)amino]pyridine-3-carboxamide (Compound 61), or pharmaceutically acceptable salt thereof; and 3-(6-(1-(2,2- difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(1,2-dimethylpentoxy)-6-(3-fluoro-5-isobutoxy-phenyl)pyridine-3-carboxamide (Compound 62), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-butoxy-6-(3-fluoro-5-isobutoxy-phenyl)pyridine-3-carboxamide (Compound 63), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[methyl(propyl)amino]pyridine-3-carboxamide (Compound 64), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[(1R)-2-methoxy-1-methyl-ethoxy]pyridine-3-carboxamide (Compound 65), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[methyl(2,2,2-trifluoroethyl)amino]pyridine-3-carboxamide (Compound 66), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-[ethyl(methyl)amino]-6-(3-fluoro-5-isobutoxy-phenyl)pyridine-3-carboxamide (Compound 67), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(1-isopropyl-2,2-dimethyl-propoxy)pyridine-3-carboxamide (Compound 68), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-[1-ethylpropyl(methyl)amino]-6-(3-fluoro-5-isobutoxy-phenyl)pyridine-3-carboxamide (Compound 69), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(2-ethoxy-1-methyl-ethoxy)-6-(3-fluoro-5-isobutoxy-phenyl)pyridine-3-carboxamide (Compound 71), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(2,2,2-trifluoro-1-methyl-ethoxy)pyridine-3-carboxamide (Compound 73), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-[ethyl(isopropyl)amino]-6-(3-fluoro-5-isobutoxy-phenyl)pyridine-3-carboxamide (Compound 74), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[methyl-[(1R)-2,2,2-trifluoro-1-methyl-ethyl]amino]pyridine-3-carboxamide (Compound 75), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(1,2-dimethylpropyl)-6-(3-fluoro-5-isobutoxy-phenyl)pyridine-3-carboxamide (Compound 76), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(3,3-dimethylpentoxy)-6-(3-fluoro-5-isobutoxy-phenyl)pyridine-3-carboxamide (Compound 77), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[(2S)-2-methoxypropoxy]pyridine-3-carboxamide (Compound 78), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises 6-(3-fluoro-5-isobutoxy-phenyl)-2-[isopropyl(methyl)amino]-N-(1H-pyrazol-5-ylsulfonyl)pyridine-3-carboxamide (Compound 79), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(3,3,3-trifluoroporoxy)pyridine-3-carboxamide (Compound 81), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(4,4,4-trifluorobutoxy)pyridine-3-carboxamide (Compound 82), or pharmaceutically acceptable salt thereof; and 3-(6-(1-(2,2-difluorobenzo[d][1,3]dioxol-5-yl)cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[(E)-4,4,4-trifluorobut-2-enoxy]pyridine-3-carboxamide (Compound 83), or pharmaceutically acceptable salt thereof; and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In one embodiment, the above recited pharmaceutical compositions contain a pharmaceutically acceptable prodrug of the compound of the present disclosure.

In another embodiment, the pharmaceutical composition of the present disclosure comprises a compound of formulas I to IIa-ii-2, or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises a compound of Table 1, or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-2-[2,2-difluoroethyl(methyl)amino]-6-(3-fluoro-5-isobutoxy-phenyl)pyridine-3-carboxamide (Compound 1), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-isopentyloxy-pyridine-3-carboxamide (Compound 2), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-2-(3,3-dimethylbutoxy)-6-(3-fluoro-5-isobutoxy-phenyl)pyridine-3-carboxamide (Compound 3), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-2-(2-tert-butoxyethoxy)-6-(3-fluoro-5-isobutoxy-phenyl)pyridine-3-carboxamide (Compound 4), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-isopropoxy-pyridine-3-carboxamide (Compound 5), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(2,2,3,3-tetrafluoro-1-methyl-propoxy)pyridine-3-carboxamide (Compound 6), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-5-(3-fluoro-5-isobutoxy-phenyl)-2-(trifluoromethyl)imidazo[1,2-a]pyridine-8-carboxamide (Compound 7), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(3,3,3-trifluoro-1-methyl-propoxy)pyridine-3-carboxamide (Compound 9), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-methoxy-pyridine-3-carboxamide (Compound 10), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-pentoxy-pyridine-3-carboxamide (Compound 11), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-2-(1,2-dimethylbutoxy)-6-(3-fluoro-5-isobutoxy-phenyl)pyridine-3-carboxamide (Compound 12), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan- 2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl) sulfonyl]-2-(2-ethoxyethoxy)-6-(3-fluoro-5-isobutoxy-phenyl)pyridine-3-carboxamide (Compound 13), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-2-[ethyl(isopropyl)amino]-6-(6-isopropoxy-3-pyridyl)pyridine-3-carboxamide (Compound 14), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-tert-butyl-2-(2,2-dimethylpropoxy)pyridine-3-carboxamide (Compound 15), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises 2-[ethyl(isopropyl)amino]-6-(3-fluoro-5-isobutoxy-phenyl)-N-(1H-pyrazol-5-ylsulfonyl)pyridine-3-carboxamide (Compound 16), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[methyl-[(1S)-2,2,2-trifluoro-1-methyl-ethyl]amino]pyridine-3-carboxamide (Compound 17), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[1-(methoxymethyl)propoxy]pyridine-3-carboxamide (Compound 18), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-2-(dimethylamino)-6-(3-fluoro-5-isobutoxy-phenyl)pyridine-3-carboxamide (Compound 19), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[(1S)-2-methoxy-1-methyl-ethoxy]pyridine-3-carboxamide (Compound 20), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(3-methoxypropoxy)pyridine-3-carboxamide (Compound 21), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(3-methoxy-3-methyl-butoxy)pyridine-3-carboxamide (Compound 22), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-2-(1,3-dimethylbutoxy)-6-(3-fluoro-5-isobutoxy-phenyl)pyridine-3-carboxamide (Compound 24), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(1,2,2-trimethylpropoxy)pyridine-3-carboxamide (Compound 25), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(1-isopropyl-2-methyl-propoxy)pyridine-3-carboxamide (Compound 26), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-propoxy-pyridine-3-carboxamide (Compound 27), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-2-[(E)-but-2-enoxy]-6-(3-fluoro-5-isobutoxy-phenyl)pyridine-3-carboxamide (Compound 28), or pharmaceutically acceptable salt thereof; and (R)-1-(2,2-difluorobenzo[d][1,3]dioxol-5-yl)-N-(1-(2,3-dihydroxypropyl)-6-fluoro- 2-(1-hydroxy-2-methylpropan-2-yl)-1H-indol-5-yl) cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[(1S)-1-methylpropoxy]pyridine-3-carboxamide (Compound 29), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-2-ethoxy-6-(3-fluoro-5-isobutoxy-phenyl)pyridine-3-carboxamide (Compound 30), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[isopropyl(methyl)amino]pyridine-3-carboxamide (Compound 31), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-2-(2,2-dimethylpropoxy)-6-(3-fluoro-5-isobutoxy-phenyl)pyridine-3-carboxamide (Compound 32), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[2,2,2-trifluoro-1-(trifluoromethyl)ethoxy]pyridine-3-carboxamide (Compound 33), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-2-(diethylamino)-6-(6-isopropoxy-3-pyridyl)pyridine-3-carboxamide (Compound 34), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-pent-3-ynoxy-pyridine-3-carboxamide (Compound 35), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(1,3,3-trimethylbutoxy)pyridine-3-carboxamide (Compound 36), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-2-(1,2-dimethylprop-1-enyl)-6-(3-fluoro-5-isobutoxy-phenyl)pyridine-3-carboxamide (Compound 37), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises 6-(3-fluoro-5-isobutoxy-phenyl)-2-(propylamino)-N-[[6-(propylamino)-2-pyridyl]sulfonyl]pyridine-3-carboxamide (Compound 39), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-2-(1-ethyl-2-methyl-propoxy)-6-(3-fluoro-5-isobutoxy-phenyl)pyridine-3-carboxamide (Compound 40), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-2-(diisopropylamino)-6-(3-fluoro-5-isobutoxy-phenyl)pyridine-3-carboxamide (Compound 41), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(1-methylallyloxy)pyridine-3-carboxamide (Compound 42), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises 2-allyloxy-N-[(6-amino-2-pyridyl)sulfonyl]-6-(3-fluoro-5-isobutoxy-phenyl)pyridine-3-carboxamide (Compound 43), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-2-(1,1-dimethylpropoxy)-6-(3-fluoro-5-isobutoxy-phenyl)pyridine-3-carboxamide (Compound 44), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises 2-(diethylamino)-6-(3-fluoro-5-isobutoxy-phenyl)-N-(1H-pyrazol-5-yl sulfonyl)pyridine-3-carboxamide (Compound 46), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropane carboxamide, or pharmaceutically acceptable salt thereof.

In another embodiment, the pharmaceutical composition of the present disclosure comprises N-[(6-amino-2-pyridyl)sulfonyl]-2-(1-ethylpropoxy)-6-(3-fluoro-5-isobutoxy-phenyl)pyridine-3-carboxamide (Compound 47), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(2-methylallyloxy)pyridine-3-carboxamide (Compound 49), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(2-methoxy-1,1-dimethyl-ethoxy)pyridine-3-carboxamide (Compound 51), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-2-[2,2-dimethylpropyl(methyl)amino]-6-(3-fluoro-5-isobutoxy-phenyl)pyridine-3-carboxamide (Compound 52), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-2-(diethylamino)-6-(3-fluoro-5-isobutoxy-phenyl)pyridine-3-carboxamide (Compound 53), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(2-isopropoxyethoxy)pyridine-3-carboxamide (Compound 55), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(1-methylbutoxy)pyridine-3-carboxamide (Compound 56), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-2-(2,2-difluoropropoxy)-6-(3-fluoro-5-isobutoxy-phenyl)pyridine-3-carboxamide (Compound 57), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-2-(tert-butylamino)-6-(3-fluoro-5-isobutoxy-phenyl)pyridine-3-carboxamide (Compound 58), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[(1R)-1-methylpropoxy]pyridine-3-carboxamide (Compound 59), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(2-methoxyethoxy)pyridine-3-carboxamide (Compound 60), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[isobutyl(methyl)amino]pyridine-3-carboxamide (Compound 61), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-2-(1,2-dimethylpentoxy)-6-(3-fluoro-5-isobutoxy-phenyl)pyridine-3-carboxamide (Compound 62), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-2-butoxy-6-(3-fluoro-5-isobutoxy-phenyl)pyridine-3-carboxamide (Compound 63), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[methyl(propyl)amino]pyridine-3-carboxamide (Compound 64), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[(1R)-2-methoxy-1-methyl-ethoxy]pyridine-3-carboxamide (Compound 65), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[methyl(2,2,2-trifluoroethyl)amino]pyridine-3-carboxamide (Compound 66), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-2-[ethyl(methyl)amino]-6-(3-fluoro-5-isobutoxy-phenyl)pyridine-3-carboxamide (Compound 67), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(1-isopropyl-2,2-dimethyl-propoxy)pyridine-3-carboxamide (Compound 68), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-2-[1-ethylpropyl(methyl)amino]-6-(3-fluoro-5-isobutoxy-phenyl)pyridine-3-carboxamide (Compound 69), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-2-(2-ethoxy-1-methyl-ethoxy)-6-(3-fluoro-5-isobutoxy-phenyl)pyridine-3-carboxamide (Compound 71), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(2,2,2-trifluoro-1-methyl-ethoxy)pyridine-3-carboxamide (Compound 73), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-2-[ethyl(isopropyl)amino]-6-(3-fluoro-5-isobutoxy-phenyl)pyridine-3-carboxamide (Compound 74), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[methyl-[(1R)-2,2,2-trifluoro-1-methyl-ethyl]amino]pyridine-3-carboxamide (Compound 75), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-2-(1,2-dimethylpropyl)-6-(3-fluoro-5-isobutoxy-phenyl)pyridine-3-carboxamide (Compound 76), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-2-(3,3-dimethylpentoxy)-6-(3-fluoro-5-isobutoxy-phenyl)pyridine-3-carboxamide (Compound 77), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[(2S)-2-methoxypropoxy]pyridine-3-carboxamide (Compound 78), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises 6-(3-fluoro-5-isobutoxy-phenyl)-2-[isopropyl(methyl)amino]-N-(1H-pyrazol-5-ylsulfonyl)pyridine-3-carboxamide (Compound 79), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(3,3,3-trifluoropropoxy)pyridine-3-carboxamide (Compound 81), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(4,4,4-trifluorobutoxy)pyridine-3-carboxamide (Compound 82), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[(E)-4,4,4-trifluorobut-2-enoxy]pyridine-3-carboxamide (Compound 83), or pharmaceutically acceptable salt thereof; and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, or pharmaceutically acceptable salt thereof.

In another embodiment, the above recited pharmaceutical compositions contain a pharmaceutically acceptable prodrug of the compound of the present disclosure.

In another embodiment, the pharmaceutical composition of the present disclosure comprises a compound of formulas I to IIa-ii-2, or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises a compound of Table 1, or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-2-[2,2-difluoroethyl(methyl)amino]-6-(3-fluoro-5-isobutoxy-phenyl)pyridine-3-carboxamide (Compound 1), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-isopentyloxy-pyridine-3-carboxamide (Compound 2), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-2-(3,3-dimethylbutoxy)-6-(3-fluoro-5-isobutoxy-phenyl)pyridine-3-carboxamide (Compound 3), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-2-(2-tert-butoxyethoxy)-6-(3-fluoro-5-isobutoxy-phenyl)pyridine-3-carboxamide (Compound 4), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-isopropoxy-pyridine-3-carboxamide (Compound 5), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(2,2,3,3-tetrafluoro-1-methyl-propoxy)pyridine-3-carboxamide (Compound 6), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-5-(3-fluoro-5-isobutoxy-phenyl)-2-(trifluoromethyl)imidazo[1,2-a]pyridine-8-carboxamide (Compound 7), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(3,3,3-trifluoro-1-methyl-propoxy)pyridine-3-carboxamide (Compound 9), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-methoxy-pyridine-3-carboxamide (Compound 10), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-pentoxy-pyridine-3-carboxamide (Compound 11), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-2-(1,2-dimethylbutoxy)-6-(3-fluoro-5-isobutoxy-phenyl)pyridine-3-carboxamide (Compound 12), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-2-(2-ethoxyethoxy)-6-(3-fluoro-5-isobutoxy-phenyl)pyridine-3-carboxamide (Compound 13), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-2-[ethyl(isopropyl)amino]-6-(6-isopropoxy-3-pyridyl)pyridine-3-carboxamide (Compound 14), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-tert-butyl-2-(2,2-dimethylpropoxy)pyridine-3-carboxamide (Compound 15), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises 2-[ethyl(isopropyl)amino]-6-(3-fluoro-5-isobutoxy-phenyl)-N-(1H-pyrazol-5-ylsulfonyl)pyridine-3-carboxamide (Compound 16), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[methyl-[(1S)-2,2,2-trifluoro-1-methyl-ethyl]amino]pyridine-3-carboxamide (Compound 17), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[1-(methoxymethyl)propoxy]pyridine-3-carboxamide (Compound 18), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-2-(dimethylamino)-6-(3-fluoro-5-isobutoxy-phenyl)pyridine-3-carboxamide (Compound 19), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[(1S)-2-methoxy-1-methyl-ethoxy]pyridine-3-carboxamide (Compound 20), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(3-methoxypropoxy)pyridine-3-carboxamide (Compound 21), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(3-methoxy-3-methyl-butoxy)pyridine-3-carboxamide (Compound 22), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-2-(1,3-dimethylbutoxy)-6-(3-fluoro-5-isobutoxy-phenyl)pyridine-3-carboxamide (Compound 24), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(1,2,2-trimethylpropoxy)pyridine-3-carboxamide (Compound 25), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(1-isopropyl-2-methyl-propoxy)pyridine-3-carboxamide (Compound 26), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-propoxy-pyridine-3-carboxamide (Compound 27), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-2-[(E)-but-2-enoxy]-6-(3-fluoro-5-isobutoxy-phenyl)pyridine-3-carboxamide (Compound 28), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[(1S)-1-methylpropoxy]pyridine-3-carboxamide (Compound 29), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-2-ethoxy-6-(3-fluoro-5-isobutoxy-phenyl)pyridine-3-carboxamide (Compound 30), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[isopropyl(methyl)amino]pyridine-3-carboxamide (Compound 31), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-2-(2,2-dimethylpropoxy)-6-(3-fluoro-5-isobutoxy-phenyl)pyridine-3-carboxamide (Compound 32), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[2,2,2-trifluoro-1-(trifluoromethyl)ethoxy]pyridine-3-carboxamide (Compound 33), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-2-(diethylamino)-6-(6-isopropoxy-3-pyridyl)pyridine-3-carboxamide (Compound 34), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-pent-3-ynoxy-pyridine-3-carboxamide (Compound 35), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(1,3,3-trimethylbutoxy)pyridine-3-carboxamide (Compound 36), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-2-(1,2-dimethylprop-1-enyl)-6-(3-fluoro-5-isobutoxy-phenyl)pyridine-3-carboxamide (Compound 37), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises 6-(3-fluoro-5-isobutoxy-phenyl)-2-(propylamino)-N-[[6-(propylamino)-2-pyridyl]sulfonyl]pyridine-3-carboxamide (Compound 39), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-2-(1-ethyl-2-methyl-propoxy)-6-(3-fluoro-5-isobutoxy-phenyl)pyridine-3-carboxamide (Compound 40), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-2-(diisopropylamino)-6-(3-fluoro-5-isobutoxy-phenyl)pyridine-3-carboxamide (Compound 41), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(1-methylallyloxy)pyridine-3-carboxamide (Compound 42), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises 2-allyloxy-N-[(6-amino-2-pyridyl)sulfonyl]-6-(3-fluoro-5-isobutoxy-phenyl)pyridine-3-carboxamide (Compound 43), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-2-(1,1-dimethylpropoxy)-6-(3-fluoro-5-isobutoxy-phenyl)pyridine-3-carboxamide (Compound 44), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises 2-(diethylamino)-6-(3-fluoro-5-isobutoxy-phenyl)-N-(1H-pyrazol-5-yl sulfonyl)pyridine-3-carboxamide (Compound 46), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-2-(1-ethylpropoxy)-6-(3-fluoro-5-isobutoxy-phenyl)pyridine-3-carboxamide (Compound 47), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(2-methylallyloxy)pyridine-3-carboxamide (Compound 49), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(2-methoxy-1,1-dimethyl-ethoxy)pyridine-3-carboxamide (Compound 51), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-2-[2,2-dimethylpropyl(methyl)amino]-6-(3-fluoro-5-isobutoxy-phenyl)pyridine-3-carboxamide (Compound 52), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-2-(diethylamino)-6-(3-fluoro-5-isobutoxy-phenyl)pyridine-3-carboxamide (Compound 53), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(2-isopropoxyethoxy)pyridine-3-carboxamide (Compound 55), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(1-methylbutoxy)pyridine-3-carboxamide (Compound 56), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-2-(2,2-difluoropropoxy)-6-(3-fluoro-5-isobutoxy-phenyl)pyridine-3-carboxamide (Compound 57), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-2-(tert-butylamino)-6-(3-fluoro-5-isobutoxy-phenyl)pyridine-3-carboxamide (Compound 58), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[(1R)-1-methylpropoxy]pyridine-3-carboxamide (Compound 59), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(2-methoxyethoxy)pyridine-3-carboxamide (Compound 60), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[isobutyl(methyl)amino]pyridine-3-carboxamide (Compound 61), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-2-(1,2-dimethylpentoxy)-6-(3-fluoro-5-isobutoxy-phenyl)pyridine-3-carboxamide (Compound 62), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-2-butoxy-6-(3-fluoro-5-isobutoxy-phenyl)pyridine-3-carboxamide (Compound 63), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[methyl(propyl)amino]pyridine-3-carboxamide (Compound 64), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[(1R)-2-methoxy-1-methyl-ethoxy]pyridine-3-carboxamide (Compound 65), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[methyl(2,2,2-trifluoroethyl)amino]pyridine-3-carboxamide (Compound 66), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-2-[ethyl(methyl)amino]-6-(3-fluoro-5-isobutoxy-phenyl)pyridine-3-carboxamide (Compound 67), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(1-isopropyl-2,2-dimethyl-propoxy)pyridine-3-carboxamide (Compound 68), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-2-[1-ethylpropyl(methyl)amino]-6-(3-fluoro-5-isobutoxy-phenyl)pyridine-3-carboxamide (Compound 69), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-2-(2-ethoxy-1-methyl-ethoxy)-6-(3-fluoro-5-isobutoxy-phenyl)pyridine-3-carboxamide (Compound 71), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(2,2,2-trifluoro-1-methyl-ethoxy)pyridine-3-carboxamide (Compound 73), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-2-[ethyl(isopropyl)amino]-6-(3-fluoro-5-isobutoxy-phenyl)pyridine-3-carboxamide (Compound 74), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[methyl-[(1R)-2,2,2-trifluoro-1-methyl-ethyl]amino]pyridine-3-carboxamide (Compound 75), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-2-(1,2-dimethylpropyl)-6-(3-fluoro-5-isobutoxy-phenyl)pyridine-3-carboxamide (Compound 76), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-2-(3,3-dimethylpentoxy)-6-(3-fluoro-5-isobutoxy-phenyl)pyridine-3-carboxamide (Compound 77), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[(2S)-2-methoxypropoxy]pyridine-3-carboxamide (Compound 78), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises 6-(3-fluoro-5-isobutoxy-phenyl)-2-[isopropyl(methyl)amino]-N-(1H-pyrazol-5-ylsulfonyl)pyridine-3-carboxamide (Compound 79), or pharmaceutically acceptable salt thereof; and N-(5-hydroxy-2,4- ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(4,4,4-trifluorobutoxy)pyridine-3-carboxamide (Compound 82), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(4,4,4-trifluorobutoxy)pyridine-3-carboxamide (Compound 82), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[(E)-4,4,4-trifluorobut-2-enoxy]pyridine-3-carboxamide (Compound 83), or pharmaceutically acceptable salt thereof; and N-(5-hydroxy-2,4-ditert-butyl-phenyl)-4-oxo-1H-quinoline-3-carboxamide, or pharmaceutically acceptable salt thereof.

In another embodiment, the above recited pharmaceutical compositions contain a pharmaceutically acceptable prodrug of the compound of the present disclosure.

In another embodiment, the additional therapeutic agent is selected from the following table:

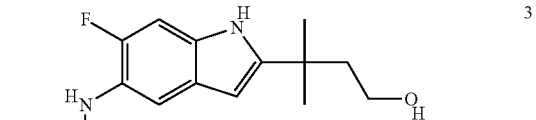

1

2

3

4

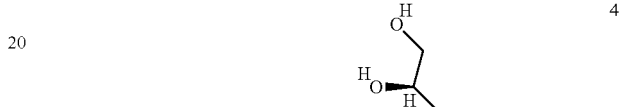

5

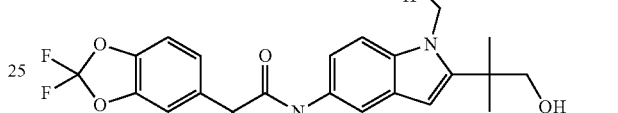

6

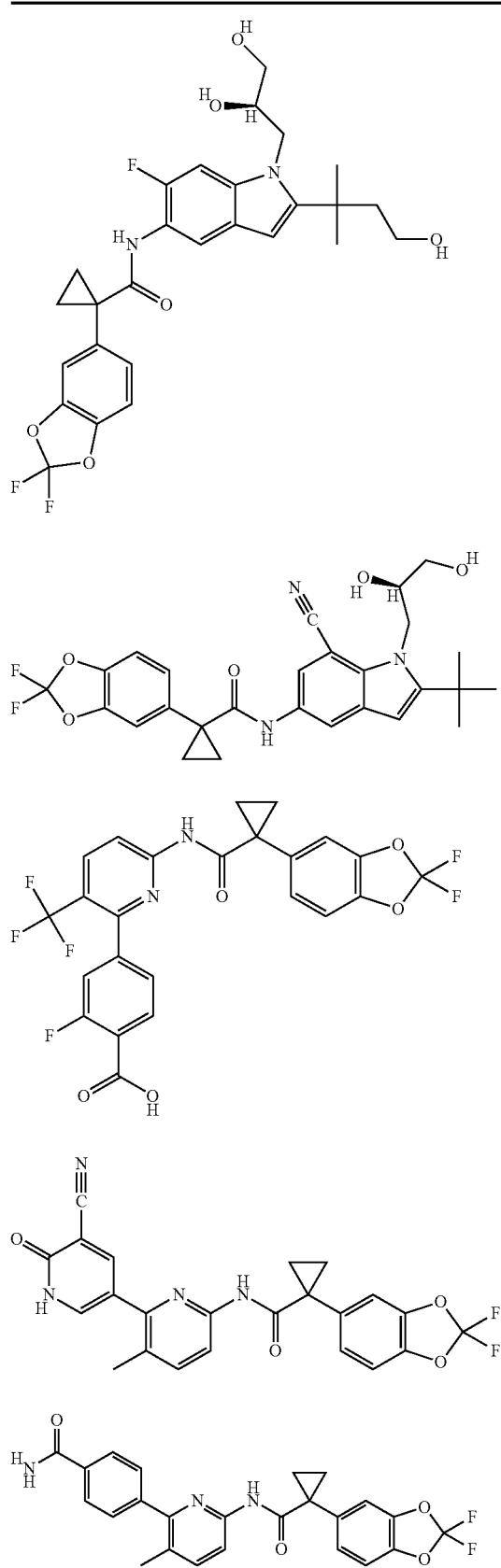
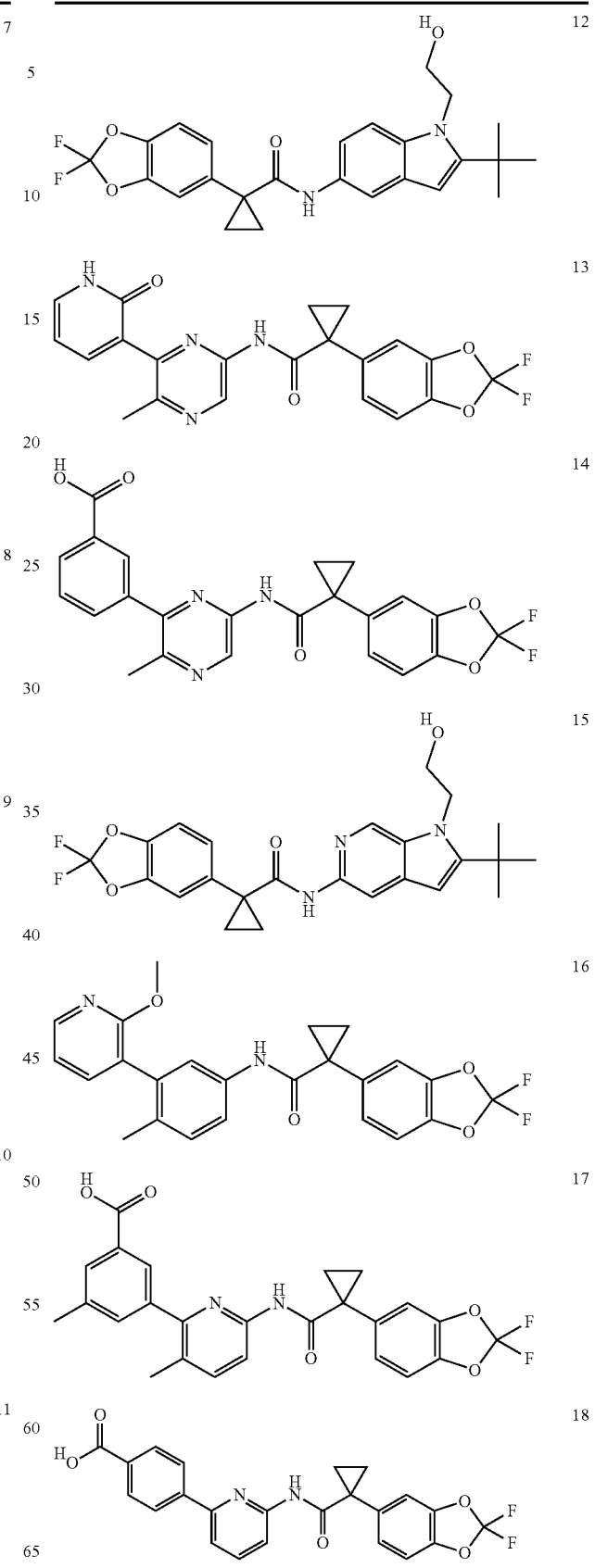

-continued

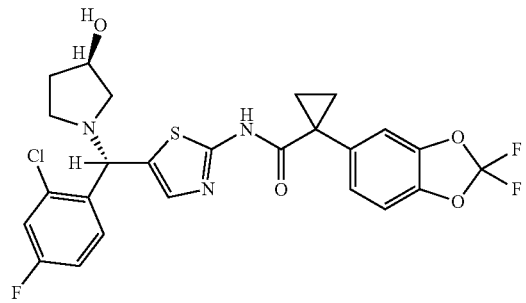

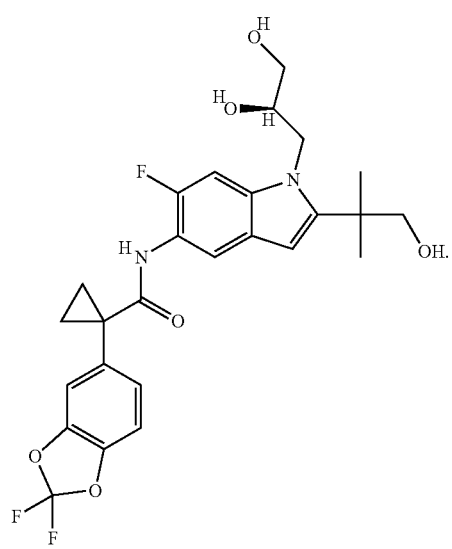

In one embodiment, the additional therapeutic agent is selected from the following table:

Compounds disclosed in U.S. Pat. No. 7,407,976 (Col 13, ln 35- col 66, ln 67; Compounds 1-100 in Table 1 at col 67, ln 1-col 127, ln 42)
Compounds disclosed in U.S. Pat. No. 7,645,789 (Col 16, ln 52-col 50, ln 22; Compounds 1-322 in Table 1 at col 50, ln 24-col 167, ln 42)
Compounds disclosed in U.S. Pat. No. 7,659,268 (Col 16, ln 20-col 70, ln 52; Compounds 1-528 in Table 1 at col 70, ln 53-col 331, ln 34)
Compounds disclosed in U.S. Pat. No. 7,671,221 (Col 16, ln 12-col 54, ln 48; Compounds 1-1216 in Table 1 at col 54, ln 49-col 699, ln 27)
Compounds disclosed in U.S. Pat. No. 7,691,902 (Col 16, ln 11-col 54, ln 29; Compounds 1-959 in Table 1 at col 54, ln 29-col 683, ln 44)
Compounds disclosed in U.S. Pat. No. 7,741,321 (Col 16, ln 25-col 72, ln 17; Compounds 1-422 in Table 1 at col 72, ln 20-col 279, ln 15)
Compounds disclosed in U.S. Pat. No. 7,754,739 (Col 16, ln 1-col 22, ln 47; Compounds 1-2 in Table 1 at col 18, ln 26-65)
Compounds disclosed in U.S. Pat. No. 7,776,905 (Col 16, ln 23-col 38, ln 40; Compounds 1-306 in Table 1 at col 38, ln 45-col 96, ln 40)
Compounds disclosed in U.S. Pat. No. 7,973,169 (Col 9, ln 16-col 40, ln 40; Compounds 1-289 in Table 1 at col. 40, ln 41-col 289, ln 39)
Compounds disclosed in U.S. Pat. No. 7,977,322 (Col 6, ln 26-col 37, ln 47; Compounds 1-498 in Table 1 at col 37, ln 50-col 141, ln 40)
Compounds disclosed in U.S. Pat. No. 7,999,113 (Col 6, ln 13-col 10, ln 67; Compounds 1-13 in Table 1 at col 11, ln 5-col 13, ln 65)
Compounds disclosed in U.S. Pat. No. 8,227,615 (Col 6, ln 10-col 29, ln 66; Compounds 1-78 in Table 1 at col 30, ln 1-col 46, ln 48)
Compounds disclosed in U.S. Pat. No. 8,299,099 (Col 6, ln 10-col 34, ln 18; Compounds 1-47 in Table 1 at col 34, ln 20-col 42, ln 35)
Compounds disclosed in US Published Application No. 2006-0052358 (Paragraphs [0034]-[0056]; [0077]-[0240]; Compounds 1-320 in Table 1 at paragraph [0241])
Compounds disclosed in US Published Application No. 2009-0143381 (Paragraphs [0102]-[0263]; Compounds 1-28 in Table 1 at paragraph [0264])
Compounds disclosed in US Published Application No. 2009-0170905 (Paragraphs [0012]-[0013]; [0030]-[0051])
Compounds disclosed in US Published Application No. 2009-0253736 (Paragraphs [0031]-[0162]; Compounds 1-15 in Table 1 at paragraph [0163])
Compounds disclosed in US Published Application No. 2011-0263654 (Paragraphs [0012]-[0013]; [0066]-[0141])
Compounds disclosed in US Published Application No. 2011-0251253 (Paragraphs [0012]-[0013]; [0054]-[0079])
Compounds disclosed in PCT application WO2008141119 (Paragraphs [0100]-[0339]; Compounds 1-117 in Table 1 at paragraph [0340])
Compounds disclosed in U.S. application Ser. No. 11/047,361
Compounds disclosed in US Published Application No. 2013-0116238 (Paragraphs [0028]-[0044]; [0117]-[0128]), or combinations thereof.

In another embodiment, the additional therapeutic agent is selected from

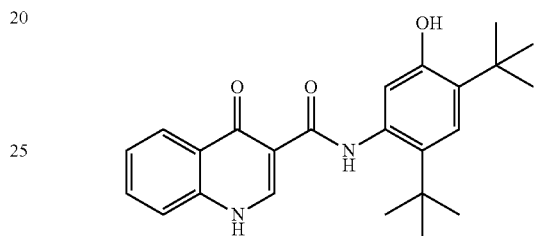

N-(5-hydroxy-2,4-ditert-butyl-phenyl)-4-oxo-1H-quinoline-3-carboxamide, or pharmaceutically acceptable salt thereof; or

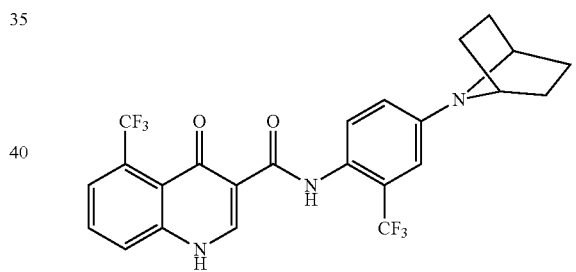

N-(4-(7-azabicyclo[2.21]heptan-7-yl)-2-(trifluoromethyl)phenyl)-4-oxo-5-(trifluoromethyl)-1,4-dihydroquinoline-3-carboxamide, or pharmaceutically acceptable salt thereof.

In another embodiment, the disclosure features a pharmaceutical composition comprising a) a compound of formulas I to IIa-ii-2, or pharmaceutically acceptable salt thereof; b) a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide, or 4-(3-(1-(2,2-difluorobenzo[d][1,3]dioxol-5-yl)cyclopropanecarboxamido) isoquinolin-1-yl)benzoic acid; and c) a compound selected from N-(5-hydroxy-2,4-ditert-butyl-phenyl)-4-oxo-1H-quinoline-3-carboxamide or N-(4-(7-azabicyclo[2.21]heptan-7-yl)-2-(trifluoromethyl)phenyl)-4-oxo-5-(trifluoromethyl)-1,4-dihydroquinoline-3-carboxamide.

In another embodiment, the disclosure features a pharmaceutical composition comprising a) a compound of Table 1, or pharmaceutically acceptable salt thereof; b) a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide, or 4-(3-(1-(2,2-difluorobenzo[d][1,3]dioxol-5-yl)cyclopropanecarboxamido) isoquinolin-1-yl)benzoic acid; and c) a compound selected from N-(5-hydroxy-2,4-ditert-butyl-phenyl)-4-oxo-1H-quinoline-3-carboxamide or N-(4-(7-azabicyclo[2.21]heptan-7-yl)-2-(trifluoromethyl)phenyl)-4-oxo-5-(trifluoromethyl)-1,4-dihydroquinoline-3-carboxamide.

In another embodiment, the above recited pharmaceutical compositions contain a pharmaceutically acceptable prodrug of the compound of the present disclosure.

In another embodiment, the additional therapeutic agent is selected from the following table:

Compounds disclosed in US Published Application No. 2005-0113423 (Paragraph [00146]; Compounds IA-1-IA-136 and Compounds I-1-I-21 in Tables 1 and 2 at paragraphs [0391]-[0392])
Compounds disclosed in US Published Application No. 2005-0059687 (Paragraphs [00100]-[00101]; Compounds 1-405 in Table 1 at paragraph [0169])
Compounds 1-108 disclosed in U.S. Pat. No. 7,598,412 (Col 22, ln 14-col 79, ln 20; Table 1)
Compounds 1-485 disclosed in U.S. Pat. No. 7,495,103 (Col 51, ln 1-col 63, ln 43; Table 1)
Compounds 1-718 disclosed in U.S. Pat. No. 8,354,427 (Col 51, ln 3-col 71, ln 46; Table 1)
Compounds 1-233 disclosed in US Published Application No. 2007-0105833 (Paragraph [00145]; Table 1)
Compounds 1-26 disclosed in U.S. Pat. No. 8,242,149 (Col 46, ln 47-col 57, ln 37; Table 1)
Compounds 1-18 disclosed in U.S. Pat. No. 8,314,256 (Col 21, ln 1-col 26, ln 19)
Compounds 1-14 disclosed in U.S. Pat. No. 8,399,479 (Col 36, ln 20-col 38, ln 40; Table 1)
Compounds 1-18 disclosed in U.S. Pat. No. 8,188,283 (Col 38, ln 43-col 43, ln 36; Table 1)
Compounds 1-16 disclosed in US Published Application No. 2010-0249180 (Paragraph [0173]; Table 1)
Compounds 1-19 disclosed in US Published Application No. 2011-0008259 (Paragraph [0172]; Table 1)
Compounds 1-129 disclosed in U.S. Pat. No. 8,367,660 (Col 57, ln 31-col 81, ln 24; Table1)
Compounds 1-2747 disclosed in U.S. patent application No. 14/876,525 (Paragraph [00525]; Table 1)

In another embodiment, the disclosure features a pharmaceutical composition comprising a) a compound of formulas I to IIa-ii-2, or pharmaceutically acceptable salt thereof; b) a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide, or 4-(3-(1-(2,2-difluorobenzo[d][1,3]dioxol-5-yl)cyclopropanecarboxamido) isoquinolin-1-yl)benzoic acid; and c) a compound selected from N-(5-hydroxy-2,4-ditert-butyl-phenyl)-4-oxo-1H-quinoline-3-carboxamide or N-(4-(7-azabicyclo[2.21]heptan-7-yl)-2-(trifluoromethyl)phenyl)-4-oxo-5-(trifluoromethyl)-1,4-dihydroquinoline-3-carboxamide.

In another embodiment, the disclosure features a pharmaceutical composition comprising a) a compound of Table 1, or pharmaceutically acceptable salt thereof; b) a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide, or 4-(3-(1-(2,2-difluorobenzo[d][1,3]dioxol-5-yl)cyclopropanecarboxamido) isoquinolin-1-yl)benzoic acid; and c) a compound selected from N-(5-hydroxy-2,4-ditert-butyl-phenyl)-4-oxo-1H-quinoline-3-carboxamide or N-(4-(7-azabicyclo[2.21]heptan-7-yl)-2-(trifluoromethyl)phenyl)-4-oxo-5-(trifluoromethyl)-1,4-dihydroquinoline-3-carboxamide.

In another embodiment, the above recited pharmaceutical compositions contain a pharmaceutically acceptable prodrug of the compound of the present disclosure.

In another embodiment, the disclosure features a pharmaceutical composition comprising a) a compound of formulas I to IIa-ii-2, or pharmaceutically acceptable salt thereof; b) a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide, or 4-(3-(1-(2,2-difluorobenzo[d][1,3]dioxol-5-yl)cyclopropanecarboxamido) isoquinolin-1-yl)benzoic acid; and c) a compound selected from certain flavones and isoflavones, such as genistein, which are capable of stimulating CFTR-mediated chloride transport in epithelial tissues in a cyclic-AMP independent manner (See U.S. Pat. No. 6,329,422, incorporated herein by reference in its entirety); phenylglycine-01 (2-[(2-1H-indol-3-yl-acetyl)-methylamino]-N-(4-isopropylphenyl)-2-phenylacetamide); felodipine (Ethyl methyl 4-(2,3-dichlorophenyl)-2,6-dimethyl-1,4-dihydro-3,5-pyridinedicarboxylate); sulfonamide SF-01 (6-(ethylphenylsulfamoyl)-4-oxo-1,4-dihydroquinoline-3-carboxylic acid cycloheptylamide); and UCCF-152 (3-[2-(benzyloxy)phenyl]-5-(chloromethyl)isoxazole).

In another embodiment, the disclosure features a pharmaceutical composition comprising a) a compound of formulas I to IIa-ii-2, or pharmaceutically acceptable salt thereof; b) 3-(6-(1-(2,2-difluorobenzo[d][1,3]dioxol-5-yl) cyclopropanecarboxamido)-3-methylpyridin-2-yl)benzoic acid; and c) N-(5-hydroxy-2,4-ditert-butyl-phenyl)-4-oxo-1H-quinoline-3-carboxamide.

In another embodiment, the disclosure features a pharmaceutical composition comprising a) a compound of Table 1, or pharmaceutically acceptable salt thereof; b) 3-(6-(1-(2,2-difluorobenzo[d][1,3]dioxol-5-yl) cyclopropanecarboxamido)-3-methylpyridin-2-yl)benzoic acid; and c) N-(5-hydroxy-2,4-ditert-butyl-phenyl)-4-oxo-1H-quinoline-3-carboxamide.

In another embodiment, the disclosure features a pharmaceutical composition comprising a) a compound of formulas I to IIa-ii-2, or pharmaceutically acceptable salt thereof; b) (R)-1-(2,2-difluorobenzo[d][1,3]dioxol-5-yl)-N-(1-(2,3-dihydroxypropyl)-6-fluoro-2-(1-hydroxy-2-methyl-propan-2-yl)-1H-indol-5-yl)cyclopropanecarboxamide; and c) N-(5-hydroxy-2,4-ditert-butyl-phenyl)-4-oxo-1H-quinoline-3-carboxamide.

In another embodiment, the disclosure features a pharmaceutical composition comprising a) a compound of Table 1, or pharmaceutically acceptable salt thereof; b) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide; and c) N-(5-hydroxy-2,4-ditert-butyl-phenyl)-4-oxo-1H-quinoline-3-carboxamide.

In another embodiment, the disclosure features a pharmaceutical composition comprising a) a compound of formulas I to IIa-ii-2, or pharmaceutically acceptable salt thereof; b) 4-(3-(1-(2,2-difluorobenzo[d][1,3]dioxol-5-yl)

cyclopropanecarboxamido) isoquinolin-1-yl)benzoic acid; and c) N-(5-hydroxy-2,4-ditert-butyl-phenyl)-4-oxo-1H-quinoline-3-carboxamide.

In another embodiment, the disclosure features a pharmaceutical composition comprising a) a compound of Table 1, or pharmaceutically acceptable salt thereof; b) 4-(3-(1-(2,2-difluorobenzo[d][1,3]dioxol-5-yl)cyclopropanecarboxamido) isoquinolin-1-yl)benzoic acid; and c) N-(5-hydroxy-2,4-ditert-butyl-phenyl)-4-oxo-1H-quinoline-3-carboxamide.

In another embodiment, the above recited pharmaceutical compositions contain a pharmaceutically acceptable prodrug of the compound of the present disclosure.

In another embodiment, the pharmaceutical composition of the present disclosure comprises a) N-[(6-amino-2-pyridyl)sulfonyl]-2-[2,2-difluoroethyl(methyl)amino]-6-(3-fluoro-5-isobutoxy-phenyl)pyridine-3-carboxamide (Compound 1), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-isopentyloxy-pyridine-3-carboxamide (Compound 2), b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(3,3-dimethylbutoxy)-6-(3-fluoro-5-isobutoxy-phenyl)pyridine-3-carboxamide (Compound 3), b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(2-tert-butoxyethoxy)-6-(3-fluoro-5-isobutoxy-phenyl)pyridine-3-carboxamide (Compound 4), b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-isopropoxy-pyridine-3-carboxamide (Compound 5), b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(2,2,3,3-tetrafluoro-1-methyl-propoxy)pyridine-3-carboxamide (Compound 6), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-5-(3-fluoro-5-isobutoxy-phenyl)-2-(trifluoromethyl)imidazo[1,2-a]pyridine-8-carboxamide (Compound 7), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(3,3,3-trifluoro-1-methyl-propoxy)pyridine-3-carboxamide (Compound 9), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-methoxy-pyridine-3-carboxamide (Compound 10), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-pentoxy-pyridine-3-carboxamide (Compound 11), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(1,2-dimethylbutoxy)-6-(3-fluoro-5-isobutoxy-phenyl)pyridine-3-carboxamide (Compound 12), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(2-ethoxyethoxy)-6-(3-fluoro-5-isobutoxy-phenyl)pyridine-3-carboxamide (Compound 13), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-[ethyl(isopropyl)amino]-6-(6-isopropoxy-3-pyridyl)pyridine-3-carboxamide (Compound 14), or pharmaceutically acceptable salt thereof; b) N-(5-hydroxy-2,4- ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-tert-butyl-2-(2,2-dimethylpropoxy)pyridine-3-carboxamide (Compound 15), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises 2-[ethyl(isopropyl)amino]-6-(3-fluoro-5-isobutoxy-phenyl)-N-(1H-pyrazol-5-ylsulfonyl)pyridine-3-carboxamide (Compound 16), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[methyl-[(1S)-2,2,2-trifluoro-1-methyl-ethyl]amino]pyridine-3-carboxamide (Compound 17), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[1-(methoxymethyl)propoxy]pyridine-3-carboxamide (Compound 18), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(dimethylamino)-6-(3-fluoro-5-isobutoxy-phenyl)pyridine-3-carboxamide (Compound 19), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[(1S)-2-methoxy-1-methyl-ethoxy]pyridine-3-carboxamide (Compound 20), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(3-methoxypropoxy)pyridine-3-carboxamide (Compound 21), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(3-methoxy-3-methyl-butoxy)pyridine-3-carboxamide (Compound 22), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(1,3-dimethylbutoxy)-6-(3-fluoro-5-isobutoxy-phenyl)pyridine-3-carboxamide (Compound 24), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(1,2,2-trimethylpropoxy)pyridine-3-carboxamide (Compound 25), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(1-isopropyl-2-methyl-propoxy)pyridine-3-carboxamide (Compound 26), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-propoxy-pyridine-3-carboxamide (Compound 27), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-[(E)-but-2-enoxy]-6-(3-fluoro-5-isobutoxy-phenyl)pyridine-3-carboxamide (Compound 28), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2, 2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl) sulfonyl]-6-(3-fluoro-5-isobutoxy-phenyl)-2-[(1S)-1-methylpropoxy]pyridine-3-carboxamide (Compound 29), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl) sulfonyl]-2-ethoxy-6-(3-fluoro-5-isobutoxy-phenyl)pyridine-3-carboxamide (Compound 30), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl) sulfonyl]-6-(3-fluoro-5-isobutoxy-phenyl)-2-[isopropyl(methyl)amino]pyridine-3-carboxamide (Compound 31), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl) sulfonyl]-2-(2,2-dimethylpropoxy)-6-(3-fluoro-5-isobutoxy-phenyl)pyridine-3-carboxamide (Compound 32), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl) sulfonyl]-6-(3-fluoro-5-isobutoxy-phenyl)-2-[2,2,2-trifluoro-1-(trifluoromethyl)ethoxy]pyridine-3-carboxamide (Compound 33), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl) sulfonyl]-2-(diethylamino)-6-(6-isopropoxy-3-pyridyl)pyridine-3-carboxamide (Compound 34), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl) sulfonyl]-6-(3-fluoro-5-isobutoxy-phenyl)-2-pent-3-ynoxy-pyridine-3-carboxamide (Compound 35), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl) sulfonyl]-6-(3-fluoro-5-isobutoxy-phenyl)-2-(1,3,3-trimethylbutoxy)pyridine-3-carboxamide (Compound 36), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl) sulfonyl]-2-(1,2-dimethylprop-1-enyl)-6-(3-fluoro-5-isobutoxy-phenyl)pyridine-3-carboxamide (Compound 37), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises 6-(3-fluoro-5-isobutoxy-phenyl)-2-(propylamino)-N-[[6-(propylamino)-2-pyridyl] sulfonyl]pyridine-3-carboxamide (Compound 39), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl) sulfonyl]-2-(1-ethyl-2-methyl-propoxy)-6-(3-fluoro-5-isobutoxy-phenyl)pyridine-3-carboxamide (Compound 40), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl) sulfonyl]-2-(diisopropylamino)-6-(3-fluoro-5-isobutoxy-phenyl)pyridine-3-carboxamide (Compound 41), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl) sulfonyl]-6-(3-fluoro-5-isobutoxy-phenyl)-2-(1-methylallyloxy)pyridine-3-carboxamide (Compound 42), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises 2-allyloxy-N-[(6-amino-2-pyridyl)sulfonyl]-6-(3-fluoro-5-isobutoxy-phenyl)pyridine-3-carboxamide (Compound 43), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(1,1-dimethylpropoxy)-6-(3-fluoro-5-isobutoxy-phenyl)pyridine-3-carboxamide (Compound 44), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises 2-(diethylamino)-6-(3-fluoro-5-isobutoxy-phenyl)-N-(1H-pyrazol-5-yl sulfonyl)pyridine-3-carboxamide (Compound 46), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(1-ethylpropoxy)-6-(3-fluoro-5-isobutoxy-phenyl)pyridine-3-carboxamide (Compound 47), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(2-methylallyloxy)pyridine-3-carboxamide (Compound 49), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(2-methoxy-1,1-dimethyl-ethoxy)pyridine-3-carboxamide (Compound 51), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-[2,2-dimethylpropyl(methyl)amino]-6-(3-fluoro-5-isobutoxy-phenyl)pyridine-3-carboxamide (Compound 52), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(diethylamino)-6-(3-fluoro-5-isobutoxy-phenyl)pyridine-3-carboxamide (Compound 53), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(2-isopropoxyethoxy)pyridine-3-carboxamide (Compound 55), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(1-methylbutoxy)pyridine-3-carboxamide (Compound 56), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(2,2-difluoropropoxy)-6-(3-fluoro-5-isobutoxy-phenyl)pyridine-3-carboxamide (Compound 57), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(tert-butylamino)-6-(3-fluoro-5-isobutoxy-phenyl)pyridine-3-carboxamide (Compound 58), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[(1R)-1-methylpropoxy]pyridine-3-carboxamide (Compound 59), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(2-methoxyethoxy)pyridine-3-carboxamide (Compound 60), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[isobutyl(methyl)amino]pyridine-3-carboxamide (Compound 61), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(1,2-dimethylpentoxy)-6-(3-fluoro-5-isobutoxy-phenyl)pyridine-3-carboxamide (Compound 62), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-butoxy-6-(3-fluoro-5-isobutoxy-phenyl)pyridine-3-carboxamide (Compound 63), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[methyl(propyl)amino]pyridine-3-carboxamide (Compound 64), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[(1R)-2-methoxy-1-methyl-ethoxy]pyridine-3-carboxamide (Compound 65), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[methyl(2,2,2-trifluoroethyl)amino]pyridine-3-carboxamide (Compound 66), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-[ethyl(methyl)amino]-6-(3-fluoro-5-isobutoxy-phenyl)pyridine-3-carboxamide (Compound 67), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(1-isopropyl-2,2-dimethyl-propoxy)pyridine-3-carboxamide (Compound 68), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-[1-ethylpropyl(methyl)amino]-6-(3-fluoro-5-isobutoxy-phenyl)pyridine-3-carboxamide (Compound 69), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-(2-ethoxy-1-methyl-ethoxy)-6-(3-fluoro-5-isobutoxy-phenyl)pyridine-3-carboxamide (Compound 71), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(2,2,2-trifluoro-1-methyl-ethoxy)pyridine-3-carboxamide (Compound 73), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-2-[ethyl(isopropyl)amino]-6-(3-fluoro-5-isobutoxy-phenyl)pyridine-3-carboxamide (Compound 74), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[methyl-[(1R)-2,2,2-trifluoro-1-methyl-ethyl]amino]pyridine-3-carboxamide (Compound 75), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl) sulfonyl]-2-(1,2-dimethylpropyl)-6-(3-fluoro-5-isobutoxyphenyl)pyridine-3-carboxamide (Compound 76), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl) sulfonyl]-2-(3,3-dimethylpentoxy)-6-(3-fluoro-5-isobutoxy-phenyl)pyridine-3-carboxamide (Compound 77), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl) sulfonyl]-6-(3-fluoro-5-isobutoxy-phenyl)-2-[(2S)-2-methoxypropoxy]pyridine-3-carboxamide (Compound 78), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises 6-(3-fluoro-5-isobutoxyphenyl)-2-[isopropyl(methyl)amino]-N-(1H-pyrazol-5-ylsulfonyl)pyridine-3-carboxamide (Compound 79), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl) sulfonyl]-6-(3-fluoro-5-isobutoxy-phenyl)-2-(3,3,3-trifluoropropoxy)pyridine-3-carboxamide (Compound 81), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl) sulfonyl]-6-(3-fluoro-5-isobutoxy-phenyl)-2-(4,4,4-trifluorobutoxy)pyridine-3-carboxamide (Compound 82), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present disclosure comprises N-[(6-amino-2-pyridyl) sulfonyl]-6-(3-fluoro-5-isobutoxy-phenyl)-2-[(E)-4,4,4-trifluorobut-2-enoxy]pyridine-3-carboxamide (Compound 83), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the above recited pharmaceutical compositions contain a pharmaceutically acceptable prodrug of the compound of the present disclosure.

In another embodiment, the pharmaceutical composition of the present disclosure comprises a) N-[(6-amino-2-pyridyl)sulfonyl]-2-[2,2-difluoroethyl(methyl)amino]-6-(3-fluoro-5-isobutoxy-phenyl)pyridine-3-carboxamide (Compound 1), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl) sulfonyl]-6-(3-fluoro-5-isobutoxy-phenyl)-2-isopentyloxypyridine-3-carboxamide (Compound 2), b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl) sulfonyl]-2-(3,3-dimethylbutoxy)-6-(3-fluoro-5-isobutoxy-phenyl)pyridine-3-carboxamide (Compound 3), b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl) sulfonyl]-2-(2-tert-butoxyethoxy)-6-(3-fluoro-5-isobutoxy-phenyl)pyridine-3-carboxamide (Compound 4), b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl) sulfonyl]-6-(3-fluoro-5-isobutoxy-phenyl)-2-isopropoxypyridine-3-carboxamide (Compound 5), b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl) sulfonyl]-6-(3-fluoro-5-isobutoxy-phenyl)-2-(2,2,3,3-tetrafluoro-1-methyl-propoxy)pyridine-3-carboxamide (Compound 6), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-5-(3-fluoro-5-isobutoxy-phenyl)-2-(trifluoromethyl)imidazo[1,2-a]pyridine-8-carboxamide (Compound 7), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(3,3,3-trifluoro-1-methyl-propoxy)pyridine-3-carboxamide (Compound 9), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-methoxy-pyridine-3-carboxamide (Compound 10), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-pentoxy-pyridine-3-carboxamide (Compound 11), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-2-(1,2-dimethylbutoxy)-6-(3-fluoro-5-isobutoxy-phenyl)pyridine-3-carboxamide (Compound 12), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-2-(2-ethoxyethoxy)-6-(3-fluoro-5-isobutoxy-phenyl)pyridine-3-carboxamide (Compound 13), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-2-[ethyl(isopropyl)amino]-6-(6-isopropoxy-3-pyridyl)pyridine-3-carboxamide (Compound 14), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-6-tert-butyl-2-(2,2-dimethylpropoxy)pyridine-3-carboxamide (Compound 15), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises 2-[ethyl(isopropyl)amino]-6-(3-fluoro-5-isobutoxy-phenyl)-N-(1H-pyrazol-5-ylsulfonyl)pyridine-3-carboxamide (Compound 16), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[methyl-[(1 S)-2,2,2-trifluoro-1-methyl-ethyl]amino]pyridine-3-carboxamide (Compound 17), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[1-(methoxymethyl)propoxy]pyridine-3-carboxamide (Compound 18), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-2-(dimethylamino)-6-(3-fluoro-5-isobutoxy-phenyl)pyridine-3-carboxamide (Compound 19), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl) sulfonyl]-6-(3-fluoro-5-isobutoxy-phenyl)-2-[(1S)-2-methoxy-1-methyl-ethoxy]pyridine-3-carboxamide (Compound 20), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl) sulfonyl]-6-(3-fluoro-5-isobutoxy-phenyl)-2-(3-methoxypropoxy)pyridine-3-carboxamide (Compound 21), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl) sulfonyl]-6-(3-fluoro-5-isobutoxy-phenyl)-2-(3-methoxy-3-methyl-butoxy)pyridine-3-carboxamide (Compound 22), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl) sulfonyl]-2-(1,3-dimethylbutoxy)-6-(3-fluoro-5-isobutoxy-phenyl)pyridine-3-carboxamide (Compound 24), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl) sulfonyl]-6-(3-fluoro-5-isobutoxy-phenyl)-2-(1,2,2-trimethylpropoxy)pyridine-3-carboxamide (Compound 25), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl) sulfonyl]-6-(3-fluoro-5-isobutoxy-phenyl)-2-(1-isopropyl-2-methyl-propoxy)pyridine-3-carboxamide (Compound 26), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl) sulfonyl]-6-(3-fluoro-5-isobutoxy-phenyl)-2-propoxy-pyridine-3-carboxamide (Compound 27), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide, or pharmaceutically acceptable salt thereof.

In another embodiment, the pharmaceutical composition of the present disclosure comprises N-[(6-amino-2-pyridyl) sulfonyl]-2-[(E)-but-2-enoxy]-6-(3-fluoro-5-isobutoxy-phenyl)pyridine-3-carboxamide (Compound 28), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl) sulfonyl]-6-(3-fluoro-5-isobutoxy-phenyl)-2-[(1S)-1-methylpropoxy]pyridine-3-carboxamide (Compound 29), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl) sulfonyl]-2-ethoxy-6-(3-fluoro-5-isobutoxy-phenyl)pyridine-3-carboxamide (Compound 30), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide, or pharmaceutically acceptable salt thereof.

In another embodiment, the pharmaceutical composition of the present disclosure comprises N-[(6-amino-2-pyridyl) sulfonyl]-6-(3-fluoro-5-isobutoxy-phenyl)-2-[isopropyl (methyl)amino]pyridine-3-carboxamide (Compound 31), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl) sulfonyl]-2-(2,2-dimethylpropoxy)-6-(3-fluoro-5-isobutoxy-phenyl)pyridine-3-carboxamide (Compound 32), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2- yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[2,2,2-trifluoro-1-(trifluoromethyl)ethoxy]pyridine-3-carboxamide (Compound 33), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-2-(diethylamino)-6-(6-isopropoxy-3-pyridyl)pyridine-3-carboxamide (Compound 34), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-pent-3-ynoxy-pyridine-3-carboxamide (Compound 35), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(1,3,3-trimethylbutoxy)pyridine-3-carboxamide (Compound 36), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-2-(1,2-dimethylprop-1-enyl)-6-(3-fluoro-5-isobutoxy-phenyl)pyridine-3-carboxamide (Compound 37), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises 6-(3-fluoro-5-isobutoxy-phenyl)-2-(propylamino)-N-[[6-(propylamino)-2-pyridyl]sulfonyl]pyridine-3-carboxamide (Compound 39), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-2-(1-ethyl-2-methyl-propoxy)-6-(3-fluoro-5-isobutoxy-phenyl)pyridine-3-carboxamide (Compound 40), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-2-(diisopropylamino)-6-(3-fluoro-5-isobutoxy-phenyl)pyridine-3-carboxamide (Compound 41), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(1-methylallyloxy)pyridine-3-carboxamide (Compound 42), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises 2-allyloxy-N-[(6-amino-2-pyridyl)sulfonyl]-6-(3-fluoro-5-isobutoxy-phenyl)pyridine-3-carboxamide (Compound 43), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-2-(1,1-dimethylpropoxy)-6-(3-fluoro-5-isobutoxy-phenyl)pyridine-3-carboxamide (Compound 44), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises 2-(diethylamino)-6-(3-fluoro-5-isobutoxy-phenyl)-N-(1H-pyrazol-5-yl sulfonyl)pyridine-3-carboxamide (Compound 46), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl) sulfonyl]-2-(1-ethylpropoxy)-6-(3-fluoro-5-isobutoxy-phenyl)pyridine-3-carboxamide (Compound 47), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl) sulfonyl]-6-(3-fluoro-5-isobutoxy-phenyl)-2-(2-methylallyloxy)pyridine-3-carboxamide (Compound 49), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl) sulfonyl]-6-(3-fluoro-5-isobutoxy-phenyl)-2-(2-methoxy-1,1-dimethyl-ethoxy)pyridine-3-carboxamide (Compound 51), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl) sulfonyl]-2-[2,2-dimethylpropyl(methyl)amino]-6-(3-fluoro-5-isobutoxy-phenyl)pyridine-3-carboxamide (Compound 52), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl) sulfonyl]-2-(diethylamino)-6-(3-fluoro-5-isobutoxy-phenyl) pyridine-3-carboxamide (Compound 53), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl) sulfonyl]-6-(3-fluoro-5-isobutoxy-phenyl)-2-(2-isopropoxyethoxy)pyridine-3-carboxamide (Compound 55), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl) sulfonyl]-6-(3-fluoro-5-isobutoxy-phenyl)-2-(1-methylbutoxy)pyridine-3-carboxamide (Compound 56), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl) sulfonyl]-2-(2,2-difluoropropoxy)-6-(3-fluoro-5-isobutoxy-phenyl)pyridine-3-carboxamide (Compound 57), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl) sulfonyl]-2-(tert-butylamino)-6-(3-fluoro-5-isobutoxy-phenyl)pyridine-3-carboxamide (Compound 58), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl) sulfonyl]-6-(3-fluoro-5-isobutoxy-phenyl)-2-[(1R)-1-methylpropoxy]pyridine-3-carboxamide (Compound 59), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl) sulfonyl]-6-(3-fluoro-5-isobutoxy-phenyl)-2-(2-methoxyethoxy)pyridine-3-carboxamide (Compound 60), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl) sulfonyl]-6-(3-fluoro-5-isobutoxy-phenyl)-2-[isobutyl (methyl)amino]pyridine-3-carboxamide (Compound 61), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2- yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-2-(1,2-dimethylpentoxy)-6-(3-fluoro-5-isobutoxy-phenyl)pyridine-3-carboxamide (Compound 62), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-2-butoxy-6-(3-fluoro-5-isobutoxy-phenyl)pyridine-3-carboxamide (Compound 63), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[methyl(propyl)amino]pyridine-3-carboxamide (Compound 64), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[(1R)-2-methoxy-1-methyl-ethoxy]pyridine-3-carboxamide (Compound 65), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[methyl(2,2,2-trifluoroethyl)amino]pyridine-3-carboxamide (Compound 66), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-2-[ethyl(methyl)amino]-6-(3-fluoro-5-isobutoxy-phenyl)pyridine-3-carboxamide (Compound 67), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(1-isopropyl-2,2-dimethyl-propoxy)pyridine-3-carboxamide (Compound 68), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-2-[1-ethylpropyl(methyl)amino]-6-(3-fluoro-5-isobutoxy-phenyl)pyridine-3-carboxamide (Compound 69), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-2-(2-ethoxy-1-methyl-ethoxy)-6-(3-fluoro-5-isobutoxy-phenyl)pyridine-3-carboxamide (Compound 71), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(2,2,2-trifluoro-1-methyl-ethoxy)pyridine-3-carboxamide (Compound 73), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-2-[ethyl(isopropyl)amino]-6-(3-fluoro-5-isobutoxy-phenyl)pyridine-3-carboxamide (Compound 74), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[methyl-[(1R)-2,2,2-trifluoro-1-methyl-ethyl]amino]pyridine-3-carboxamide (Compound 75), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1- hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-2-(1,2-dimethylpropyl)-6-(3-fluoro-5-isobutoxy-phenyl)pyridine-3-carboxamide (Compound 76), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-2-(3,3-dimethylpentoxy)-6-(3-fluoro-5-isobutoxy-phenyl)pyridine-3-carboxamide (Compound 77), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[(2S)-2-methoxypropoxy]pyridine-3-carboxamide (Compound 78), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises 6-(3-fluoro-5-isobutoxy-phenyl)-2-[isopropyl(methyl)amino]-N-(1H-pyrazol-5-ylsulfonyl)pyridine-3-carboxamide (Compound 79), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(3,3,3-trifluoropropoxy)pyridine-3-carboxamide (Compound 81), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-(4,4,4-trifluorobutoxy)pyridine-3-carboxamide (Compound 82), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present disclosure comprises N-[(6-amino-2-pyridyl)sulfonyl]-6-(3-fluoro-5-isobutoxy-phenyl)-2-[(E)-4,4,4-trifluorobut-2-enoxy]pyridine-3-carboxamide (Compound 83), or pharmaceutically acceptable salt thereof; b) N-(5-hydroxy-2,4-ditert-butyl-phenyl)-4-oxo-1H-quinoline-3-carboxamide, or pharmaceutically acceptable salt thereof; and c) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the above recited pharmaceutical compositions contain a pharmaceutically acceptable prodrug of the compound of the present disclosure.

In another embodiment, the present disclosure features a pharmaceutical composition comprising a) a compound of formulas I to IIa-ii-2, or pharmaceutically acceptable salt thereof; b) a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide, or 4-(3-(1-(2,2-difluorobenzo[d][1,3]dioxol-5-yl)cyclopropanecarboxamido) isoquinolin-1-yl)benzoic acid; and c) an additional CFTR corrector.

In another embodiment, the present disclosure features a pharmaceutical composition comprising a) a compound of Table 1, or pharmaceutically acceptable salt thereof; b) a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide, or 4-(3-(1-(2,2-difluorobenzo[d][1,3]dioxol-5-yl)cyclopropanecarboxamido) isoquinolin-1-yl)benzoic acid; and c) an additional CFTR corrector.

In another embodiment, the above recited pharmaceutical composition contain a pharmaceutically acceptable prodrug of the compound of the present disclosure.

In another embodiment, the additional CFTR corrector from above is (N-(2-(5-chloro-2-methoxy-phenylamino)-4'-methyl-[4,5']bithiazolyl-2'-yl)-benzamide (corr-4a). In another embodiment, the additional CFTR corrector is a compound disclosed in published International Patent Application WO2014081820 or U.S. Pat. No. 9,221,840, incorporated herein in its entirety by reference.

In another embodiment, the present disclosure features a pharmaceutical composition comprising a) a compound of formulas I to IIa-ii-2, or pharmaceutically acceptable salt thereof; b) N-(5-hydroxy-2,4-ditert-butyl-phenyl)-4-oxo-1H-quinoline-3-carboxamide or N-(4-(7-azabicyclo[2.21]heptan-7-yl)-2-(trifluoromethyl)phenyl)-4-oxo-5-(trifluoromethyl)-1,4-dihydroquinoline-3-carboxamide; and a CFTR corrector selected from (N-(2-(5-chloro-2-methoxy-phenylamino)-4'-methyl-[4,5']bithiazolyl-2'-yl)-benzamide (corr-4a), a compound disclosed in published International Patent Application WO2014081820 incorporated herein in its entirety by reference, a compound disclosed in Published International Patent Application No. WO2014086687, or a compound disclosed in U.S. Pat. No. 8,247,436 or 8,476,269; U.S. patent application Ser. No. 13/923,349; or Published International Patent Application No: WO2011113894, WO2013038373, WO2013038378, WO2013038381, WO2013038386, or WO2013038390; all US patents, US patent applications, and published international patent applications are hereby incorporated in their entirety by reference.

In another embodiment, the present disclosure features a pharmaceutical composition comprising a) a compound of formulas I to IIa-ii-2, or pharmaceutically acceptable salt thereof; b) a compound selected from certain flavones and isoflavones, such as genistein, which are capable of stimulating CFTR-mediated chloride transport in epithelial tissues in a cyclic-AMP independent manner (See U.S. Pat. No. 6,329,422, incorporated herein by reference in its entirety); phenylglycine-01 (2-[(2-1H-indol-3-yl-acetyl)-methylamino]-N-(4-isopropylphenyl)-2-phenylacetamide); felodipine (Ethyl methyl 4-(2,3-dichlorophenyl)-2,6-dimethyl-1,4-dihydro-3,5-pyridinedicarboxylate); sulfonamide SF-01 (6-(ethylphenylsulfamoyl)-4-oxo-1,4-dihydroquinoline-3-carboxylic acid cycloheptylamine); and UCCF-152 (3-[2-(benzyloxy)phenyl]-5-(chloromethyl)isoxazole); and c) a CFTR corrector selected from (N-(2-(5-chloro-2-methoxyphenylamino)-4'-methyl-[4,5']bithiazolyl-2'-yl)-benzamide (corr-4a), a compound disclosed in published International Patent Application WO2014081820 incorporated herein in its entirety by reference, or a compound disclosed in U.S. Pat. No. 8,247,436 or 8,476,269; U.S. patent application Ser. No. 13/923,349; or Published International Patent Application No: WO2011113894, WO2013038373, WO2013038378, WO2013038381, WO2013038386, or WO2013038390; all US patents, US patent applications, and published international patent applications are hereby incorporated in their entirety by reference.

In another embodiment, the present disclosure features the pharmaceutical composition described above comprising a) a compound of formulas I to IIa-ii-2, or pharmaceutically acceptable salt thereof; b) a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or 4-(3-(1-(2,2-difluorobenzo[d][1,3]dioxol-5-yl) cyclopropanecarboxamido) isoquinolin-1-yl)benzoic acid; and c) an additional CFTR corrector, such as those, for example, specifically listed above; and further comprising d) a CFTR potentiator.

In another embodiment, the CFTR potentiator from above is N-(5-hydroxy-2,4-ditert-butyl-phenyl)-4-oxo-1H-quinoline-3-carboxamide or N-(4-(7-azabicyclo[2.21]heptan-7-yl)-2-(trifluoromethyl)phenyl)-4-oxo-5-(trifluoromethyl)-1,4-dihydroquinoline-3-carboxamide. In another embodiment, the CFTR potentiator from above is N-(5-hydroxy-2,4-ditert-butyl-phenyl)-4-oxo-1H-quinoline-3-carboxamide.

In another embodiment, the CFTR potentiator from above is selected from certain flavones and isoflavones, such as genistein, which are capable of stimulating CFTR-mediated chloride transport in epithelial tissues in a cyclic-AMP independent manner (See U.S. Pat. No. 6,329,422, incorporated herein by reference in its entirety); phenylglycine-01 (2-[(2-1H-indol-3-yl-acetyl)-methylamino]-N-(4-isopropylphenyl)-2-phenylacetamide); felodipine (Ethyl methyl 4-(2,3-dichlorophenyl)-2,6-dimethyl-1,4-dihydro-3,5-pyridinedicarboxylate); sulfonamide SF-01 (6-(ethylphenylsulfamoyl)-4-oxo-1,4-dihydroquinoline-3-carboxylic acid cycloheptylamine); and UCCF-152 (3-[2-(benzyloxy)phenyl]-5-(chloromethyl)isoxazole).

In one embodiment, the additional therapeutic agent is selected from a compound disclosed in Published International Patent Application No. WO2014078842 or WO2012158885, or in United States Published Application No. US20140073667; all published international patent applications and published US patent application are hereby incorporated in their entirety by reference.

In one embodiment, the additional therapeutic agent is selected from a compound disclosed in Published International Patent Application No: WO2012078909; WO2012154880; WO2012154888; WO2012154967; WO2013112651; WO2013112699; WO2012078902; WO2015138934, WO2015138909; or WO2015196071, all published international patent applications are hereby incorporated in their entirety by reference.

In one embodiment, the additional therapeutic agent is selected from a compound disclosed in U.S. Pat. No. 8,247,436 or 8,476,269; U.S. patent application Ser. No. 13/923,349; and Published International Patent Application No: WO2011113894, WO2013038373, WO2013038378, WO2013038381, WO2013038386, or WO2013038390; all US patents, US patent applications, and published international patent applications are hereby incorporated in their entirety by reference.

In one embodiment, the additional therapeutic agent is selected from a compound disclosed in WO2014210159 or WO2014152213; all published international patent applications are hereby incorporated in their entirety by reference.

In one embodiment, the additional therapeutic agent is selected from a compound disclosed in Published International Patent Application No.: WO2015003083, WO2015007517, WO2015007519, or WO2015007516; all published international patent applications are hereby incorporated in their entirety by reference.

In another embodiment, the disclosure features a pharmaceutical composition comprising a) a compound of formulas I to IIa-ii-2, or pharmaceutically acceptable salt thereof; b) 3-(6-(1-(2,2-difluorobenzo[d][1,3]dioxol-5-yl) cyclopropanecarboxamido)-3-methylpyridin-2-yl)benzoic acid; and c) a compound disclosed in U.S. Pat. No. 8,247,436 or 8,476,269; U.S. patent application Ser. No. 13/923,349; and Published International Patent Application No: WO2011113894, WO2013038373, WO2013038378, WO2013038381, WO2013038386, or WO2013038390; all US patents, US patent applications, and published international patent applications are hereby incorporated in their entirety by reference.

In another embodiment, the disclosure features a pharmaceutical composition comprising a) a compound of formulas I to IIa-ii-2, or pharmaceutically acceptable salt thereof; b) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide; and c) a compound disclosed in U.S. Pat. No. 8,247,436 or 8,476,269; U.S. patent application Ser. No. 13/923,349; and Published International Patent Application No: WO2011113894, WO2013038373, WO2013038378, WO2013038381, WO2013038386, or WO2013038390; all US patents, US patent applications, and published international patent applications are hereby incorporated in their entirety by reference.

In another embodiment, the disclosure features a pharmaceutical composition comprising a) a compound of formulas I to IIa-ii-2, or pharmaceutically acceptable salt thereof; b) 4-(3-(1-(2,2-difluorobenzo[d][1,3]dioxol-5-yl) cyclopropanecarboxamido) isoquinolin-1-yl)benzoic acid; and c) a compound disclosed in U.S. Pat. No. 8,247,436 or 8,476,269; U.S. patent application Ser. No. 13/923,349; and Published International Patent Application No: WO2011113894, WO2013038373, WO2013038378, WO2013038381, WO2013038386, or WO2013038390; all US patents, US patent applications, and published international patent applications are hereby incorporated in their entirety by reference.

In another embodiment, the disclosure features a pharmaceutical composition comprising a) a compound of formulas I to IIa-ii-2, or pharmaceutically acceptable salt thereof; b) a compound disclosed in U.S. Pat. No. 8,247,436 or 8,476,269; U.S. patent application Ser. No. 13/923,349; and Published International Patent Application No: WO2011113894, WO2013038373, WO2013038378, WO2013038381, WO2013038386, or WO2013038390; all US patents, US patent applications, and published international patent applications are hereby incorporated in their entirety by reference; and c) N-(5-hydroxy-2,4-ditert-butyl-phenyl)-4-oxo-1H-quinoline-3-carboxamide.

In another embodiment, the disclosure features a pharmaceutical composition comprising a) a compound of formulas I to IIa-ii-2, or pharmaceutically acceptable salt thereof; b) 3-(6-(1-(2,2-difluorobenzo[d][1,3]dioxol-5-yl) cyclopropanecarboxamido)-3-methylpyridin-2-yl)benzoic acid; c) a compound disclosed in U.S. Pat. No. 8,247,436 or 8,476,269; U.S. patent application Ser. No. 13/923,349; and Published International Patent Application No: WO2011113894, WO2013038373, WO2013038378, WO2013038381, WO2013038386, or WO2013038390; all US patents, US patent applications, and published international patent applications are hereby incorporated in their entirety by reference; and d) N-(5-hydroxy-2,4-ditert-butyl-phenyl)-4-oxo-1H-quinoline-3-carboxamide.

In another embodiment, the disclosure features a pharmaceutical composition comprising a) a compound of formulas I to IIa-ii-2, or pharmaceutically acceptable salt thereof; b) (R)-1-(2,2-difluorobenzo[d][1,3]dioxol-5-yl)-N-(1-(2,3-dihydroxypropyl)-6-fluoro-2-(1-hydroxy-2-methyl-propan-2-yl)-1H-indol-5-yl)cyclopropanecarboxamide; c) a compound disclosed in U.S. Pat. No. 8,247,436 or 8,476,269; U.S. patent application Ser. No. 13/923,349; and Published International Patent Application No: WO2011113894, WO2013038373, WO2013038378, WO2013038381, WO2013038386, or WO2013038390; all US patents, US patent applications, and published international patent applications are hereby incorporated in their entirety by reference; and d) N-(5-hydroxy-2,4-ditert-butyl-phenyl)-4-oxo-1H-quinoline-3-carboxamide.

In another embodiment, the disclosure features a pharmaceutical composition comprising a) a compound of formulas I to IIa-ii-2, or pharmaceutically acceptable salt thereof; b) 4-(3-(1-(2,2-difluorobenzo[d][1,3]dioxol-5-yl) cyclopropanecarboxamido) isoquinolin-1-yl)benzoic acid; c) a compound disclosed in U.S. Pat. No. 8,247,436 or 8,476,269; U.S. patent application Ser. No. 13/923,349; and Published International Patent Application No: WO2011113894, WO2013038373, WO2013038378, WO2013038381, WO2013038386, or WO2013038390; all US patents, US patent applications, and published international patent applications are hereby incorporated in their entirety by reference; and d) N-(5-hydroxy-2,4-ditert-butyl-phenyl)-4-oxo-1H-quinoline-3-carboxamide.

In another embodiment, the disclosure features a pharmaceutical composition comprising a) a compound of formulas I to IIa-ii-2, or pharmaceutically acceptable salt thereof; b) 3-(6-(1-(2,2-difluorobenzo[d][1,3]dioxol-5-yl) cyclopropanecarboxamido)-3-methylpyridin-2-yl)benzoic acid; and c) a compound disclosed in Published International Patent Application No: WO2012078909; WO2012154880; WO2012154888; WO2012154967; WO2013112651; WO2013112699; or WO2012078902; all published international patent applications are hereby incorporated in their entirety by reference.

In another embodiment, the disclosure features a pharmaceutical composition comprising a) a compound of formulas I to IIa-ii-2, or pharmaceutically acceptable salt thereof; b) (R)-1-(2,2-difluorobenzo[d][1,3]dioxol-5-yl)-N-(1-(2,3-dihydroxypropyl)-6-fluoro-2-(1-hydroxy-2-methyl-propan-2-yl)-1H-indol-5-yl)cyclopropanecarboxamide; and c) a compound disclosed in Published International Patent Application No: WO2012078909; WO2012154880; WO2012154888; WO2012154967; WO2013112651; WO2013112699; or WO2012078902; all published international patent applications are hereby incorporated in their entirety by reference.

In another embodiment, the disclosure features a pharmaceutical composition comprising a) a compound of formulas I to IIa-ii-2, or pharmaceutically acceptable salt thereof; b) 4-(3-(1-(2,2-difluorobenzo[d][1,3]dioxol-5-yl) cyclopropanecarboxamido) isoquinolin-1-yl)benzoic acid; and c) a compound disclosed in Published International Patent Application No: WO2012078909; WO2012154880; WO2012154888; WO2012154967; WO2013112651; WO2013112699; or WO2012078902; all published international patent applications are hereby incorporated in their entirety by reference.

In another embodiment, the disclosure features a pharmaceutical composition comprising a) a compound of formulas I to IIa-ii-2, or pharmaceutically acceptable salt thereof; b) 3-(6-(1-(2,2-difluorobenzo[d][1,3]dioxol-5-yl) cyclopropanecarboxamido)-3-methylpyridin-2-yl)benzoic acid; c) a compound disclosed in Published International Patent Application No: WO2012078909; WO2012154880; WO2012154888; WO2012154967; WO2013112651; WO2013112699; or WO2012078902; all published international patent applications are hereby incorporated in their entirety by reference; and d) N-(5-hydroxy-2,4-ditert-butyl-phenyl)-4-oxo-1H-quinoline-3-carboxamide.

In another embodiment, the disclosure features a pharmaceutical composition comprising a) a compound of formulas I to IIa-ii-2, or pharmaceutically acceptable salt thereof; b) (R)-1-(2,2-difluorobenzo[d][1,3]dioxol-5-yl)-N-(1-(2,3-dihydroxypropyl)-6-fluoro-2-(1-hydroxy-2-methyl-propan-2-yl)-1H-indol-5-yl)cyclopropanecarboxamide; c) a compound disclosed in Published International Patent Application No: WO2012078909; WO2012154880; WO2012154888; WO2012154967; WO2013112651; WO2013112699; or WO2012078902; all published international patent applications are hereby incorporated in their entirety by reference; and d) N-(5-hydroxy-2,4-ditert-butyl-phenyl)-4-oxo-1H-quinoline-3-carboxamide.

In another embodiment, the disclosure features a pharmaceutical composition comprising a) a compound of formulas I to IIa-ii-2, or pharmaceutically acceptable salt thereof; b) 4-(3-(1-(2,2-difluorobenzo[d][1,3]dioxol-5-yl) cyclopropanecarboxamido) isoquinolin-1-yl)benzoic acid; c) a compound disclosed in Published International Patent Application No: WO2012078909; WO2012154880; WO2012154888; WO2012154967; WO2013112651; WO2013112699; or WO2012078902; all published international patent applications are hereby incorporated in their entirety by reference; and d) N-(5-hydroxy-2,4-ditert-butyl-phenyl)-4-oxo-1H-quinoline-3-carboxamide.

In another embodiment, the additional therapeutic agent is a compound disclosed in Published International Patent Application No. WO2014099673 hereby incorporated in its entirety by reference, including but not limited to the following compounds:

P-1
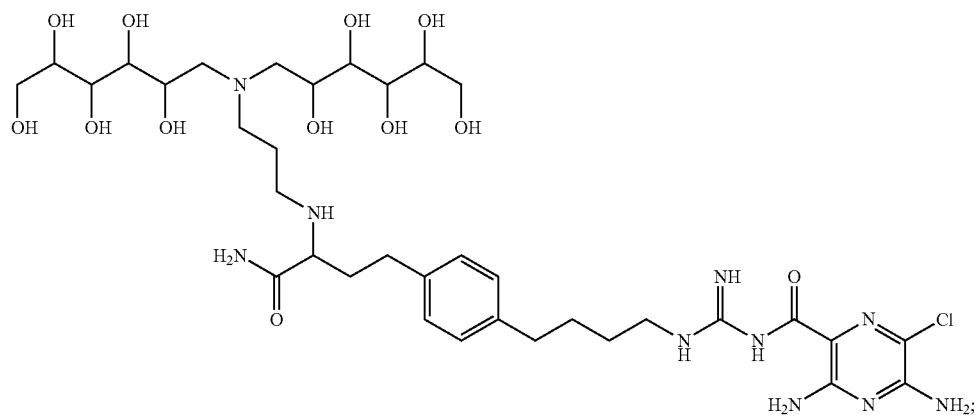
P-2
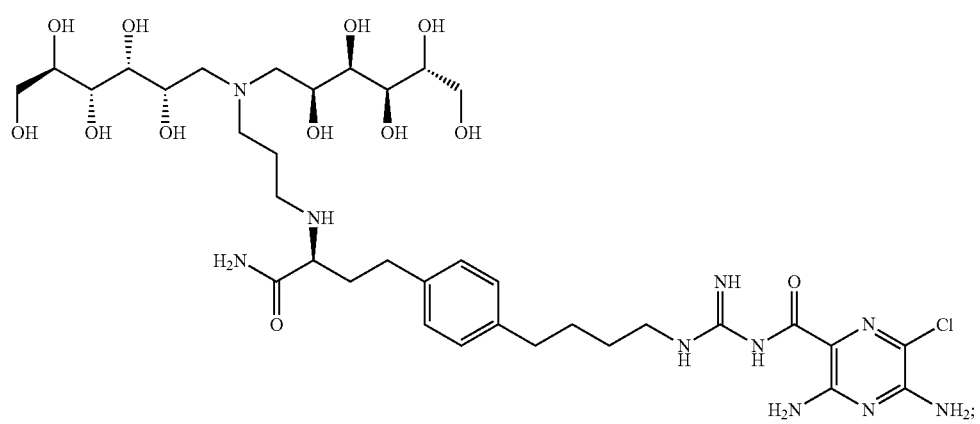
P-3
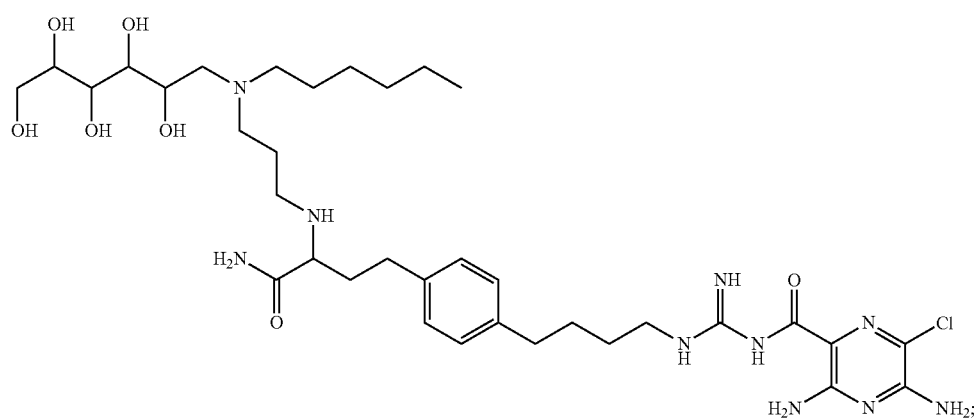
P-4
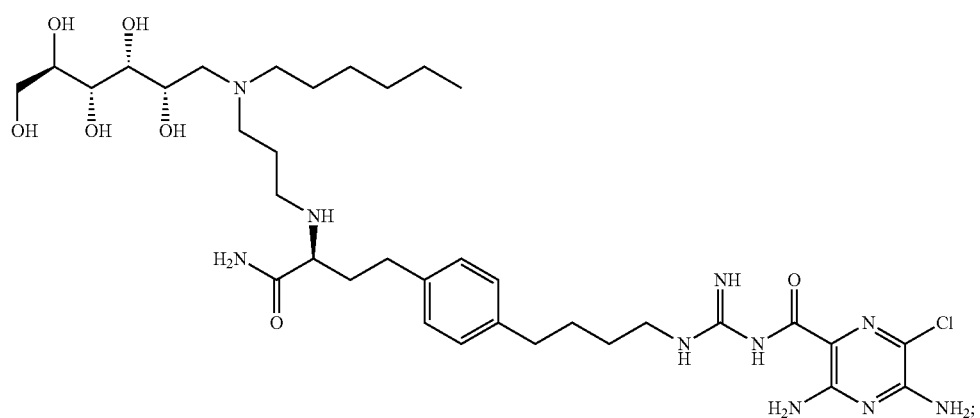

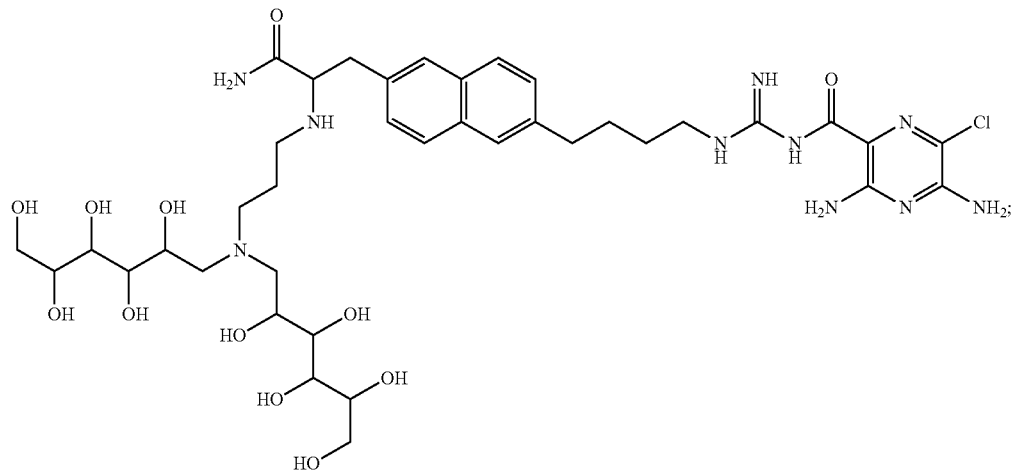
P-5
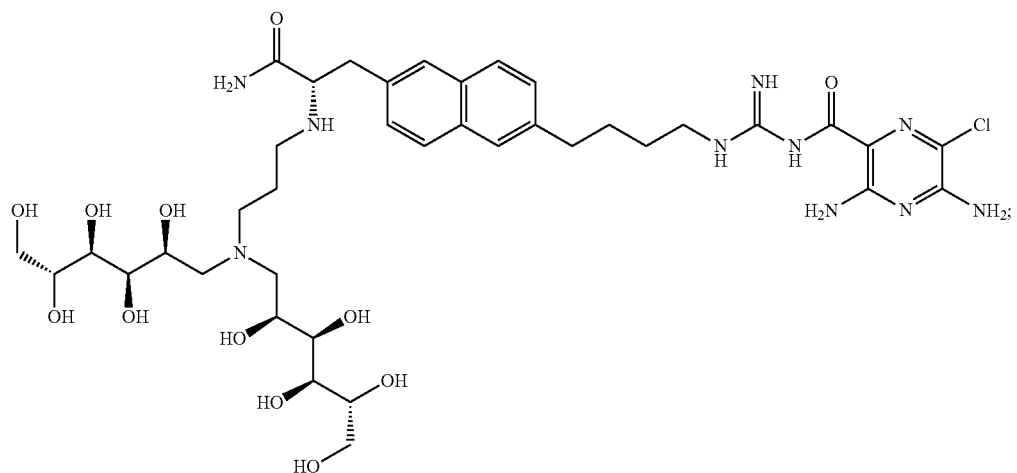
P-6
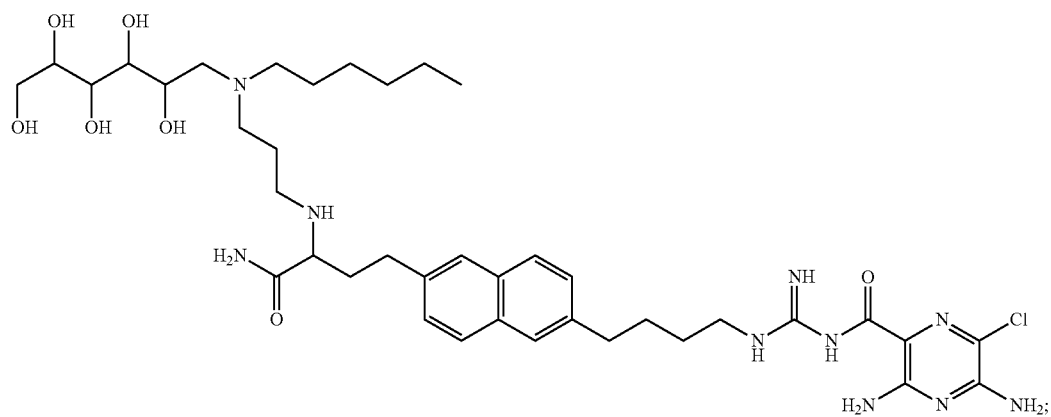
P-7

-continued
P-8
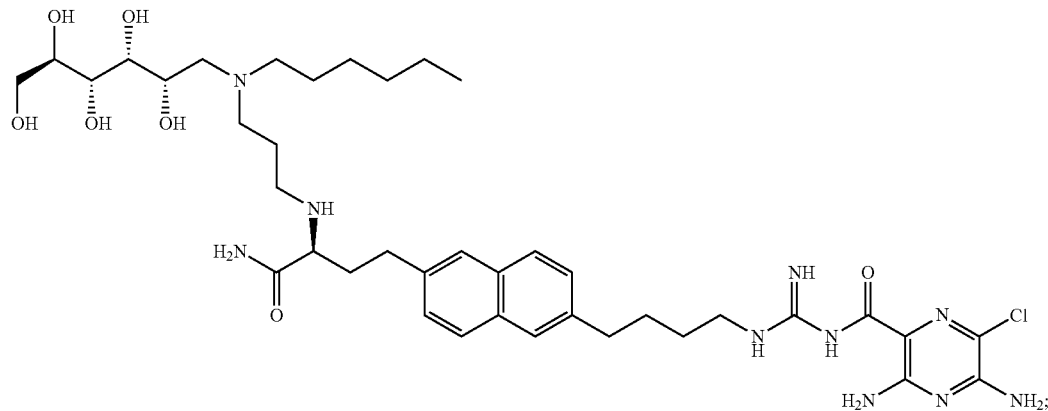
P-9
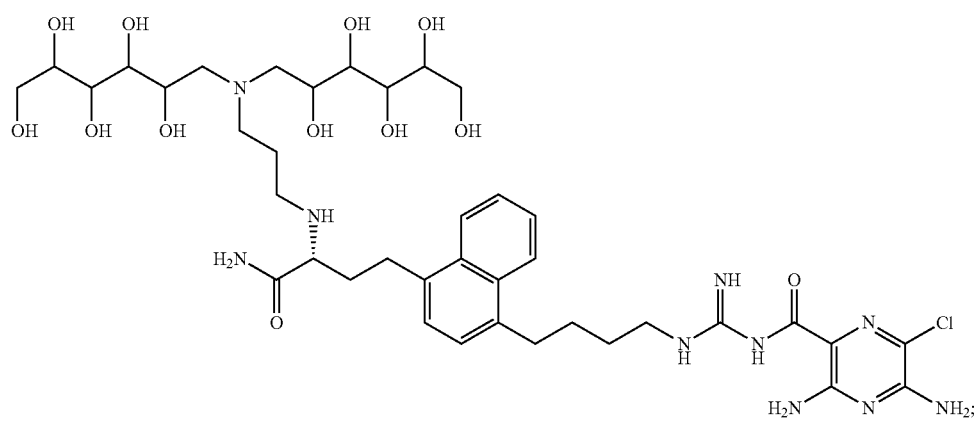
P-10
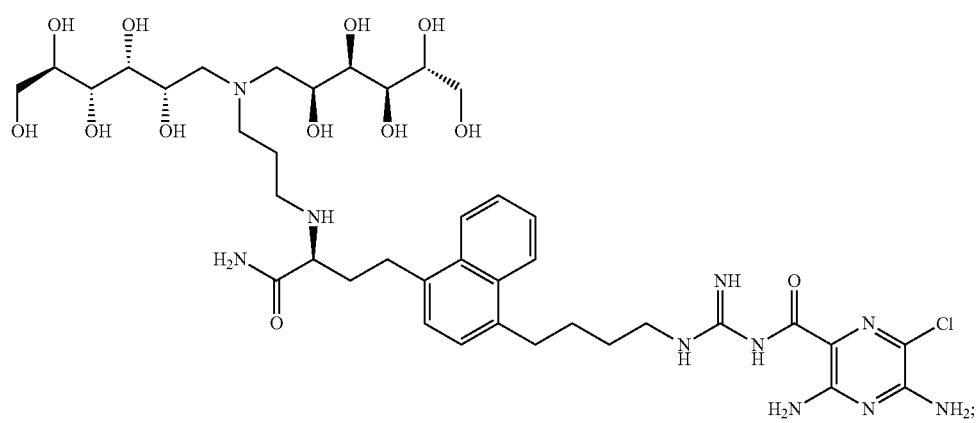
P-11
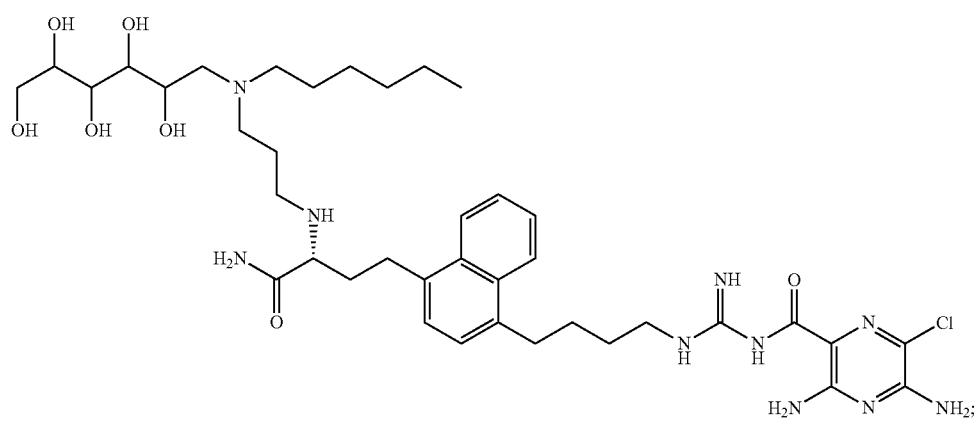

-continued
P-12
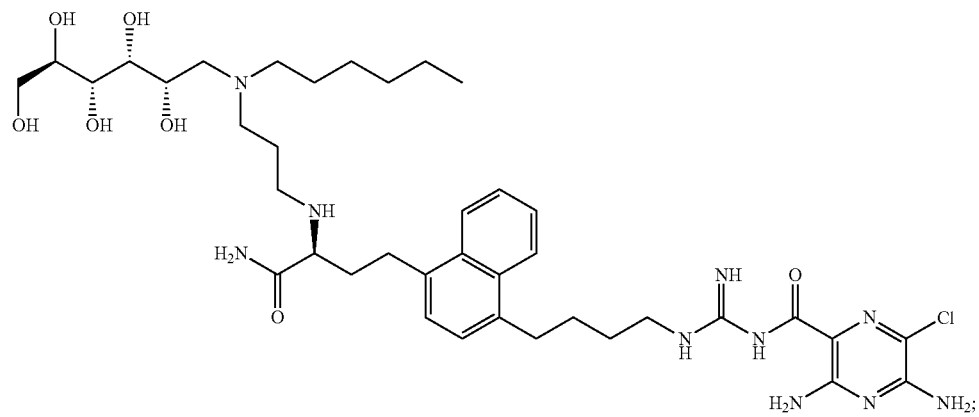
P-13
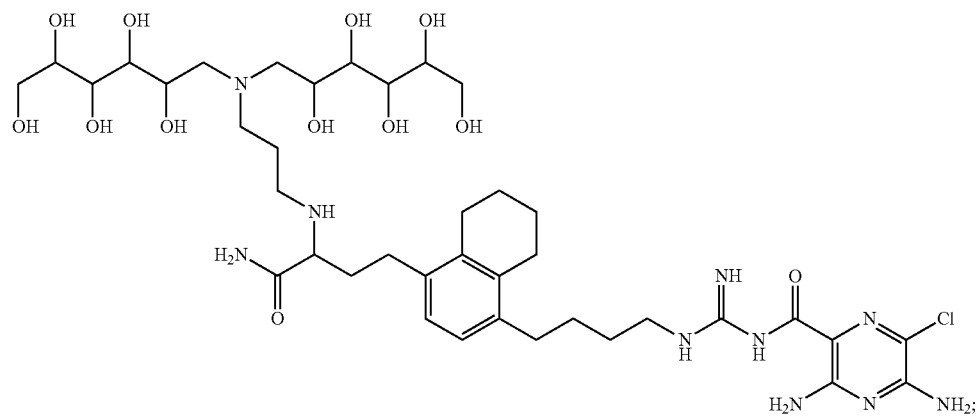
P-14
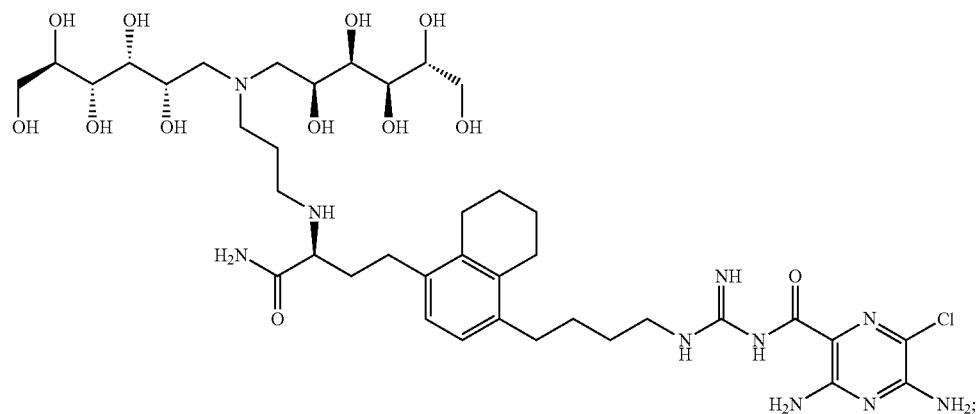
P-15
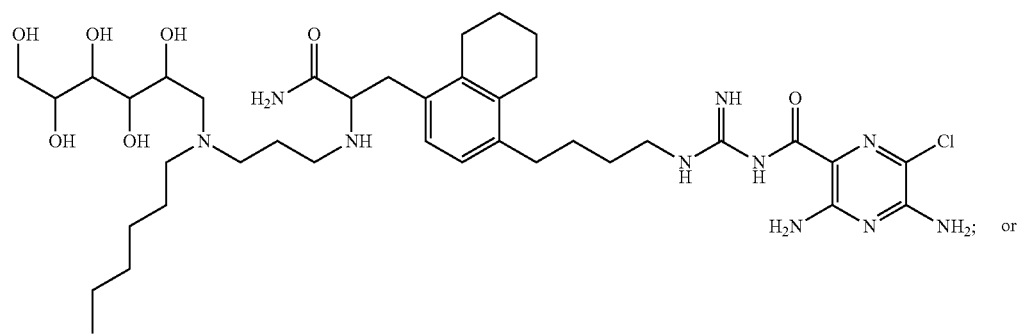
or

P-16

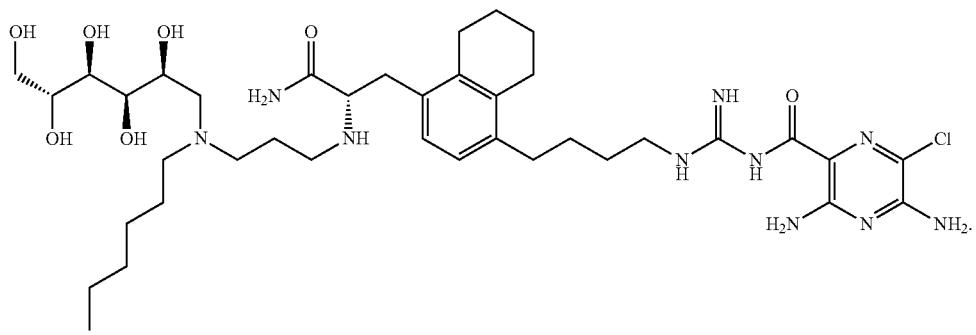

In another embodiment, the disclosure features a pharmaceutical composition comprising a) a compound of formulas I to IIa-ii-2, or pharmaceutically acceptable salt thereof; b) 3-(6-(1-(2,2-difluorobenzo[d][1,3]dioxol-5-yl) cyclopropanecarboxamido)-3-methylpyridin-2-yl)benzoic acid; and c) a compound selected from P-1 to P-16 disclosed above.

In another embodiment, the disclosure features a pharmaceutical composition comprising a) a compound of Table 1, or pharmaceutically acceptable salt thereof; b) 3-(6-(1-(2,2-difluorobenzo[d][1,3]dioxol-5-yl) cyclopropanecarboxamido)-3-methylpyridin-2-yl)benzoic acid; and c) a compound selected from P-1 to P-16 disclosed above.

In another embodiment, the disclosure features a pharmaceutical composition comprising a) a compound of formulas I to IIa-ii-2, or pharmaceutically acceptable salt thereof; b) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide; and c) a compound selected from P-1 to P-16 disclosed above.

In another embodiment, the disclosure features a pharmaceutical composition comprising a) a compound of Table 1, or pharmaceutically acceptable salt thereof; b) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide; and c) a compound selected from P-1 to P-16 disclosed above.

In another embodiment, the disclosure features a pharmaceutical composition comprising a) a compound of formulas I to IIa-ii-2, or pharmaceutically acceptable salt thereof; b) 4-(3-(1-(2,2-difluorobenzo[d][1,3]dioxol-5-yl) cyclopropanecarboxamido) isoquinolin-1-yl)benzoic acid; and c) a compound selected from P-1 to P-16 disclosed above.

In another embodiment, the disclosure features a pharmaceutical composition comprising a) a compound of Table 1, or pharmaceutically acceptable salt thereof; b) 4-(3-(1-(2,2-difluorobenzo[d][1,3]dioxol-5-yl)cyclopropanecarboxamido) isoquinolin-1-yl)benzoic acid; and c) a compound selected from P-1 to P-16 disclosed above.

In another embodiment, the disclosure features a pharmaceutical composition comprising a) a compound of formulas I to IIa-ii-2, or pharmaceutically acceptable salt thereof; b) 3-(6-(1-(2,2-difluorobenzo[d][1,3]dioxol-5-yl) cyclopropanecarboxamido)-3-methylpyridin-2-yl)benzoic acid; c) a compound selected from P-1 to P-16 disclosed above; and d) N-(5-hydroxy-2,4-ditert-butyl-phenyl)-4-oxo-1H-quinoline-3-carboxamide.

In another embodiment, the disclosure features a pharmaceutical composition comprising a) a compound of Table 1, or pharmaceutically acceptable salt thereof; b) 3-(6-(1-(2,2-difluorobenzo[d][1,3]dioxol-5-yl) cyclopropanecarboxamido)-3-methylpyridin-2-yl)benzoic acid; c) a compound selected from P-1 to P-16 disclosed above; and d) N-(5-hydroxy-2,4-ditert-butyl-phenyl)-4-oxo-1H-quinoline-3-carboxamide.

In another embodiment, the disclosure features a pharmaceutical composition comprising a) a compound of formulas I to IIa-ii-2, or pharmaceutically acceptable salt thereof; b) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide; c) a compound selected from P-1 to P-16 disclosed above; and d) N-(5-hydroxy-2,4-ditert-butyl-phenyl)-4-oxo-1H-quinoline-3-carboxamide.

In another embodiment, the disclosure features a pharmaceutical composition comprising a) a compound of formulas I to IIa-ii-2, or pharmaceutically acceptable salt thereof; b) 4-(3-(1-(2,2-difluorobenzo[d][1,3]dioxol-5-yl) cyclopropanecarboxamido) isoquinolin-1-yl)benzoic acid; c) a compound selected from P-1 to P-16 disclosed above; and d) N-(5-hydroxy-2,4-ditert-butyl-phenyl)-4-oxo-1H-quinoline-3-carboxamide.

In another embodiment, the above recited pharmaceutical compositions contain a pharmaceutically acceptable prodrug of the compound of the present disclosure.

In some embodiments, the disclosure features a pharmaceutical composition comprising a) a compound of formulas I to IIa-ii-2, or pharmaceutically acceptable salt thereof; and b) a compound disclosed in U.S. Pat. No. 8,865,902. In some embodiments, the disclosure features a pharmaceutical composition comprising a) a compound of Table 1, or pharmaceutically acceptable salt thereof; and b) a compound disclosed in U.S. Pat. No. 8,865,902. In another embodiment, the compound disclosed in U.S. Pat. No. 8,865,902 has the following structure:

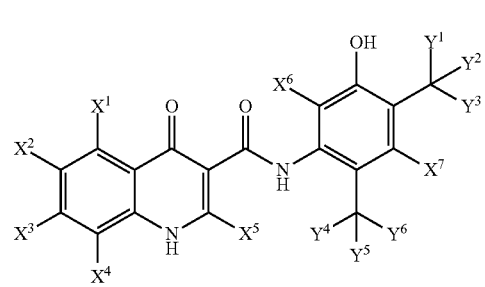

wherein the compound disclosed in U.S. Pat. No. 8,865,902 is any one of the compounds of the following table:

| $X^1$ | $X^2$ | $X^3$ | $X^4$ | $X^5$ | $X^6$ | $X^7$ | $Y^1$ | $Y^2$ | $Y^3$ | $Y^4$ | $Y^5$ | $Y^6$ |
|---|---|---|---|---|---|---|---|---|---|---|---|---|
| D | D | D | D | D | D | D | $CD_3$ | $CD_3$ | $CD_3$ | $CD_3$ | $CD_3$ | $CD_3$ |
| H | H | H | H | D | H | H | $CD_3$ | $CD_3$ | $CD_3$ | $CD_3$ | $CD_3$ | $CD_3$ |
| H | H | H | H | D | H | H | $CH_3$ | $CH_3$ | $CH_3$ | $CD_3$ | $CD_3$ | $CH_3$ |
| H | H | H | H | D | H | H | $CH_3$ | $CH_3$ | $CH_3$ | $CD_3$ | $CD_3$ | $CD_3$ |
| H | H | H | H | D | H | H | $CH_3$ | $CH_3$ | $CH_3$ | $CH_3$ | $CH_3$ | $CH_3$ |
| H | H | H | H | H | H | H | $CD_3$ | $CD_3$ | $CD_3$ | $CD_3$ | $CD_3$ | $CD_3$ |
| H | H | H | H | H | H | H | $CD_3$ | $CD_3$ | $CD_3$ | $CD_3$ | $CD_3$ | $CD_3$ |
| H | H | H | H | H | H | H | $CH_3$ | $CH_3$ | $CH_3$ | $CD_3$ | $CD_3$ | $CD_3$ |

In another embodiment, the compound disclosed in U.S. Pat. No. 8,865,902 is any one of the compounds of the following table:

| $X^1$ | $X^2$ | $X^3$ | $X^4$ | $X^5$ | $X^6$ | $X^7$ | $Y^1$ | $Y^2$ | $Y^3$ | $Y^4$ | $Y^5$ | $Y^6$ |
|---|---|---|---|---|---|---|---|---|---|---|---|---|
| H | H | H | H | H | D | D | $CD_3$ | $CD_3$ | $CD_3$ | $CD_3$ | $CD_3$ | $CD_3$ |
| H | H | H | H | D | D | D | $CD_3$ | $CD_3$ | $CD_3$ | $CD_3$ | $CD_3$ | $CD_3$ |
| H | H | H | H | D | D | D | $CH_3$ | $CH_3$ | $CH_3$ | $CD_3$ | $CD_3$ | $CH_3$ |
| H | H | H | H | D | D | D | $CH_3$ | $CH_3$ | $CH_3$ | $CD_3$ | $CD_3$ | $CD_3$ |
| H | H | H | H | D | D | D | $CH_3$ | $CH_3$ | $CH_3$ | $CH_3$ | $CH_3$ | $CH_3$ |
| H | H | H | H | H | D | D | $CD_3$ | $CD_3$ | $CD_3$ | $CH_3$ | $CH_3$ | $CH_3$ |
| H | H | H | H | H | D | D | $CD_3$ | $CD_3$ | $CD_3$ | $CD_3$ | $CD_3$ | $CD_3$ |
| D | D | D | D | D | D | D | $CD_3$ | $CD_3$ | $CD_3$ | $CH_3$ | $CH_3$ | $CH_3$ |
| D | D | D | D | D | D | D | $CH_3$ | $CH_3$ | $CH_3$ | $CD_3$ | $CD_3$ | $CD_3$ |
| D | D | D | D | D | H | H | $CD_3$ | $CD_3$ | $CD_3$ | $CH_3$ | $CH_3$ | $CH_3$ |
| D | D | D | D | D | H | H | $CD_3$ | $CD_3$ | $CD_3$ | $CD_3$ | $CD_3$ | $CD_3$ |
| H | H | H | H | H | H | D | $CD_3$ | $CD_3$ | $CD_3$ | $CD_3$ | $CD_3$ | $CD_3$ |
| H | H | H | H | H | H | D | $CD_3$ | $CD_3$ | $CD_3$ | $CH_3$ | $CH_3$ | $CH_3$ |
| H | H | H | H | H | H | D | $CH_3$ | $CH_3$ | $CH_3$ | $CD_3$ | $CD_3$ | $CD_3$ |
| H | H | H | H | D | H | H | $CD_3$ | $CD_3$ | $CD_3$ | $CD_3$ | $CD_3$ | $CD_3$ |
| H | H | H | H | D | H | H | $CD_3$ | $CD_3$ | $CD_3$ | $CH_3$ | $CH_3$ | $CH_3$ |
| H | H | H | H | D | H | H | $CH_3$ | $CH_3$ | $CH_3$ | $CD_3$ | $CD_3$ | $CD_3$ |
| H | H | H | H | D | H | H | $CH_3$ | $CH_3$ | $CH_3$ | $CD_3$ | $CD_3$ | $CD_3$ |

In another embodiment, the compound disclosed in U.S. Pat. No. 8,865,902 is any one of the compounds of the following table:

| $X^1$ | $X^2$ | $X^3$ | $X^4$ | $X^5$ | $X^6$ | $X^7$ | $Y^1$ | $Y^2$ | $Y^3$ | $Y^4$ | $Y^5$ | $Y^6$ |
|---|---|---|---|---|---|---|---|---|---|---|---|---|
| D | D | D | D | D | H | H | $CD_3$ | $CD_3$ | $CD_3$ | $CD_3$ | $CD_3$ | $CD_3$ |
| D | D | D | D | D | D | D | $CH_3$ | $CH_3$ | $CH_3$ | $CH_3$ | $CH_3$ | $CH_3$ |
| D | D | D | D | D | H | H | $CH_3$ | $CH_3$ | $CH_3$ | $CH_3$ | $CH_3$ | $CH_3$ |
| D | D | D | D | H | D | D | $CD_3$ | $CD_3$ | $CD_3$ | $CD_3$ | $CD_3$ | $CD_3$ |
| D | D | D | D | H | H | H | $CD_3$ | $CD_3$ | $CD_3$ | $CD_3$ | $CD_3$ | $CD_3$ |
| D | D | D | D | H | D | H | $CH_3$ | $CH_3$ | $CH_3$ | $CH_3$ | $CH_3$ | $CH_3$ |
| D | D | D | D | H | H | H | $CH_3$ | $CH_3$ | $CH_3$ | $CH_3$ | $CH_3$ | $CH_3$ |
| H | H | H | H | H | D | D | $CH_3$ | $CH_3$ | $CH_3$ | $CH_3$ | $CH_3$ | $CH_3$ |

In some embodiments, the disclosure features a pharmaceutical composition comprising a) a compound of formulas I to IIa-ii-2, or pharmaceutically acceptable salt thereof; and b) the compound:

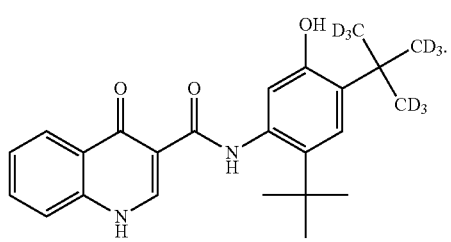 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

In some embodiments, the disclosure features a pharmaceutical composition comprising a) a compound of Table 1, or pharmaceutically acceptable salt thereof; and b) the compound:

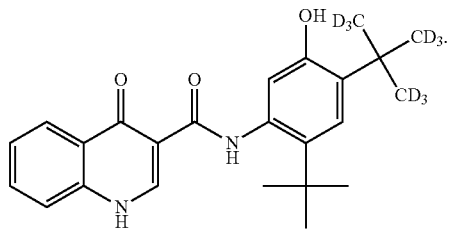 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

In some embodiments, the disclosure features a pharmaceutical composition comprising a) a compound of formulas I to IIa-ii-2, or pharmaceutically acceptable salt thereof; b) 3-(6-(1-(2,2-difluorobenzo[d][1,3]dioxol-5-yl) cyclopropanecarboxamido)-3-methylpyridin-2-yl)benzoic acid; and c) the compound:

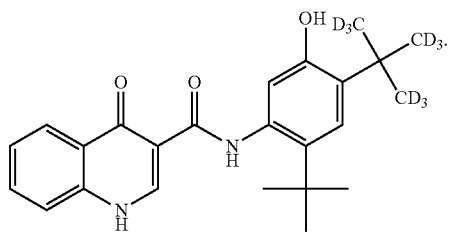 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

In some embodiments, the disclosure features a pharmaceutical composition comprising a) a compound of Table 1, or pharmaceutically acceptable salt thereof; b) 3-(6-(1-(2,2-difluorobenzo[d][1,3]dioxol-5-yl) cyclopropanecarboxamido)-3-methylpyridin-2-yl)benzoic acid; and c) the compound:

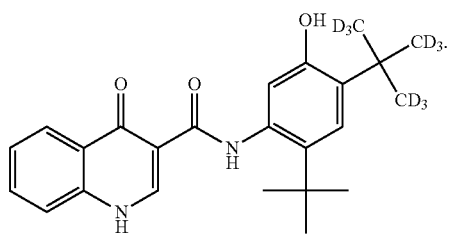

In some embodiments, the disclosure features a pharmaceutical composition comprising a) a compound selected from Compound 1, Compound 2, Compound 3, Compound 4, Compound 5, Compound 6, Compound 7, Compound 9, Compound 10, Compound 11, Compound 12, Compound 13, Compound 14, Compound 15, Compound 16, Compound 17, Compound 18, Compound 19, Compound 20, Compound 21, Compound 22, Compound 24, Compound 25, Compound 26, Compound 27, Compound 28, Compound 29, Compound 30, Compound 31, Compound 32, Compound 33, Compound 34, Compound 35, Compound 36, Compound 37, Compound 40, Compound 41, Compound 42, Compound 43, Compound 44, Compound 46, Compound 47, Compound 49, Compound 51, Compound 52, Compound 53, Compound 55, Compound 56, Compound 57, Compound 58, Compound 59, Compound 60, Compound 61, Compound 62, Compound 63, Compound 64, Compound 65, Compound 66, Compound 67, Compound 68, Compound 69, Compound 71, Compound 73, Compound 74, Compound 75, Compound 76, Compound 77, Compound 78, Compound 79, Compound 81, Compound 82 or Compound 83; b) 3-(6-(1-(2,2-difluorobenzo[d][1,3]dioxol-5-yl) cyclopropanecarboxamido)-3-methylpyridin-2-yl)benzoic acid; and c) the compound:

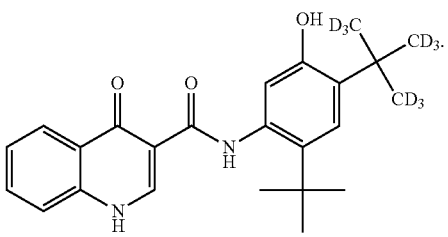 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

In some embodiments, the disclosure features a pharmaceutical composition comprising a) a compound of formulas I to IIa-ii-2, or pharmaceutically acceptable salt thereof; b) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide; and c) the compound:

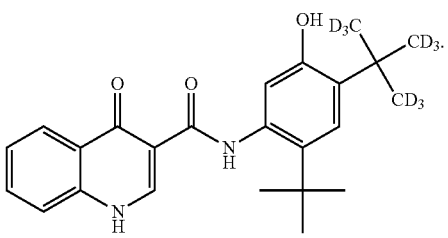 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

In some embodiments, the disclosure features a pharmaceutical composition comprising a) a compound of Table 1, or pharmaceutically acceptable salt thereof; b) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide; and c) the compound:

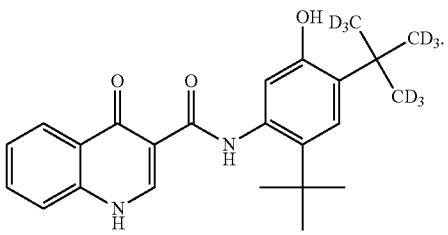 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

In some embodiments, the disclosure features a pharmaceutical composition comprising a) a compound selected from Compound 1, Compound 2, Compound 3, Compound 4, Compound 5, Compound 6, Compound 7, Compound 9, Compound 10, Compound 11, Compound 12, Compound 13, Compound 14, Compound 15, Compound 16, Compound 17, Compound 18, Compound 19, Compound 20, Compound 21, Compound 22, Compound 24, Compound 25, Compound 26, Compound 27, Compound 28, Compound 29, Compound 30, Compound 31, Compound 32, Compound 33, Compound 34, Compound 35, Compound 36, Compound 37, Compound 40, Compound 41, Compound 42, Compound 43, Compound 44, Compound 46, Compound 47, Compound 49, Compound 51, Compound 52, Compound 53, Compound 55, Compound 56, Compound 57, Compound 58, Compound 59, Compound 60, Compound 61, Compound 62, Compound 63, Compound 64, Compound 65, Compound 66, Compound 67, Compound 68, Compound 69, Compound 71, Compound 73, Compound 74, Compound 75, Compound 76, Compound 77, Compound 78, Compound 79, Compound 81, Compound 82 or Compound 83; b) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide; and c) the compound:

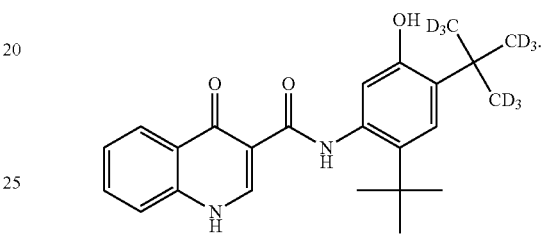

In another embodiment, the above recited pharmaceutical compositions contain a pharmaceutically acceptable prodrug of the compound of the present disclosure.

In one embodiment, any of the below therapeutic agents can be used alone with a compound of formulas I to IIa-ii-2, or in combination with any of the above described pharmaceutical compositions, or as a component in any of the above described pharmaceutical compositions.

In one embodiment, the additional therapeutic agent is selected from a mucolytic agent, bronchodialator, an antibiotic, an anti-infective agent, a CFTR modulator, or an anti-inflammatory agent.

In one embodiment, any of the below therapeutic agents, which predominantly treat the symptoms a CFTR mediated disease, such as cystic fibrosis, rather than its underlying cause, can be used alone with a compound of formulas I to IIa-ii-2, or pharmaceutically acceptable salt thereof, or in combination with any of the above described pharmaceutical compositions, or as a component in any of the above described pharmaceutical compositions.

In one embodiment, the additional therapeutic agent is an antibiotic. Exemplary antibiotics useful herein include tobramycin, including tobramycin inhaled powder (TIP), azithromycin, cayston, aztreonam, including the aerosolized form of aztreonam, amikacin, including liposomal formulations thereof, ciprofloxacin, including formulations thereof suitable for administration by inhalation, levoflaxacin, including aerosolized formulations thereof, and combinations of two antibiotics, e.g., fosfomycin and tobramycin.

In another embodiment, the additional therapeutic agent is a mucolyte. Exemplary mucolytes useful herein includes Pulmozyme®.

In another embodiment, the additional therapeutic agent is a bronchodialator. Exemplary bronchodialtors include albuterol, metaproternol sulfate, pirbuterol acetate, salmeterol, or tetrabuline sulfate.

In another embodiment, the additional therapeutic agent is effective in restoring lung airway surface liquid. Such agents improve the movement of salt in and out of cells, allowing mucus in the lung airway to be more hydrated and, therefore, cleared more easily. Exemplary such agents include hypertonic saline, denufosol tetrasodium ([[(3 S,5R)-5-(4-amino-2-oxopyrimidin-1-yl)-3-hydroxyoxolan-2-yl]methoxy-hydroxyphosphoryl] [[[(2R,3S,4R,5R)-5-(2,4-dioxopyrimidin-1-yl)-3, 4-dihydroxyoxolan-2-yl]methoxy-hydroxyphosphoryl]oxy-hydroxyphosphoryl] hydrogen phosphate), or bronchitol (inhaled formulation of mannitol).

In another embodiment, the additional therapeutic agent is an anti-inflammatory agent, i.e., an agent that can reduce the inflammation in the lungs. Exemplary such agents useful herein include ibuprofen, docosahexanoic acid (DHA), sildenafil, inhaled glutathione, pioglitazone, hydroxychloroquine, or simavastatin.

In another embodiment, the additional therapeutic agent is a compound that augments or induces CFTR activity other than a compound of formulas I to IIa-ii-2, or pharmaceutically acceptable salt thereof. Exemplary such agents include ataluren ("PTC124®"; 3-[5-(2-fluorophenyl)-1,2,4-oxadiazol-3-yl]benzoic acid), sinapultide, lancovutide, depelestat (a human recombinant neutrophil elastase inhibitor), and cobiprostone (7-{(2R,4aR,5R, 7aR)-2-[(3)-1,1-difluoro-3-methylpentyl]-2-hydroxy-6-oxooctahydrocyclopenta[b]pyran-5-yl}heptanoic acid).

In another embodiment, the additional therapeutic agent is a nutritional agent. Exemplary nutritional agents include pancrelipase (pancreating enzyme replacement), including Pancrease®, Pancreacarb®, Ultrase®, or Creon®, Liprotomase® (formerly Trizytek®), Aquadeks®, or glutathione inhalation. In one embodiment, the additional nutritional agent is pancrelipase.

In another embodiment, the additional therapeutic agent is a compound selected from gentamicin, curcumin, cyclophosphamide, 4-phenylbutyrate, miglustat, felodipine, nimodipine, Philoxin B, geniestein, Apigenin, cAMP/cGMP inducers such as rolipram, sildenafil, milrinone, tadalafil, amrinone, isoproterenol, albuterol, and almeterol, deoxyspergualin, HSP 90 inhibitors, HSP 70 inhibitors, proteosome inhibitors such as epoxomicin, lactacystin, etc.

In other embodiments, the additional therapeutic agent is a compound disclosed in WO2004028480, WO2004110352, WO2005094374, WO2005120497, or WO2006101740, incorporated herein in their entirety by reference. In another embodiment, the additional agent is a benzo[c]quinolizinium derivative that exhibits CFTR inducing or augmenting activity or a benzopyran derivative that exhibits CFTR inducing or augmenting activity. In another embodiment, the additional agent is a compound disclosed in U.S. Pat. Nos. 7,202,262, 6,992,096, US20060148864, US20060148863, US20060035943, US20050164973, WO2006110483, WO2006044456, WO2006044682, WO2006044505, WO2006044503, WO2006044502, or WO2004091502, incorporated herein in their entirety by reference. In another embodiment, the additional agent is a compound disclosed in WO2004080972, WO2004111014, WO2005035514, WO2005049018, WO2006099256, WO2006127588, or WO2007044560, incorporated herein in their entirety by reference.

In another embodiment, the additional therapeutic agent is a compound disclosed in WO2014180562, WO2015018823, or US20140274933, incorporated herein in their entirety by reference.

In another embodiment, the additional therapeutic agent is selected from the categories ENaC inhibitors, betamimetics, anticholinergics, corticosteroids, PDE4-inhibitors, LTD4-antagonists, EGFR-inhibitors, dopamine agonists, H1-antihistamines, PAF-antagonists, MAP-kinase inhibitors, MPR4-Inhibitors, iNOS-Inhibitors, or SYK-Inhibitors, or double or triple combinations thereof.

In another embodiment, the additional therapeutic agent is a potentiator selected from 3-amino-6-(4-fluoro-phenyl)-5-trifluoromethyl-pyridine-2-carboxylic acid (3,3,3-trifluoro-2-hydroxy-2-methyl-propyl)-amide;

5-amino-6'-methyl-3-trifluoromethyl-[2,3]bipyridinyl-6-carboxylic acid (3,3,3-trifluoro-2-hydroxy-2-methyl-propyl)-amide;

3-amino-6-cyclopropyl-N-(3,3,3-trifluoro-2-hydroxy-2-methylpropyl)-5-(trifluoromethyl)picolinamide; 3-amino-6-methoxy-N-(3,3,3-trifluoro-2-hydroxy-2-(trifluoromethyl)propyl)-5-(trifluoro methyl)picolinamide;

3-amino-6-(4-fluoro-phenyl)-5-trifluoromethyl-pyridine-2-carboxylic acid ((S)-3,3,3-trifluoro-2-hydroxy-2-methyl-propyl)-amide;

3-amino-6-methoxy-5-trifluoromethyl-pyridine-2-carboxylic acid((S-3,3,3-trifluoro-2-hydroxy-2-methyl-propyl)-amide;

3-amino-6-methoxy-5-trifluoromethyl-pyridine-2-carboxylic acid ((R)-3,3,3-trifluoro-2-hydroxy-2-methyl-propyl)-amide;

3-amino-6-(2,4-dichloro-phenyl)-5-trifluoromethyl-pyridine-2-carboxylic acid ((S)-3,3,3-trifluoro-2-hydroxy-2-methyl-propyl)-amide;

3-amino-6-(2,4-dichloro-phenyl)-5-trifluoromethyl-pyridine-2-carboxylic acid ((R)-3,3,3-trifluoro-2-hydroxy-2-methyl-propyl)-amide;

3-amino-6-(4-fluoro-phenyl)-5-trifluoromethyl-pyridine-2-carboxylic acid (2-hydroxy-2-methyl-propyl)-amide;

3-amino-5,6-bis-trifluoromethyl-pyridine-2-carboxylic acid ((S)-3,3,3-trifluoro-2-hydroxy-2-methyl-propyl)-amide;

3-amino-5,6-bis-trifluoromethyl-pyridine-2-carboxylic acid ((R)-3,3,3-trifluoro-2-hydroxy-2-methyl-propyl)-amide;

(S)-3-amino-6-ethoxy-N-(3,3,3-trifluoro-2-hydroxy-2-methylpropyl)-5-(trifluoro methyl)picolinamide;

3-amino-6-methoxy-5-trifluoromethyl-pyridine-2-carboxylic acid ((S)-3,3,3-trifluoro-2-hydroxy-2-methyl-propyl)-amide;

3-amino-6-methoxy-5-trifluoromethyl-pyridine-2-carboxylic acid ((R)-3,3,3-trifluoro-2-hydroxy-2-methyl-propyl)-amide;

3-amino-6-(4-fluoro-phenyl)-5-trifluoromethyl-pyridine-2-carboxylic acid (3,3,3-trifluoro-2-hydroxy-2-methyl-propyl)-amide;

3-amino-5,6-bis-trifluoromethyl-pyridine-2-carboxylic acid ((S)-3,3,3-trifluoro-2-hydroxy-2-methyl-propyl)-amide;

3-amino-5,6-bis-trifluoromethyl-pyridine-2-carboxylic acid ((R)-3,3,3-trifluoro-2-hydroxy-2-methyl-propyl)-amide, or pharmaceutically acceptable salts thereof.

In another embodiment, the additional agent is a compound disclosed in U.S. Pat. No. 8,247,436 and International PCT Publication WO2011113894, incorporated herein in their entirety by reference.

In another embodiment, the additional therapeutic agent is a betamimetic selected from Albuterole, Arformoterole, Bambuterole, Bitolterole, Broxaterole, Carbuterole, Clenbuterole, Fenoterole, Formoterole, Hexoprenaline, Ibuterole, Isoetharine, Isoprenaline, Levosalbutamole, Mabuterole, Meluadrine, Metaproterenole, Milveterol, Orciprenaline, Pirbuterole, Procaterole, Reproterole, Rimiterole, Ritodrine, Salmefamole, Salmeterole, Soterenole, Sulphonterole, Terbutaline, Tiaramide, Tolubuterole, Zinterole, Nolomirole, and
1-(2-chloro-4-hydroxyphenyl)-t-butylaminoethanole;
(–)-2-[7(S)-[2(R)-Hydroxy-2-(4-hydroxyphenyl)-ethylamino]-5,6,7,8-tetrahydro-2-naphthyloxy]-N,N-dimethylacetamide hydrochloride monohydrate;
3-(4-{6-[2-Hydroxy-2-(4-hydroxy-3-hydroxymethyl-phenyl)-ethylamino]-hexyl-oxy}-butyl)-benzyl-sulfonamide;
5-[2-(5,6-Diethyl-indan-2-ylamino)-1-hydroxy-ethyl]-8-hydroxy-1H-quinoline-2-one;
4-Hydroxy-7-[2-{[2-{[3-(2-phenylethoxy)propyl]sulphonyl}ethyl]-amino}ethyl]-2(3H)-benzothiazolone;
1-(2-Fluoro-4-hydroxyphenyl)-2-[4-(1-benzimidazolyl)-2-methyl-2-butylamino]ethanol;
1-[3-(4-Methoxybenzyl-amino)-4-hydroxyphenyl]-2-[4-(1-benzimidazolyl)-2-m-ethyl-2-butylamino]ethanol;
1-[2H-5-hydroxy-3-oxo-4H-1,4-benzoxazin-8-yl]-2-[3-(4-N,N-dimethylaminophenyl)-2-methyl-2-propylamino]ethanol;
1-[2H-5-hydroxy-3-oxo-4H-1,4-benzoxazin-8-yl]-2-[3-(4-methoxyphenyl)-2-methyl-2-propylamino]ethanol;
1-[2H-5-hydroxy-3-oxo-4H-1,4-benzoxazin-8-yl]-2-[3-(4-n-butyloxyphenyl)-2-methyl-2-propylamino]ethanol;
1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol;
5-Hydroxy-8-(1-hydroxy-2-isopropylaminobutyl)-2H-1,4-benzoxazin-3-(4H)-one;
1-(4-Amino-3-chloro-5-trifluoromethylphenyl)-2-tert.-butylamino)ethanol;
6-Hydroxy-8-{1-hydroxy-2-[2-(4-methoxy-phenyl)-1,1-dimethyl-ethylamino]-ethyl}-4H-benzo[1,4]oxazin-3-one;
6-Hydroxy-8-{1-hydroxy-2-[2-(4-phenoxy-acetic acid ethylester)-1,1-dimethyl-ethylamino]-ethyl}-4H-benzo[1,4]oxazin-3-one;
6-Hydroxy-8-{1-hydroxy-2-[2-(4-phenoxy-acetic acid)-1,1-dimethyl-ethylamino]-ethyl}-4H-benzo[1,4]oxazin-3-one;
8-{2-[1,1-Dimethyl-2-(2,4,6-trimethylphenyl)-ethylamino]-1-hydroxy-ethyl})-6-hydroxy-4H-benzo[1,4]oxazin-3-one;
6-Hydroxy-8-{1-hydroxy-2-[2-(4-hydroxy-phenyl)-1,1-dimethyl-ethylamino]-ethyl}-4H-benzo[1,4]oxazin-3-one;
6-Hydroxy-8-{1-hydroxy-2-[2-(4-isopropyl-phenyl)-1,1-dimethyl-ethylamino]-ethyl}-4H-benzo[1,4]oxazin-3-one;
8-{2-[2-(4-Ethyl-phenyl)-1,1-dimethyl-ethylamino]-1-hydroxy-ethyl}-6-hydroxy-4H-benzo[1,4]oxazin-3-one;
8-{2-[2-(4-Ethoxy-phenyl)-1,1-dimethyl-ethylamino]-1-hydroxy-ethyl}-6-hydroxy-4H-benzo[1,4]oxazin-3-one;
4-(4-{2-[2-Hydroxy-2-(6-hydroxy-3-oxo-3,4-dihydro-2H-benzo[1,4]oxazin-8-yl)-ethylamino]-2-methyl-propyl}-phenoxy)-butyric acid;
8-{2-[2-(3,4-Difluoro-phenyl)-1,1-dimethyl-ethylamino]-1-hydroxy-ethyl}-6-hydroxy-4H-benzo[1,4]oxazin-3-one;
1-(4-Ethoxy-carbonylamino-3-cyano-5-fluorophenyl)-2-(tert-butylamino)ethanol;
N-[2-Hydroxy-5-(1-hydroxy-2-{2-[4-(2-hydroxy-2-phenyl-ethylamino)-phenyl]-ethylamino}-ethyl)-phenyl]-formamide;
8-Hydroxy-5-(1-hydroxy-2-{2-[4-(6-methoxy-biphenyl-3-ylamino)-phenyl]-eth-ylamino}-ethyl)-1H-quinolin-2-one;
8-Hydroxy-5-[1-hydroxy-2-(6-phenethylamino-hexylamino)-ethyl]-1H-quinolin-2-one;
5-[2-(2-{4-[4-(2-Amino-2-methyl-propoxy)-phenylamino]-phenyl}-ethylamino)-1-hydroxy-ethyl]-8-hydroxy-1H-quinolin-2-one;
[3-(4-{6-[2-Hydroxy-2-(4-hydroxy-3-hydroxymethyl-phenyl)-ethylamino]hexyl-oxy}-butyl)-5-methyl-phenyl]-urea;
4-(2-{6-[2-(2,6-Dichloro-benzyloxy)-ethoxy]-hexylamino}-1-hydroxy-ethyl)-2-hydroxymethyl-phenole;
3-(4-{6-[2-Hydroxy-2-(4-hydroxy-3-hydroxymethyl-phenyl)-ethylamino]-hexyl-oxy}-butyl)-benzenesulfonamide;
3-(3-{7-[2-Hydroxy-2-(4-hydroxy-3-hydroxymethyl-phenyl)-ethylamino]-hepty-loxy}-propyl)-benzenesulfonamide;
4-(2-{6-[4-(3-Cyclopentanesulfonyl-phenyl)-butoxy]-hexylamino}-1-hydroxy-ethyl)-2-hydroxymethyl-phenole;
N-Adamantan-2-yl-2-(3-{2-[2-hydroxy-2-(4-hydroxy-3-hydroxymethyl-phenyl)-ethylamino]-propyl}-phenyl)-acetamide;
(R,S)-4-(2-{[6-(2,2-Difluoro-4-phenylbutoxy)hexyl]amino}-1-hydroxy-ethyl)-2-(hydroxymethyl)phenol;
(R,S)-4-(2-{[6-(2,2-Difluoro-2-phenylethoxy)hexyl]amino}-1-hydroxy-ethyl)-2-(hydroxymethyl)phenol;
(R,S)-4-(2-{[4,4-Difluoro-6-(4-phenylbutoxy)hexyl]amino}-1-hydroxy-ethyl)-2-(hydroxy-methyl)phenol;
(R,S)-4-(2-{[6-(4,4-Difluoro-4-phenylbutoxy)hexyl]amino}-1-hydroxy-ethyl)-2-(hydroxymethyl)phenol;
(R,S)-5-(2-{[6-(2,2-Difluoro-2-phenylethoxy)hexyl]amino}-1-hydroxy-ethyl)-8-hydroxyquinolin-2(1H)-one;
(R,S)-[2-({6-[2,2-Difluoro-2-(3-methylphenyl)ethoxy]hexyl}amino)-1-hydroxyethyl]-2-(hydroxymethyl)phenol;
4-(1R)-2-{[6-(2,2-Difluoro-2-phenylethoxy)hexyl]amino}-1-hydroxyethyl)-2-(hydroxymethyl)phenol;
(R,S)-2-(Hydroxymethyl)-4-(1-hydroxy-2-{[4,4,515-tetrafluoro-6-(3-phenylpropoxy)-hexyl]amino}ethyl)phenol;
(R,S)-[5-(2-{[6-(2,2-Difluoro-2-phenylethoxy)hexyl]amino}-1-hydroxy-ethyl-)-2-hydroxy-phenyl]formamide;
(R,S)-4-[2-({6-[2-(3-Bromophenyl)-2,2-difluoroethoxy]hexyl}amino)-1-hydro-xyethyl]-2-(hydroxymethyl)phenol;
(R,S)—N-[3-(1,1-Difluoro-2-{[6-({2-hydroxy-2-[4-hydroxy-3-(hydroxymethyl)-phenyl]-ethyl}amino)hexyl]oxy}ethyl)phenyl]urea;
3-[3-(1,1-difluoro-2-{[6-({2-hydroxy-2-[4-hydroxy-3-(hydroxymethyl)phenyl]ethyl}-amino)hexyl]oxy}ethyl)phenyl]imidazolidine-2,4-dione;
(R,S)-4-(2-({6-[2,2-difluoro-2-(3-methoxyphenyl)ethoxy]hexyl}amino)-1-hydroxyethyl]-2-(hydroxymethyl)phenol;
5-((1R)-2-{[6-(2,2-difluoro-2-phenylethoxy)hexyl]amino}-1-hydroxyethyl)-8-hydroxyquinolin-2(1H)-one;
4-((1R)-2-{[4,4-Difluoro-6-(4-phenylbutoxy)hexyl]amino}-1-hydroxy-ethyl)-2-(hydroxymethyl)phenol;
(R,S)-4-(2-{[6-(3,3-Difluoro-3-phenylpropoxy)hexyl]amino}-1-hydroxy-ethyl-)-2-(hydroxymethyl)phenol;
(R,S)-(2-{[6-(2,2-Difluoro-2-phenylethoxy)-4,4-difluorohexyl]amino}-1-hydroxyethyl)-2-(hydroxymethyl)phenol;
(R,S)-4-(2-{[6-(2,2-difluoro-3-phenylpropoxy)hexyl]amino}-1-hydroxyethyl)-2-(hydroxy-methyl)phenol;
3-[2-(3-Chloro-phenyl)-ethoxy]-N-(2-diethylamino-ethyl)-N-{2-[2-(4-hydroxy-2-oxo-2,3-dihydro-benzothiazol-7-yl)-ethylamino]-ethyl}-propionamide;

N-(2-Diethylamino-ethyl)-N-{2-[2-(4-hydroxy-2-oxo-2,3-dihydro-benzothiazol-7-yl)-ethylamino]-ethyl}-3-(2-naphthalen-1-yl-ethoxy)-propionamide;

7-[2-(2-{3-[2-(2-Chloro-phenyl)-ethylamino]-propylsulfanyl}-ethylamino)-1-hydroxy-ethyl]-4-hydroxy-3H-benzothiazol-2-one; or 7-[(1R)-2-(2-{3-[2-(2-Chloro-phenyl)-ethylamino]-propylsulfanyl})-ethylamino)-1-hydroxyethyl]-4-hydroxy-3H-benzothiazol-2-one; optionally in racemic form, as enantiomers, diastereomeres or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

In one embodiment, the additional therapeutic agent is an anticholinergic selected from Tiotropium salts, preferably the bromide salt, Oxitropium salts, preferably the bromide salt, Flutropium salts, preferably the bromide salt, Ipratropium salts, preferably the bromide salt, Aclidinium salts, preferably the bromide salt, Glycopyrronium salts, preferably the bromide salt, Trospium salts, preferably the chloride salt, Tolterodin. From the above mentioned salts the pharmaceutically active part is the cation, possible anions are chloride, bromide, iodide, sulfate, phosphate, methansulfonate, nitrate, maleate, acetate, citrate, fumarate, tartrate, oxalate, succinate, benzoate or p-toluenesulfonate. Further examples of preferred anticholinergics are selected from among 2,2-Diphenylpropionic acid tropenole ester-methobromide;
2,2-Diphenylpropionic acid scopine ester-methobromide;
2-Fluor-2,2-Diphenylacetic acid scopine ester-methobromide;
2-Fluor-2,2-Diphenylacetic acid tropenole ester-methobromide;
3,3',4,4'-Tetrafluorbenzil acid tropenole ester-methobromide;
3,3',4,4'-Tetrafluorbenzil acid scopine ester-methobromide;
4,4'-Difluorbenzil acid tropenole ester-methobromide;
4,4'-Difluorbenzil acid scopine ester-methobromide;
3,3'-Difluorbenzil acid tropenole ester-methobromide;
3,3'-Difluorbenzil acid scopine ester-methobromide;
9-Hydroxy-fluorene-9-carbon acid tropenole ester-methobromide;
9-Fluor-fluorene-9-carbon acid tropenole ester-methobromide;
9-Hydroxy-fluorene-9-carbon acid scopine ester-methobromide;
9-Fluor-fluorene-9-carbon acid scopine ester methobromide;
9-Methyl-fluorene-9-carbon acid tropenole estermethobromide;
9-Methyl-fluorene-9-carbon acid scopine estermethobromide;
Benzil acid cyclopropyl tropine ester-methobromide;
2,2-Diphenylpropionic acid cyclopropyl tropine ester-methobromide;
9-Hydroxy-xanthene-9-carbon acid cyclopropyl tropine ester-methobromide;
9-Methyl-fluorene-9-carbon acid cyclopropyl tropine ester-methobromide;
9-Methyl-xanthene-9-carbon acid cyclopropyl tropine ester-methobromide;
9-Hydroxy-fluorene-9-carbon acid cyclopropyl tropine ester-methobromide;
4,4'-Difluorbenzil acid methylester cyclopropyl tropine ester-methobromide;
9-Hydroxy-xanthene-9-carbon acid tropenole ester-methobromide;
9-Hydroxy-xanthene-9-carbon acid scopine ester methobromide;
9-Methyl-xanthene-9-carbon acid tropenole ester-methobromide;
9-Methyl-xanthene-9-carbon acid scopine estermethobromide;
9-Ethyl-xanthene-9-carbon acid tropenole ester methobromide;
9-Difluoromethyl-xanthene-9-carbon acid tropenole ester-methobromide; or
9-Hydroxymethyl-xanthene-9-carbon acid scopine ester methobromide.

In one embodiment, the additional therapeutic agent is a corticosteroid selected from Beclomethasone, Betamethasone, Budesonide, Butixocorte, Ciclesonide, Deflazacorte, Dexamethasone, Etiprednole, Flunisolide, Fluticasone, Loteprednole, Mometasone, Prednisolone, Prednisone, Rofleponide, Triamcinolone, Tipredane, {20R-16alpha, 17alpha-[butylidenebis(oxy)]-6alpha,9alpha-difluoro-11 beta-hydroxy-17beta-(methylthio)androsta-4-en-3-one};
9-fluoro-11beta, 17,21-trihydroxy-16alpha-methylpregna-1,4-diene-3,20-dione 21-cyclohexanecarboxylate 17-cyclopropanecarboxylate;
16,17-butylidenedioxy-6,9-difluoro-11-hydroxy-17-(methylthio)androst-4-en-3-one;
Flunisolide-21-[4'-(nitrooxymethyl)benzoate];
6,9-Difluoro-17-[(2-furanylcarbonyl)oxy]-11-hydroxy-16-methyl-3-oxo-androsta-1,4-dien-17-carbothion acid (S)-fluoromethylester;
6,9-Difluoro-11-hydroxy-16-methyl-3-oxo-17-propionyloxy-androsta-1,4-dien-17-carbothion acid (S)-(2-oxotetrahydro-furan-3 S-yl)ester; or
6alpha,9alpha-difluoro-11beta-hydroxy-16alpha-methyl-3-oxo-17alpha-(2,2,3,3-tertamethylcyclopropylcarbonyl)oxy-androsta-1,4-diene-17beta-carboxylic acid cyanomethyl ester; optionally in racemic form, as enantiomers, diastereomeres or as pharmaceutically acceptable salts, solvates or hydrates. Examples for preferred salts and derivatives are alkali salts, i.e. sodium or potassium salts, sulfobenzoates, phosphates, isonicotinates, acetates, dichloroacetates, propionates, dihydrogenphosphates, palmitates, pivalates or furoates.

In one embodiment, the additional therapeutic agent is a PDE4-inhibitor selected from Enprofylline, Theophylline, Roflumilaste, Ariflo (Cilomilaste), Tofimilaste, Pumafentrine, Lirimilaste, Apremilaste, Arofylline, Atizorame, Oglemilastum, Tetomilaste;

5-[(N-(2,5-dichloro-3-pyridinyl)-carboxamide]-8-methoxyquinoline;
5-[N-(3,5-dichloro-1-oxido-4-pyridinyl)-carboxamide]-8-methoxy-2-(trifluoromethyl)-quinoline;
N-(3,5-dichloropyrido-4-yl)-[1-(4-fluorobenzyl)-5-hydroxy-indole-3-yl]glyoxyl acid amide);
9-[(2-fluorophenyl)methyl]-N-methyl-2-(trifluoromethyl)-9H-purine-6-amine;
4-[(2R)-2-[3-(cyclopentyloxy)-4-methoxyphenyl]-2-phenylethyl]-pyridine;
N-[(3R)-3,4,6,7-tetrahydro-9-methyl-4-oxo-1-phenylpyrrolo[3,2,1-jk]-[1,4]benzodiazepin-3-yl]-4-Pyridinecarboxamide;
4-[6,7-diethoxy-2,3-bis(hydroxymethyl)-1-naphthalenyl]-1-(2-methoxyethyl)-2(1H)-pyridinone;

2-[4-[6,7-diethoxy-2,3-bis(hydroxymethyl)-1-naphthalenyl]-2-pyridinyl]-4-(3-pyridinyl)-1 (2H)-Phthalazinone;

(3-(3-cyclopenyloxy-4-methoxybenzyl)-6-ethylamino-8-isopropyl-3H-purine;

beta-[3-(cyclopentyloxy)-4-methoxyphenyl]-1,3-dihydro-1,3-dioxo-2H-isoindole-2-propanamide;

9-ethyl-2-methoxy-7-methyl-5-propyl-imidazo[1,5-a]pyrido[3,2-e]pyrazin-6(-5H)-one;

5-[3-(cyclopentyloxy)-4-methoxyphenyl]-3-[(3-methylphenyl)methyl](3S,5S)-2-piperidinone;

4-[1-[3,4-bis(difluoromethoxy)phenyl]-2-(3-methyl-1-oxido-4-pyridinyl)ethyl]-alpha,alpha-bis(trifluoromethyl)-Benzenemethanol;

N-(3,5-Dichloro-1-oxo-pyridine-4-yl)-4-difluoromethoxy-3-cyclopropylmethoxy-benzamide;

(−)p-[(4aR*,10bS*)-9-Ethoxy-1,2,3,4,4a, 10b-hexahydro-8-methoxy-2-methyl-benzo[s][1,6]naphthyridin-6-yl]-N,N-diisopropylbenzamide;

(R)-(+)-1-(4-Bromobenzyl)-4-[(3-cyclopentyloxy)-4-methoxyphenyl]-2-pyrrolidone;

3-(Cyclopentyloxy-4-methoxyphenyl)-1-(4-N'—[N-2-cyano-S-methyl-isothioureido]-benzyl)-2-pyrrolidone;

cis[4-Cyano-4-(3-cyclopentyloxy-4-methoxyphenyl)cyclohexan-1-carbon acid];

2-Carbomethoxy-4-cyano-4-(3-cyclopropylmethoxy-4-difluoromethoxyphenyl)-cyclohexan-1-one;

cis[4-Cyano-4-(3-cyclopropylmethoxy-4-difluoromethoxyphenyl)cyclohexan-1-ol];

(R)-(+)-Ethyl[4-(3-cyclopentyloxy-4-methoxyphenyl)pyrrolidine-2-yliden]acetate;

(S)-(−)-Ethyl[4-(3-cyclopentyloxy-4-methoxyphenyl)pyrrolidine-2-yliden]acetate;

9-Cyclopentyl-5,6-dihydro-7-ethyl-3-(2-thienyl)-9H-pyrazolo[3,4-c]-1,2,4-triazolo[4,3-a]pyridine; or 9-Cyclopentyl-5,6-dihydro-7-ethyl-3-(tert-butyl)-9H-pyrazolo[3,4-c]-1,2,4-triazolo[4,3-a]pyridine; optionally in racemic form, as enantiomers, diastereomeres or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

In one embodiment, the additional therapeutic agent is a LTD4-antagonist selected from Montelukast, Pranlukast, Zafirlukast, Masikulast, L-733321 (see compound 2ab of D. Guay et al, Bioorg. Med. Chem. Lett. 8 (1998) 453-458);

(E)-8-[2-[4-[4-(4-Fluorophenyl)butoxy]phenyl]ethenyl]-2-(1H-tetrazole-5-yl)-4H-1-benzopyran-4-one;

4-[6-Acetyl-3-[3-(4-acetyl-3-hydroxy-2-propylphenylthio)propoxy]-2-propyl-phenoxy]-butyric acid;

1-(((R)-(3-(2-(6,7-Difluoro-2-quinolinyl)ethenyl)phenyl)-3-(2-(2-hydroxy-2-propyl)phenyl)thio)methylcyclopropane-acetic acid;

1-(((1 (R)-3 (3-(2-(2,3-Dichlorothieno[3,2-b]pyridin-5-yl)-(E)-ethenyl)phenyl)-3-(2-(1-hydroxy-1-methylethyl)phenyl)propyl)thio)methyl)cyclopropane acetic acid; or

[2-[[2-(4-tert-Butyl-2-thiazolyl)-5-benzofuranyl]oxymethyl]phenyl]acetic acid; optionally in racemic form, as enantiomers, diastereomeres or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate. Further examples for optionally preferred salts and derivatives are alkali salts, i.e. sodium or potassium salts, sulfobenzoates, phosphates, isonicotinates, acetates, propionates, dihydrogenphosphates, palmitates, pivalates or furoates.

In one embodiment, the additional therapeutic agent is an EGFR-inhibitor selected from Cetuximab, Trastuzumab, Panitumumab Gefitinib, Canertinib, Erlotinib, Mab ICR-62;

4-[(3-Chlor-4-fluorophenyl)amino]-6-{[4-(morpholine-4-yl)-1-oxo-2-butene-1-yl]amino}-7-cyclopropylmethoxy-quinazoline;

4-[(3-Chlor-4-fluorophenyl)amino]-6-{[4-(N,N-diethylamino)-1-oxo-2-butene-1-yl]amino}-7-cyclopropyl-methoxy-quinazoline;

4-[(3-Chlor-4-fluorophenyl)amino]-6-{[4-(N,N-dimethylamino)-1-oxo-2-butene-1-yl]amino}-7-cyclopropyl-methoxy-quinazoline;

4-[(R)-(1-Phenyl-ethyl)amino]-6-{[4-(morpholine-4-yl)-1-oxo-2-butene-1-yl-]amino}-7-cyclopentyloxy-quinazoline;

4-[(3-Chlor-4-fluorophenyl)amino]-6-{[4-((R)-6-methyl-2-oxo-morpholine-4-yl)-1-oxo-2-butene-1-yl]amino}-7-cyclopropylmethoxy-quinazoline;

4-[(3-Chlor-4-fluorophenyl)amino]-6-{[4-((R)-6-methyl-2-oxo-morpholine-4-yl)-1-oxo-2-butene-1-yl]amino}-7-[(S)-(tetrahydrofuran-3-yl)oxy]-quinazoline;

4-[(3-Chlor-4-fluorophenyl)amino]-6-{[4-((R)-2-methoxymethyl-6-oxo-morpholine-4-yl)-1-oxo-2-butene-1-yl]amino}-7-cyclopropylmethoxy-quinazoline;

4-[(3-Chlor-4-fluorophenyl)amino]-6-[2-((S)-6-methyl-2-oxo-morpholine-4-yl)-ethoxy]-7-methoxy-quinazoline;

4-[(3-Chlor-4-fluorophenyl)amino]-6-({4-[N-(2-methoxyethyl)-N-methyl-amino]-1-oxo-2-butene-1-yl}amino)-7-cyclopropylmethoxy-quinazoline;

4-[(3-Chlor-4-fluorophenyl)amino]-6-{[4-(N,N-dimethylamino)-1-oxo-2-butene-1-yl]amino}-7-cyclopentyloxy-quinazoline;

4-[(R)-(1-Phenyl-ethyl)amino]-6-{[4-(N,N-bis-(2-methoxyethyl)-amino)-1-oxo-2-butene-1-yl]amino}-7-cyclopropylmethoxy-quinazoline;

4-[(R)-(1-Phenyl-ethyl)amino]-6-({4-[N-(2-methoxyethyl)-N-ethyl-amino]-1-oxo-2-butene-1-yl}amino)-7-cyclopropylmethoxy-quinazoline;

4-[(R)-(1-Phenyl-ethyl)amino]-6-({4-[N-(2-methoxyethyl)-N-methyl-amino]-1-oxo-2-butene-1-yl}amino)-7-cyclopropylmethoxy-quinazoline;

4-[(R)-(1-Phenyl-ethyl)amino]-6-({4-[N-(tetrahydropyran-4-yl)-N-methyl-amino]-1-oxo-2-butene-1-yl}amino)-7-cyclopropylmethoxy-quinazoline;

4-[(3-Chlor-4-fluorophenyl)amino]-6-{[4-(N,N-dimethylamino)-1-oxo-2-butene-1-yl]amino}-7-((R)-tetrahydrofuran-3-yloxy)-quinazoline;

4-[(3-Chlor-4-fluorophenyl)amino]-6-{[4-(N,N-dimethylamino)-1-oxo-2-butene-1-yl]amino}-7-((S)-tetrahydrofuran-3-yloxy)-quinazoline;

4-[(3-Chlor-4-fluorophenyl)amino]-6-({4-[N-(2-methoxyethyl)-N-methyl-amino]-1-oxo-2-butene-1-yl}amino)-7-cyclopentyloxy-quinazoline;

4-[(3-Chlor-4-fluorophenyl)amino]-6-{[4-(N-cyclopropyl-N-methyl-amino)-1-oxo-2-butene-1-yl]amino}-7-cyclopentyloxy-quinazoline;

4-[(3-Chlor-4-fluorophenyl)amino]-6-{[4-(N,N-dimethylamino)-1-oxo-2-butene-1-yl]amino}-7-[(R)-(tetrahydrofuran-2-yl)methoxy]-quinazoline;

4-[(3-Chlor-4-fluorophenyl)amino]-6-{[4-(N,N-dimethylamino)-1-oxo-2-butene-1-yl]amino}-7-[(S)-(tetrahydrofuran-2-yl)methoxy]-quinazoline;

4-[(3-Ethinyl-phenyl)amino]-6,7-bis-(2-methoxy-ethoxy)-quinazoline;

4-[(3-Chlor-4-fluorophenyl)amino]-7-[3-(morpholine-4-yl)-propyloxy]-6-[(vinylcarbonyl)amino]-quinazoline;

4-[(R)-(1-Phenyl-ethyl)amino]-6-(4-hydroxy-phenyl)-7H-pyrrolo[2,3-d]pyrimidine;

3-Cyano-4-[(3-chlor-4-fluorophenyl)amino]-6-{[4-(N,N-dimethylamino)-1-oxo-2-butene-1-yl]amino}-7-ethoxy-quinoline;

4-{[3-Chlor-4-(3-fluor-benzyloxy)-phenyl]amino}-6-(5-{[(2-methansulfonyl-ethyl)amino]methyl}-furan-2-yl)quinazoline;

4-[(R)-(1-Phenyl-ethyl)amino]-6-{[4-((R)-6-methyl-2-oxo-morpholine-4-yl)-1-oxo-2-butene-1-yl]amino}-7-methoxy-quinazoline;

4-[(3-Chlor-4-fluorophenyl)amino]-6-{[4-(morpholine-4-yl)-1-oxo-2-butene-1-yl]amino}-7-[(tetrahydrofuran-2-yl)methoxy]-quinazoline;

4-[(3-Chlor-4-fluorophenyl)amino]-6-({4-[N,N-bis-(2-methoxy-ethyl)-amino]-1-oxo-2-butene-1-yl}amino)-7-[(tetrahydrofuran-2-yl)methoxy]-quinazoline;

4-[(3-Ethinyl-phenyl)amino]-6-{[4-(5,5-dimethyl-2-oxo-morpholine-4-yl)-1-oxo-2-butene-1-yl]amino}-quinazoline;

4-[(3-Chlor-4-fluorophenyl)amino]-6-[2-(2,2-dimethyl-6-oxo-morpholine-4-yl)-ethoxy]-7-methoxy-quinazoline;

4-[(3-Chlor-4-fluorophenyl)amino]-6-[2-(2,2-dimethyl-6-oxo-morpholine-4-yl)-ethoxy]-7-[(R)-(tetrahydrofuran-2-yl)methoxy]-quinazoline;

4-[(3-Chlor-4-fluorophenyl)amino]-7-[2-(2,2-dimethyl-6-oxo-morpholine-4-yl)-ethoxy]-6-[(S)-(tetrahydrofuran-2-yl)methoxy]-quinazoline;

4-[(3-Chlor-4-fluorophenyl)amino]-6-{2-[4-(2-oxo-morpholine-4-yl)-piperidin-1-yl]-ethoxy}-7-methoxy-quinazoline;

4-[(3-Chlor-4-fluorophenyl)amino]-6-[1-(tert-butyloxycarbonyl)-piperidine-4-yloxy]-7-methoxy-quinazoline;

4-[(3-Chlor-4-fluorophenyl)amino]-6-(trans-4-amino-cyclohexane-1-yloxy)-7-methoxy-quinazoline;

4-[(3-Chlor-4-fluorophenyl)amino]-6-(trans-4-methansulfonylamino-cyclohexane-1-yloxy)-7-methoxy-quinazoline;

4-[(3-Chlor-4-fluorophenyl)amino]-6-(tetrahydropyran-3-yloxy)-7-methoxy-quinazoline;

4-[(3-Chlor-4-fluorophenyl)amino]-6-(1-methyl-piperidine-4-yloxy)-7-methoxy-quinazoline;

4-[(3-Chlor-4-fluorophenyl)amino]-6-{1-[(morpholine-4-yl)carbonyl]-piperidine-4-yloxy}-7-methoxy-quinazoline;

4-[(3-Chlor-4-fluorophenyl)amino]-6-{1-[(methoxymethyl)carbonyl]-piperidine-4-yloxy}-7-methoxy-quinazoline;

4-[(3-Chlor-4-fluorophenyl)amino]-6-(piperidine-3-yloxy)-7-methoxy-quinazoline;

4-[(3-Chlor-4-fluorophenyl)amino]-6-[1-(2-acetylamino-ethyl)-piperidine-4-yloxy]-7-methoxy-quinazoline;

4-[(3-Chlor-4-fluorophenyl)amino]-6-(tetrahydropyran-4-yloxy)-7-ethoxy-quinazoline;

4-[(3-Chlor-4-fluorophenyl)amino]-6-((S)-tetrahydrofuran-3-yloxy)-7-hydroxy-quinazoline;

4-[(3-Chlor-4-fluorophenyl)amino]-6-(tetrahydropyran-4-yloxy)-7-(2-methoxy-ethoxy)-quinazoline;

4-[(3-Chlor-4-fluorophenyl)amino]-6-{trans-4-[(dimethylamino)sulfonylamino]-cyclohexane-1-yloxy}-7-methoxy-quinazoline;

4-[(3-Chlor-4-fluorophenyl)amino]-6-{trans-4-[(morpholine-4-yl)carbonylamino]-cyclohexane-1-yloxy}-7-methoxy-quinazoline;

4-[(3-Chlor-4-fluorophenyl)amino]-6-{trans-4-[(morpholine-4-yl)sulfonylamino]-cyclohexane-1-yloxy}-7-methoxy-quinazoline;

4-[(3-Chlor-4-fluorophenyl)amino]-6-(tetrahydropyran-4-yloxy)-7-(2-acetyl-amino-ethoxy)-quinazoline;

4-[(3-Chlor-4-fluorophenyl)amino]-6-(tetrahydropyran-4-yloxy)-7-(2-methane-sulfonylamino-ethoxy)-quinazoline;

4-[(3-Chlor-4-fluorophenyl)amino]-6-{1-[(piperidine-1-yl)carbonyl]-piperidine-4-yloxy}-7-methoxy-quinazoline;

4-[(3-Chlor-4-fluorophenyl)amino]-6-(1-aminocarbonylmethyl-piperidine-4-yloxy)-7-methoxy-quinazoline;

4-[(3-Chlor-4-fluorophenyl)amino]-6-(cis-4-{N-[(tetrahydropyran-4-yl)carbonyl]-N-methyl-amino}-cyclohexane-1-yloxy)-7-methoxy-quinazoline;

4-[(3-Chlor-4-fluorophenyl)amino]-6-(cis-4-{N-[(morpholine-4-yl)carbonyl]-N-methyl-amino}-cyclohexane-1-yloxy)-7-methoxy-quinazoline;

4-[(3-Chlor-4-fluorophenyl)amino]-6-(cis-4-{N-[(morpholine-4-yl)sulfonyl]-N-methyl-amino}-cyclohexane-1-yloxy)-7-methoxy-quinazoline;

4-[(3-Chlor-4-fluorophenyl)amino]-6-(trans-4-ethanesulfonylamino-cyclohexane-1-yloxy)-7-methoxy-quinazoline;

4-[(3-Chlor-4-fluorophenyl)amino]-6-(1-methansulfonyl-piperidine-4-yloxy)-7-ethoxy-quinazoline;

4-[(3-Chlor-4-fluorophenyl)amino]-6-(1-methansulfonyl-piperidine-4-yloxy)-7-(2-methoxy-ethoxy)-quinazoline;

4-[(3-Chlor-4-fluorophenyl)amino]-6-[1-(2-methoxy-acetyl)-piperidine-4-yl-oxy]-7-(2-methoxy-ethoxy)-quinazoline;

4-[(3-Chlor-4-fluorophenyl)amino]-6-(cis-4-acetylamino-cyclohexane-1-yloxy)-7-methoxy-quinazoline;

4-[(3-Ethinyl-phenyl)amino]-6-[1-(tert-butyloxycarbonyl)-piperidine-4-yloxy]-7-methoxy-quinazoline;

4-[(3-Ethinyl-phenyl)amino]-6-(tetrahydropyran-4-yloxy]-7-methoxy-quinazoline;

4-[(3-Chlor-4-fluorophenyl)amino]-6-(cis-4-{N-[(piperidine-1-yl)carbonyl]-N-methyl-amino}-cyclohexane-1-yloxy)-7-methoxy-quinazoline;

4-[(3-Chlor-4-fluorophenyl)amino]-6-(cis-4-({N-[(4-methyl-piperazine-1-yl)-carbonyl]-N-methyl-amino}-cyclohexane-1-yloxy)-7-methoxy-quinazoline;

4-[(3-Chlor-4-fluorophenyl)amino]-6-{cis-4-[(morpholine-4-yl)carbonylamino-cyclohexane-1-yloxy}-7-methoxy-quinazoline;

4-[(3-Chlor-4-fluorophenyl)amino]-6-{1-[2-(2-oxopyrrolidine-1-yl)ethyl]-piperidine-4-yloxy}-7-methoxy-quinazoline;

4-[(3-Chlor-4-fluorophenyl)amino]-6-{1-[(morpholine-4-yl)carbonyl]-piperidine-4-yloxy}-7-(2-methoxy-ethoxy)-quinazoline;

4-[(3-Ethinyl-phenyl)amino]-6-(1-acetyl-piperidine-4-yloxy)-7-methoxy-quinazoline;

4-[(3-Ethinyl-phenyl)amino]-6-(1-methyl-piperidine-4-yloxy)-7-methoxy-quinazoline;

4-[(3-Ethinyl-phenyl)amino]-6-(1-methansulfonyl-piperidine-4-yloxy)-7-methoxy-quinazoline;

4-[(3-Chlor-4-fluorophenyl)amino]-6-(1-methyl-piperidine-4-yloxy)-7-(2-methoxy-ethoxy)-quinazoline;

4-[(3-Chlor-4-fluorophenyl)amino]-6-(1-isopropyloxycarbonyl-piperidine-4-yloxy)-7-methoxy-quinazoline;

4-[(3-Chlor-4-fluorophenyl)amino]-6-(cis-4-methylamino-cyclohexane-1-yloxy)-7-methoxy-chinazoline;

4-[(3-Chlor-4-fluorophenyl)amino]-6-{cis-4-[N-(2-methoxy-acetyl)-N-methyl-amino-cyclohexane-1-yloxy}-7-methoxy-quinazoline;

4-[(3-Ethinyl-phenyl)amino]-6-(piperidine-4-yloxy)-7-methoxy-quinazoline;
4-[(3-Ethinyl-phenyl)amino]-6-[1-(2-methoxy-acetyl)-piperidine-4-yloxy]-7-methoxy-quinazoline;
4-[(3-Ethinyl-phenyl)amino]-6-{1-[(morpholine-4-yl)carbonyl]-piperidine-4-yloxy}-7-methoxy-quinazoline;
4-[(3-Chlor-4-fluorophenyl)amino]-6-{1-[cis-2,6-dimethyl-morpholine-4-yl)-carbonyl]-piperidine-4-yloxy}-7-methoxy-quinazoline;
4-[(3-Chlor-4-fluorophenyl)amino]-6-{1-[(2-methyl-morpholine-4-yl)carbonyl-1]-piperidine-4-yloxy}-7-methoxy-quinazoline;
4-[(3-Chlor-4-fluorophenyl)amino]-6-{1-[(S,S)-(2-oxa-5-aza-bicyclo[2.2.1]-hept-5-yl)carbonyl]-piperidine-4-yloxy}-7-methoxy-quinazoline;
4-[(3-Chlor-4-fluorophenyl)amino]-6-{1-[(N-methyl-N-2-methoxyethyl-amino)-carbonyl]-piperidine-4-yloxy}-7-methoxy-quinazoline;
4-[(3-Chlor-4-fluorophenyl)amino]-6-(1-ethyl-piperidine-4-yloxy)-7-methoxy-quinazoline;
4-[(3-Chlor-4-fluorophenyl)amino]-6-{1-[(2-methoxyethyl)carbonyl]-piperidine-4-yloxy}-7-methoxy-quinazoline;
4-[(3-Chlor-4-fluorophenyl)amino]-6-{1-[(3-methoxypropyl-amino)-carbonyl]-piperidine-4-yloxy}-7-methoxy-quinazoline;
4-[(3-Chlor-4-fluorophenyl)amino]-6-[cis-4-(N-methansulfonyl-N-methyl-amino)-cyclohexane-1-yloxy]-7-methoxy-quinazoline;
4-[(3-Chlor-4-fluorophenyl)amino]-6-[cis-4-(N-acetyl-N-methyl-amino)-cyclohexane-1-yloxy]-7-methoxy-quinazoline;
4-[(3-Chlor-4-fluorophenyl)amino]-6-(trans-4-methyl-amino-cyclohexane-1-yloxy)-7-methoxy-quinazoline;
4-[(3-Chlor-4-fluorophenyl)amino]-6-[trans-4-(N-methansulfonyl-N-methyl-amino)-cyclohexane-1-yloxy]-7-methoxy-quinazoline;
4-[(3-Chlor-4-fluorophenyl)amino]-6-(trans-4-dimethyl-amino-cyclohexane-1-yloxy)-7-methoxy-quinazoline;
4-[(3-Chlor-4-fluorophenyl)amino]-6-(trans-4-{N-[(morpholine-4-yl)carbonyl]-N-methyl-amino}-cyclohexane-1-yloxy)-7-methoxy-quinazoline;
4-[(3-Chlor-4-fluorophenyl)amino]-6-[2-(2,2-dimethyl-6-oxo-morpholine-4-yl)-ethoxy]-7-[(S)-(tetrahydrofuran-2-yl)methoxy]-quinazoline;
4-[(3-Chlor-4-fluorophenyl)amino]-6-(1-methansulfonyl-piperidine-4-yloxy)-7-methoxy-quinazoline; or
4-[(3-Chlor-4-fluorophenyl)amino]-6-(1-cyano-piperidine-4-yloxy)-7-methoxy-quinazoline; optionally in racemic form, as enantiomers, diastereomeres or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

In another embodiment, the additional therapeutic agent is a dopamine antagonist selected from Bromocriptine, Cabergoline, Alpha-Dihydroergocryptine, Lisuride, Pergolide, Pramipexole, Roxindole, Ropinirole, Talipexole, Terguride and Viozane, optionally in racemic form, as enantiomers, diastereomeres or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

In another embodiment, the additional therapeutic agent is an antiallergic agent selected from Epinastine, Cetirizine, Azelastine, Fexofenadine, Levocabastine, Loratadine, Mizolastine, Ketotifene, Emedastine, Dimetindene, Clemastine, Bamipine, Cexchlorpheniramine, Pheniramine, Doxylamine, Chlorphenoxamine, Dimenhydrinate, Diphenhydramine, Promethazine, Ebastine, Olopatadine, Desloratidine and Meclozine, optionally in racemic form, as enantiomers, diastereomeres or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

In one embodiment, the additional therapeutic agent is an MAP kinase inhibitor selected from Bentamapimod, Doramapimod, 5-Carbamoylindole, 6-[(aminocarbonyl)(2,6-difluorophenyl)amino]-2-(2,4-difluorophenyl)-3-pyridine carboxamide, alpha-[2-[[2-(3-pyridinyl)ethyl]amino]-4-pyrimidinyl]-2-benzothiazole acetonitrile, 9,12-Epoxy-1H-diindolo[1,2,3-fg:3',2',1'-kl]pyrrolo[3,4-i][1,6]benzodiazocine-10-Carboxylic acid, or 4-[3-(4-chlorophenyl)-5-(1-methyl-4-piperidinyl)-1H-pyrazole-4-yl]-pyrimidine, optionally in racemic form, as enantiomers, diastereomeres or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

In one embodiment, the additional therapeutic agent is an MRP4-Inhibitor selected from N-Acetyl-dinitrophenyl-Cysteine, cGMP, Cholate, Diclofenac, Dehydroepiandrosterone 3-glucuronide, Dehydroepiandrosterone 3-sulphate, Dilazep, Dinitrophenyl-S-glutathione, Estradiol 17-beta-glucuronide, Estradiol 3,17-disulphate, Estradiol 3-glucuronide, Estradiol 3-sulphate, Estrone 3-sulphate, Flurbiprofen, Folate, N5-formyl-tetrahydrofolate, Glycocholate, Glycolithocholic acid sulphate, Ibuprofen, Indomethacin, Indoprofen, Ketoprofen, Lithocholic acid sulphate, Methotrexate, (E)-3-[[[[3-[2-(7-Chloro-2-quinolinyl)ethenyl]phenyl]-[3-dimethylamino)-3-oxopropyl]thio]methyl]thio]-propanoic acid, alpha-Naphthyl-beta-D-glucuronide, Nitrobenzyl mercaptopurine riboside, Probenecid, Valspodar, Sildenafil, Sulfinpyrazone, Taurochenodeoxycholate, Taurocholate, Taurodeoxycholate, Taurolithocholate, Taurolithocholic acid sulphate, Topotecan, Trequinsin, Zaprinast or Dipyridamol, optionally in racemic form, as enantiomers, diastereomers or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

In one embodiment, the additional therapeutic is an iNOS-Inhibitor selected from S-(2-Aminoethyl)isothiourea, Aminoguanidine, 2-Aminomethylpyridine, 5,6-dihydro-6-methyl-4H-1,3-thiazine-2-amine (AMT), L-Canavanin, 2-Iminopiperidine, S-Isopropylisothiourea, S-Methylisothiourea, S-Ethylisothiourea, S-Methylthiocitrulline, S-Ethylthiocitrulline, L-NA ($N^G$-Nitro-L-arginine), L-NAME (N^G-Nitro-L-argininemethylester), L-NMMA (N^G-Monomethyl-L-arginine), L-NIO (N^G-Iminoethyl-L-ornithine), L-NIL (N^G-iminoethyl-lysine),
(S)-6-Acetimidoylamino-2-amino-hexanoic acid (1H-tetrazole-5-yl)-amide;
N-[[3-(aminomethyl)phenyl]methyl]-ethanimidamide;
(S)-4-(2-acetimidoylamino-ethylsulfanyl)-2-amino-buturic acid;
2-[2-(4-Methoxy-pyridine-2-yl)-ethyl]-3H-imidazo[4,5-b]pyridine;
2-((R)-3-amino-1-phenyl-propoxy)-4-chlor-5-fluorbenzonitrile;
2-((1R,3S)-3-amino-4-hydroxy-1-thiazole-5-yl-butylsulfanyl)-6-trifluoromethyl-nicotinonitrile;
2-((1R,3S)-3-amino-4-hydroxy-1-thiazole-5-yl-butylsulfanyl)-4-chlor-benzonitrile;
2-((1R,3S)-3-amino-4-hydroxy-1-thiazole-5-yl-butylsulfanyl)-5-chlor-benzonitrile;
(2S,4R)-2-amino-4-(2-chlor-5-trifluoromethyl-phenylsulfanyl)-4-thiazole-5-yl-butane-1-ol;
2-((1R,3S)-3-amino-4-hydroxy-1-thiazole-5-yl-butylsulfanyl)-5-chlor-nicotinonitrile;
4-((S)-3-amino-4-hydroxy-1-phenyl-butylsulfanyl)-6-methoxy-nicotinonitrile; or substituted 3-phenyl-3,4-dihydro-1-isoquinolinamine as for instance 1S,5S,6R)-7-Chlor-5-methyl-2-aza-bicyclo[4.1.0]hept-2-ene-3-ylamin (4R,5R)-5-Ethyl-4-methyl-thiazolidine-2-ylideneamine, (1S,5S,6R)-7-Chlor-5-methyl-2-aza-bicyclo[4.1.0]hept-2-ene-3-ylamin, (4R,5R)-5-Ethyl-4-methyl-thiazolidine-2-ylideneamine, (4R,5R)-5-Ethyl-4-methyl-selenazolidine-2-ylideneamine, 4-Aminotetrahydrobiopterine, (E)-3-(4-Chlor-phenyl)-N-(1-{2-oxo-2-[4-(6-trifluormethyl-pyrimidine-4-yloxy)-piperidine-1-yl]-ethylcarbamoyl}-2-pyridine-2-yl-ethyl)-acrylamide, 3-(2,4-Difluor-phenyl)-6-[2-(4-imidazole-1-ylmethyl-phenoxy)-ethoxy]-2-phenyl-pyridine, 3-{[(Benzo[1,3]dioxol-5-ylmethyl)-carbamoyl]-methyl}-4-(2-imidazole-1-yl-pyrimidine-4-yl)-piperazine-1-carbon acid methylester, or (R)-1-(2-imidazole-1-yl-6-methyl-pyrimidine-4-yl)-pyrrolidine-2-carbon acid (2-benzo[1,3]dioxol-5-yl-ethyl)-amide, optionally in racemic form, as enantiomers, diastereomeres or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate. Further examples of preferred iNOS-Inhibitors which may be mentioned include antisense-Oligonucleotide, especially those antisense-Oligonucleotide binding iNOS-coding nucleic acids, examples therefore are disclosed in WO01/52902, incorporated herein by reference in its entirety.

In another embodiment, the additional therapeutic agent is a SYK-inhibitor selected from
2-[(2-aminoethyl)amino]-4-[(3-bromophenyl)amino]-5-pyrimidinecarboxamide;
2-[[7-(3,4-dimethoxyphenyl)imidazo[1,2-c]pyrimidine-5-yl]amino]-3-pyridinecarboxamide;
6-[[5-fluoro-2-[3,4,5-trimethoxyphenyl)amino]-4-pyrimidinyl]amino]-2,2-dimethyl-2H-pyrido[3,2-b]-1,4-oxazin-3(4H)-one;
N-[3-bromo-7-(4-methoxyphenyl)-1,6-naphthyridine-5-yl]-1,3-propanediamine;
7-(4-methoxyphenyl)-N-methyl-1,6-naphthyridine-5-amine;
N-[7-(4-methoxyphenyl)-1,6-naphthyridine-5-yl]-1,3-propanediamine;
N-[7-(2-thienyl)-1,6-naphthyridine-5-yl-1,3-propanediamine;
N-[7-[4-(dimethylamino)phenyl]-1,6-naphthyridine-5-yl]-1,2-ethanediamine;
N-[7-(4-methoxyphenyl)-2-(trifluoromethyl)-1,6-naphthyridine-5-yl]-1,3-propanediamine;
N-[7-(4-methoxyphenyl)-3-phenyl-1,6-naphthyridine-5-yl]-1,3-propanediamine;
N-(7-phenyl-1,6-naphthyridine-5-yl)-1,3-propanediamine;
N-[7-(3-fluorophenyl)-1,6-naphthyridine-5-yl]-1,3-propanediamine;
N-[7-(3-chlorophenyl)-1,6-naphthyridine-5-yl]-1,3-propanediamine;
N-[7-[3-(trifluoromethoxy)phenyl]-1,6-naphthyridine-5yl]-1,3-propanediamine;
N-[7-(4-fluorophenyl)-1,6-naphthyridine-5-yl]-1,3-propanediamine;
N-[7-(4-fluorophenyl)-1,6-naphthyridine-5-yl]-1,3-propanediamine;
N-[7-(4-chlorophenyl)-1,6-naphthyridine-5-yl]-1,3-propanediamine;
N-[7-(4'-methyl[1,1'-biphenyl]-4-yl)-1,6-naphthyridine-1,3-propane-diamine;
N-[7-[4-(dimethylamino)phenyl]-1,6-naphthyridine-5-yl]-1,3-propanediamine;
N-[7-[4-(diethylamino)phenyl]-1,6-naphthyridine-5-yl]-1,3-propane-diamine;
N-[7-[4-(4-morpholinyl)phenyl]-1,6-naphthyridine-5-yl]-1,3-propanediamine;
N-[7-[4-[[2-(dimethylamino)ethyl]methylamino]phenyl]-1,6-naphthyridine-5-yl]-1,3-propanediamine;
N-[7-(4-bromophenyl)-1,6-naphthyridine-5-yl]-1,3-propanediamine;
N-[7-(4-methylphenyl)-1,6-naphthyridine-5-yl]-1,3-propanediamine;
N-[7-[4-(methylthio)phenyl]-1,6-naphthyridine-5-yl]-1,3-propanediamine;
N-[7-[4-(1-methylethyl)phenyl]-1,6-naphthyridine-5-yl]-1,3-propanediamine;
7-[4-(dimethylamino)phenyl]-N-methyl-1,6-naphthyridine-5-amine;
7-[4-(dimethylamino)phenyl]-N,N-dimethyl-1,6-naphthyridine-5-amine;
N-[7-[4-(dimethylamino)phenyl]-1,6-naphthyridine-5-yl]-1,4-butanediamine;
N-[7-[4-(dimethylamino)phenyl]-1,6-naphthyridine-5-yl]-1,5-pentanediamine;
3-[[7-[4-(dimethylamino)phenyl]-1,6-naphthyridine-5-yl]oxy]-1-propanole;
4-[5-(4-aminobutoxy)-1,6-naphthyridine-7-yl]-N,N-dimethyl-benzenamine;
4-[[7-[4-(dimethylamino)phenyl]-1,6-naphthyridine-5-yl]amino]-1-butanole;
N-[7-[4-(dimethylamino)phenyl]-1,6-naphthyridine-5-yl]-N-methyl-1,3-propanediamine;
N-[7-[4-(dimethylamino)phenyl]-1,6-naphthyridine-5-yl]-N'-methyl-1,3-propanediamine;
N-[7-[4-(dimethylamino)phenyl]-1,6-naphthyridine-5-yl]-N,N'-dimethyl-1,3-propanediamine;
1-amino-3-[[7-[4-(dimethylamino)phenyl]-1,6-naphthyridine-5-yl]amino]-2-propanole;
N-[7-[4-(dimethylamino)phenyl]-1,6-naphthyridine-5-yl]-2,2-dimethyl-1,3-propanediamine;
7-[4-(dimethylamino)phenyl]-N-(3-pyridinylmethyl)-1,6-naphthyridine-5-amine;

N-[(2-aminophenyl)methyl]-7-[4-(dimethylamino)phenyl]-1,6-naphthyridine-5-amine;
N-[7-[6-(dimethylamino)[1,1'-biphenyl]-3-yl]-1,6-naphthyridine-5-yl]-1,3-propanediamine;
N-[7-[3-chloro-4-(diethylamino)phenyl]-1,6-naphthyridine-5-yl]-1,3-propanediamine;
N-[7-[4-(dimethylamino)-3-methoxyphenyl]-1,6-naphthyridine-5-yl]-1,3-propanediamine;
N-[7-[4-(diethylamino)phenyl]-3-methyl-1,6-naphthyridine-5-yl]-1,3-propanediamine;
N-[7-(3'-fluoro[1,1'-biphenyl]-3-yl)-1,6-naphthyridine-5-yl]-1,2-ethanediamine;
N-[7-(4-methoxyphenyl)-1,6-naphthyridine-5-yl]-1,6-naphthyridine-1,3-propanediamine;
N,N'-bis(3-aminopropyl)-7-(4-methoxyphenyl)-2,5-diamine;
N-[7-(4-methoxyphenyl)-2-(phenylmethoxy)-1,6-naphthyridine-5-yl]-1,6-naphthyridine-1,3-propanediamine;
N5-(3-aminopropyl)-7-(4-methoxyphenyl)-N2-(phenylmethyl)-2,5-diamine;
N-[7-(2-naphthalenyl)-1,6-naphthyridine-5-yl]-1,3-propanediamine;
N-[7-(2'-fluoro[1,1'-biphenyl]-4-yl)-1,6-naphthyridine-5-yl]-1,3-propanediamine;
N-[7-(3,4,5-trimethoxyphenyl)-1,6-naphthyridine-5-yl]-1,3-propanediamine;
N-[7-(3,4-dimethylphenyl)-1,6-naphthyridine-5-yl]-1,3-propanediamine;
1-amino-3-[[7-(2-naphthalenyl)-1,6-naphthyridine-5-yl]amino]-2-propanole;
1-amino-3-[[7-(2'-fluoro[1,1'-biphenyl]-4-yl)-1,6-naphthyridine-5-yl]amino]-2-propanole;
1-amino-3-[[7-(4'-methoxy[1,1'-biphenyl]-4-yl)-1,6-naphthyridine-5-yl]amino]-2-propanole;
1-amino-3-[[7-(3,4,5-trimethoxyphenyl)-1,6-naphthyridine-5-yl]amino]-2-propanole;
1-amino-3-[[7-(4-bromophenyl)-1,6-naphthyridine-5-yl]amino]-2-propanole;
N-[7-(4'-methoxy[1,1'-biphenyl]-4-yl)-1,6-naphthyridine-5-yl]-2,2-dimethyl-1,3-propanediamine;
1-[[7-[4-(dimethylamino)phenyl]-1,6-naphthyridine-5-yl]amino]-2-propanole;
2-[[2-[[7-[4-(dimethylamino)phenyl]-1,6-naphthyridine-5-yl]amino]-ethyl]thio]-ethanole;
7-[4-(dimethylamino)phenyl]-N-(3-methyl-5-isoxazolyl)-1,6-naphthyridine-5-amine;
7-[4-(dimethylamino)phenyl]-N-4-pyrimidinyl-1,6-naphthyridine-5-amine;
N-[7-[4-(dimethylamino)phenyl]-1,6-naphthyridine-5-yl]-1,3-cyclohexane diamine;
N,N-dimethyl-4-[5-(1-piperazinyl)-1,6-naphthyridine-7-yl]-benzenamine;
4-[5-(2-methoxyethoxy)-1,6-naphthyridine-7-yl]-N,N-dimethyl-benzeneamine;
1-[7-[4-(dimethylamino)phenyl]-1,6-naphthyridine-5-yl]-4-piperidinole;
1-[7-[4-(dimethylamino)phenyl]-1,6-naphthyridine-5-yl]-3-pyrrolidinole;
7-[4-(dimethylamino)phenyl]-N-(2-furanylmethyl)-1,6-naphthyridine-5-amine;
7-[4-(dimethylamino)phenyl]-N-[3-(1H-imidazole-1-yl)propyl]-1,6-naphthyridine-5-amine;
1-[7-[4-(dimethylamino)phenyl]-1,6-naphthyridine-5-yl]-4-piperidine carboxamide;
1-[3-[[7-[4-(dimethylamino)phenyl]-1,6-naphthyridine-5-yl]amino]propyl]-2-pyrrolidinone;
N-[3'-[5-[(3-aminopropyl)amino]-1,6-naphthyridine-7-yl][1,1'-biphenyl]-3-yl]-acetamide;
N-[7-(4'-fluoro[1,1'-biphenyl]-4-yl)-1,6-naphthyridine-5-yl]-1,3-propanediamine;
N-[4'-[5-[(3-aminopropyl)amino]-1,6-naphthyridine-7-yl][1,1'-biphenyl]-3-yl]-acetamide;
N-[7-[4-(1,3-benzodioxol-5-yl)phenyl]-1,6-naphthyridine-5-yl]-1,3-propanediamine;
N-[7-[4-(2-thienyl)phenyl]-1,6-naphthyridine-5-yl]-1,3-propanediamine;
N-[7-[4-fluoro-3-(trifluoromethyl)phenyl]-1,6-naphthyridine-5-yl]-1,3-propanediamine;
N-[7-[4-(3-pyridinyl)phenyl]-1,6-naphthyridine-5-yl]-1,3-propanediamine;
N-[7-(1,3-benzodioxol-5-yl)-1,6-naphthyridine-5-yl]-1,3-propanediamine;
N-[7-(6-methoxy-2-naphthalenyl)-1,6-naphthyridine-5-yl]-1,3-propanediamine;
7-[4-(dimethylamino)phenyl]-N-(4-pyridinylmethyl)-1,6-naphthyridine-5-amine;
3-[[7-[4-(dimethylamino)phenyl]-1,6-naphthyridine-5-yl]methylamino]-propanenitrile;
7-[4-(dimethylamino)phenyl]-N-[1-(phenylmethyl)-4-piperidinyl]-1,6-naphthyridine-5-amine;
N-[7-[4-(dimethylamino)phenyl]-1,6-naphthyridine-5-yl]-1,2-cyclohexanediamine;
N-[7-[4-(dimethylamino)phenyl]-1,6-naphthyridine-5-yl]-1,2-cyclohexanediamine, (1R,2S)-rel-;
N-[7-[4-(dimethylamino)phenyl]-1,6-naphthyridine-5-yl]-1,2-benzene dimethanamine;
N-[7-[4-(diethylamino)phenyl]-1,6-naphthyridine-5-yl]-1,4-butanediamine;
N-[7-[3',5'-bis(trifluoromethyl)[1,1'-biphenyl]-4-yl]-1,6-naphthyridine-5-yl]-3-propanediamine;
N-[7-(3'-methoxy[1,1'-biphenyl]-4-yl)-1,6-naphthyridine-5-yl]-1,3-propane-diamine;
N-[7-(3'-fluoro[1,1'-biphenyl]-4-yl)-1,6-naphthyridine-5-yl]-1,3-propanediamine;
4-[[7-[4-(dimethylamino)phenyl]-1,6-naphthyridine-5-yl]oxy]-1-butanole;
N-[7-[4-(dimethylamino)phenyl]-1,6-naphthyridine-5-yl]-1,4-cyclohexanediamine;
7-[4-(dimethylamino)phenyl]-N-(2,2,6,6-tetramethyl-4-piperidinyl)-1,6-naphthyridine-5-amine;
N-[7-[3-bromo-4-(dimethylamino)phenyl]-1,6-naphthyridine-5-yl]-1,3-propanediamine;
N-[7-(1-methyl-1H-indole-5-yl)-1,6-naphthyridine-5-yl]-1,3-propanediamine;
N-[7-[3-(trifluoromethyl)phenyl]-1,6-naphthyridine-5-yl]-1,3-propanediamine;
N-[7-[4-(trifluoromethyl)phenyl]-1,6-naphthyridine-5-yl]-1,3-propanediamine;
N-[7-(3-bromo-4-methoxyphenyl)-1,6-naphthyridine-5-yl]-1,3-propanediamine;
N-[7-[4-[[3-(dimethylamino)propyl]methylamino]phenyl]-1,6-naphthyridine-5-yl]-1,4-cyclohexanediamine;
N-[7-[4-[[2-(dimethylamino)ethyl]methylamino]phenyl]-1,6-naphthyridine-5-yl]-1,4-cyclohexanediamine;
N-[7-[4-(dimethylamino)-3-methoxyphenyl]-1,6-naphthyridine-5-yl]-1,4-cyclohexanediamine;
N-[7-[4-(4-morpholinyl)phenyl]-1,6-naphthyridine-5-yl]-1,4-cyclohexanediamine;
N-[7-[3-bromo-4-(4-morpholinyl)phenyl]-1,6-naphthyridine-5-yl]-1,4-cyclohexane-diamine;
4-[[7-[4-[[2-(dimethylamino)ethyl]methylamino]phenyl]-1,6-naphthyridine-5-yl]oxy]-cyclohexanole;

N-[7-[3-bromo-4-(4-morpholinyl)phenyl]-1,6-naphthyridine-5-yl]-1,3-propane-diamine;

N,N-dimethyl-4-[5-(4-methyl-1-piperazinyl)-1,6-naphthyridine-7-yl]-benzenamine;

4-[[7-[4-[[3-(dimethylamino)propyl]methylamino]phenyl]-1,6-naphthyridine-5-yl]oxy]-cyclohexanole;

N-[7-[4-[[2-(dimethylamino)ethyl]methylamino]phenyl]-1,6-naphthyridine-5-yl]-1,4-butanediamine; or

[3-[[5-[(3-aminopropyl)amino]-7-(4-methoxyphenyl)-1,6-naphthyridine-2-yl]-amino]propyl]-carbamic acid-1,1-dimethylethyl ester, optionally in racemic form, as enantiomers, diastereomers or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

In another embodiment, the additional therapeutic agent is an agent that inhibits the interaction between CAL (also known as CFTR-associated ligand) and mutant CFTR proteins. In one embodiment, the agent that inhibits interaction between CAL and mutant CFTR proteins is a peptide or peptidomimetic (e.g., 6 to 20 residues in length). In another embodiment, the agent that inhibits interaction between CAL and mutant CFTR proteins is a peptide or peptidomimetic disclosed in US Published Patent Application No. US2014/0100155 A1, incorporated herein by reference in its entirety.

In another embodiment, the above recited pharmaceutical compositions contain a pharmaceutically acceptable prodrug of the compound of the present disclosure.

In one aspect, the pharmaceutical compositions of the disclosure can be administered to a patient once daily or about every twenty four hours. Alternatively, the pharmaceutical compositions of the disclosure can be administered to a patient twice daily. Alternatively, the pharmaceutical composition of the disclosure can be administered about every twelve hours. These pharmaceutical compositions are administered as oral formulations containing about 25 mg, 50 mg, 100 mg, 125 mg, 150 mg, 200 mg, 250 mg, 300 mg, or 400 mg of a compound of Formula I. In this aspect, the pharmaceutical compositions further comprise a filler; a disintegrant; a surfactant; a binder; or a lubricant, or combinations thereof.

It will also be appreciated that the pharmaceutical compositions of the disclosure, including the pharmaceutical compositions comprising combinations described previously, can be employed in combination therapies; that is, the compositions can be administered concurrently with, prior to, or subsequent to, one or more other desired therapeutic agents or medical procedures.

These combinations are useful for treating the diseases described herein including cystic fibrosis. These combinations are also useful in the kits described herein.

The amount of additional therapeutic agent present in or with the compositions of this disclosure will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Therapeutic Uses of the Compounds of Formulas I-IIa-ii-2 and Pharmaceutical Compositions Thereof In one aspect, the disclosure also provides a method of treating, lessening the severity of, or symptomatically treating a disease in a patient, the method comprising administering an effective amount of the pharmaceutical composition of the disclosure to the patient, preferably a mammal, wherein the disease is selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency and Type 1 hereditary angioedema, lipid processing deficiencies (such as familial hypercholesterolemia, Type 1 chylomicronemia, and abetalipoproteinemia), lysosomal storage diseases (such as I-cell disease/pseudo-Hurler), mucopolysaccharidoses, Sandhof/Tay-Sachs, Crigler-Najjar type II, polyendocrinopathy/hyperinsulinemia, Diabetes mellitus, Laron dwarfism, myeloperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurohypophyseal DI, nephrogenic DI, Charcot-Marie Tooth syndrome, Pelizaeus-Merzbacher disease, neurodegenerative diseases (such as Alzheimer's disease, Parkinson's disease, amyotrophic lateral sclerosis, progressive supranuclear palsy, and Pick's disease), several polyglutamine neurological disorders (such as Huntington's, spinocerebellar ataxia type I, spinal and bulbar muscular atrophy, dentatorubral pallidoluysian atrophy, and myotonic dystrophy), spongiform encephalopathies (such as hereditary Creutzfeldt-Jakob disease (due to prion protein processing defect)), Fabry disease, Gerstmann-Straussler-Scheinker syndrome, COPD, dry-eye disease, or Sjogren's disease, osteoporosis, osteopenia, bone healing and bone growth (including bone repair, bone regeneration, reducing bone resorption and increasing bone deposition), Gorham's Syndrome, chloride channelopathies such as myotonia congenita (Thomson and Becker forms), Bartter's syndrome type III, Dent's disease, epilepsy, lysosomal storage disease, Angelman syndrome, and Primary Ciliary Dyskinesia (PCD), a term for inherited disorders of the structure and/or function of cilia, including PCD with situs inversus (also known as Kartagener syndrome), PCD without situs inversus and ciliary aplasia.

In one aspect, the disclosure also provides a method of treating, lessening the severity of, or symptomatically treating a disease in a patient comprising administering an effective amount of the pharmaceutical composition or tablet of the disclosure to the patient, preferably a mammal, wherein the disease is selected from generalized epilepsy with ferbrile seizures plus (GEFS+), general epilepsy with ferbrile and aferbrile seizures, myotonia, paramyotonia congenital, potassium-aggravated myotonia, hyperkalemic periodic paralysis, LQTS, LQTS/Brugada syndrome, autosomal-dominant LQTS with deafness, autosomal-recessive LQTS, LQTS with dysmorphic features, congenital and acquired LQTS, Timothy syndrome, persistent hyperinsulinemic hypolglycemia of infancy, dilated cardiomyopathy, autosomal-dominant LQTS, Dent disease, Osteopetrosis, Bartter syndrome type III, central core disease, malignant hyperthermia, and catecholaminergic polymorphic tachycardia.

In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation N1303K, ΔI507, or R560T.

In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation G551D. In another embodiment, the patient is homozygous in G551D. In another embodiment, the patient is heterozygous in G551D. In another embodiment, the patient is heterozygous in G551D, wherein the other CFTR genetic mutation is any one of F508del, G542X, N1303K, W1282X, R117H, R553X, 1717-1G→A, 621+1G→T, 2789+5G→A, 3849+10kbC→T, R1162X, G85E, 3120+1G→A, AI507, 1898+1G→A, 3659delC, R347P, R560T, R334W, A455E, 2184delA, or 711+1G→T. In another embodiment, the patient is heterozygous in G551D, wherein the other CFTR genetic mutation is F508del. In another embodiment, the patient is heterozygous in G551D, wherein the other CFTR genetic mutation is R117H.

In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation F508del. In another embodiment, the patient is homozygous in F508del. In another embodiment, the patient is heterozygous in F508del. In another embodiment, the patient is heterozygous in F508del, wherein the other CFTR genetic mutation is any one of G551D, G542X, N1303K, W1282X, R117H, R553X, 1717-1G→A, 621+1G→T, 2789+5G→A, 3849+10kbC→T, R1162X, G85E, 3120+1G→A, AI507, 1898+1G→A, 3659delC, R347P, R560T, R334W, A455E, 2184delA, or 711+1G→T. In another embodiment, the patient is heterozygous in F508del, wherein the other CFTR genetic mutation is G551D. In another embodiment, the patient is heterozygous in F508del, wherein the other CFTR genetic mutation is R117H.

In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G.

In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from G178R, G551S, G970R, G1244E, S1255P, G1349D, S549N, S549R, S1251N, E193K, F1052V and G1069R. In one embodiment of this aspect, the disclosure provides a method of treating CFTR comprising administering a compound of the present application to a patient possessing a human CFTR mutation selected from G178R, G551S, G970R, G1244E, S1255P, G1349D, S549N, S549R and S1251N. In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from E193K, F1052V and G1069R. In some embodiments of this aspect, the method produces a greater than 10-fold increase in chloride transport relative to baseline chloride transport.

In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from R117C, D110H, R347H, R352Q, E56K, P67L, L206W, A455E, D579G, S1235R, S945L, R1070W, F1074L, D110E, D1270N and D1152H. In one embodiment of this aspect, the method produces an increase in chloride transport which is greater or equal to 10% above the baseline chloride transport.

In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G. In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from 1717-1G→A, 1811+1.6kbA→G, 2789+5G→A, 3272-26A→G and 3849+10kbC→T. In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from 2789+5G→A and 3272-26A→G.

In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G, and a human CFTR mutation selected from F508del, R117H, and G551D.

In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from G178R, G551S, G970R, G1244E, S1255P, G1349D, S549N, S549R, S1251N, E193K, F1052V and G1069R, and a human CFTR mutation selected from F508del, R117H, and G551D. In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from G178R, G551S, G970R, G1244E, S1255P, G1349D, S549N, S549R and S1251N, and a human CFTR mutation selected from F508del, R117H, and G551D. In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from E193K, F1052V and G1069R, and a human CFTR mutation selected from F508del, R117H, and G551D. In some embodiments of this aspect, the method produces a greater than 10-fold increase in chloride transport relative to baseline chloride transport.

In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from R117C, D110H, R347H, R352Q, E56K, P67L, L206W, A455E, D579G, S1235R, S945L, R1070W, F1074L, D110E, D1270N and D 1152H, and a human CFTR mutation selected from F508del, R117H, and G551D. In one embodiment of this aspect, the method produces an increase in chloride transport which is greater or equal to 10% above the baseline chloride transport.

In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G, and a human CFTR mutation selected from F508del, R117H, and G551D.

In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from 1717-1G→A, 1811+1.6kbA→G, 2789+5G→A, 3272-26A→G and 3849+10kbC→T, and a human CFTR mutation selected from F508del, R117H, and G551D. In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from 2789+5G→A and 3272-26A→G, and a human CFTR mutation selected from F508del, R117H.

In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G, and a human CFTR mutation selected from F508del, R117H, and G551D.

In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from G178R, G551S, G970R, G1244E, S1255P, G1349D, S549N, S549R, S1251N, E193K, F1052V and G1069R. In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from G178R, G551S, G970R, G1244E, S1255P, G1349D, S549N, S549R and S1251N. In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from E193K, F1052V and G1069R. In some embodiments of this aspect, the method produces a greater than 10-fold increase in chloride transport relative to baseline chloride transport.

In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from R117C, D110H, R347H, R352Q, E56K, P67L, L206W, A455E, D579G, S1235R, S945L, R1070W, F1074L, D110E, D1270N and D1152H. In one embodiment of this aspect, the method produces an increase in chloride transport which is greater or equal to 10% above the baseline chloride transport.

In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G. In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from 1717-1G→A, 1811+1.6kbA→G, 2789+5G→A, 3272-26A→G and 3849+10kbC→T. In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from 2789+5G→A and 3272-26A→G.

In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G, and a human CFTR mutation selected from F508del, R117H, and G551D, and one or more human CFTR mutations selected from F508del, R117H, and G551D.

In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from G178R, G551S, G970R, G1244E, S1255P, G1349D, S549N, S549R, S1251N, E193K, F1052V and G1069R, and one or more human CFTR mutations selected from F508del, R117H, and G551D. In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from G178R, G551S, G970R, G1244E, S1255P, G1349D, S549N, S549R and S1251N, and one or more human CFTR mutations selected from F508del, R117H, and G551D. In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from E193K, F1052V and G1069R, and one or more human CFTR mutations selected from F508del, R117H, and G551D. In some embodiments of this aspect, the method produces a greater than 10-fold increase in chloride transport relative to baseline chloride transport.

In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from R117C, D110H, R347H, R352Q, E56K, P67L, L206W, A455E, D579G, S1235R, S945L, R1070W, F1074L, D110E, D1270N and D1152H, and one or more human CFTR mutations selected from F508del, R117H, and G551D. In one embodiment of this aspect, the method produces an increase in chloride transport which is greater or equal to 10% above the baseline chloride transport.

In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+

5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G, and one or more human CFTR mutations selected from F508del, R117H, and G551D. In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from 1717-1G→A, 1811+1.6kbA→G, 2789+5G→A, 3272-26A→G and 3849+10kbC→T, and one or more human CFTR mutations selected from F508del, R117H, and G551D. In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation is selected from 2789+5G→A and 3272-26A→G, and one or more human CFTR mutations selected from F508del, R117H, and G551D.

In one aspect, the present disclosure is directed to a method of treating, lessening the severity of, or symptomatically treating cystic fibrosis in a patient comprising administering an effective amount of the pharmaceutical composition or tablet of the disclosure to the patient, preferably a mammal, wherein the patient possesses the CFTR genetic mutation selected from FIG. 1.

In certain embodiments, the composition of the present disclosure is useful for treating, lessening the severity of, or symptomatically treating cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary Cl⁻ concentrations, or ex vivo biochemical or histochemical techniques to monitor cell surface density. Using such methods, residual CFTR activity can be readily detected in patients heterozygous or homozygous for a variety of different mutations, including patients homozygous or heterozygous for the most common mutation, F508del, as well as other mutations such as the G551D mutation, or the R117H mutation. In certain embodiments, compositions of the present disclosure are useful for treating, lessening the severity of, or symptomatically treating cystic fibrosis in patients who exhibit little to no residual CFTR activity. In certain embodiments, compositions of the present disclosure are useful for treating, lessening the severity of, or symptomatically treating cystic fibrosis in patients who exhibit little to no residual CFTR activity in the apical membrane of respiratory epithelia.

In another embodiment, the compositions of the present disclosure are useful for treating or lessening the severity of cystic fibrosis in patients who exhibit residual CFTR activity using pharmacological methods. In another embodiment, the compositions of the present disclosure are useful for treating or lessening the severity of cystic fibrosis in patients who have residual CFTR activity using gene therapy. Such methods increase the amount of CFTR present at the cell surface, thereby inducing a hitherto absent CFTR activity in a patient or augmenting the existing level of residual CFTR activity in a patient.

In one embodiment, the compositions of the present disclosure are useful for treating or lessening the severity of cystic fibrosis in patients within certain genotypes exhibiting residual CFTR activity, e.g., Class I mutations (not synthesized), class II mutation (misfolding), class III mutations (impaired regulation or gating), class IV mutations (altered conductance), or class V mutations (reduced synthesis).

In one embodiment, compositions of the present disclosure are useful for treating, lessening the severity of, or symptomatically treating cystic fibrosis in patients within certain clinical phenotypes, e.g., a moderate to mild clinical phenotype that typically correlates with the amount of residual CFTR activity in the apical membrane of epithelia. Such phenotypes include patients exhibiting pancreatic sufficiency.

In one embodiment, the compositions of the present disclosure are useful for treating, lessening the severity of, or symptomatically treating patients diagnosed with pancreatic sufficiency, idiopathic pancreatitis and congenital bilateral absence of the vas deferens, or mild lung disease wherein the patient exhibits residual CFTR activity.

In one embodiment, the compositions of the present disclosure are useful for treating, lessening the severity of, or symptomatically treating patients diagnosed with pancreatic sufficiency, idiopathic pancreatitis and congenital bilateral absence of the vas deferens, or mild lung disease wherein the patient has wild type CFTR.

In addition to cystic fibrosis, modulation of CFTR activity may be beneficial for other diseases not directly caused by mutations in CFTR, such as secretory diseases and other protein folding diseases mediated by CFTR. These include, but are not limited to, chronic obstructive pulmonary disease (COPD), dry eye disease, and Sjögren's Syndrome. COPD is characterized by airflow limitation that is progressive and not fully reversible. The airflow limitation is due to mucus hypersecretion, emphysema, and bronchiolitis. Activators of mutant or wild-type CFTR offer a potential treatment of mucus hypersecretion and impaired mucociliary clearance that is common in COPD. Specifically, increasing anion secretion across CFTR may facilitate fluid transport into the airway surface liquid to hydrate the mucus and improved periciliary fluid viscosity. This would lead to enhanced mucociliary clearance and a reduction in the symptoms associated with COPD. Dry eye disease is characterized by a decrease in tear aqueous production and abnormal tear film lipid, protein and mucin profiles. There are many causes of dry eye, some of which include age, Lasik eye surgery, arthritis, medications, chemical/thermal burns, allergies, and diseases, such as cystic fibrosis and Sjögrens's syndrome. Increasing anion secretion via CFTR would enhance fluid transport from the corneal endothelial cells and secretory glands surrounding the eye to increase corneal hydration. This would help to alleviate the symptoms associated with dry eye disease. Sjögrens's syndrome is an autoimmune disease in which the immune system attacks moisture-producing glands throughout the body, including the eye, mouth, skin, respiratory tissue, liver, vagina, and gut. Symptoms, include, dry eye, mouth, and vagina, as well as lung disease. The disease is also associated with rheumatoid arthritis, systemic lupus, systemic sclerosis, and polymyositis/dermatomyositis. Defective protein trafficking is believed to cause the disease, for which treatment options are limited. Modulators of CFTR activity may hydrate the various organs afflicted by the disease and help to elevate the associated symptoms.

In one embodiment, the disclosure relates to a method of augmenting or inducing anion channel activity in vitro or in vivo, comprising contacting the channel with a composition of the present disclosure. In another embodiment, the anion channel is a chloride channel or a bicarbonate channel. In another embodiment, the anion channel is a chloride channel.

The exact amount required will vary from subject to subject, depending on the species, age, and general condition of the subject, the severity of the infection, the particular agent, its mode of administration, and the like. The compounds of the disclosure are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

In recent years a number of attempts have been made to treat cystic fibrosis using gene therapy. Gene therapy is the insertion, alteration, or removal of genes within an individual's cells and biological tissues to treat disease. It is a technique for correcting defective genes that are responsible for disease development. The most common form of gene therapy involves the insertion of functional genes into an unspecified genomic location in order to replace a mutated gene, but other forms involve directly correcting the mutation or modifying normal gene that enables a viral infection. Although the technology is still in its infancy, it has been used with some success.

Cystic fibrosis is a good candidate for gene therapy as it is primarily caused by mutations in a single gene. A normal copy of the gene could be delivered to patients via topical delivery to the lung, not requiring invasive techniques or surgery. A gene complementation approach would also directly target the cause of the disease and could correct many aspects of the complex lung pathology.

Soon after the cloning of the CFTR gene, proof-of-principle was established when the Cl-conductance defect was corrected after delivery of a functional copy of human wild-type CFTR DNA to cells isolated from cystic fibrosis patients. To date, a number of trials for cystic fibrosis gene therapy have been tested in humans. These early studies were concerned mainly with safety issues.

In one embodiment, the disclosure features a method of treating cystic fibrosis comprising administering to the patient a compound of formulas I to IIa-ii-2 in conjunction with gene therapy. The gene therapy can be as disclosed in Internation Published Patent Application No. WO2013061091, incorporated herein in its entirety by reference. Administration may be prior, concomitant, or subsequent administration of a compound of formulas I to IIa-ii-2, or any of the pharmaceutical compositions of the present disclosure.

In another embodiment, the gene therapy features administering to the patient 1 mL to less than 10 mLs of a complex of (i) a non-viral CpG dinucleotide-free plasmid comprising nucleic acid encoding a CFTR polypeptide operatively linked to hCEF1 promoter, wherein the plasmid is at a concentration of 2 mg/mL to 3 mg/mL, and (ii) GL67A lipid mixture at a concentration of 10 mg/mL to 20 mg/mL.

In one embodiment, gene therapy is administered to a patient with cystic fibrosis prior, concomitant, or subsequent administration of a pharmaceutical composition comprising (i) a compound of formulas I to IIa-ii-2, or pharmaceutically acceptable salt thereof and (ii) 3-(6-(1-(2,2-difluorobenzo[d][1,3]dioxol-5-yl) cyclopropanecarboxamido)-3-methylpyridin-2-yl)benzoic acid.

In one embodiment, gene therapy is administered to a patient with cystic fibrosis prior, concomitant, or subsequent administration of a pharmaceutical composition comprising (i) a compound of formulas I to IIa-ii-2, or pharmaceutically acceptable salt thereof and (ii) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide.

In one embodiment, gene therapy is administered to a patient with cystic fibrosis prior, concomitant, or subsequent administration of a pharmaceutical composition comprising (i) a compound of formulas I to IIa-ii-2, or pharmaceutically acceptable salt thereof and (ii) 4-(3-(1-(2,2-difluorobenzo[d][1,3]dioxol-5-yl)cyclopropanecarboxamido) isoquinolin-1-yl)benzoic acid.

In one embodiment, gene therapy is administered to a patient with cystic fibrosis prior, concomitant, or subsequent administration of a pharmaceutical composition comprising (i) a compound of formulas I to IIa-ii-2, or pharmaceutically acceptable salt thereof; (ii) 3-(6-(1-(2,2-difluorobenzo[d][1,3]dioxol-5-yl) cyclopropanecarboxamido)-3-methylpyridin-2-yl)benzoic acid; and (iii) N-(5-hydroxy-2,4-ditert-butyl-phenyl)-4-oxo-1H-quinoline-3-carboxamide.

In one embodiment, gene therapy is administered to a patient with cystic fibrosis prior, concomitant, or subsequent administration of a pharmaceutical composition comprising (i) a compound of formulas I to IIa-ii-2, or pharmaceutically acceptable salt thereof; (ii) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide; and (iii)N-(5-hydroxy-2,4-ditert-butyl-phenyl)-4-oxo-1H-quinoline-3-carboxamide.

In one embodiment, gene therapy is administered to a patient with cystic fibrosis prior, concomitant, or subsequent administration of a pharmaceutical composition comprising (i) a compound of formulas I to IIa-ii-2, or pharmaceutically acceptable salt thereof; (ii) 4-(3-(1-(2,2-difluorobenzo[d][1,3]dioxol-5-yl)cyclopropanecarboxamido) isoquinolin-1-yl) benzoic acid; and (iii)N-(5-hydroxy-2,4-ditert-butyl-phenyl)-4-oxo-1H-quinoline-3-carboxamide.

Kits

In another aspect, the present disclosure features a kit comprising a compound and/or pharmaceutical composition of the present disclosure and instructions for use thereof.

In another embodiment, the kits of the present disclosure further comprise one or more additional therapeutic agent(s). In another embodiment, the additional therapeutic agent is selected from a mucolytic agent, bronchodialator, an antibiotic, an anti-infective agent, a CFTR modulator, or an anti-inflammatory agent. In another embodiment, the additional therapeutic agent is a CFTR modulator. In another embodiment, the additional therapeutic agent is a CFTR corrector.

In another embodiment, the additional therapeutic agent is

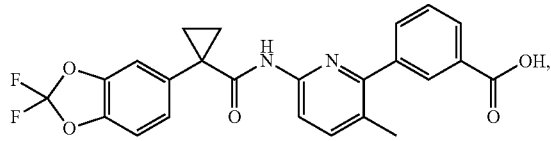 [SMILES: Cc1ccc(NC(=O)C2(c3ccc4c(c3)OC(F)(F)O4)CC2)nc1-c1cccc(C(=O)O)c1]

or a pharmaceutically acceptable salt thereof.

In another embodiment, the additional therapeutic agent is

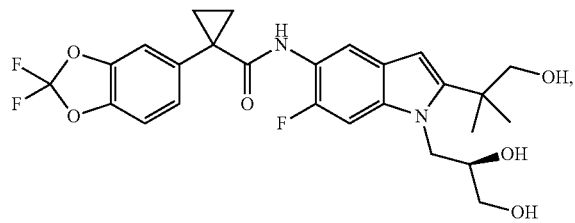 [SMILES: CC(C)(CO)c1cc2cc(NC(=O)C3(c4ccc5c(c4)OC(F)(F)O5)CC3)c(F)cc2n1C[C@@H](O)CO]

or a pharmaceutically acceptable salt thereof.

In another embodiment, the additional therapeutic agent is

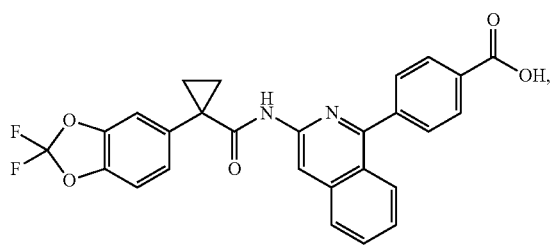

or a pharmaceutically acceptable salt thereof.

In another embodiment, the additional therapeutic agent is a CFTR potentiator.

In another embodiment, the additional therapeutic agent is

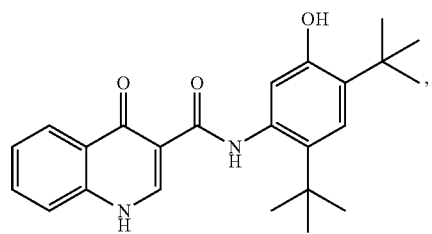 [SMILES: CC(C)(C)c1cc(C(C)(C)C)c(NC(=O)c2c[nH]c3ccccc3c2=O)cc1O ; ","]

or a pharmaceutically acceptable salt thereof.

In another embodiment, the additional therapeutic agents are a CFTR corrector and a CFTR potentiator.

In another embodiment, the additional therapeutic agents are

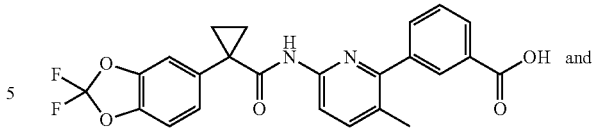

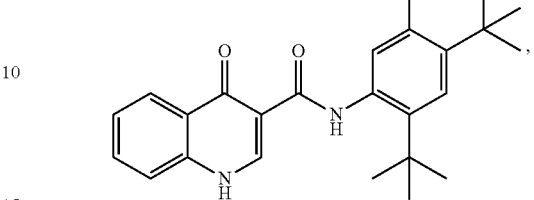

pharmaceutically acceptable salts thereof.

In another embodiment, the additional therapeutic agents are

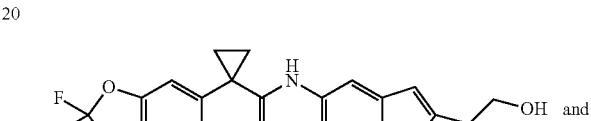

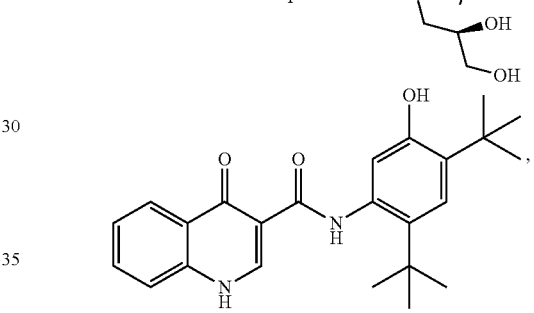

or pharmaceutically acceptable salts thereof.

In another embodiment, the additional therapeutic agents are

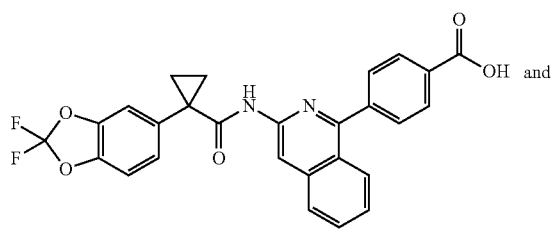

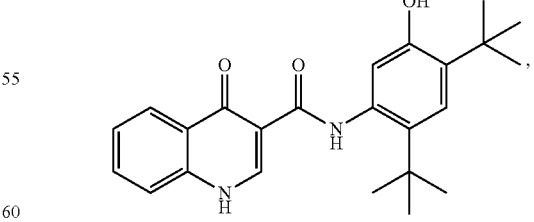

or pharmaceutically acceptable salts thereof.

In another embodiment, the kits of the present disclosure are drawn to kits wherein the compounds or the pharmaceutical compositions of the present disclosure and the one or more additional therapeutic agent(s) are in separate containers.

In another embodiment, the kits of the present disclosure are drawn to kits wherein the compounds or the pharmaceutical compositions of the present disclosure and the one or more additional therapeutic agent(s) are in the same container.

In another embodiment, the container is a bottle, vial, or blister pack, or combination thereof.

Anywhere in the present application where a name of a compound may not correctly describe the structure of the compound, the structure supersedes the name and governs.

EXAMPLES

The compounds of the disclosure can be made by any suitable method known in the art and the specific exemplary methods shown below in Preparations 1-17.

Preparation 1: N-[(6-amino-2-pyridyl)sulfonyl]-6-(3-fluoro-5-isobutoxy-phenyl)-2-(pentylamino)pyridine-3-carboxamide (Compound 84)

Step 1: tert-Butyl 2-chloro-6-(3-fluoro-5-isobutoxy-phenyl)pyridine-3-carboxylate

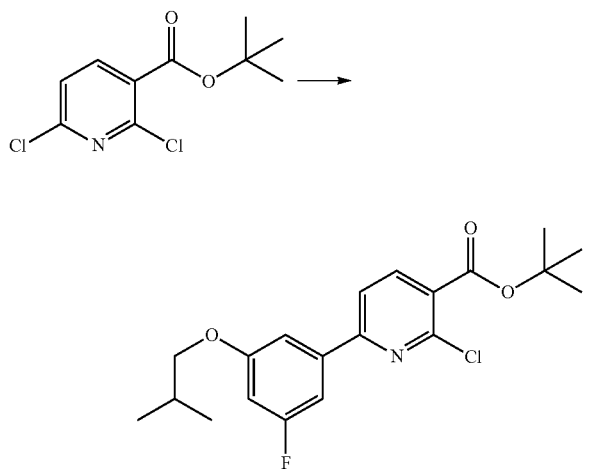

tert-Butyl 2,6-dichloropyridine-3-carboxylate (15.0 g, 60.5 mmol) and (3-fluoro-5-isobutoxy-phenyl)boronic acid (13.46 g, 63.48 mmol) were combined and fully dissolved in ethanol (150 mL) and toluene (150 mL). A suspension of sodium carbonate (19.23 g, 181.4 mmol) in water (30 mL) was added. Tetrakis(triphenylphosphine)palladium (0) (2.096 g, 1.814 mmol) was added under nitrogen. The reaction mixture was allowed to stir at 60° C. for 16 hours. Volatiles were removed under reduced pressure. The remaining solids were partitioned between water (100 mL) and ethyl acetate (100 mL). The organic layer was washed with brine (1×100 mL), dried over sodium sulfate, filtered and concentrated under reduced pressure. The material was subjected to silica gel column chromatography on a 330 gram silica gel column, 0 to 20% ethyl acetate in hexanes gradient. The material was re-purified on a 220 gram silica gel column, isocratic 100% hexane for 10 minutes, then a 0 to 5% ethyl acetate in hexanes gradient to yield tert-butyl 2-chloro-6-(3-fluoro-5-isobutoxy-phenyl)pyridine-3-carboxylate (18.87 g, 49.68 mmol, 82%) was obtained as a colorless oil. $^1$H NMR (400 MHz, DMSO-$d_6$) δ 8.24 (d, J=8.0 Hz, 1H), 8.16 (d, J=8.1 Hz, 1H), 7.48 (dd, J=9.4, 2.0 Hz, 2H), 6.99 (dt, J=10.8, 2.2 Hz, 1H), 3.86 (d, J=6.5 Hz, 2H), 2.05 (dt, J=13.3, 6.6 Hz, 1H), 1.57 (d, J=9.3 Hz, 9H), 1.00 (t, J=5.5 Hz, 6H). ESI-MS m/z calc. 379.13504, found 380.2 (M+1)+; Retention time: 2.57 minutes.

The following compound can be made in a manner analogous to that described in preparation 1: ethyl 2-chloro-6-(3-fluoro-5-isobutoxy-phenyl)pyridine-3-carboxylate.

Step 2: 2-Chloro-6-(3-fluoro-5-isobutoxy-phenyl)pyridine-3-carboxylic Acid

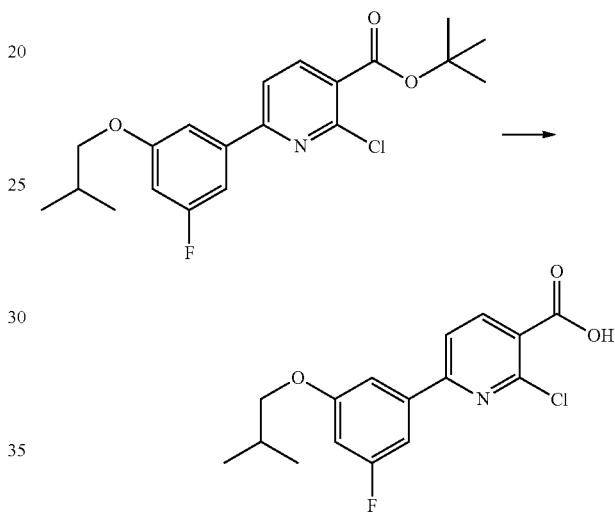

tert-Butyl 2-chloro-6-(3-fluoro-5-isobutoxy-phenyl)pyridine-3-carboxylate (18.57 g, 48.89 mmol) was dissolved in dichloromethane (200 mL). Trifluoroacetic acid (60. mL, 780 mmol) was added and the reaction mixture was allowed to stir at room temperature for 1 hour. The reaction mixture was stirred at 40° C. for 2 hours. The reaction mixture was concentrated under reduced pressure and taken up in ethyl acetate (100 mL). It was washed with a saturated aqueous sodium bicarbonate solution (1×100 mL) and brine (1×100 mL), dried over sodium sulfate, filtered and concentrated under reduced pressure. The crude product was suspended in ethyl acetate (75 mL) and washed with aqueous hydrochloric acid (1 N, 1×75 mL). The organic layer was dried over sodium sulfate, filtered and concentrated under reduced pressure. The remaining solid (17.7 g) was stirred as a slurry in dichloromethane (35 mL) at 40° C. for 30 minutes. After cooling to room temperature, the remaining slurry was filtered, and then rinsed with cold dichloromethane to give 2-chloro-6-(3-fluoro-5-isobutoxy-phenyl)pyridine-3-carboxylic acid (11.35 g, 35.06 mmol, 72%) as a white solid. $^1$H NMR (400 MHz, DMSO-$d_6$) δ 13.76 (s, 1H), 8.31 (d, J=8.0 Hz, 1H), 8.17 (d, J=8.1 Hz, 1H), 7.54-7.47 (m, 2H), 7.00 (dt, J=10.8, 2.3 Hz, 1H), 3.87 (d, J=6.5 Hz, 2H), 2.05 (dt, J=13.3, 6.6 Hz, 1H), 1.01 (d, J=6.7 Hz, 6H). ESI-MS m/z calc. 323.07245, found 324.1 (M+1)+; Retention time: 1.96 minute.

Step 3: N-[(6-Amino-2-pyridyl)sulfonyl]-2-chloro-6-(3-fluoro-5-isobutoxy-phenyl)pyridine-3-carboxamide

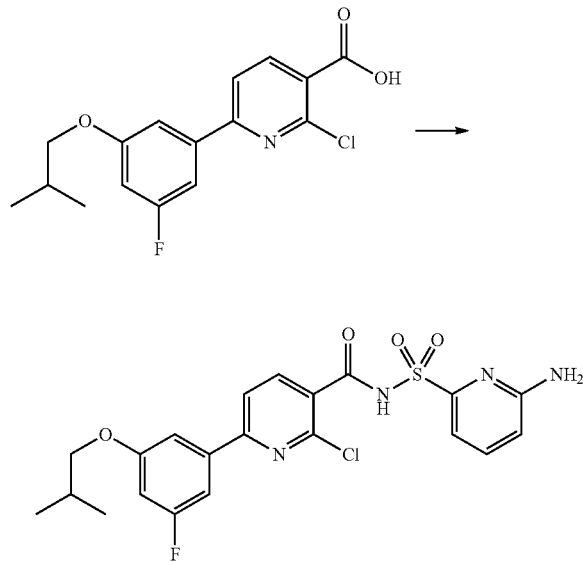

2-Chloro-6-(3-fluoro-5-isobutoxy-phenyl)pyridine-3-carboxylic acid (3.00 g, 9.27 mmol) was dissolved in N,N-dimethylformamide (30.00 mL), and 1,1'-carbonyldiimidazole (2.254 g, 13.90 mmol) was added to the solution. The solution was allowed to stir at 65° C. for 1 hour. In a separate flask, sodium hydride (444.8 mg, 11.12 mmol) was added to a solution of 6-aminopyridine-2-sulfonamide (1.926 g, 11.12 mmol) in N,N-dimethylformamide (15.00 mL). This mixture was stirred for one hour before being added to the prior reaction mixture. The final reaction mixture was stirred at 65° C. for 15 minutes. Volatiles were removed under reduced pressure. The remaining oil was taken up in ethyl acetate and washed with aqueous hydrochloric acid (1 N, 1×75 mL) and brine (3×75 mL). The organic layer was dried over sodium sulfate, filtered and concentrated under reduced pressure. The remaining white solid (4.7 g) was fully dissolved in isopropanol (120 mL) in an 85° C. water bath. The colorless solution was allowed to slowly cool to room temperature with slow stirring over 16 hours. The crystalline solids that had formed were collected by vacuum filtration, and then rinsed with cold isopropanol (50 mL). Upon drying, N-[(6-amino-2-pyridyl)sulfonyl]-2-chloro-6-(3-fluoro-5-isobutoxy-phenyl)pyridine-3-carboxamide (3.24 g, 6.76 mmol, 73%) was obtained as a white solid. $^1$H NMR (400 MHz, DMSO-$d_6$) δ 12.78 (s, 1H), 8.15 (d, J=8.0 Hz, 1H), 8.09 (d, J=7.9 Hz, 1H), 7.73-7.63 (m, 1H), 7.49 (dd, J=8.6, 1.9 Hz, 2H), 7.21 (d, J=7.3 Hz, 1H), 6.99 (dt, J=10.7, 2.2 Hz, 1H), 6.74 (d, J=8.4 Hz, 1H), 6.64 (s, 2H), 3.86 (d, J=6.5 Hz, 2H), 2.05 (dp, J=13.3, 6.5 Hz, 1H), 1.02 (dd, J=12.7, 6.4 Hz, 6H).

The following compounds can be synthesized using the procedures described herein:

N-((1H-pyrazol-5-yl)sulfonyl)-2-chloro-6-(3-fluoro-5-isobutoxyphenyl)nicotinamide;
N-((6-aminopyridin-2-yl)sulfonyl)-6-chloro-6'-isopropoxy-[2,3'-bipyridine]-5-carboxamide; and
2-chloro-6-(3-fluoro-5-isobutoxy-phenyl)-N-[(6-fluoro-2-pyridyl)sulfonyl]pyridine-3-carboxamide.

Step 4: N-[(6-Amino-2-pyridyl)sulfonyl]-6-(3-fluoro-5-isobutoxy-phenyl)-2-(pentylamino)pyridine-3-carboxamide (Compound 84)

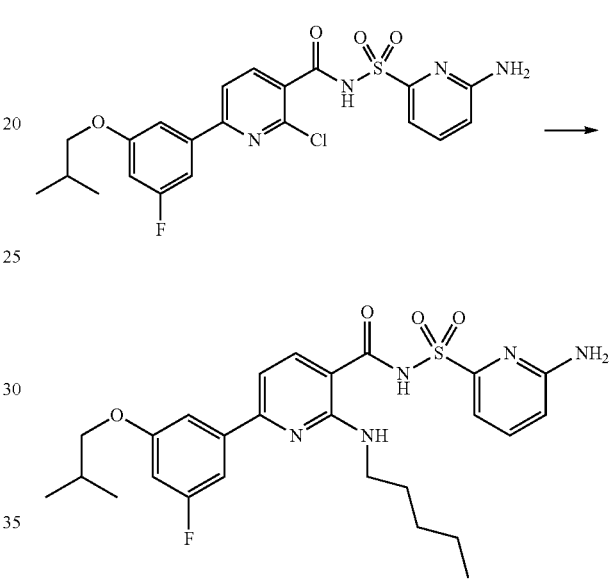

A 5 mL vial was charged with N-[(6-amino-2-pyridyl)sulfonyl]-2-chloro-6-(3-fluoro-5-isobutoxy-phenyl)pyridine-3-carboxamide (40. mg, 0.084 mmol), and cesium fluoride (76.12 mg, 0.5011 mmol) in dimethylsulfoxide (131.4 μL) followed by potassium carbonate (115.4 mg, 0.8352 mmol) and pentan-1-amine (29.12 mg, 38.72 μL, 0.3341 mmol). The vial was purged with nitrogen, capped, and stirred at 120° C. in an oil bath for 16 hours. The reaction mixture was filtered and then purified directly by reverse-phase preparative chromatography utilizing a C18 column and a gradient of 30 to 99% acetonitrile in water containing 5 mM hydrochloric acid to afford N-[(6-amino-2-pyridyl)sulfonyl]-6-(3-fluoro-5-isobutoxy-phenyl)-2-(pentylamino)pyridine-3-carboxamide (32.2 mg, 0.0602 mmol, 72%) as a light yellow solid ESI-MS m/z calc. 529.2159, found 530.4 (M+1)+; Retention time: 2.23 minutes. $^1$H NMR (400 MHz, DMSO-$d_6$) δ 8.31 (d, J=8.2 Hz, 1H), 7.66 (t, J=7.9 Hz, 1H), 7.55 (d, J=1.3 Hz, 1H), 7.50 (dd, J=10.2, 1.2 Hz, 1H), 7.27 (d, J=8.2 Hz, 1H), 7.19 (d, J=7.3 Hz, 1H), 6.92 (d, J=10.7 Hz, 1H), 6.71 (d, J=8.4 Hz, 1H), 6.59 (s, 2H), 3.84 (d, J=6.5 Hz, 2H), 3.47 (t, J=7.2 Hz, 2H), 3.37 (s, 2H), 2.07-1.95 (m, 1H), 1.64-1.50 (m, 2H), 1.30 (dd, J=10.6, 7.3 Hz, 4H), 1.00 (d, J=6.7 Hz, 6H), 0.85 (t, J=6.9 Hz, 3H).

The following compound can be synthesized using the procedures described herein:

379

N-[(6-amino-2-pyridyl)sulfonyl]-6-(3-fluoro-5-isobutoxy-phenyl)-2-[(3-hydroxy-3-methyl-butyl)amino]pyridine-3-carboxamide (Compound 80).

Preparation 2: N-[(6-Amino-2-pyridyl)sulfonyl]-2-(dimethylamino)-6-(3-fluoro-5-isobutoxy-phenyl)pyridine-3-carboxamide hydrochloride (Compound 19)

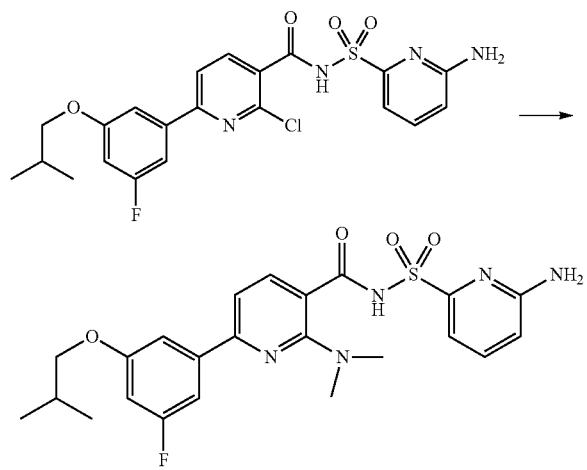

To a solution of N-[(6-amino-2-pyridyl)sulfonyl]-2-chloro-6-(3-fluoro-5-isobutoxy-phenyl)pyridine-3-carboxamide (35 mg, 0.073 mmol) in a 4 mL vial in N,N-dimethylformamide (0.8 mL) was added N,N-diisopropyl ethyl amine (37.78 mg, 50.92 µL, 0.2923 mmol) and the vial was capped under nitrogen and heated in an oil bath at 150° C. for 12 hours. The material was filtered through a syringe filter disk and purified using reverse-phase preparative HPLC utilizing a gradient of 1 to 99% acetonitrile in water containing 5 mM hydrochloric acid over 30 minutes to yield N-[(6-amino-2-pyridyl)sulfonyl]-2-(dimethylamino)-6-(3-fluoro-5-isobutoxy-phenyl)pyridine-3-carboxamide hydrochloride (9.2 mg, 0.017 mmol, 24%)$^1$H NMR (400 MHz, DMSO-$d_6$) δ 12.53 (s, 1H), 7.78 (d, J=7.9 Hz, 1H), 7.64 (dd, J=8.4, 7.3 Hz, 1H), 7.45 (dd, J=8.4, 1.8 Hz, 2H), 7.33 (d, J=7.9 Hz, 1H), 7.20 (d, J=7.1 Hz, 1H), 6.90 (dt, J=10.8, 2.4 Hz, 1H), 6.70 (d, J=8.2 Hz, 1H), 3.84 (d, J=6.5 Hz, 2H), 2.88 (s, 6H), 2.04 (hept, J=6.7 Hz, 1H), 1.00 (d, J=6.7 Hz, 6H). ESI-MS m/z calc. 487.16895, found 488.5 (M+1)+; Retention time: 1.71 minutes.

Preparation 3: N-((6-Aminopyridin-2-yl)sulfonyl)-2-(diethylamino)-6-(3-fluoro-5-isobutoxyphenyl)nicotinamide hydrochloride (Compound 53)

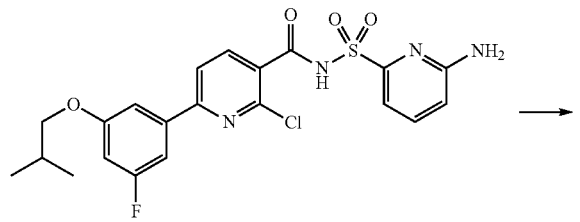

380

-continued

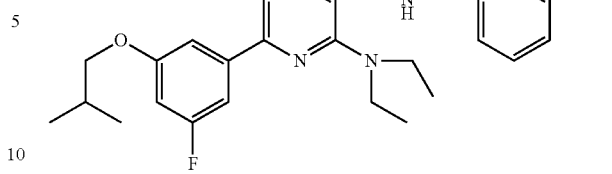

To a stirred solution of N-[(6-amino-2-pyridyl)sulfonyl]-2-chloro-6-(3-fluoro-5-isobutoxy-phenyl)pyridine-3-carboxamide (30. mg, 0.063 mmol) in anhydrous N-methyl-pyrrolidone (0.8 mL) was added N,N-diethylamine and N,N-diisopropyl ethyl amine, in that order. The vial was capped and the solution was heated to 150° C. for 12 hours. The cooled solution was filtered through a syringe filter disk and purified using reverse-phase preparative HPLC utilizing a gradient of 1 to 99% acetonitrile in water containing 5 mM hydrochloric acid over 30 minutes to yield N-((6-aminopyridin-2-yl)sulfonyl)-2-(diethylamino)-6-(3-fluoro-5-isobutoxyphenyl)nicotinamide hydrochloride (8.3 mg, 0.015 mmol, 24%). ESI-MS m/z calc. 515.20, found 516.3 (M+1)+; Retention time: 1.71 minutes.

Preparation 4: N-((6-Aminopyridin-2-yl)sulfonyl)-2-(tert-butylamino)-6-(3-fluoro-5-isobutoxyphenyl)nicotinamide hydrochloride (Compound 58)

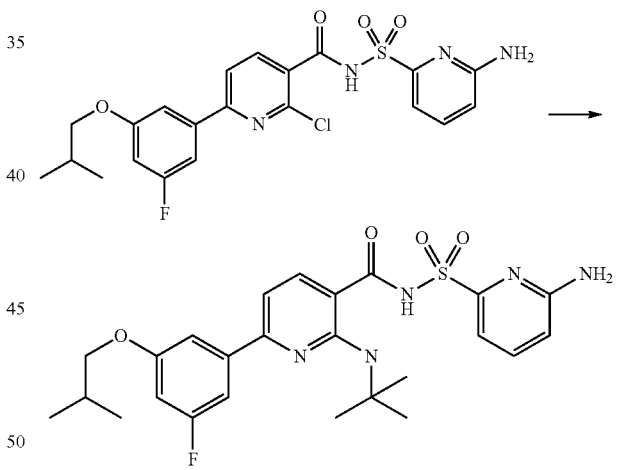

N-[(6-amino-2-pyridyl)sulfonyl]-2-chloro-6-(3-fluoro-5-isobutoxy-phenyl)pyridine-3-carboxamide (25 mg, 0.052 mmol) was mixed with potassium carbonate (72 mg, 0.52 mmol) and 2-methylpropane-2-amine (19 mg, 0.26 mmol) in dimethylsulfoxide (300 µL) and reaction mixture was heated to 150° C. for 16 hours. The cooled reaction was filtered and purified using reverse-phase preparative HPLC utilizing a gradient of 1 to 99% acetonitrile in water containing 5 mM hydrochloric acid over 30 minutes to yield N-((6-aminopyridin-2-yl)sulfonyl)-2-(tert-butylamino)-6-(3-fluoro-5-isobutoxyphenyl)nicotinamide hydrochloride (1 mg, 0.002 mmol, 4%). $^1$H NMR (400 MHz, DMSO-$d_6$) δ 8.32 (d, J=8.3 Hz, 1H), 8.21 (s, 1H), 7.67 (dd, J=8.5, 7.3 Hz, 1H), 7.55 (t, J=1.8 Hz, 1H), 7.48 (dt, J=10.1, 1.9 Hz, 1H), 7.29 (d, J=8.2 Hz, 1H), 7.20 (d, J=7.2 Hz, 1H), 6.93 (dt, J=10.6, 2.3 Hz, 1H), 6.72 (d, J=8.5 Hz, 1H), 6.62 (s, 2H), 3.85 (d, J=6.6 Hz, 2H), 2.12-1.98 (m, 1H), 1.46 (s, 9H), 0.99 (d, J=6.7 Hz, 6H). ESI-MS m/z calc. 515.20, found 516.3 (M+1)+; Retention time: 3.16 minutes.

The following compound can be synthesized using the procedures described herein:

N-[(6-amino-2-pyridyl)sulfonyl]-6-(3-fluoro-5-isobutoxy-phenyl)-2-[isopropyl(methyl)amino]pyridine-3-carboxamide (Compound 31);

N-[(6-amino-2-pyridyl)sulfonyl]-2-(1,2-dimethylpropylamino)-6-(3-fluoro-5-isobutoxy-phenyl)pyridine-3-carboxamide (Compound 54);

N-[(6-amino-2-pyridyl)sulfonyl]-2-[ethyl(methyl)amino]-6-(3-fluoro-5-isobutoxy-phenyl)pyridine-3-carboxamide (Compound 67);

N-[(6-amino-2-pyridyl)sulfonyl]-6-(3-fluoro-5-isobutoxy-phenyl)-2-[methyl(propyl)amino]pyridine-3-carboxamide (Compound 64);

N-[(6-amino-2-pyridyl)sulfonyl]-6-(3-fluoro-5-isobutoxy-phenyl)-2-[isobutyl(methyl)amino]pyridine-3-carboxamide (Compound 61);

N-[(6-amino-2-pyridyl)sulfonyl]-2-[2,2-dimethylpropyl(methyl)amino]-6-(3-fluoro-5-isobutoxy-phenyl)pyridine-3-carboxamide (Compound 52);

N-[(6-amino-2-pyridyl)sulfonyl]-2-[ethyl(isopropyl)amino]-6-(3-fluoro-5-isobutoxy-phenyl)pyridine-3-carboxamide (Compound 74);

N-[(6-amino-2-pyridyl)sulfonyl]-6-(3-fluoro-5-isobutoxy-phenyl)-2-[methyl(2,2,2-trifluoroethyl)amino]pyridine-3-carboxamide (Compound 66);

N-[(6-amino-2-pyridyl)sulfonyl]-2-[1-ethylpropyl(methyl)amino]-6-(3-fluoro-5-isobutoxy-phenyl)pyridine-3-carboxamide (Compound 69);

2-(3,3-dimethylbutylamino)-6-(3-fluoro-5-isobutoxy-phenyl)-N-(1H-pyrazol-5-ylsulfonyl)pyridine-3-carboxamide (Compound 50);

2-(2,2-dimethylpropylamino)-6-(3-fluoro-5-isobutoxy-phenyl)-N-(1H-pyrazol-5-ylsulfonyl)pyridine-3-carboxamide (Compound 72); and N-[(6-amino-2-pyridyl)sulfonyl]-2-[ethyl(isopropyl)amino]-6-(6-isopropoxy-3-pyridyl)pyridine-3-carboxamide (Compound 14).

The following compounds can be made in a manner analogous to that described in preparation 4 using sodium carbonate in place of potassium carbonate:

6-(3-fluoro-5-isobutoxy-phenyl)-2-[isopropyl(methyl)amino]-N-(1H-pyrazol-5-ylsulfonyl)pyridine-3-carboxamide (Compound 79);

2-[ethyl(isopropyl)amino]-6-(3-fluoro-5-isobutoxy-phenyl)-N-(1H-pyrazol-5-ylsulfonyl)pyridine-3-carboxamide (Compound 16); and 2-(diethylamino)-6-(3-fluoro-5-isobutoxy-phenyl)-N-(1H-pyrazol-5-ylsulfonyl)pyridine-3-carboxamide (Compound 46).

The following compound can be made in a manner analogous to that described in preparation 4 except the reaction mixture was heated to 170° C. for 2 hours and then 150° C. for 1 hour: N-[(6-amino-2-pyridyl)sulfonyl]-6-(6-isopropoxy-3-pyridyl)-2-[isopropyl(methyl)amino]pyridine-3-carboxamide (Compound 70).

Preparation 5: N-((6-Aminopyridin-2-yl)sulfonyl)-2-fluoro-6-(3-fluoro-5-isobutoxyphenyl)nicotinamide

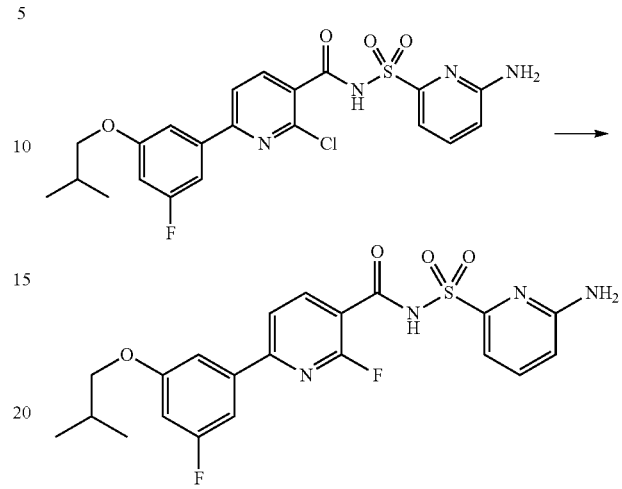

N-[(6-amino-2-pyridyl)sulfonyl]-2-chloro-6-(3-fluoro-5-isobutoxy-phenyl)pyridine-3-carboxamide (5.2 g, 11 mmol) and cesium fluoride (8.248 g, 54.30 mmol) in dimethylsulfoxide (35 mL) was stirred at 150° C. for 24 hours. A second aliquot of cesium fluoride (1.650 g, 10.86 mmol) was added and the mixture was heated at 155° C. for 6 hours. The cooled reaction was diluted with ice water and washed with ethyl acetate. The combined organic layers were washed with brine, dried over sodium sulfate, and concentrated under reduced pressure to an orange oil. The crude material was purified using silica gel column chromatography eluting with 0 to 10% ethyl acetate in hexanes to give N-[(6-amino-2-pyridyl)sulfonyl]-2-fluoro-6-(3-fluoro-5-isobutoxy-phenyl)pyridine-3-carboxamide (1.72 g, 3.46 mmol, 32%) ESI-MS m/z calc. 462.11734, found 463.2 (M+1)+; Retention time: 1.71 minutes.

Preparation 6: N-[(6-Amino-2-pyridyl)sulfonyl]-2-(diisopropylamino)-6-(3-fluoro-5-isobutoxy-phenyl)pyridine-3-carboxamide (Compound 41)

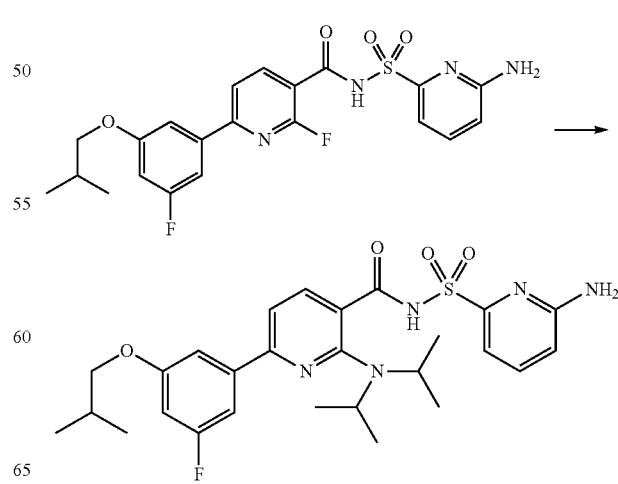

N-[(6-amino-2-pyridyl)sulfonyl]-2-fluoro-6-(3-fluoro-5-isobutoxy-phenyl)pyridine-3-carboxamide (25 mg, 0.054 mmol) was mixed with potassium carbonate (75 mg, 0.54 mmol) and diisopropylamine (27 mg, 38 µL, 0.27 mmol) in dimethylsulfoxide (300 µL) and reaction mixture was heated to 150° C. overnight. The reaction mixture was cooled to room temperature, filtered, and purified by reverse-phase preparative chromatography utilizing a C18 column and a gradient of 1 to 99% acetonitrile in water containing 5 mM hydrochloric acid over 15 minutes to yield N-((6-aminopyridin-2-yl)sulfonyl)-2-fluoro-6-(3-fluoro-5-isobutoxyphenyl)nicotinamide (4.0 mg, 0.0069 mmol, 13%) as a hydrochloric acid salt. ESI-MS m/z calc. 543.23, found 544.4 (M+1)+; Retention time: 2.48 minutes.

The following compounds can be synthesized using the procedures described herein:
N-[(6-amino-2-pyridyl)sulfonyl]-6-(3-fluoro-5-isobutoxy-phenyl)-2-[methyl-[(1R)-2,2,2-trifluoro-1-methyl-ethyl]amino]pyridine-3-carboxamide (Compound 75);
N-[(6-amino-2-pyridyl)sulfonyl]-2-[2,2-difluoroethyl(methyl)amino]-6-(3-fluoro-5-isobutoxy-phenyl)pyridine-3-carboxamide (Compound 1); and
N-[(6-amino-2-pyridyl)sulfonyl]-6-(3-fluoro-5-isobutoxy-phenyl)-2-[methyl-[(1 S)-2,2,2-trifluoro-1-methyl-ethyl]amino]pyridine-3-carboxamide (Compound 17).

Preparation 7: N-[(6-Amino-2-pyridyl)sulfonyl]-6-(3-fluoro-5-isobutoxy-phenyl)-2-methoxy-pyridine-3-carboxamide (Compound 10)

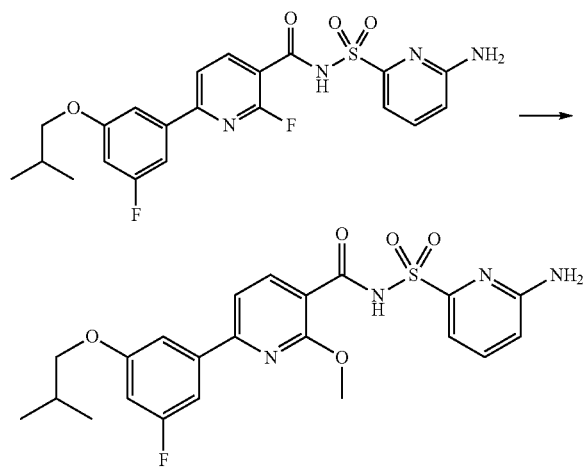

Methanol (5.5 mg, 7.0 µL, 0.17 mmol) was dissolved in dimethylsulfoxide (300 µL) and treated with sodium hydride (60% by weight, 6.9 mg, 0.17 mmol). After stirring at room temperature for 5 minutes, a solution of N-[(6-amino-2-pyridyl)sulfonyl]-2-fluoro-6-(3-fluoro-5-isobutoxy-phenyl)pyridine-3-carboxamide (40. mg, 0.086 mmol) in dioxane (300 µL) was added to the reaction mixture. After another 5 minutes of stirring at room temperature, the reaction vessel was sealed under nitrogen gas and heated in a microwave reactor to 110° C. for 30 minutes. The reaction mixture was cooled to room temperature, filtered, and purified by reverse-phase preparative chromatography utilizing a C18 column and a gradient of 1 to 99% acetonitrile in water containing 5 mM hydrochloric acid over 15 minutes to yield N-[(6-amino-2-pyridyl)sulfonyl]-6-(3-fluoro-5-isobutoxy-phenyl)-2-methoxy-pyridine-3-carboxamide (5.9 mg, 0.012 mmol, 73%) as a hydrochloric acid salt. ESI-MS m/z calc. 474.14, found 475.04 (M+1)+; Retention time: 2.02 minutes.

The following compound can be synthesized using the procedures described herein:
N-[(6-amino-2-pyridyl)sulfonyl]-6-(3-fluoro-5-isobutoxy-phenyl)-2-[(1 S)-1-methylpropoxy]pyridine-3-carboxamide (Compound 29);
N-[(6-amino-2-pyridyl)sulfonyl]-2-(3,3-dimethylpentoxy)-6-(3-fluoro-5-isobutoxy-phenyl)pyridine-3-carboxamide (Compound 77);
N-[(6-amino-2-pyridyl)sulfonyl]-2-(3,3-dimethylbutoxy)-6-(3-fluoro-5-isobutoxy-phenyl)pyridine-3-carboxamide (Compound 3);
N-[(6-amino-2-pyridyl)sulfonyl]-6-(3-fluoro-5-isobutoxy-phenyl)-2-[2,2,2-trifluoro-1-(trifluoromethyl)ethoxy]pyridine-3-carboxamide (Compound 33);
N-[(6-amino-2-pyridyl)sulfonyl]-2-(1-ethyl-2-methyl-propoxy)-6-(3-fluoro-5-isobutoxy-phenyl)pyridine-3-carboxamide (Compound 40);
N-[(6-amino-2-pyridyl)sulfonyl]-6-(3-fluoro-5-isobutoxy-phenyl)-2-(1-isopropyl-2-methyl-propoxy)pyridine-3-carboxamide (Compound 26);
N-[(6-amino-2-pyridyl)sulfonyl]-6-(3-fluoro-5-isobutoxy-phenyl)-2-pent-3-ynoxy-pyridine-3-carboxamide (Compound 35);
N-[(6-amino-2-pyridyl)sulfonyl]-6-(3-fluoro-5-isobutoxy-phenyl)-2-(3,3,3-trifluoro-1-methyl-propoxy)pyridine-3-carboxamide (Compound 9);
N-[(6-amino-2-pyridyl)sulfonyl]-6-(3-fluoro-5-isobutoxy-phenyl)-2-(1-isopropyl-2,2-dimethyl-propoxy)pyridine-3-carboxamide (Compound 68);
N-[(6-amino-2-pyridyl)sulfonyl]-6-(3-fluoro-5-isobutoxy-phenyl)-2-(2-methoxyethoxy)pyridine-3-carboxamide (Compound 60);
N-[(6-amino-2-pyridyl)sulfonyl]-2-butoxy-6-(3-fluoro-5-isobutoxy-phenyl)pyridine-3-carboxamide (Compound 63);
N-[(6-amino-2-pyridyl)sulfonyl]-6-(3-fluoro-5-isobutoxy-phenyl)-2-(3-methoxy-3-methyl-butoxy)pyridine-3-carboxamide (Compound 22);
N-[(6-amino-2-pyridyl)sulfonyl]-6-(3-fluoro-5-isobutoxy-phenyl)-2-(3-methoxypropoxy)pyridine-3-carboxamide (Compound 21);
N-[(6-amino-2-pyridyl)sulfonyl]-2-(2,2-difluoropropoxy)-6-(3-fluoro-5-isobutoxy-phenyl)pyridine-3-carboxamide (Compound 57);
N-[(6-amino-2-pyridyl)sulfonyl]-6-(3-fluoro-5-isobutoxy-phenyl)-2-isopentyloxy-pyridine-3-carboxamide (Compound 2);
N-[(6-amino-2-pyridyl)sulfonyl]-2-(2-tert-butoxyethoxy)-6-(3-fluoro-5-isobutoxy-phenyl)pyridine-3-carboxamide (Compound 4);
N-[(6-amino-2-pyridyl)sulfonyl]-2-(1,2-dimethylpentoxy)-6-(3-fluoro-5-isobutoxy-phenyl)pyridine-3-carboxamide (Compound 62);
N-[(6-amino-2-pyridyl)sulfonyl]-6-(3-fluoro-5-isobutoxy-phenyl)-2-(2,2,3,3-tetrafluoro-1-methyl-propoxy)pyridine-3-carboxamide (Compound 6);
N-[(6-amino-2-pyridyl)sulfonyl]-2-(1,1-dimethylpropoxy)-6-(3-fluoro-5-isobutoxy-phenyl)pyridine-3-carboxamide (Compound 44);
N-[(6-amino-2-pyridyl)sulfonyl]-2-(1,2-dimethylbutoxy)-6-(3-fluoro-5-isobutoxy-phenyl)pyridine-3-carboxamide (Compound 12);

N-[(6-amino-2-pyridyl)sulfonyl]-6-(3-fluoro-5-isobutoxy-phenyl)-2-pentoxy-pyridine-3-carboxamide (Compound 11);

N-[(6-amino-2-pyridyl)sulfonyl]-6-(3-fluoro-5-isobutoxy-phenyl)-2-[(1R)-1-methylpropoxy]pyridine-3-carboxamide (Compound 59);

N-[(6-amino-2-pyridyl)sulfonyl]-6-(3-fluoro-5-isobutoxy-phenyl)-2-(3,3,3-trifluoropropoxy)pyridine-3-carboxamide (Compound 81);

N-[(6-amino-2-pyridyl)sulfonyl]-6-(3-fluoro-5-isobutoxy-phenyl)-2-(2-methoxy-1,1-dimethyl-ethoxy)pyridine-3-carboxamide (Compound 51);

N-[(6-amino-2-pyridyl)sulfonyl]-2-(2-ethoxy-1-methyl-ethoxy)-6-(3-fluoro-5-isobutoxy-phenyl)pyridine-3-carboxamide (Compound 71);

N-[(6-amino-2-pyridyl)sulfonyl]-6-(3-fluoro-5-isobutoxy-phenyl)-2-propoxy-pyridine-3-carboxamide (Compound 27); and N-[(6-amino-2-pyridyl)sulfonyl]-2-(2-ethoxyethoxy)-6-(3-fluoro-5-isobutoxy-phenyl)pyridine-3-carboxamide (Compound 13).

Preparation 8: N-((6-Aminopyridin-2-yl)sulfonyl)-2-ethoxy-6-(3-fluoro-5-isobutoxyphenyl)nicotinamide (Compound 30)

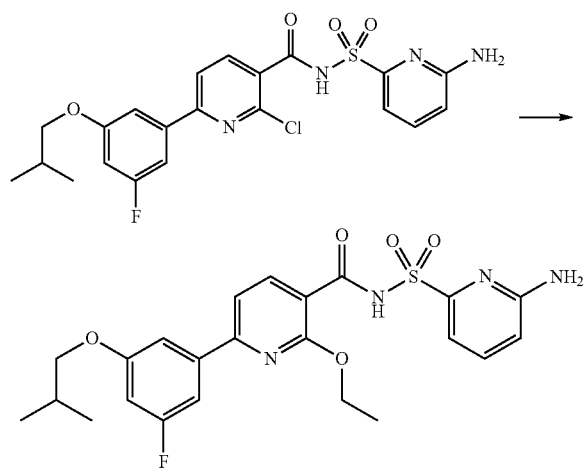

N-[(6-amino-2-pyridyl)sulfonyl]-2-chloro-6-(3-fluoro-5-isobutoxy-phenyl)pyridine-3-carboxamide (50. mg 0.10 mmol) was dissolved in dimethylsulfoxide (300 µL), and cesium fluoride (47 mg, 0.31 mmol) was added. The reaction mixture was allowed to stir in a 150° C. oil bath for 3 to 16 hours. In separate microwave reactor vials, sodium hydride (8 mg, 0.20 mmol, 60% by weight in oil) was added to ethanol (9.6 mg, 12 µL, 0.21 mmol) dissolved in dioxane (300 µL). After stirring for 5 minutes, the reaction mixture in dimethylsulfoxide described above was added as a 300 µL aliquot. The final reaction mixture was heated under microwave irradiation in a microwave reactor to 110° C. for 30 minutes. The reaction mixture was cooled to room temperature, filtered, and purified by reverse-phase preparative chromatography utilizing a C18 column and a gradient of 1 to 99% acetonitrile in water containing 5 mM hydrochloric acid over 15 minutes to yield N-((6-aminopyridin-2-yl)sulfonyl)-2-ethoxy-6-(3-fluoro-5-isobutoxyphenyl)nicotinamide (15 mg, 0.031 mmol, 31%). $^1$H NMR (400 MHz, DMSO) δ 7.89 (d, J=7.7 Hz, 1H), 7.54 (d, J=7.7 Hz, 1H), 7.52-7.39 (m, 3H), 7.06 (d, J=7.3 Hz, 1H), 6.93-6.83 (m, 1H), 6.45 (d, J=8.2 Hz, 1H), 6.07 (s, 2H), 4.41 (q, J=7.0 Hz, 2H), 3.85 (d, J=6.5 Hz, 2H), 2.05 (dt, J=13.2, 6.7 Hz, 1H), 1.34 (t, J=7.0 Hz, 3H), 1.00 (d, J=6.7 Hz, 6H). ESI-MS m/z calc. 488.15, found 489.4 (M+1)+; Retention time: 2.15 minutes.

The following compound can be synthesized using the procedures described herein:

N-[(6-amino-2-pyridyl)sulfonyl]-6-(3-fluoro-5-isobutoxy-phenyl)-2-(1-methylallyloxy)pyridine-3-carboxamide (Compound 42);

N-[(6-amino-2-pyridyl)sulfonyl]-6-(3-fluoro-5-isobutoxy-phenyl)-2-[(E)-4,4,4-trifluorobut-2-enoxy]pyridine-3-carboxamide (Compound 83);

N-[(6-amino-2-pyridyl)sulfonyl]-2-(1-ethylpropoxy)-6-(3-fluoro-5-isobutoxy-phenyl)pyridine-3-carboxamide (Compound 47);

N-[(6-amino-2-pyridyl)sulfonyl]-6-(3-fluoro-5-isobutoxy-phenyl)-2-(2-methylallyloxy)pyridine-3-carboxamide (Compound 49);

N-[(6-amino-2-pyridyl)sulfonyl]-2-(2,2-dimethylpropoxy)-6-(3-fluoro-5-isobutoxy-phenyl)pyridine-3-carboxamide (Compound 32);

2-allyloxy-N-[(6-amino-2-pyridyl)sulfonyl]-6-(3-fluoro-5-isobutoxy-phenyl)pyridine-3-carboxamide (Compound 43);

N-[(6-amino-2-pyridyl)sulfonyl]-2-[(E)-but-2-enoxy]-6-(3-fluoro-5-isobutoxy-phenyl)pyridine-3-carboxamide (Compound 28);

N-[(6-amino-2-pyridyl)sulfonyl]-6-(3-fluoro-5-isobutoxy-phenyl)-2-isopropoxy-pyridine-3-carboxamide (Compound 5);

N-[(6-amino-2-pyridyl)sulfonyl]-6-(3-fluoro-5-isobutoxy-phenyl)-2-(2,2,2-trifluoro-1-methyl-ethoxy)pyridine-3-carboxamide (Compound 73); and N-[(6-amino-2-pyridyl)sulfonyl]-6-(3-fluoro-5-isobutoxy-phenyl)-2-(2,2,2-trifluoroethoxy)pyridine-3-carboxamide (Compound 48).

Preparation 9: N-((6-Aminopyridin-2-yl)sulfonyl)-6-(3-fluoro-5-isobutoxyphenyl)-2-(4,4,4-trifluorobutoxy)nicotinamide (Compound 82)

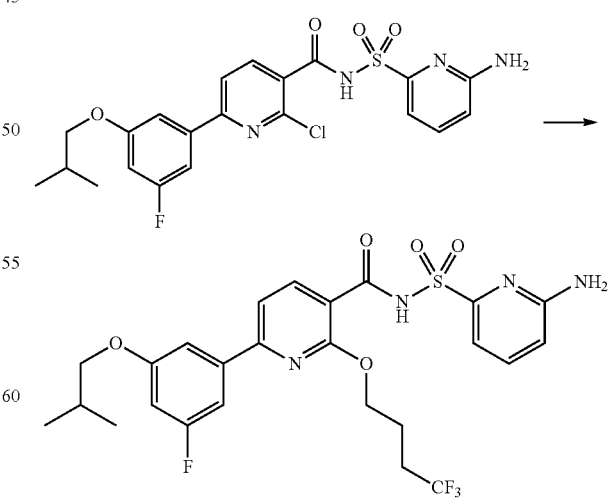

To a solution of 4,4,4-trifluorobutan-1-ol (21 mg, 0.16 mmol) in N-methylpyrrolidone (200 µL) was added sodium hydride (4 mg, 0.16 mmol, 60% by weight in oil). After stirring at room temperature for 5 minutes, a solution of N-[(6-amino-2-pyridyl)sulfonyl]-2-chloro-6-(3-fluoro-5-isobutoxy-phenyl)pyridine-3-carboxamide (40. mg, 0.080 mmol) in dioxane (200 µL) was added. After an additional 5 minutes of stirring at room temperature, the reaction vial was sealed and heated in a microwave reactor to 110° C. for 30 minutes. The reaction mixture was cooled to room temperature, filtered, and purified by reverse-phase preparative chromatography utilizing a C18 column and a gradient of 1 to 99% acetonitrile in water containing 5 mM hydrochloric acid over 15 minutes to yield N-((6-aminopyridin-2-yl)sulfonyl)-6-(3-fluoro-5-isobutoxyphenyl)-2-(4,4,4-trifluorobutoxy)nicotinamide (15 mg, 0.026 mmol, 33%). ESI-MS m/z calc. 570.16, found 571.2 (M+1)+; Retention time: 2.18 minutes.

The following compound can be synthesized using the procedures described herein:

N-[(6-amino-2-pyridyl)sulfonyl]-6-(3-fluoro-5-isobutoxy-phenyl)-2-(1,2,2-trimethylpropoxy)pyridine-3-carboxamide (Compound 25);

N-[(6-amino-2-pyridyl)sulfonyl]-6-(3-fluoro-5-isobutoxy-phenyl)-2-[1-(methoxymethyl)propoxy]pyridine-3-carboxamide (Compound 18);

N-[(6-amino-2-pyridyl)sulfonyl]-2-(1,3-dimethylbutoxy)-6-(3-fluoro-5-isobutoxy-phenyl)pyridine-3-carboxamide (Compound 24);

N-[(6-amino-2-pyridyl)sulfonyl]-6-(3-fluoro-5-isobutoxy-phenyl)-2-(1-methylbutoxy)pyridine-3-carboxamide (Compound 56);

N-[(6-amino-2-pyridyl)sulfonyl]-6-(3-fluoro-5-isobutoxy-phenyl)-2-(2-methoxy-1-methyl-ethoxy)pyridine-3-carboxamide (Compound 23);

N-[(6-amino-2-pyridyl)sulfonyl]-6-(3-fluoro-5-isobutoxy-phenyl)-2-(2-isopropoxyethoxy)pyridine-3-carboxamide (Compound 55);

N-[(6-amino-2-pyridyl)sulfonyl]-6-(3-fluoro-5-isobutoxy-phenyl)-2-[(1R)-2-methoxy-1-methyl-ethoxy]pyridine-3-carboxamide (Compound 65);

N-[(6-amino-2-pyridyl)sulfonyl]-6-(3-fluoro-5-isobutoxy-phenyl)-2-[(2S)-2-methoxypropoxy]pyridine-3-carboxamide (Compound 78);

N-[(6-amino-2-pyridyl)sulfonyl]-2-(1-ethyl-2,2-dimethyl-propoxy)-6-(3-fluoro-5-isobutoxy-phenyl)pyridine-3-carboxamide (Compound 34);

N-[(6-amino-2-pyridyl)sulfonyl]-6-(3-fluoro-5-isobutoxy-phenyl)-2-[(1 S)-2-methoxy-1-methyl-ethoxy]pyridine-3-carboxamide (Compound 20);

N-[(6-amino-2-pyridyl)sulfonyl]-6-(3-fluoro-5-isobutoxy-phenyl)-2-(1,3,3-trimethylbutoxy)pyridine-3-carboxamide (Compound 36); and N-[(6-amino-2-pyridyl)sulfonyl]-2-(2,2-difluoroethoxy)-6-(3-fluoro-5-isobutoxy-phenyl)pyridine-3-carboxamide (Compound 38).

The following compounds can be made in a manner analogous to that described in preparation 9 except the reaction mixture was heated to 120° C. for 30 minutes:

N-[(6-amino-2-pyridyl)sulfonyl]-6-tert-butyl-2-(2,2-dimethylpropoxy)pyridine-3-carboxamide (Compound 15); and N-[(6-amino-2-pyridyl)sulfonyl]-6-tert-butyl-2-isopropoxy-pyridine-3-carboxamide (Compound 45).

Preparation 10: N-((6-Aminopyridin-2-yl)sulfonyl)-6-(diethylamino)-6'-isopropoxy-[2,3'-bipyridine]-5-carboxamide (Compound 8)

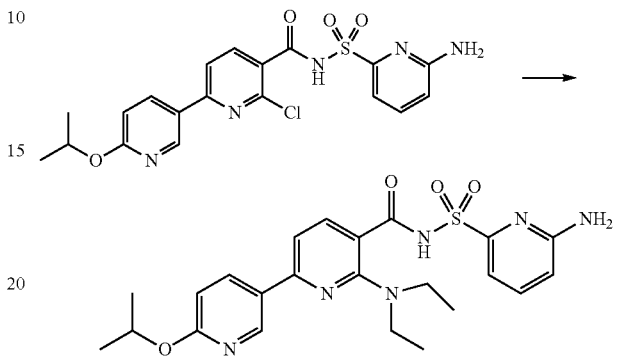

A mixture of N-[(6-amino-2-pyridyl)sulfonyl]-2-chloro-6-(6-isopropoxy-3-pyridyl)pyridine-3-carboxamide (25 mg, 0.056 mmol) and N-ethylethanamine (41 mg, 0.56 mmol) was heated at 100° C. for 1 hour. The mixture was cooled to room temperature, diluted with N,N-dimethylformamide and subjected to preparatory HPLC utilizing a C18 column and a gradient of 1 to 99% acetonitrile in water containing 5 mM hydrochloric acid over 15 minutes to yield N-((6-aminopyridin-2-yl)sulfonyl)-6-(diethylamino)-6'-isopropoxy-[2,3'-bipyridine]-5-carboxamide (13 mg, 0.027 mmol, 48%). ESI-MS m/z calc. 484.19, found 485.2 (M+1)+; Retention time: 1.31 minutes.

Preparation 11: N-((6-Aminopyridin-2-yl)sulfonyl)-6-(diethylamino)-6'-isopropoxy-[2,3'-bipyridine]-5-carboxamide (Compound 39)

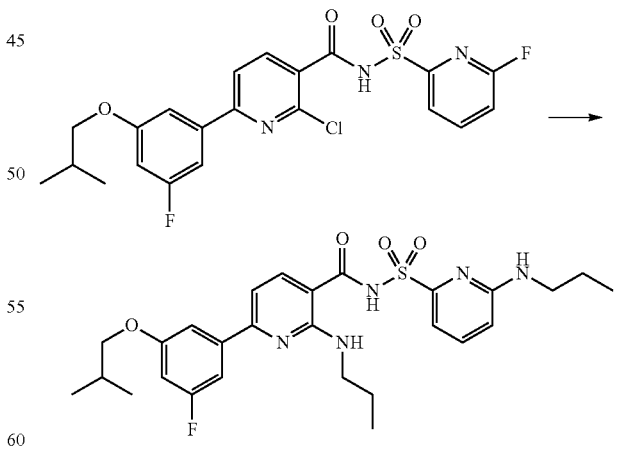

To a microwave vial was added 2-chloro-6-(3-fluoro-5-isobutoxy-phenyl)-N-[(6-fluoro-2-pyridyl)sulfonyl]pyridine-3-carboxamide (25 mg, 0.052 mmol), potassium carbonate (36 mg, 0.26 mmol), dimethylsulfoxide (1 mL), and propylamine (12 mg, 17 µL, 0.21 mmol). The reaction was heated at 150° C. for 3 hours. The reaction was filtered and purified via utilizing a C18 column and a gradient of 1 to 99% acetonitrile in water containing 5 mM hydrochloric acid over 15 minutes to yield 6-(3-fluoro-5-isobutoxy-phenyl)-2-(propylamino)-N-[[6-(propylamino)-2-pyridyl]sulfonyl]pyridine-3-carboxamide (8 mg, 0.015 mmol, 28%) as a solid. ESI-MS m/z calc. 543.23157, found 544.3 (M+1)+; Retention time: 2.33 minutes.

Preparation 12: N-[(6-Amino-2-pyridyl)sulfonyl]-6-tert-butyl-2-fluoro-pyridine-3-carboxamide Step 1: 6-tert-Butyl-2-fluoro-pyridine-3-carbonitrile

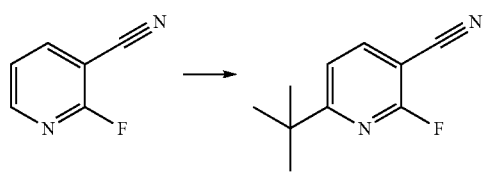

2,2-dimethylpropanoic acid (20.92 g, 11.76 mL, 204.8 mmol), 2-fluoropyridine-3-carbonitrile (5.00 g, 40.95 mmol), and silver nitrate (1.740 g, 10.24 mmol) were suspended in 10% sulfuric acid in water (100 mL). A solution of ammonium persulfate (17.29 g, 81.90 mmol) in water (113.5 mL) was added dropwise through an addition funnel. The mixture was stirred at room temperature for 2 days. The pH of reaction mixture was adjusted to ~8-9 with concentrated ammonium hydroxide (~60 mL) and extracted with ethyl acetate (3×100 mL). The combined organic layers were extracted with brine, dried over sodium sulfate, and concentrated. The crude was purified on silica using ethyl acetate/hexane; product came out ~5% ethyl acetate. The fractions were concentrated to give a clear oil (5.5 grams). It was dissolved in ethyl acetate (75 mL) and washed with aqueous sodium hydroxide (1 N, 4×75 mL). The organic layer was dried over sodium sulfate, filtered and concentrated under reduced pressure to provide 6-tert-butyl-2-fluoro-pyridine-3-carbonitrile (1.75 g, 9.820 mmol, 24%) as a clear colorless oil. $^1$H NMR (400 MHz, CDCl$_3$) δ 7.98 (dd, J=8.7, 8.0 Hz, 1H), 7.34 (dd, J=7.9, 2.0 Hz, 1H), 1.36 (s, 9H). ESI-MS m/z calc. 178.09062, found 179.4 (M+1)+; Retention time: 1.25 minutes.

Step 2: 6-tert-Butyl-2-fluoro-pyridine-3-carbaldehyde

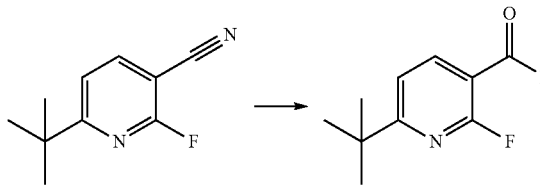

6-tert-butyl-2-fluoro-pyridine-3-carbonitrile (1.75 g, 9.820 mmol) was dissolved in dichloromethane (30 mL), and the solution was cooled to 0° C. Diisobutylaluminum (19.64 mL of 1 M in hexanes, 19.64 mmol) was slowly added dropwise. The ice bath was allowed to slowly melt, and the reaction was allowed to stir overnight at room temperature. The reaction mixture was again cooled to 0° C.

Aqueous citric acid solution (30 mL) was very slowly and carefully added to the reaction mixture. After stirring at room temperature for 1 hour, the mixture was extracted with ethyl acetate (3×75 mL) (aqueous 1 N sodium hydroxide was added to the aqueous layer to help break up lithium-aluminum salts). The combined organic layers were washed with brine (1×75 mL), dried over sodium sulfate, filtered and concentrated under reduced pressure. The product was isolated by silica gel column chromatography. $^1$H NMR (400 MHz, CDCl$_3$) δ 10.27 (s, 1H), 8.22 (dd, J=9.6, 7.9 Hz, 1H), 7.37 (ddd, J=7.9, 2.0, 0.7 Hz, 1H), 1.38 (s, 9H). ESI-MS m/z calc. 181.09029, found 182.4 (M+1)+; Retention time: 1.144 minutes.

Step 3: 6-tert-butyl-2-fluoro-pyridine-3-carboxylic Acid

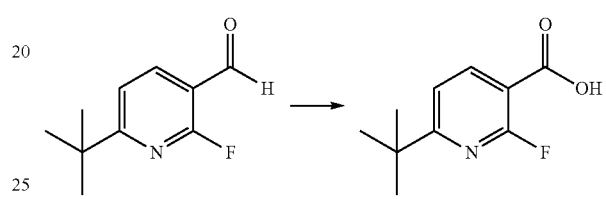

A solution of sodium dihydrogen phosphate monohydrate (5.412 g, 39.22 mmol) in water (5 mL) was added to a solution of 6-tert-butyl-2-fluoro-pyridine-3-carbaldehyde (646 mg, 3.56 mmol) and 2-methylbut-2-ene (2.5 g, 3.8 mL, 37 mmol) in tert-butanol (35 mL). Sodium chlorite (1.6 g, 18 mmol) was added portionwise. The reaction mixture was allowed to stir at room temperature overnight. The reaction mixture was diluted with water (20 mL) and adjusted to pH 2 with the addition of aqueous 1 N hydrochloric acid. It was extracted with ethyl acetate (3×75 mL). The organic layer was dried over sodium sulfate, filtered and concentrated under reduced pressure. The product was isolated by silica gel column chromatography: 0 to 70% ethyl acetate/hexane gradient; product eluted at 25%. 6-tert-butyl-2-fluoro-pyridine-3-carboxylic acid (626 mg, 3.17 mmol, 89%) was obtained as a white crystalline solid. $^1$H NMR (400 MHz, CDCl$_3$) δ 8.38 (dd, J=9.6, 7.9 Hz, 1H), 7.33 (dd, J=7.9, 2.0 Hz, 1H), 1.38 (s, 9H). ESI-MS m/z calc. 197.0852, found 198.3 (M+1)+; Retention time: 0.96 minutes.

Step 4: 6-tert-Butyl-2-fluoro-N-[(6-nitro-2-pyridyl)sulfonyl]pyridine-3-carboxamide

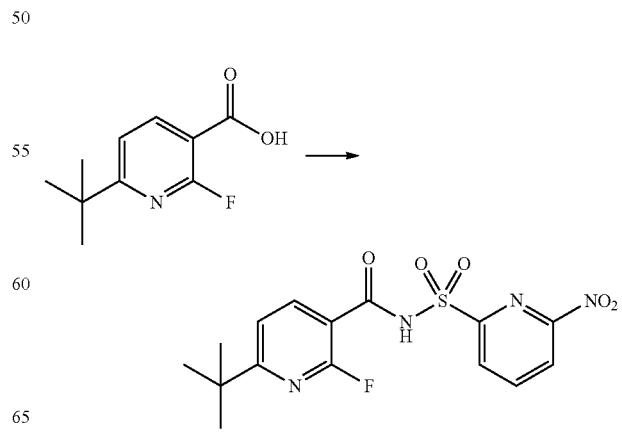

6-tert-Butyl-2-fluoro-pyridine-3-carboxylic acid (500. mg, 2.53 mmol) and 6-nitropyridine-2-sulfonamide (566.7 mg, 2.789 mmol) were combined and dissolved in N,N-dimethylformamide (10 mL). 1-[Bis(dimethylamino)methylene]-1H-1,2,3-triazolo[4,5-b]pyridinium 3-oxide hexafluorophosphate (1.060 g, 2.789 mmol) was added followed by potassium carbonate (1.051 g, 7.605 mmol). The reaction mixture was allowed to stir at 80° C. for 30 minutes. Additional 1-[bis(dimethylamino)methylene]-1H-1,2,3-triazolo[4,5-b]pyridinium 3-oxide hexafluorophosphate (337.3 mg, 0.8872 mmol) was added, and the reaction mixture was allowed to further stir at 80° C. overnight. The reaction mixture was diluted with ethyl acetate (75 mL) and washed with water (1×75 mL). The aqueous layer was extracted with ethyl acetate (2×50 mL). All organic layers were combined and washed with brine (1×75 mL). The organic layer was dried over sodium sulfate, filtered and concentrated to yield 6-tert-butyl-2-fluoro-N-[(6-nitro-2-pyridyl)sulfonyl]pyridine-3-carboxamide (744 mg, 1.95 mmol, 77%) $^1$H NMR (400 MHz, DMSO) δ 8.35 (s, 3H), 8.18 (dd, J=10.2, 7.8 Hz, 1H), 7.31 (dd, J=7.8, 2.1 Hz, 1H), 1.28 (s, 9H). ESI-MS m/z calc. 382.0747, found 383.3 (M+1)+; Retention time: 1.36 minutes.

Step 5: N-[(6-Amino-2-pyridyl)sulfonyl]-6-tert-butyl-2-fluoro-pyridine-3-carboxamide

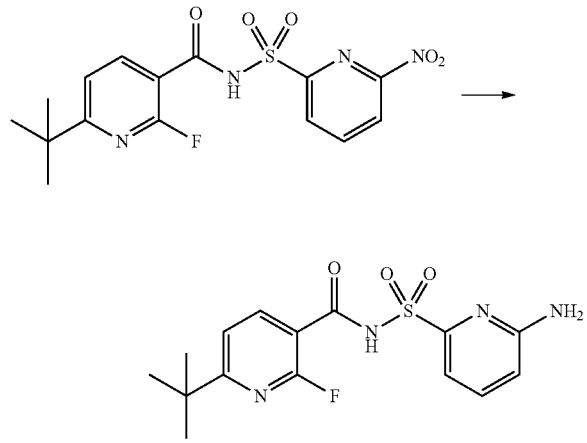

6-tert-butyl-2-fluoro-N-[(6-nitro-2-pyridyl)sulfonyl]pyridine-3-carboxamide (1.65 g, 4.31 mmol) was dissolved in tetrahydrofuran (33 mL) and ethanol (16.5 mL). Aqueous hydrochloric acid (7.2 mL of 6 M, 43 mmol) was added followed by powdered iron (2.41 g, 43.1 mmol). The reaction mixture was allowed to stir at 50° C. for 1 hour. Solids were removed by vacuum filtration, and the filtrate was concentrated under reduced pressure. The remaining residue was re-dissolved in a 1:1 mixture of tetrahydrofuran/methanol at 60° C. and concentrated onto silica gel. Purification was done via silica gel column chromatography utilizing a gradient of 20 to 70% ethyl acetate in hexanes to yield N-[(6-amino-2-pyridyl)sulfonyl]-6-tert-butyl-2-fluoro-pyridine-3-carboxamide (2.30 g, 6.53 mmol, 151%) as a yellow solid and it was used without further purification. ESI-MS m/z calc. 352.10052, found 353.1 (M+1)+; Retention time: 0.95 minutes.

Preparation 13: N-((6-Aminopyridin-2-yl)sulfonyl)-6-(3-fluoro-5-isobutoxyphenyl)-2-(3-methylbut-2-en-2-yl)nicotinamide (Compound 37)

Step 1: Ethyl 6-(3-fluoro-5-isobutoxyphenyl)-2-(3-methylbut-2-en-2-yl)nicotinate

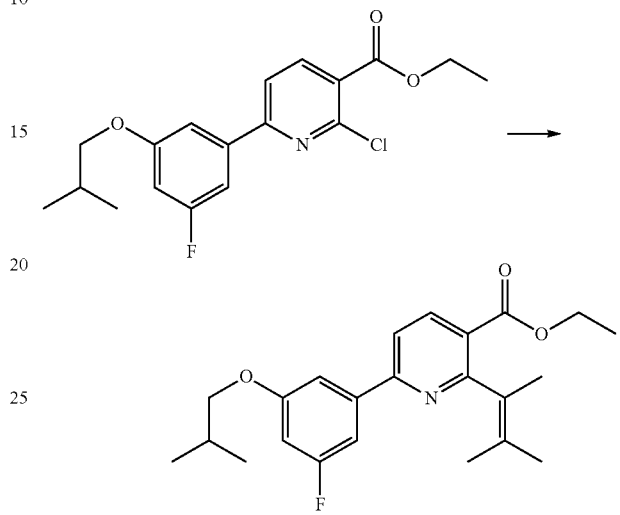

A mixture of ethyl 2-chloro-6-(3-fluoro-5-isobutoxy-phenyl)pyridine-3-carboxylate (141 mg, 0.401 mmol), potassium 3-methyl-2-buten-2-yltrifluoroborate (91.5 mg, 0.520 mmol), [1,1'-bis(diphenylphosphino)ferrocene]dichloropalladium(II), complex with dichloromethane (29 mg, 0.040 mmol), and sodium carbonate (127 mg, 1.20 mmol) in dioxane (1.8 mL) and water (200.0 μL) was degassed under a stream of nitrogen and stirred at 150° C. for 16 hours. The reaction combined with another reaction that was run at 0.1 mmol scale of ethyl 2-chloro-6-(3-fluoro-5-isobutoxy-phenyl)pyridine-3-carboxylate. The combined reactions were filtered and the solids were washed with ethyl acetate. The combined extracts were washed with brine and water, dried over sodium sulfate, and evaporated. The residue was purified by silica gel chromatography with 0 to 30% ethyl acetate in hexanes to give 0.16 g (0.41 mmol) of product as a colorless oil (83% yield for two reactions combined). ESI-MS m/z calc. 385.21, found 386.5 (M+1)+; Retention time: 0.93 minutes.

Step 2: 2-(1,2-Dimethylprop-1-enyl)-6-(3-fluoro-5-isobutoxy-phenyl)pyridine-3-carboxylic Acid

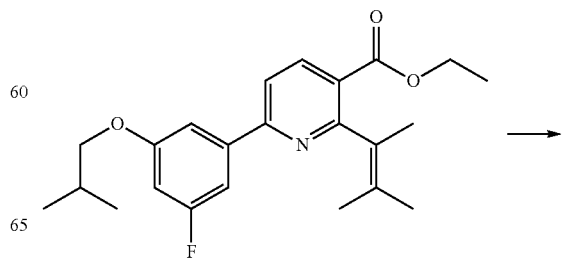

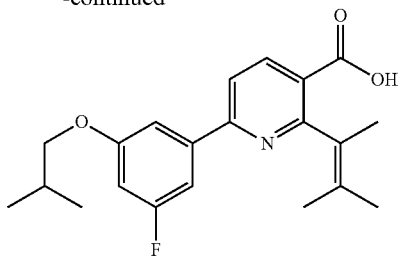

A solution of ethyl 6-(3-fluoro-5-isobutoxyphenyl)-2-(3-methylbut-2-en-2-yl)nicotinate (0.16 g, 0.41 mmol) and lithium hydroxide monohydrate (87 mg, 2.1 mmol) in tetrahydrofuran (1.0 mL) and water (1.0 mL) was stirred for 15 hours. A second aliquot of lithium hydroxide monohydrate (87 mg, 2.1 mmol) was added, and the reaction was stirred at 40° C. for three hours. The reaction was then stirred at 70° C. for 20 hours. The reaction was diluted with water, neutralized with 4 mL 1 M aqueous hydrochloric acid, and extracted with ethyl acetate. The combined extracts were dried over sodium sulfate and evaporated to give 2-(1,2-dimethylprop-1-enyl)-6-(3-fluoro-5-isobutoxy-phenyl)pyridine-3-carboxylic acid (0.14 g, 0.39 mmol, 94%) as a colorless foam. ESI-MS m/z calc. 357.17, found 358.4 (M+1)+; Retention time: 0.80 minutes.

Step 3: N-((6-Aminopyridin-2-yl)sulfonyl)-6-(3-fluoro-5-isobutoxyphenyl)-2-(3-methylbut-2-en-2-yl)nicotinamide (Compound 37)

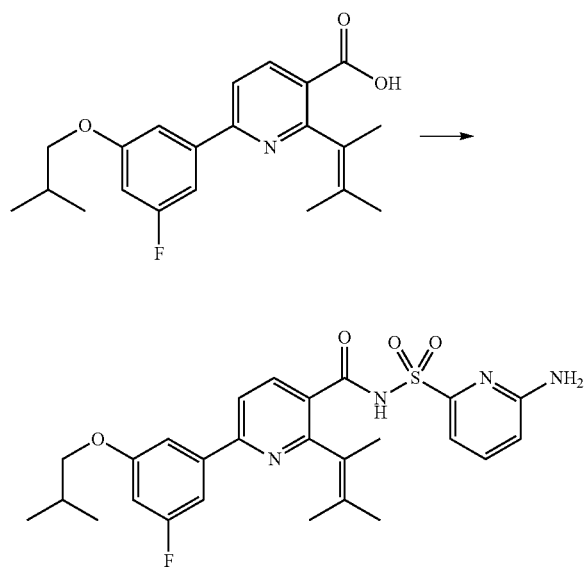

A solution of 2-(1,2-dimethylprop-1-enyl)-6-(3-fluoro-5-isobutoxy-phenyl)pyridine-3-carboxylic acid (20. mg, 0.056 mmol) and 1,1'-carbonyldiimidazole (11 mg, 0.070 mmol) in N,N-dimethylformamide (0.4 mL) was stirred at 45° C. for 90 minutes, and a solution of 6-aminopyridine-2-sulfonamide (12 mg, 0.070 mmol) and sodium bis(trimethylsilyl)amide (70. L of 1 M, 0.070 mmol) in N,N-dimethylformamide (0.4 mL) was stirred at 45° C. for 45 minutes. The two solutions were combined and stirred at 45° C. for two hours. The reaction was purified using a reverse phase HPLC-MS method using a Luna C18 column (75×30 mm, 5 μm particle size) sold by Phenomenex (pn: 00C-4252-U0-AX), and a dual gradient run from 30 to 99% acetonitrile in water containing 5 mM hydrochloric acid to yield N-((6-aminopyridin-2-yl)sulfonyl)-6-(3-fluoro-5-isobutoxyphenyl)-2-(3-methylbut-2-en-2-yl)nicotinamide (14 mg, 0.027 mmol, 49%). ESI-MS m/z calc. 512.19, found 513.4 (M+1)+; Retention time: 1.94 minutes.

The following compound can be made in a manner analogous to that described in preparation 13:

N-[(6-amino-2-pyridyl)sulfonyl]-2-(1,2-dimethylpropyl)-6-(3-fluoro-5-isobutoxy-phenyl)pyridine-3-carboxamide (Compound 76).

Preparation 14: 6-(3-Fluoro-5-isobutoxyphenyl)-2-(3-methylbutan-2-yl)nicotinic Acid

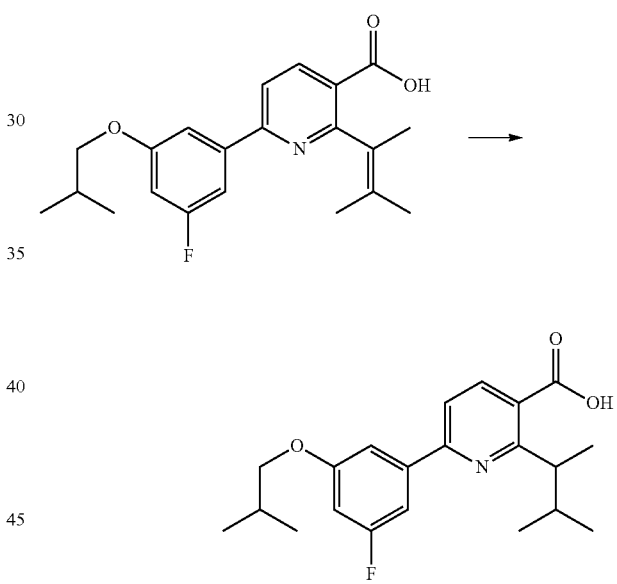

A suspension of 2-(1,2-dimethylprop-1-enyl)-6-(3-fluoro-5-isobutoxy-phenyl)pyridine-3-carboxylic acid (0.14 g, 0.39 mmol), dihydroxypalladium (55 mg, 0.39 mmol), ammonium formate (247 mg, 3.92 mmol) and ethanol (4 mL) was heated to reflux. The reaction was stirred at reflux, and ammonium formate (247 mg, 3.92 mmol) was added every few hours until the reaction was mostly complete. Six more additions were required. The reaction was filtered and evaporated, and the residue was purified using a reverse phase HPLC-MS method using a Luna C18 column (75×30 mm, 5 m particle size) sold by Phenomenex (pn: 00C-4252-U0-AX), and a dual gradient run from 30 to 99% acetonitrile in water containing 5 mM hydrochloric acid over 15.0 minutes to yield 6-(3-fluoro-5-isobutoxyphenyl)-2-(3-methylbutan-2-yl)nicotinic acid (58 mg, 0.16 mmol, 41%). ESI-MS m/z calc. 359.19, found 360.4 (M+1)+; Retention time: 0.87 minutes.

Preparation 15: N-((6-Aminopyridin-2-yl)sulfonyl)-5-(3-fluoro-5-isobutoxyphenyl)-2-(trifluoromethyl)imidazo[1,2-a]pyridine-8-carboxamide (Compound 7)

Step 1: 2-Fluoro-6-(3-fluoro-5-isobutoxy-phenyl)pyridine-3-carboxylic Acid

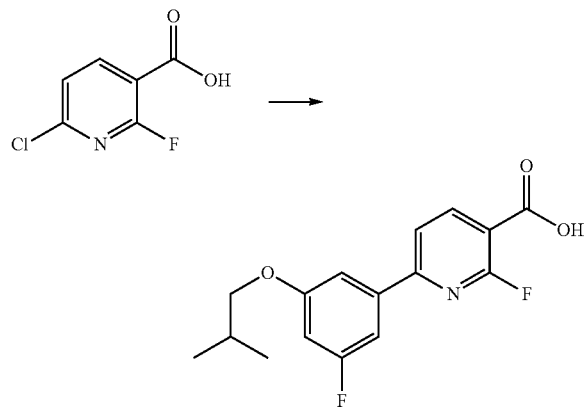

6-Chloro-2-fluoro-pyridine-3-carboxylic acid (2.0 g, 11 mmol), (3-fluoro-5-isobutoxy-phenyl)boronic acid (2.898 g, 13.67 mmol), tetrakis(triphenylphosphine)palladium(0) (1.3 g, 1.1 mmol), and sodium carbonate (23 mL of 2 M in water, 46 mmol) were combined in N,N-dimethylformamide (40 mL) and heated to 100° C. for 4 hours. The reaction was evaporated to one half the volume and the resulting material was partitioned between ethyl acetate and 1 N aqueous hydrochloric acid (pH=1). The organic layer was separated, washed with brine, dried over sodium sulfate and evaporated to an oil. The crude material was purified by silica gel chromatography eluting with 0 to 10% methanol in dichloromethane giving some pure product and some mixed fractions. Mixed fractions were subjected to a second column starting with a shallow gradient from 100% hexanes to 100% ethyl acetate followed by a shallow gradient from 100% dichloromethane to 20% methanol in dichloromethane. The combined fractions gave 2-fluoro-6-(3-fluoro-5-isobutoxy-phenyl)pyridine-3-carboxylic acid (1.33 g, 4.33 mmol, 38%). $^1$H NMR (400 MHz, DMSO) δ 13.61 (s, 1H), 8.45 (dd, J=9.7, 8.0 Hz, 1H), 8.14 (dd, J=7.9, 1.7 Hz, 1H), 7.55-7.47 (m, 2H), 7.00 (dt, J=10.8, 2.3 Hz, 1H), 3.87 (d, J=6.5 Hz, 2H), 2.10-1.95 (m, 1H), 1.02 (s, 3H), 1.00 (s, 3H).

Step 2: 2-Amino-6-(3-fluoro-5-isobutoxy-phenyl)pyridine-3-carboxylic Acid

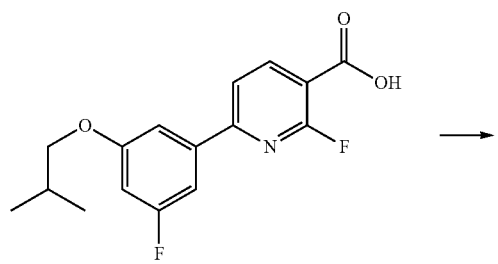

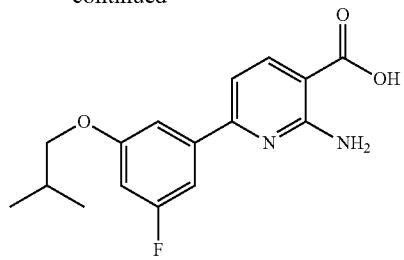

2-Fluoro-6-(3-fluoro-5-isobutoxy-phenyl)pyridine-3-carboxylic acid (1.05 g, 3.42 mmol), ammonium hydroxide (11 g, 12 mL, 310 mmol) and 1,4-dioxane (2.6 mL) were heated in a sealed vial to 150° C. for 2 hours. The reaction mixture was partitioned between ethyl acetate and 1N aqueous hydrochloric acid. The organic layer was evaporated to dryness to give crude 2-amino-6-(3-fluoro-5-isobutoxy-phenyl)pyridine-3-carboxylic acid (1.42 g) which was used directly in the next step.

Step 3: Methyl 2-amino-6-(3-fluoro-5-isobutoxy-phenyl)pyridine-3-carboxylate

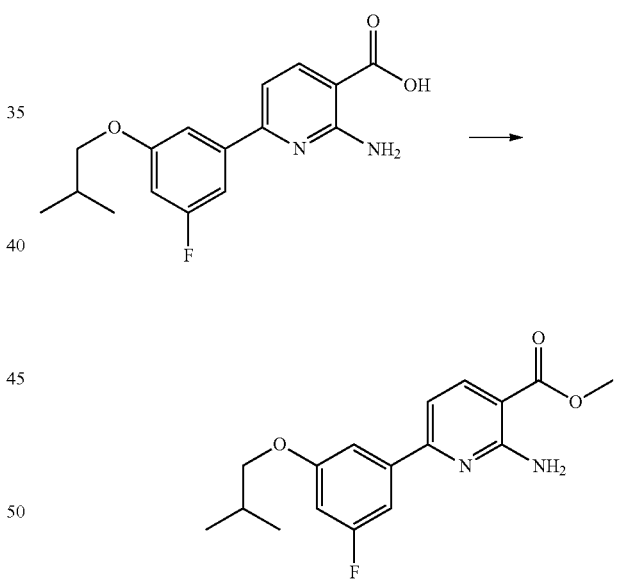

To a stirring solution under a nitrogen atmosphere of 2-amino-6-(3-fluoro-5-isobutoxy-phenyl)pyridine-3-carboxylic acid (1.193 g, 2.862 mmol) in methanol (9 mL) at 0° C. was slowly added the diazomethyl(trimethyl)silane (4.472 mL of 2 M, 8.944 mmol) (gas evolution on addition and eventually yellow color persists). The reaction mixture was warmed to room temperature and stirred for 3 hours. A small amount of acetic acid (~1 mL, CAUTION: Gas evolution) was added which removed the yellow color and then the solution was stirred for 2 minutes and evaporated to dryness to give crude methyl 2-amino-6-(3-fluoro-5-isobutoxy-phenyl)pyridine-3-carboxylate (561 mg) which was used directly in the next step.

Step 4: 5-(3-Fluoro-5-isobutoxy-phenyl)-2-(trifluoromethyl)imidazo[1,2-a]pyridine-8-carboxylic Acid

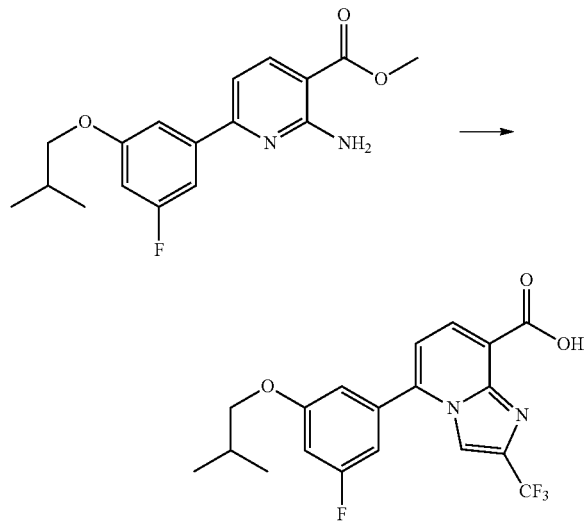

The methyl 2-amino-6-(3-fluoro-5-isobutoxy-phenyl)pyridine-3-carboxylate (150 mg, 0.47 mmol), 3-bromo-1,1,1-trifluoro-propan-2-one (101 mg, 0.530 mmol) and ethanol (375.0 μL) were combined in a sealed vial and stirred at 85° C. overnight. The reaction mixture was then heated to 100° C. and stirred overnight. A second aliquot of 3-bromo-1,1,1-trifluoro-propan-2-one (101 mg, 0.530 mmol) was added and the reaction mixture was stirred at 120° C. overnight. The reaction mixture was cooled to room temperature and methanol (0.5 mL), tetrahydrofuran (0.5 mL), and aqueous sodium hydroxide (1.2 mL of 1 M, 1.2 mmol) were added to the reaction mixture. After stirring for 90 minutes the reaction mixture was diluted with 1N aqueous hydrochloric acid and extracted twice with ethyl acetate. The combined organic layers were dried over sodium sulfate, filtered, and concentrated to give an orange/brown oil. The crude material was purified by silica gel chromatography using a gradient from 100% dichloromethane to 20% methanol in dichloromethane to yield 5-(3-fluoro-5-isobutoxy-phenyl)-2-(trifluoromethyl)imidazo[1,2-a]pyridine-8-carboxylic acid (134 mg, 0.300, 64%).

Step 5: N-((6-Aminopyridin-2-yl)sulfonyl)-5-(3-fluoro-5-isobutoxyphenyl)-2-(trifluoromethyl)imidazo[1,2-a]pyridine-8-carboxamide (Compound 7)

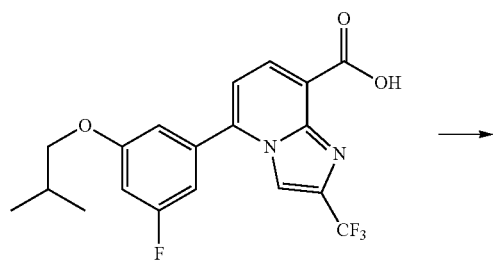

-continued

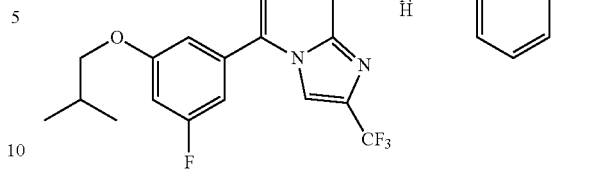

5-(3-fluoro-5-isobutoxy-phenyl)-2-(trifluoromethyl)imidazo[1,2-a]pyridine-8-carboxylic acid (66.9 mg, 0.1502 mmol) was dissolved in N,N-dimethylformamide (0.6 mL), and 1,1'-carbonyldiimidazole (36.5 mg, 0.225 mmol) was added to the solution. The solution was allowed to stir at 45° C. for 45 minutes. In a separate flask, sodium hydride (12 mg, 0.30 mmol) was added to a solution of 6-aminopyridine-2-sulfonamide (52 mg, 0.30 mmol) in N,N-dimethylformamide (0.3 mL). This mixture was stirred for 45 minutes at 45° C. before being added to the prior reaction mixture. The final reaction mixture was stirred at 45° C. for 16 hours. The reaction mixture was cooled to room temperature, filtered, and purified by reverse-phase preparative chromatography utilizing a C18 column and a gradient of 1 to 99% acetonitrile in water containing 5 mM hydrochloric acid over 15 minutes to yield N-((6-aminopyridin-2-yl)sulfonyl)-5-(3-fluoro-5-isobutoxyphenyl)-2-(trifluoromethyl)imidazo[1,2-a]pyridine-8-carboxamide (47 mg, 0.081 mmol, 54%). ESI-MS m/z calc. 551.13, found 552.3 (M+1)+; Retention time: 2.05 minutes.

Preparation 16: 4-[[3-(benzenesulfonylcarbamoyl)-6-(3-fluoro-5-isobutoxy-phenyl)-2-pyridyl]-methyl-amino]butanoic Acid (Compound 86)

N-(benzenesulfonyl)-2-chloro-6-(3-fluoro-5-isobutoxyphenyl)pyridine-3-carboxamide (500 mg, 1.08 mmol) and (4S)-2,2,4-trimethylpyrrolidine (245 mg, 2.16 mmol) in N-methyl pyrrolidinone (2.0 mL) was treated with lithium hydroxide mono hydrate (136 mg, 3.24 mmol) and heated at 125° C. for 21 hours. UPLC analysis showed complete conversion with 43% AUC product along with 25% AUC of a major impurity. The impurity was isolated by purifying an aliquot of the reaction mixture by reverse phase preparative chromatography using a C18 column and a gradient eluent of 25 to 75% acetonitrile in water containing 5 mM hydrochloric acid to give 4-[[3-(benzenesulfonylcarbamoyl)-6-(3-fluoro-5-isobutoxy-phenyl)-2-pyridyl]-methyl-amino]butanoic acid (5 mg), 1H NMR (400 MHz, DMSO-d6) δ 12.62 (s, 1H), 12.01 (s, 1H), 8.06-7.97 (m, 2H), 7.78-7.70 (m, 2H), 7.66 (t, J=7.6 Hz, 2H), 7.44 (dd, J=10.4, 2.3 Hz, 2H), 7.33 (d, J=7.9 Hz, 1H), 6.88 (dt, J=10.7, 2.3 Hz, 1H), 3.83 (d, J=6.5 Hz, 2H), 3.52-3.41 (m, 2H), 2.14 (t, J=7.5 Hz, 2H), 2.02 (dt, J=13.3, 6.6 Hz, 1H), 1.76 (q, J=7.4 Hz, 2H), 0.99 (d, J=6.7 Hz, 6H). ESI-MS m/z calc. 543.18, found 544.25 (M+1)+; Retention time: 2.65 minutes as a cream solid.

Preparation 17: 2-(2,2-dimethylpropyl)-4-ethoxy-1-methyl-N-[(6-oxo-1H-pyridin-2-yl)sulfonyl]isoindoline-1-carboxamide (Compound 85)

Benzoyl benzenecarboperoxoate (approximately 2.252 g, 9.299 mmol) was added to a solution of 1-bromo-3-ethoxy-2-methyl-benzene (20 g, 92.99 mmol) and NBS (approximately 19.86 g, 111.6 mmol) in CCl₄ (200.0 mL). The reaction was heated at reflux (probe temperature 80 OC) overnight. The solution was then cooled to room and filtered to isolate the precipitate. The precipitate was concentrated and purified on silica using a gradient of hexane/ethyl acetate, to give 1-bromo-2-(bromomethyl)-3-ethoxy-benzene as a clear oil (18.3 g). $^1$H NMR (400 MHz, CDCl$_3$) δ 7.16 (d, J=8.1 Hz, 1H), 7.11 (s, 1H), 6.81 (d, J=8.1 Hz, 1H), 4.75 (s, 2H), 4.10 (s, 2H), 1.47 (s, 3H).

1-bromo-2-(bromomethyl)-3-ethoxy-benzene (18.3 g, 62.25 mmol) in acetonitrile (200 ml) was added dropwise to a mixture of tert-butyl (2R)-2-aminopropanoate (hydrochloride salt) (approximately 14.13 g, 77.81 mmol), tert-butyl (2S)-2-aminopropanoate (hydrochloride salt) (approximately 14.13 g, 77.81 mmol), and potassium carbonate (approximately 12.91 g, 93.38 mmol) in acetonitrile (500 ml) at 50° C. The reaction was stirred overnight, and then the solvent was removed. The mixture was then repartitioned between ethyl acetate and water. The aqueous layer was extracted three times with ethyl acetate, and the resulting organic extractions were combined. The extractions were then washed with brine, dried over Na$_2$SO$_4$, filtered, and concentrated to dryness. The residue was purified by column chromatography using a gradient of ethyl acetate/hexane to give tert-butyl 2-[(2-bromo-6-ethoxy-phenyl)methylamino]propanoate (12.6 g, 56%)$^1$H NMR (400 MHz, CDCl$_3$) δ 7.08 (d, J=38.7 Hz, 2H), 6.79 (s, 1H), 4.06 (s, 4H), 3.31 (s, 1H), 1.41 (s, 13H), 1.30 (s, 3H). ESI-MS m/z calc. 357.09396, found 358.0 (M+1)+; Retention time: 1.14 minutes (3 minute run).

N,N-Diisopropylethylamine (DIEA) (approximately 6.818 g, 9.189 mL, 52.75 mmol) was added to a solution of tert-butyl 2-[(2-bromo-6-ethoxy-phenyl)methylamino]propanoate (12.6 g, 35.17 mmol) in DCM (252.0 mL). Benzyl carbonochloridate (approximately 7.199 g, 6.024 mL, 42.20 mmol) was then added dropwise at 0° C. to this solution. The mixture was stirred at room temperature for 4 hours. At this point LC/MS indicated a mixture of starting material and the desired product. The solution was diluted with DCM, washed twice with saturated citric acid and brine, then dried over MgSO$_4$. The solution was then filtered and concentrated to dryness. The residue was purified by column chromatography to give tert-butyl 2-[benzyloxycarbonyl-[(2-bromo-6-ethoxy-phenyl)methyl]amino]propanoate (15.4 g, 88%)$^1$H NMR (400 MHz, CD$_3$OD) δ 7.35 (s, 5H), 7.19 (s, 2H), 6.98 (s, 1H), 5.23 (d, J=12.5 Hz, 1H), 5.08 (dd, J=32.3, 12.4 Hz, 1H), 4.90 (s, 1H), 4.76 (d, J=14.0 Hz, 1H), 4.05 (s, 2H), 3.59 (s, 1H), 1.35 (s, 12H), 1.16 (s, 3H). ESI-MS m/z calc. 491.13074, found 493.0 (M+1); Retention time: 2.2 minutes (3 minute run).

A solution of tert-butyl 2-[benzyloxycarbonyl-[(2-bromo-6-ethoxy-phenyl)methyl]amino]propanoate (15.4 g, 30.96 mmol) in dioxane (91.87 mL) was purged with nitrogen for 2 min. 2-(2-diphenylphosphanylphenyl)-N,N-dimethyl-aniline (approximately 1.181 g, 3.096 mmol), was added under nitrogen followed by the addition of Pd$_2$(dba)$_3$ (approximately 1.418 g, 1.548 mmol). Then, 2-methylpropan-2-olate (Lithium salt) (approximately 4.957 g, 61.92 mmol) was added. The mixture was heated at 90° C. overnight, diluted with EtOAc and then filtered. The filtrate was concentrated to dryness. The residue was purified by column chromatography to give 2-benzyl 1-(tert-butyl) 4-ethoxy-1-methyl-isoindoline-1,2-dicarboxylate (8.1 g, 57%) as a yellow solid. $^1$H NMR (400 MHz, DMSO) δ 7.37 (t, J=20.7 Hz, 7H), 6.95 (d, J=10.9 Hz, 1H), 6.81 (d, J=7.7 Hz, 1H), 5.28-5.17 (m, 1H), 5.08 (d, J=16.2 Hz, 1H), 4.68-4.57 (m, 2H), 4.09 (s, 2H), 1.73 (s, 3H), 1.33 (s, 4H), 1.21 (d, J=5.4 Hz, 9H). ESI-MS m/z calc. 411.20456, found 412.0 (M+1); Retention time: 2.14 minutes (3 minute run).

O2-benzyl O1-tert-butyl 4-ethoxy-1-methyl-isoindoline-1,2-dicarboxylate (2 g, 4.617 mmol) was stirred overnight in HCl (approximately 4.618 mL of 4 M, 18.47 mmol) (in dioxane) at 65° C. The reaction mixture was concentrated to remove solvent, and re-dissolved in ethyl acetate/toluene (repeated 3 times) to remove the acid. The crude product was purified on reverse phase HPLC (Waters, HCl, 25-75% ACN-H$_2$O) to give 2-benzyloxycarbonyl-4-ethoxy-1-methyl-isoindoline-1-carboxylic acid (969 mg).

A solution of 2-benzyloxycarbonyl-4-ethoxy-1-methyl-isoindoline-1-carboxylic acid (554 mg, 1.559 mmol), 6-fluoropyridine-2-sulfonamide (approximately 329.6 mg, 1.871 mmol) in DMF was combined with HATU (approximately 889.4 mg, 2.339 mmol), and K$_2$CO$_3$ (approximately 646.4 mg, 4.677 mmol). The solution was stirred overnight at room temperature. LC/MS showed activated starting material. The reaction mixture was then heated at 70° C. for 5 hours. The reaction mixture was then filtered and purified by LC/MS to give benzyl 4-ethoxy-1-[(6-fluoro-2-pyridyl)sulfonylcarbamoyl]-1-methyl-isoindoline-2-carboxylate. (436.3 mg). $^1$H NMR (400 MHz, DMSO) δ 12.38 (s, 1H), 8.27 (s, 1H), 7.98 (s, 1H), 7.57-7.19 (m, 8H), 6.98 (d, J=8.1 Hz, 1H), 6.40 (dd, J=19.1, 7.5 Hz, 1H), 5.28 (d, J=12.9 Hz, 1H), 5.16 (s, 1H), 4.94 (s, 1H), 4.49 (s, 1H), 4.11 (s, 2H), 1.51 (d, J=12.8 Hz, 3H), 1.37 (s, 3H).

Benzyl 4-ethoxy-1-[(6-fluoro-2-pyridyl)sulfonylcarbamoyl]-1-methyl-isoindoline-2-carboxylate (436.3 mg) was suspended in ethanol (10 mL), followed by the addition of palladium on carbon (approximately 331.8 mg of 5% w/w, 0.1559 mmol). The mixture was stirred at room temperature over night under positive pressure of hydrogen. The reaction mixture was filtered, and concentrated to give 4-ethoxy-N-[(6-fluoro-2-pyridyl)sulfonyl]-1-methyl-isoindoline-1-carboxamide (40 mg, 0.1054 mmol).

4-ethoxy-N-[(6-fluoro-2-pyridyl)sulfonyl]-1-methyl-isoindoline-1-carboxamide (40 mg, 0.1054 mmol) was mixed with K$_2$CO$_3$ and 1-bromo-2,2-dimethyl-propane (approximately 47.76 mg, 0.3162 mmol) in DMSO (800.0 µL). The reaction mixture was heated at 100° C. overnight. Then Cs$_2$CO$_3$ (approximately 171.7 mg, 0.5270 mmol) and additional 1-bromo-2,2-dimethyl-propane (approximately 47.76 mg, 0.3162 mmol) were added. The reaction was heated to 130° C. and left overnight. The reaction mixture was then filtered and purified on reverse phase HPLC (Waters, HCl, 10-60% ACN-H$_2$O) to give 2-(2,2-dimethylpropyl)-4-ethoxy-1-methyl-N-[(6-oxo-1H-pyridin-2-yl)sulfonyl]isoindoline-1-carboxamide (2.6 mg). $^1$H NMR (400 MHz, DMSO) δ 9.67 (s, 1H), 9.15 (s, 1H), 7.75 (s, 1H), 7.40 (d, J=7.3 Hz, 1H), 7.31 (s, 1H), 7.14 (d, J=7.6 Hz, 1H), 6.97 (d, J=8.2 Hz, 1H), 6.83 (d, J=8.3 Hz, 1H), 4.39 (d, J=12.9 Hz, 2H), 4.08 (d, J=13.9 Hz, 2H), 3.76 (s, 2H), 1.69 (s, 3H), 1.32 (s, 3H), 0.95 (s, 10H). ESI-MS m/z calc. 447.1828, found 448.0 (M+1); Retention time: 1.36 minutes (3 minute run).

Table 2 below recites the analytical data for the compounds of Table 1.

TABLE 2

| Cmpd No. | LC/MS M + 1 | LC/RT min | NMR |
|---|---|---|---|
| 1 | 538.30 | 2.84 | |
| 2 | 531.11 | 2.46 | |
| 3 | 545.14 | 2.48 | |
| 4 | 561.11 | 2.37 | |
| 5 | 503.20 | 2.23 | |
| 6 | 589.21 | 2.13 | |
| 7 | 552.30 | 2.05 | $^1$H NMR (400 MHz, DMSO) δ 12.63 (s, 1H), 8.63 (s, 1H), 8.24 (d, J = 7.5 Hz, 1H), 7.67 (t, J = 7.9 Hz, 1H), 7.32 (s, 2H), 7.17 (s, 3H), 6.71 (d, J = 8.4 Hz, 1H), 6.64 (s, 2H), 3.86 (d, J = 6.5 Hz, 2H), 2.04 (dt, J = 13.3, 6.7 Hz, 1H), 1.99 (s, 1H), 0.99 (d, J = 6.7 Hz, 6H). |
| 8 | 485.20 | 1.31 | |
| 9 | 571.18 | 2.17 | |
| 10 | 475.04 | 2.02 | |
| 11 | 531.11 | 2.46 | |
| 12 | 545.25 | 2.38 | |
| 13 | 533.00 | 2.26 | |
| 14 | 499.16 | 1.37 | |
| 15 | 421.20 | 2.06 | |
| 16 | 504.26 | 1.74 | |
| 17 | 570.40 | 3.04 | |
| 18 | 547.31 | 2.18 | |
| 19 | 488.50 | 1.71 | 1H NMR (400 MHz, DMSO-d6) δ 12.53 (s, 1H), 7.78 (d, J = 7.9 Hz, 1H), 7.64 (dd, J = 8.4, 7.3 Hz, 1H), 7.45 (dd, J = 8.4, 1.8 Hz, 2H), 7.33 (d, J = 7.9 Hz, 1H), 7.20 (d, J = 7.1 Hz, 1H), 6.90 (dt, J = 10.8, 2.4 Hz, 1H), 6.70 (d, J = 8.2 Hz, 1H), 3.84 (d, J = 6.5 Hz, 2H), 2.88 (s, 6H), 2.04 (hept, J = 6.7 Hz, 1H), 1.00 (d, J = 6.7 Hz, 6H). |
| 20 | 533.24 | 2.12 | |
| 21 | 533.04 | 2.23 | |
| 22 | 561.04 | 2.34 | |
| 23 | 533.28 | 2.17 | |
| 24 | 545.25 | 2.38 | |
| 25 | 545.25 | 2.35 | |
| 26 | 559.29 | 2.39 | |
| 27 | 503.20 | 2.21 | |
| 28 | 515.20 | 2.22 | |
| 29 | 517.11 | 2.38 | |
| 30 | 489.40 | 2.15 | 1H NMR (400 MHz, DMSO) δ 7.89 (d, J = 7.7 Hz, 1H), 7.54 (d, J = 7.7 Hz, 1H), 7.52-7.39 (m, 3H), 7.06 (d, J = 7.3 Hz, 1H), 6.93-6.83 (m, 1H), 6.45 (d, J = 8.2 Hz, 1H), 6.07 (s, 2H), 4.41 (q, J = 7.0 Hz, 2H), 3.85 (d, J = 6.5 Hz, 2H), 2.05 (dt, J = 13.2, 6.7 Hz, 1H), 1.34 (t, J = 7.0 Hz, 3H), 1.00 (d, J = 6.7 Hz, 6H). |
| 31 | 516.40 | 2.45 | |
| 32 | 531.20 | 2.39 | |
| 33 | 611.11 | 2.11 | |
| 34 | 559.28 | 2.40 | |
| 35 | 527.02 | 2.29 | |
| 36 | 559.25 | 2.42 | |
| 37 | 513.40 | 1.94 | |
| 38 | 525.19 | 2.05 | |
| 39 | 544.30 | 2.33 | |
| 40 | 545.25 | 2.36 | |
| 41 | 544.40 | 2.48 | 1H NMR (400 MHz, Chloroform-d) δ 15.89 (s, 1H), 8.72 (d, J = 8.2 Hz, 1H), 7.88 (d, J = 8.1 Hz, 1H), 7.70 (t, J = 7.6 Hz, 1H), 7.56 (d, J = 7.1 Hz, 1H), 7.40-7.29 (m, 2H), 7.00 (d, J = 8.8 Hz, 1H), 6.74 (dt, J = 10.3, 2.2 Hz, 1H), 4.45-4.27 (m, 2H), 3.78 (d, J = 6.5 Hz, 2H), 2.13 (hept, J = 6.7 Hz, 2H), 1.39 (d, J = 6.4 Hz, 16H), 1.05 (d, J = 6.7 Hz, 6H). |
| 42 | 515.20 | 2.20 | |
| 43 | 501.20 | 2.13 | |
| 44 | 531.08 | 2.45 | |
| 45 | 393.17 | 1.88 | |
| 46 | 490.23 | 1.70 | |
| 47 | 531.20 | 2.38 | |
| 48 | 543.00 | 2.12 | |
| 49 | 515.20 | 2.20 | |
| 50 | 518.30 | 2.38 | |
| 51 | 547.24 | 2.20 | |
| 52 | 544.40 | 3.02 | 1H NMR (400 MHz, DMSO-d6) δ 12.55 (s, 1H), 7.83 (d, J = 7.9 Hz, 1H), 7.64 (dd, J = 8.4, 7.3 Hz, 1H), 7.53-7.47 (m, 1H), 7.42 (ddd, J = 10.2, 2.3, 1.3 Hz, 1H), 7.33 (d, J = 7.9 Hz, 1H), 7.21 (dd, J = 7.3, 0.7 Hz, 1H), 6.88 (dt, J = 10.7, 2.3 Hz, 1H), 6.70 (dd, J = 8.3, 0.8 Hz, 1H), 6.45 (s, 2H), 4.32 (s, 1H, iPrOH), 3.83 (d, J = 6.6 |

TABLE 2-continued

| Cmpd No. | LC/MS M + 1 | LC/RT min | NMR |
|---|---|---|---|
|  |  |  | Hz, 2H), 3.81-3.75 (m, 1H, iPrOH), 3.73 (d, J = 8.6 Hz, 2H), 2.73 (s, 3H), 2.05 (hept, J = 6.7 Hz, 1H), 1.04 (d, J = 6.1 Hz, 6H, iPrOH), 0.99 (d, J = 6.6 Hz, 6H), 0.85 (s, 9H). |
| 53 | 516.26 | 1.71 |  |
| 54 | 530.40 | 3.24 |  |
| 55 | 547.28 | 2.17 |  |
| 56 | 531.25 | 2.30 |  |
| 57 | 539.06 | 2.23 |  |
| 58 | 516.30 | 3.16 | 1H NMR (400 MHz, DMSO-d6) δ 8.32 (d, J = 8.3 Hz, 1H), 8.21 (s, 1H), 7.67 (dd, J = 8.5, 7.3 Hz, 1H), 7.55 (t, J = 1.8 Hz, 1H), 7.48 (dt, J = 10.1, 1.9 Hz, 1H), 7.29 (d, J = 8.2 Hz, 1H), 7.20 (d, J = 7.2 Hz, 1H), 6.93 (dt, J = 10.6, 2.3 Hz, 1H), 6.72 (d, J = 8.5 Hz, 1H), 6.62 (s, 2H), 3.85 (d, J = 6.6 Hz, 2H), 2.12-1.98 (m, 1H), 1.46 (s, 9H), 0.99 (d, J = 6.7 Hz, 6H). |
| 59 | 517.18 | 2.37 |  |
| 60 | 518.95 | 2.19 |  |
| 61 | 530.22 | 2.13 |  |
| 62 | 559.28 | 2.45 |  |
| 63 | 517.11 | 2.41 |  |
| 64 | 516.21 | 2.02 |  |
| 65 | 533.24 | 2.11 |  |
| 66 | 556.24 | 2.08 |  |
| 67 | 502.30 | 2.39 |  |
| 68 | 573.29 | 2.45 |  |
| 69 | 544.34 | 2.14 |  |
| 70 | 485.20 | 1.39 |  |
| 71 | 547.25 | 2.17 |  |
| 72 | 504.30 | 2.27 |  |
| 73 | 557.20 | 2.18 |  |
| 74 | 530.30 | 2.45 |  |
| 75 | 570.40 | 3.04 |  |
| 76 | 515.50 | 2.11 |  |
| 77 | 559.35 | 2.52 |  |
| 78 | 533.24 | 2.09 |  |
| 79 | 490.23 | 1.77 |  |
| 80 | 546.40 | 1.85 |  |
| 81 | 557.05 | 2.25 |  |
| 82 | 571.22 | 2.18 |  |
| 83 | 569.20 | 2.16 |  |
| 84 | 530.40 | 2.23 | 1H NMR (400 MHz, DMSO) δ 8.31 (d, J = 8.2 Hz, 1H), 7.66 (t, J = 7.9 Hz, 1H), 7.55 (d, J = 1.3 Hz, 1H), 7.50 (dd, J = 10.2, 1.2 Hz, 1H), 7.27 (d, J = 8.2 Hz, 1H), 7.19 (d, J = 7.3 Hz, 1H), 6.92 (d, J = 10.7 Hz, 1H), 6.71 (d, J = 8.4 Hz, 1H), 6.59 (s, 2H), 3.84 (d, J = 6.5 Hz, 2H), 3.47 (t, J = 7.2 Hz, 2H), 3.37 (s, 2H), 2.07-1.95 (m, 1H), 1.64-1.50 (m, 2H), 1.30 (dd, J = 10.6, 7.3 Hz, 4H), 1.00 (d, J = 6.7 Hz, 6H), 0.85 (t, J = 6.9 Hz, 3H). |
| 85 | 448 | 1.36 | 1H NMR (400 MHz, DMSO) δ 9.67 (s, 1H), 9.15 (s, 1H), 7.75 (s, 1H), 7.40 (d, J = 7.3 Hz, 1H), 7.31 (s, 1H), 7.14 (d, J = 7.6 Hz, 1H), 6.97 (d, J = 8.2 Hz, 1H), 6.83 (d, J = 8.3 Hz, 1H), 4.39 (d, J = 12.9 Hz, 2H), 4.08 (d, J = 13.9 Hz, 2H), 3.76 (s, 2H), 1.69 (s, 3H), 1.32 (s, 3H), 0.95 (s, 10H). |
| 86 | 543.18 | 2.65 | 1H NMR (400 MHz, DMSO-d6) δ 12.62 (s, 1H), 12.01 (s, 1H), 8.06-7.97 (m, 2H), 7.78-7.70 (m, 2H), 7.66 (t, J = 7.6 Hz, 2H), 7.44 (dd, J = 10.4, 2.3 Hz, 2H), 7.33 (d, J = 7.9 Hz, 1H), 6.88 (dt, J = 10.7, 2.3 Hz, 1H), 3.83 (d, J = 6.5 Hz, 2H), 3.52-3.41 (m, 2H), 2.14 (t, J = 7.5 Hz, 2H), 2.02 (dt, J = 13.3, 6.6 Hz, 1H), 1.76 (q, J = 7.4 Hz, 2H), 0.99 (d, J = 6.7 Hz, 6H) |

Assays

Protocol 1

Assays for Detecting and Measuring F508del Potentiation Properties of Compounds

Membrane Potential Optical Methods for Assaying F508del Modulation Properties of Compounds The assay utilizes fluorescent voltage sensing dyes to measure changes in membrane potential using a fluorescent plate reader (e.g., FLIPR III, Molecular Devices, Inc.) as a readout for increase in functional F508del in NIH 3T3 cells. The driving force for the response is the creation of a chloride ion gradient in conjunction with channel activation and concurrent with compound treatment by a single liquid addition step after the cells have previously been loaded with a voltage sensing dye.

Identification of Potentiator Compounds

To identify potentiators of F508del, a fluorescence based HTS assay format was developed. This HTS assay utilizes fluorescent voltage sensing dyes to measure changes in membrane potential on the FLIPR III as a measurement for increase in gating (conductance) of F508del NIH 3T3 cells. The driving force for the response is the creation of a chloride ion gradient in conjunction with channel activation and concurrent with compound treatment by a single liquid addition step after the cells have previously been loaded with a voltage sensing dye.

Solutions

Bath Solution #1:

(in mM) NaCl 160, KCl 4.5, CaCl$_2$ 2, MgCl$_2$ 1, HEPES 10, pH 7.4 with NaOH, Glucose 10.

Chloride-Free Bath Solution:

Chloride salts in Bath Solution #1 (above) are substituted with gluconate salts.

Cell Culture

NIH3T3 mouse fibroblasts stably expressing F508del are used for optical measurements of membrane potential. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm$^2$ culture flasks. For all optical assays, the cells were seeded at 12,000 cells/well in 384-well matrigel-coated plates and cultured for 18-24 hrs at 37° C. for the potentiator assay. For the correction assays, the cells are cultured at 37° C. with and without compounds for 18-24 hours.

Electrophysiological Assays for assaying F508del modulation properties of compounds.

Using Chamber Assay

Using chamber experiments were performed on polarized airway epithelial cells expressing F508del to further characterize the F508del modulators identified in the optical assays. Non-CF and CF airway epithelia were isolated from bronchial tissue, cultured as previously described (Galietta, L. J. V., Lantero, S., Gazzolo, A., Sacco, O., Romano, L., Rossi, G. A., & Zegarra-Moran, O. (1998) In Vitro Cell. Dev. Biol. 34, 478-481), and plated onto Costar® Snapwell™ filters that were precoated with NIH3T3-conditioned media. After four days the apical media was removed and the cells were grown at an air liquid interface for >14 days prior to use. This resulted in a monolayer of fully differentiated columnar cells that were ciliated, features that are characteristic of airway epithelia. Non-CF HBE were isolated from non-smokers that did not have any known lung disease. CF-HBE were isolated from patients homozygous for F508del.

HBE grown on Costar® Snapwell™ cell culture inserts were mounted in an Using chamber (Physiologic Instruments, Inc., San Diego, Calif.), and the transepithelial resistance and short-circuit current in the presence of a basolateral to apical Cl$^-$ gradient ($I_{SC}$) were measured using a voltage-clamp system (Department of Bioengineering, University of Iowa, Iowa). Briefly, HBE were examined under voltage-clamp recording conditions ($V_{hold}$=0 mV) at 37° C. The basolateral solution contained (in mM) 145 NaCl, 0.83 K$_2$HPO$_4$, 3.3 KH$_2$PO$_4$, 1.2 MgCl$_2$, 1.2 CaCl$_2$, 10 Glucose, 10 HEPES (pH adjusted to 7.35 with NaOH) and the apical solution contained (in mM) 145 NaGluconate, 1.2 MgCl$_2$, 1.2 CaCl$_2$, 10 glucose, 10 HEPES (pH adjusted to 7.35 with NaOH).

Identification of Potentiator Compounds

Typical protocol utilized a basolateral to apical membrane Cl$^-$ concentration gradient. To set up this gradient, normal ringers was used on the basolateral membrane, whereas apical NaCl was replaced by equimolar sodium gluconate (titrated to pH 7.4 with NaOH) to give a large Cl$^-$ concentration gradient across the epithelium. Forskolin (10 μM) and all test compounds were added to the apical side of the cell culture inserts. The efficacy of the putative F508del potentiators was compared to that of the known potentiator, genistein.

Patch-Clamp Recordings

Total Cl$^-$ current in F508del-NIH3T3 cells was monitored using the perforated-patch recording configuration as previously described (Rae, J., Cooper, K., Gates, P., & Watsky, M. (1991) J. Neurosci. Methods 37, 15-26). Voltage-clamp recordings were performed at 22° C. using an Axopatch 200B patch-clamp amplifier (Axon Instruments Inc., Foster City, Calif.). The pipette solution contained (in mM) 150 N-methyl-D-glucamine (NMDG)-Cl, 2 MgCl$_2$, 2 CaCl$_2$, 10 EGTA, 10 HEPES, and 240 g/mL amphotericin-B (pH adjusted to 7.35 with HCl). The extracellular medium contained (in mM) 150 NMDG-Cl, 2 MgCl$_2$, 2 CaCl$_2$, 10 HEPES (pH adjusted to 7.35 with HCl). Pulse generation, data acquisition, and analysis were performed using a PC equipped with a Digidata 1320 A/D interface in conjunction with Clampex 8 (Axon Instruments Inc.). To activate F508del, 10 μM forskolin and 20 μM genistein were added to the bath and the current-voltage relation was monitored every 30 sec.

Identification of Potentiator Compounds

The ability of F508del potentiators to increase the macroscopic F508del Cl$^-$ current ($I_{F508del}$) in NIH3T3 cells stably expressing F508del was also investigated using perforated-patch-recording techniques. The potentiators identified from the optical assays evoked a dose-dependent increase in $I\Delta_{F508}$ with similar potency and efficacy observed in the optical assays. In all cells examined, the reversal potential before and during potentiator application was around −30 mV, which is the calculated $E_{Cl}$ (−28 mV).

Cell Culture

NIH3T3 mouse fibroblasts stably expressing F508del are used for whole-cell recordings. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm$^2$ culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

Single-Channel Recordings

Gating activity of wt-CFTR and temperature-corrected F508del expressed in NIH3T3 cells was observed using excised inside-out membrane patch recordings as previously described (Dalemans, W., Barbry, P., Champigny, G., Jallat, S., Dott, K., Dreyer, D., Crystal, R. G., Pavirani, A., Lecocq, J-P., Lazdunski, M. (1991) Nature 354, 526-528) using an Axopatch 200B patch-clamp amplifier (Axon Instruments Inc.). The pipette contained (in mM): 150 NMDG, 150 aspartic acid, 5 CaCl$_2$, 2 MgCl$_2$, and 10 HEPES (pH adjusted to 7.35 with Tris base). The bath contained (in mM): 150 NMDG-Cl, 2 MgCl$_2$, 5 EGTA, 10 TES, and 14 Tris base (pH adjusted to 7.35 with HCl). After excision, both wt- and F508del were activated by adding 1 mM Mg-ATP, 75 nM of the catalytic subunit of cAMP-dependent protein kinase (PKA; Promega Corp. Madison, Wis.), and 10 mM NaF to inhibit protein phosphatases, which prevented current rundown. The pipette potential was maintained at 80 mV. Channel activity was analyzed from membrane patches containing ≤2 active channels. The maximum number of simultaneous openings determined the number of active channels during the course of an experiment. To determine the single-channel current amplitude, the data recorded from 120 sec of F508del activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o=I/i(N)$, where I=mean current, i=single-channel current amplitude, and N=number of active channels in patch.

Cell Culture

NIH3T3 mouse fibroblasts stably expressing F508del are used for excised-membrane patch-clamp recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For single channel recordings, 2,500-5,000 cells were seeded on poly-L-lysine-coated glass coverslips and cultured for 24-48 hrs at 27° C. before use.

Protocol 2

Assays for Detecting and Measuring F508del Correction Properties of Compounds

Membrane potential optical methods for assaying F508del modulation properties of compounds.

The optical membrane potential assay utilized voltage-sensitive FRET sensors described by Gonzalez and Tsien (See Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See, Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, $DiSBAC_2(3)$, and a fluorescent phospholipid, CC2-DMPE, which is attached to the outer leaflet of the plasma membrane and acts as a FRET donor. Changes in membrane potential (Vm) cause the negatively charged $DiSBAC_2(3)$ to redistribute across the plasma membrane and the amount of energy transfer from CC2-DMPE changes accordingly. The changes in fluorescence emission were monitored using VIPR™ II, which is an integrated liquid handler and fluorescent detector designed to conduct cell-based screens in 96- or 384-well microtiter plates.

Identification of Correction Compounds

To identify small molecules that correct the trafficking defect associated with F508del; a single-addition HTS assay format was developed. The cells were incubated in serum-free medium for 16 hrs at 37° C. in the presence or absence (negative control) of test compound. As a positive control, cells plated in 384-well plates were incubated for 16 hrs at 27° C. to "temperature-correct" F508del. The cells were subsequently rinsed 3× with Krebs Ringers solution and loaded with the voltage-sensitive dyes. To activate F508del, 10 μM forskolin and the CFTR potentiator, genistein (20 μM), were added along with Cl⁻-free medium to each well. The addition of Cl⁻-free medium promoted Cl⁻ efflux in response to F508del activation and the resulting membrane depolarization was optically monitored using the FRET-based voltage-sensor dyes.

Identification of Potentiator Compounds

To identify potentiators of F508del, a double-addition HTS assay format was developed. During the first addition, a Cl⁻-free medium with or without test compound was added to each well. After 22 sec, a second addition of Cl⁻-free medium containing 2-10 μM forskolin was added to activate F508del. The extracellular Cl⁻ concentration following both additions was 28 mM, which promoted Cl⁻ efflux in response to F508del activation and the resulting membrane depolarization was optically monitored using the FRET-based voltage-sensor dyes.

Solutions

Bath Solution #1: (in mM) NaCl 160, KCl 4.5, $CaCl_2$ 2, $MgCl_2$ 1, HEPES 10, pH 7.4 with NaOH.

Chloride-free bath solution: Chloride salts in Bath Solution #1 (above) are substituted with gluconate salts.

CC2-DMPE: Prepared as a 10 mM stock solution in DMSO and stored at −20° C.

$DiSBAC_2(3)$: Prepared as a 10 mM stock in DMSO and stored at −20° C.

Cell Culture

NIH3T3 mouse fibroblasts stably expressing F508del are used for optical measurements of membrane potential. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For all optical assays, the cells were seeded at 30,000/well in 384-well matrigel-coated plates and cultured for 2 hrs at 37° C. before culturing at 27° C. for 24 hrs for the potentiator assay. For the correction assays, the cells are cultured at 27° C. or 37° C. with and without compounds for 16-24 hours.

Electrophysiological Assays for assaying F508del modulation properties of compounds Using Chamber Assay Using chamber experiments were performed on polarized epithelial cells expressing F508del to further characterize the F508del modulators identified in the optical assays. $FRT^{F508del}$ epithelial cells grown on Costar Snapwell cell culture inserts were mounted in an Using chamber (Physiologic Instruments, Inc., San Diego, Calif.), and the monolayers were continuously short-circuited using a Voltage-clamp System (Department of Bioengineering, University of Iowa, Iowa, and, Physiologic Instruments, Inc., San Diego, Calif.). Transepithelial resistance was measured by applying a 2-mV pulse. Under these conditions, the FRT epithelia demonstrated resistances of 4 KΩ/cm² or more. The solutions were maintained at 27° C. and bubbled with air. The electrode offset potential and fluid resistance were corrected using a cell-free insert. Under these conditions, the current reflects the flow of Cl⁻ through F508del expressed in the apical membrane. The $I_{SC}$ was digitally acquired using an MP100A-CE interface and AcqKnowledge software (v3.2.6; BIOPAC Systems, Santa Barbara, Calif.).

Identification of Correction Compounds

Typical protocol utilized a basolateral to apical membrane Cl⁻ concentration gradient. To set up this gradient, normal ringer was used on the basolateral membrane, whereas apical NaCl was replaced by equimolar sodium gluconate (titrated to pH 7.4 with NaOH) to give a large Cl⁻ concentration gradient across the epithelium. All experiments were performed with intact monolayers. To fully activate F508del, forskolin (10 μM) and the PDE inhibitor, IBMX (100 μM), were applied followed by the addition of the CFTR potentiator, genistein (50 μM).

As observed in other cell types, incubation at low temperatures of FRT cells stably expressing F508del increases the functional density of CFTR in the plasma membrane. To determine the activity of correction compounds, the cells were incubated with 10 µM of the test compound for 24 hours at 37° C. and were subsequently washed 3× prior to recording. The cAMP- and genistein-mediated $I_{SC}$ in compound-treated cells was normalized to the 27° C. and 37° C. controls and expressed as percentage activity. Preincubation of the cells with the correction compound significantly increased the cAMP- and genistein-mediated $I_{SC}$ compared to the 37° C. controls.

Identification of Potentiator Compounds

Typical protocol utilized a basolateral to apical membrane Cl⁻ concentration gradient. To set up this gradient, normal ringers was used on the basolateral membrane and was permeabilized with nystatin (360 µg/ml), whereas apical NaCl was replaced by equimolar sodium gluconate (titrated to pH 7.4 with NaOH) to give a large Cl⁻ concentration gradient across the epithelium. All experiments were performed 30 min after nystatin permeabilization. Forskolin (10 µM) and all test compounds were added to both sides of the cell culture inserts. The efficacy of the putative F508del potentiators was compared to that of the known potentiator, genistein.

Solutions

Basolateral solution (in mM): NaCl (135), $CaCl_2$ (1.2), $MgCl_2$ (1.2), $K_2HPO_4$ (2.4), $KHPO_4$ (0.6), N-2-hydroxyethylpiperazine-N'-2-ethanesulfonic acid (HEPES) (10), and dextrose (10). The solution was titrated to pH 7.4 with NaOH.

Apical solution (in mM): Same as basolateral solution with NaCl replaced with Na Gluconate (135).

Cell Culture

Fisher rat epithelial (FRT) cells expressing F508del ($FRT^{F508del}$) were used for Using chamber experiments for the putative F508del modulators identified from our optical assays. The cells were cultured on Costar Snapwell cell culture inserts and cultured for five days at 37° C. and 5% $CO_2$ in Coon's modified Ham's F-12 medium supplemented with 5% fetal calf serum, 100 U/ml penicillin, and 100 µg/ml streptomycin. Prior to use for characterizing the potentiator activity of compounds, the cells were incubated at 27° C. for 16-48 hrs to correct for the F508del. To determine the activity of corrections compounds, the cells were incubated at 27° C. or 37° C. with and without the compounds for 24 hours.

Whole-Cell Recordings

The macroscopic F508del current ($I_{F508del}$) in temperature- and test compound-corrected NIH3T3 cells stably expressing F508del were monitored using the perforated-patch, whole-cell recording. Briefly, voltage-clamp recordings of $I_{F508del}$ were performed at room temperature using an Axopatch 200B patch-clamp amplifier (Axon Instruments Inc., Foster City, Calif.). All recordings were acquired at a sampling frequency of 10 kHz and low-pass filtered at 1 kHz. Pipettes had a resistance of 5-6 MΩ when filled with the intracellular solution. Under these recording conditions, the calculated reversal potential for Cl⁻ ($E_{Cl}$) at room temperature was −28 mV. All recordings had a seal resistance >20 GΩ and a series resistance <15 MΩ. Pulse generation, data acquisition, and analysis were performed using a PC equipped with a Digidata 1320 A/D interface in conjunction with Clampex 8 (Axon Instruments Inc.). The bath contained <250 µl of saline and was continuously perifused at a rate of 2 ml/min using a gravity-driven perfusion system.

Identification of Correction Compounds

To determine the activity of correction compounds for increasing the density of functional F508del in the plasma membrane, we used the above-described perforated-patch-recording techniques to measure the current density following 24-hr treatment with the correction compounds. To fully activate F508del, 10 µM forskolin and 20 µM genistein were added to the cells. Under our recording conditions, the current density following 24-hr incubation at 27° C. was higher than that observed following 24-hr incubation at 37° C. These results are consistent with the known effects of low-temperature incubation on the density of F508del in the plasma membrane. To determine the effects of correction compounds on CFTR current density, the cells were incubated with 10 µM of the test compound for 24 hours at 37° C. and the current density was compared to the 27° C. and 37° C. controls (% activity). Prior to recording, the cells were washed 3× with extracellular recording medium to remove any remaining test compound. Preincubation with 10 µM of correction compounds significantly increased the cAMP- and genistein-dependent current compared to the 37° C. controls.

Identification of Potentiator Compounds

The ability of F508del potentiators to increase the macroscopic F508del Cl⁻ current ($I_{F508del}$) in NIH3T3 cells stably expressing F508del was also investigated using perforated-patch-recording techniques. The potentiators identified from the optical assays evoked a dose-dependent increase in $I_{F508del}$ with similar potency and efficacy observed in the optical assays. In all cells examined, the reversal potential before and during potentiator application was around −30 mV, which is the calculated $E_{Cl}$ (−28 mV).

Solutions

Intracellular solution (in mM): Cs-aspartate (90), CsCl (50), $MgCl_2$ (1), HEPES (10), and 240 µg/ml amphotericin-B (pH adjusted to 7.35 with CsOH).

Extracellular solution (in mM): N-methyl-D-glucamine (NMDG)-Cl (150), $MgCl_2$ (2), $CaCl_2$ (2), HEPES (10) (pH adjusted to 7.35 with HCl).

Cell Culture

NIH3T3 mouse fibroblasts stably expressing F508del are used for whole-cell recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

Single-Channel Recordings

The single-channel activities of temperature-corrected F508del stably expressed in NIH3T3 cells and activities of potentiator compounds were observed using excised inside-out membrane patch. Briefly, voltage-clamp recordings of single-channel activity were performed at room temperature with an Axopatch 200B patch-clamp amplifier (Axon Instruments Inc.). All recordings were acquired at a sampling frequency of 10 kHz and low-pass filtered at 400 Hz. Patch pipettes were fabricated from Corning Kovar Sealing #7052 glass (World Precision Instruments, Inc., Sarasota, Fla.) and had a resistance of 5-8 MS when filled with the extracellular solution. The F508del was activated after excision, by adding 1 mM Mg-ATP, and 75 nM of the cAMP-dependent protein kinase, catalytic subunit (PKA; Promega Corp. Madison, Wis.). After channel activity stabilized, the patch was perifused using a gravity-driven microperfusion system.

The inflow was placed adjacent to the patch, resulting in complete solution exchange within 1-2 sec. To maintain F508del activity during the rapid perifusion, the nonspecific phosphatase inhibitor $F^-$ (10 mM NaF) was added to the bath solution. Under these recording conditions, channel activity remained constant throughout the duration of the patch recording (up to 60 min). Currents produced by positive charge moving from the intra- to extracellular solutions (anions moving in the opposite direction) are shown as positive currents. The pipette potential ($V_p$) was maintained at 80 mV.

Channel activity was analyzed from membrane patches containing ≤2 active channels. The maximum number of simultaneous openings determined the number of active channels during the course of an experiment. To determine the single-channel current amplitude, the data recorded from 120 sec of F508del activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o=I/i(N)$, where I=mean current, i=single-channel current amplitude, and N=number of active channels in patch.

Solutions

Extracellular solution (in mM): NMDG (150), aspartic acid (150), $CaCl_2$ (5), $MgCl_2$ (2), and HEPES (10) (pH adjusted to 7.35 with Tris base).

Intracellular solution (in mM): NMDG-Cl (150), $MgCl_2$ (2), EGTA (5), TES (10), and Tris base (14) (pH adjusted to 7.35 with HCl).

Cell Culture

NIH3T3 mouse fibroblasts stably expressing F508del are used for excised-membrane patch-clamp recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For single channel recordings, 2,500-5,000 cells were seeded on poly-L-lysine-coated glass coverslips and cultured for 24-48 hrs at 27° C. before use.

The compounds of formula I are useful as modulators of CFTR activity. Table 3 below illustrates the EC50 of the compounds of Table 1 using procedures described above. In Table 3 below, the following meanings apply. EC50: "+++" means <3.0 uM; "++" means between 3.0 uM and 10.0 uM; "+" means greater than 10.0 uM.

TABLE 3

| Cmpd. No. | EC50 (μM) |
| --- | --- |
| 1 | +++ |
| 2 | +++ |
| 3 | +++ |
| 4 | +++ |
| 5 | +++ |
| 6 | +++ |
| 7 | +++ |
| 8 | ++ |
| 9 | +++ |
| 10 | +++ |
| 11 | +++ |
| 12 | +++ |
| 13 | +++ |
| 14 | +++ |
| 15 | +++ |
| 16 | +++ |
| 17 | +++ |
| 18 | +++ |
| 19 | +++ |
| 20 | +++ |
| 21 | +++ |
| 22 | +++ |
| 23 | ++ |
| 24 | +++ |
| 25 | +++ |
| 26 | +++ |
| 27 | +++ |
| 28 | +++ |
| 29 | +++ |
| 30 | +++ |
| 31 | +++ |
| 32 | +++ |
| 33 | +++ |
| 34 | +++ |
| 35 | +++ |
| 36 | +++ |
| 37 | +++ |
| 38 | ++ |
| 39 | +++ |
| 40 | +++ |
| 41 | +++ |
| 42 | +++ |
| 43 | +++ |
| 44 | +++ |
| 45 | ++ |
| 46 | +++ |
| 47 | +++ |
| 48 | ++ |
| 49 | +++ |
| 50 | ++ |
| 51 | +++ |
| 52 | +++ |
| 53 | +++ |
| 54 | ++ |
| 55 | +++ |
| 56 | +++ |
| 57 | +++ |
| 58 | +++ |
| 59 | +++ |
| 60 | +++ |
| 61 | +++ |
| 62 | +++ |
| 63 | +++ |
| 64 | +++ |
| 65 | +++ |
| 66 | +++ |
| 67 | +++ |
| 68 | +++ |
| 69 | +++ |
| 70 | ++ |
| 71 | +++ |
| 72 | ++ |
| 73 | +++ |
| 74 | +++ |
| 75 | +++ |
| 76 | +++ |
| 77 | +++ |
| 78 | +++ |
| 79 | +++ |
| 80 | + |
| 81 | +++ |
| 82 | +++ |
| 83 | +++ |
| 84 | ++ |
| 85 | + |
| 86 | + |

Table 4 below illustrates the maximum efficacy of the compounds of Table 1 using the procedures described above. In Table 4 below, the following meanings apply. Maximum efficacy: "+++" means >80.0; "++" means >30.0 and <=80.0; "+" means <=30.0.

TABLE 4

| Cmpd. No. | Max Efficacy (%) |
|---|---|
| 1 | +++ |
| 2 | +++ |
| 3 | +++ |
| 4 | ++ |
| 5 | +++ |
| 6 | ++ |
| 7 | ++ |
| 8 | ++ |
| 9 | ++ |
| 10 | ++ |
| 11 | +++ |
| 12 | +++ |
| 13 | ++ |
| 14 | ++ |
| 15 | ++ |
| 16 | +++ |
| 17 | +++ |
| 18 | ++ |
| 19 | +++ |
| 20 | ++ |
| 21 | ++ |
| 22 | ++ |
| 23 | ++ |
| 24 | +++ |
| 25 | ++ |
| 26 | ++ |
| 27 | +++ |
| 28 | ++ |
| 29 | ++ |
| 30 | ++ |
| 31 | +++ |
| 32 | +++ |
| 33 | ++ |
| 34 | +++ |
| 35 | ++ |
| 36 | ++ |
| 37 | ++ |
| 38 | ++ |
| 39 | ++ |
| 40 | ++ |
| 41 | +++ |
| 42 | +++ |
| 43 | ++ |
| 44 | +++ |
| 45 | ++ |
| 46 | ++ |
| 47 | +++ |
| 48 | ++ |
| 49 | +++ |
| 50 | ++ |
| 51 | ++ |
| 52 | +++ |
| 53 | +++ |
| 54 | ++ |
| 55 | ++ |
| 56 | +++ |
| 57 | ++ |
| 58 | +++ |
| 59 | ++ |
| 60 | ++ |
| 61 | +++ |
| 62 | ++ |
| 63 | +++ |
| 64 | +++ |
| 65 | ++ |
| 66 | +++ |
| 67 | +++ |
| 68 | ++ |
| 69 | +++ |
| 70 | ++ |
| 71 | ++ |
| 72 | ++ |
| 73 | ++ |
| 74 | +++ |
| 75 | +++ |
| 76 | ++ |
| 77 | ++ |
| 78 | ++ |

TABLE 4-continued

| Cmpd. No. | Max Efficacy (%) |
|---|---|
| 79 | +++ |
| 80 | ++ |
| 81 | ++ |
| 82 | ++ |
| 83 | ++ |
| 84 | +++ |
| 85 | + |
| 86 | + |

Other Embodiments

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the disclosure. One skilled in the art will readily recognize from such discussion and from the accompanying drawings and claims, that various changes, modifications and variations can be made therein without departing from the spirit and scope of the disclosure as defined in the following claims.

The invention claimed is:

1. A compound of formula I:

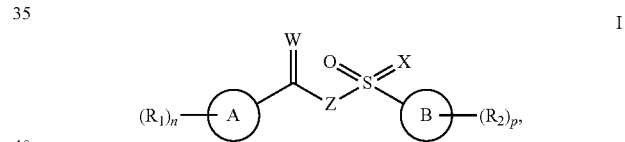

or a pharmaceutically acceptable salt thereof, wherein, independently for each occurrence:

Ring A is a $C_3$-$C_{14}$ heteroaryl or heterocyclic ring wherein anywhere from 1 to 4 ring atoms are independently O, S, N, or NR;

Ring B is a $C_3$-$C_{10}$ cycloalkyl ring; a $C_6$-$C_{10}$ aryl ring; or a $C_3$-$C_{10}$ heteroaryl or $C_3$-$C_{10}$ heterocyclic ring wherein anywhere from 1 to 4 ring atoms are independently O, S, N, or NR;

W is O, S, or NR;

X is O or NR;

Z is NR or $C(R)_2$;

$R_1$ is halo; CN; NRR; $C_1$-$C_6$ alkyl or $C_1$-$C_6$ fluoroalkyl; $C_3$-$C_6$ cycloalkyl; $C_1$-$C_8$ alkoxy or $C_1$-$C_8$ fluoroalkoxy; $C_2$-$C_6$ alkenyl; $C_2$-$C_6$ alkynyl; ($C_1$-$C_9$ alkylene)-$R_3$ wherein up to four $CH_2$ units are independently replaced with O, CO, S, SO, $SO_2$ or NR; $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_2$ is halo; NRR; CN; $CO_2R$; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four CH₂ units are optionally and independently replaced with O, CO, S, SO, SO₂ or NR;

or two R₂ may form a =CH₂ or =O group;

R₃ is H; CF₃; CHF₂; OR; C≡CH; CO₂R; OH; C₆-C₁₀ aryl; C₃-C₁₀ heteroaryl or heterocycloalkyl wherein anywhere from 1 to 4 ring atoms are independently O, S, N, or NR; C₃-C₁₀ cycloalkyl; NRR, NRCOR, CONRR, CN, halo, or SO₂R;

R is independently H; OH; CO₂H; CO₂C₁-C₆ alkyl; C₁-C₆ alkyl; C₂-C₆ alkenyl; C₂-C₆ alkynyl; C₆-C₁₀ aryl; C₃-C₁₀ heteroaryl or heterocycloalkyl wherein anywhere from 1 to 4 ring atoms are independently O, S, or N; or C₃-C₁₀ cycloalkyl;

n is 2 or 3;

p is 0, 1, 2, or 3; and

Provided that 1) when R₁ is adjacent to the C=W attached to Ring A, R₁ does not contain a ring moiety, 2) at least one R₁ is adjacent to the C=W attached to Ring A, and at least one R₁ is C₁-C₆ alkyl or C₁-C₆ fluoroalkyl, C₆-C₁₀ aryl; C₃-C₁₀ heteroaryl or C₃-C₁₀ heterocyclic ring wherein anywhere from 1 to 4 ring atoms are independently O, S, N, or NR; or C₃-C₁₀ cycloalkyl; 3) when Ring A is phenyl or six-membered mono-heteroaryl wherein anywhere from 1 to 3 ring atoms are N, R₁ is not 4,5-dihydroisoxazole; 4) when Ring A is phenyl, R₁ is not

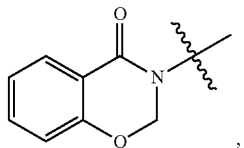 [SMILES: *N1COc2ccccc2C1=O ; ","]

ureido, or aminocarbonyl; 5) when Ring A and the at least one R₁ is pyridine, R₁ (pyridine) is not further substituted by —CONHSO₂—; and 6) when Ring A is pyridine or thiazole, and C=W wherein W is O in formula I is adjacent to the N on the pyridine or thiazole, R₁ which is adjacent to the N on the pyridine or on the thiazole is not

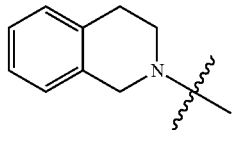

wherein said compound of formula I modulates cystic fibrosis transmembrane conductance receptor activity.

2. The compound of claim 1 or a pharmaceutically acceptable salt thereof, wherein Ring A is pyridyl, indole, indoline, isoindoline, pyrazole, pyrimidine, 1,2,3,4-tetrahydroquinoline, quinoline, 5,6,7,8-tetrahydroquinoline, 1,2,3,4-tetrahydroisoquinoline, pyrrolodine, aza-indole, pyrrole, thiophene, oxazole, pyrazine, triazole, thiazole, indazole, 2,3,4,5-tetrahydro-1H-benzo[d]azepine, 1H-benzo[d]imidazole, imidazo[1,2-a]pyridine, or imidazole ring.

3. The compound of claim 1 or a pharmaceutically acceptable salt thereof, wherein Ring A is

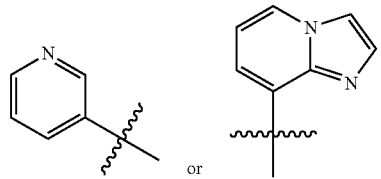

wherein the wavy line ⌇ indicates point of attachment of Ring A to the C=W.

4. The compound of claim 1 or a pharmaceutically acceptable salt thereof, wherein Ring B is a pyridyl, pyridine-2(1H)-one, pyrazole, indole, pyrrole, indoline, thiophene, dihydrobenzofuran, tetrahydrofuran, furan, pyrazine, indazole, thiazole, pyridine-4(1H)-one, pyrrolidinone, 3-azabicyclo[3.1.0]hexane, (1R,4R)-2-oxa-5-azabicyclo[2.2.1]heptane, pyrrolidine, azetidine, piperidine, piperazine, imidazo[1,2-a]pyridine, or quinoline.

5. The compound of claim 1 or a pharmaceutically acceptable salt thereof, wherein Ring B is

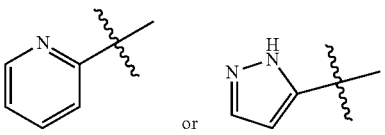

wherein the wavy line ⌇ indicates point of attachment of Ring B to the X=S=O.

6. The compound of claim 1 or a pharmaceutically acceptable salt thereof, wherein R₁ is independently halo, amino, OH, C₂-C₆ alkenyl; C₂-C₆ alkynyl, C₁-C₆ fluoroalkyl, CN, C₁-C₆ alkyl, C₁-C₈ alkoxy or C₁-C₈ fluoroalkoxy, a phenyl, C₃-C₆ mono-cycloalkly, mono-C₄-C₆ heterocyclic ring, 1,2,3,4-tetrahydroisoquinoline, pyridyl, pyrimidine, indole, aza-indole, pyrazole, pyrrole, or thiophene ring, or a (C₁-C₉ alkylene)-R₃, wherein up to four CH₂ units are independently replaced with O, CO, S, SO, SO₂ or NR.

7. The compound of claim 1 or a pharmaceutically acceptable salt thereof, wherein R₁ is CHF₂CH₂(CH₃)N—, (CH₃)₂CHCH₂CH₂O—, (CH₃)₃CCH₂CH₂O—, (CH₃)₃COCH₂CH₂O—, (CH₃)₂CHO, CHF₂CHF₂CH(CH₃)O—, —CF₃, (CH₃CH₂)₂N—, CF₃CH₂CH(CH₃)O—, CH₃O—, CH₃(CH₂)₄O—, CH₃CH₂CH(CH₃)CH(CH₃)O—, CH₃CH₂OCH₂CH₂O—, CH₃CH₂NCH(CH₃)₂, (CH₃)₃CH₂O—, (R)—CH₃NCH(CH₃)(CF₃), CH₃OCH₂CH (CH₂CH₃)O—, (CH₃)₂N—, (S)—CH₃OCH₂CH(CH₃)O—, CH₃O(CH₂)₃O—, CH₃OC(CH₃)₂(CH₂)₂O, CH₃OCH₂CH (CH₃)O, CH₃CH(CH₃)CH₂CH(CH₃)O—, (CH₃)₃CCH (CH₃)O, ((CH₃)₂CH)₂CHO—, CH₃CH₂CH₂O, CH₃CH=CHCH₂O—, (S)—CH₃CH₂CH(CH₃)O—, CH₃CH₂O, (CH₃)₂CHNCH₃, (CH₃)₃CCH₂O, (CF₃)₂CHO—, (CH₃)₃CCH(CH₂CH₃)O, CH₃C≡CCH₂CH₂O, (CH₃)₃CCH₂CH(CH₃)O—, (CH₃)₂C=C(CH₃), CHF₂CH₂O—, CH₃CH₂CH₂NH, (CH₃)₂CHCH(CH₂CH₃) O, ((CH₃)₂CH)₂N, CH₂=CHCH(CH₃)O, CH₂=CHCH₂O—, CH₃CH₂C(CH₃)₂O, (CH₃CH₂)₂CHO, CF₃CH₂O, CH₃C(=CH₂)CH₂O, (CH₃)₃CCH₂CH₂NH, CH₃OCH₂C(CH₃)₂O, (CH₃)₃CCH₂N(CH₃), (CH₃)₂CHCH (CH₃)NH, (CH₃)₂CHO(CH₂)₂O, CH₃CH₂CH₂CH(CH₃)O, CH₃CF₂CH₂O, (CH₃)₃CNH, (R)—CH₃CH₂CH(CH₃)O, CH₃OCH₂CH₂O, (CH₃)₂CHCH₂N(CH₃), CH₃CH₂CH₂CH (CH₃)CH(CH₃)O, CH₃CH₂CH₂O, CH₃CH₂CH₂N (CH₃), (R)—CH₃OCH₂CH(CH₃)O, CF₃CH₂N(CH₃), CH₃CH₂N(CH₃), ((CH₃)₃C)₂CHO, (CH₃CH₂)₂CHN(CH₃), (CH₃)₂CHN(CH₃), CH₃CH₂OCH₂CH(CH₃)O, (CH₃)₃CCH₂NH, CF₃CH(CH₃)O, CH₃CH₂NCH(CH₃)₂, (R)—CF₃CH(CH₃)N(CH₃), (CH₃)₂CHCH(CH₃), CH₃CH₂(CH₃)₂CHCH₂CH₂O, (S)—CH₃OCH(CH₃)CH₂O, HOCH(CH₃)₂CH₂CH₂NH, CF₃CH₂CH₂O, CF₃CH₂CH₂CH₂O, CF₃CH=CHCH₂O, CH₃CH₂CH₂CH₂CH₂NH, CH₃, Cl, F, CN, CH₂CH₃, CH(CH₃)₂, OCH₂CH₂OCH₂CH₃,
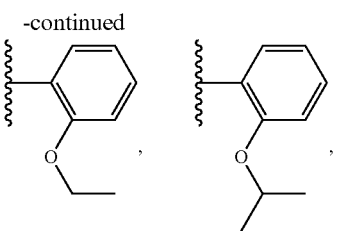
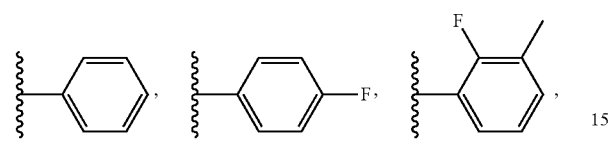
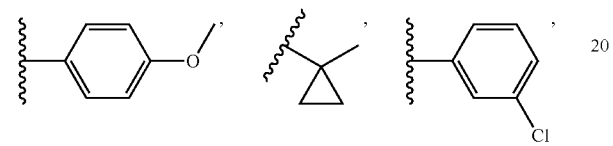
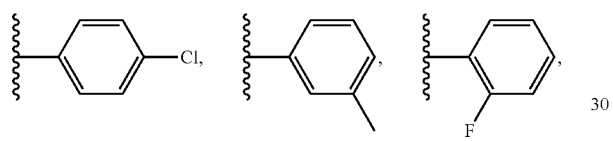
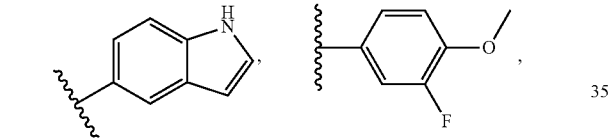
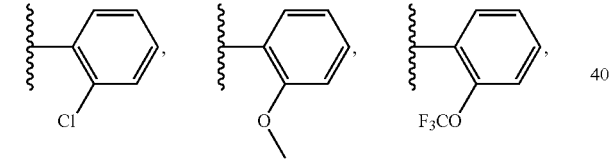
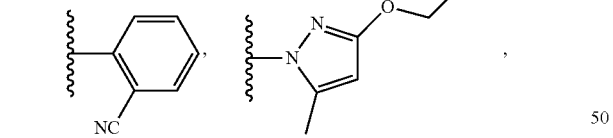
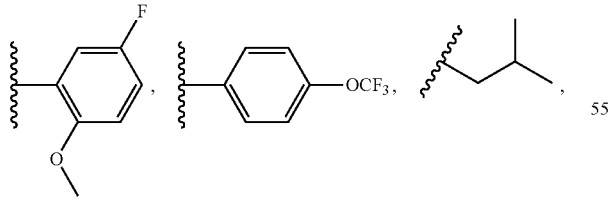
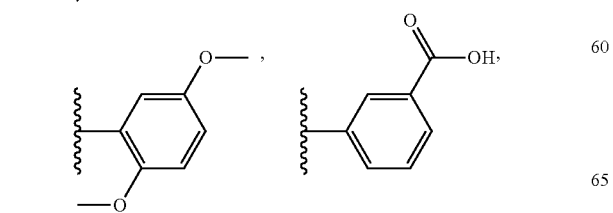

-continued
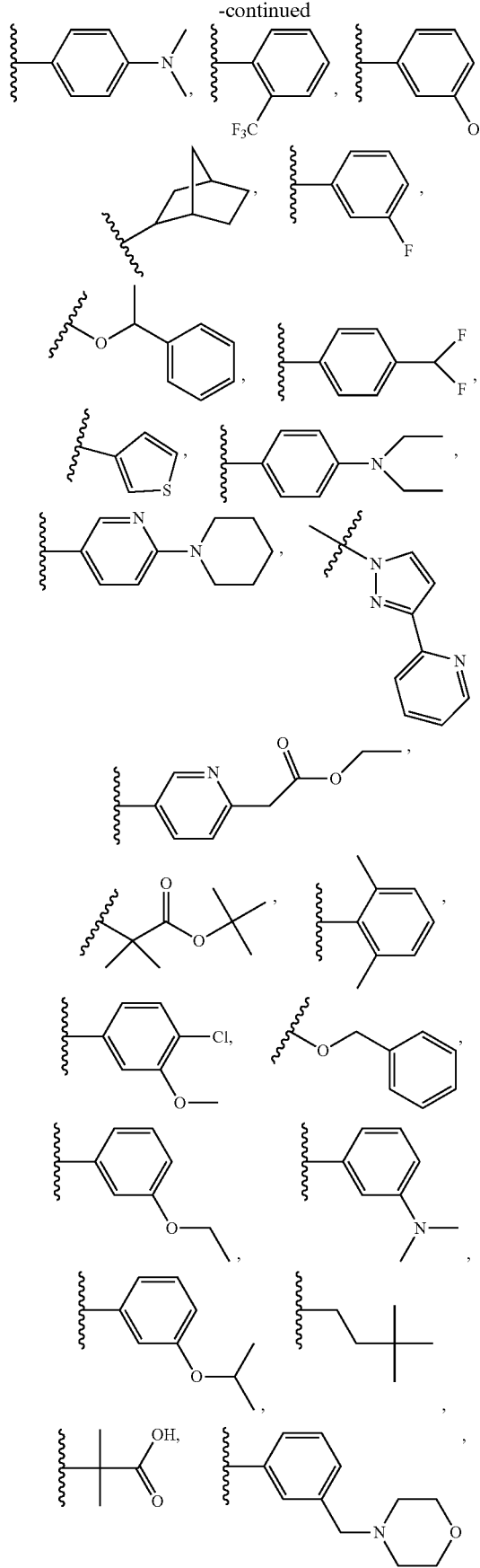
-continued
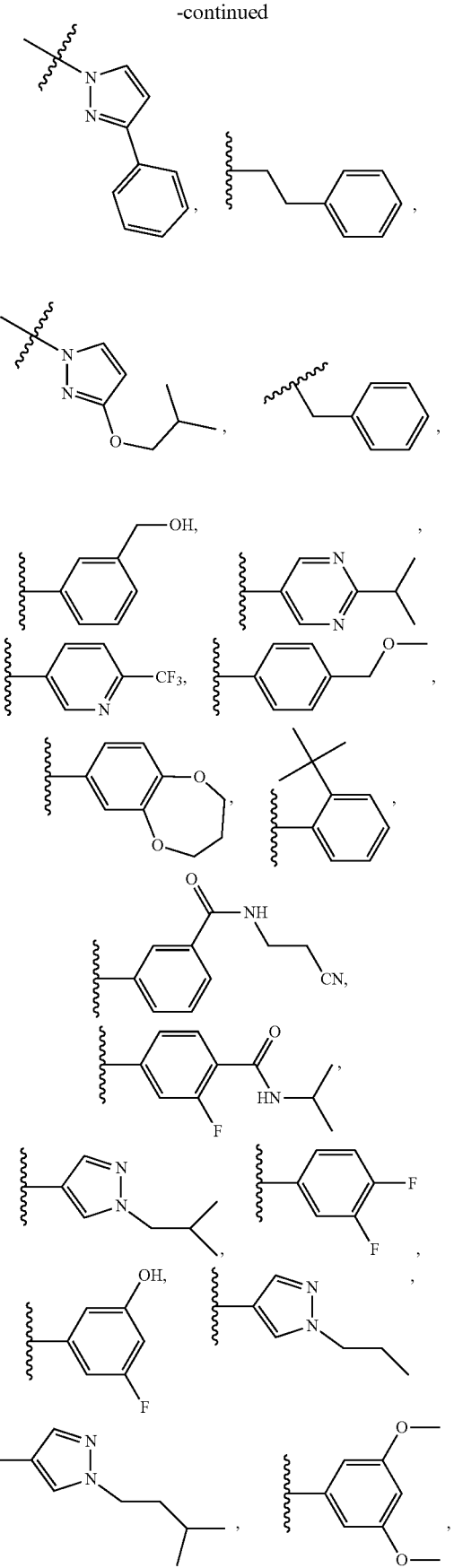

421
-continued
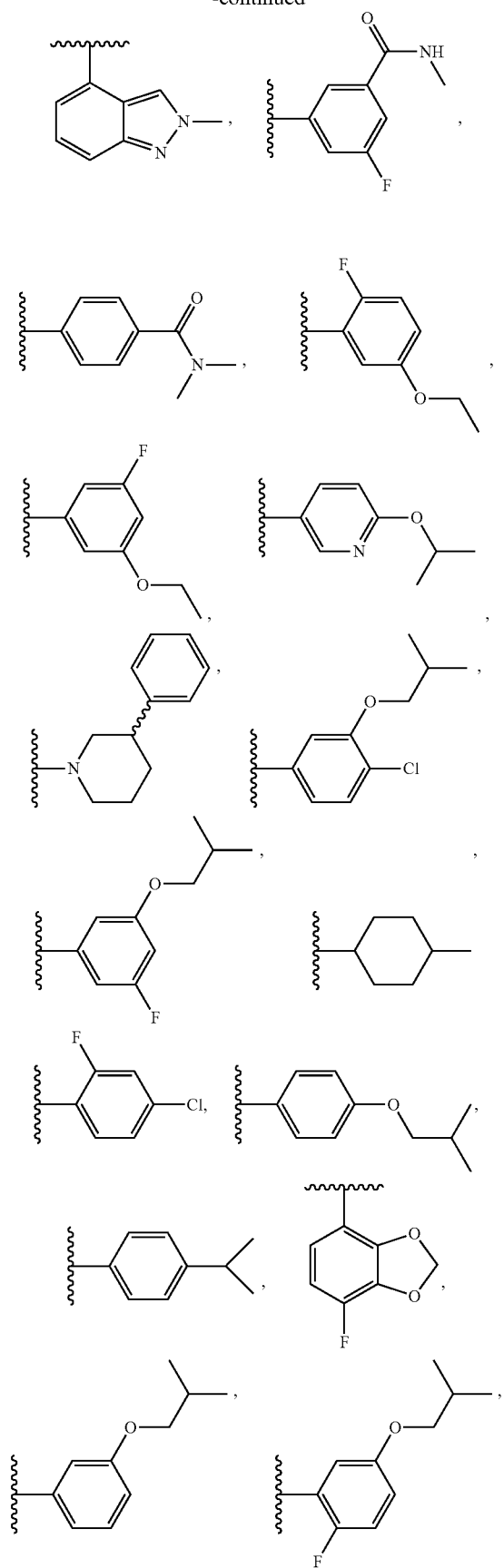
422
-continued
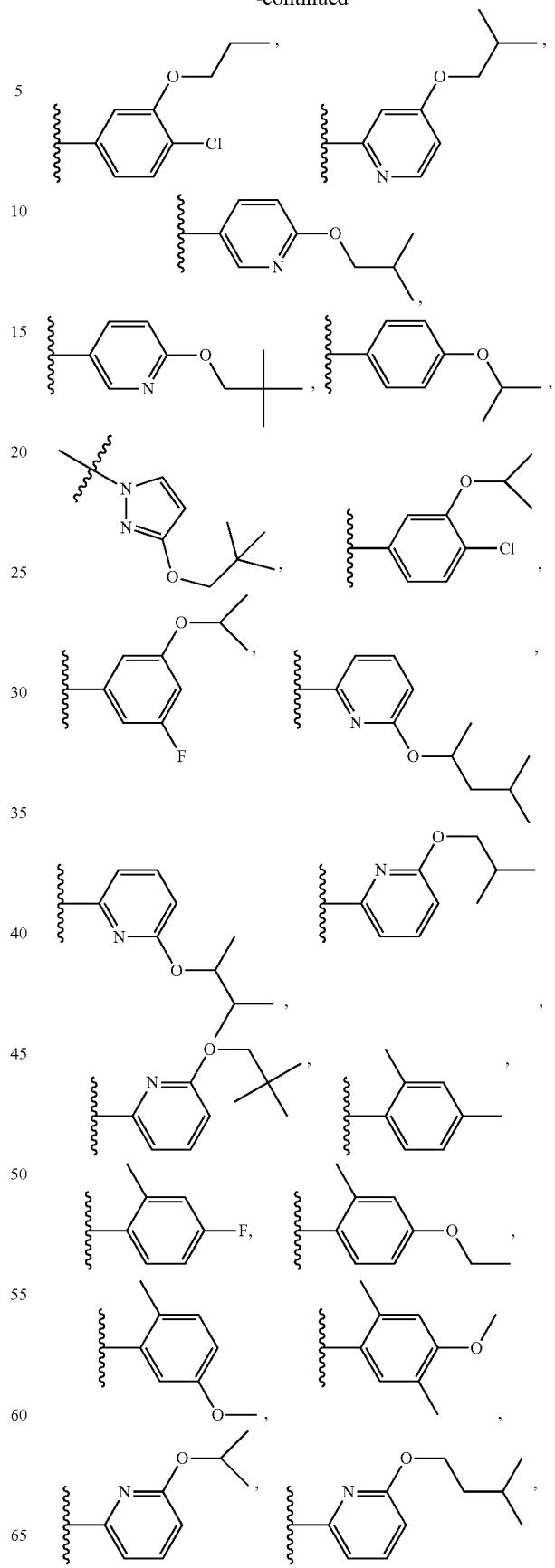

-continued

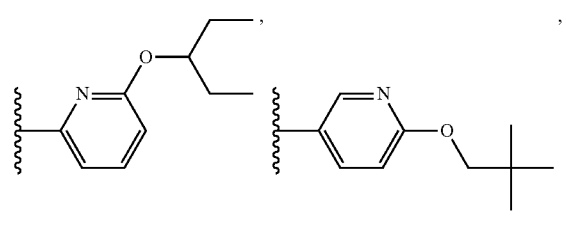

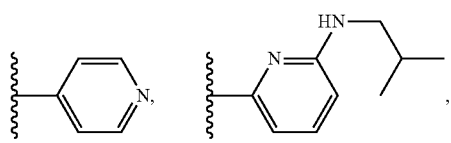

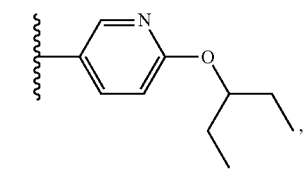

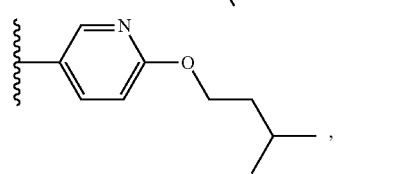

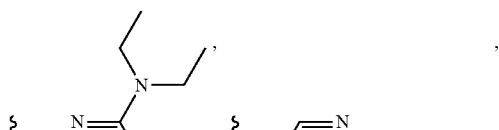

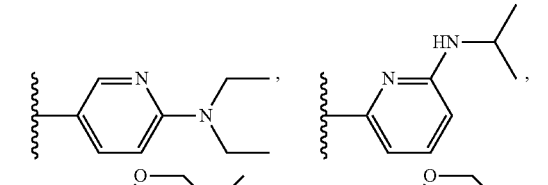

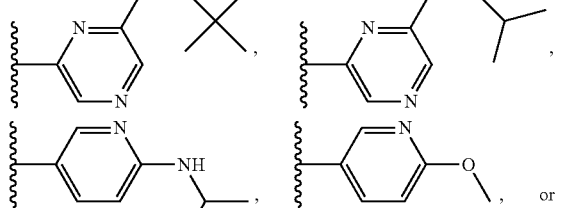

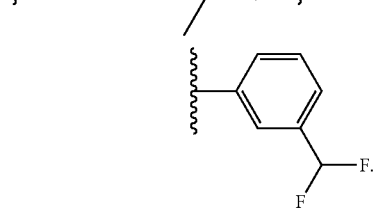

8. The compound of claim 1 or a pharmaceutically acceptable salt thereof, wherein $R_1$ is tBu,

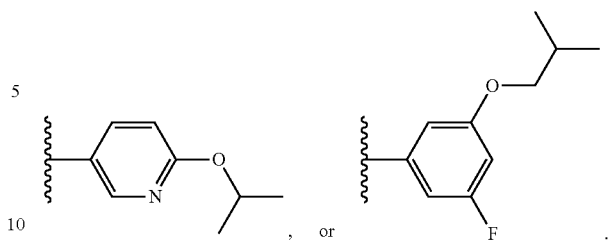

9. The compound of claim 1 or a pharmaceutically acceptable salt thereof, wherein $R_2$ is halo, OH, CN, amino, $C_1$-$C_6$ alkyl or $C_1$-$C_6$ fluoroalkyl, $C_1$-$C_6$ alkoxy or $C_1$-$C_6$ fluoroalkoxy, $C_3$-$C_{10}$ heterocyclic ring wherein anywhere from 1 to 4 carbon atoms are independently O, S, N, or NR; or a ($C_1$-$C_9$ alkylene)-$R_3$ wherein up to four $CH_2$ units are optionally and independently replaced with O, CO, S, SO, $SO_2$ or NR.

10. The compound of claim 1 or a pharmaceutically acceptable salt thereof, wherein $R_2$ is $NH_2$, or $NHCH_2CH_2CH_3$.

11. The compound of claim 1 or a pharmaceutically acceptable salt thereof, wherein n is 2.

12. The compound of claim 1 or a pharmaceutically acceptable salt thereof, wherein p is 0.

13. The compound of claim 1 or a pharmaceutically acceptable salt thereof, wherein p is 1.

14. The compound of claim 1 or a pharmaceutically acceptable salt thereof, wherein W is O.

15. The compound of claim 1 or a pharmaceutically acceptable salt thereof, wherein Z is NH.

16. The compound of claim 1 or a pharmaceutically acceptable salt thereof, wherein X is O.

17. The compound of claim 1 or a pharmaceutically acceptable salt thereof, where in Ring A is

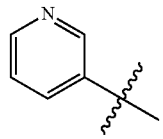 [SMILES: *c1cccnc1]

and n is 2.

18. The compound of claim 1 or a pharmaceutically acceptable salt thereof, wherein Ring A is

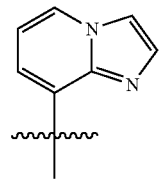 [SMILES: *c1cccn2ccnc12]

and n is 2.

19. The compound of any claim 1 or a pharmaceutically acceptable salt thereof, wherein Ring A is

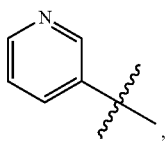

and at least one $R_1$ is phenyl.

20. The compound of claim 1 or a pharmaceutically acceptable salt thereof, wherein Ring A is

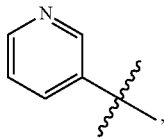

and at least one $R_1$ is tert-butyl.

21. The compound of claim 1 or a pharmaceutically acceptable salt thereof, wherein Ring A is

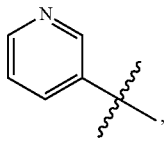

and at least one $R_1$ is pyridinyl.

22. The compound of claim 1 or a pharmaceutically acceptable salt thereof, wherein one or more hydrogen atoms is replaced by a deuterium atom.

23. The compound of claim 1 or a pharmaceutically acceptable salt thereof, wherein the compound of formula I or a pharmaceutically acceptable salt thereof is a compound of formula I-i:

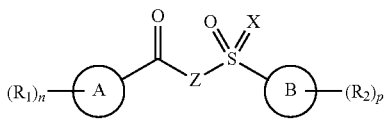

I-i or a pharmaceutically acceptable salt thereof, wherein, independently for each occurrence:

Ring A is a $C_3$-$C_{14}$ heteroaryl or heterocyclic ring wherein anywhere from 1 to 4 ring atoms are independently O, S, N, or NR;

Ring B is a $C_3$-$C_{10}$ heteroaryl or $C_3$-$C_{10}$ heterocyclic ring wherein anywhere from 1 to 4 ring atoms are independently O, S, N, or NR;

X is O or NR;

Z is NR;

$R_1$ is halo; CN; NRR; $C_1$-$C_6$ alkyl or $C_1$-$C_6$ fluoroalkyl; $C_3$-$C_6$ cycloalkyl; $C_1$-$C_8$ alkoxy or $C_1$-$C_8$ fluoroalkoxy; $C_2$-$C_6$ alkenyl; $C_2$-$C_6$ alkynyl; ($C_1$-$C_9$ alkylene)-$R_3$ wherein up to four $CH_2$ units are independently replaced with O, CO, S, SO, $SO_2$ or NR; $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_2$ is halo; NRR; CN; $CO_2R$; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four $CH_2$ units are optionally and independently replaced with O, CO, S, SO, $SO_2$ or NR;

or two $R_2$ may form a $=CH_2$ or $=O$ group;

$R_3$ is H; $CF_3$; $CHF_2$; OR; C≡CH; $CO_2R$; OH; $C_6$-$C_{10}$ aryl, $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or $SO_2R$;

R is independently H; OH; $CO_2H$; $CO_2C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, or N; or $C_3$-$C_{10}$ cycloalkyl;

n is 2 or 3; and p is 0, 1, 2, or 3.

24. The compound of claim 1 or a pharmaceutically acceptable salt thereof, wherein the compound of formula I or a pharmaceutically acceptable salt thereof is a compound of formula Ia:

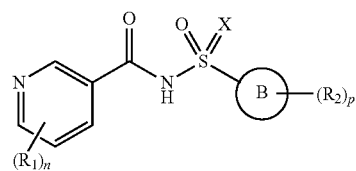

Ia or a pharmaceutically acceptable salt thereof, wherein, independently for each occurrence:

Ring B is a $C_3$-$C_{10}$ cycloalkyl ring; a $C_6$-$C_{10}$ aryl ring; or a $C_3$-$C_{10}$ heteroaryl or $C_3$-$C_{10}$ heterocyclic ring wherein anywhere from 1 to 4 ring atoms are independently O, S, N, or NR;

X is O or NR;

$R_1$ is halo; CN; NRR; $C_1$-$C_6$ alkyl or $C_1$-$C_6$ fluoroalkyl; $C_3$-$C_6$ cycloalkyl; $C_1$-$C_8$ alkoxy or $C_1$-$C_8$ fluoroalkoxy; $C_2$-$C_6$ alkenyl; $C_2$-$C_6$ alkynyl; ($C_1$-$C_9$ alkylene)-$R_3$ wherein up to four $CH_2$ units are independently replaced with O, CO, S, SO, $SO_2$ or NR; $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_2$ is halo; NRR; CN; $CO_2R$; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four $CH_2$ units are optionally and independently replaced with O, CO, S, SO, $SO_2$ or NR;

or two $R_2$ may form a $=CH_2$ or $=O$ group;

$R_3$ is H; $CF_3$; $CHF_2$; OR; C≡CH; $CO_2R$; OH; $C_6$-$C_{10}$ aryl, $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or $SO_2R$;

R is independently H; OH; $CO_2H$; $CO_2C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, or N; or $C_3-C_{10}$ cycloalkyl;

n is 2 or 3; and p is 0, 1, 2, or 3.

25. The compound of claim 24 or a pharmaceutically acceptable salt thereof, wherein the compounds of formula Ia or a pharmaceutically acceptable salt thereof is a compound of formula Ia-i

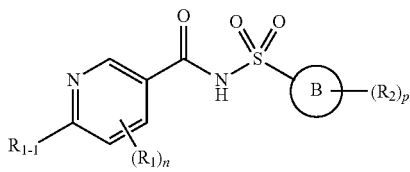

Ia-i or a pharmaceutically acceptable salt thereof, wherein, independently for each occurrence:

Ring B is a $C_3-C_{10}$ cycloalkyl ring; a $C_6-C_{10}$ aryl ring; or a $C_3-C_{10}$ heteroaryl or $C_3-C_{10}$ heterocyclic ring wherein anywhere from 1 to 4 ring atoms are independently O, S, N, or NR;

$R_1$ is halo; CN; NRR; $C_1-C_6$ alkyl or $C_1-C_6$ fluoroalkyl; $C_3-C_6$ cycloalkyl; $C_1-C_8$ alkoxy or $C_1-C_8$ fluoroalkoxy; $C_2-C_6$ alkenyl; $C_2-C_6$ alkynyl; $(C_1-C_9$ alkylene)-$R_3$ wherein up to four $CH_2$ units are independently replaced with O, CO, S, SO, $SO_2$ or NR; $C_6-C_{10}$ aryl; $C_3-C_{10}$ heteroaryl or $C_3-C_{10}$ heterocyclic ring wherein anywhere from 1 to 4 ring atoms are independently O, S, N, or NR; or $C_3-C_{10}$ cycloalkyl;

$R_{1-1}$ is $C_1-C_6$ alkyl or $C_1-C_6$ fluoroalkyl, $C_6-C_{10}$ aryl; $C_3-C_{10}$ heteroaryl or $C_3-C_{10}$ heterocyclic ring wherein anywhere from 1 to 4 ring atoms are independently O, S, N, or NR; or $C_3-C_{10}$ cycloalkyl;

$R_2$ is halo; NRR; CN; $CO_2R$; $C_1-C_6$ alkyl or $C_1-C_6$ fluoroalkyl; $C_1-C_6$ alkoxy or $C_1-C_6$ fluoroalkoxy; $C_2-C_6$ alkenyl; $C_2-C_6$ alkynyl; $C_6-C_{10}$ aryl; $C_3-C_{13}$ heteroaryl or heterocyclic ring wherein anywhere from 1 to 4 ring atoms are independently O, S, N, or NR; $C_3-C_{10}$ cycloalkyl; or a $(C_1-C_9$ alkylene)-$R_3$ wherein up to four $CH_2$ units are optionally and independently replaced with O, CO, S, SO, $SO_2$ or NR;

or two $R_2$ may form a $=CH_2$ or $=O$ group;

$R_3$ is H; $CF_3$; $CHF_2$; OR; C≡CH; $CO_2R$; OH; $C_6-C_{10}$ aryl, $C_3-C_{10}$ heteroaryl or heterocycloalkyl wherein anywhere from 1 to 4 ring atoms are independently O, S, N, or NR; $C_3-C_{10}$ cycloalkyl; NRR, NRCOR, CONRR, CN, halo, or $SO_2R$;

R is independently H; OH; $CO_2H$; $CO_2C_1-C_6$ alkyl; $C_1-C_6$ alkyl; $C_2-C_6$ alkenyl; $C_2-C_6$ alkynyl; $C_6-C_{10}$ aryl; $C_3-C_{10}$ heteroaryl or heterocycloalkyl wherein anywhere from 1 to 4 ring atoms are independently O, S, or N; or $C_3-C_{10}$ cycloalkyl;

n is 1 or 2; and p is 0, 1, 2, or 3.

26. The compound of claim 25 or a pharmaceutically acceptable salt thereof, wherein the compounds of formula Ia-i or a pharmaceutically acceptable salt thereof is a compound of formula Ia-i-1

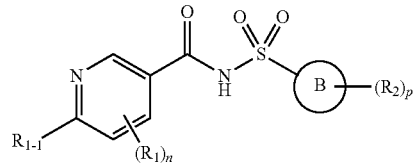

Ia-i-1 or a pharmaceutically acceptable salt thereof, wherein, independently for each occurrence:

Ring B is a $C_3-C_{10}$ heteroaryl or $C_3-C_{10}$ heterocyclic ring wherein anywhere from 1 to 4 ring atoms are independently O, S, N, or NR;

$R_1$ is halo; CN; NRR; $C_1-C_6$ alkyl or $C_1-C_6$ fluoroalkyl; $C_3-C_6$ cycloalkyl; $C_1-C_8$ alkoxy or $C_1-C_8$ fluoroalkoxy; $C_2-C_6$ alkenyl; $C_2-C_6$ alkynyl; $(C_1-C_9$ alkylene)-$R_3$ wherein up to four $CH_2$ units are independently replaced with O, CO, S, SO, $SO_2$ or NR; $C_6-C_{10}$ aryl; $C_3-C_{10}$ heteroaryl or $C_3-C_{10}$ heterocyclic ring wherein anywhere from 1 to 4 ring atoms are independently O, S, N, or NR; or $C_3-C_{10}$ cycloalkyl;

$R_{1-1}$ is $C_1-C_6$ alkyl or $C_1-C_6$ fluoroalkyl, $C_6-C_{10}$ aryl; $C_3-C_{10}$ heteroaryl or $C_3-C_{10}$ heterocyclic ring wherein anywhere from 1 to 4 ring atoms are independently O, S, N, or NR; or $C_3-C_{10}$ cycloalkyl;

$R_2$ is halo; NRR; CN; $CO_2R$; $C_1-C_6$ alkyl or $C_1-C_6$ fluoroalkyl; $C_1-C_6$ alkoxy or $C_1-C_6$ fluoroalkoxy; $C_2-C_6$ alkenyl; $C_2-C_6$ alkynyl; $C_6-C_{10}$ aryl; $C_3-C_{13}$ heteroaryl or heterocyclic ring wherein anywhere from 1 to 4 ring atoms are independently O, S, N, or NR; $C_3-C_{10}$ cycloalkyl; or a $(C_1-C_9$ alkylene)-$R_3$ wherein up to four $CH_2$ units are optionally and independently replaced with O, CO, S, SO, $SO_2$ or NR;

or two $R_2$ may form a $=CH_2$ or $=O$ group;

$R_3$ is H; $CF_3$; $CHF_2$; OR; C≡CH; $CO_2R$; OH; $C_6-C_{10}$ aryl, $C_3-C_{10}$ heteroaryl or heterocycloalkyl wherein anywhere from 1 to 4 ring atoms are independently O, S, N, or NR; $C_3-C_{10}$ cycloalkyl; NRR, NRCOR, CONRR, CN, halo, or $SO_2R$;

R is independently H; OH; $CO_2H$; $CO_2C_1-C_6$ alkyl; $C_1-C_6$ alkyl; $C_2-C_6$ alkenyl; $C_2-C_6$ alkynyl; $C_6-C_{10}$ aryl; $C_3-C_{10}$ heteroaryl or heterocycloalkyl wherein anywhere from 1 to 4 ring atoms are independently O, S, or N; or $C_3-C_{10}$ cycloalkyl;

n is 1 or 2; and p is 0, 1, 2, or 3.

27. The compound of claim 26 or a pharmaceutically acceptable salt thereof, wherein the compound of formula Ia-i-1 or a pharmaceutically acceptable salt thereof is a compound of formula Ia-i-2

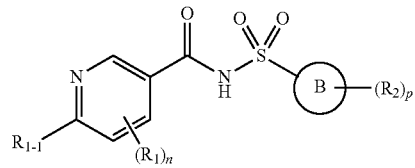

Ia-i-2 or a pharmaceutically acceptable salt thereof, wherein, independently for each occurrence:

Ring B is a pyridinyl;

R$_1$ is halo; CN; NRR; C$_1$-C$_6$ alkyl or C$_1$-C$_6$ fluoroalkyl; C$_3$-C$_6$ cycloalkyl; C$_1$-C$_8$ alkoxy or C$_1$-C$_8$ fluoroalkoxy; C$_2$-C$_6$ alkenyl; C$_2$-C$_6$ alkynyl; (C$_1$-C$_9$ alkylene)-R$_3$ wherein up to four CH$_2$ units are independently replaced with O, CO, S, SO, SO$_2$ or NR; C$_6$-C$_{10}$ aryl, C$_3$-C$_{10}$ heteroaryl or C$_3$-C$_{10}$ heterocyclic ring wherein anywhere from 1 to 4 ring atoms are independently O, S, N, or NR; or C$_3$-C$_{10}$ cycloalkyl;

R$_{1\text{-}1}$ is C$_1$-C$_6$ alkyl or C$_1$-C$_6$ fluoroalkyl, C$_6$-C$_{10}$ aryl; C$_3$-C$_{10}$ heteroaryl or C$_3$-C$_{10}$ heterocyclic ring wherein anywhere from 1 to 4 ring atoms are independently O, S, N, or NR; or C$_3$-C$_{10}$ cycloalkyl;

R$_2$ is halo; NRR; CN; CO$_2$R; C$_1$-C$_6$ alkyl or C$_1$-C$_6$ fluoroalkyl; C$_1$-C$_6$ alkoxy or C$_1$-C$_6$ fluoroalkoxy; C$_2$-C$_6$ alkenyl; C$_2$-C$_6$ alkynyl; C$_6$-C$_{10}$ aryl; C$_3$-C$_{13}$ heteroaryl or heterocyclic ring wherein anywhere from 1 to 4 ring atoms are independently O, S, N, or NR; C$_3$-C$_{10}$ cycloalkyl; or a (C$_1$-C$_9$ alkylene)-R$_3$ wherein up to four CH$_2$ units are optionally and independently replaced with O, CO, S, SO, SO$_2$ or NR;

or two R$_2$ may form a =CH$_2$ or =O group;

R$_3$ is H; CF$_3$; CHF$_2$; OR; C≡CH; CO$_2$R; OH; C$_6$-C$_{10}$ aryl, C$_3$-C$_{10}$ heteroaryl or heterocycloalkyl wherein anywhere from 1 to 4 ring atoms are independently O, S, N, or NR; C$_3$-C$_{10}$ cycloalkyl; NRR, NRCOR, CONRR, CN, halo, or SO$_2$R;

R is independently H; OH; CO$_2$H; CO$_2$C$_1$-C$_6$ alkyl; C$_1$-C$_6$ alkyl; C$_2$-C$_6$ alkenyl; C$_2$-C$_6$ alkynyl; C$_6$-C$_{10}$ aryl; C$_3$-C$_{10}$ heteroaryl or heterocycloalkyl wherein anywhere from 1 to 4 ring atoms are independently O, S, or N; or C$_3$-C$_{10}$ cycloalkyl;

n is 1 or 2; and p is 0, 1, 2, or 3.

28. The compound of claim 24 or a pharmaceutically acceptable salt thereof, wherein the compounds of formula Ia or a pharmaceutically acceptable salt thereof is a compound of formula Ia-ii

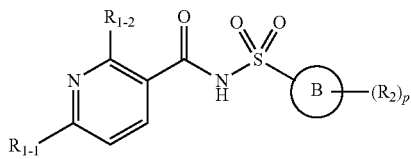

Ia-ii or a pharmaceutically acceptable salt thereof, wherein, independently for each occurrence:

Ring B is a C$_3$-C$_{10}$ cycloalkyl ring; a C$_6$-C$_{10}$ aryl ring; or a C$_3$-C$_{10}$ heteroaryl or C$_3$-C$_{10}$ heterocyclic ring wherein anywhere from 1 to 4 ring atoms are independently O, S, N, or NR;

R$_{1\text{-}2}$ is halo; CN; NRR; C$_1$-C$_6$ alkyl or C$_1$-C$_6$ fluoroalkyl; C$_1$-C$_8$ alkoxy or C$_1$-C$_8$ fluoroalkoxy; C$_2$-C$_6$ alkenyl; C$_2$-C$_6$ alkynyl; or (C$_1$-C$_9$ alkylene)-R$_3$ wherein up to four CH$_2$ units are independently replaced with O, CO, S, SO, SO$_2$ or NR;

R$_{1\text{-}1}$ is C$_1$-C$_6$ alkyl or C$_1$-C$_6$ fluoroalkyl, C$_6$-C$_{10}$ aryl; C$_3$-C$_{10}$ heteroaryl or C$_3$-C$_{10}$ heterocyclic ring wherein anywhere from 1 to 4 ring atoms are independently O, S, N, or NR; or C$_3$-C$_{10}$ cycloalkyl;

R$_2$ is halo; NRR; CN; CO$_2$R; C$_1$-C$_6$ alkyl or C$_1$-C$_6$ fluoroalkyl; C$_1$-C$_6$ alkoxy or C$_1$-C$_6$ fluoroalkoxy; C$_2$-C$_6$ alkenyl; C$_2$-C$_6$ alkynyl; C$_6$-C$_{10}$ aryl; C$_3$-C$_{13}$ heteroaryl or heterocyclic ring wherein anywhere from 1 to 4 ring atoms are independently O, S, N, or NR; C$_3$-C$_{10}$ cycloalkyl; or a (C$_1$-C$_9$ alkylene)-R$_3$ wherein up to four CH$_2$ units are optionally and independently replaced with O, CO, S, SO, SO$_2$ or NR;

or two R$_2$ may form a =CH$_2$ or =O group;

R$_3$ is H; CF$_3$; CHF$_2$; OR; C≡CH; CO$_2$R; OH; C$_6$-C$_{10}$ aryl, C$_3$-C$_{10}$ heteroaryl or heterocycloalkyl wherein anywhere from 1 to 4 ring atoms are independently O, S, N, or NR; C$_3$-C$_{10}$ cycloalkyl; NRR, NRCOR, CONRR, CN, halo, or SO$_2$R;

R is independently H; OH; CO$_2$H; CO$_2$C$_1$-C$_6$ alkyl; C$_1$-C$_6$ alkyl; C$_2$-C$_6$ alkenyl; C$_2$-C$_6$ alkynyl; C$_6$-C$_{10}$ aryl; C$_3$-C$_{10}$ heteroaryl or heterocycloalkyl wherein anywhere from 1 to 4 ring atoms are independently O, S, or N; or C$_3$-C$_{10}$ cycloalkyl; and p is 0, 1, 2, or 3.

29. The compound of claim 28 or a pharmaceutically acceptable salt thereof, wherein the compounds of formula Ia-ii or a pharmaceutically acceptable salt thereof is a compound of formula Ia-ii-1

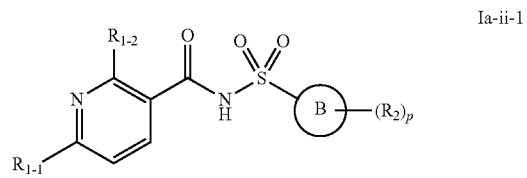

Ia-ii-1 or a pharmaceutically acceptable salt thereof, wherein, independently for each occurrence:

Ring B is a C$_3$-C$_{10}$ heteroaryl or C$_3$-C$_{10}$ heterocyclic ring wherein anywhere from 1 to 4 ring atoms are independently O, S, N, or NR;

R$_{1\text{-}2}$ is halo; CN; NRR; C$_1$-C$_6$ alkyl or C$_1$-C$_6$ fluoroalkyl; C$_1$-C$_8$ alkoxy or C$_1$-C$_8$ fluoroalkoxy; C$_2$-C$_6$ alkenyl; C$_2$-C$_6$ alkynyl; or (C$_1$-C$_9$ alkylene)-R$_3$ wherein up to four CH$_2$ units are independently replaced with O, CO, S, SO, SO$_2$ or NR;

R$_{1\text{-}1}$ is C$_1$-C$_6$ alkyl or C$_1$-C$_6$ fluoroalkyl, C$_6$-C$_{10}$ aryl; C$_3$-C$_{10}$ heteroaryl or C$_3$-C$_{10}$ heterocyclic ring wherein anywhere from 1 to 4 ring atoms are independently O, S, N, or NR; or C$_3$-C$_{10}$ cycloalkyl;

R$_2$ is halo; NRR; CN; CO$_2$R; C$_1$-C$_6$ alkyl or C$_1$-C$_6$ fluoroalkyl; C$_1$-C$_6$ alkoxy or C$_1$-C$_6$ fluoroalkoxy; C$_2$-C$_6$ alkenyl; C$_2$-C$_6$ alkynyl; C$_6$-C$_{10}$ aryl; C$_3$-C$_{13}$ heteroaryl or heterocyclic ring wherein anywhere from 1 to 4 ring atoms are independently O, S, N, or NR; C$_3$-C$_{10}$ cycloalkyl; or a (C$_1$-C$_9$ alkylene)-R$_3$ wherein up to four CH$_2$ units are optionally and independently replaced with O, CO, S, SO, SO$_2$ or NR;

or two R$_2$ may form a =CH$_2$ or =O group;

R$_3$ is H; CF$_3$; CHF$_2$; OR; C≡CH; CO$_2$R; OH; C$_6$-C$_{10}$ aryl, C$_3$-C$_{10}$ heteroaryl or heterocycloalkyl wherein anywhere from 1 to 4 ring atoms are independently O, S, N, or NR; C$_3$-C$_{10}$ cycloalkyl; NRR, NRCOR, CONRR, CN, halo, or SO$_2$R;

R is independently H; OH; CO$_2$H; CO$_2$C$_1$-C$_6$ alkyl; C$_1$-C$_6$ alkyl; C$_2$-C$_6$ alkenyl; C$_2$-C$_6$ alkynyl; C$_6$-C$_{10}$ aryl; C$_3$-C$_{10}$ heteroaryl or heterocycloalkyl wherein anywhere from 1 to 4 ring atoms are independently O, S, or N; or C$_3$-C$_{10}$ cycloalkyl; and p is 0, 1, 2, or 3.

30. The compound of claim 29 or a pharmaceutically acceptable salt thereof, wherein the compounds of formula Ia-ii-1 or a pharmaceutically acceptable salt thereof is a compound of formula Ia-ii-2

Ia-ii-2

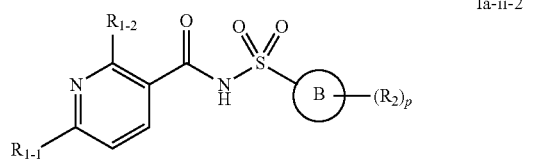

or a pharmaceutically acceptable salt thereof, wherein, independently for each occurrence:

Ring B is a pyridinyl;

$R_{1-2}$ is halo; CN; NRR; $C_1$-$C_6$ alkyl or $C_1$-$C_6$ fluoroalkyl; $C_1$-$C_8$ alkoxy or $C_1$-$C_8$ fluoroalkoxy; $C_2$-$C_6$ alkenyl; $C_2$-$C_6$ alkynyl; or ($C_1$-$C_9$ alkylene)-$R_3$ wherein up to four $CH_2$ units are independently replaced with O, CO, S, SO, $SO_2$ or NR;

$R_{1-1}$ is $C_1$-$C_6$ alkyl or $C_1$-$C_6$ fluoroalkyl, $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;

$R_2$ is halo; NRR; CN; $CO_2R$; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four $CH_2$ units are optionally and independently replaced with O, CO, S, SO, $SO_2$ or NR;

or two $R_2$ may form a $=CH_2$ or $=O$ group;

$R_3$ is H; $CF_3$; $CHF_2$; OR; C≡CH; $CO_2R$; OH; $C_6$-$C_{10}$ aryl, $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or $SO_2R$;

R is independently H; OH; $CO_2H$; $CO_2C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, or N; or $C_3$-$C_{10}$ cycloalkyl; and p is 0, 1, 2, or 3.

31. A compound selected from:

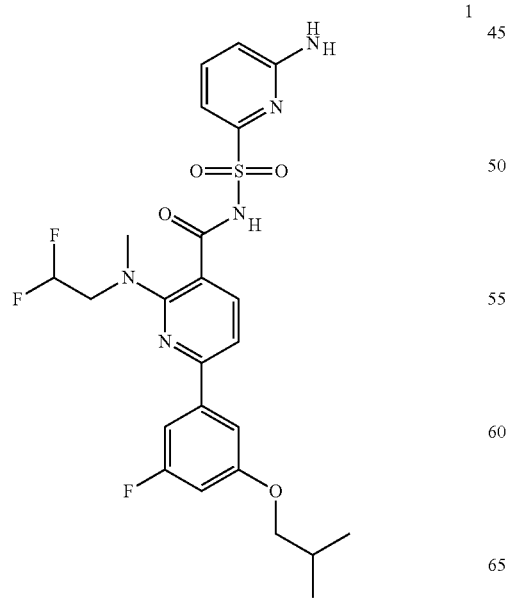

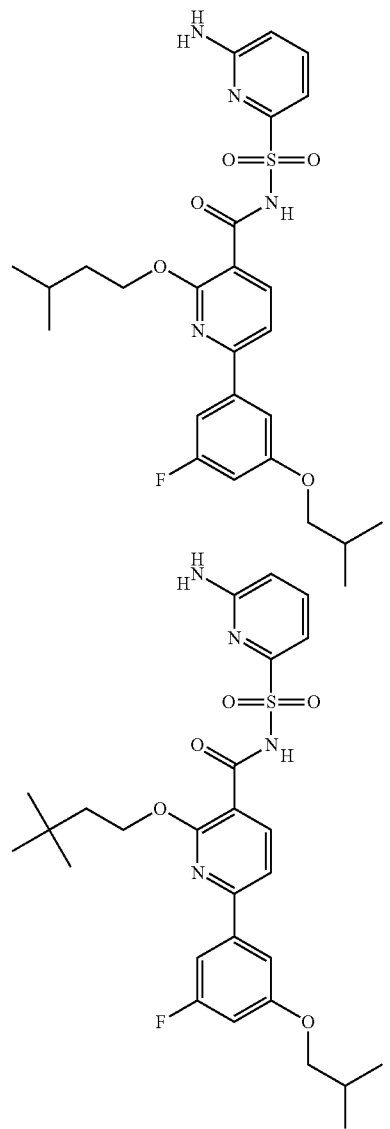

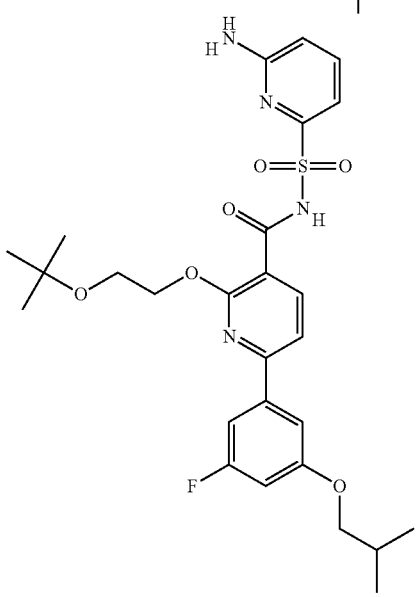

433
-continued
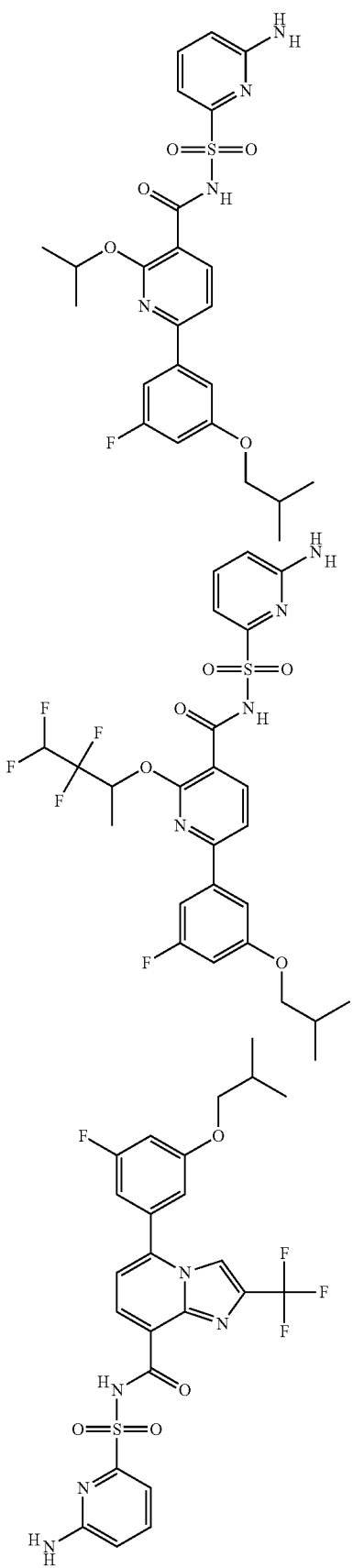
434
-continued
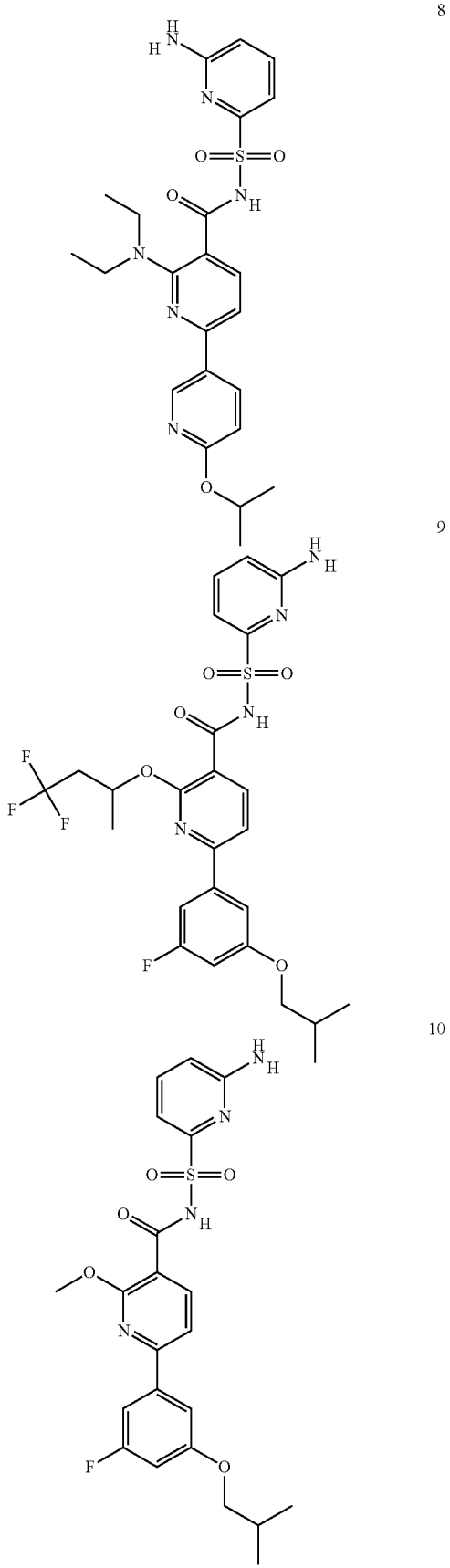

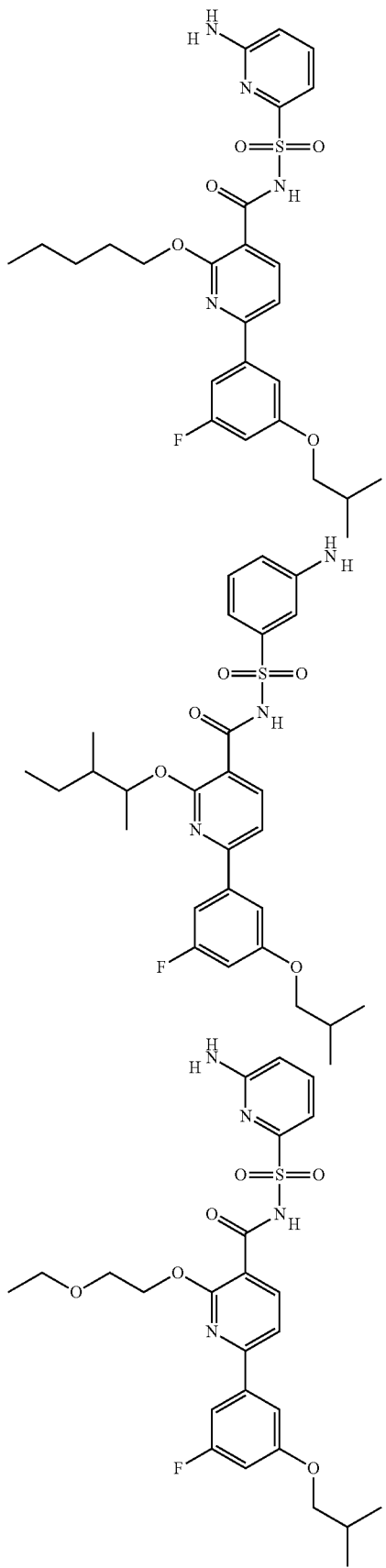
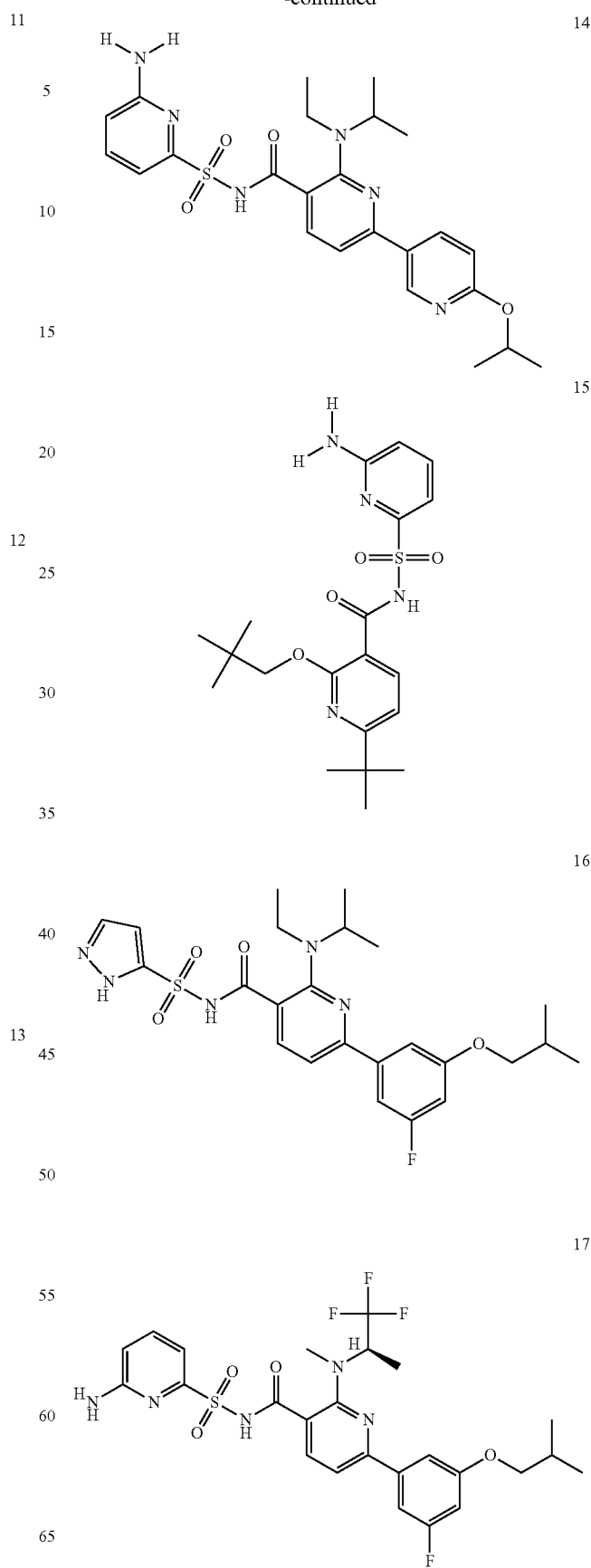

437
-continued
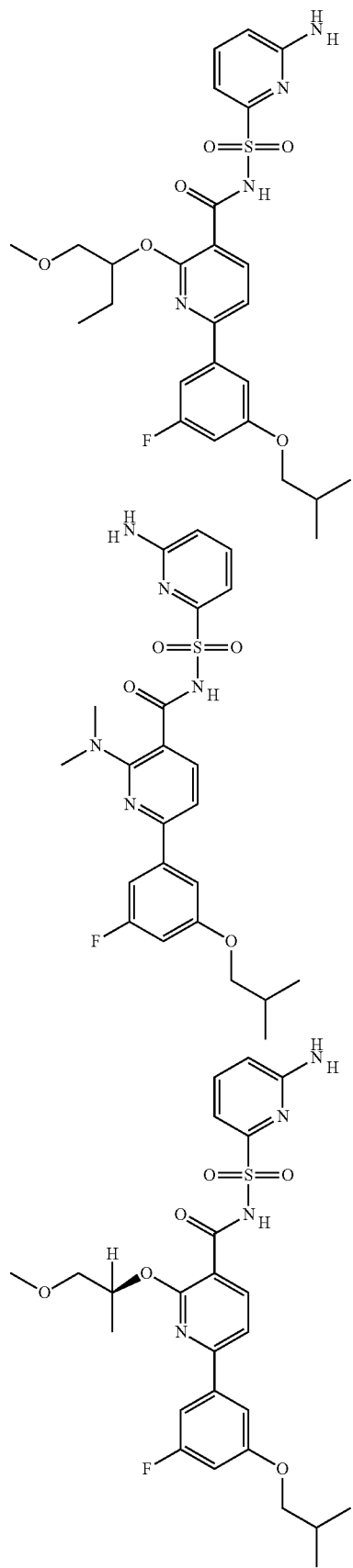
438
-continued
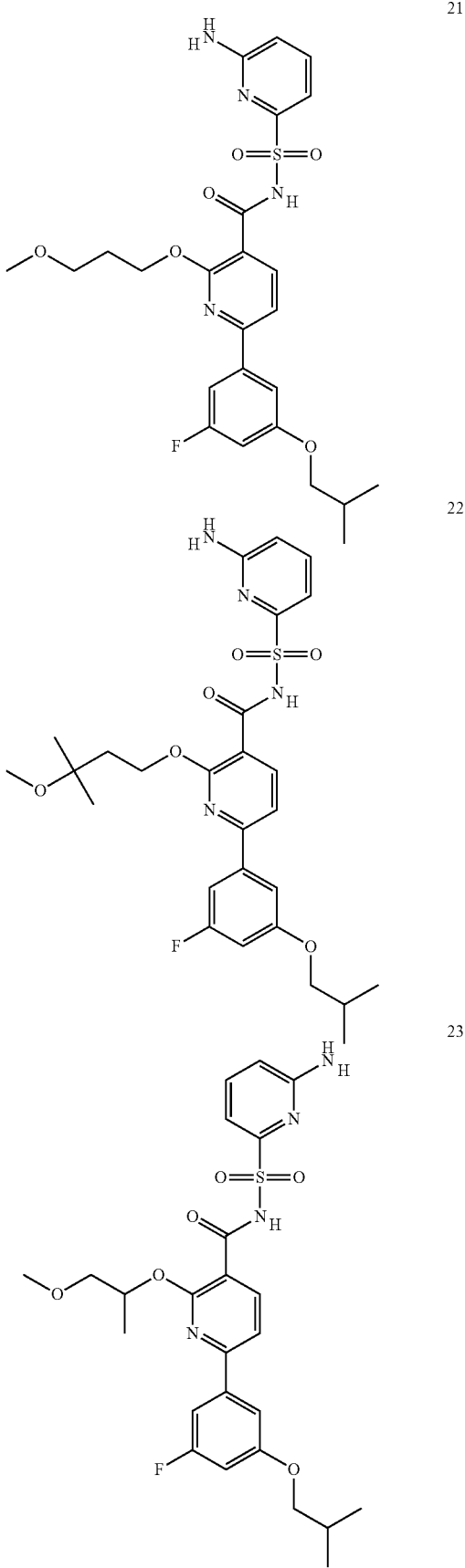

439
-continued
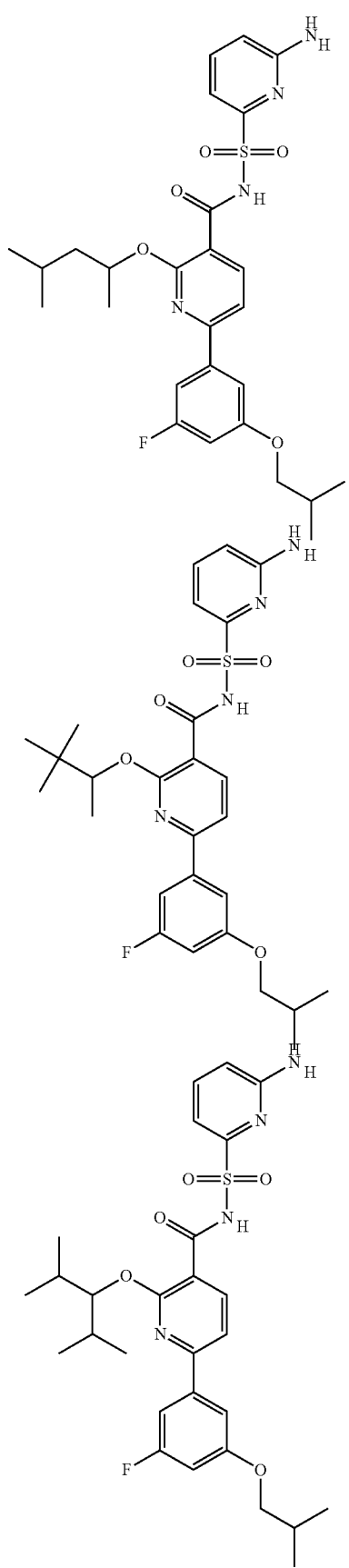
440
-continued
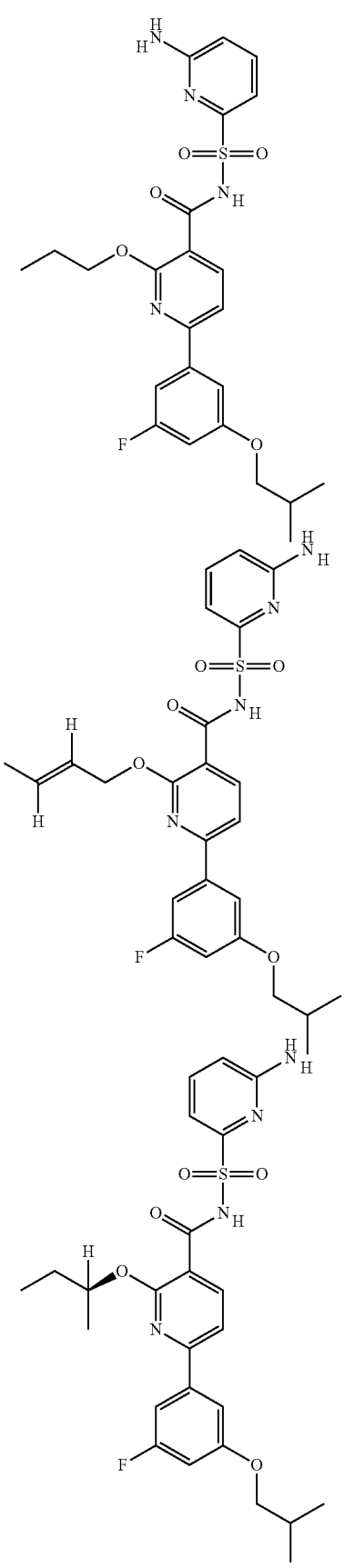

441
-continued
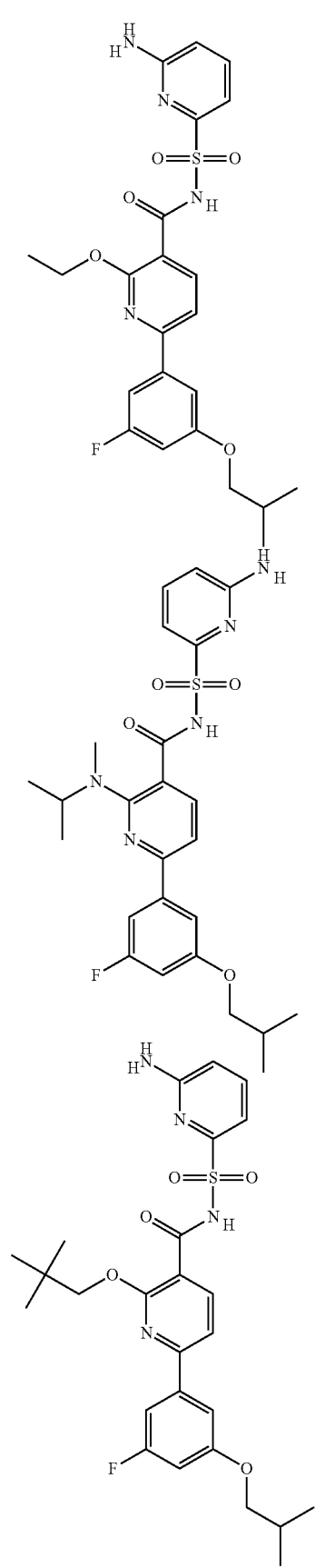
30
31
32
442
-continued
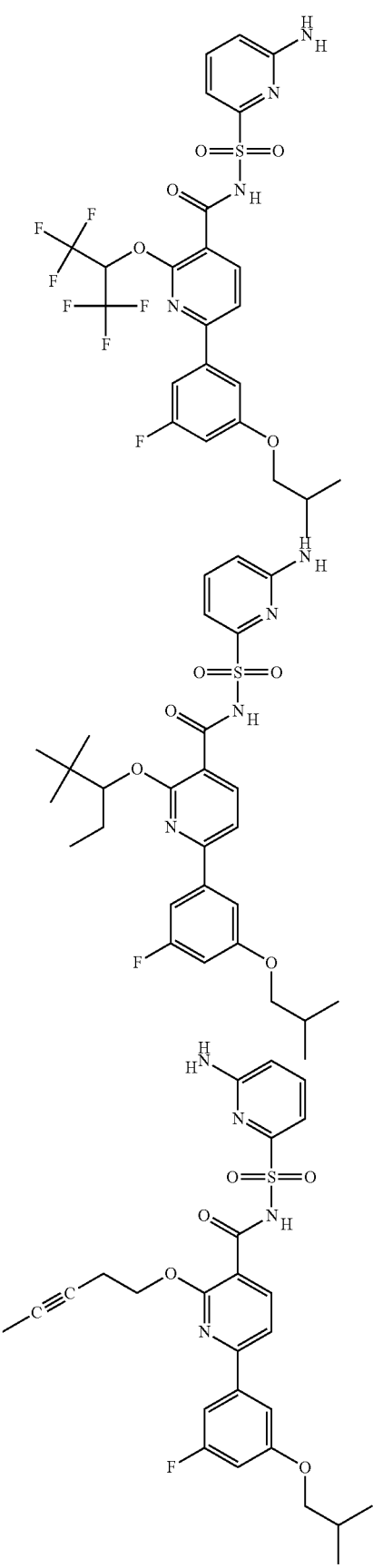
33
34
35

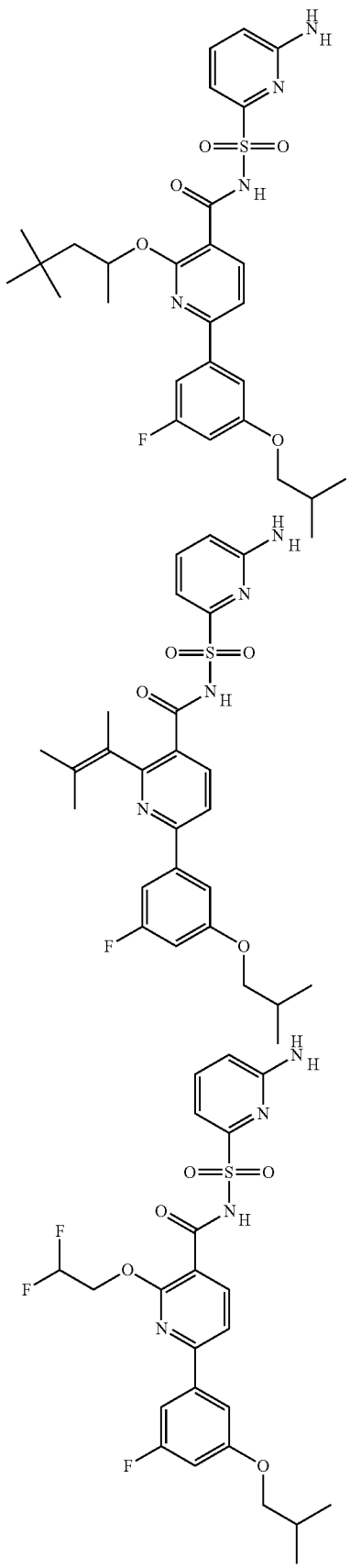
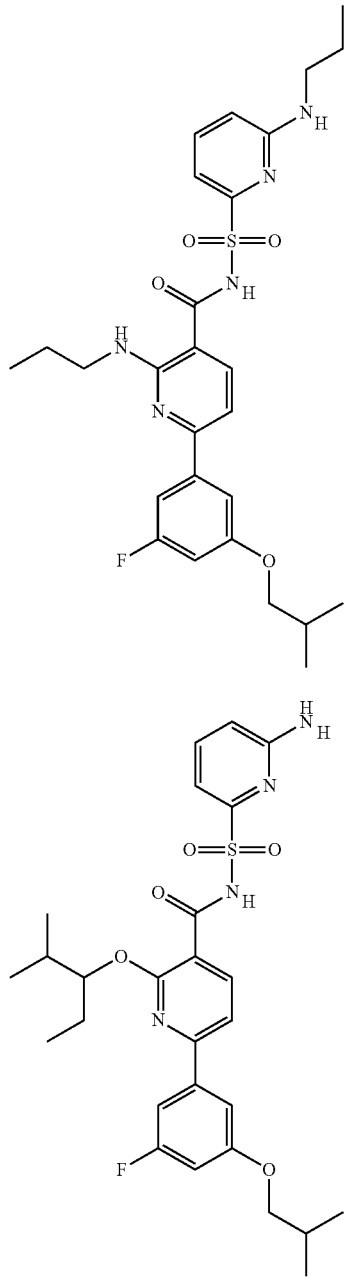
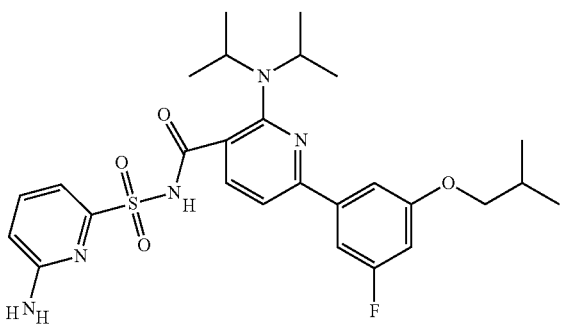

445
-continued
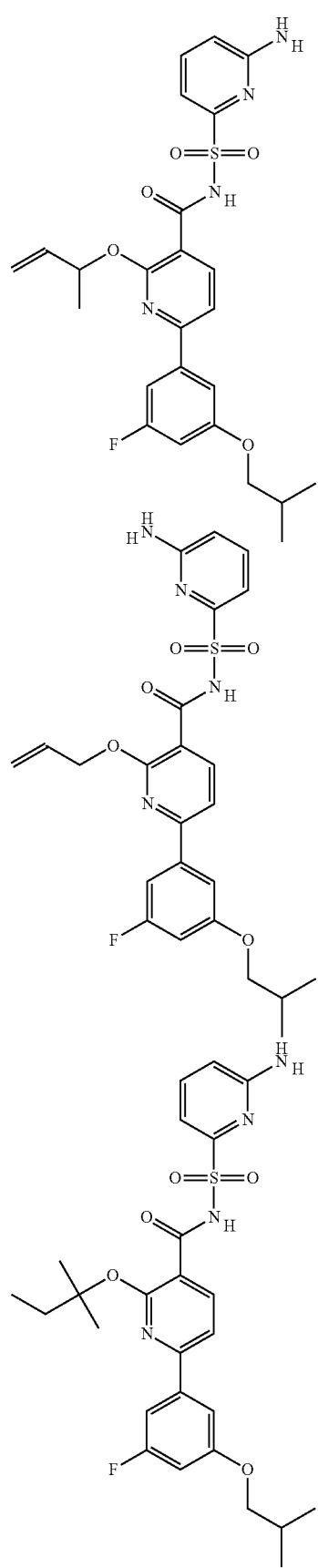
446
-continued
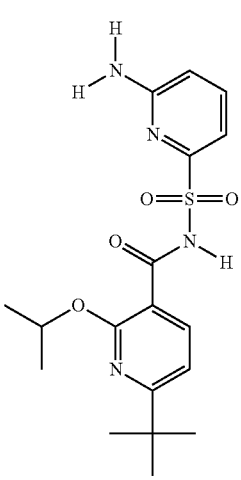
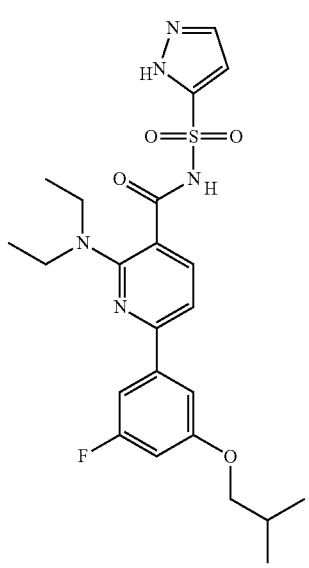
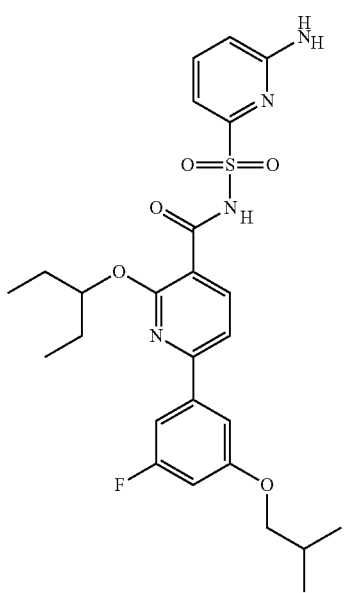

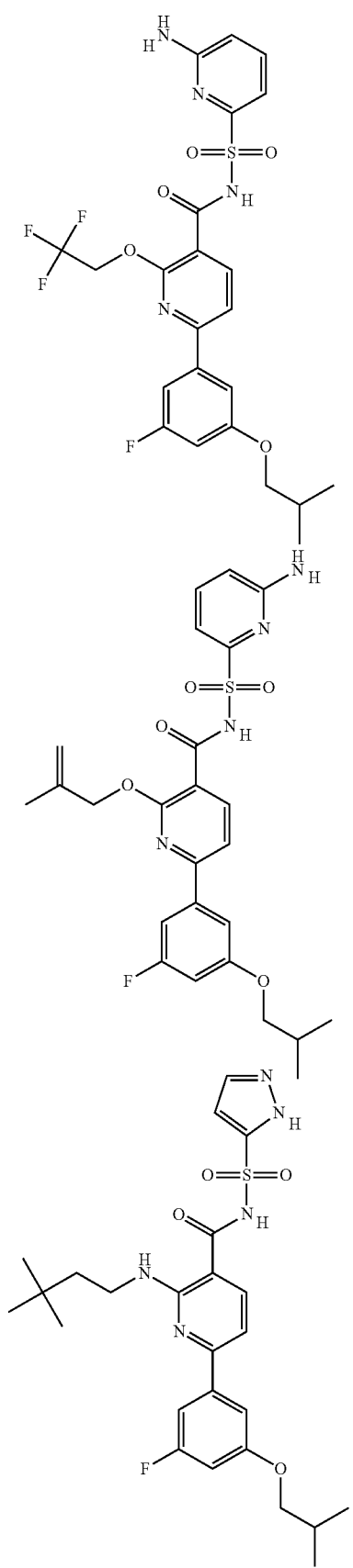
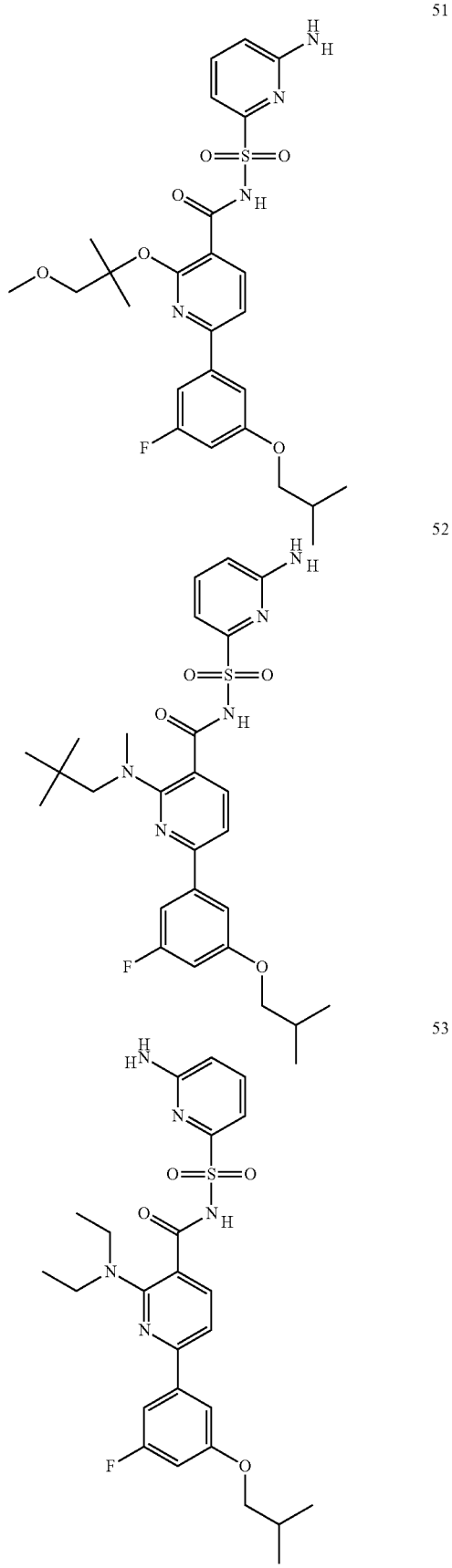

54
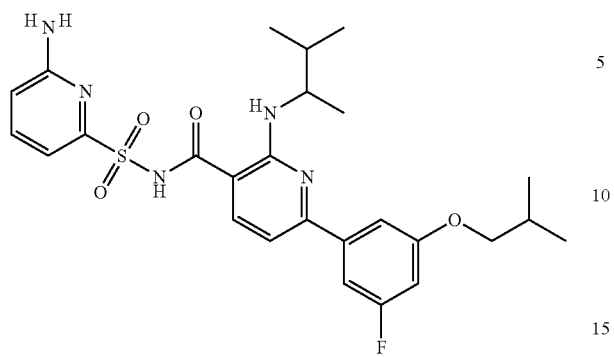
55
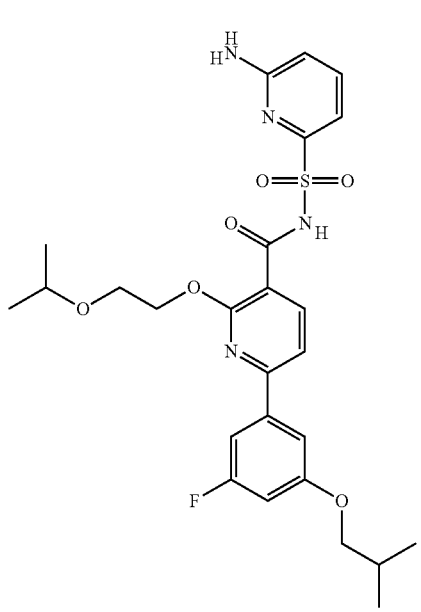
56
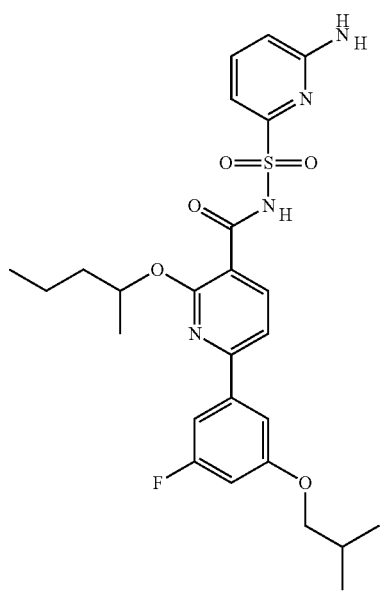
57
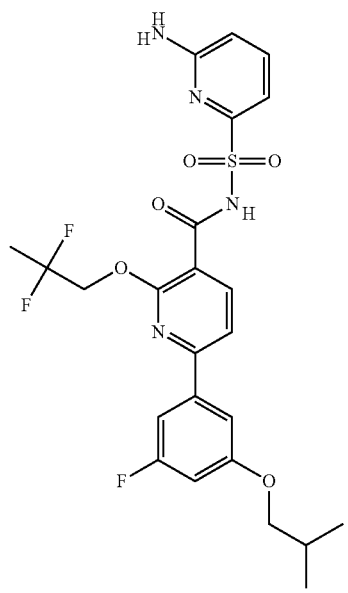
58
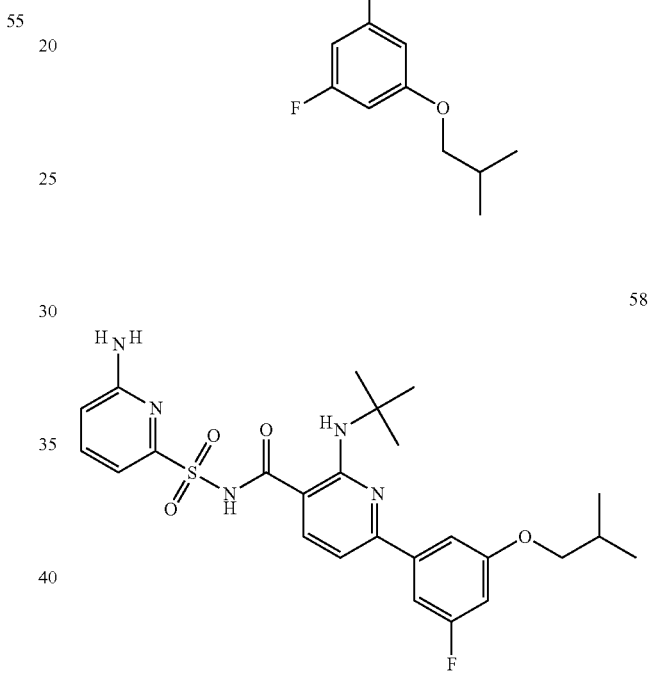
59

451
-continued
60
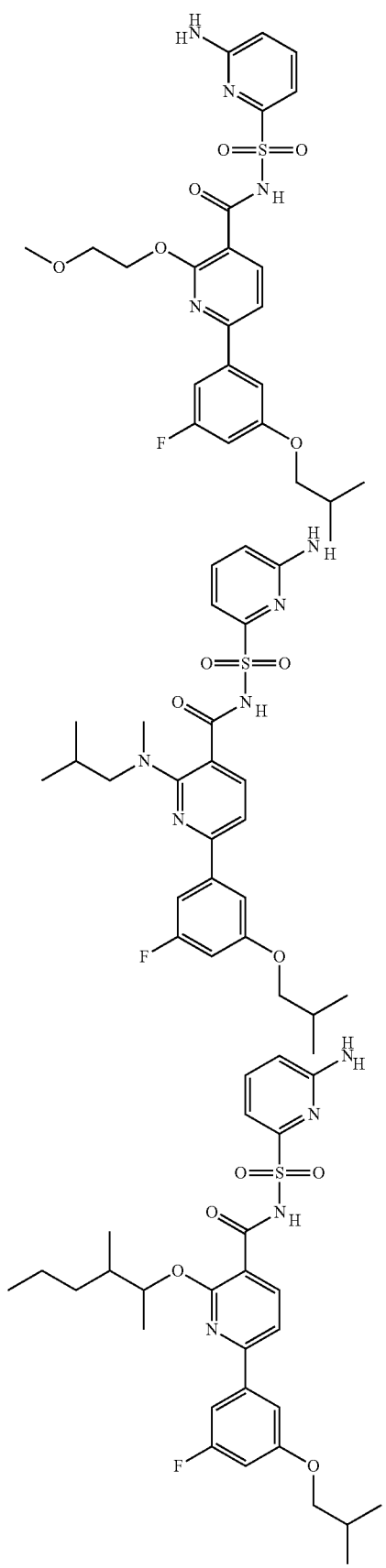
452
-continued
63
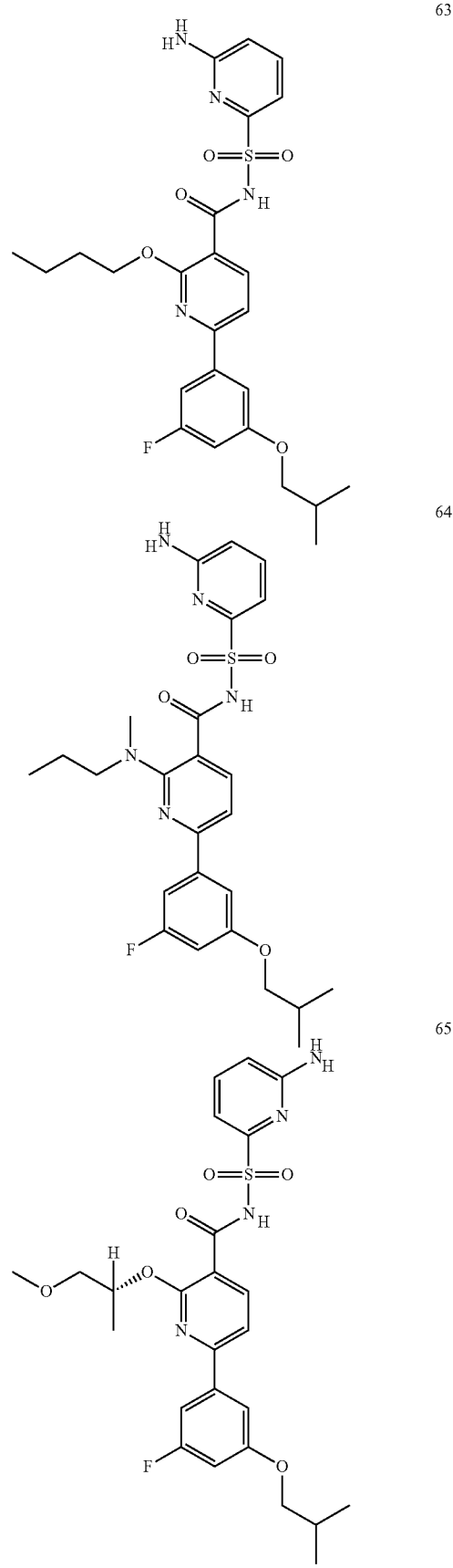

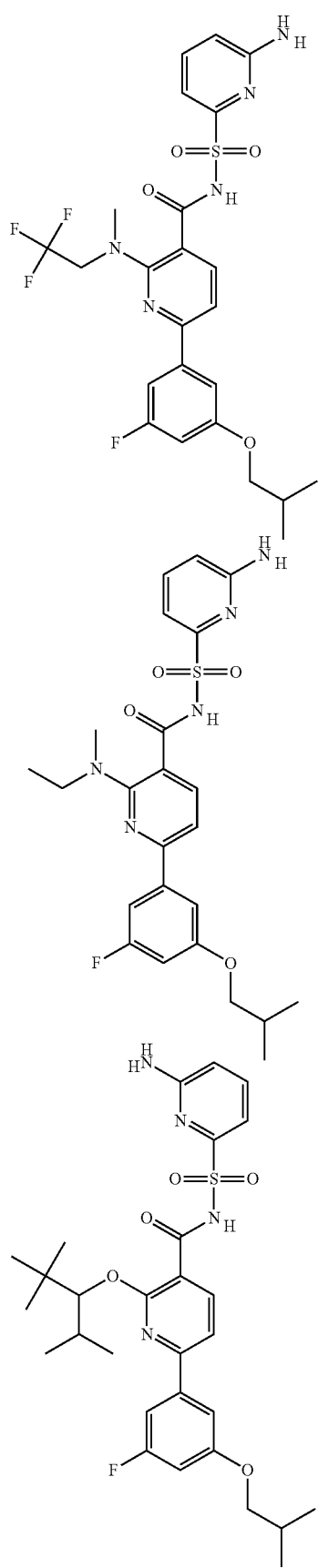
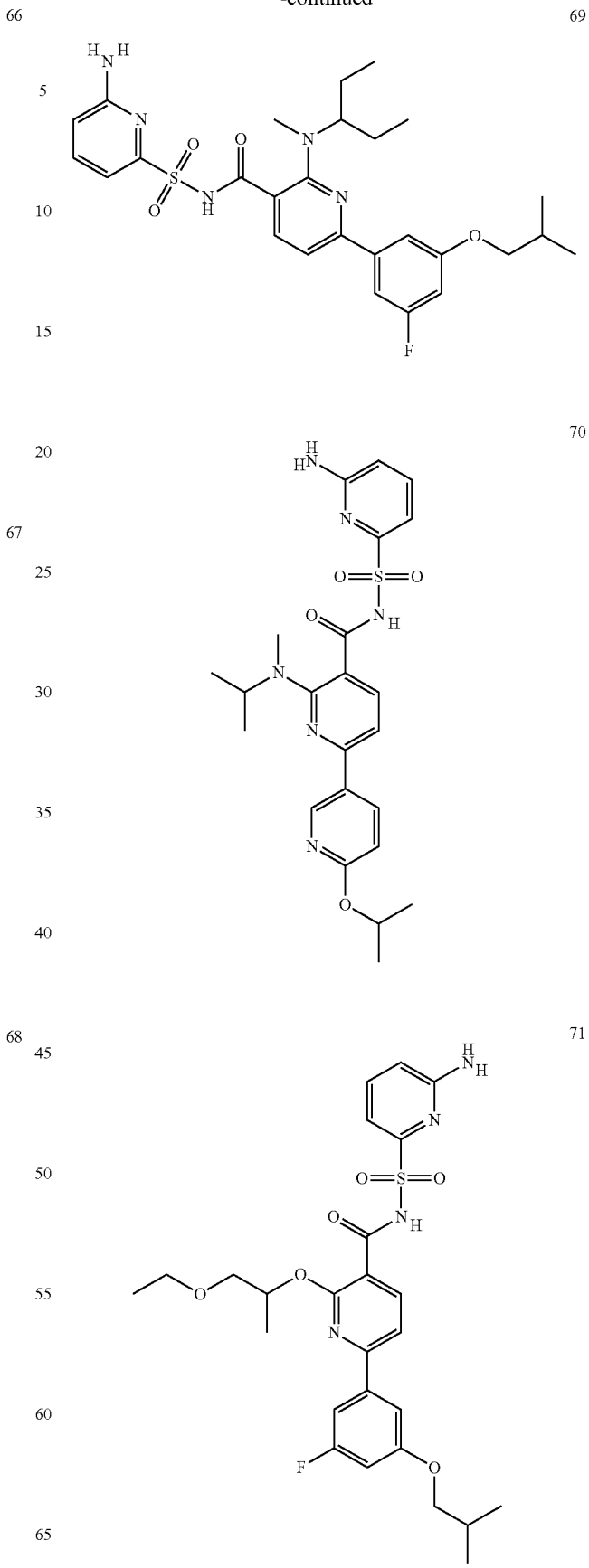

72
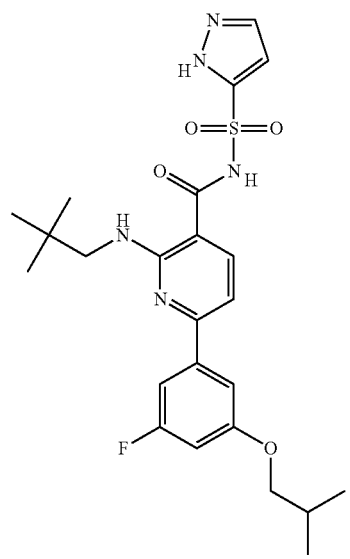
73
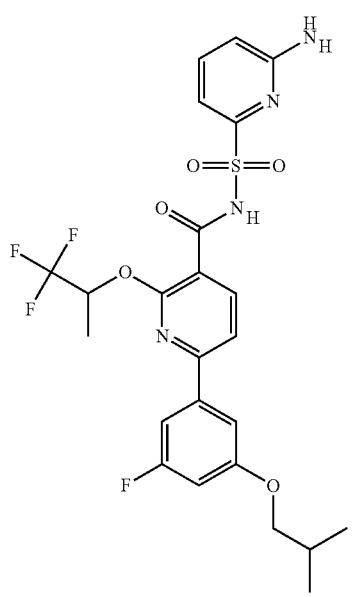
74
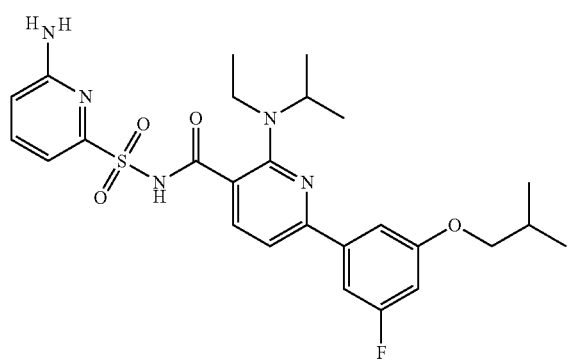
75
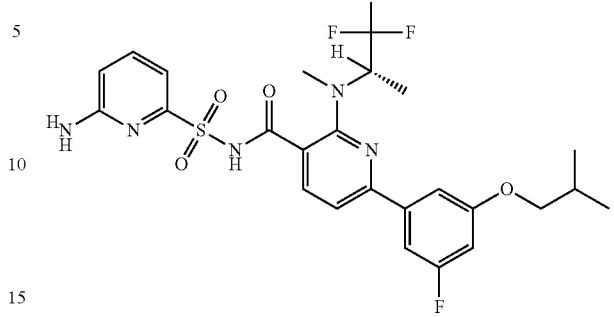
76
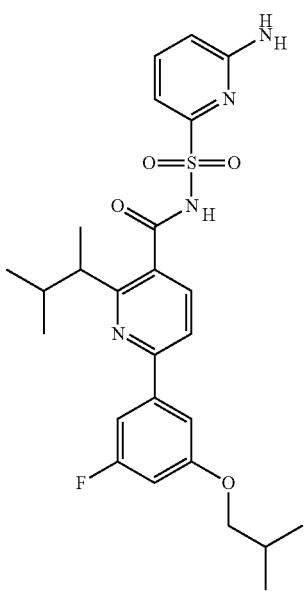
77
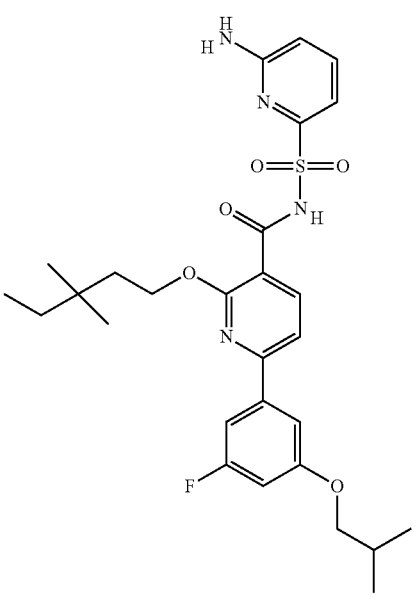

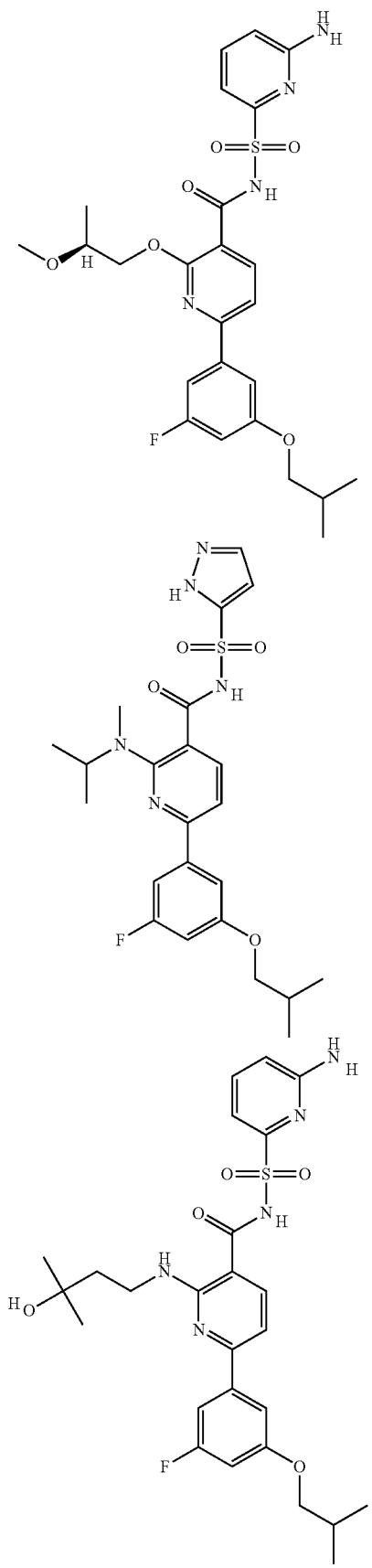
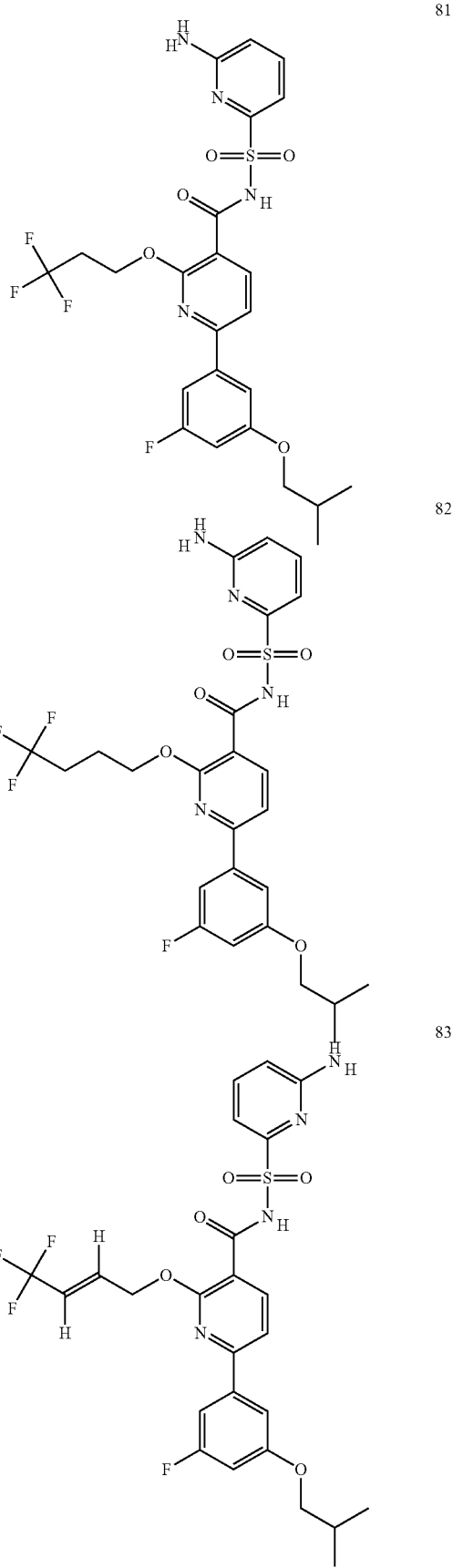

-continued

84

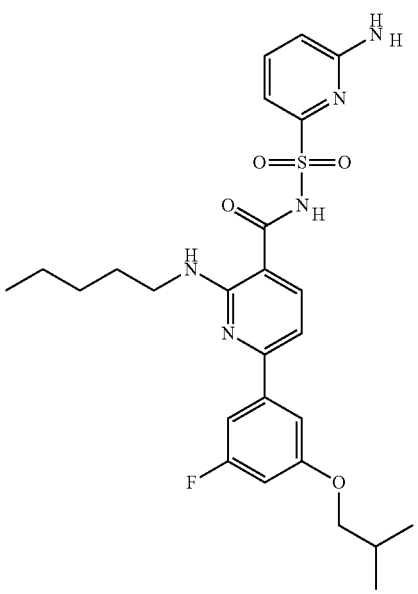

and pharmaceutically acceptable salts thereof.

32. A pharmaceutically acceptable salt of a compound of claim 1.

33. A pharmaceutically acceptable salt of a compound of claim 31.

34. A pharmaceutical composition comprising the compound of claim 1, and a pharmaceutically acceptable carrier.

35. The pharmaceutical composition of claim 34, further comprising one or more additional therapeutic agent(s).

36. The pharmaceutical composition of claim 35, wherein the one or more additional therapeutic agent(s) comprises a CFTR modulator.

37. The pharmaceutical composition of claim 35, wherein at least one additional therapeutic agent is

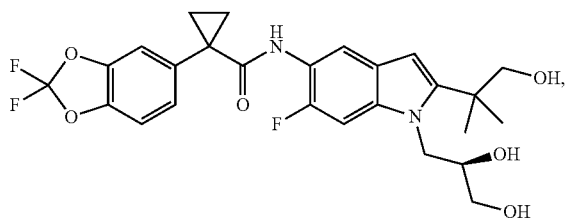 [SMILES: CC(C)(CO)c1cc2cc(NC(=O)C3(c4ccc5c(c4)OC(F)(F)O5)CC3)c(F)cc2n1C[C@@H](O)CO]

or a pharmaceutically acceptable salt thereof.

38. The pharmaceutical composition of claim 35, wherein at least one additional therapeutic agent is

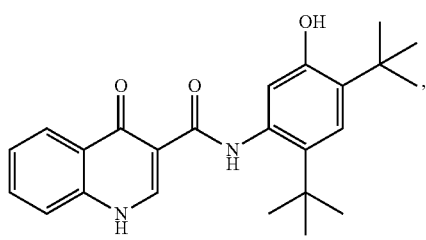

or pharmaceutically acceptable salt thereof.

39. A pharmaceutical composition comprising the compound of claim 31, and a pharmaceutically acceptable carrier.

40. The pharmaceutical composition of claim 39, further comprising one or more additional therapeutic agent(s).

41. The pharmaceutical composition of claim 40, wherein the one or more additional therapeutic agent(s) comprises a CFTR modulator.

42. The pharmaceutical composition of claim 40, wherein at least one additional therapeutic agent is

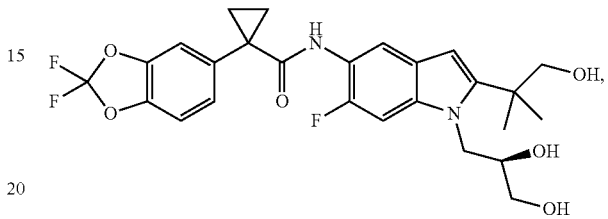

or a pharmaceutically acceptable salt thereof.

43. The pharmaceutical composition of claim 40, wherein at least one additional therapeutic agent is

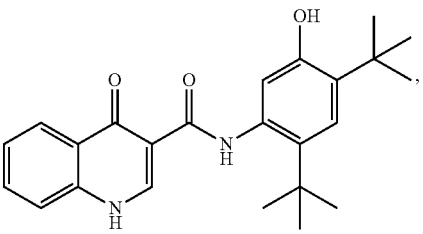

or pharmaceutically acceptable salt thereof.

44. A method of modulating cystic fibrosis transmembrane conductance regulator (CFTR) activity in a patient comprising administering to the patient in need thereof an effective amount of a compound according to claim 1.

45. A method of modulating cystic fibrosis transmembrane conductance regulator (CFTR) activity in a patient comprising administering to the patient in need thereof an effective amount of a compound according to claim 31.

46. A method of modulating cystic fibrosis transmembrane conductance regulator (CFTR) activity in a patient comprising administering to the patient in need thereof an effective amount of a composition according to claim 34.

47. A method of modulating cystic fibrosis transmembrane conductance regulator (CFTR) activity in a patient comprising administering to the patient in need thereof an effective amount of a composition according to claim 39.

48. A method of modulating cystic fibrosis transmembrane conductance regulator (CFTR) activity in a patient comprising administering to the patient in need thereof an effective amount of 1) a compound of formula II or a pharmaceutically acceptable salt thereof, or 2) a pharmaceutical composition comprising a pharmaceutically acceptable excipient and a compound of formula II or a pharmaceutically acceptable salt thereof:

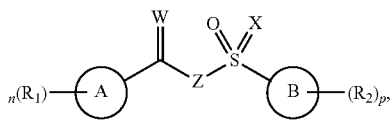

II wherein, independently for each occurrence:
  Ring A is a $C_3$-$C_{14}$ heteroaryl or heterocyclic ring wherein anywhere from 1 to 4 ring atoms are independently O, S, N, or NR;
  Ring B is a $C_3$-$C_{10}$ cycloalkyl ring; a $C_6$-$C_{10}$ aryl ring; or a $C_3$-$C_{10}$ heteroaryl or $C_3$-$C_{10}$ heterocyclic ring wherein anywhere from 1 to 4 ring atoms are independently O, S, N, or NR;
  W is O, S, or NR;
  X is O or NR;
  Z is NR;
  $R_1$ is halo; CN; NRR; $C_1$-$C_6$ alkyl or $C_1$-$C_6$ fluoroalkyl; $C_3$-$C_6$ cycloalkyl; $C_1$-$C_8$ alkoxy or $C_1$-$C_8$ fluoroalkoxy; $C_2$-$C_6$ alkenyl; $C_2$-$C_6$ alkynyl; ($C_1$-$C_9$ alkylene)-$R_3$ wherein up to four $CH_2$ units are independently replaced with O, CO, S, SO, $SO_2$ or NR; $C_6$-$C_{10}$ aryl; $C_3$-$C_{10}$ heteroaryl or $C_3$-$C_{10}$ heterocyclic ring wherein anywhere from 1 to 4 ring atoms are independently O, S, N, or NR; or $C_3$-$C_{10}$ cycloalkyl;
  $R_2$ is halo; NRR; CN; $CO_2R$; $C_1$-$C_6$ alkyl or $C_1$-$C_6$ fluoroalkyl; $C_1$-$C_6$ alkoxy or $C_1$-$C_6$ fluoroalkoxy; $C_2$-$C_6$ alkenyl; $C_2$-$C_6$ alkynyl; $C_6$-$C_{10}$ aryl; $C_3$-$C_{13}$ heteroaryl or heterocyclic ring wherein anywhere from 1 to 4 ring atoms are independently O, S, N, or NR; $C_3$-$C_{10}$ cycloalkyl; or a ($C_1$-$C_9$ alkylene)-$R_3$ wherein up to four $CH_2$ units are optionally and independently replaced with O, CO, S, SO, $SO_2$ or NR;
  or two $R_2$ may form a $=CH_2$ or $=O$ group;
  $R_3$ is H; $CF_3$; $CHF_2$; OR; C≡CH; $CO_2R$; OH; $C_6$-$C_{10}$ aryl, $C_3$-$C_{10}$ heteroaryl or heterocycloalkyl wherein anywhere from 1 to 4 ring atoms are independently O, S, N, or NR; $C_3$-$C_{10}$ cycloalkyl; NRR, NRCOR, CONRR, CN, halo, or $SO_2R$;
  R is independently H; OH; $CO_2H$; $CO_2C_1$-$C_6$ alkyl; $C_1$-$C_6$ alkyl; $C_2$-$C_6$ alkenyl; $C_2$-$C_6$ alkynyl; $C_6$-$C_{10}$ aryl; $C_3$-$C_{10}$ heteroaryl or heterocycloalkyl wherein anywhere from 1 to 4 ring atoms are independently O, S, or N; or $C_3$-$C_{10}$ cycloalkyl;
  n is 2 or 3;
  p is 0, 1, 2, or 3; and
  provided that 1) when $R_1$ is adjacent to C=W attached to Ring A, $R_1$ does not contain a ring moiety, and 2) at least one $R_1$ is adjacent to the C=W attached to Ring A.

* * * * *

UNITED STATES PATENT AND TRADEMARK OFFICE
CERTIFICATE OF CORRECTION

PATENT NO. : 10,738,030 B2
APPLICATION NO. : 16/089703
DATED : August 11, 2020
INVENTOR(S) : Brian Bear et al.

It is certified that error appears in the above-identified patent and that said Letters Patent is hereby corrected as shown below:

In the Claims

Claim 19, Column 424, Line 66, "The compound of any claim 1" should read --The compound of claim 1--.

Signed and Sealed this
Twenty-seventh Day of April, 2021

Drew Hirshfeld
*Performing the Functions and Duties of the
Under Secretary of Commerce for Intellectual Property and
Director of the United States Patent and Trademark Office*